US012157896B2

(12) United States Patent
Hewezi et al.

(10) Patent No.: US 12,157,896 B2
(45) Date of Patent: Dec. 3, 2024

(54) DISCOVERY OF SOYBEAN CYST NEMATODE RESISTANCE GENES BASED ON EPIGENETIC ANALYSIS

(71) Applicant: UNIVERSITY OF TENNESSEE RESEARCH FOUNDATION, Knoxville, TN (US)

(72) Inventors: Tarek Abdelfattah Hewezi, Knoxville, TN (US); Aditi Rambani, Knoxville, TN (US); Vincent R. Pantalone, Knoxville, TN (US); J. Hollis Rice, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 106 days.

(21) Appl. No.: 17/278,346

(22) PCT Filed: Sep. 27, 2019

(86) PCT No.: PCT/US2019/053329

§ 371 (c)(1),
(2) Date: Mar. 22, 2021

(87) PCT Pub. No.: WO2020/069241

PCT Pub. Date: Apr. 2, 2020

(65) Prior Publication Data

US 2022/0033841 A1 Feb. 3, 2022

Related U.S. Application Data

(60) Provisional application No. 62/860,451, filed on Jun. 12, 2019, provisional application No. 62/737,383, filed on Sep. 27, 2018.

(51) Int. Cl.
*C12N 15/82* (2006.01)
*C07K 14/415* (2006.01)

(52) U.S. Cl.
CPC ........ *C12N 15/8285* (2013.01); *C07K 14/415* (2013.01); *C12N 15/8213* (2013.01)

(58) Field of Classification Search
CPC .......................... C12N 15/8285; C07K 14/415
See application file for complete search history.

(56) References Cited

U.S. PATENT DOCUMENTS

| | | | |
|---|---|---|---|
| 7,569,389 | B2 | 8/2009 | Feldmann et al. |
| 9,062,322 | B2 | 6/2015 | Hatzfeld |
| 10,457,956 | B2 | 10/2019 | Hewezi et al. |

FOREIGN PATENT DOCUMENTS

| | | | | |
|---|---|---|---|---|
| WO | WO-2012149316 A2 * | 11/2012 | ......... | C12N 15/8218 |
| WO | WO 2016/109619 | 7/2016 | | |

OTHER PUBLICATIONS

Yokogawa et al (Mitochondrial phylogeny certified PGL (Paternal Genome Loss) is of single origin and haplodiploidy sensu stricto (arrhenotoky) did not evolve from PGL in the scale insects. Genes Genet. Syst. 84, 57-66, 2009) (Year: 2009).*
SeedQuest—Seed biotechnologies_2023 (Year: 2023).*
Zhang et al.(Transcriptome analysis of Kentucky bluegrass subject to drought and ethephon treatment. PLOS One. p. 1-22, Dec. 16, 2021). (Year: 2021).*
Tang et al (Populus euphratica: the transcriptomic response to drought stress. Plant Mol Biol. 83:539-557, 2013). (Year: 2013).*
Calvo-Garrido et al (Vacuole membrane protein 1, autophagy and much more. Autophagy 4:6, 835-837, 2008). (Year: 2008).*
Forster et al (Transcriptome Analysis in Tardigrade Species Reveals Specific Molecular Pathways for Stress Adaptations. Bioinformatics and Biology Insights 6 69-96, 2012). (Year: 2012).*
Database GenBank [Online] Accession No. AB439528.1, "*Asterodiaspis* sp. TY265, mitochondrial COX1 gene for cytochrome oxidase subunit 1 and COX2 gene, partial cds and partial sequence" Jul. 24, 2016, pp. 1-2.
Database EMBL [Online] Accession No. KRH70140, "Glycine max (soybean) hypothetical protein" Aug. 6, 2018, pp. 1-3.
Database GenBank [Online] Accession No. NR_048814.1, "Glycine max microRNA MIR5032 (MIR5032), microRNA," Feb. 18, 2016, pp. 1-2.
Yuan, C.-P. et al. "DNA sequence polymorphism of the Rhg4 candidate gene conferring resistance to soybean cyst nematode in Chinese domesticated and wild soybeans" *Mol Breeding*, 2012, pp. 1155-1162, vol. 30.
Written Opinion in International Application No. PCT/US2019/053329, Jan. 9, 2020, pp. 1-6.
Cook, D. E. et al. "Distinct Copy Number, Coding Sequence, and Locus Methylation Patterns Underlie Rhg1-Mediated Soybean Resistance to Soybean Cyst Nematode" *Plant Physiology*, Jun. 2014, pp. 630-647, vol. 165.
Rambani, A. et al. "The Methylome of Soybean Roots during the Compatible Interaction with the Soybean Cyst Nematode" *Plant Physiology*, Aug. 2015, pp. 1364-1377, vol. 168.

* cited by examiner

*Primary Examiner* — Charles Logsdon
*Assistant Examiner* — Wayne Zhong
(74) *Attorney, Agent, or Firm* — SALIWANCHIK, LLOYD & EISENSCHENK

(57) ABSTRACT

The invention relates to genes which may be utilized to induce resistance to soybean cyst nematode (SCN). More specifically the present disclosure provides genes that, when inactivated or overexpressed in a plant, particularly, a soybean plant, can confer upon the plant resistance to SCN. Methods of using these genes to obtain plants, particularly, soybean plants, that are resistant to SCN are also provided.

14 Claims, 42 Drawing Sheets
(41 of 42 Drawing Sheet(s) Filed in Color)

Specification includes a Sequence Listing.

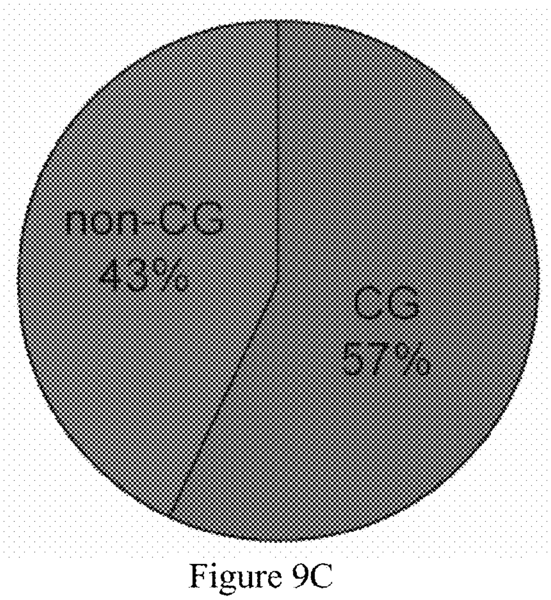
Figure 9C
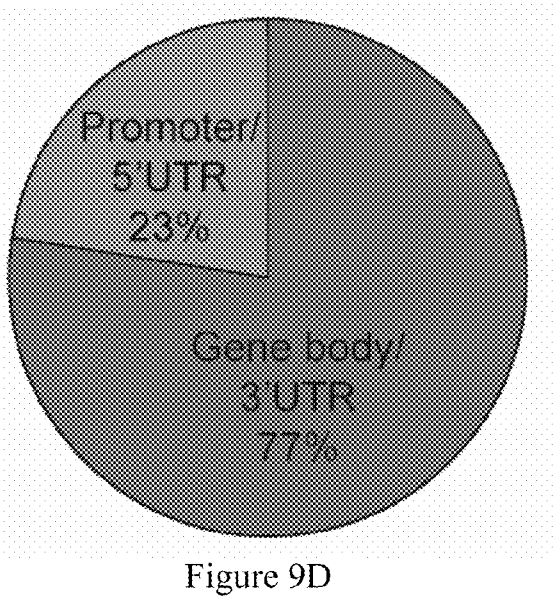
Figure 9D
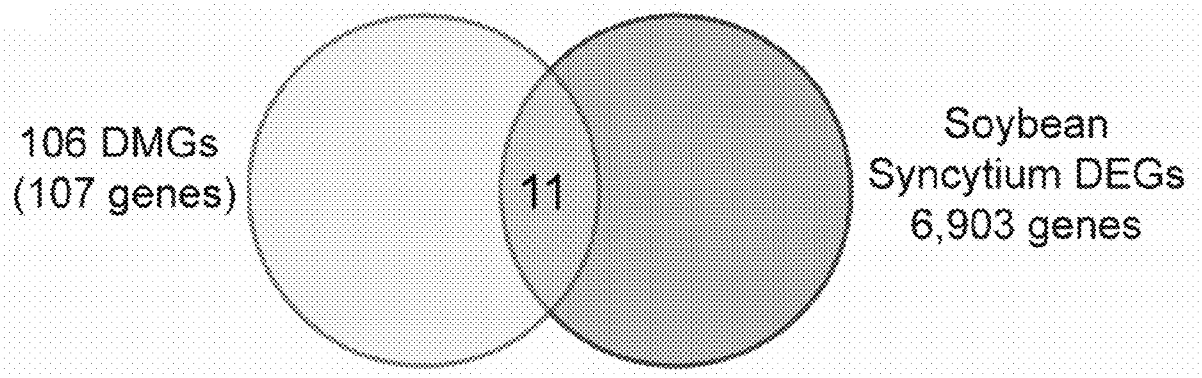
Figure 9E
Glyma.04G221900 Glyma.07G243600
Glyma.09G190500 Glyma.09G198900
Glyma.10G028800 Glyma.13G056100
Glyma.13G355400 Glyma.14G138300
Glyma.17G008600 Glyma.17G205100
Glyma.18G220700
Figure 9F

DISCOVERY OF SOYBEAN CYST NEMATODE RESISTANCE GENES BASED ON EPIGENETIC ANALYSIS

CROSS-REFERENCE TO RELATED APPLICATIONS

This application is the U.S. National Stage Application of International Patent Application No. PCT/US2019/053329, filed on Sep. 27, 2019, which claims the benefit of U.S. Provisional Ser. No. 62/737,383, filed Sep. 27, 2018, and U.S. Provisional Ser. No. 62/860,451, filed Jun. 12, 2019, the disclosures of which are hereby incorporated by reference in their entireties, including all figures, tables and amino acid or nucleic acid sequences.

The Sequence Listing for this application is labeled "SeqList_ST25.txt" which was created on Sep. 20, 2019, and is 463 KB. The Sequence Listing is incorporated herein by reference in its entirety.

FIELD OF THE INVENTION

This disclosure relates to genes that may be overexpressed or inactivated in a plant to induce resistance in the plant to soybean cyst nematode (SCN). The present disclosure also relates to methods of identification of gene(s) that can confer upon a soybean plant resistance to SCN and the methods of overexpressing or inactivating the genes so identified to obtain soybean plants that are resistant to SCN.

BACKGROUND OF THE INVENTION

DNA methylation is a consequential epigenetic change that impacts gene expression, transposon mobility, genomic stability and imprinting. Previous studies identified key enzymes that carry-out cytosine DNA methylation in various sequence contexts. After DNA replication cytosine methylation in CG and CHG is maintained through the activity of Methyltransferasel (MET1) and Chromomethylase3 (CMT3), respectively. Also, a small portion of CHH methylation can be maintained by CMT2 following DNA replication, but the large majority of CHH methylation sites are reestablished de novo. De novo DNA methylation in CG and non-CG contexts is carried-out through the synchronized activity of the RNA-directed DNA methylation (RdDM) pathway and Domains Rearranged Methyltransferase 2. Failure to faithfully maintain DNA methylation status by the maintenance enzymes after fertilization may cause spontaneous DNA methylation polymorphisms referred to as epialleles. Epialleles can be induced by developmental and environmental stimuli as well as through transposon insertions and genome rearrangements that induce directed chromatin modifications.

DNA methylation patterns of *Arabidopsis* lines generated through single-seed descent for 30 generations with their ancestral lines revealed that spontaneous loss and gain of DNA methylation at individual cytosine sites occur at high levels mainly in the genic regions in the CG sequence context. Regions with continuous cytosine methylation polymorphisms were also found but at relatively lower rate. Studies of inheritance and stability of DNA methylation patterns in maize and soybean using populations of recombinant inbred lines (RILs) provided additional evidences for transgenerational inheritance of DNA methylation variants over several generations in the segregating populations.

Similar to spontaneously generated DNA methylation variants experimentally induced DNA methylation changes may result in generation of novel non-parental DNA methylation polymorphisms that are heritable. For example, DNA hypomethylation induced by mutation in the *Arabidopsis* DDM1 gene was stably transmitted over several generations. Similarly, ddm1-induced hypermethylation of BONSAI gene was consistently maintained in the ddm1 after recurrent self-pollination. More comprehensive studies of transgenerational inheritance of DNA methylation variants were conducted in *Arabidopsis* using epigenetic recombinant inbred lines known as epiRILs that were generated by crossing the hypomethylated mutants met1 or ddm1 with wild-type plants. Analysis of DNA methylation profiles in these epiRILs documented the transgenerational inheritance of parental DNA methylation patterns in addition to the presence of newly acquired non-parental methylation variants. Furthermore, phenotypic analysis of the epiRILs for various traits including plant growth, plant height, flowering time and response to biotic and abiotic stresses revealed high degree of heritability, indicating that epiallelic variations may contribute to the heritability of complex traits. Combining hypomethylated and normally methylated genomes in F1 plants triggers substantial reprogramming of plant methylomes that may result in novel and heritable epialleles. Therefore, interference with DNA methylation programs may spontaneously trigger heritable epigenetic variations that may be conditioned by cis- and/or trans-acting differences.

In soybean, SCN (*Heterodera glycines*) is a damaging pathogen, causing significant yield and quality losses. SCN induces vascular root cells to fuse and form a permanent feeding structure, the syncytium, essential for nematode development and maturity. Resistance to SCN is conferred by two main loci, Rhg1 (for resistance to *H. glycines*) and Rhg4, at chromosome 18 and 8, respectively. The Rhg1 locus contains three genes within a 31-kb repeat region that encode an α-SNAP protein, a putative amino acid transporter, and a wound-inducible protein. Increased expression of these three genes, mediated by high copy number, was found to contribute to SCN resistance in an additive manner. Rhg4 locus contains only one gene encoding serine hydroxymethyltransferase (GmSHMT08). SCN resistance in commercially available soybean cultivars is gained from two main sources that include plant introduction (PI) 88788 and Peking. (PI) 88788-derived resistance is mediated by high copy number of rhg1-b allele (7 to 10 copies), and cultivars produced from this source display slow degeneration of the nematode feeding site, leading to delayed arrest of nematode development. Peking-derived resistance requires both Rhg4 and rhg1-a alleles, and cultivars produced from this source display stronger and faster resistance response, leading to rapid arrest of nematode development at the infective juvenile stage. However, molecular mechanisms through which Rhg1 and Rhg4 mediate SCN resistance remain to be elucidated.

Serine hydroxymethyltransferases (SHMTs) are key enzymes involved in one-carbon metabolism, a housekeeping cellular function that supports various physiological processes including redox defense and DNA methylation. The anticipated function of Rhg4 (GmSHMT08) in redox defense is consistent with the activation of significant numbers of genes associated with oxidative stress, hypersensitive responses and programmed cell death in the syncytium formed in Peking. The potential implication of Rhg4 in modulating plant DNA methylation landscape is striking since recent studies indicated that level and pattern of plant DNA methylation are considerably modulated during cyst nematode infection.

Therefore, discovery of proteins and genes that modulate plant DNA methylation pattern to confer genetic resistance to cyst nematode infection is warranted.

SUMMARY OF THE INVENTION

The instant invention pertains to the function of Rhg4 and Rhg1 loci in establishing DNA methylome landscapes of soybean roots during SCN infection. Highly homozygous near-isogenic lines (NILs) differing at Rhg4 and Rgh1 loci were analyzed to obtain insights into the role of GmSHMT08 and GmSNAP18 in reprograming soybean methylomes that may prime a plant's response to SCN parasitism.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A-9F: Identification of novel non-parental DMRs specific to the resistant isogenic line. A: Heat map of 102 DMRs showing methylation patterns specific to TN09-29. B: Example of a DMR overlapping with a protein coding gene (Glyma.18g33500) and showing methylation patterns specific to TN09-29. The region was hypermethylated in TN09-29 but hypomethylated in TN09-16 and the parental lines Fowler and Anand. C and D: Proportions for methylation contexts (C) and overlapping genic features of the identified 102 DMrs (D). E. Identification of 11 genes overlapping between the 100 DMR-associated genes and the previously identified syncytium DEGs. F: Accession numbers of the 11 overlapping genes.

DETAILED DESCRIPTION OF THE INVENTION

Figure 1:
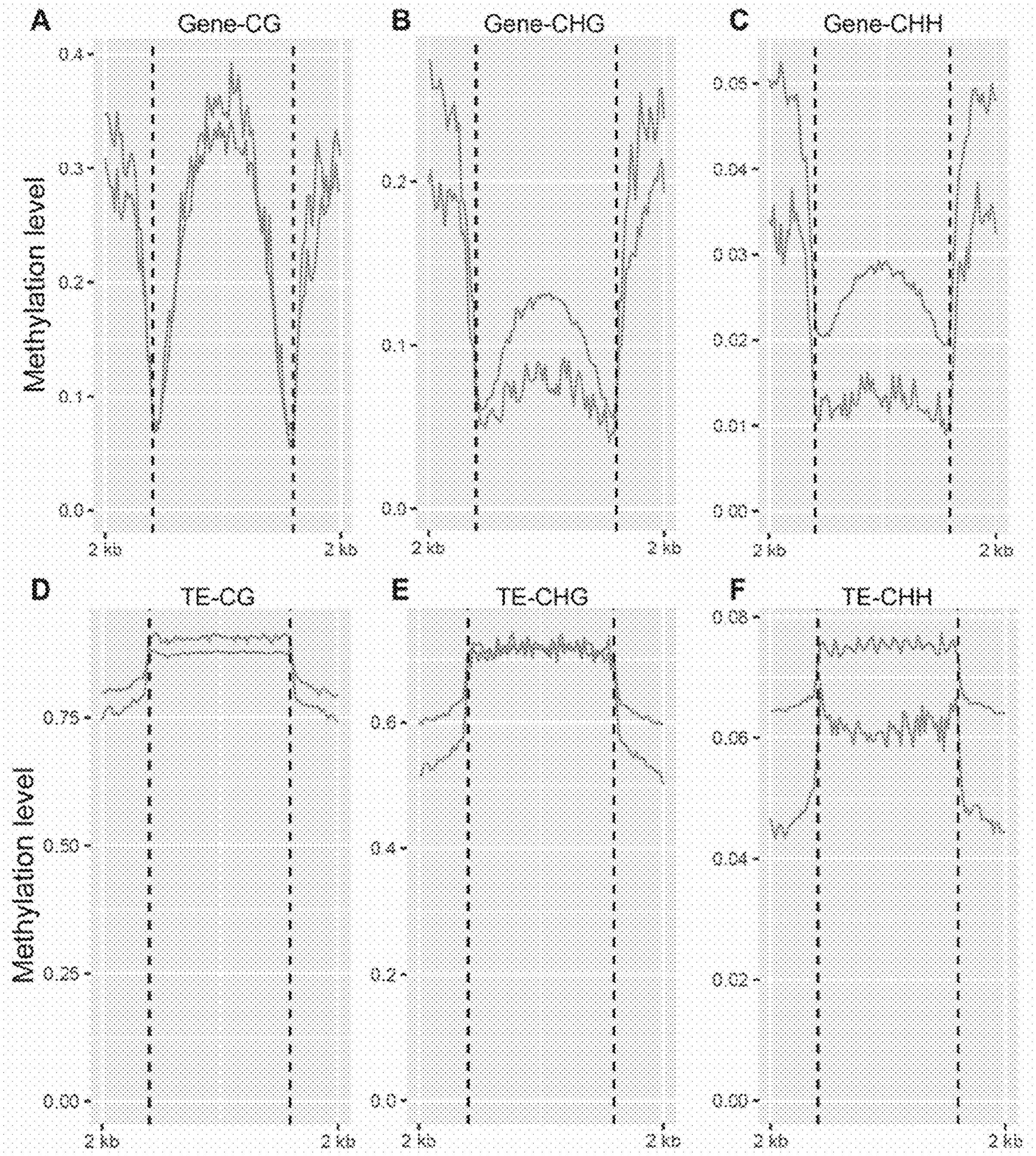
FIG. 1: Comparison of global DNA methylation levels between TN09-16 and TN09-29 over genes and TEs in various sequence contexts under non-infected conditions. Global DNA methylation levels over protein-coding genes (A-C) and TEs (D-F) in the CG, CHG, and CHH sequence contexts.

The present invention relates to a novel and useful methods for introducing in a reliable and predictable manner SCN resistance into non-resistant soybean germplasm. The method involves the genetic-mapping of loci associated with SCN resistance based on epigenetic analysis of parent and progeny lines that are resistant or susceptible to SCN. The genetic loci identified to be associated with the SCN resistance can be overexpressed or inactivated in a plant to render it resistant to SCN.

Epigenetics can be defined as the biochemical modifications of DNA and associated proteins that regulate gene expression and chromosome structure and function, without changing DNA nucleotide sequences. DNA methylation, the most common epigenetic modifications, is the addition or removal of a methyl group ($CH_3$), mostly where cytosine bases occur repeatedly. In plants, DNA methylation occurs in symmetric (CG and CHG) and asymmetric (CHH) contexts where H refers to any nucleotide but G. The CG and CHG patterns are symmetric across the two DNA strands, which are believed to be important for the maintenance of methylation at these sites following DNA replication. DNA cytosine methylation, as the main epigenetic mark, controls gene expression networks and hence plays essential roles in different aspects of plant growth, development, and response to biotic stress (Zhang et al., 2010; He et al., 2011, Dowen et al. 2012). While DNA methylation has been initially reported to control various developmental processes in plants, recent studies revealed that this silencing pathway plays a key role in modulating plant defense responses during biotrophic interactions (Yu et al., 2013; Dowen et al. 2012; Luna et al., 2012). Recently, Dowen et al. (2012) provided a clear evidence of dynamic changes in DNA methylation in response to infection by the bacterial pathogen *Pseudomonas syringae* pv. tomato DC3000 (Pst). Using deep sequencing of bisulfite treated DNA, they found that differentially methylated regions (DMRs) are preferentially associated with genes involved in defense response, and that hypomethylation in DMRs is frequently accompanied by activation of the proximal genes, specifically those with defense response function. Similarly, another recent study indicated that DNA demethylation restricts the multiplication and vascular propagation of the Pst and, consequently some immune response genes, are repressed by DNA methylation (Yu et al., 2013). Chemical demethylation of the silenced resistance Xa21G gene in rice reestablished its resistance function against Xanthomomonas *oryzae* (Akimoto et al., 2007). Similarly, induced DNA hypomethylation at the NBS-LRR gene clusters by the tobacco mosaic virus was associated with increased genomic rearrangements at these genomic loci (Boyko et al., 2007). The expression difference between the resistant alleles of the *Medicago truncatula* REP1 gene, which confers resistance against the powdery mildew disease caused by the biotrophic fungus *Erysiphe pisi*, was found to be correlated with the methylation status at the promoter regions (Yang et al., 2013). In soybean, differential hypermethylation patterns at the genomic regions that contain multiple copies of SCN resistance gene Rhg1 have been recently identified (Cook et al., 2014). Collectively these results indicate that DNA methylation plays a crucial role in regulating the immune system in response to pathogen infection including cyst nematodes.

Epigenetic variation is when the phenotypic traits of an individual vary without altering the primary sequence of its DNA. This can occur through changes in the expression of particular genes via processes such as DNA methylation and chromatin remodeling, and by influencing the activity of RNA structures which regulate levels of gene expression.

Epigenetic changes in gene expression enable an individual to respond to changes in the environment and adjust the synthesis of proteins accordingly. It has become apparent that while many of the epigenetic modifications to the genome are reset during the process of meiosis, some epigenetic information can be transmitted between generations, so that the phenotypic traits of offspring are affected without altering the primary structure of the DNA. Thus offspring can inherit tolerance to a particular environmental condition before they have been exposed.

In this disclosure the term "isolated nucleic acid" molecule means a nucleic acid molecule that is separated from other nucleic acid molecules that are usually associated with the isolated nucleic acid molecule. Thus, an "isolated nucleic acid molecule" includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated nucleic acid".

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)). The term nucleic acid is used interchangeably with gene, cDNA, and mRNA encoded by a gene.

The term "gene" means the segment of DNA involved in producing a polypeptide chain or a microRNA (miRNA); it includes regions preceding and following the coding region (leader and trailer) involved in the transcription/translation of the gene product and the regulation of the transcription/translation, as well as intervening sequences (introns) between individual coding segments (exons).

In this application, the terms "polypeptide", "peptide", and "protein" are used interchangeably herein to refer to a polymer of amino acids. The terms apply to amino acid polymers in which one or more amino acid residues are artificial chemical mimetic of a corresponding naturally occurring amino acids, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used in herein, the terms "identical" or percent "identity", in the context of describing two or more polynucleotide or amino acid sequences, refer to two or more sequences or subsequences that are the same or have a specified percentage of amino acid residues or nucleotides that are the same (for example, a variant protein used in the method of this invention has at least 80% sequence identity, preferably 85%, 90%, 91%, 92%, 93, 94%, 95%, 96%, 97%, 98%, 99%, or 100% identity, to a reference sequence), when compared and aligned for maximum correspondence over a comparison window, or designated region as measured using one of the following sequence comparison algorithms or by manual alignment and visual inspection. Such sequences are then said to be "substantially identical". With regard to polynucleotide sequences, this definition also refers to the complement of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists".

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed.

In the present disclosure, ranges are stated in shorthand, to avoid having to set out at length and describe each and every value within the range. Any appropriate value within the range can be selected, where appropriate, as the upper value, lower value, or the terminus of the range. For example, a range of 1-10 represents the terminal values of 1 and 10, as well as the intermediate values of 2, 3, 4, 5, 6, 7, 8, 9, and all intermediate ranges encompassed within 1-10, such as 2-5, 2-8, and 7-10. Also, when ranges are used herein, combinations and sub-combinations of ranges (e.g., subranges within the disclosed range) and specific embodiments therein are intended to be explicitly included.

An endogenous nucleic acid is a nucleic acid that is naturally present in a cell. For example, a nucleic acid present in the genomic DNA of a cell is an endogenous nucleic acid.

An exogenous nucleic acid is any nucleic acid that is not naturally present in a cell. For example, a nucleic acid vector introduced into a cell constitutes an exogenous nucleic acid.

The subject invention provides for the use of "homologous nucleic acid sequences" or "homologs of nucleic acid sequences". Homologs of nucleic acid sequences will be understood to mean any nucleotide sequence obtained by mutagenesis according to techniques well known to persons skilled in the art, and exhibiting modifications in relation to the parent sequences. For example, mutations in the regulatory and/or promoter sequences for the expression of a polypeptide that result in a modification of the level of expression of a polypeptide according to the invention provide for a "homolog of a nucleotide sequence". Likewise, substitutions, deletions, or additions of nucleic acid to the polynucleotides of the invention provide for "homologs" of nucleotide sequences. In various embodiments, "homologs" of nucleic acid sequences have substantially the same biological activity as the corresponding reference gene, i.e., a gene homologous to a native gene would encode for a protein having the same biological activity as the corresponding protein encoded by the naturally occurring gene. Typically, a homolog of a gene shares a sequence identity with the gene of at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. These percentages are purely statistical and differences between two nucleic acid sequences can be distributed randomly and over the entire sequence length.

Likewise, the subject invention also provides for the use of "homologs of proteins". Homologs of proteins will be understood to mean any proteins obtained by mutagenesis according to techniques well known to persons skilled in the art, and exhibiting modifications in relation to the parent protein. Such modifications in a protein sequence include substitutions, deletions, or additions of amino acids to produce homologs of proteins. In various embodiments, a homolog of a protein has substantially the same biological activity as the protein, i.e., a protein homolog of a native protein would have the same biological activity as the native protein. Typically, a homolog of a reference protein shares a sequence identity with the reference protein of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. These percentages are purely statistical and differences between two nucleic acid sequences can be distributed randomly and over the entire sequence length.

Rhg4 is a major locus required for SCN resistance in certain soybean accessions. Rhg4 encodes a serine hydroxymethyltransferase (GmSHMT08), whose function in nematode resistance remains mostly unknown. A key role of GmSHMT08 in reprograming soybean methylome during SCN infection is demonstrated using a pair of highly homozygous NILs containing the resistant or susceptible Rhg4 allele. Under non-infected conditions, the genomes of the NILs were considerably differentially methylated. The substantial differences in DNA methylation patterns between the NILs were associated with differential gene expression that may prime their response to SCN parasitism. In response to SCN infection, the NILs exhibited contrasted DNA methylation patterns with the methylome of the susceptible line being more dynamic than that of the resistant line.

Analysis of the methylome landscapes mediated by the SCN resistance gene Rhg4 was facilitated by using highly genetically identical NILs differing in Rhg4 locus and showing opposite responses to SCN infection. A key role of Rhg4 in establishing the root methylomes of the isogenic lines was demonstrated by the finding that the genomes of the isogenic lines were substantially differentially methylated both under non-infected and SCN-infected conditions. Rhg4 is believed to be the key factor mediating these differences since no gene involved in DNA methylation machinery was identified as differentially expressed when the root transcriptome of the isogenic lines were compared. This disclosure also indicates that methylome differences in the isogenic lines were established de novo since only 59 genetic regions showing opposite methylation patterns in these lines were inherited from the parents.

Under non-infected conditions, a general trend was observed of increased global DNA methylation in the SCN susceptible line relative to the SCN resistant line, specifically in the CHG and CHH contexts over protein-coding genes and TEs. However, the resistant line exhibited increased DNA methylation over the body of protein-coding genes and TEs in the CG context. This finding suggests that global decrease in CHG and CHH methylation in the resistant line complemented with an increase of CG methylation. Unlike other plant species in which gene body methylation occurs exclusively at CG sites, a significant number of CHG-DMRs were observed in the body of protein-coding genes when the methylomes of the two isogenic lines were compared under non-infected conditions. This could be the results of high insertion rate of short TEs in the introns of these genes. However, only 32% of the body CHG-methylated genes possess DMTEs inside their transcribed regions. Another possibility is that CHG methylation in gene body may be linked to the activity of various histone demethylases that function in eliminating methylation at histone H3 lysine 9 (H3K9me). In *Arabidopsis*, loss-of-function of the H3K9 demethylase IBM1 (Increase in BONSAI Methylation1) induced CHG methylation in the body of thousands of highly expressed genes. Thus, differential accumulation of H3K9me in the body of actively transcribed genes may be responsible for CMT3-mediated differential genic CHG methylation between the isogenic lines. If CHG-methylation in gene body was mechanistically associated with CG or CHH methylation was also examined. Interestingly, only 24 and 3% of body CHG-methylated genes showed differential methylation in CG or CHH contexts, respectively. This finding suggests that CHG methylation in transcribed regions is mostly independent of CG and CHH methylation.

The isogenic lines also exhibited high level of differential DNA methylation in TEs, particularly LTR-type in the CHG context. This result may reflect differences in the transposition dynamics of Copia and Gypsy retrotransposons, which tend to be more vulnerable to DNA methylation than other types of TEs.

Rhg4-mediated methylome changes in the isogenic lines under non-infected conditions appeared to significantly impact the methylation patterns of several genes involved in epigenetic regulation. Various epigenetic components including DNA methylation, histone modification and siRNA accumulation are highly interconnected. Thus, differential methylation of key genes involved in these pathways may be a part of epigenetic feedback regulatory mechanisms that maintain epigenetic information. Maintenance of epigenetic information could contribute to priming of plant defense responses. The RNA-seq analysis of the NILs under non-infected conditions pointed into a possible difference in some type of defense priming between the lines. This possibility was further reinforced by a number of findings. First, the DEGs were highly enriched for genes involved in defense responses and biological processes associated with nematode susceptibility. Second, about one-third of the DEGs were previously shown to change expression in SCN-induced syncytium. Third, the DEGs included numerous marker genes of defense priming, including several WRKY transcription factors, ROS-related genes, and lipoxygenases. *Arabidopsis* hyper- and hypomethylated mutants developed opposite responses to pathogen infection that were dependent on the mutants' ability to prime salicylic acid-mediated defense responses and callose deposition. In this context, DNA methylation can prime defense responses in a way that alters chromatin structure to expedite gene transcription.

The role of GmSHMT08 in establishing the methylomes of the isogenic lines became more evident when the methylomes of isogenic lines were determined under SCN-infected conditions. Consistent with the role of SHMT enzymes in cellular methylation, the susceptible line, which contains a non-functional allele of Rhg4, exhibited reduced global methylation levels in both protein-coding regions and TEs, whereas the resistant line showed the opposite response of increased global methylation levels. This trend was observed in all three methylation contexts, suggesting that the SHMT enzymes may have significant impact the whole methylation pathway. Also, the methylome of the susceptible line is more dynamic than that of the resistant line in response to SCN infection. 50,040 DMRs were identified in the susceptible line compared to only 5,080 DMRs in the resistant line. This dynamic can be explained by the many cellular processes that accompany syncytium formation and development during the susceptible interaction compared to localized cell death that occurs during the resistant interaction. In addition to the dramatic differences between the isogenic lines in term of methylation level and direction, differential DNA methylation patterns within protein-coding genes and TEs demonstrated remarkable level of specificity as only 74 DMRs were found common to both lines.

A low overlap was observed between the DEGs and the DMGs in the resistant line during SCN infection. This may be due to the dilution of localized gene expression changes at the infection sites by using whole roots as analyzed here. Because DNA methylation can precede gene expression changes during cyst nematode infections, the DMGs may associate with gene transcription at later stage of infection. Alternatively, DNA methylation patterns may regulate the steady-state expression of these genes, preventing their induction or repression during the resistant response. A role of DNA methylation as a secondary stabilizer of gene expression has been recently proposed. Also, DNA methylation function mutually with other epigenetic modification and hence, one can anticipate that methylation status of these genes may necessitate additional epigenetic marks to influence gene transcription to the level of significance.

In contrast to the resistant interaction, DNA methylation reprograming during the susceptible interaction seem to directly impact gene transcription levels. A set of 147 differentially expressed genes (DEGs) and differentially methylated genes (DMGs) was identified. Differential DNA methylation seems to impact cellular functions that are directly modulated by cyst nematode effectors. For example, genes involved in pectin demethylesterification and polyamine oxidation, which are targeted by the cyst nematode effectors cellulose binding protein and 10A06, respectively, were among the 147 DEGs/DMGs. The potential effect of DNA methylation on gene transcription was obvious in many situations as in the case of an adaptin family protein gene, which was hypomethylated in the promoter, gene body, and 3'UTR in various sequence contexts and highly induced in response to SCN infection. Adaptin family proteins are involved in intracellular protein trafficking and thus hypomethylation-mediated upregulation of this gene may facilitate assimilate flow to the syncytium. Another example of the impact of DNA methylation is the down-regulation of cycling DOF factor 2 (CDF2), which was hypomethylated in gene body in the CG context, but was hypermethylated in the promoter region in the CHH context. In *Arabidopsis*, CDF2 has been reported to regulate the expression of a number of miRNA genes at both transcriptional and posttranscriptional levels by direct binding to miRNA promoters or through modulation of DCL1-mediated processing of primary miRNA transcripts. Thus, reprogramming of DNA methylation patterns may function in concert with other epigenetic pathways during SCN parasitism.

Increased activity of metabolism pathways is known to play central role in successful nematode parasitism. This disclosure demonstrates that DNA methylation contributes to the regulation of the transcriptional activity of several key genes specifically associated with the metabolic processes of carbohydrate, glucan and malate, presumably to maintain metabolite levels at an active physiological status compatible with nematode feeding and development. Associations between hyper- and hypomethylation and significant changes in gene expression were also observed for several genes involved in the biogenesis of primary and secondary cell walls, organization of actin and microtubules, defense responses, and signal transduction. Thus, cyst nematode-induced differential methylation during the susceptible interaction appears to regulate similar cellular processes in various plant species.

Figure 11:
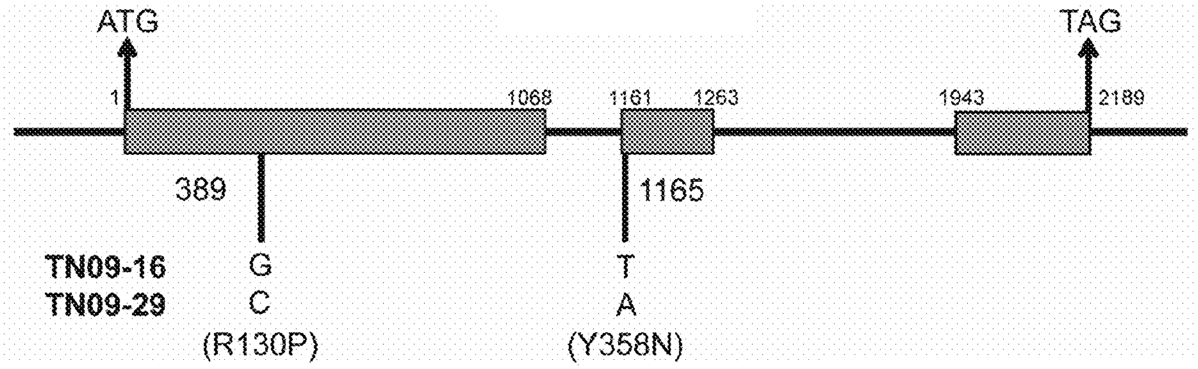
FIG. 11: Schematic representation of the two single nucleotide polymorphisms identified in the susceptible line TN09-16 leading to R130P and Y358N amino acid substitutions.

Two near isogenic lines (NILs), TN09-16 and TN09-29, respectively containing the susceptible and resistant allele of Rhg4, were generated. These NILs are highly homozygous recombinant inbred lines derived from individual F13 generation single plants from a cross between the SCN-resistant variety Fowler and the SCN-susceptible variety Anand. Homozygosity level of these NILs was estimated to be 0.9998 based on the number of inbreeding generations after the creation of F1. SCN resistance in the parental line Fowler was acquired from the Plant Introduction (PI) 437654. PI 437654, which exhibit 'Peking-type' resistance, has been shown to carry the SCN resistance gene Rhg4 and three copies of rhg1a. Initially, Simple Sequence Repeat (SSR) markers associated with rhg1 (Satt309) and Rhg4 (Satt162 and Satt632) were used to test potential genetic differences between these two NILs at rhg1 and Rhg4 loci. The resistant line TN09-29 inherited the two resistant alleles from its Hartwig ancestry. The susceptible line TN09-016, however, did not inherit the Rhg4 allele but did receive the Rhg1 resistant allele. The SCN resistance genes soluble NSF attachment proteins (GmSNAP18) and the serine hydroxymethyltransferase (GmSHMT08) at the rhg1 and Rhg4 loci, respectively, were cloned and sequenced from the isogenic lines. While the nucleotide sequences of GmSNAP18 were identical in both lines, GmSHMT08 showed two single nucleotide polymorphisms (SNPs), leading to R130P and Y358N amino acid substitutions between the TN09-29 and TN09-16 (FIG. 11). These two amino acid substitutions were previously reported to establish the difference between the resistant and susceptible alleles of Rhg4.

The methylome analysis of the parental lines and the two isogenic lines revealed 56 and 102 genetic regions that exhibit novel non-parental methylation patterns unique to TN09-16 and TN09-29, respectively. Gain or loss of DNA methylation in these regions seem to occur to a similar extent with preference observed for CG and CHG contexts. Gain of DNA methylation appears to be introduced in the isogenic lines, whether environmentally or genetically, during the 13 generations of breeding and was faithfully maintained through the activity of MET1 and CMT3. In contrast, loss of DNA methylation in certain genic regions could be the result of absence of corrective DNA methylation mechanisms that can restore DNA methylation. Failure to reestablish DNA methylation in specific genic regions may be due to the loss of the repressive histone mark H3K9me2, which has been shown to be directly or indirectly linked to the activity of MET1 and CMT3-mediated DNA methylation in CG and non-CG contexts.

The non-parental methylation patterns in these genic regions could be induced by transposons located in proximity to these DMR-associated genes, specifically those transposons that are prone to DNA methylation change under infected conditions. 12 of the 56 DMRs found to be unique to the susceptible line TN09-16 were located within 2 Kb of differentially methylated TEs identified in TN09-16 in response to SCN infection. Previously, it has been shown that TEs can induce heritable epialleles by bringing neighboring genes under their own regulation. Whether these 56 DMRs are particularly vulnerable to DNA methylation changes under SCN infected conditions was examined. Interestingly, 18 of these DMRs were found to be among those identified in TN09-16 in response to SCN infection. Similarly, 20 of the 102 DMRs that were unique to TN09-29 were among those showing differential methylation under SCN infection. Together, these findings suggest that the non-parental methylation patterns occur in regions that are vulnerable to methylation changes and that some introduced variations in DNA methylation pattern can be inherited and stably transmitted to offspring. A small portion of stress-induced DNA methylation changes can be faithfully transmitted to next generations. However, the association of these regions with genes previously shown to change expression in the syncytium highlight sheds lights into a role of these regions in SCN parasitism of soybean.

Thus, comparing the methylomes of the parental lines with that of the NILs resulted in the identification of heritable as well as novel non-parental differentially methylated regions overlapping with genes related to SCN parasitism of soybean. Thus, the disclosure provides the genes involved in biochemical basis of Rhg4 function in SCN resistance.

The disclosure provides that the genes listed in Table 1 (SEQ ID NOs: 1-210) provide resistance or susceptibility to a plant cell or a plant, particularly, a soybean plant cell or a soybean plant. For example, overexpressing in a plant cell or a plant, particularly, a soybean plant cell or a soybean plant, one or more genes comprising a protein coding sequence selected from SEQ ID NOs: 1-209 or homologs thereof renders the plant cell or the plant, particularly, the soybean plant cell or the soybean plant, resistance to SCN. Similarly, overexpressing in a plant cell or a plant, particularly, a soybean plant cell or a soybean plant, the gene encoding the miRNA having the sequence of SEQ ID NO: 210 (gma-miR5032) or a homolog thereof renders the plant cell or the plant, particularly, the soybean plant cell or the soybean plant, resistance to SCN. Also, inactivating in a plant cell or a plant, particularly, a soybean plant cell or a soybean plant, one or more genes comprising a protein coding sequence selected from SEQ ID NOs: 1-209 or homologs thereof renders the plant cell or the plant, particularly, the soybean plant cell or the soybean plant, resistance to SCN.

TABLE 1

SEQ ID NOs: 1 to 210 providing candidate genes that confer SCN resistance when overexpressed or inactivated.

| Glyma ID No. | SEQ ID NO: |
|---|---|
| Glyma.11G004900 | 1 |
| Glyma.14G142500 | 2 |
| Glyma.17G216000 | 3 |
| Glyma.09G171300 | 4 |
| Glyma.10G083800 | 5 |
| Glyma.U040800 | 6 |
| Glyma.17G017300 | 7 |
| Glyma.17G223100 | 8 |
| Glyma.09G094000 | 9 |
| Glyma.09G198400 | 10 |
| Glyma.09G123300 | 11 |
| Glyma.09G132300 | 12 |
| Glyma.09G133900 | 13 |
| Glyma.09G129600 | 14 |
| Glyma.04G157200 | 15 |
| Glyma.04G191800 | 16 |
| Glyma.04G036000 | 17 |
| Glyma.07G168900 | 18 |
| Glyma.15G015100 | 19 |
| Glyma.13G228800 | 20 |
| Glyma.13G234600 | 21 |
| Glyma.13G288000 | 22 |
| Glyma.13G005900 | 23 |
| Glyma.13G320100 | 24 |
| Glyma.13G339600 | 25 |
| Glyma.19G044300 | 26 |
| Glyma.19G136000 | 27 |
| Glyma.03G131000 | 28 |
| Glyma.03G085300 | 29 |
| Glyma.03G129100 | 30 |
| Glyma.20G052100 | 31 |
| Glyma.05G093400 | 32 |
| Glyma.05G132100 | 33 |
| Glyma.05G203000 | 34 |
| Glyma.05G092300 | 35 |
| Glyma.11G092400 | 36 |
| Glyma.14G103300 | 37 |
| Glyma.08G078200 | 38 |
| Glyma.08G028400 | 39 |
| Glyma.08G060200 | 40 |
| Glyma.08G314100 | 41 |
| Glyma.08G100300 | 42 |
| Glyma.01G154500 | 43 |

TABLE 1-continued

SEQ ID NOs: 1 to 210 providing candidate genes that confer SCN resistance when overexpressed or inactivated.

| Glyma ID No. | SEQ ID NO: |
|---|---|
| Glyma.12G060400 | 44 |
| Glyma.12G121100 | 45 |
| Glyma.06G251700 | 46 |
| Glyma.06G228100 | 47 |
| Glyma.06G148300 | 48 |
| Glyma.18G168000 | 49 |
| Glyma.16G088900 | 50 |
| Glyma.16G065300 | 51 |
| Glyma.04g041900 | 52 |
| Glyma.10g104900 | 53 |
| Glyma.12g081900 | 54 |
| Glyma.14g021300 | 55 |
| Glyma.17g091700 | 56 |
| Glyma.20g126100 | 57 |
| Glyma.20g134300 | 58 |
| Glyma.10G067400 | 59 |
| Glyma.10G289000 | 60 |
| Glyma.17G193800 | 61 |
| Glyma.17G214800 | 62 |
| Glyma.17G057300 | 63 |
| Glyma.09G002300 | 64 |
| Glyma.04G174100 | 65 |
| Glyma.04G238800 | 66 |
| Glyma.04G149700 | 67 |
| Glyma.04G095300 | 68 |
| Glyma.04G029400 | 69 |
| Glyma.04G033600 | 70 |
| Glyma.04G241200 | 71 |
| Glyma.07G132300 | 72 |
| Glyma.07G118800 | 73 |
| Glyma.15G204600 | 74 |
| Glyma.15G219000 | 75 |
| Glyma.13G010200 | 76 |
| Glyma.13G137000 | 77 |
| Glyma.02G236000 | 78 |
| Glyma.02G181200 | 79 |
| Glyma.19G130000 | 80 |
| Glyma.03G240800 | 81 |
| Glyma.03G100000 | 82 |
| Glyma.03G243400 | 83 |
| Glyma.03G205600 | 84 |
| Glyma.20G219600 | 85 |
| Glyma.20G237500 | 86 |
| Glyma.20G212100 | 87 |
| Glyma.05G142200 | 88 |
| Glyma.11G164700 | 89 |
| Glyma.11G181300 | 90 |
| Glyma.11G229600 | 91 |
| Glyma.14G047400 | 92 |
| Glyma.08G269900 | 93 |
| Glyma.08G238200 | 94 |
| Glyma.08G237500 | 95 |
| Glyma.08G226000 | 96 |
| Glyma.08G079300 | 97 |
| Glyma.08G168000 | 98 |
| Glyma.01G060200 | 99 |
| Glyma.01G008900 | 100 |
| Glyma.01G218100 | 101 |
| Glyma.12G173100 | 102 |
| Glyma.06G233300 | 103 |
| Glyma.18G279400 | 104 |
| Glyma.18G073400 | 105 |
| Glyma.16G088200 | 106 |
| Glyma.16G174500 | 107 |
| Glyma.16G164500 | 108 |
| Glyma.19g104100 | 109 |
| Glyma.20g189700 | 110 |
| Glyma.10G098700 | 111 |
| Glyma.10G028800 | 112 |
| Glyma.10G238200 | 113 |
| Glyma.10G066100 | 114 |
| Glyma.10G076500 | 115 |
| Glyma.10G073100 | 116 |

TABLE 1-continued

SEQ ID NOs: 1 to 210 providing candidate genes that confer SCN resistance when overexpressed or inactivated.

| Glyma ID No. | SEQ ID NO: |
|---|---|
| Glyma.17G008600 | 117 |
| Glyma.17G032500 | 118 |
| Glyma.17G135500 | 119 |
| Glyma.17G049500 | 120 |
| Glyma.17G012400 | 121 |
| Glyma.17G038800 | 122 |
| Glyma.09G159500 | 123 |
| Glyma.09G198900 | 124 |
| Glyma.09G190500 | 125 |
| Glyma.04G220100 | 126 |
| Glyma.04G221900 | 127 |
| Glyma.04G136700 | 128 |
| Glyma.04G177000 | 129 |
| Glyma.04G094900 | 130 |
| Glyma.04G140800 | 131 |
| Glyma.04G149400 | 132 |
| Glyma.04G111200 | 133 |
| Glyma.04G245700 | 134 |
| Glyma.07G243600 | 135 |
| Glyma.07G188300 | 136 |
| Glyma.07G000600 | 137 |
| Glyma.07G156900 | 138 |
| Glyma.07G166000 | 139 |
| Glyma.15G136000 | 140 |
| Glyma.15G125100 | 141 |
| Glyma.13G355400 | 142 |
| Glyma.13G056100 | 143 |
| Glyma.02G093000 | 144 |
| Glyma.02G129200 | 145 |
| Glyma.02G221300 | 146 |
| Glyma.02G164300 | 147 |
| Glyma.19G018100 | 148 |
| Glyma.19G153500 | 149 |
| Glyma.19G023000 | 150 |
| Glyma.19G164800 | 151 |
| Glyma.19G036100 | 152 |
| Glyma.03G058300 | 153 |
| Glyma.03G034500 | 154 |
| Glyma.03G107700 | 155 |
| Glyma.03G064800 | 156 |
| Glyma.05G185300 | 157 |
| Glyma.05G098000 | 158 |
| Glyma.05G003500 | 159 |
| Glyma.05G084500 | 160 |
| Glyma.05G100700 | 161 |
| Glyma.05G035100 | 162 |
| Glyma.05G092600 | 163 |
| Glyma.05G012700 | 164 |
| Glyma.11G125600 | 165 |
| Glyma.14G193900 | 166 |
| Glyma.14G098600 | 167 |
| Glyma.14G122700 | 168 |
| Glyma.14G138300 | 169 |
| Glyma.14G065500 | 170 |
| Glyma.14G104300 | 171 |
| Glyma.14G193600 | 172 |
| Glyma.08G190600 | 173 |
| Glyma.08G014300 | 174 |
| Glyma.08G238800 | 175 |
| Glyma.08G167600 | 176 |
| Glyma.08G258600 | 177 |
| Glyma.01G102900 | 178 |
| Glyma.01G244700 | 179 |
| Glyma.01G112600 | 180 |
| Glyma.12G136700 | 181 |
| Glyma.12G146400 | 182 |
| Glyma.06G286900 | 183 |
| Glyma.06G196500 | 184 |
| Glyma.06G180700 | 185 |
| Glyma.06G092500 | 186 |
| Glyma.06G231200 | 187 |
| Glyma.18G033500 | 188 |
| Glyma.18G168500 | 189 |

TABLE 1-continued

SEQ ID NOs: 1 to 210 providing candidate genes that confer SCN resistance when overexpressed or inactivated.

| Glyma ID No. | SEQ ID NO: |
|---|---|
| Glyma.18G077700 | 190 |
| Glyma.18G179600 | 191 |
| Glyma.18G066700 | 192 |
| Glyma.18G131100 | 193 |
| Glyma.18G220700 | 194 |
| Glyma.16G135200 | 195 |
| Glyma.16G214100 | 196 |
| Glyma.02g041600 | 197 |
| Glyma.02g071300 | 198 |
| Glyma.09g001700 | 199 |
| Glyma.10g105800 | 200 |
| Glyma.10g145700 | 201 |
| Glyma.10g168000 | 202 |
| Glyma.10g181600 | 203 |
| Glyma.10g192400 | 204 |
| Glyma.11g000100 | 205 |
| Glyma.14g009100 | 206 |
| Glyma.14g011600 | 207 |
| Glyma.17g205100 | 208 |
| Glyma.20g071200 | 209 |
| gma-miR5032 | 210 |

Accordingly, certain embodiments of the invention provide a method of producing an SCN resistant plant cell or a plant comprising overexpressing in the plant one or more genes comprising a protein coding sequence selected from SEQ ID NOs: 1-209 or homologs thereof. Further embodiments of the invention provide a method of producing an SCN resistant plant cell or a plant comprising overexpressing in the plant cell or the plant a gene encoding the miRNA having the sequence of SEQ ID NO: 210 (miR5032) or a homolog thereof. In preferred embodiments, the plant cell or a plant is a soybean plant cell or soybean plant.

As used herein, the term "overexpressing a gene" or grammatical variations thereof refer to a condition in a genetically modified plant cell or a genetically modified plant wherein the gene encodes for a protein or an miRNA at a level higher than the parent plant cell or the plant without the genetic modification. Thus, a parent plant cell or a parent plant is genetically modified to produce a modified plant cell or modified plant that expresses a gene to produce a protein or an miRNA at a higher level compared to the parent plant cell or parent plant.

Typically, overexpressing a gene in a plant cell or a plant comprises introducing into the plant cell or a plant, a nucleic acid construct comprising the gene. The nucleic acid construct is designed to induce the expression of the protein or the miRNA encoded by the gene. Methods of producing and introducing various nucleic acid constructs comprising genes of interest into a plant cell or a plant to overexpress the genes are well known to a person of ordinary skill in the art and such embodiments are within the purview of the invention. Certain such embodiments are identified below.

A gene is referred to as "operably linked" when it is placed into a functional relationship with another DNA segment (for example, a promoter that is operably linked to any one of SEQ ID NOs: 1-209 or homologs thereof or a sequence encoding miR5032 of SEQ ID NO: 210 or a homolog thereof). However, enhancers need not be contiguous with the coding sequences whose transcription they control. Linking is accomplished by ligation at convenient restriction sites or at adapters or linkers inserted in lieu thereof. The expression cassette can include one or more enhancers in addition to the promoter. By "enhancer" is intended a cis-acting sequence that increases the utilization of a promoter. Such enhancers can be native to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938, which is hereby incorporated by reference in its entirety.

The promoter for driving expression of the genes of interest may be selected based on a number of criteria including, but not limited to, what the desired use is for the operably linked polynucleotide, what location in the plant is expression of the gene of interest desired, and at what level is expression of gene of interest desired or whether it needs to be controlled in another spatial or temporal manner. In one aspect, a promoter that directs expression to particular tissue may be desirable. When referring to a promoter that directs expression to a particular tissue is meant to include promoters referred to as tissue specific or tissue preferred. Included within the scope of the invention are promoters that express highly in the plant tissue, express more in the plant tissue than in other plant tissue, or express exclusively in the plant tissue. For example, "seed-specific" promoters may be employed to drive expression. Specific-seed promoters include those promoters active during seed development, promoters active during seed germination, and/or that are expressed only in the seed. Seed-specific promoters, such as annexin, P34, beta-phaseolin, alpha subunit of beta-conglycinin, oleosin, zein, napin promoters have been identified in many plant species such as maize, wheat, rice and barley. See U.S. Pat. Nos. 7,157,629, 7,129,089, and 7,109,392. Such seed-preferred promoters further include, but are not limited to, Cim1 (cytokinin-induced message); cZ19B1 (maize 19 kDa zein); and mi1ps (myo-inositol-1-phosphate synthase); (see WO 00/11177, herein incorporated by reference). The 27 kDa gamma-zein promoter is a preferred endosperm-specific promoter. The maize globulin-1 and oleosin promoters are preferred embryo-specific promoters. For dicots, seed-specific promoters include, but are not limited to, bean beta phaseolin, napin, beta-conglycinin, soybean lectin, cruciferin, and the like. For monocots, seed-specific promoters include, but are not limited to, promoters of the 15 kDa beta-zein, 22 kDa alpha-zein, 27 kDa gamma-zein, waxy, shrunken 1, shrunken 2, globulin 1, an Ltp1, an Ltp2, and oleosin genes. See also WO 00/12733, where seed-preferred promoters from end1 and end2 genes are disclosed; herein incorporated by reference. Each of these aforementioned references is hereby incorporated by reference in its entirety, particularly as it relates to the promoters disclosed within the reference.

In preferred embodiments, a promoter used in the present invention is a promoter for soybean ubiquitin promoters, for example, the promoters for soybean ubiquitin B (UBB)/ubiquitin C (UBC) gene. Certain examples of soybean ubiquitin promoters that could be used in the present invention are described in United States patent application publication numbers 20140053296 and 20100186119. Each of these publications is incorporated by reference in its entirety, particularly, the sequence listing.

The promoters useful in the present invention can also include constitutive, inducible or tissue-specific (preferred) promoters that are operably linked to a gene comprising a protein coding sequence of any one of SEQ ID NOs: 1-209 or homologs thereof or a sequence encoding miR5032 or a homolog thereof and are heterologous to the nucleic acid sequences to which they are operably linked. In other words, the promoters are not those found operably linked to a gene comprising a protein coding sequence of SEQ ID NOs: 1-209 or homologs thereof or a sequence encoding miR5032 or a homolog thereof in their native context within a plant, such as a soybean plant. Constitutive promoters, generally, are active in most or all tissues of a plant; inducible promoters, which generally are inactive or exhibit a low basal level of expression, and can be induced to a relatively high activity upon contact of cells with an appropriate inducing agent; tissue-specific (or tissue-preferred) promoters, which generally are expressed in only one or a few particular cell types (e.g., root cells); and developmental-or stage-specific promoters, which are active only during a defined period during the growth or development of a plant. Often promoters can be modified, if necessary, to vary the expression level. Certain embodiments comprise promoters exogenous to the species being manipulated (e.g. a soybean plant).

Non-limiting examples of root-specific promoters (a subset of tissue-specific promoters) include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1B10 promoter (WO06055487, published May 26, 2006), the CRWAQ81 (WO05035770, published Apr. 21, 2005) and the maize ZRP2.47 promoter (NCBI accession number: U38790; GI No. 1063664). Each of these aforementioned references is hereby incorporated by reference in its entirety, particularly as it relates to the promoters disclosed within the reference.

Exemplary constitutive promoters include the 35S cauliflower mosaic virus (CaMV) promoter (Odell et al. (1985) Nature 313:810-812), the maize ubiquitin promoter (Christensen et al. (1989) Plant Mol. Biol. 12:619-632 and Christensen et al. (1992) Plant Mol. Biol. 18:675-689); the core promoter of the Rsyn7 promoter and other constitutive promoters disclosed in WO 99/43838 and U.S. Pat. No. 6,072,050; rice actin (McElroy et al. (1990) Plant Cell 2:163-171); pEMU (Last et al. (1991) Theor. Appl. Genet. 81:581-588); MAS (Velten et al. (1984) EMBO J. 3:2723-2730); ALS promoter (U.S. Pat. No. 5,659,026); rice actin promoter (U.S. Pat. No. 5,641,876; WO 00/70067), maize histone promoter (Brignon et al., Plant Mol Bio 22(6):1007-1015 (1993); Rasco-Gaunt et al., Plant Cell Rep. 21(6):569-576 (2003)) and the like. Other constitutive promoters include, for example, those described in U.S. Pat. Nos. 5,608,144 and 6,177,611, and PCT publication WO 03/102198. Each of these aforementioned references is hereby incorporated by reference in its entirety, particularly as it relates to the promoters disclosed within the reference.

An inducible promoter/regulatory element is one that is capable of directly or indirectly activating transcription of a gene comprising a protein coding sequence of one or more of SEQ ID NOs: 1-209 or a sequence encoding miR5032 or a homolog thereof in response to an inducer. The inducer can be a chemical agent such as a protein, metabolite, growth regulator, herbicide or phenolic compound; or a physiological stress, such as that imposed directly by heat, cold, salt, or toxic elements, or indirectly through the action of a pathogen or disease agent such as a virus; or other biological or physical agent or environmental condition. A plant cell containing an inducible promoter/regulatory element may be exposed to an inducer by externally applying the inducer to the cell or plant such as by spraying, watering, heating or similar methods. An inducing agent useful for inducing expression from an inducible promoter is selected based on the particular inducible regulatory element. In response to exposure to an inducing agent, transcription from the inducible regulatory element generally is initiated de novo or is increased above a basal or constitutive level of expression.

Any inducible promoter/regulatory element can be used in the instant invention (See Ward et al., Plant Mol. Biol. 22: 361-366, 1993). Non-limiting examples of such promoters/regulatory elements include: a metallothionein regulatory element, a copper-inducible regulatory element, or a tetracycline-inducible regulatory element, the transcription from which can be effected in response to divalent metal ions, copper or tetracycline, respectively (Furst et al., Cell 55:705-717, 1988; Mett et al., Proc. Natl. Acad. Sci., USA 90:4567-4571, 1993; Gatz et al., Plant J. 2:397-404, 1992; Roder et al., Mol. Gen. Genet. 243:32-38, 1994). Inducible promoters/regulatory elements also include an ecdysone regulatory element or a glucocorticoid regulatory element, the transcription from which can be effected in response to ecdysone or other steroid (Christopherson et al., Proc. Natl. Acad. Sci., USA 89:6314-6318, 1992; Schena et al., Proc. Natl. Acad. Sci., USA 88:10421-10425, 1991; U.S. Pat. No. 6,504,082); a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6): 1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible promoter/regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as P5CS (Zang et al. (1997) Plant Sciences 129:81-89); cold-inducible promoters, such as, cor15a (Hajela et al. (1990) Plant Physiol. 93:1246-1252), cor15b (Wilhelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), ci21A (Schneider et al. (1997) Plant Physiol. 113:335-45); drought-inducible promoters, such as, Trg-31 (Chaudhary et al (1996) Plant Mol. Biol. 30:1247-57), rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); and heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the *Agrobacterium* pmas promoter (Guevara-Garcia et al. (1993) Plant J. 4(3):495-505) and the *Agrobacterium* ORF13 promoter (Hansen et al., (1997) Mol. Gen. Genet. 254(3):337-343). Each of these aforementioned references is hereby incorporated by reference in its entirety, particularly as it relates to the promoters disclosed within the reference.

Overexpression of a gene comprising a protein coding sequence selected from SEQ ID NOs: 1-209 or homologs thereof or a sequence encoding miR5032 or a homolog thereof can also be achieved by one or one or more mutations in the endogenous promoter of the gene, wherein the one or more mutations increase the expression of the gene. For a particular gene, a skilled artisan can identify one or more mutations that would increase the expression of the gene and such embodiments are within the purview of the invention.

Certain preferred embodiments of the invention provide a method of producing a plant cell or a plant that is resistant to SCN, the method comprising overexpressing in the plant cell or the plant a gene comprising a protein coding sequence of a sulfite exporter TauE/SafE protein and/or overexpressing a gene comprising a protein coding sequence of a SNARE associated Golgi protein. The overexpressed gene encoding the SNARE associated Golgi protein can comprise a protein coding sequence of Glyma. 11G004900, according to SEQ ID NO: 1, or a homolog thereof.

The overexpressed gene encoding the sulfite exporter TauE/SafE protein can comprise a protein coding sequence of Glyma. 14G142500, according to SEQ ID NO: 2, or a homolog thereof.

Additional embodiments of the invention also provide a plant cell comprising an overexpressed gene comprising a protein coding sequence selected from SEQ ID NOs: 1-209 or homologs thereof or a sequence encoding miR5032 or a homolog thereof. The plant cell or the plant can be a soybean plant cell or soybean plant.

In preferred embodiments, the plant cell or the plant overexpresses a gene encoding a sulfite exporter TauE/SafE protein and/or a gene encoding a SNARE associated Golgi protein. The overexpressed gene encoding the SNARE associated Golgi protein can comprise a protein coding sequence of Glyma. 11G004900, according to SEQ ID NO: 1, or a homolog thereof. The overexpressed gene encoding the sulfite exporter TauE/SafE protein can comprise a protein coding sequence of Glyma. 14G142500, according to SEQ ID NO: 2, or a homolog thereof. The plant cell or a plant can also comprise overexpression of a gene encoding the SNARE associated Golgi protein of the protein coding sequence of Glyma. 11G004900, according to SEQ ID NO: 1, or a homolog thereof and overexpression of a gene encoding the sulfite exporter TauE/SafE protein of the prteoin coding sequence of Glyma. 14G142500, according to SEQ ID NO: 2, or a homolog thereof.

In further embodiments, the plant cell or the plant overexpresses a gene encoding a sequence encoding miR5032 or a homolog thereof. The plant cell or a plant can also further comprise overexpression of a gene comprising a protein coding sequence of SEQ ID NO: 1 or a homolog thereof and/or a gene comprising a protein coding sequence of SEQ ID NO: 2 or a homolog thereof. In addition to these modifications, the plant cell or a plant can also further comprise an inactivation of a gene comprising a protein coding sequence of Glyma. 17G216000, according to SEQ ID NO: 3, or a homolog thereof and an inactivation of a gene comprising a protein coding sequence of Glyma.02G071300, according to SEQ ID NO: 4, or a homolog thereof.

Further embodiments of the invention provide a method of producing an SCN resistant plant cell or a plant comprising inactivating in the plant one or more genes comprising a protein coding sequence selected from SEQ ID NOs: 1-209 or homologs thereof. In preferred embodiments, the plant cell or a plant is a soybean plant cell or soybean plant.

Typically, inactivating a gene in a plant cell or a plant comprises introducing into the gene one or more mutations that inhibit or abolish the expression of an active protein from the gene. Mutations in a gene that inhibit or abolish the expression of a protein from the gene can be achieved either by deleting the entire coding region of the gene or a portion of the coding region of the gene, by introducing a frame shift mutation within the coding region of the gene, by introducing a missense mutation, insertion of sequences that disrupt the activity of the protein encoded by the gene, by introducing a stop codon or any combination of the aforementioned gene mutations. Inactivating a gene can also be performed by using molecular markers or other traditional breeding methods to integrate activated or inhibited genes in any soybean germplasm. Further, overexpressing one or more genes can be performed by introducing and/or expressing the one or more genes under soybean endogenous promoters and/or any exogenous promoters.

Methods of inactivating a gene of interest in a plant cell or a plant to inhibit or abolish the expression of an active protein from the gene are well known to a person of ordinary skill in the art and such embodiments are within the purview of the invention. Certain such embodiments are identified below.

Sanagala et al. (2017), Journal of Genetic Engineering and Biotechnology; 15(2):317-321, describe several methods of inactivating a gene, for example, by implementing homologous recombination, zinc finger nucleases, Transcription activator-like effector nucleases (TALENs), and the clustered regularly interspaced short palindromic repeats/CRISPR-associated (CRISPR/Cas) system. The Sanagala et al. reference is incorporated herein by reference in its entirety.

In preferred embodiments, inactivating a gene of interest is performed using the CRISPR/Cas system. An example of such system to inactivate genes in a plant cell or a plant is provided by Ordon et al. (2017), The Plant Journal; 89:155-168. The Ordon et al. reference is incorporated herein by reference in its entirety.

Typically, a CRISPR/Cas system mediated inactivation of a gene involves the use of a guide RNA targeted to a gene of interest. A DNA oligomer targeted to a gene of interest can be transcribed into single guide RNA (sgRNA). sgRNA guides the Cas9 DNA endonuclease to the gene of interest by sgRNA hybridization to the target site. The endonuclease Cas9 makes a double strand break 3 bp upstream of Palindromic Adjacent Motif (PAM). The DNA breakage engages the repair mechanism, such as homologous recombination (HR) or the non-homologous end joining (NHEJ) mechanism. The NHEJ mechanism is a major double strand break repair pathway in plants and is known to be error prone. NHEJ DNA repair process introduces errors in the DNA repair, which causes irreversible mutations at the gene of interest. The chances of errors in DNA repair can be increased by providing multiple sgRNA. Based on the sequence of a gene comprising a protein coding sequence selected from SEQ ID NOs: 1-209 or homologs thereof, a person of ordinary skill in the art can design and perform inactivation of the gene using the CRISPR/Cas system and such embodiments are within the purview of the invention.

Methods of inactivating a gene of interest in a plant cell or a plant to inhibit or abolish the expression of an active protein from the gene also include introduction into the plant cell or the plant one or more inhibitory oligonucleotides, such as small interfering RNA (siRNA) or short hairpin RNAs (shRNA). Methods of producing and introducing inhibitory RNA are also well known to a person of ordinary skill in the art and such embodiments are within the purview of the invention.

Certain preferred embodiments of the invention provide a method of producing a plant cell or a plant that is resistant to SCN, the method comprising inactivating in the plant cell or the plant a gene encoding an aspartate aminotransferase protein and/or a gene encoding a transcription regulator of the NOT2/NOT3/NOT5 protein. The inactivated gene encoding the aspartate aminotransferase protein can comprise a protein coding sequence of Glyma.17G216000, according to SEQ ID NO: 3, or a homolog thereof. The inactivated gene encoding the transcription regulator of the NOT2/NOT3/NOT5 can comprise a protein coding sequence of Glyma.02G071300, according to SEQ ID NO: 4, or a homolog thereof. A gene comprising a protein coding sequence of Glyma. 17G216000, according to SEQ ID NO: 3, or a homolog thereof and a gene comprising a protein coding sequence of Glyma.02G071300, according to SEQ ID NO: 4, or a homolog thereof can also be inactivated.

Additional embodiments of the invention also provide a plant cell comprising an inactivated gene comprising a protein coding sequence selected from SEQ ID NOs: 1-209 or homologs thereof. The plant cell or the plant can be a soybean plant cell or soybean plant.

In preferred embodiments, the plant cell or the plant comprises inactivation of a gene encoding an aspartate aminotransferase protein and/or inactivation of a gene encoding a transcription regulator of the NOT2/NOT3/NOT5 protein. The inactivated gene encoding the aspartate aminotransferase protein can comprise a protein coding sequence of Glyma. 17G216000.

according to SEQ ID NO: 3, or a homolog thereof. The inactivated gene encoding the transcription regulator of the NOT2/NOT3/NOT5 can comprise a protein coding sequence of Glyma.02G071300, according to SEQ ID NO: 4, or a homolog thereof. A plant cell or plant can also contain an inactivation of a gene comprising a protein coding sequence of Glyma. 17G216000, according to SEQ ID NO: 3, or a homolog thereof and an inactivation of a gene comprising a protein coding sequence of Glyma.02G071300, according to SEQ ID NO: 4, or a homolog thereof.

In the methods of producing a plant cell described herein the plant cell can be in a plant part, for example, a seed, endosperm, ovule or pollen. The plant can be a soybean plant.

Further embodiments of the invention provide methods for identifying a gene that induces SCN resistance in a plant cell or a plant when overexpressed or inactivated, the method comprising the steps of: (a) overexpressing a gene in a plant cell or a plant, compared to the expression in a plant cell or a plant known to be susceptible to SCN, or inactivating a gene in a plant cell or a plant known to be resistant to SCN, (b) testing the SCN resistance in the plant cell or the plant comprising the overexpressed or inactivated gene, and (c) identifying the gene that induces resistance in the plant cell or the plant when overexpressed or inactivated.

In preferred embodiments, an overexpressed or inactivated gene comprises a protein coding sequence selected from SEQ ID NOs: 1-209 or homologs thereof or a sequence encoding miR5032 or a homolog thereof. In some embodiments, one or more genes comprising protein coding sequences selected from SEQ ID NOs: 1-209 or homologs thereof or a sequence encoding miR5032 or a homolog thereof are overexpressed and/or one or more genes comprising protein coding sequences selected from SEQ ID NOs: 1-209 or homologs thereof are inactivated.

The plant cell or the plant can be a soybean plant cell or a soybean plant.

The details discussed above for overexpressing and inactivating genes in a plant cell or a plant are also applicable to the methods of identifying a gene that induces SCN resistance in a plant cell or a plant when overexpressed or inactivated and such embodiments are within the purview of the invention.

Modifications to the promoter regions of the genes comprising protein coding sequences selected from SEQ ID NOs: 1 to 209 or a sequence encoding miR5032 or a homolog thereof can affect the SCN susceptibility of a plant. To identify genomic changes that render soybean plants resistant to SCN infection, ninety nine completely sequenced soybean accessions were phenotyped against five races of SCN (race 1, 2, 3, 5, and 14). The DNA sequences of the promoter regions of the genes Glyma.11G004900, Glyma.14G142500, and gma-miR5032 were retrieved from these 99 soybean accessions and analyzed for potential genetic differences and polymorphisms linked with resistance against five SCN races. Certain nucleotide polymorphisms associated with resistance to SCN infection are provided in Tables 5-8.

In a polymorphism as described in Tables 5-8, the nucleotide to the left of "I" describes the genomic sequence in an SCN susceptible plant and the nucleotide to the right of "/" describes the genomic sequence in an SCN resistant plant. For example, a single nucleotide polymorphism (SNP) A/T at position 500 indicates that a soybean plant having A at the $500^{th}$ position would be susceptible to SCN infection and a soybean plant having T at the $500^{th}$ position would be resistant to SCN infection.

Also, in a polymorphism as described in Tables 5-8, the nucleotide position can be described relative to the transcription start site (TSS) for the miRNA and ATG start codon for the protein. For example, a nucleotide at position −100 corresponds to the $100^{th}$ nucleotide upstream of the TSS or the ATG codon. Particularly, for SEQ ID NO: 211, TAC codon at positions 2001-2003 corresponds to the ATG codon on the opposite strand, which encodes the protein. For SEQ ID NO: 212, the protein coding sequence begins with the ATG codon at positions 2001-2003. For SEQ ID NO: 213, TSS for the miRNA is at the position 2300.

Thirteen polymorphisms in the promoter region and one polymorphism in the gene body (K/P) of the gene Glyma.11G004900 were identified to be associated with soybean resistance against one or more SCN races (Table 5). The sequence of the Glyma.11G004900 gene, including the promoter region and the protein coding region is provided in SEQ ID NO: 211. In the SEQ ID NO: 211, the corresponding nucleotides are on the negative strand, i.e., on the strand that does not encode the protein. Therefore, in the promoter sequence of the coding strand as provided in SEQ ID NO: 211, the corresponding polymorphisms contain the nucleotides that are complementary to the nucleotides indicated in Table 5.

The sequence of SEQ ID NO: 211 corresponds to the sequence having the relevant polymorphisms as found in the SCN susceptible plants. Therefore, when the nucleotides at the relevant positions of the susceptible genotype are replaced with the nucleotides of the resistant genotype as shown in Table 5, an SCN susceptible plant is converted in to an SCN resistant plant.

Ten polymorphisms in the promoter region of the gene Glyma.14G142500 were identified (Table 6). Six of these polymorphisms were found to be statistically significantly associated with resistance against SCN race 3, 5, and 14 (Table 6).

Seven polymorphisms in the promoter region of the gene encoding for miR5032 were identified (Table 7). Three polymorphisms were statistically linked to SCN resistance. The "insert" provided in Table 7 at the −309 position ("n" at the $1991^{st}$ position of SEQ ID NO: 213) represents a sequence of between 3 and 13 nucleotides.

Table 8 provides a list of polymorphisms from Tables 5-7 that are associated with susceptibility/resistance against an SCN infection. Accordingly, certain embodiments of the invention provide a method of producing an SCN resistant plant cell or a plant comprising one or more polymorphisms from Table 8. In preferred embodiments, the plant cell or a plant is a soybean plant cell or soybean plant.

The methods disclosed herein for producing an SCN resistant plant includes editing a genome to replace one or more nucleotides in an SCN susceptible plant cell or a plant with one or more nucleotides that confer resistant to an SCN infection.

Several techniques for editing a genome to replace one or more nucleotide with different one or more nucleotides are known in the art and are within the purview of the invention. Such techniques include homologous recombination using sequences that flank a genomic site to replace a native sequence with a non-native sequence. Additional such techniques include genome editing using CRISPR-Cas9 system, Zinc Finger based nuclease (ZFN) system, Transcription Activator-Like Effector Nucleases (TALEN) system, viral systems, such as recombinant adeno-associated viruses (rAAV), and transposons. Details of using these systems are known in the art and a person of ordinary skill in the art can design appropriate machinery to edit a genome and such embodiments are within the purview of this invention. Additional techniques of genome editing are also known in the art and such embodiments are within the purview of the invention.

Further embodiments of the invention provide an isolated nucleic acid sequence comprising a sequence of SEQ ID NO: 211, 212 or 213 or a fragment thereof. As discussed above, one or more nucleotides in SEQ ID NO: 211, 212 or 213 contain polymorphisms as provided in Tables 5-8, some of which are associated with susceptibility or resistance to an SCN infection. Accordingly, preferred embodiments of the invention provide an isolated nucleic acid sequence comprising SEQ ID NO: 211, 212 or 213 or a fragment thereof, wherein the sequence comprises one or more polymorphisms that are associated with resistance to SCN infection.

The fragment of SEQ ID NO: 211, 212 or 213 can be a fragment from the promoter region or the coding region.

For SEQ ID NO: 211, the promoter region is from the nucleotide at position 1 to the nucleotide at position 2000.

For SEQ ID NO: 212, the promoter region is from the nucleotide at position 1 to the nucleotide at position 2000.

For SEQ ID NO: 213, the promoter region is from the nucleotide at position 1 to the nucleotide at position 2298.

Further embodiments of the invention provide a combination of one or more probes that are suitable for predicting susceptibility or resistance of a plant cell or a plant to an SCN infection. The one or more probes are designed to determine in a plant cell or a plant the genomic sequence corresponding to SEQ ID NO: 211, 212 or 213, particularly, the genomic sequence corresponding to one or more polymorphisms described in Tables 5-8. A person of ordinary skill in the art can design one or more probes to identify in a genomic sequence one or more polymorphisms from Tables 5-8.

A genomic sequence can be detected using techniques known in the art, for example, using a labeled probe complementary to a sequence of a polymorphism. For example, a polymorphism can be detected based a labeled probe specific for that polymorphism.

The term "label" refers to a molecule detectable by spectroscopic, photochemical, biochemical, immunochemical, chemical, or other physical means. For example, useful labels include fluorescent dyes (fluorophores), fluorescent quenchers, luminescent agents, electron-dense reagents, biotin, digoxigenin, $^{32}P$ and other isotopes or other molecules that can be made detectable, e.g., by incorporating into an oligonucleotide. The term includes combinations of labeling agents, e.g., a combination of fluorophores each providing a unique detectable signature, e.g., at a particular wavelength or combination of wavelengths.

Exemplary fluorophores include, but are not limited to, Alexa dyes (e.g., Alexa 350, Alexa 430, Alexa 488, etc.), AMCA, BODIPY 630/650, BODIPY 650/665, BODIPY-FL, BODIPY-R6G, BODIPY-TMR, BODIPY-TRX, Cascade Blue, Cy2, Cy3, Cy5, Cy5.5, Cy7, Cy7.5, Dylight dyes (Dylight405, Dylight488, Dylight549, Dylight550, Dylight 649, Dylight680, Dylight750, Dylight800), 6-FAM, fluorescein, FITC, HEX, 6-JOE, Oregon Green 488, Oregon Green 500, Oregon Green 514, Pacific Blue, REG, Rhodamine Green, Rhodamine Red, ROX, R-Phycoerythrin (R-PE), Starbright Blue Dyes (e.g., Starbright Blue 520, Starbright Blue 700), TAMRA, TET, Tetramethylrhodamine, Texas Red, and TRITC.

Accordingly, methods of determining susceptibility or resistance of a plant cell or a plant to an SCN infection are also envisioned. Such methods comprise determining in a plant cell or a plant the genomic sequences corresponding one to more polymorphisms provided in Tables 5-8 and determining, based on the genomic sequences, whether a plant cell or a plant is resistant or susceptible to an SCN infection.

As discussed above, comparing the methylomes of the parental lines that are resistant or susceptible to SCN with that of the NILs that are resistant or susceptible to SCN resulted in the identification of heritable as well as novel non-parental differentially methylated regions overlapping with genes related to SCN parasitism of soybean. Thus, the disclosure provides the genes involved in biochemical basis of Rhg4 function in SCN resistance. Such comparisons can also be used to identify genes involved in conferring traits other than SCN resistance.

Accordingly, certain embodiments of the invention provide a method of identifying one or more genes that confer a trait to a plant when expressed or inactivated, the method comprising the steps of:

a) providing two NILs, one of the two NILs having one or more genetic loci known to confer the trait and the other NIL not having the one or more genetic loci known to confer the trait;
b) analyzing the methylation status of a plurality of genetic loci within the genomes of the two NILs,
c) comparing the methylation status of the plurality of genetic loci between the two NILs to identify a plurality of genetic loci that are differentially methylated between the two NILs,
d) comparing the mRNA expression profiles of the two NILs and identifying a plurality of mRNAs that are differentially expressed between the two NILs,
e) identifying a plurality of genetic loci that is differentially methylated between the two NILs and that encodes differentially expressed mRNAs,
f) expressing or inactivating in a plant cell each of a plurality of genes located in the plurality of genetic loci that is differentially methylated between the two NILs and that encodes differentially expressed mRNAs; and
g) identifying one or more genes that confer the trait to the plant when expressed or inactivated.

Additional genes that confer a trait to a plant when expressed or inactivated can be identified by further steps of:

h) comparing the methylation status of the plurality of genetic loci between the two NILs and the two parent lines to identify a plurality of genetic loci that are differentially methylated in one of the two NILs compared to the other NIL and the two parent lines,
i) identifying a plurality of genes located in the plurality of genetic loci that are differentially methylated in one of the two NILs compared to the other NIL and the two parent lines,
j) expressing or inactivating in a plant cell each of the plurality of genes identified in step i), and
k) identifying one or more genes from the genes expressed or inactivated step i) that impart the trait to the plant when expressed or inactivated.

As used herein, the phrase "a gene confers a trait" or grammatical variations thereof indicates that a plant containing the gene exhibits the trait and an otherwise genetically identical plant lacking the gene does not exhibit the trait. Thus, in two otherwise genetically identical plants, the presence of a trait in the plant containing the gene and the absence of the trait in the plant not containing the gene is attributed to the presence or the absence of the gene.

The differentially methylated regions can be located in the protein coding regions or transposon elements. The differential methylation can be differential CG-methylation, differential CHG-methylation, or differential CHH-methylation.

In preferred embodiments, the two NILs are derived from a parent line having the trait and a parent line not having the trait by repeated back-crossing.

In preferred embodiments of the invention, the plant is a soybean plant and the trait is resistance to SCN. Also, the one or more genetic loci known to confer the SCN resistance encodes a serine hydroxymethyltransferase, an α-SNAP protein, a putative amino acid transporter, a wound-inducible protein, or a combination thereof.

Exemplary embodiments of such methods are described in Examples 1 to 9 below. A skilled artisan can implement such methods to identify genes that confer a trait of interest in a plant and such embodiments are within the purview of the invention.

Materials and Methods

Developing Near-Isogenic Soybean Lines Differing in GmSHMT08 Gene

Two NILs, TN09-16 and TN09-29, which exhibit susceptible and resistant responses, respectively, to SCN HG type 0 (race 3) were developed. These NILs are highly homozygous recombinant inbred lines derived from individual F13 generation single plants from the cross 'Fowler'×'Anand'. Anand was developed from the cross Holladay×Hartwig by the Missouri Agricultural Experiment Station and released in 1999 (Anand et al., 2001). Fowler was developed from the cross Hartwig×Holladay by the USDA-ARS at Jackson, TN, and released in 1999 (Young LD. 2001). Hartwig derived its resistance from Plant Introduction (PI) 437654. Simple sequence repeat (SSR) markers associated with rhg1 (Satt309) and Rhg4 (Satt162 and Satt632) were initially used to examine the genetic differences between these two NILs. In addition, the SCN resistance genes soluble NSF attachment proteins (GmSNAP18) and the serine hydroxymethyltransferase (GmSHMT08) at the rhg1-b and RHg4 loci, respectively, were amplified, ligated into pGMT-easy vector (Promega), and sequenced to further confirm the genetic differences between the NILs at GmSHMT08 locus.

Nematode Inoculation and Collection of Root Tissues

Soybean seeds of TN09-16 and TN09-29 were washed for 30 minutes under running water and then soaked in 10% bleach for 10 minutes. After this surface sterilization the seeds were washed again for 30 minutes to remove bleach remnants. The seeds were then germinated on wet germination paper in dark at 26° C. for three days. Healthy looking 3 day old seedlings were selected for nematode inoculation. Freshly hatched second stage juveniles (J2s) of SCN HG type 0 (race 3) were surface-sterilized and then suspended in 0.1% sterile agarose solution at a concentration of approximately 500 J2s per 100 μL. Each seedling was inoculated with about 3000 J2s, by spreading the nematodes across the whole root of a seedling. Control plants were set up in exact same way, except mock inoculations were performed using 0.1% (w/v) agarose per seedling. Control and inoculated plants were arranged in replicates, each containing at least six plants and maintained in a controlled plant growth chamber at 26° C. with 16-h light/8-h dark conditions as previously described (Rambani et al., 2015). Five days post SCN-inoculation, roots tissues were collected from both inoculated and non-inoculated soybean roots in three biologically independent replicates resulting in a total of 12 samples. Successful infection of each replicate was confirmed by examining one-fourth of the infected seedlings using acid fuschin stain. The two parental lines (Fowler and Anand) were only mock-inoculated in the same experimental settings and a total of 6 biologically independent samples were similarly collected five days later. DNA and RNA were isolated from each sample and used construct methylC-seq and RNA-seq library.

Preparation of methylC-Seq Libraries

Genomic DNA of the infected and non-infected root samples was extracted using DNeasy Plant Mini Kit (Qiagen). Whole genome methylC-seq libraries were constructed as per protocol from Illumina TruSeq Library Prep kit (Illumina, San Diego, CA) with slight modifications of the bisulfite treatment. Briefly, about 2 μg of genomic DNA (gDNA) in addition to unmethylated lambda DNA were fragmented using Bioruptor (Diagenode Inc. USA, Denville, NJ) and then spiked with unmethylated fragmented lambda DNA (Promega, Madison, WI) that constitutes up to 2% of total concentration. Fragment size distribution of sheared DNA was verified using the Agilent Bioanalyzer 1000 DNA chip (Agilent Technologies, Santa Clara, CA). DNA fragments were then ligated to cytosine-methylated adapters (provided by Illumina) and then subjected to sodium bisulfite treatment using MethylCode™ Bisulfite Conversion Kit (Invitrogen, Grand Island, NY). DNA fragments between 400 and 500 bp were selected on the Pippin Prep system (Sage Sciences) and enriched by 10 cycles of PCR as recently described (Rambani et al., 2015). PCR products were then purified using Agencourt AMPure XP beads (Beckman Coulter, Inc., Brea, CA) and subsequently enriched using 5 additional PCR cycles according to Illumina's protocol. The PCR products were purified once more and library size distribution was examined using the Agilent Bioanalyzer 1000 DNA chip. Finally, the libraries were quantified and sequenced using Illumina HiSeq 2500 platform.

Identification of DMRs and Overlapping Genomic Regions

Sequencing adapters were trimmed from bisulfite sequencing reads (BS reads) and low quality reads below Phred threshold of 33 were removed using Trimmomatic. Then high quality paired-end reads were aligned to the soybean reference genome (Wm82.a2.v1) using Bismark with default parameters. Alignment files generated by Bismark were analyzed by the R bioconductor package methylKit to identify differentially methylated cytosines. Methylation status at each cytosine covered by at least 10 reads in the CG, CHG and CHH sequence contexts were calculated. A non-overlapping sliding window of 200 bp overall the 20 soybean chromosomes was used to identify DMRs with methylation difference of at least 50%. Significance of differentially hyper- and hypo-DMRs was determined using q-value less 1%. DMRs were mapped to various genic regions including prompter (1 kb upstream of the transcription start site), 5' and 3' untranslated regions (UTRs), and gene body (transcribed region) using Bioconductor package rtracklayer in a custom R script. Methylation cytosine report files generated by Bismark were used to visualize global methylation levels over protein-coding genes and TEs using ViewBS package (see world-wide-website: github.com/xie186/ViewBS).

The most recent assembly of soybean genome (Wm82.a2.v1) was released without annotation of TEs. Thus, sequences of previously annotated and known TEs in soybean assembly were obtained from SoyTEdb. The TE sequences were used to mask the new soybean assembly using RepeatMasker and output file with TE coordinates in the new assembly was created. Then, overlaps of DMRs with TEs belonging to various families were reported. BED tools were used to calculate the distance from DMR-associated TEs to the nearest gene.

RNA Library Preparation and Transcriptome Analysis mRNA was isolated using magnetic mRNA isolation kit (NEB). NEBnext mRNA library prep master mix (NEB) was used to build libraries following manufacturer's protocol. RNA-seq libraries were sequenced on Illumina Hiseq 2500 platform. Quality of paired-ended reads was verified with FastQC (version 0.11.4) (see world-wide-website: bioinformatics.babraham.ac.uk/projects/fastqc/). Adapter sequences and low-quality reads were removed using Trimmomatic (version 0.35). Qualified reads were then mapped to the soybean reference genome (Wm82.a2.v1) using TOPHAT v.2.0.13 with default parameters. Reads mapped to multiple loci were discarded and numbers of uniquely mapped reads per gene were determined using HTSeq. Counts generated by HTSeq were used to determine differentially expressed genes using the R bioconductor package edgeR. Genes with false discovery rate less than 0.1 or 0.05 were considered significantly differentially expressed. Separate count files were generated using the python-based package QoRTs for counting sequencing reads spanning exons for every gene. The count files were used with the bioconductor R package JunctionSeq to determine differentially spliced transcripts.

GO Terms Enrichment Analysis

GO terms enrichment analysis of differentially methylated genes and differentially expressed genes were determined using soybase tools and AgriGO database. Statistically significant enriched GO terms were calculated using Fisher's exact test and Bonferroni multi-test adjustment with a q value less than 0.05. GO terms were clustered based on semantic similarity to other GO terms in Uniprot database using REVIGO.

Generation of Transgenic Hairy Roots and Nematode Infection Assay

The coding sequences of four soybean genes were amplified from root cDNA and cloned under the control of a soybean ubiquitin promoter and the RuBisCO small subunit terminator in the binary vector pG2RNAi2, which contains the superfolded green fluorescent protein (sGFP) to facilitate identification of transgenic hairy roots. All constructs were confirmed by sequencing. Each of the four constructs as well GFP-only control vector were transformed into *Agrobacterium rhizogenes* strain K599 and used for generation of transgenic soybean hairy roots Transgenic hairy roots overexpressing these constructs were generated in seven-day-old seedlings of the susceptible isogenic line TN09-016 using the method previously described by Kereszt et al. (2007). Three weeks after *A. rhizogenes* inoculation, the transgenic hairy roots (3 per plant) were selected using an epifluorescent microscope (Olympus, model SZX12) equipped with GFP filter. Transgenic hairy roots expressing the empty vector containing only the GFP marker gene were used as control. In all cases, non-transgenic hairy roots as well as the main root system were removed. The composite transgenic plants were then planted in 656 $cm^3$ cone-tainers (6.4 cm×25.4 cm) containing steam-sterilized sand mixed with top soil (3:1) and arranged in a randomized complete block design. Two days after planting, each composite plant was inoculated with about 3000 eggs of SCN race 3 (HG Type 0). The plants were maintained under controlled growth conditions (16-h day length and 26° C.) in Percival reach-in plant growth chambers. Five weeks after inoculation, the cysts were extracted from each plant separately and counted under a stereoscope. The number of cysts was used to calculate the female index as a percentage of the average number of cysts determined on the test lines relative to those determined on the control line. Nematode susceptibility assays of the isogenic lines and their parents were conducted in the greenhouse using SCN HG type 0 (race 3). Seeds of each line were planted in pots (2 seeds per pot) containing soil:sand (1:1) mixture and organized in a randomized complete block design. Each pot was inoculated with approximately 4,000 eggs at seeding. Approximately 5 weeks after planting the cysts were blasted off the roots and counted under the microscope. Statistically significant differences between the lines were calculated using t-tests with P value<0.001.

The sequences of the genes identified by the Glyma IDs provided throughout this disclosure can be found in the soybean genome database (see the website: soybase.org) and the sequences associated with the Glyma IDs within the soybean genome database are hereby incorporated by reference in their entireties.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Developing Near-Isogenic Soybean Lines Differing at the SCN Resistance Gene Rhg4

Two near isogenic lines (NILs), TN09-16 and TN09-29, respectively containing the susceptible and resistant allele of RHg4, were generated. These NILs are highly homozygous recombinant inbred lines derived from individual F13 generation single plants from a cross between the SCN-resistant variety Fowler and the SCN-susceptible variety Anand. Homozygosity level of these NILs was estimated to be 0.9998 based on the number of inbreeding generations after the creation of F1. SCN resistance in the parental line Fowler was acquired from the Plant Introduction (PI) 437654. PI 437654, which exhibit 'Peking-type' resistance, has been shown to carry the SCN resistance gene Rhg4 and three copies of rhg1a. Initially, Simple Sequence Repeat (SSR) markers associated with rhg1 (Satt309) and Rhg4 (Satt162 and Satt632) were used to test potential genetic differences between these two NILs at rhg1 and Rhg4 loci. The resistant line TN09-29 inherited the two resistant alleles from its Hartwig ancestry. The susceptible line TN09-016, however, did not inherit the Rhg4 allele but did receive the rhg1 resistant allele. The SCN resistance genes soluble NSF attachment proteins (GmSNAP18) and the serine hydroxymethyltransferase (GmSHMT08) at the rhg1 and Rhg4 loci, respectively, were cloned and sequenced from the isogenic lines. While the nucleotide sequences of GmSNAP18 were identical in both lines, GmSHMT08 showed two single nucleotide polymorphisms (SNPs), leading to R130P and Y358N amino acid substitutions between the TN09-29 and TN09-16 (FIG. 11). These two amino acid substitutions were previously reported to establish the difference between the resistant and susceptible alleles of Rhg4.

Figure 12:
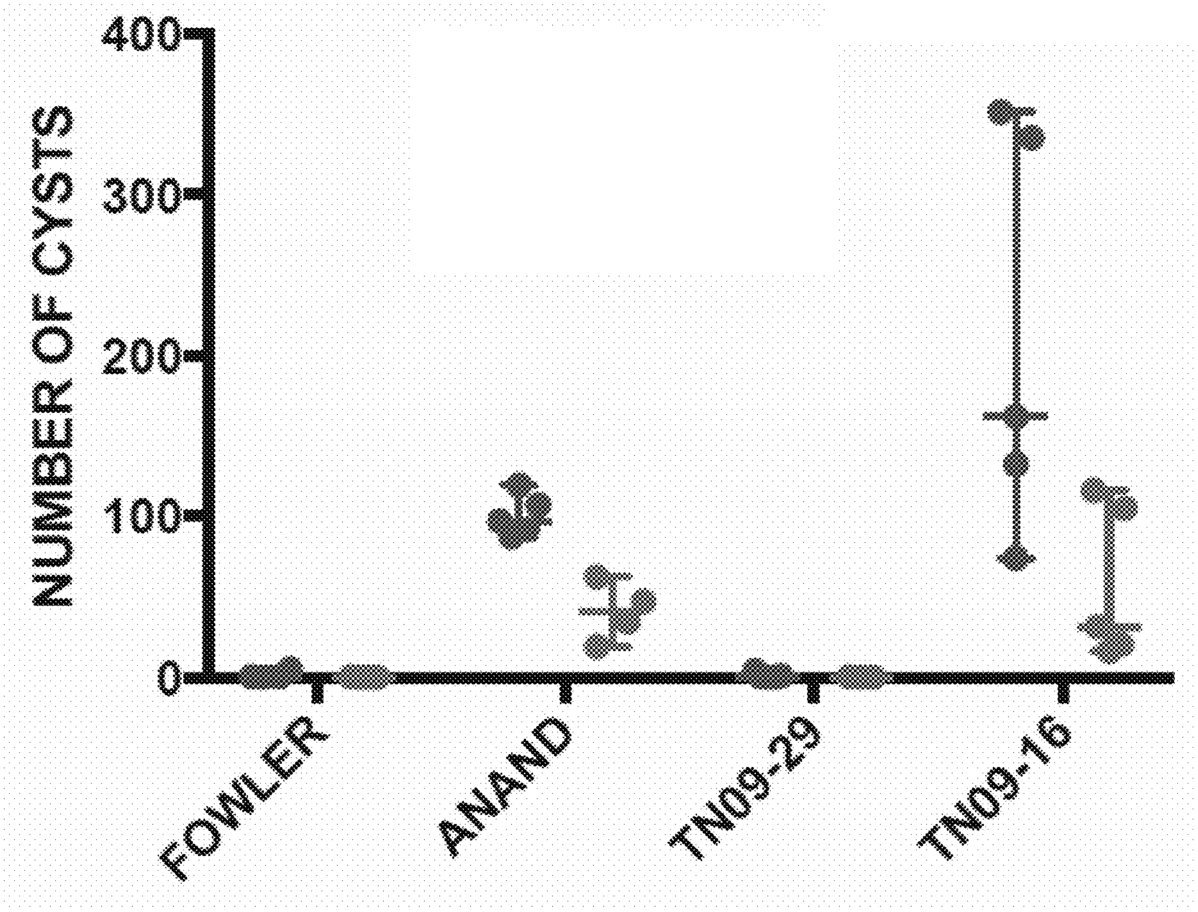
FIG. 12: Responses of TN09-16, TN09-29, and the parental lines Fowler and Anand to infection by the soybean cyst nematode race 3 (HG type 0). The number of cysts was determined five weeks post inoculation. Data from two experiments (highlighted in red and blue), each with at least 10 plants per line are shown. Each data point represents the mean of cyst numbers obtained from two plants.

Nematode susceptibility assays of the parental lines and the NILs were conducted against SCN HG Type 0 (race 3). The parental line Anand showed very high level of SCN susceptibility with more than 100 cysts per plants. In contrast, Fowler showed high level of resistance with only one or two cysts in the inoculated plants (FIG. 12). Similarly, the NILs showed completely opposite responses to SCN infection. TN09-16 showed very high level of susceptibility, whereas TN09-29 showed complete resistance to SCN (FIG. 12). TN09-16 and TN09-29 were also evaluated for SCN resistance in the USDA Southern Uniform Soybean Test program. TN09-29 showed strong resistance to race 2 (HG Type 1.2.5.7), race 3, and race 5 (HG Type 2.5.7) with the highest possible resistant score ratings (1, 1, 1). In contrast, TN09-16 showed high level of susceptibility rated at scores of 4, 4, and 4, for SCN races 2, 3, and 5, respectively. Thus, Rhg4 is required for complete resistance against SCN in the PI 437654-derived germplasms.

Example 2—the Genomes of the Near Isogenic Lines are Substantially Differentially Methylated Taking into consideration the function of GmSHMT08 in cellular methylation, its potential impact on the methylome of the NILs under non-infected conditions was examined. Seeds of the NILs TN09-16 and TN09-29 were germinated and root tissues of non-infected one-week-old seedlings were collected in three biological independent samples. DNA were isolated from these six samples and used to prepare methylC-seq libraries. The libraries were sequenced using Illumina HiSeq 2500 sequencing platform. 1.190E+09 100-bp reads were obtained for the susceptible TN09-16 line and 1.159E+09 reads were obtained for the resistant TN09-29 line, providing more than 100× coverage of the soybean genomes. Bisulfite conversion rate was estimated using the λ phage genome and found to be greater than 99.7%. Differentially methylated cytosines in the CG, CHH and CHG sequence contexts were considered for downstream analyses only if they covered by at least 10 high-quality reads. The global methylation levels were compared between TN09-16 and TN09-29 over genes and transposable elements (TEs) in the CG, CHG, and CHH contexts. Interestingly, differences in the global methylation levels between the two lines were detected in gene body as well as upstream and downstream regions in all sequence contexts (FIGS. 1A-1C). The susceptible line TN09-16 showed higher methylation levels than the resistant TN09-29 line over gene body and the flanking regions in the CHG and CHH contexts (FIGS. 1B and 1C). In the CG context, TN09-16 showed higher methylation level in the flanking regions but lower methylation in gene body (FIG. 1A). Differences in the global methylation levels between the two lines were also observed in TEs (FIGS. 1D-1F). TN09-16 showed higher methylation levels than TN09-29 in the TE flaking regions in all sequence contexts (FIGS. 1D-1F). Over the body of TEs, the global methylation levels of TN09-16 and TN09-29 in the CHG context were comparable (FIG. 1E). In CG and CHH, however, the differences between the two lines were noticeable. TN09-16 showed higher CHH-methylation and lower CG-methylation than TN09-29 (FIGS. 1D and 1F). These analyses indicate that the genomes of these NILs are considerably differentially methylated.

Figure 2:
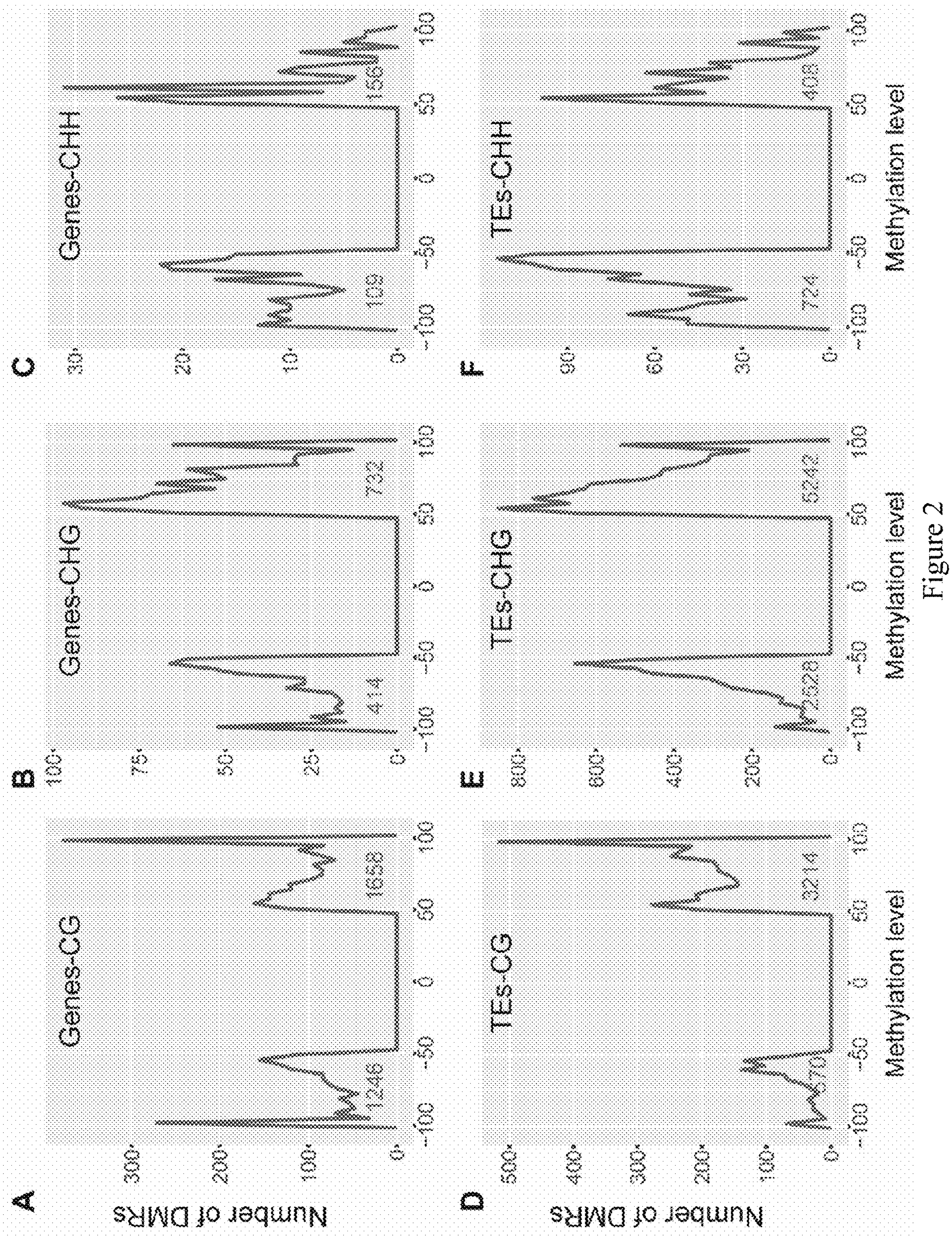
FIG. 2: Characterization of the differentially methylated regions between TN09-16 and TN09-29. A-C, Differentially methylated regions overlapping with protein-coding genes in the CG, CHG, and CHH sequence contexts. D-F, Differentially methylated regions overlapping with TEs in the CG, CHG, and CHH sequence contexts.
Figure 13:
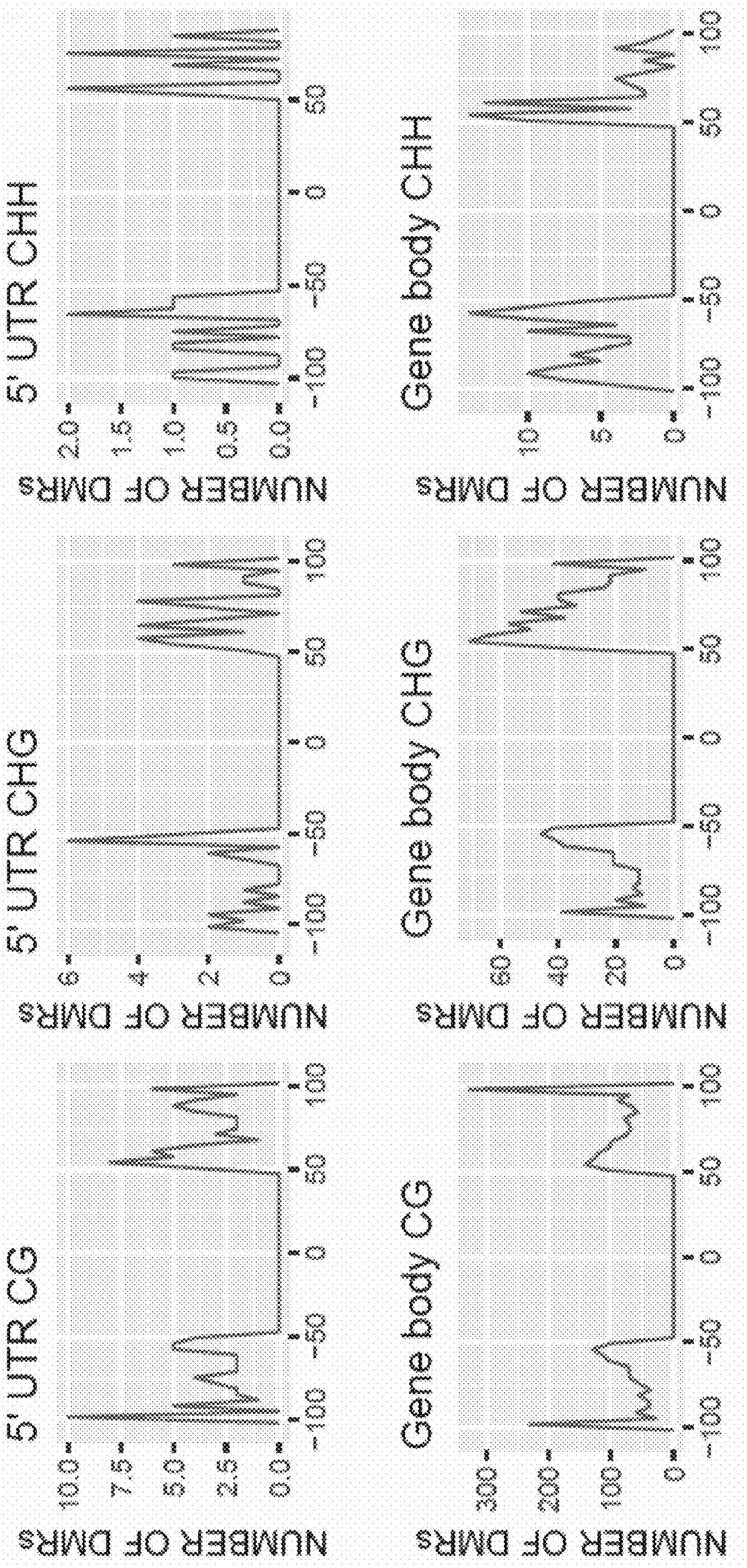
FIG. 13: Mapping DMRs identified between TN09-16 and TN09-29 under non-infected conditions to various annotated features of protein-coding genes, including promoter, gene body, and 5' and 3'UTRs.
Figure 13:
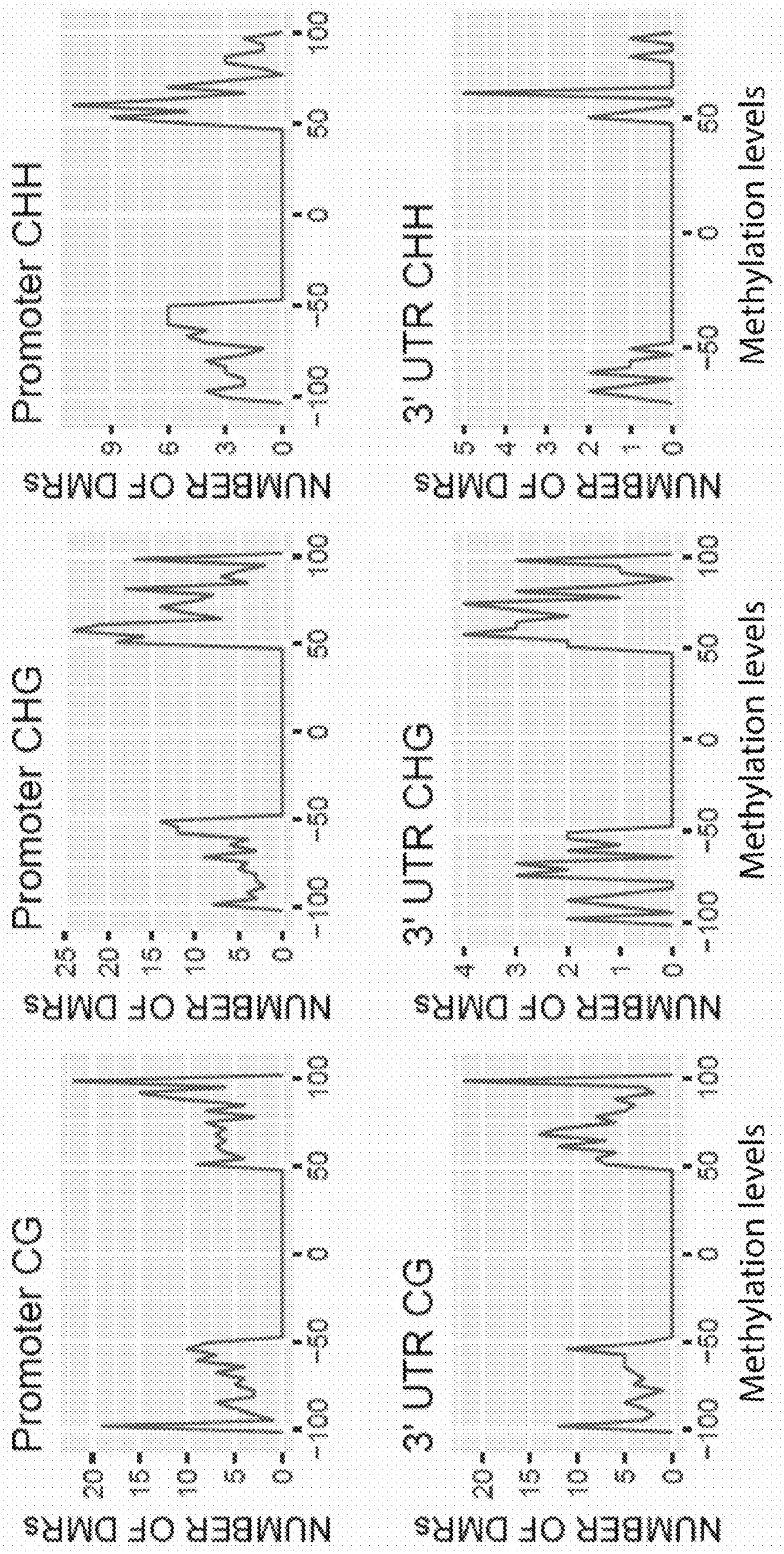
Figure 14:
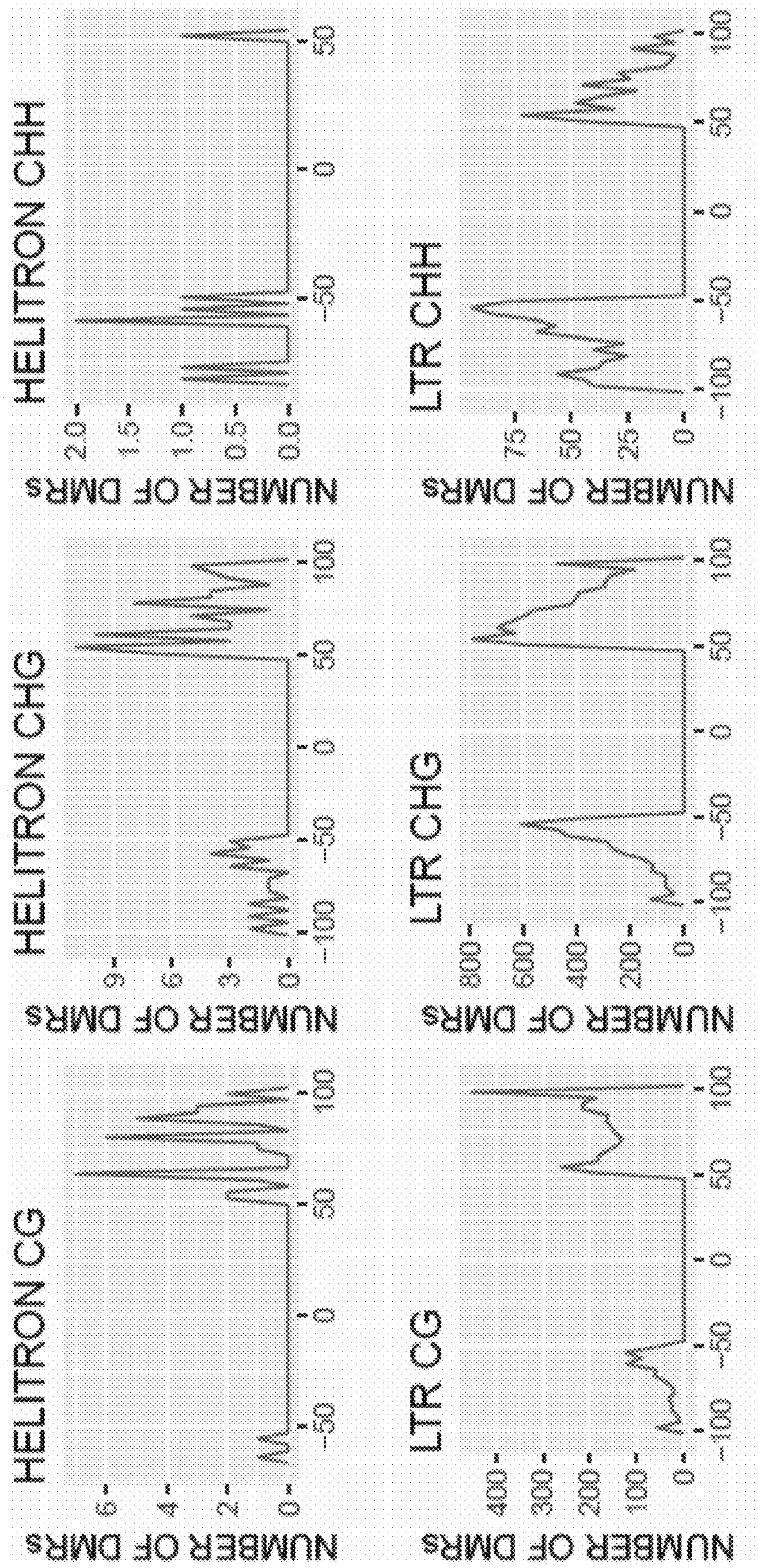
FIG. 14: Mapping DMRs identified between TN09-16 and TN09-29 under non-infected conditions to various transposon families, including Helitron, TIR, LTR, and Line.
Figure 14:
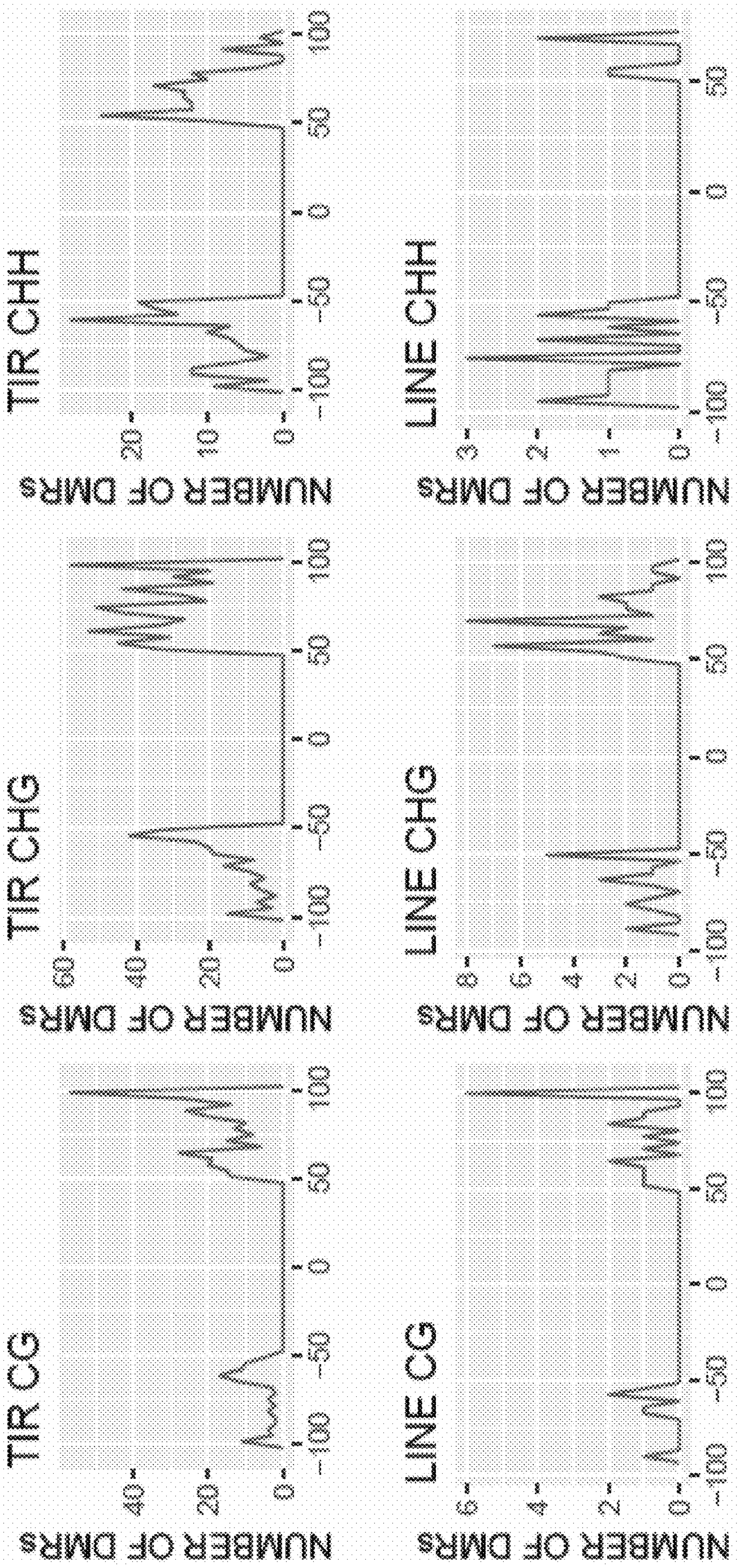

To identify genomic regions with the most significant methylation differences, the genomes of these two lines were divided into 200-bp non-overlapping bins and then differentially methylated regions (DMRs) with at least 50% methylation differences were identified using a false discovery rate (FDR) of 0.01. Using these stringent criteria, 21,852 unique DMRs between TN09-16 and TN09-29 were identified. Of these 4,180 and 11,211 DMRs overlapped with protein-coding genes and TEs, respectively (FIG. 2). The remaining DMRs are located in unannotated regions of the genome. As shown in FIG. 2, the majority of these DMRs occurred in the CHG and CG contexts, with approximately two-thirds of these regions being hypermethylated in the susceptible line TN09-16 compared with the resistant line TN09-29. When the 4,180 DMRs were mapped to various annotated features of protein-coding genes CG-DMRs were found to occur mostly in gene body and to a much lesser extent in gene promoters and 5' and 3' untranslated regions (UTRs) (FIG. 13). Notably, 70% of CHG-DMRs were found in gene body (FIG. 13). In contrast to CG- and CHG-DMRs, the number of CHH-DMRs overlapping with gene features was relatively small (FIG. 11). TE-associated DMRs were mapped to various transposon families. Remarkably, 88% of these DMRs were associated with long terminal repeat (LTR) retrotransposons (FIG. 14). DMRs overlapping with the DNA transposons Helitron and TIR constituted about 10% of the total number of TE-associated DMRs (FIG. 14).

Figure 3A:
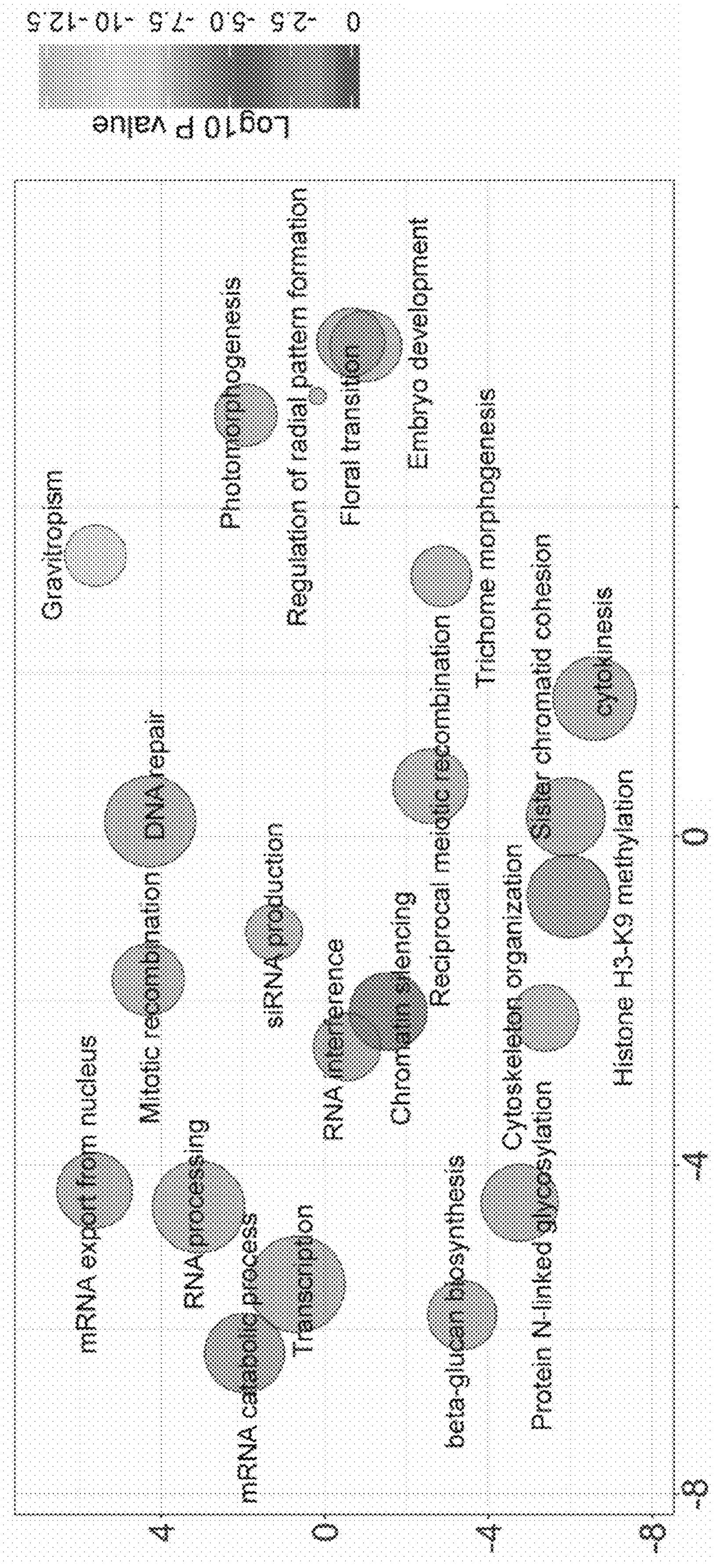
FIGS. 3A-3D: Functional classification of the differentially methylated and differentially expressed genes between TN09-16 and TN09-29. A and B: Gene Ontology enrichment analysis of the differentially methylated genes (A) and differentially expressed genes (B). C: Venn diagram demonstrating the overlap between differentially methylated genes and differentially expressed genes. D: Genome browser image showing DNA hypermethylation in the promoter and gene body regions of Glyma.09G133900 in TN09-16. The hypermethylation of Glyma.09G133900 was associated with gene downregulation. Promoter region, 1 kb upstream of ATG, is highlighted.

Gene Ontology (GO) enrichment analysis of the 3,666 differentially methylated genes (DMGs) between TN09-16 and TN09-29 revealed overrepresentation of genes involved in various biological processes (FIG. 3A). Of note is that ontologies with functions related to chromatin silencing, RNA interference, DNA repair, production of siRNAs, and histone H3-K9 methylation were significantly overrepresented. Thus, the enrichment of genes related to epigenetic modifications among the DMGs may explain the remarkable methylome differences between these two NILs.

Figure 3B:
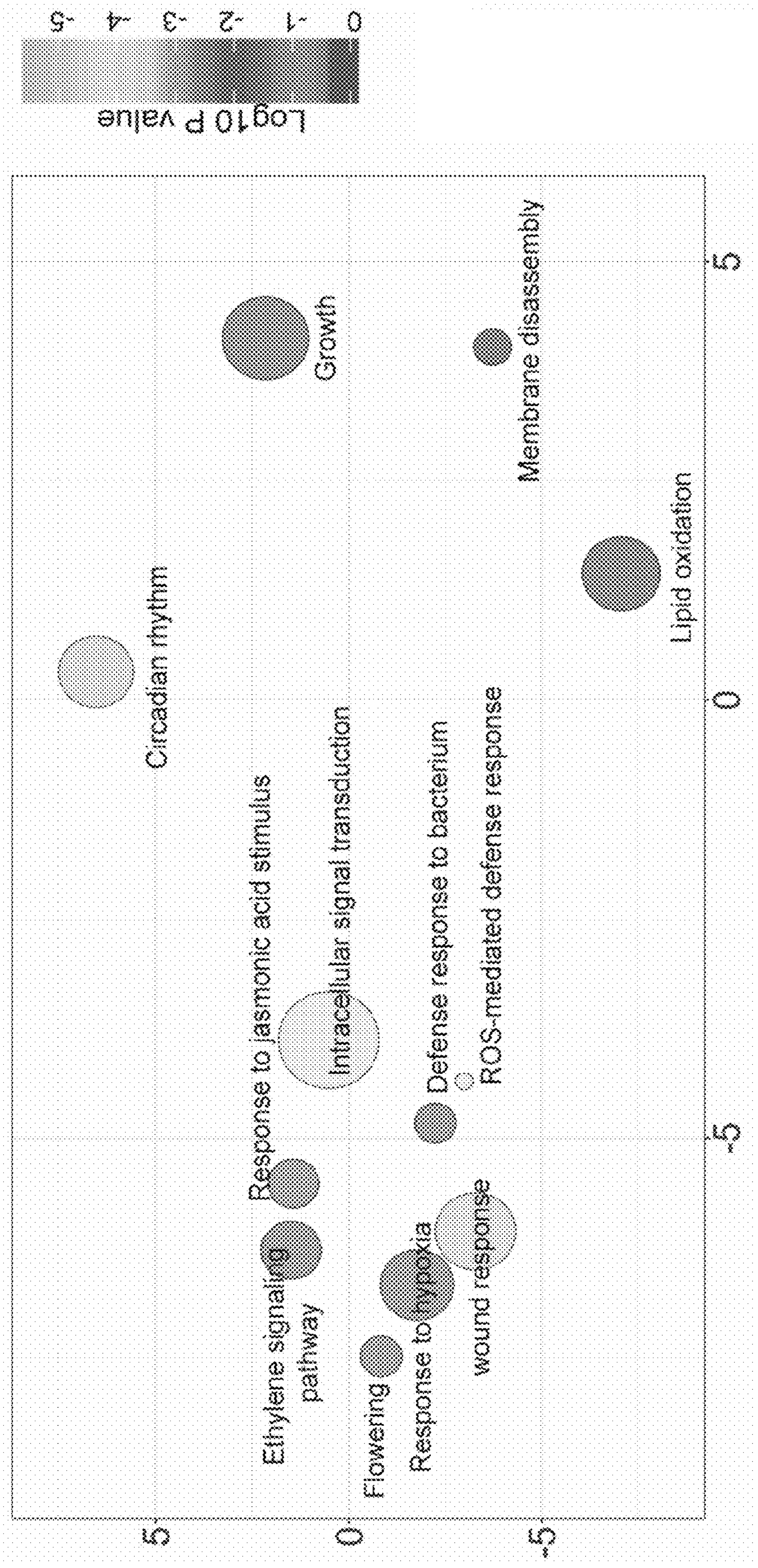
Figure 3C:
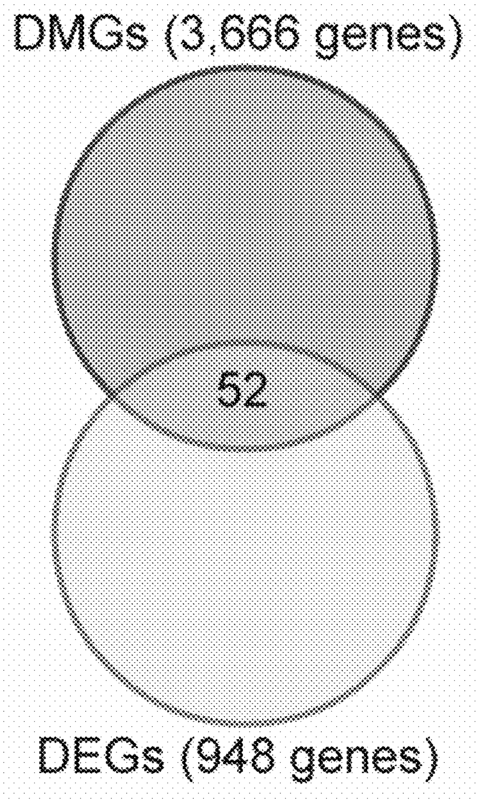
Figure 3D:
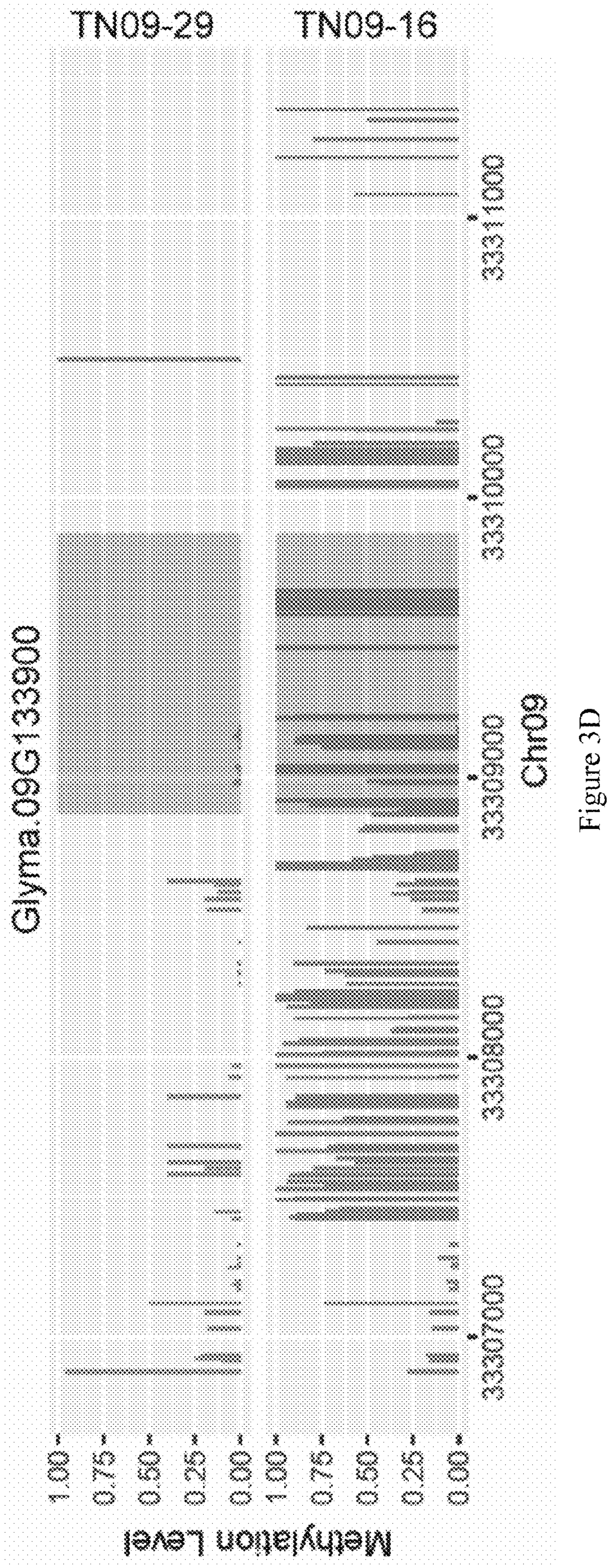

Example 3—Differential DNA Methylation Between the Isogenic Lines May Prime their Responses to SCN Infection To examine the degree to which cytosine methylation impacts gene expression in the isogenic lines, RNA-seq libraries were generated from the same root samples used for DNA methylation analysis. 948 differentially expressed genes (DEGs) were identified between TN09-16 and TN09-29 at a FDR of 0.05. GO term analysis revealed statistically significant enrichment for categories related to wounding response, defense response, membrane disassembly, and intracellular signal transduction (FIG. 3B). These findings suggest that differences in priming response between TN09-16 and TN09-29 may contribute to their contrasted response to SCN infection. To examine this suggestion the 948 DEGs were compared with a list of previously identified syncytium DEGs (6,903) and 267 genes were identified to be common between these two gene lists. This significant overlap (28.16%, $\chi 2=38.91$, P=1.81E-08) further supports that differences in priming response between TN09-16 and TN09-29 may contribute to their contrasted response to SCN infection. The 948-gene list was next compared with the 3,666 DMGs to determine if there is a significant enrichment for the DMGs among the DEGs. Fifty two genes were common to both gene lists, revealing a significant enrichment (5.48%, $\chi 2=27.76$, P=4.07E-06) for the DMGs among the DEGs (FIG. 3C). The methylation patterns of these 52 genes seem to impact their expression levels. For example, promoter and gene body hypermethylation of Glyma.09G133900 in TN09-16 was associated with a significant gene downregulation (FIG. 3D). In addition, 9 DEGs were identified that are located with 2 kb from differentially methylated TEs. Together, these data indicate that under non-infected conditions differential DNA methylation contributes to differential gene expression between the NILs that may prime their responses to SCN parasitism.

Figure 4:
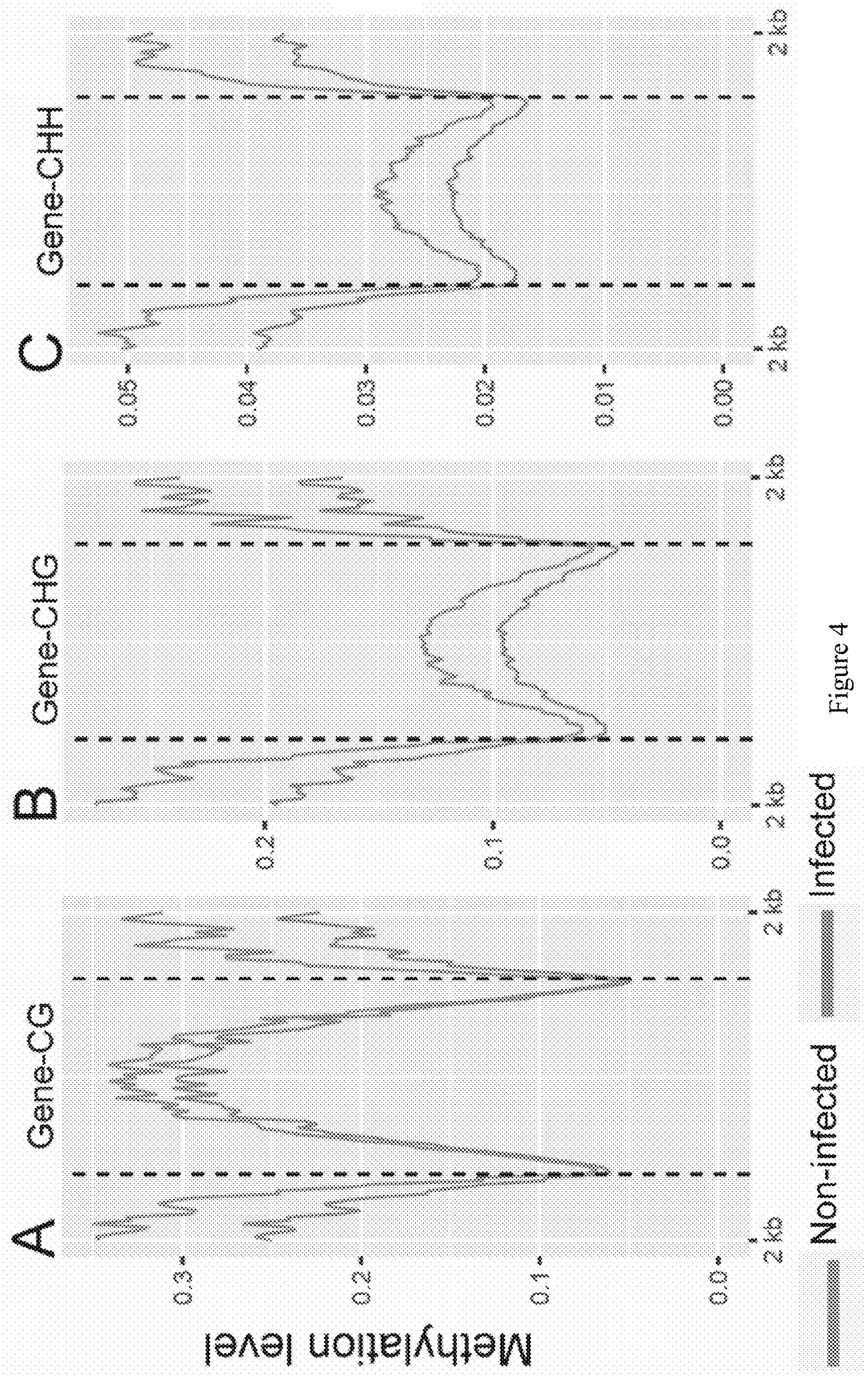
FIG. 4: Comparison of global DNA methylation levels between the isogenic lines at 5 day post SCN infection. A-F: Global DNA methylation levels over protein-coding genes (A-C) and TEs (D-F) in infected and non-infected root samples of TN09-16. G-L: Global DNA methylation levels over protein-coding genes (G-I) and TEs (J-L) in infected and non-infected root samples of TN09-29.
Figure 4:
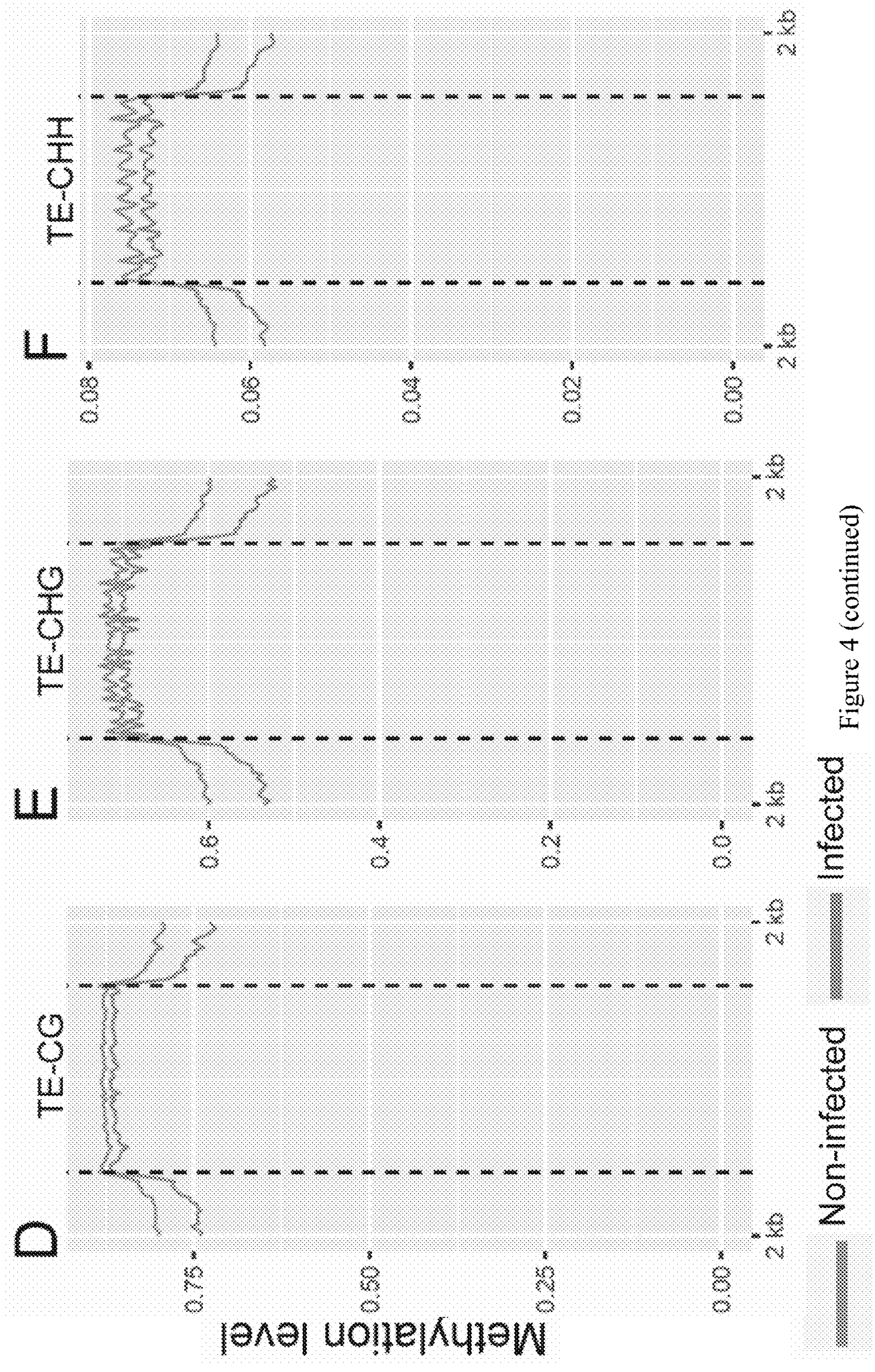
Figure 4:
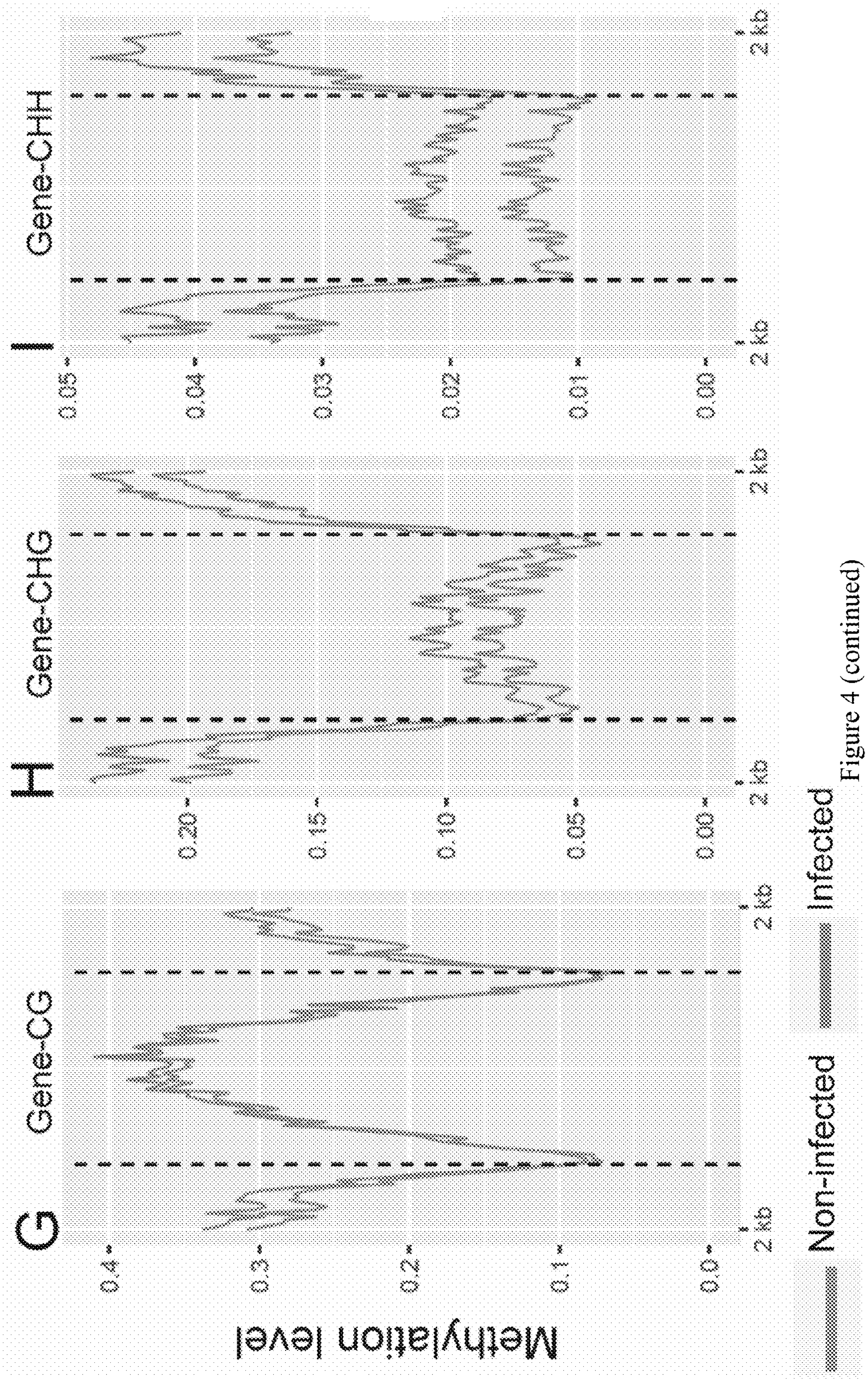
Figure 4:
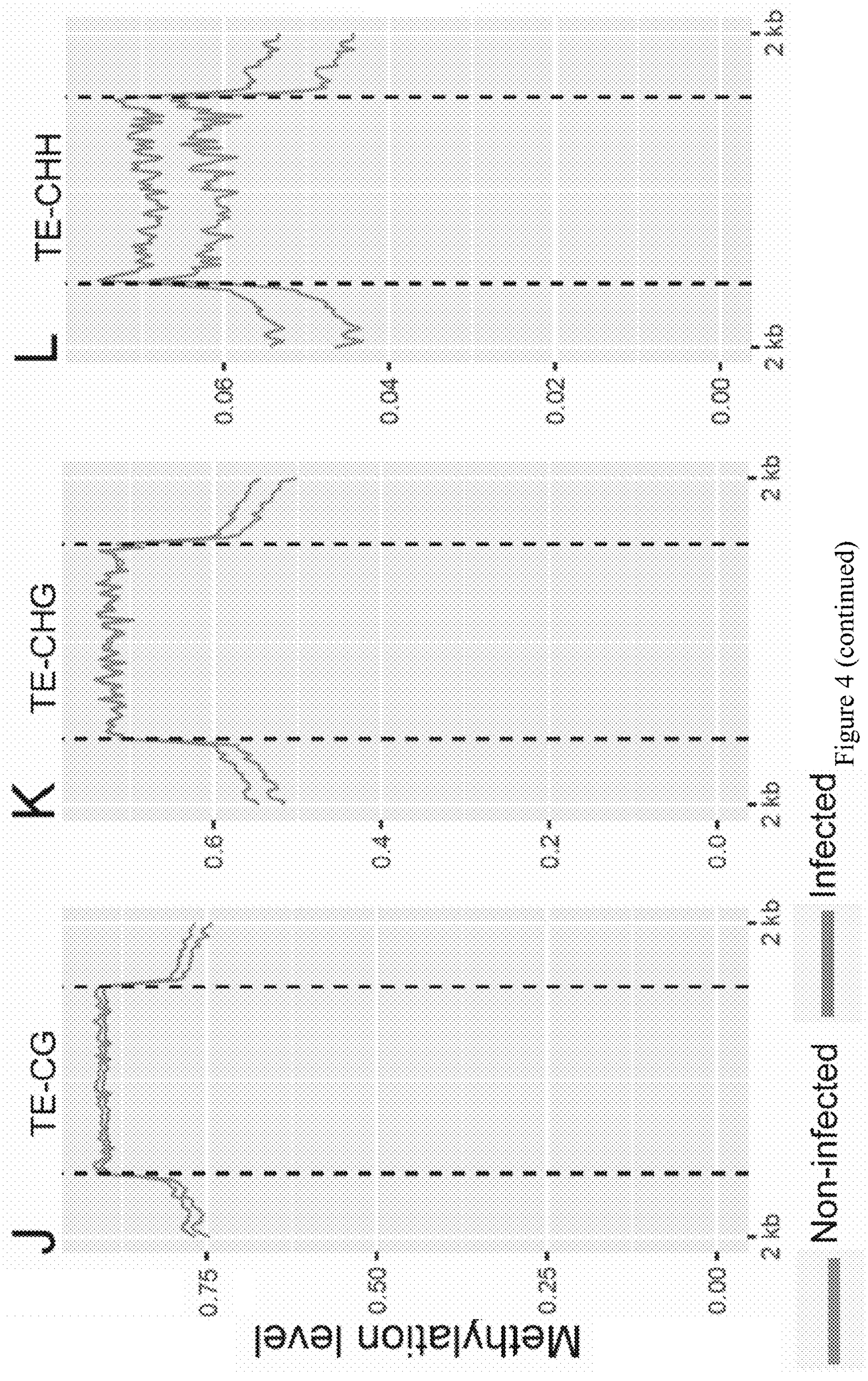

Example 4—the Susceptible and Resistant Isogenic Lines Exhibit Contrasted DNA Methylation Patterns in Response to SCN Infection Whether the methylomes of the TN09-16 and TN09-29 are similarly altered in response to SCN (race 3) infection was examined. MethylC-seq libraries were constructed from SCN-infected roots at 5 day post infection (dpi) and compared with control samples. Both infected and non-infected libraries were prepared from root tissues collected from the same experiments at the same time. Differentially methylated cytosines were identified as described above and global methylation levels were compared between infected and non-infected samples over genes and TEs in all sequence contexts. In response to SCN infection, the susceptible line TN09-16 showed reduced methylation levels over protein-coding genes in all sequence contexts compared with non-infected control (FIGS. 4A-4C). In sharp contrast, the SCN-infected samples of the resistant line TN09-29 showed increased methylation levels over protein-coding genes in all sequence contexts compared with non-infected control (FIGS. 4G-4I).

Differences in global methylation patterns over TEs in response to SCN infection were also observed between the NILs. Infected TN09-16 samples showed reduced methylation levels over the body of TEs and flaking regions in all sequence contexts in comparison with the non-infected control samples (FIGS. 4D-4F). On the contrary, infected TN09-29 samples showed increased methylation level over the body of TEs and flaking regions in CHH context relative to non-infected samples (FIG. 4L). In the CG and CHG contexts, however, increased methylation levels in the TN09-29—infected samples were observed only over the TE flaking regions (FIGS. 4J and 4K). These analyses indicate that the NILs exhibit contrasted DNA methylation patterns in response to SCN infection with hypomethylation being more predominant in the susceptible line, whereas hypermethylation being more predominant in the resistant line.

Figure 5A:
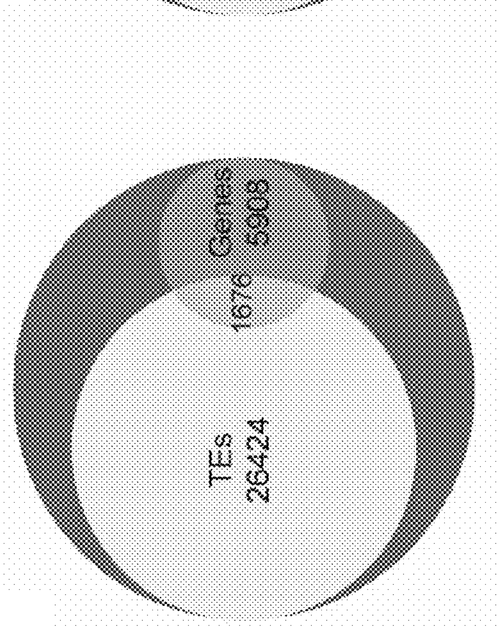
FIGS. 5A-5K: Specificity and magnitude of DNA methylation changes induced by SCN in the isogenic lines. A and B: Venn diagrams showing the numbers of DMRs overlapping with protein-coding genes and TEs in TN09-16 (A) and TN09-29 (B). C: Venn diagram showing 74 DMRs overlapping between those identified in TN09-16 and TN09-29. D and E: Gene Ontology enrichment analysis of the DMRs-associated genes identified in TN09-16 (D) and TN09-29 (E). F to K: Methylation level, direction, sequence contexts, and numbers of the DMRs overlapping with protein-coding genes (F-H) and TEs (I-K) identified in TN09-16 (blue lines) and TN09-29 (red lines) in response to infection by soybean cyst nematode.
Figure 5B:
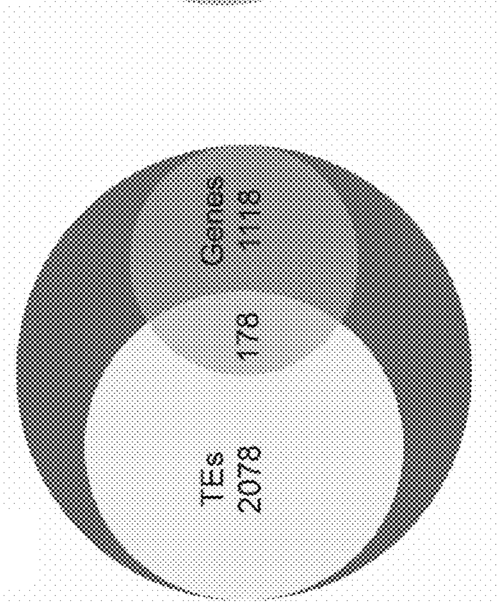
Figure 5C:
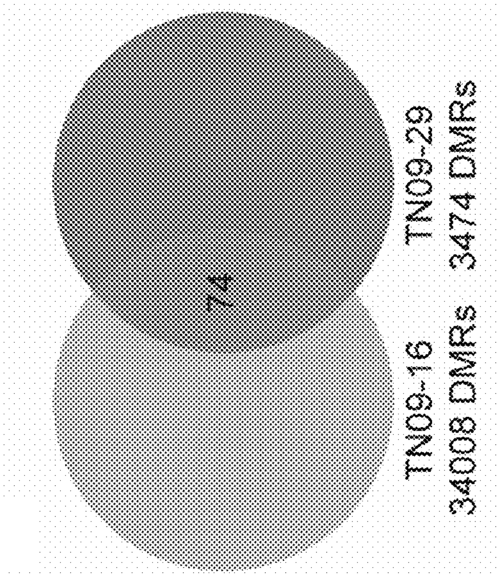
Figure 5D:
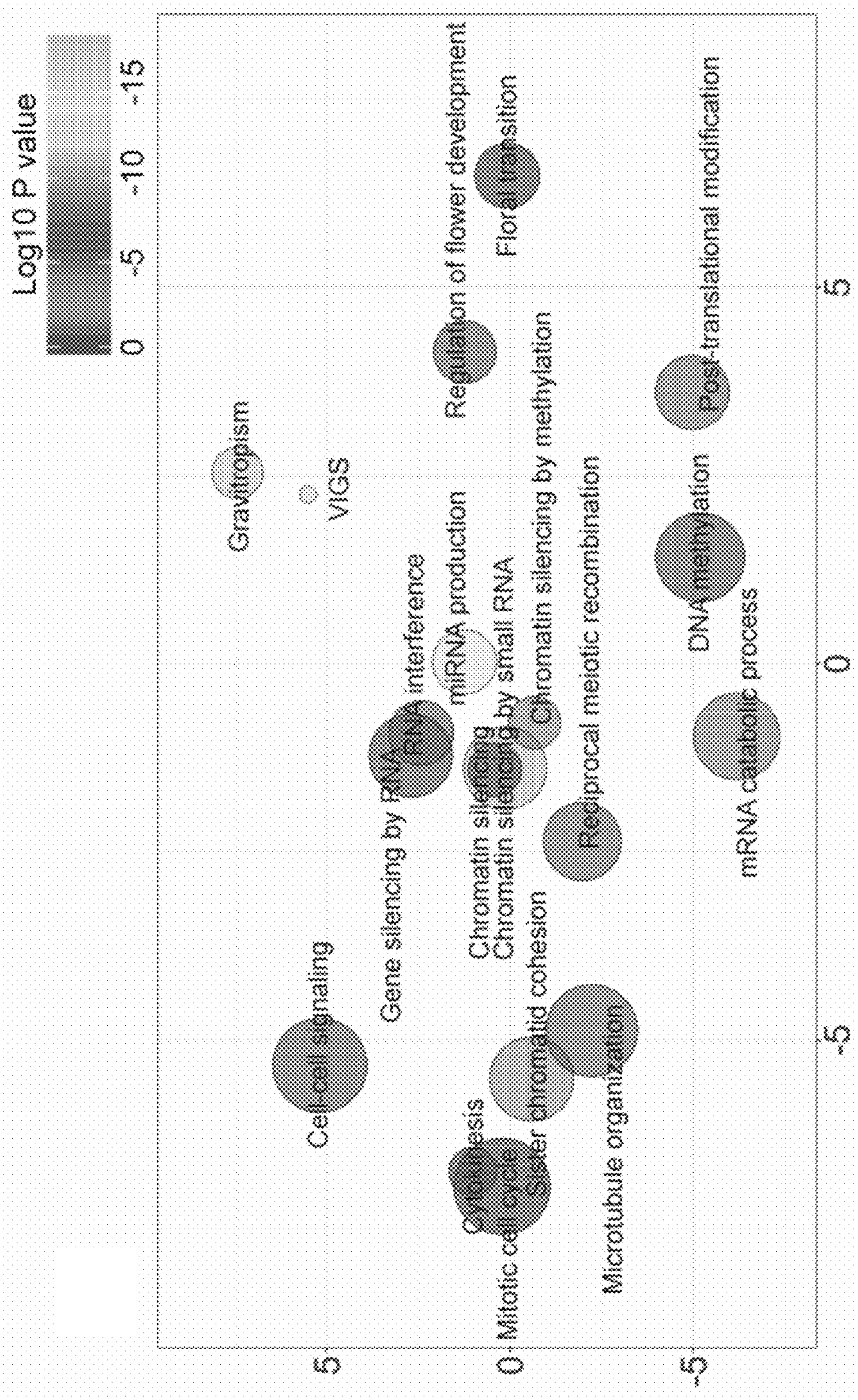
Figure 5E:
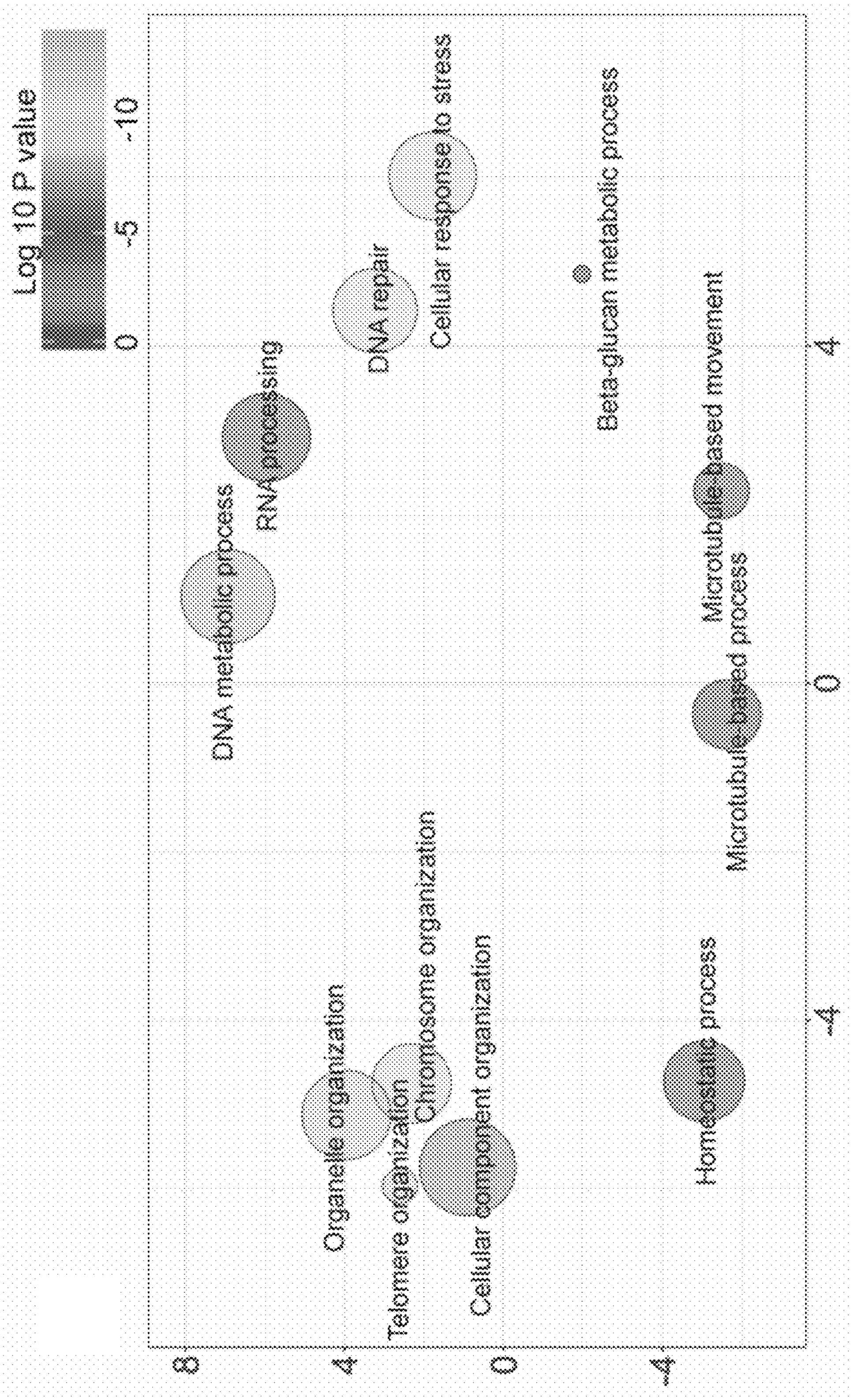
Figure 5F:
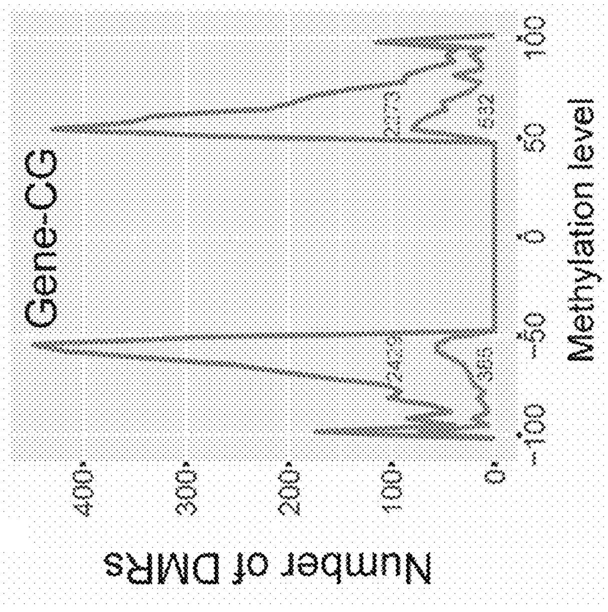
Figure 5G:
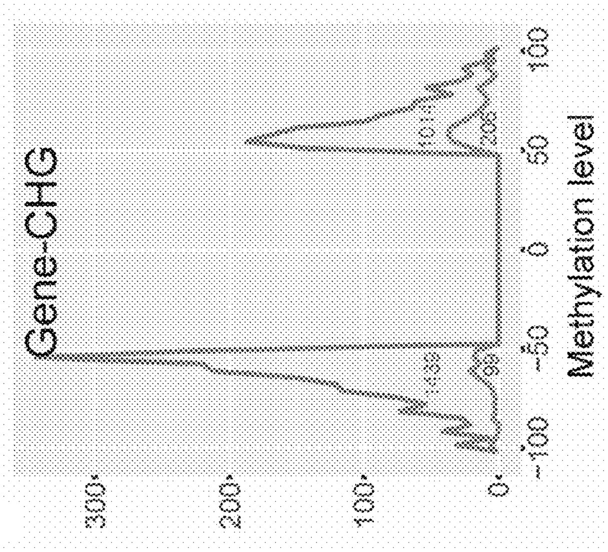
Figure 5H:
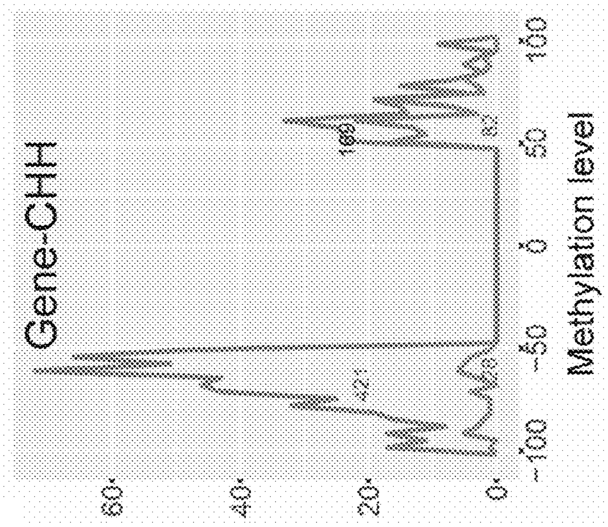
Figure 5I:
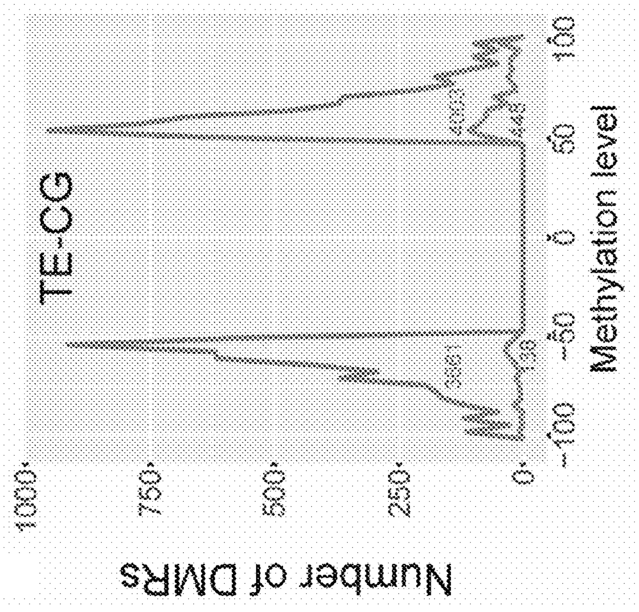
Figure 5J:
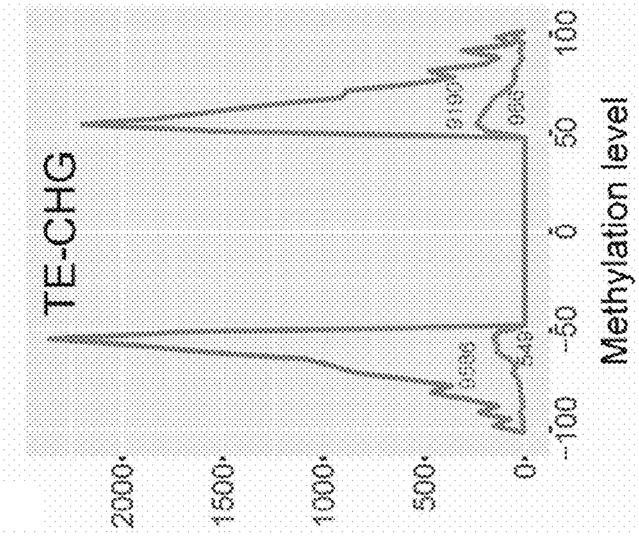

Example 5—DNA Methylation Patterns Associated with the Susceptible and Resistant Responses are Highly Specific To localize the genome-wide DNA methylation profiles induced by SCN in both lines DMRs were identified as indicated above and mapped to the annotated protein-coding genes and TEs. In response to SCN infection 50,040 DMRs were identified in TN09-016. Of these, 7,585 (15.16%) overlapped with protein-coding genes, and 28,100 (56.16%) overlapped with TEs (FIG. 5A). Of the 28,100 TE-associated DMRs 1,676 (5.96%) were located in genes. Notably, the number of DMRs in TN09-29 was dramatically lower (FIG. 5B). A total number of 5,080 DMRs were identified in the TN09-29-infected samples compared with controls (FIG. 5B). Of these, 1,296 (25.51%) overlapped with protein-coding genes, and 2,356 (46.38%) overlapped with TEs (FIG. 5B). Of the 2,356 TE-associated DMRs 178 (7.55%) were located in genes. When the DMRs overlapping with protein-coding genes or TEs were compared between the two lines, only 74 DMRs were common (FIG. 5C), indicating that DNA methylation patterns associated with the susceptible and resistant responses are highly specific. This indication was further supported by GO term enrichment analysis showing the association of the DMGs in TN09-16 and TN09-29 with different GO biological process categories (FIGS. 5D and E).

Figure 5K:
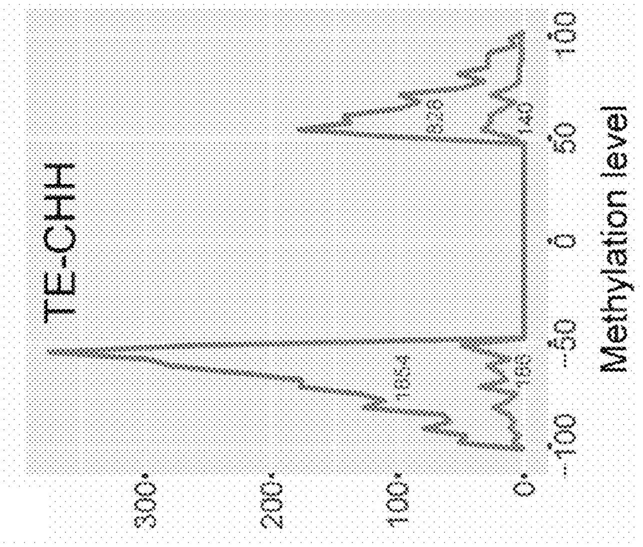
Figure 15:
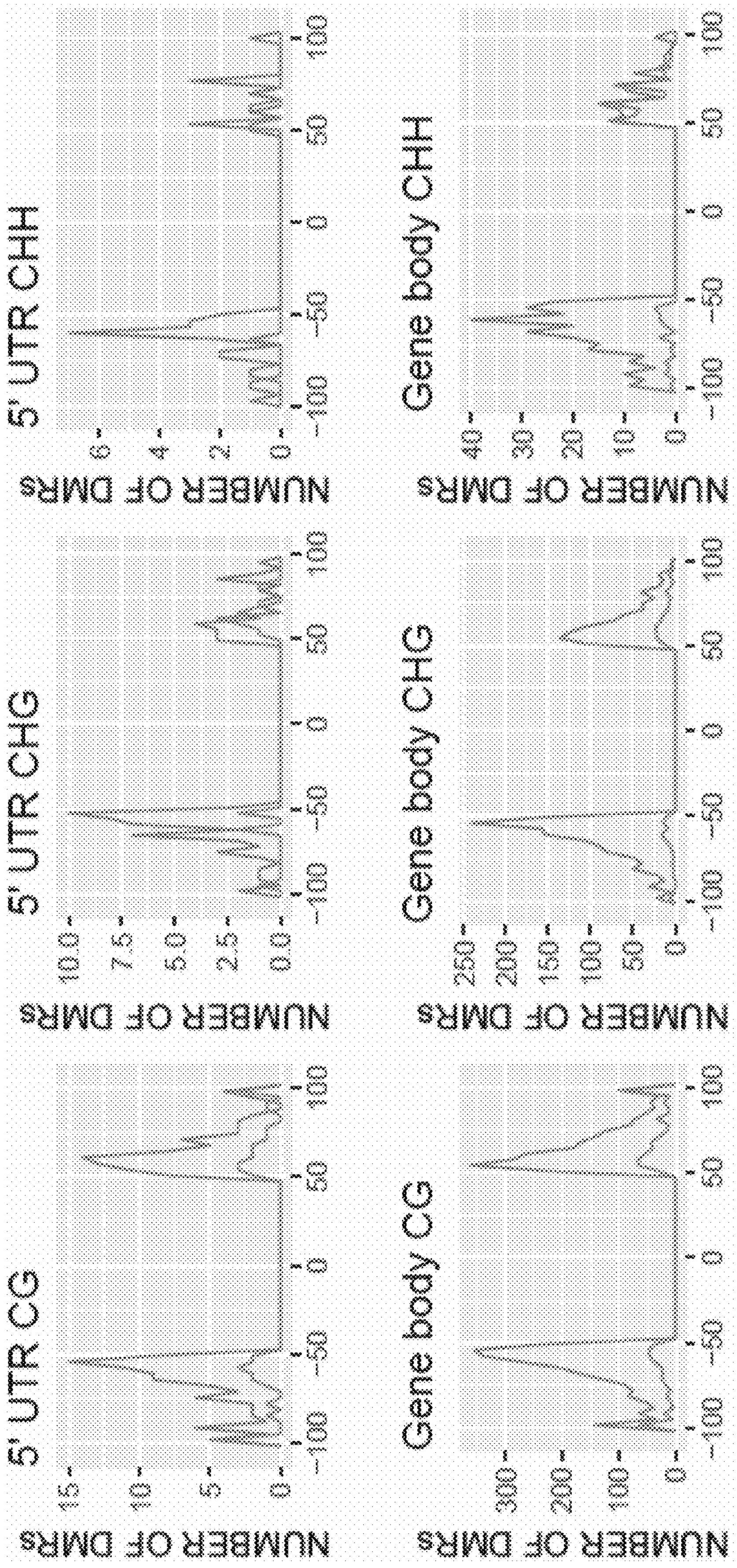
FIG. 15: Numbers and direction of the DMRs identified in TN09-16 (blue) and TN09-29 (red) in response to SCN infection and overlapping with protein-coding genes.
Figure 15:
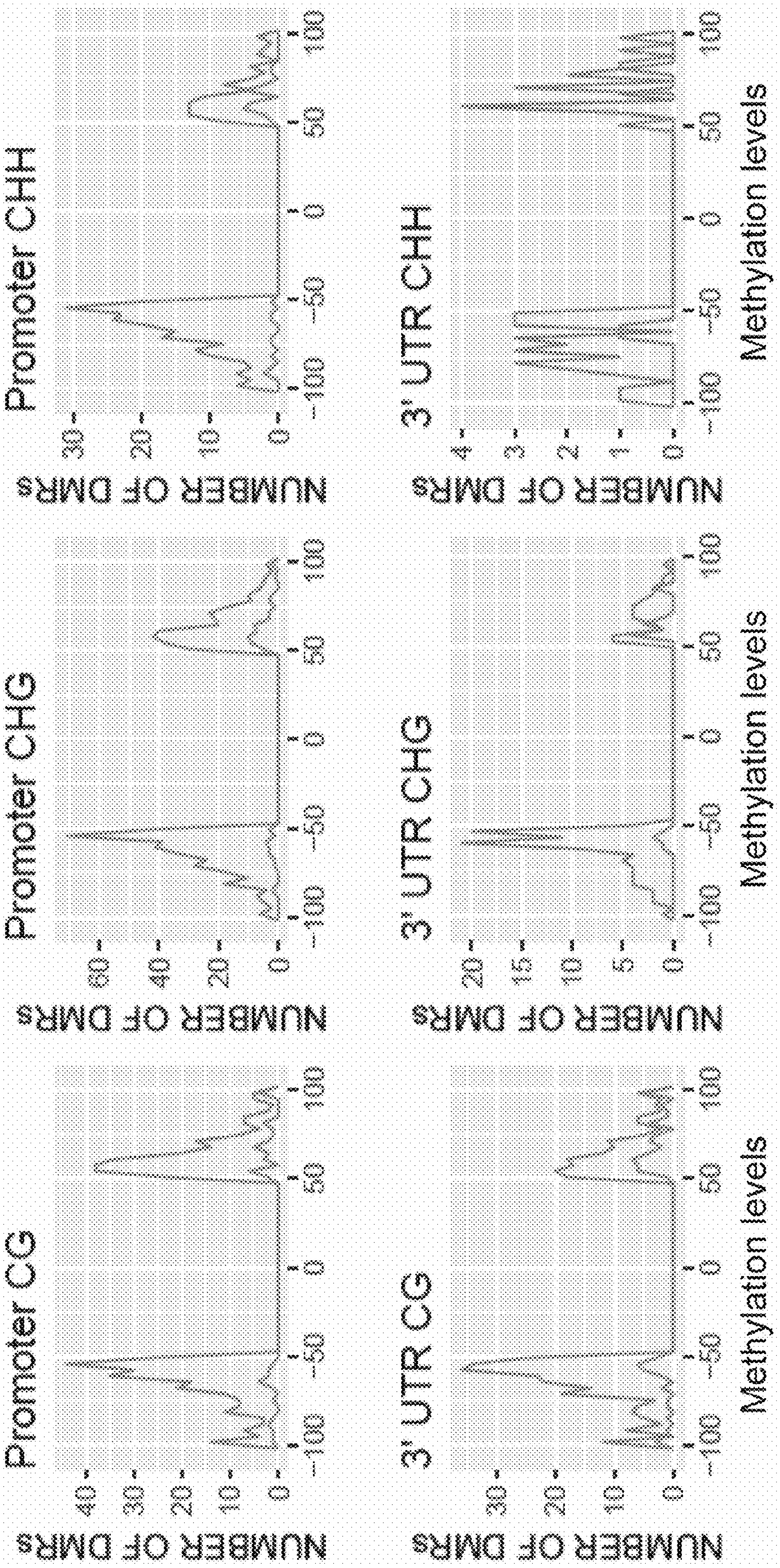
Figure 16:
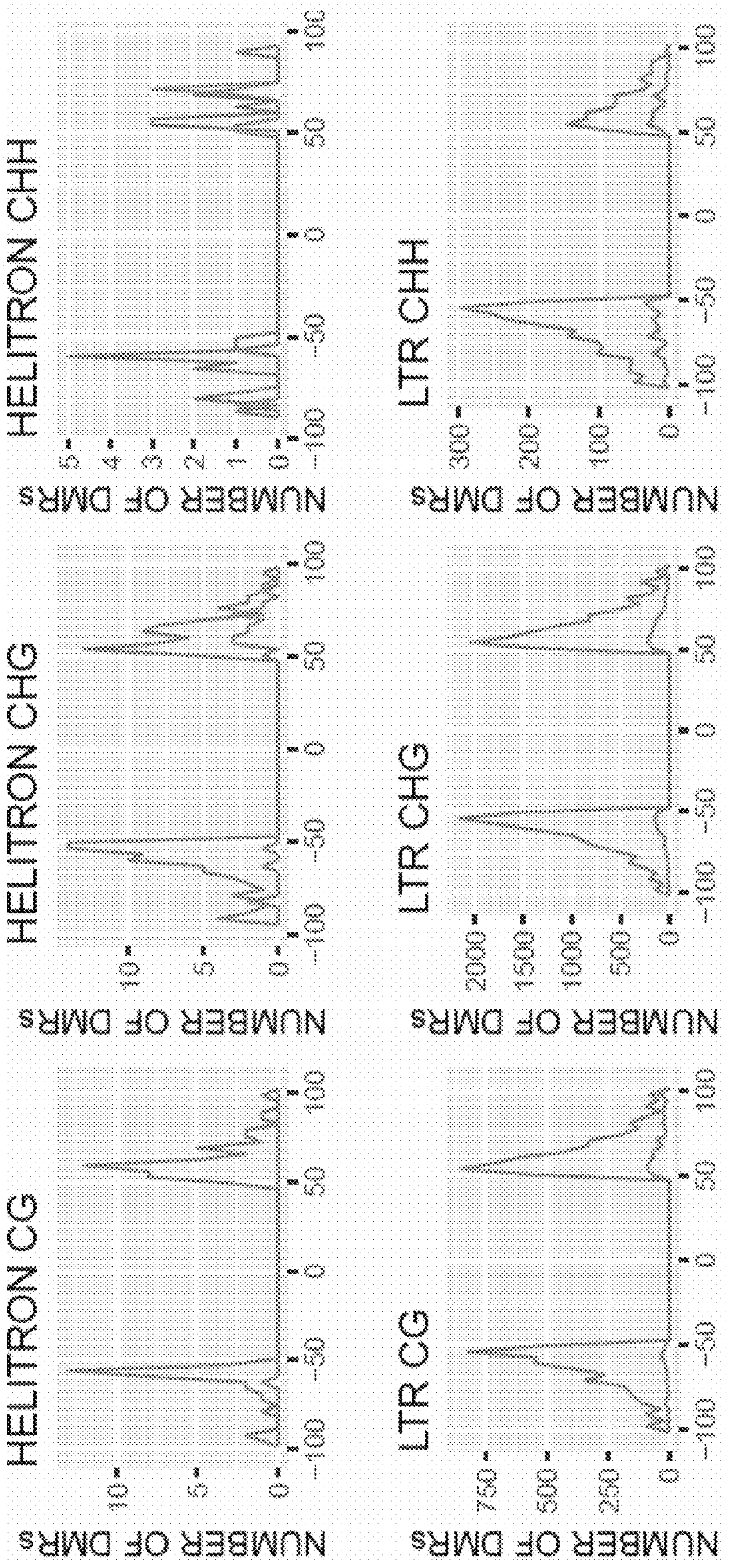
FIG. 16: Numbers and direction of the DMRs identified in TN09-16 (blue) and TN09-29 (red) in response to SCN infection and overlapping with various transposon families.
Figure 16:
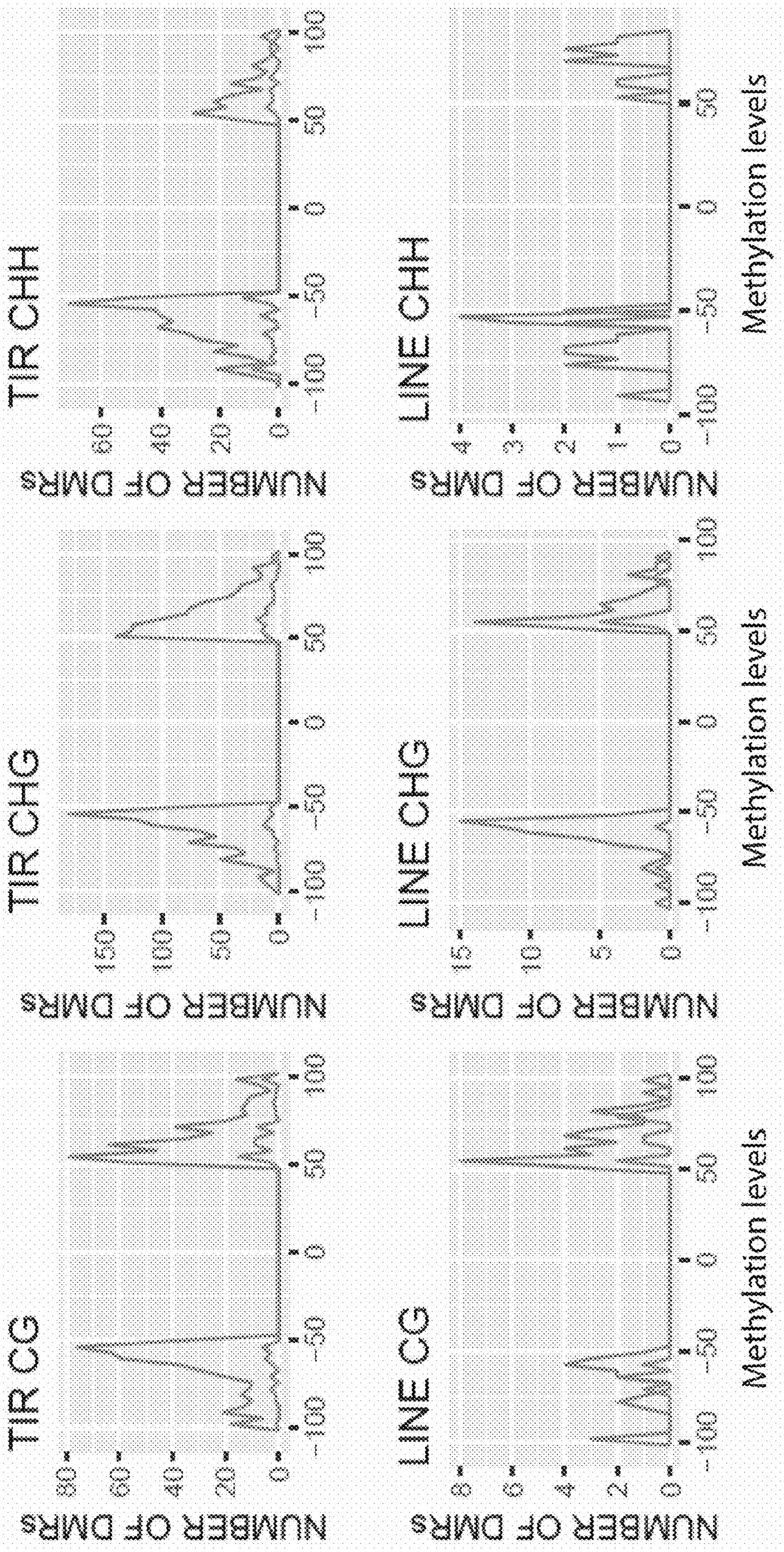

To better understand the methylation differences between TN09-16 and TN09-29 in response to SCN infection, the methylation level, direction, and sequence contexts of the DMRs were examined. The numbers of hyper- and hypo-DMRs associated with protein-coding genes and TEs in the CG, CHG and CHH contexts are shown in FIGS. 5F-5K. With the exception of the CG-DMRs overlapping with TEs (Figure SI) the numbers of hypo-DMRs in various sequence contexts in TN09-16 were higher than hyper-DMRs. In TN09-29, however, the opposite trend was observed with hyper-DMRs being more predominant than hypo-DMRs in all cases except CHH-DMRs associated with TEs (FIG. 5K). This trend is also evident when hyper- and hypo-DMRs overlapping with various annotated features of protein-coding genes (FIG. 15) and transposon families (FIG. 16) were compared within each line. Together, these data indicate that DNA methylation reprograming occurs prominently during the susceptible interaction and to a much lesser extent during the resistant interaction.

Figure 6A:
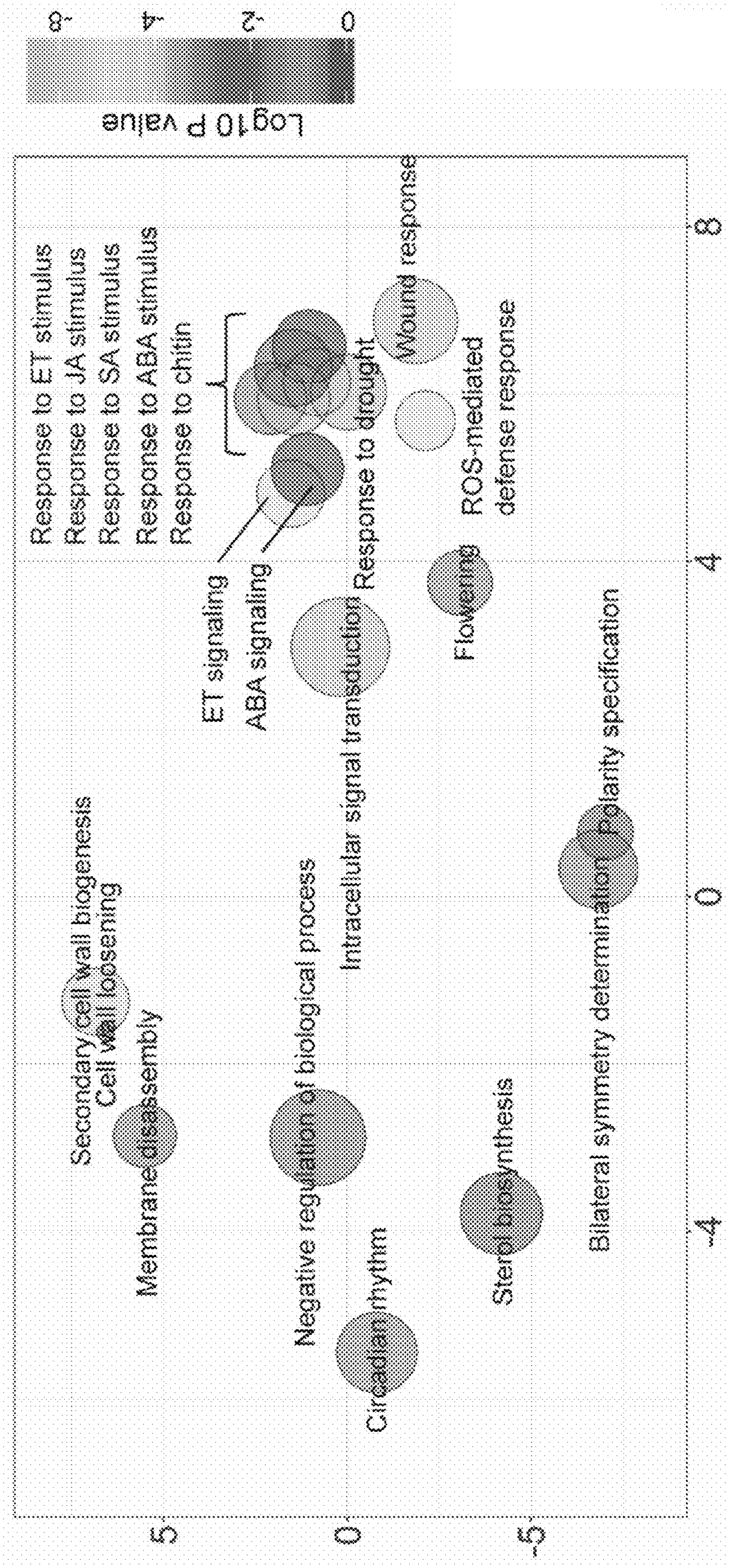
FIGS. 6A-6C: Association between DNA methylation reprograming during the susceptible interaction and gene expression changes. A: Gene Ontology enrichment analysis of the differentially expressed genes identified in the TN09-016 in response to SCN infection. B and C: Venn diagrams showing the overlaps between the DMGs, DMTE-associated genes, and DEGs identified in TN09-29 (B) and TN09-16 (C).

Example 6—DNA methylation reprograming during the susceptible interaction contributes to gene expression changes Gene expression changes were further studied in the TN09-16 and TN09-29 in response to SCN using RNA-seq approach. The RNA libraries were prepared from the same tissue samples used for DNA methylation analysis to facilitate examining the potential link between DNA methylation and transcriptome changes. Because of the heterogeneity nature of SCN-infected roots a less stringent P value cutoff of <0.05 and a FDR<0.1 to identify DEGs was used. 1,668 and 112 DEGs in TN09-16 and TN09-29, respectively, were identified at 5 d post SCN infection. The low number of the DEGs identified in the resistant lines may reflect the localized response to SCN infection compared with the susceptible line in which localized and systemic responses may occur both in the developing syncytium as well as in cells far from the infection sites. GO analysis revealed a significant enrichment of three biological process terms associated with plant responses to oxidative stress, chemical stimulus, and oxidation reduction among the TN09-29 DEGs. These results are consistent with the previous reports associating oxidoreductase activity and oxidative stress response with Peking-type resistance, and support the potential function of GmSHMT08 in redox defense. Among the TN09-16 DEGs genes a significant enrichment of biological process terms corresponding to plant response to stimulus and signaling of various phytohormones was noted, including ethylene, salicylic acid, jasmonic acid, and abscisic acid (FIG. 6A). Genes involved in ROS-mediated defense response, secondary cell wall biogenesis, cell wall loosening, membrane disassembly, and cellular responses to wounding and chitin were also overrepresented among the TN09-16 DEGs (FIG. 6A).

Figure 6B:
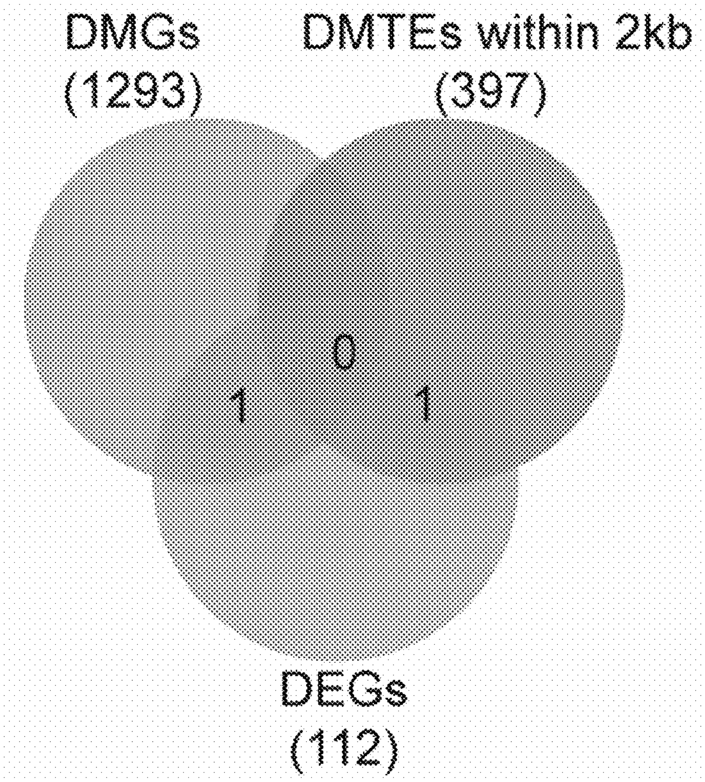
Figure 6C:
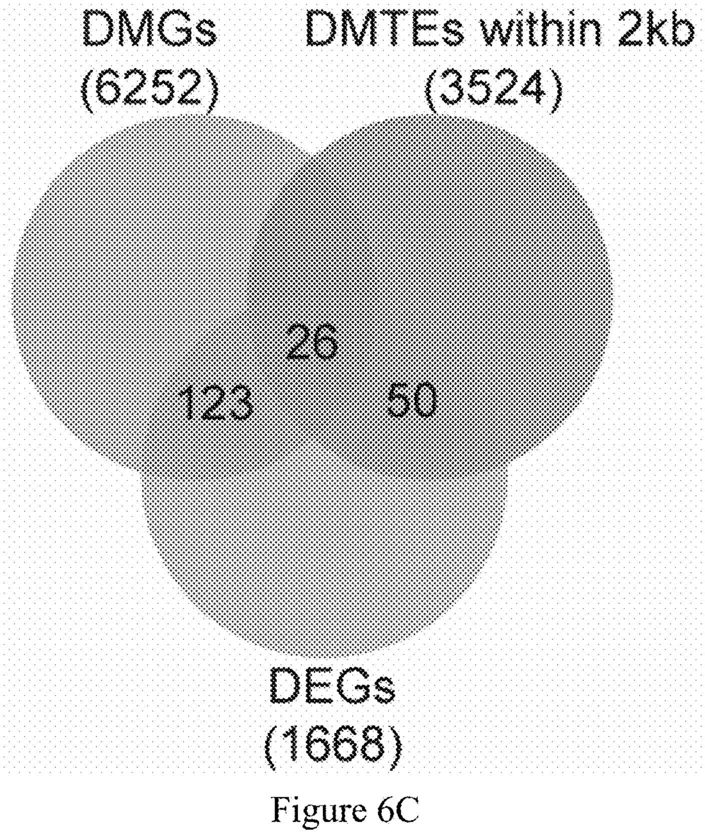

Next, the potential association between DNA methylation and gene expression changes was determined. The 112 DEGs and the 1293 DMGs identified in the TN09-29 upon SCN infection were compared and only one gene (Glyma.04G180400) was common between the two gene lists (FIG. 6B). Also, whether differentially methylated TEs are located within 2 kb upstream or downstream of the 112 DEGs was examined. Only one gene (Glyma.06G102000) was found to contain a differentially methylated TE 1.813 kb from its transcriptional start site (TSS) (FIG. 6B). These results imply that differential DNA methylation doesn't seem to directly impact gene transcription during the resistant interaction. Similarly, the 1668 DEGs and the 6252 DMGs identified in the TN09-16 after SCN infection were compared and 123 genes were common between the two gene lists (FIG. 6C), implying that DMGs are statistically significantly enriched among the DEGs (7.37%, $\chi2=140.3$, P=3.27E-30). Furthermore, 50 DEGs were identified containing differentially methylated TEs in their gene body or promoters, 2 kb upstream of the TSS, resulting in a unique list of 147 differentially expressed DMGs (FIG. 6C). Of these 147 genes, 47 have been previously shown to change expression in the SCN-induced syncytium, providing additional support for the involvement of these genes in plant-SCN interaction. Thus, unlike the resistant interaction, DNA methylation reprograming during the susceptible interaction may directly contribute to gene expression changes.

Figures 17A, 17B, 17C:
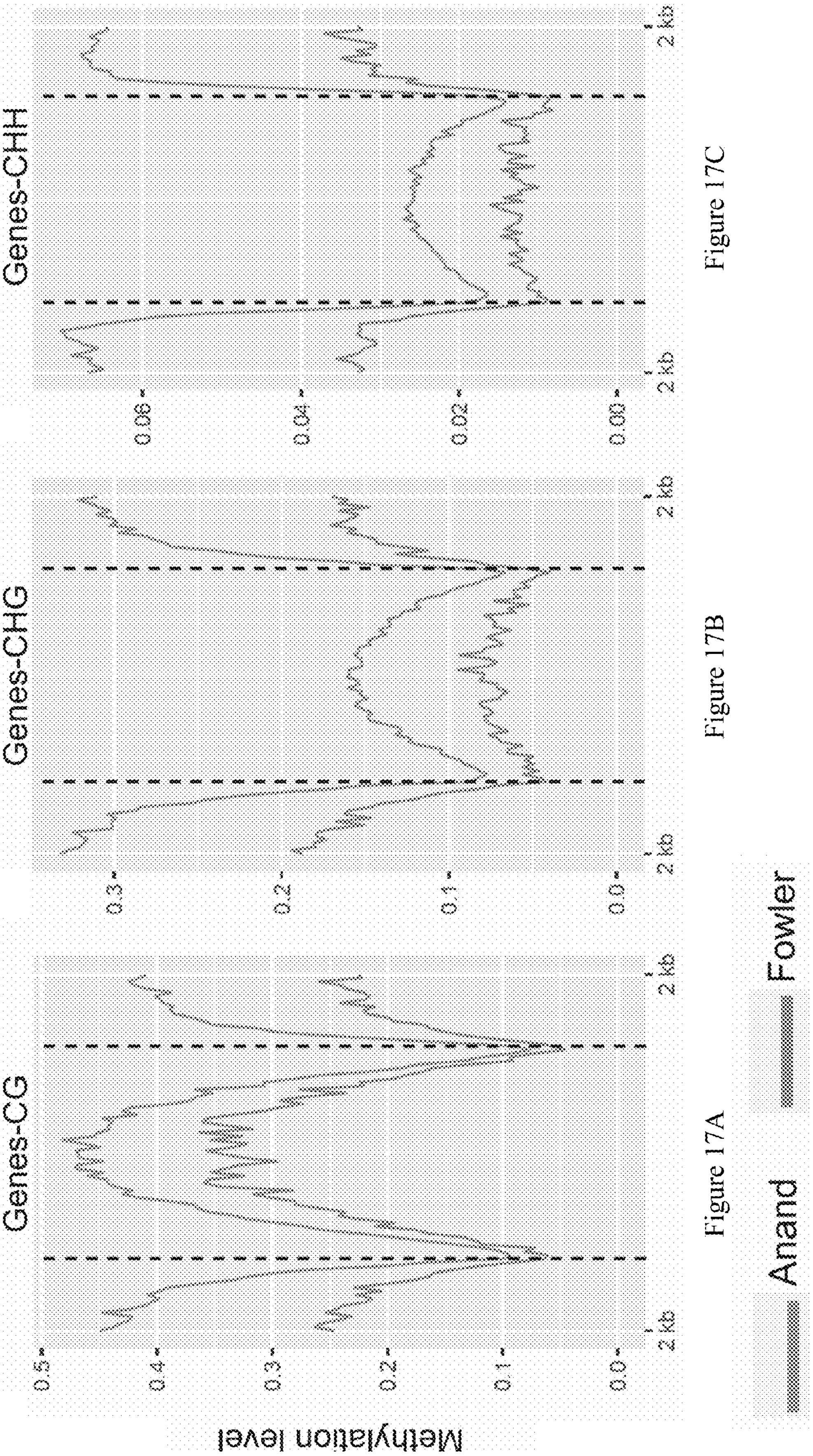
FIGS. 17A-17F: Comparison of global DNA methylation levels between the parental lines (Anand and fowler) over protein-coding genes (A to C) and TEs (D to F) in various sequence contexts under non-infected conditions.
Figures 17D, 17E, 17F:
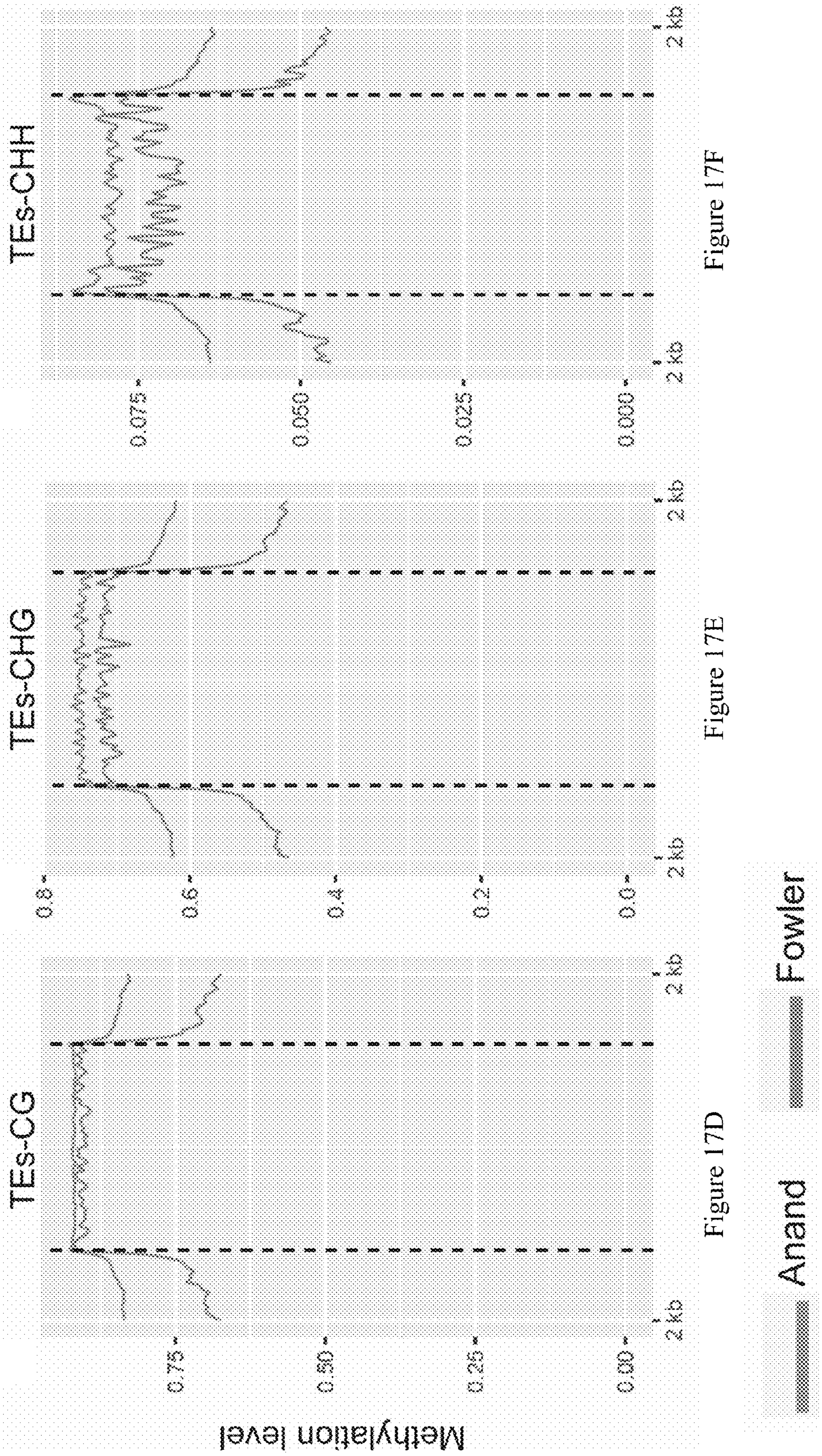

Example 7—Identification of Stably Inherited DMRs Potentially Associated with SCN Infection To identify stably inherited DMRs in the genic regions with potential association with SCN resistance/susceptibility differential methylation was searched in the isogenic lines that are inherited from the parents. In other words, DMRs with the exact genomic coordinates that are hypermethylated in the susceptible parent (Anand) and the susceptible line TN09-16 but hypomethylated in the resistant parent (Fowler) and the resistant line TN09-29, and vice versa (hypomethylated in Anand and TN09-16 but hypermethylated in Fowler and TN09-29) were pursued. Therefore, methylC-seq libraries were generated from the two parental lines Fowler and Anand using non-infected root tissues collected from the same experimental settings described above. Differentially methylated cytosines were identified and global methylation levels over genes and TEs in all sequence contexts were compared between the parental lines. Interestingly, the susceptible parent (Anand) showed higher methylation levels than the resistant parent (Fowler) over genes and TEs in all sequence contexts (FIG. 17). A significant number of DMRs between the parental lines were also detected. Of the 45,603 DMRs detected, 7,000 mapped to protein-coding genes and 21,667 mapped to TEs. Consistent with global methylation patterns, the majority (65.70%) of DMRs were hypermethylated in the susceptible parent (Anand) compared with the resistant parent (Fowler). These DNA methylation patterns are consistent with our results mentioned above and showing increased global methylation levels and hyper-DMRs in the susceptible line TN09-16 compared to the resistant line TN09-29.

Figure 7A:
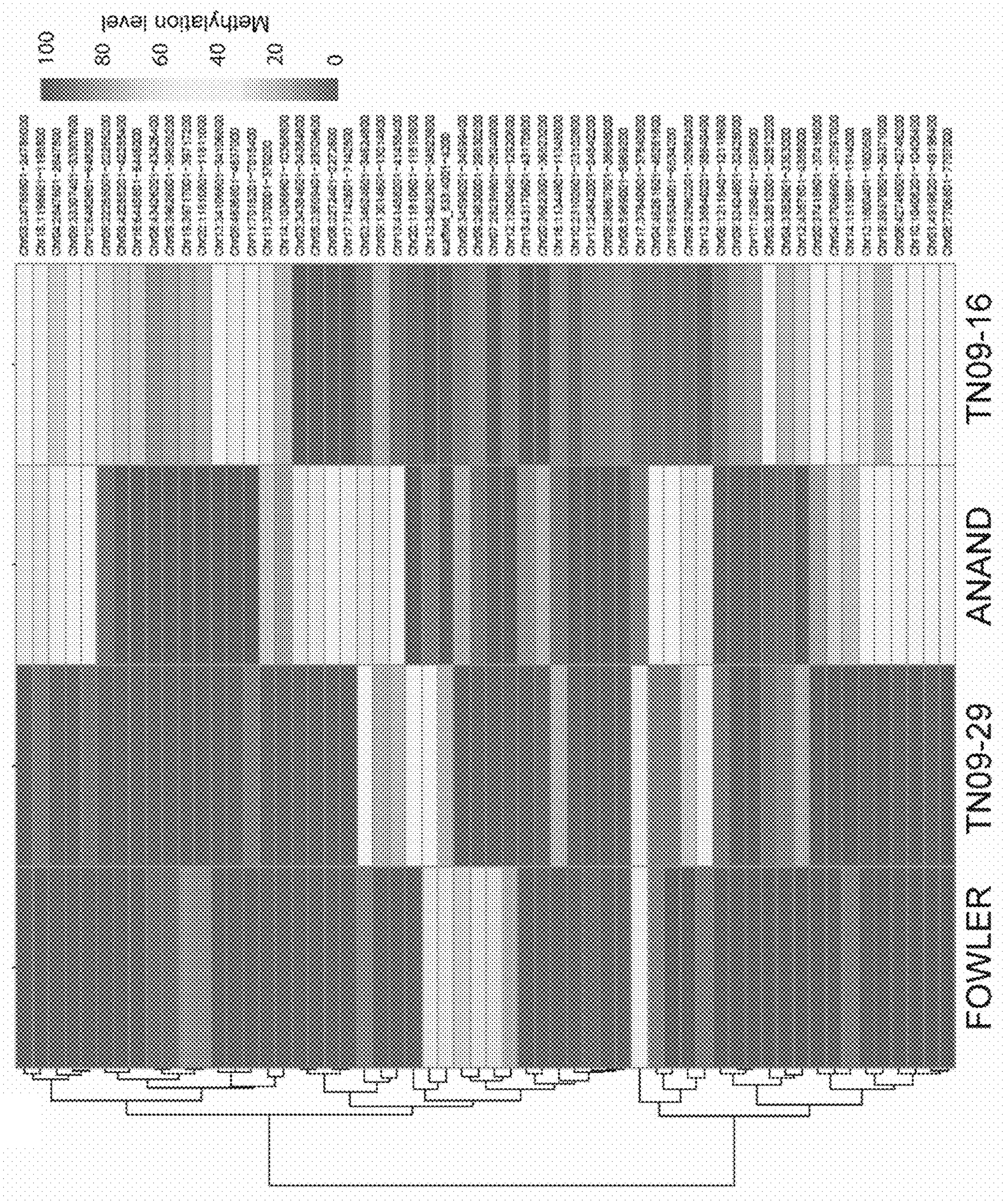
FIGS. 7A-7D: Characterization of differential methylation patterns identified in the isogenic lines that were stably inherited from the parents. A: Heat map of 58 DMRs showing the methylation patterns in TN09-29 and TN09-16 that were inherited from the parental lines Fowler and Anand, respectively. B: Example of DMRs showing hypermethylation patterns in the susceptible line TN09-16 that were inherited from the susceptible parent Anand. In contrast, the resistant line TN09-29 and the resistant parent Fowler showed hypomethylation in these regions. C and D: Proportions for methylation contexts (C) and the overlapping genic features of the 58 DMRs (D).
Figure 7B:
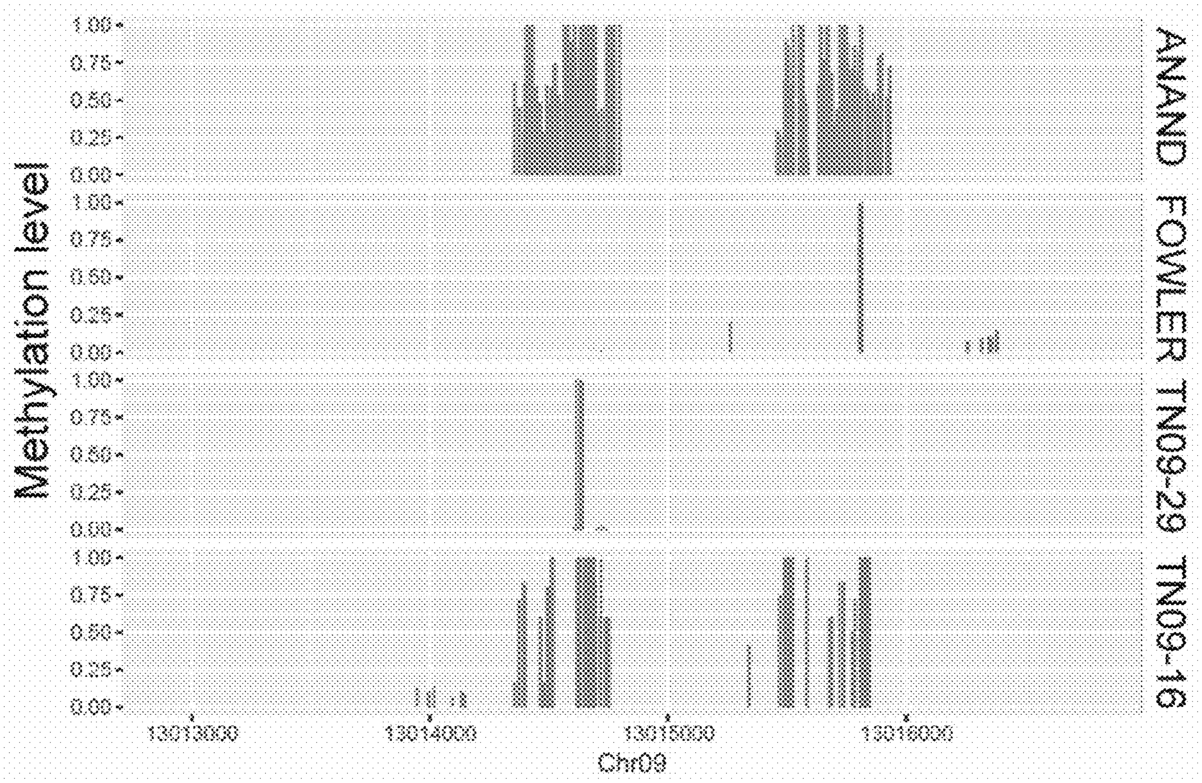
Figure 7C:
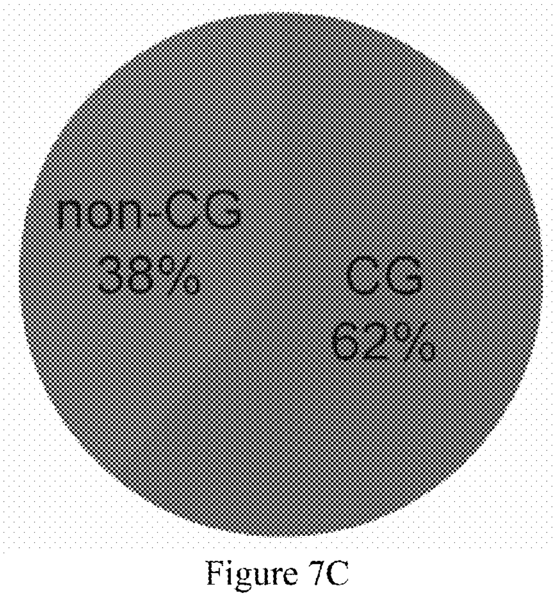
Figure 7D:
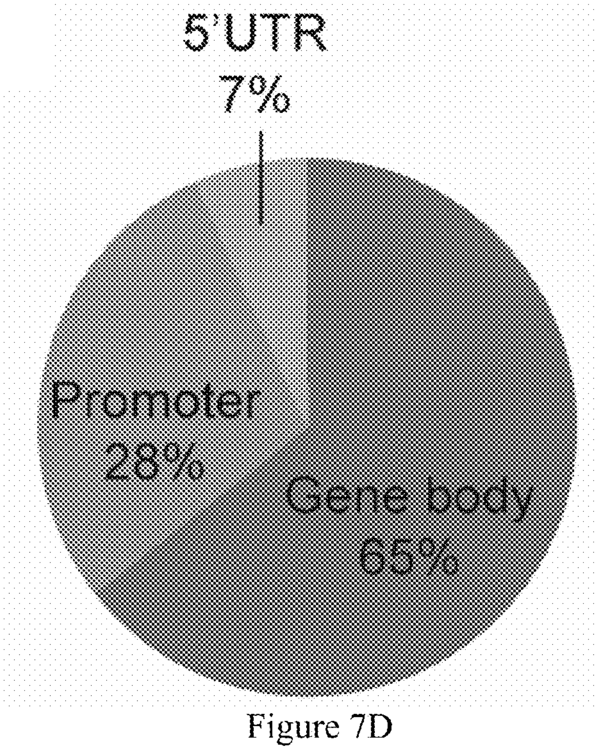

The methylomes of the parental lines and that of the isogenic lines were then compared. 59 DMRs in the isogenic lines were identified with differential methylation patterns that were inherited from the parents (FIG. 7A). As shown in FIG. 7A, the 58 DMRs are grouped into two main clusters. The first cluster contains 38 regions that were hypomethylated in Fowler and TN09-29 but hypermethylated in Anand and TN09-016. An example of these regions is highlighted in FIG. 7B. The second cluster contains 22 regions that were hypermethylated in Fowler and TN09-29 but hypomethylated in Anand and TN09-16 (FIG. 7A). These regions showed differential methylation in the CG (36) and non-CG contexts (22) and are located in the gene body (38), promoter (16) and 5'UTR (4) (FIGS. 7C and 7D). These 58 DMRs overlapped with 57 unique protein-coding genes, four of them were previously reported as differentially expressed in soybean syncytium (Table 2).

TABLE 2

57 protein-coding genes associated with DMRs in isogenic lines

| | | | |
|---|---|---|---|
| Glyma.10G083800 | Glyma.06G251700 | Glyma.11G004900 | Glyma.16G065300 |
| Glyma.01G154500 | Glyma.07G168900 | Glyma.11G092400 | Glyma.16G088900 |
| Glyma.03G085300 | Glyma.08G028400 | Glyma.11G181300 | Glyma.17G017300 |
| Glyma.03G129100 | Glyma.08G060200 | Glyma.12G060400 | Glyma.17g091700 |
| Glyma.03G131000 | Glyma.08G078200 | Glyma.12g081900 | Glyma.17G223100 |
| Glyma.04G036000 | Glyma.08G100300 | Glyma.12G121100 | Glyma.18G168000 |
| Glyma.04g041900 | Glyma.08G314100 | Glyma.13G005900 | Glyma.19G044300 |
| Glyma.04G157200 | Glyma.09G094000 | Glyma.13G228800 | Glyma.19G136000 |
| Glyma.04G191800 | Glyma.09G123300 | Glyma.13G234600 | Glyma.20G052100 |
| Glyma.05G092300 | Glyma.09G129600 | Glyma.13G288000 | Glyma.20g126100 |
| Glyma.05G093400 | Glyma.09G132300 | Glyma.13G320100 | Glyma.20g134300 |
| Glyma.05G132100 | Glyma.09G133900 | Glyma.13G339600 | Glyma.U040800 |
| Glyma.05G203000 | Glyma.09G171300 | Glyma.14g021300 | |
| Glyma.06G148300 | Glyma.09G198400 | Glyma.14G103300 | |
| Glyma.06G228100 | Glyma.10g104900 | Glyma.15G015100 | |

Figure 8A:
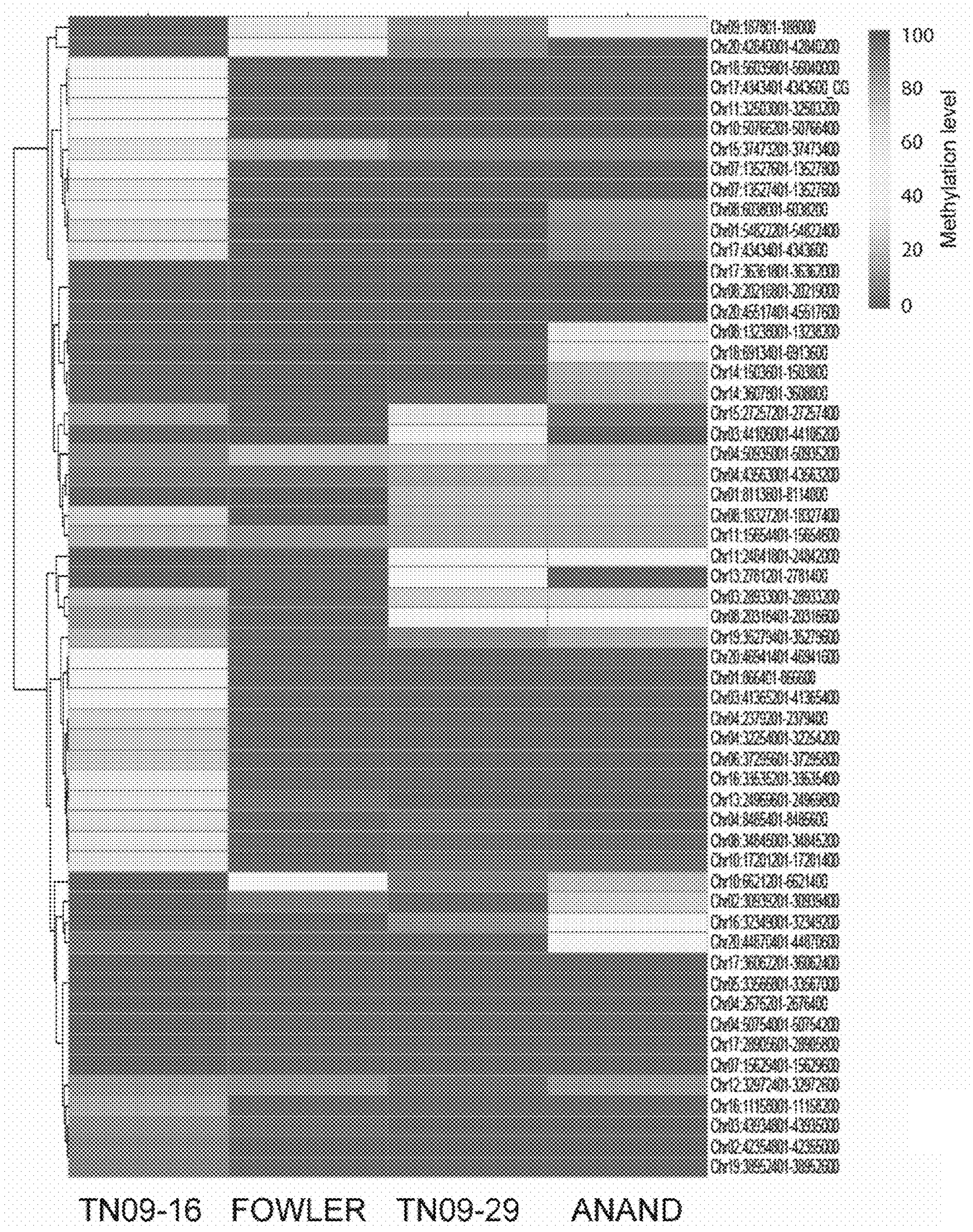
FIGS. 8A-8F: Identification of novel non-parental DMRs specific to the susceptible isogenic line. A: Heat map of 56 DMRs showing methylation patterns specific to TN09-16. B: Example of a DMR overlapping with a protein coding gene (Glyma.08g157400) and showing methylation patterns specific to TN09-16. The region was hypermethylated in TN09-16 but hypomethylated in TN09-29 and the parental lines Fowler and Anand. C and D: Proportions for methylation contexts (C) and overlapping genic features of the identified 56 DMGs (D). E: Identification of 13 significantly differentially used exons/junctions in the RNA-seq data of TN09-16 versus TN09-29 under non-infected conditions. The mean normalized coverage of each gene was plotted against fold change values and 13 significantly differentially used exons/junctions (red dots) were identified using q value less than 0.1. F: Exon/junction expression profile for the Glyma.17G149600 gene. The numbers of normalized sequencing read aligned to each exon or splice junction in TN09-16 (blue) and TN09-29 (red) were obtained from RNA-seq data under non-infected condition and were displayed as gene profile plot. A gene diagram showing the location of each exon (boxes) and the predicted junction sites (dashed lines) is included below the plot. One statistically significantly (q value=0.0072) used exon is highlighted in pink.
Figure 8B:
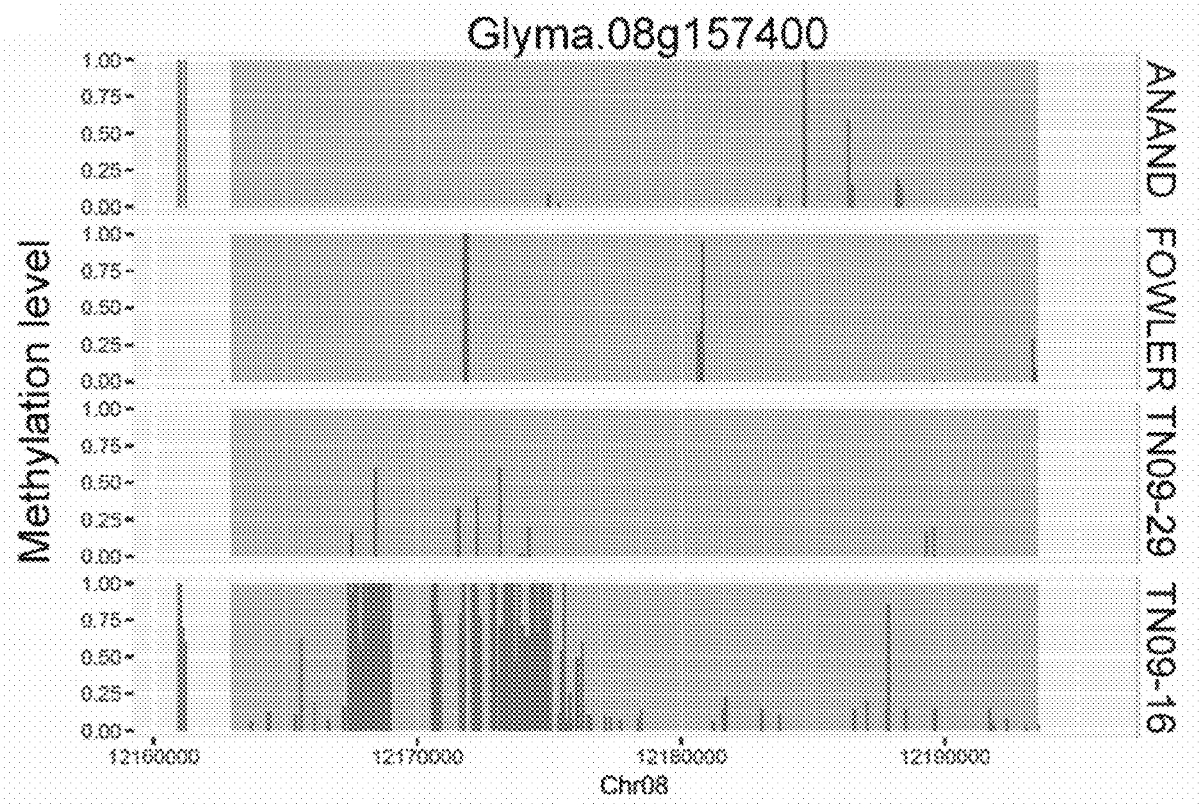
Figure 8C:
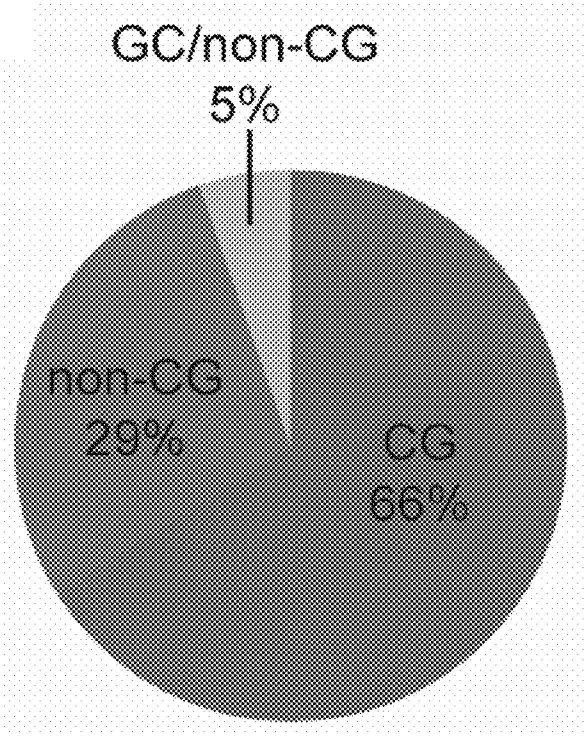
Figure 8D:
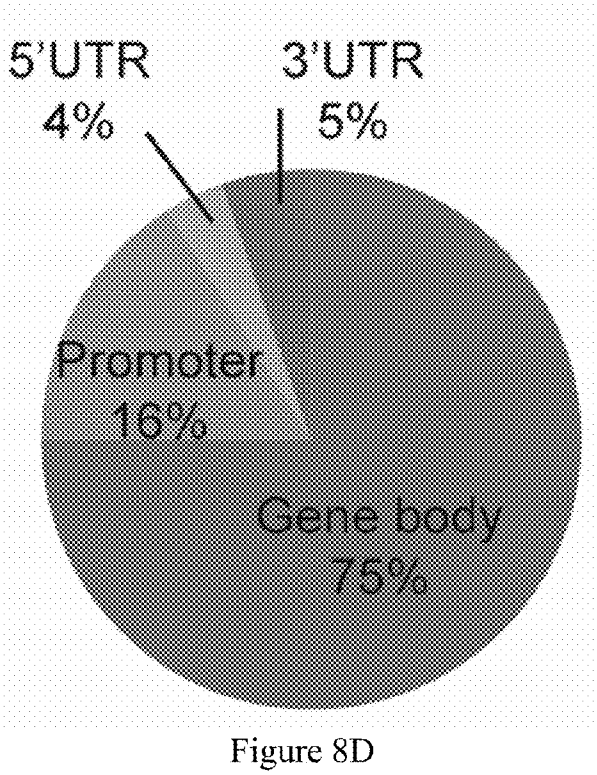
Figure 8E:
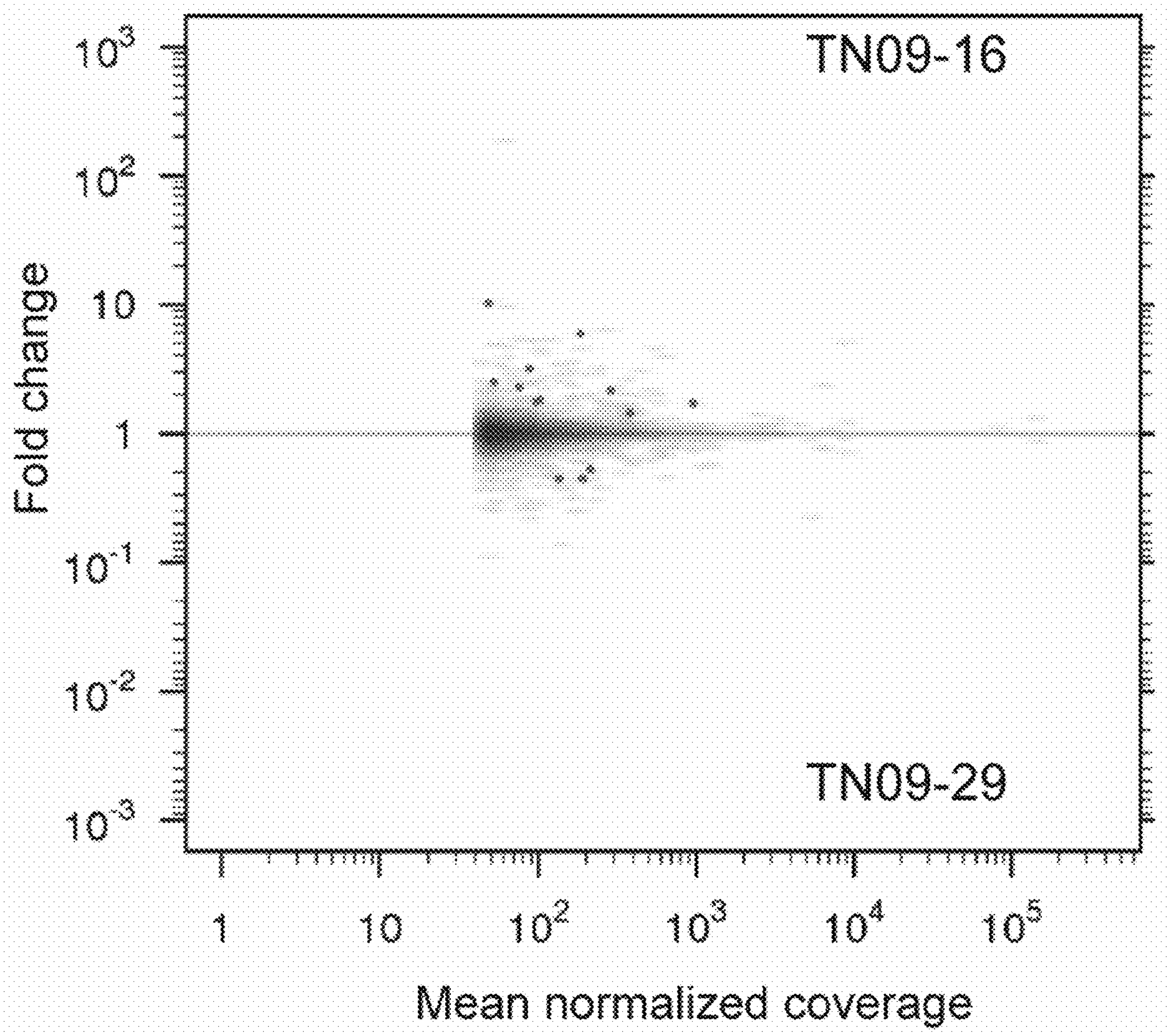
Figure 8F:
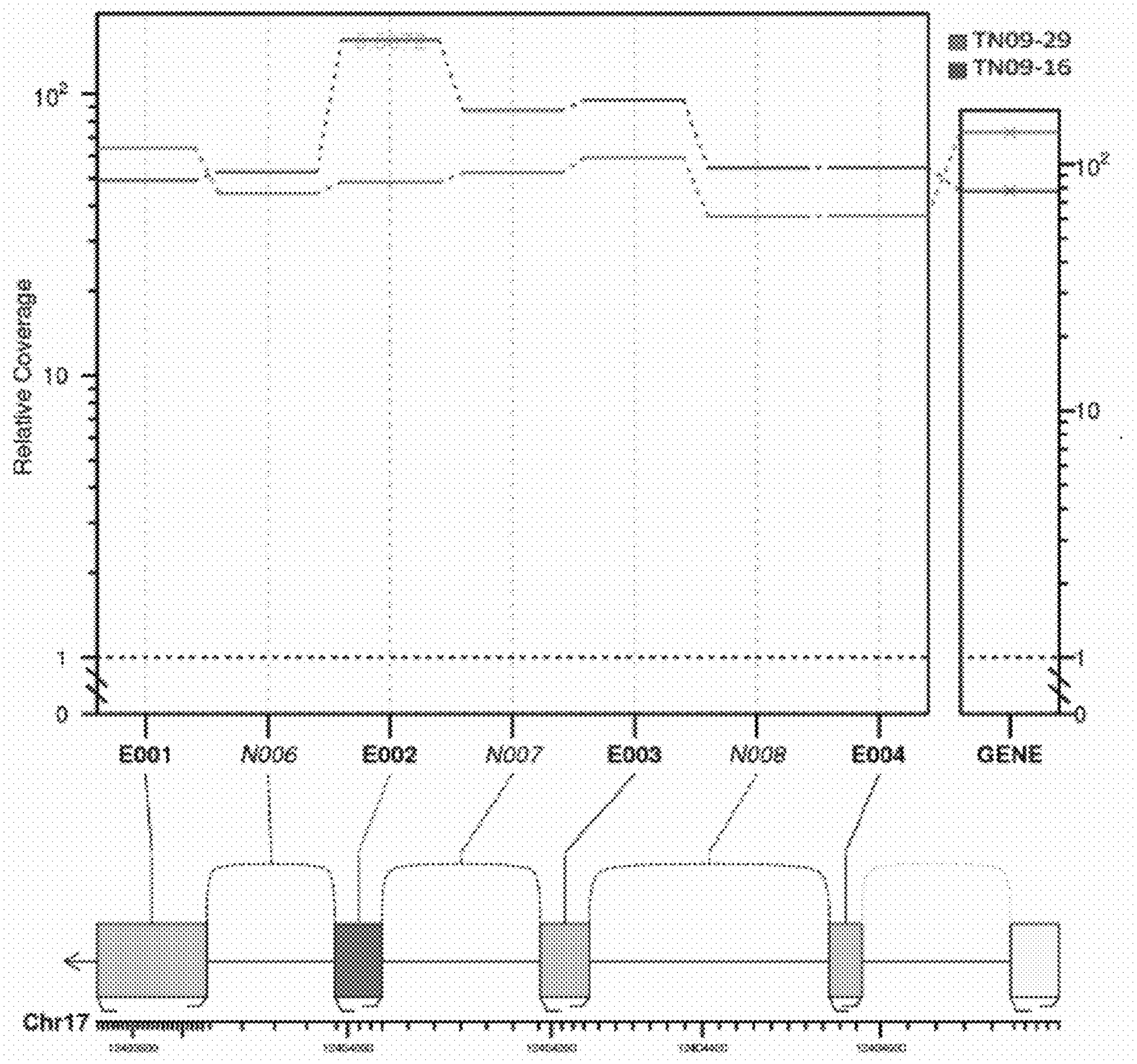

Example 8—Identification of Novel Non-Parental DMRs Specific to the Isogenic Lines These analyses were extended by comparing the methylomes of the parental lines and the isogenic lines under non-infected conditions to identify novel non-parental DMRs unique to TN09-16 or TN09-29. Interestingly, 56 DMRs unique to TN09-16 were identified. Gain or loss of DNA methylation in these regions occurred to a similar extent and was opposite of that detected in the parental lines and TN09-29 (FIG. 8A). An example of these regions is provided in FIG. 8B. The opposite methylation patterns were detected in CG (37), non-CG (16), and both CG and non-CG contexts (3) (FIG. 8C). The DMRs were located in gene body (42), gene promoters (9), and UTRs (5) (FIG. 8D). The 56 DMRs overlapped with 55 protein-coding genes (Table 3). This gene list included 9 of the previously identified syncytium DEGs, implying a role in the susceptible soybean-SCN interaction. A homolog of *Arabidopsis* mRNA splicing factor was also identified among this gene list. This finding prompted examination of RNA-seq data for differential usage of exon and exon-exon junctions using JunctionSeq package. Using a FDR cut-off of 0.1, 12 alternatively spliced genes with 13 differentially used exons/junctions were identified when the transcriptomes of TN09-16 and TN09-29 were compared under non-infected conditions (FIG. 8E). Of these exons/junctions 10 were significantly highly used in TN09-16 as in the case of Glyma17G149600 (FIG. 8F), whereas the remaining 3 were significantly highly used in TN09-29. Interestingly, 4 out of these 12 differentially spliced genes are among the syncytium DEGs, suggesting that novel non-parental hypomethylation of a splicing factor-encoding gene in TN09-16 may affect alternative splicing of syncytium DEGs. Because DNA methylation can impact splicing efficiency, these 12 genes were intersected with 3,666 genes showing differential DNA methylation between TN09-16 and TN09-29. None of these genes was common to both lists, indicating that alternative splicing of these genes occurred independently of their methylation patterns.

TABLE 3

| 55 protein-coding genes associated with DMRs unique to TN09-16 | | | |
|---|---|---|---|
| Glyma.10G067400 | Glyma.04G238800 | Glyma.11G164700 | Glyma.17G214800 |
| Glyma.01G008900 | Glyma.04G241200 | Glyma.11G181300 | Glyma.17G216000 |
| Glyma.01G060200 | Glyma.05G142200 | Glyma.11G229600 | Glyma.18G073400 |
| Glyma.01G218100 | Glyma.06G233300 | Glyma.12G173100 | Glyma.18G279400 |
| Glyma.02G181200 | Glyma.07G118800 | Glyma.13G010200 | Glyma.19g104100 |
| Glyma.02G236000 | Glyma.07G132300 | Glyma.13G137000 | Glyma.19G130000 |
| Glyma.03G100000 | Glyma.08G079300 | Glyma.14g021300 | Glyma.20g189700 |
| Glyma.03G205600 | Glyma.08G168000 | Glyma.14G047400 | Glyma.20G212100 |
| Glyma.03G240800 | Glyma.08G226000 | Glyma.15G204600 | Glyma.20G219600 |
| Glyma.03G243400 | Glyma.08G237500 | Glyma.15G219000 | Glyma.20G237500 |
| Glyma.04G029400 | Glyma.08G238200 | Glyma.16G088200 | |
| Glyma.04G033600 | Glyma.08G269900 | Glyma.16G164500 | |
| Glyma.04G095300 | Glyma.09G002300 | Glyma.16G174500 | |
| Glyma.04G149700 | Glyma.10G098700 | Glyma.17G057300 | |
| Glyma.04G174100 | Glyma.10G289000 | Glyma.17G193800 | |

Figure 9A:
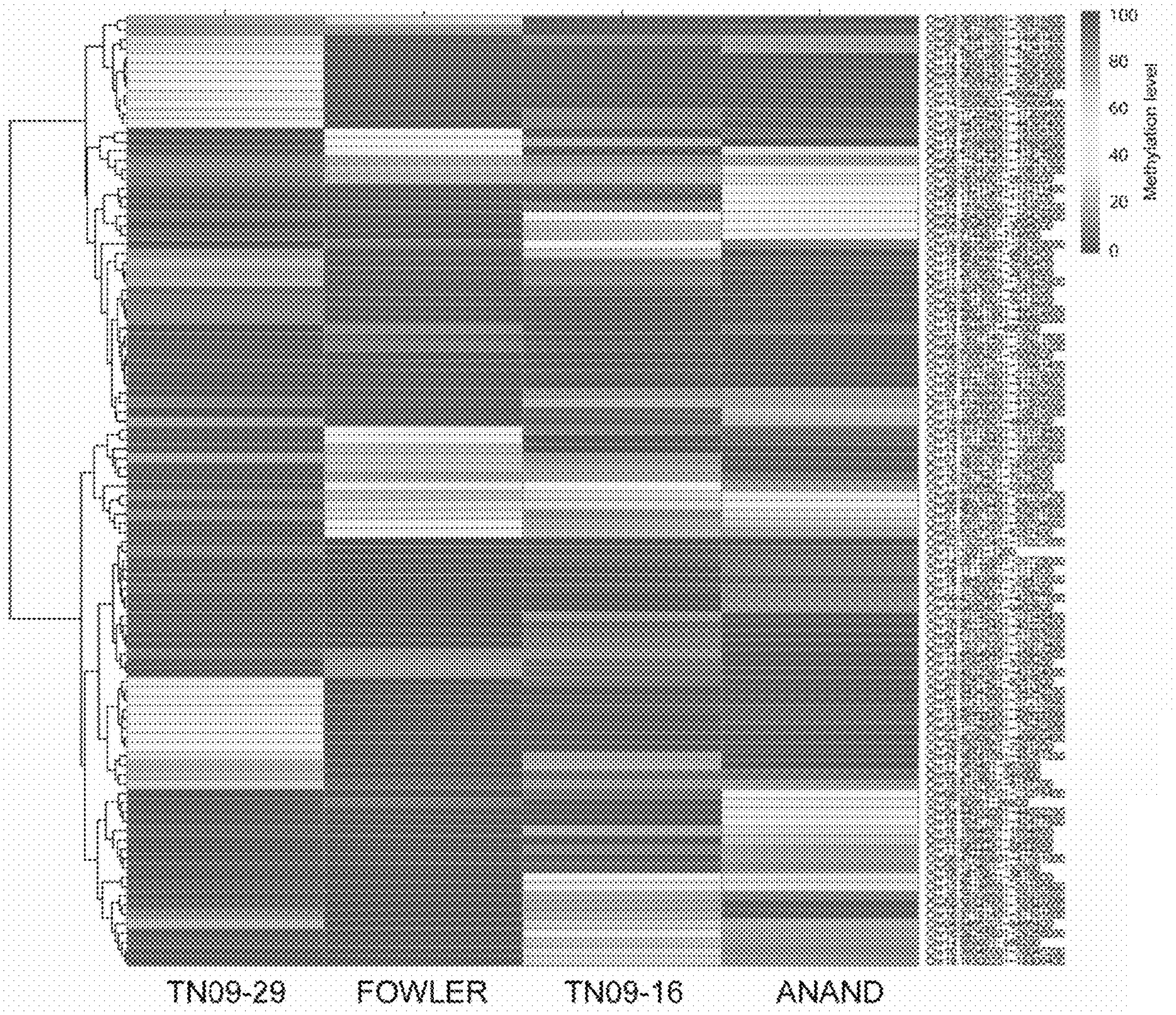
Figure 9B:
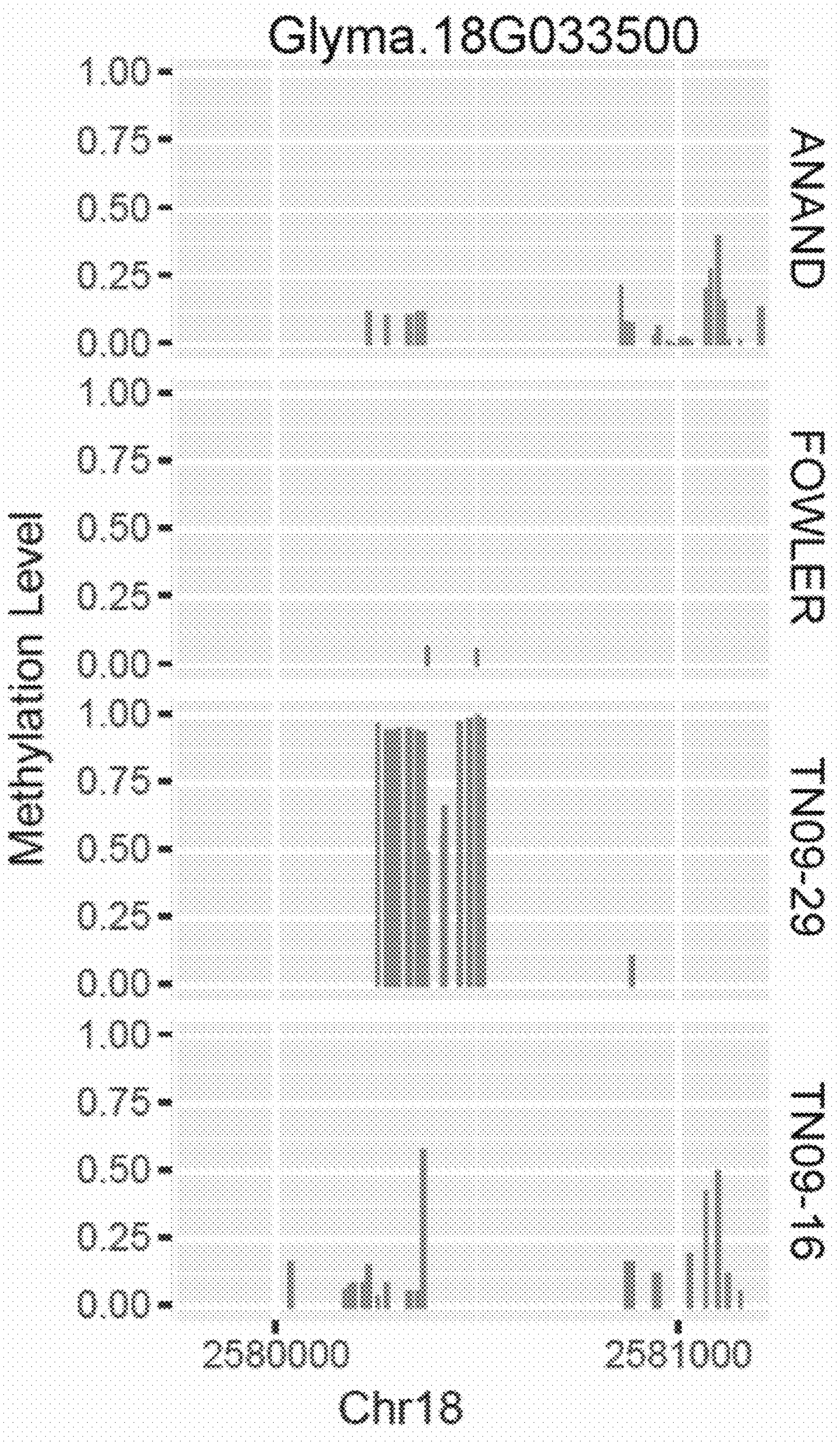

Similarly, the methylomes of the parental lines and the isogenic lines were compared under non-infected conditions to identify novel non-parental DMRs unique to TN09-29. Interestingly, 102 DMRs specific to TN09-29 were identified (FIG. 9A). Hyper- and hypomethylation in these 102 regions occurred to a similar extent and was opposite of that detected in the parental lines and TN09-16 (FIG. 9A). An example of hypermethylated region specific to TN09-29 is provided in FIG. 9B. Differential methylation of these DMRs was found in CG (58) and non-CG (44) (FIG. 9C). The opposite methylation patterns were detected in gene promoter/5'UTR (23) and gene body/3'UTR (79) (FIG. 9D). The 102 DMRs overlapped with 100 protein-coding genes (Table 4), 11 of them previously reported to change expression in SCN-induced syncytium (FIGS. 9E and 9F). Together, these data suggest that novel non-parental DMRs specific to the isogenic lines may impact gene expression in the nematode feeding sites.

TABLE 4

| 100 protein-coding genes associated with DMRs unique to TN09-29 | | | |
|---|---|---|---|
| Glyma.10G098700 | Glyma.05G035100 | Glyma.10G028800 | Glyma.14G193900 |
| Glyma.01G102900 | Glyma.05G084500 | Glyma.10G066100 | Glyma.15G125100 |
| Glyma.01G112600 | Glyma.05G092600 | Glyma.10G073100 | Glyma.15G136000 |
| Glyma.01G244700 | Glyma.05G098000 | Glyma.10G076500 | Glyma.16G135200 |
| Glyma.02g041600 | Glyma.05G100700 | Glyma.10g105800 | Glyma.16G214100 |
| Glyma.02g071300 | Glyma.05G185300 | Glyma.10g145700 | Glyma.17G008600 |
| Glyma.02G093000 | Glyma.06G092500 | Glyma.10g168000 | Glyma.17G012400 |
| Glyma.02G129200 | Glyma.06G180700 | Glyma.10g181600 | Glyma.17G032500 |
| Glyma.02G164300 | Glyma.06G196500 | Glyma.10g192400 | Glyma.17G038800 |
| Glyma.02G221300 | Glyma.06G231200 | Glyma.10G238200 | Glyma.17G049500 |
| Glyma.03G034500 | Glyma.06G286900 | Glyma.11g000100 | Glyma.17G135500 |
| Glyma.03G058300 | Glyma.07G000600 | Glyma.11G125600 | Glyma.17g205100 |
| Glyma.03G064800 | Glyma.07G156900 | Glyma.12G136700 | Glyma.18G033500 |
| Glyma.03G107700 | Glyma.07G166000 | Glyma.12G146400 | Glyma.18G066700 |
| Glyma.04G094900 | Glyma.07G188300 | Glyma.13G056100 | Glyma.18G077700 |
| Glyma.04G111200 | Glyma.07G243600 | Glyma.13G355400 | Glyma.18G131100 |
| Glyma.04G136700 | Glyma.08G014300 | Glyma.14g009100 | Glyma.18G168500 |
| Glyma.04G140800 | Glyma.08G167600 | Glyma.14g011600 | Glyma.18G179600 |
| Glyma.04G149400 | Glyma.08G190600 | Glyma.14G065500 | Glyma.18G220700 |
| Glyma.04G177000 | Glyma.08G238800 | Glyma.14G098600 | Glyma.19G018100 |
| Glyma.04G220100 | Glyma.08G258600 | Glyma.14G104300 | Glyma.19G023000 |
| Glyma.04G221900 | Glyma.09g001700 | Glyma.14G122700 | Glyma.19G036100 |
| Glyma.04G245700 | Glyma.09G159500 | Glyma.14G138300 | Glyma.19G153500 |
| Glyma.05G003500 | Glyma.09G190500 | Glyma.14G142500 | Glyma.19G164800 |
| Glyma.05G012700 | Glyma.09G198900 | Glyma.14G193600 | Glyma.20g071200 |

Figure 10A:
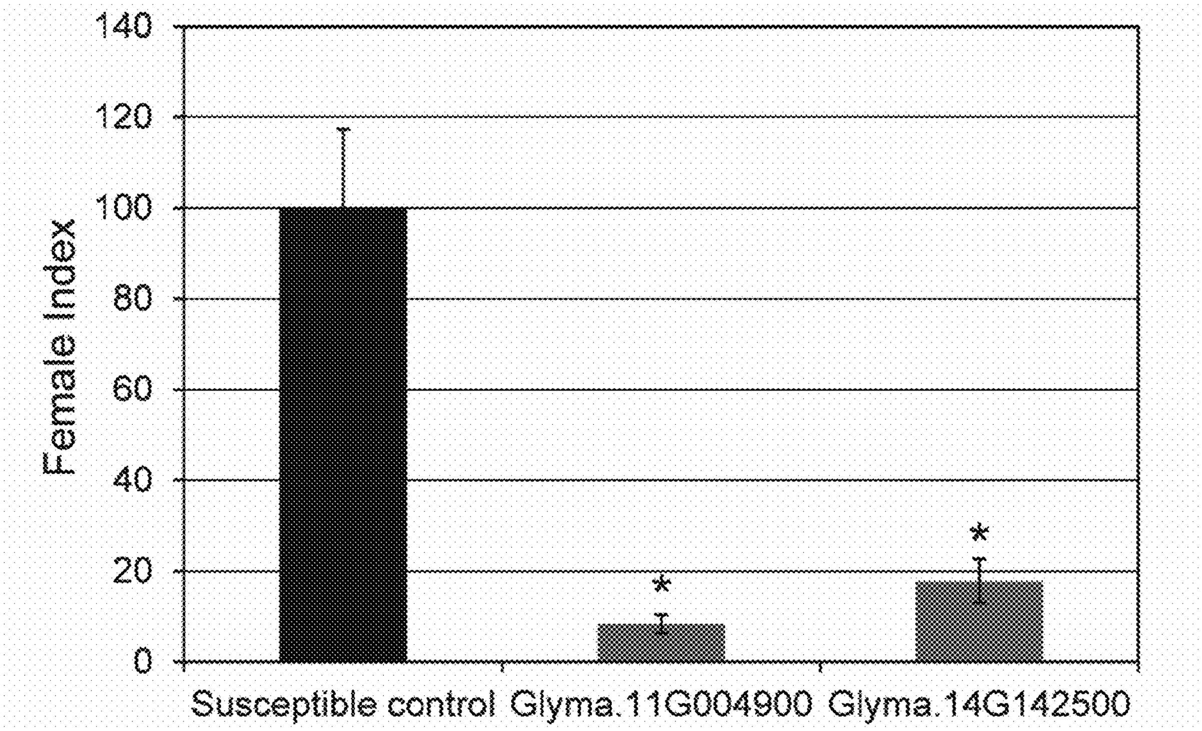
FIGS. 10A-10B: Identification of novel soybean cyst nematode resistance and susceptibility genes. A: Nematode susceptibility assays of transgenic soybean hairy root plants overexpressing two SCN resistant genes. The composite plants overexpressing a sulfite exporter TauE/SafE family protein (Glyma. 14G142500, according to SEQ ID NO: 2), a SNARE associated Golgi protein family (Glyma. 11G004900, according to SEQ ID NO: 1), or the empty vector (control) were generated in the susceptible isogenic line TN09-016 and inoculated with 3000 eggs of SCN (race 3). B: Nematode susceptibility assays of transgenic soybean hairy root plants overexpressing two SCN susceptibility genes. The composite plants overexpressing an aspartate aminotransferase 5 (Glyma.17G216000, according to SEQ ID NO: 3), a transcription regulator of the NOT2/NOT3/NOT5 family protein (Glyma.02G071300, according to SEQ ID NO: 4), or the empty vector were generated in the susceptible isogenic line TN09-016 and inoculated with 3000 eggs of SCN (race 3). The number of cysts per plant was counted 5 weeks after inoculation and used to calculate female index. Data are presented as mean value of 8 independent replicates±SE.
Figure 10B:
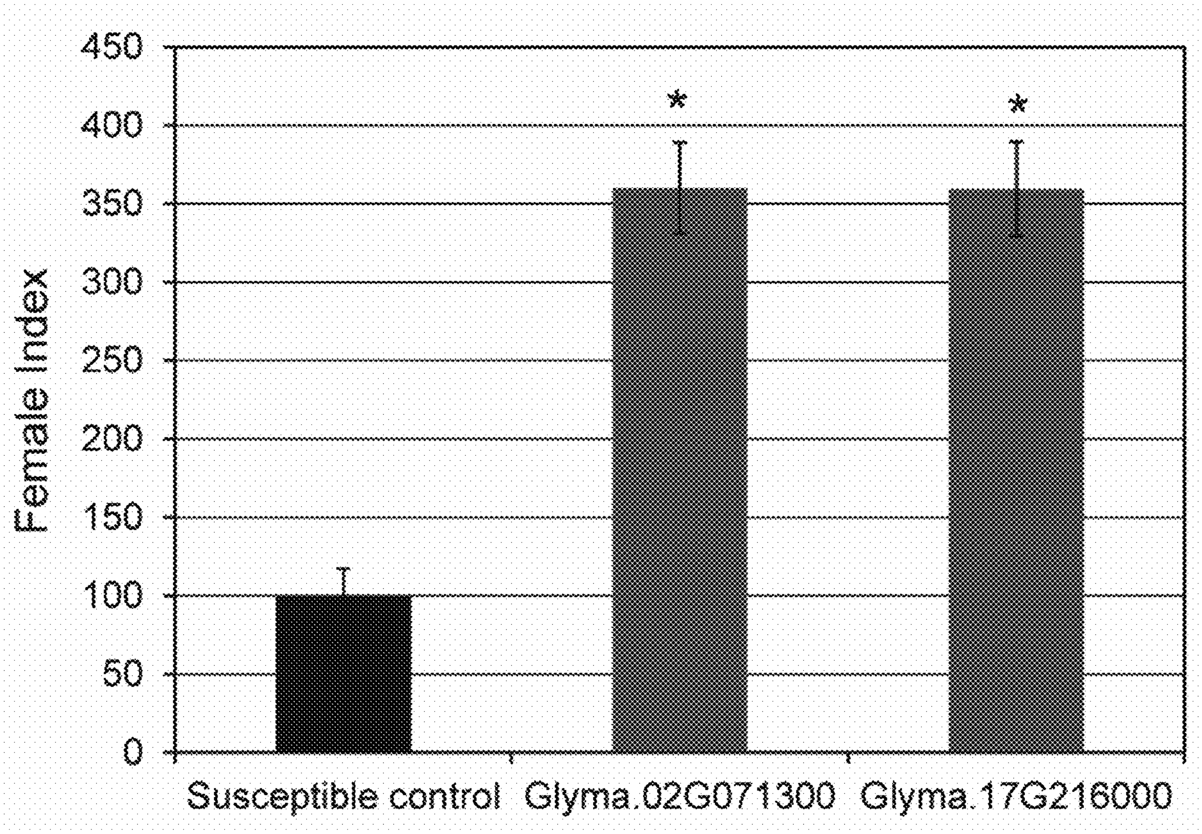

Example 9—Genes with Inherited or Introduced Differential Methylation are of Biological Significance It was examined whether the genes with inherited or introduced differential methylation are of biological significance and impact plant response to SCN. Four genes coding for a sulfite exporter TauE/SafE family protein (Glyma.14G142500), a SNARE associated Golgi protein family (Glyma.11G004900), an aspartate aminotransferase 5 (Glyma.17G216000), and a transcription regulator of the NOT2/NOT3/NOT5 family protein (Glyma.02G071300) were overexpressed in the susceptible isogenic line TN09-016 using soybean transgenic hairy root system. The composite transgenic plants were assayed for SCN (race 3) response. Interestingly, overexpression of SNARE associated Golgi protein family was able to complement the RHg4 susceptible allele coffering very high level of resistance with female index of 8% compared with the control (FIG. 10A). Overexpression of the aspartate aminotransferase also produced very high level of resistance resulting in a female index of less than 20% (FIG. 10A). Equally important, overexpression of the aspartate aminotransferase 5 and the NOT2/NOT3/NOT5 family transcription regulator dramatically increased plant susceptibility to SCN resulting in a female index of more than 350% (FIG. 10B). These results indicate that genes associated with stably inherited or introduced DNA methylation are bona fide candidate genes for enhancing plant resistance to SCN.

Example 10—Discovery of SCN Resistance Genes Based on Epigenetic Analysis

Figure 18:
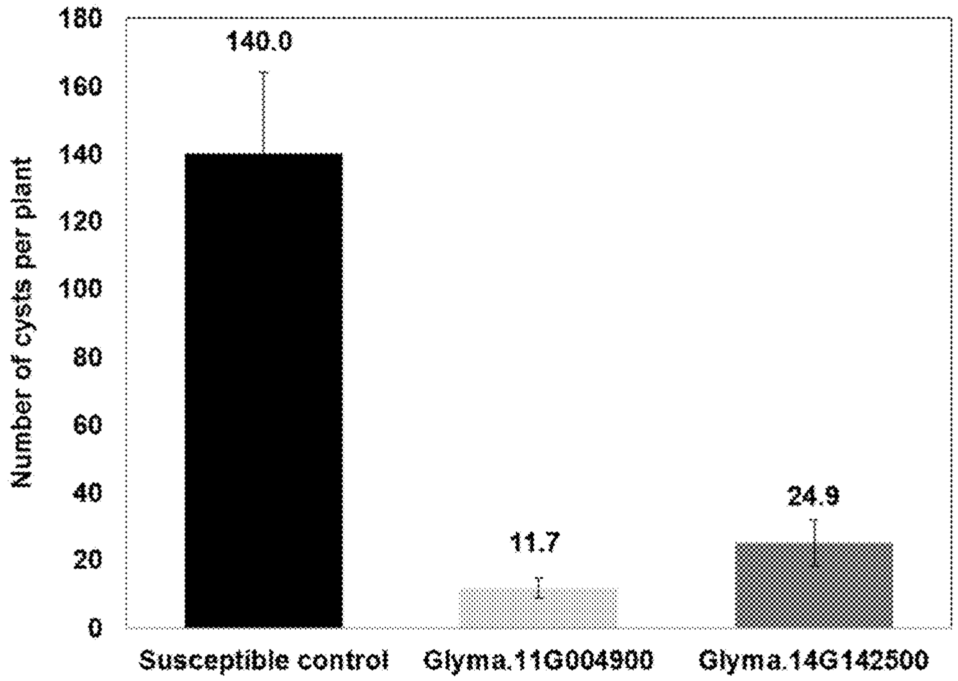
FIG. 18: Nematode susceptibility assays of transgenic soybean hairy root plants overexpressing two SCN resistance genes (Glyma.11G004900 and Glyma.14G142500). The composite plants overexpressing Glyma.11G004900, Glyma.14G142500, or the empty vector (control) were generated in a soybean susceptible line and inoculated with 3000 eggs of SCN (race 3). The numbers of cysts per plant were counted 5 weeks after inoculation. Data are presented as mean±SE of 8 independent replicates.

A novel epigenetic analysis—based approach was used to identify a SNARE associated Golgi protein family (Glyma.11G004900) and a sulfite exporter TauE/SafE family protein (Glyma.14G142500) as SCN resistance genes. The functional roles of these genes in SCN resistance were confirmed using transgenic soybean hairy root system. These genes were overexpressed in the susceptible isogenic line TN09-016 using transgenic hairy root system. The composite plants were assayed for SCN (race 3) response. Overexpression of the coding sequences of SNARE associated Golgi protein family was able to complement the Rhg4 susceptible allele coffering very high level of resistance with an average of cyst of 11.7 compared with 140.0 found in the susceptible control (FIG. 18). Similarly, overexpression of the coding sequences of the sulfite exporter TauE/SafE family protein produced very high level of resistance of about 80% (FIG. 18).

Example 11—Discovery of SCN Resistance miRNA Gene Based on Epigenetic Analysis

Figure 19:
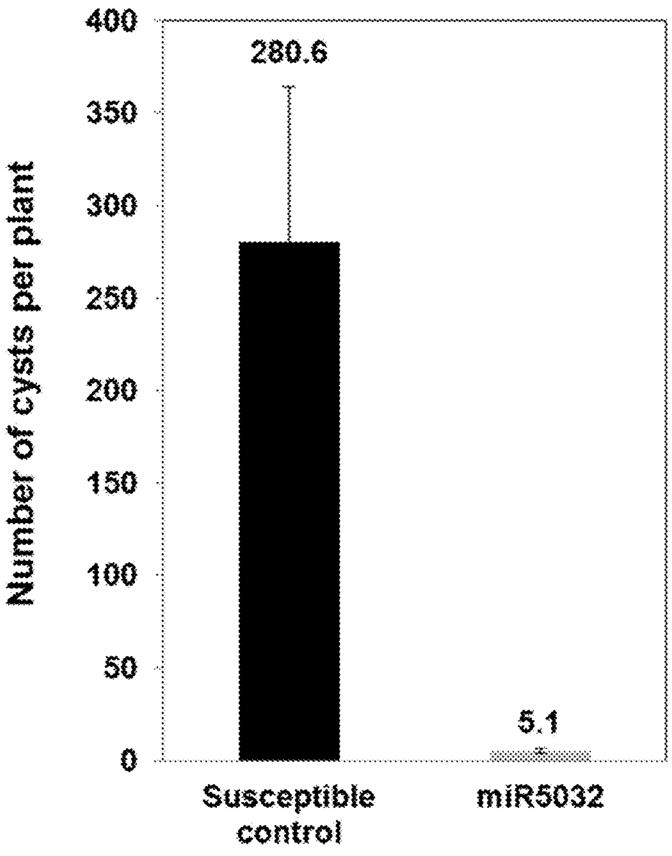
FIG. 19: Nematode susceptibility assays of transgenic soybean hairy root plants overexpressing gma-miR5032. The composite plants overexpressing gma-miR5032 or the empty vector (control) were generated in a soybean susceptible line and inoculated with 3000 eggs of SCN (race 3). The numbers of cysts per plant were counted 5 weeks after inoculation. Data are presented as mean values of 10 independent replicates±SE.

A novel epigenetic analysis—based approach was used to identify miRNA5032 as an SCN resistance gene. The functional roles of miRNA5032 in SCN resistance were confirmed using transgenic soybean hairy root system. miRNA5032 was overexpressed in the susceptible isogenic line TN09-016 using transgenic hairy root system. The composite plants were assayed for SCN (race 3) response. Overexpression of the primary transcript of the gma-miR5032 produced extreme resistance against SCN race 3 compared with the susceptible control. An average of 5.1 cysts per plant was counted on the plants containing overexpression of miRNA5032 compared to 280.6 cysts per plant recorded in the susceptible control (FIG. 19).

Thus, certain embodiments of the disclosure provide the gene encoding miR5032 provides SCN resistance to a plant cell or a plant, particularly, a soybean plant cell or a soybean plant. For example, overexpressing in a plant cell or a plant, particularly, a soybean plant cell or a soybean plant, a gene encoding an miRNA having the sequence of SEQ ID NO: 210 or homologs thereof renders the plant cell or the plant, particularly, the soybean plant cell or the soybean plant, resistance to SCN. An example of a gene encoding an miRNA having the sequence of SEQ ID NO: 210 is provided by the gene comprising the sequence of SEQ ID NO: 213.

Example 12—Identification of Genetic Polymorphisms in the Three Major SCN Resistance Genes Associated with Soybean Resistance Against Five SCN Races Ninety nine completely sequenced soybean accessions were phenotyped against five races of SCN (race 1, 2, 3, 5, and 14). The DNA sequences of the promoter regions of these three SCN resistance genes in addition to the coding sequences of the Glyma.11G004900 and Glyma.14G142500 were retrieved from these 99 soybean accessions and analyzed for potential genetic differences and polymorphisms linked with resistance against five SCN races. Genetic polymorphisms in the promoter and/or coding sequences of these three genes were identified. Statistical analysis revealed significant association between the identified genetic polymorphisms and soybean resistance against one or more races.

Figure 20A:
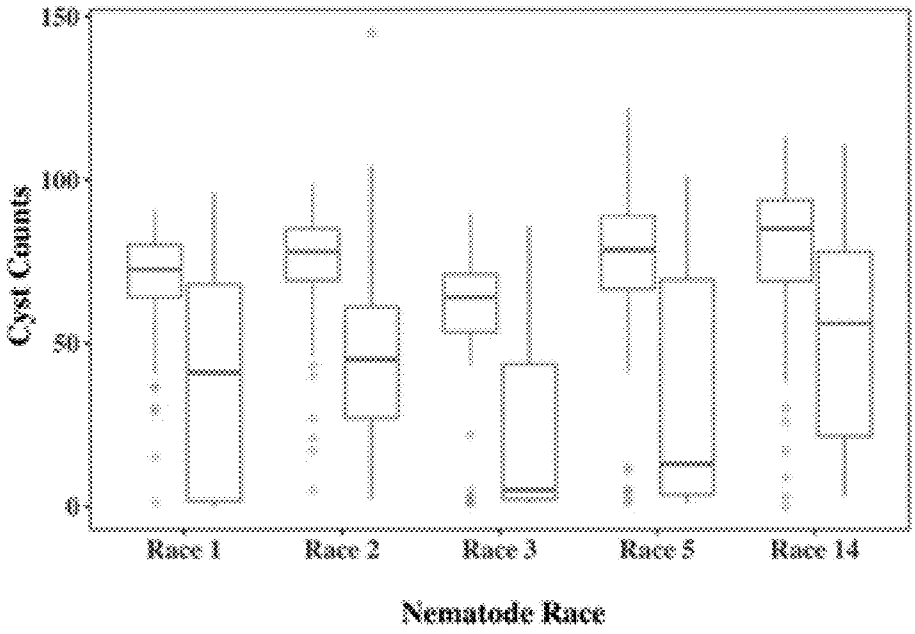
FIGS. 20A-20B: Examples of genetic polymorphisms in the SCN resistance Glyma.11G004900 associated with soybean resistance against five SCN races. A: C/T polymorphism in promoter region at the position −1020 is associated with resistance against race 1, 2, 3, 5, and 14. For each race, the bar on the left corresponds to genotype having C at the position −1020 and the bar on the right corresponds to the genotype having T at the position −1020. B: CAACAT/C polymorphism in the promoter region at positions 1718/23 is associated with resistance against race 1, 2, 3, 5, and 14. For each race, the bar on the left corresponds to genotype having C at the position 1718/23 and the bar on the right corresponds to the genotype having the sequence "CAACAT" at that position.
Figure 20B:
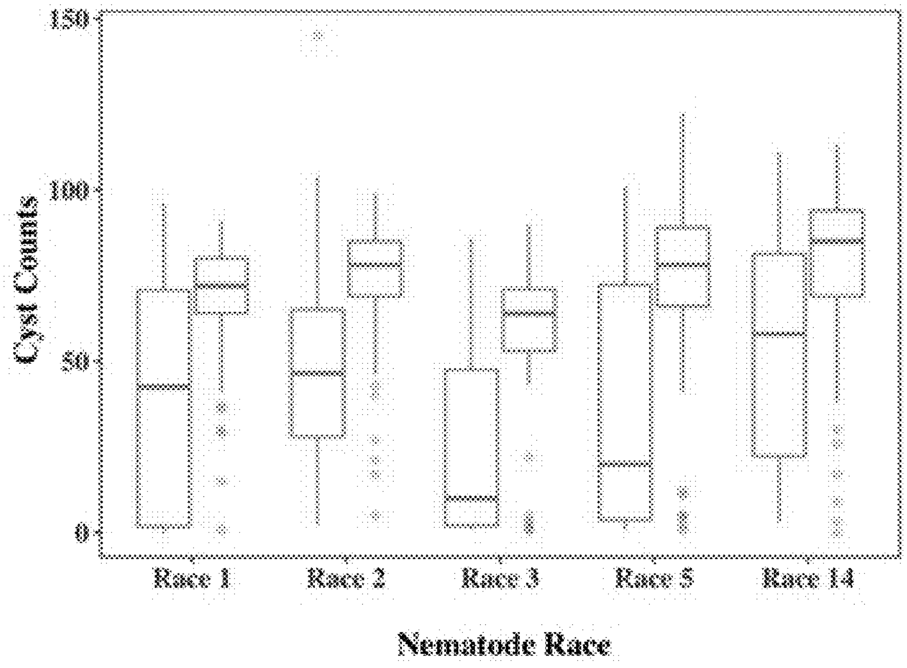

For Glyma.11G004900, fourteen single nucleotide polymorphism (SNPs) were identified to be associated with SCN resistance; one in the gene body (K/P), and 13 in the promoter region (Table 5). All of these fourteen SNPs were found to be statistically significantly associated with resistance against all the five SCN races (race 1, 2, 3, 5, and 14) (Table 5). As shown in FIGS. 20A and 20B, the C/T and CAACAT/C changes in the promoter of this gene at positions 1020 and 1718/23 upstream of the translation start codon ATG were associated with resistance against all the five SCN races tested.

TABLE 5

Genomic locations and P values of the genetic polymorphisms identified in the SCN resistance gene Glyma.11G004900.

| Genomic location | Polymorphism | P value | | | | |
|---|---|---|---|---|---|---|
| relative to ATG | Susceptibility/ Resistance | SCN Race 1 | SCN Race 2 | SCN Race 3 | SCN Race 5 | SCN Race 14 |
| Gene body, 355 | K/R | 0.00012 | 2.911E−07 | 3.552E−06 | 2.662E−06 | 0.00000 |
| Promoter, −209 | G/T | 0.00022 | 3.069E−06 | 2.368E−06 | 5.232E−06 | 0.00002 |
| Promoter, −384 | A/T | 0.00022 | 0.00039 | 0.000018 | 0.00007 | 0.00024 |
| Promoter, −460 | A/G | 0.00022 | 0.00001 | 2.499E−06 | 0.00002 | 0.00003 |
| Promoter, −823 | T/A | 0.00022 | 0.00165 | 0.00003 | 0.00171 | 0.00059 |
| Promoter, −828/29 | TA/T | 0.00022 | 0.00000 | 0.00000 | 0.00002 | 0.00004 |
| Promoter, −866 | C/A | 0.00043 | 0.00150 | 0.00001 | 0.00024 | 0.00035 |
| Promoter, −1011 | G/GTT | 0.00061 | 0.00022 | 0.00002 | 0.00030 | 0.00023 |
| Promoter, −1020 | C/T | 0.00006 | 0.00036 | 1.339E−06 | 0.00005 | 0.00020 |
| Promoter, −1155 | C/A | 0.00044 | 0.00061 | 4.592E−06 | 0.00012 | 0.00038 |
| Promoter, −1434 | T/C | 0.00031 | 0.00033 | 2.303E−06 | 0.00006 | 0.00022 |
| Promoter, −1718/23 | CAACAT/C | 0.00030 | 0.00039 | 2.757E−06 | 0.00008 | 0.00035 |
| Promoter, −1910 | T/C | 0.00203 | 0.00021 | 0.000014 | 0.00081 | 0.00029 |
| Promoter, −1969 | C/T | 0.00031 | 0.00033 | 2.303E−06 | 0.00006 | 0.00022 |

Figure 21A:
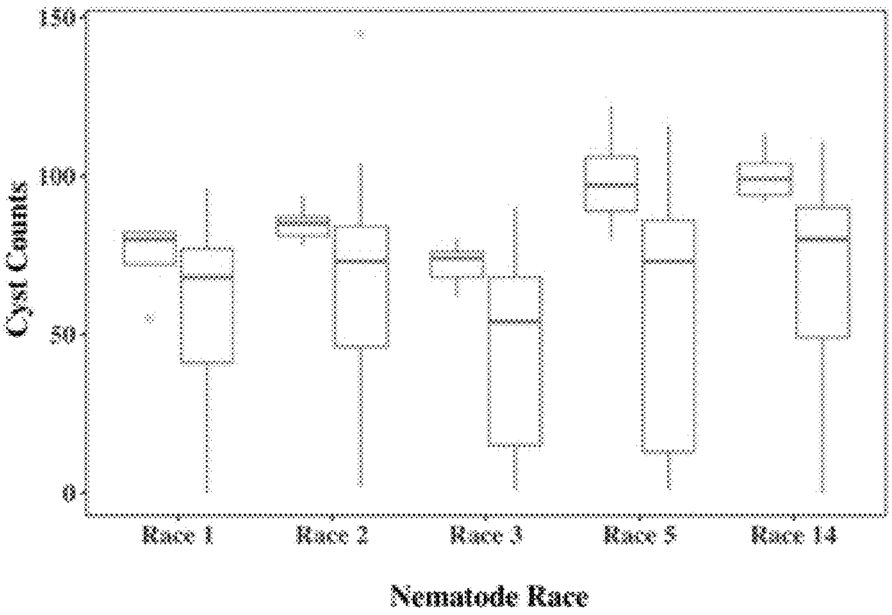
FIGS. 21A-21B: Examples of genetic polymorphisms in the SCN resistance Glyma.14G142500 associated with soybean resistance against three SCN races. A: A/AT polymorphism in promoter region at the position −482 is associated with resistance against races 3, 5, and 14. For each race, the bar on the left corresponds to genotype having A at the position −482 and the bar on the right corresponds to the genotype having AT that position. B: G/A polymorphism in the promoter region at the position −1101 is associated with resistance against race 3, 5, and 14. For each race, the bar on the left corresponds to genotype having A at the position −1101 and the bar on the right corresponds to the genotype having G at the position −1101.
Figure 21B:
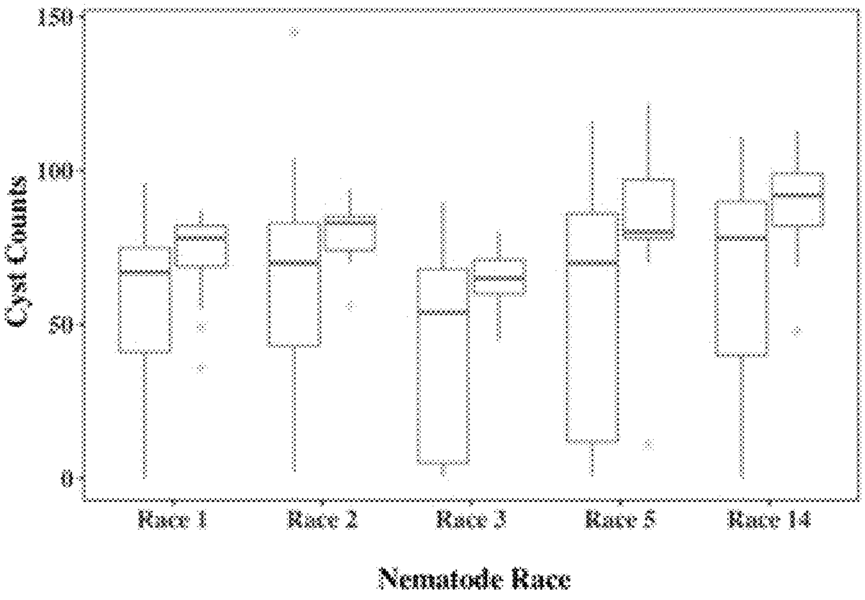

Similarly, for Glyma.14G142500, ten SNPs were identified in the promoter region (Table 6). Six of these ten SNPs were found to be statistically significantly associated with resistance against SCN race 3, 5, and 14 (Table 6). These SNPs are located at positions 166, 383, 387, 482, 1101, and 1103 upstream of the ATG. FIGS. 21A and 21B show that A/AT and G/A polymorphisms in the promoter of this gene at positions 482 and 1101, respectively were associated with resistance against SCN race 3, 5, and 14.

TABLE 6

Genomic locations and P values of the genetic polymorphisms identified in the SCN resistance gene Glyma.14G142500.

| Genomic location | Polymorphism | P value | | | | |
|---|---|---|---|---|---|---|
| relative to ATG | Susceptibility/ Resistance | SCN Race 1 | SCN Race 2 | SCN Race 3 | SCN Race 5 | SCN Race 14 |
| Promoter, −1587 | T/G | 0.14590 | 0.13690 | 0.64240 | 0.66710 | 0.29470 |
| Promoter, −1578 | G/A | 0.26320 | 0.17040 | 0.08625 | 0.10850 | 0.06291 |
| Promoter, −1103 | C/T | 0.16770 | 0.12800 | 0.01725* | 0.02008* | 0.01309* |
| Promoter, −1101 | G/A | 0.16770 | 0.12800 | 0.01725* | 0.02008* | 0.01309* |
| Promoter, −1092 | A/G | 0.14590 | 0.13690 | 0.64240 | 0.66710 | 0.29470 |
| Promoter, −556 | G/GT | 0.10790 | 0.27220 | 0.64240 | 0.66710 | 0.29470 |
| Promoter, −482 | A/AT | 0.39120 | 0.14810 | 0.01642* | 0.00493* | 0.00204* |
| Promoter, −387 | A/AT | 0.39120 | 0.14810 | 0.01642* | 0.00493* | 0.00204* |
| Promoter, −383 | A/T | 0.39120 | 0.14810 | 0.01642* | 0.00493* | 0.00204* |
| Promoter, −166 | C/A | 0.39120 | 0.14810 | 0.01642* | 0.00493* | 0.00204* |

*indicates statistically significant increase in SCN resistance.

Figure 22A:
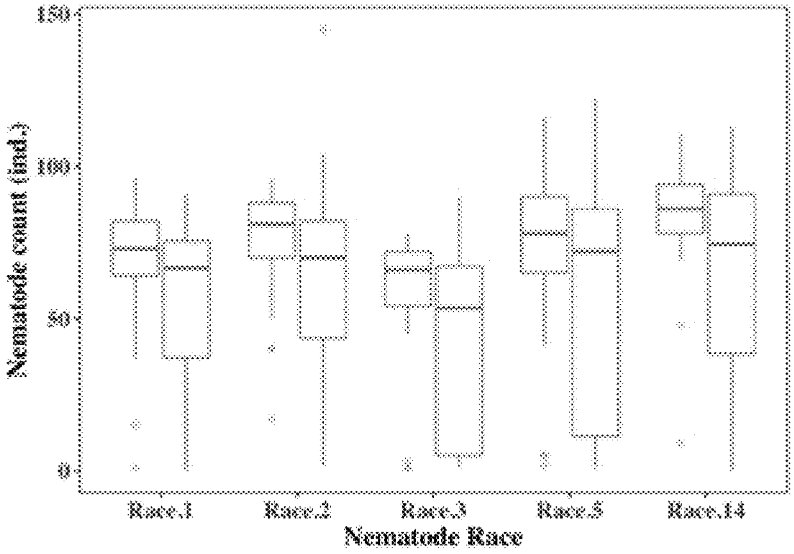
FIGS. 22A-22B: Examples of genetic polymorphisms in the gma-miR5032 associated with soybean resistance against four SCN races. A: C/T polymorphism in promoter region at the position −905 is associated with resistance against race 2. For each race, the bar on the left corresponds to the genotype having C at the position −905 and the bar on the right corresponds to the genotype having T at the position −905. B: T/G polymorphism in the promoter region at position 2051 is associated with resistance against race 1, 2, 3, and 5. For each race, the bar on the left corresponds to genotype having G at the position −2051 and the bar on the right corresponds to the genotype having T at the position −2051.
Figure 22B:
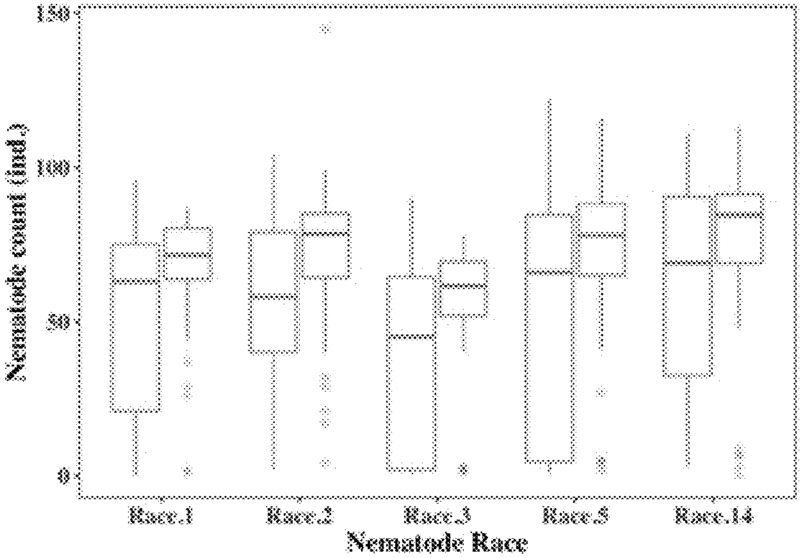

For gma-miR5032, seven SNPs were identified in the promoter region (Table 7). Only three SNPs were statistically linked to SCN resistance. The C/T and A/C changes in the promoter of this microRNA gene at positions 905 and 1259 upstream of the transcription start site (TSS) were associated with resistance against race 2 (FIG. 22A). Importantly, the T/G change in the promoter of this gene at position 2051 upstream of the transcription start site was associated with resistance against SCN races 1, 2, 3 and 5 (FIG. 22B).

TABLE 7

Genomic locations and P values of the genetic polymorphisms identified in the gma-miR5032.

| Genomic location relative to TSS | Polymorphism Susceptibility/ Resistance | P value SCN Race 1 | SCN Race 2 | SCN Race 3 | SCN Race 5 | SCN Race 14 |
|---|---|---|---|---|---|---|
| Promoter, −127 | C/G | 0.55600 | 0.54630 | 0.15510 | 0.97860 | 0.24670 |
| Promoter, −309 | Insert/A | 0.27480 | 0.18970 | 0.11880 | 0.40080 | 0.93000 |
| Promoter, −905 | C/T | 0.08572 | 0.02218 | 0.12120 | 0.13340 | 0.06569 |
| Promoter, −1259 | A/C | 0.08062 | 0.02061 | 0.17240 | 0.08697 | 0.06886 |
| Promoter, −1503 | G/A | 0.13470 | 0.05441 | 0.48540 | 0.34600 | 0.27790 |
| Promoter, −1526/27 | CA/C | 0.44120 | 0.13120 | 0.38180 | 0.52580 | 0.48150 |
| Promoter, −2051 | T/G | 0.03660 | 0.00455 | 0.01562 | 0.01090 | 0.08924 |

TABLE 8

The list of polymorphisms from Tables 5-7 that are associated with susceptibility/resistance against an SCN infection.

| Genomic location relative to start site for transcription | Polymorphism Susceptibility/Resistance |
|---|---|
| Glyma.11G004900 (SEQ ID NO: 211) | |
| Gene body, 355 | K/R |
| Promoter, −209 | G/T |
| Promoter, −384 | A/T |
| Promoter, −460 | A/G |
| Promoter, −823 | T/A |
| Promoter, −828/29 | TA/T |
| Promoter, −866 | C/A |
| Promoter, −1011 | G/GTT |
| Promoter, −1020 | C/T |
| Promoter, −1155 | C/A |
| Promoter, −1434 | T/C |
| Promoter, −1718/23 | CAACAT/C |
| Promoter, −1910 | T/C |
| Promoter, −1969 | C/T |
| Glyma.14G142500 (SEQ ID NO: 212) | |
| Promoter, −1103 | C/T |
| Promoter, −1101 | G/A |
| Promoter, −482 | A/AT |
| Promoter, −387 | A/AT |
| Promoter, −383 | A/T |
| Promoter, −166 | C/A |
| gma-miR5032 (SEQ ID NO: 211) | |
| Promoter, −905 | C/T |
| Promoter, −1259 | A/C |
| Promoter, −2051 | T/G |

REFERENCES

1. Akalin A, Kormaksson M, Li S, Garrett-Bakelman F E, Figueroa M E, Melnick A, Mason C E (2012) methylKit: a comprehensive R package for the analysis of genome-wide DNA methylation profiles. Genome Biol 13: R87.
2. Anand S C, Newman T, Fisher J. 2001. Registration of 'Anand' soybean. Crop Sci 41:919-920.
3. Anders S, Pyl P T, Huber W (2015) HTSeq—a Python framework to work with high-throughput sequencing data. Bioinformatics 31: 166-169.
4. Becker, C., Hagmann, J., Müller, J., Koenig, D., Stegle, O., Borgwardt, K. and Weigel, D., 2011. Spontaneous epigenetic variation in the *Arabidopsis thaliana* methylome. Nature, 480(7376), p. 245.
5. Bernatavichute Y V, Zhang X, Cokus S, Pellegrini M, Jacobsen S E (2008) Genome-wide association of histone H3 lysine nine methylation with CHG DNA methylation in *Arabidopsis thaliana*. PLoS One 3: e3156.
6. Boehm, M. and Bonifacino, J. S., 2001. Adaptins the final recount. Molecular biology of the cell, 12(10), pp. 2907-2920.
7. Bolger A M, Lohse M, Usadel B (2014) Trimmomatic: a flexible trimmer for Illumina sequence data. Bioinformatics 30: 2114-2120.
8. Brucker E, Carlson S, Wright E, Niblack T, Diers B (2005) Rhg1 alleles from soybean PI 437654 and P I 88788 respond differentially to isolates of *Heterodera glycines* in the greenhouse. Theor Appl Genet 111: 44-49.
9. Concibido V C, Diers B W, Arelli P R. 2004. A decade of QTL mapping for cyst nematode resistance in soybean. Crop Sci 44:1121-1131.
10. Cook D E, Bayless A M, Wang K, Guo X L, Song Q J, Jiang J M, et al. 2014. Distinct copy number, coding sequence, and locus methylation patterns underlie Rhg1-mediated soybean resistance to soybean cyst nematode. Plant Physiol 165:630-647.
11. Cook, D. E., Lee, T. G., Guo, X., Melito, S., Wang, K., Bayless, A., Wang, J., Hughes, T. J., Willis, D. K., Clemente, T. E., Diers, B. W., Jiang, J., Hudson, M. E., and Bent, A. F. 2012. Copy number variation of multiple genes at Rhg1 mediates nematode resistance in soybean. Science 338:1206-1209.
12. Daykin M E., Hussey R S. 1985. Staining and histopathological techniques in nematology. In K R Barker, C C Carter, J N Sasser, eds, An Advanced treatise on *Meloidogyne*, Vol 2. North Carolina State University Graphics, Raleigh, NC, 39-48.
13. Du J, et al. (2012) Dual binding of chromomethylase domains to H3K9me2-containing nucleosomes directs DNA methylation in plants. Cell; 151:167-180.
14. Du Z, Zhou X, Ling Y, Zhang Z, Su Z (2010) agriGO: a GO analysis toolkit for the agricultural community. Nucleic Acids Res 38: W64-W70.
15. Du, J., Johnson, L. M., Jacobsen, S. E. and Patel, D. J., 2015. DNA methylation pathways and their crosstalk with histone methylation. Nature reviews. Molecular cell biology, 16(9), p. 519-532.

16. Eichten, S. R., Briskine, R., Song, J., Li, Q., Swanson-Wagner, R., Hermanson, P. J., Waters, A. J., Starr, E., West, P. T., Tiffin, P. and Myers, C. L., 2013. Epigenetic and genetic influences on DNA methylation variation in maize populations. *The Plant Cell,* 25:2783-2797.
17. Gillen AM, Shelton GW (ed.) (2012) Uniform soybean tests, southern states, 2011. USDA-ARS, Stoneville, MS. Available at ars.usda.gov/ARSUserFiles/60661000/UniformSoybean Tests/2011 SoyBook.pdf.
18. Hartley, S. W. and Mullikin, J. C., 2015. QoRTs: a comprehensive toolset for quality control and data processing of RNA-Seq experiments. BMC bioinformatics, 16:224.
19. Hartley, S. W. and Mullikin, J. C., 2016. Detection and visualization of differential splicing in RNA-Seq data with JunctionSeq. Nucleic acids research, 44(15), pp.e127-e127.
20. He, X. J., Chen, T. and Zhu, J. K., 2011. Regulation and function of DNA methylation in plants and animals. Cell research, 21(3), p. 442.
21. Hewezi T, Lane T, Piya S, Rambani A, Rice J H, Staton M. (2017) Cyst nematode parasitism induces dynamic changes in the root epigenome. Plant Physiology. 174: 405-420.
22. Hewezi, T., Howe, P., Maier, T. R., Hussey, R. S., Mitchum, M. G., Davis, E. L., Baum, T. J. (2008). Cellulose binding protein from the parasitic nematode *Heterodera schachtii* interacts with *Arabidopsis* pectin methylesterase: cooperative cell wall modification during parasitism. Plant Cell 20: 3080-3093.
23. Hewezi, T., Howe, P. J., Maier, T. R., Hussey, R. S., Mitchum, M. G., Davis, E. L., Baum, T. J. (2010). *Arabidopsis* spermidine synthase is targeted by an effector protein of the cyst nematode *Heterodera schachtii*. Plant Physiol. 152: 968-984.
24. Hofmann J, El Ashry AelN, Anwar S, Erban A, Kopka J, Grundler F (2010) Metabolic profiling reveals local and systemic responses of host plants to nematode parasitism. Plant J 62: 1058-1071.
25. Hollister, J. D. & Gaut, B. S. Epigenetic silencing of transposable elements: a trade-off between reduced transposition and deleterious effects on neighboring gene expression. Genome Res. 19, 1419-1428 (2009).
26. Holoch, D. and Moazed, D., 2015. RNA-mediated epigenetic regulation of gene expression. Nature Reviews Genetics, 16(2), pp. 71-84.
27. Inagaki S, Miura-Kamio A, Nakamura Y, Lu F, Cui X, Cao X, Kimura H, Saze H, Kakutani T. (2010) Autocatalytic differentiation of epigenetic modifications within the *Arabidopsis* genome. EMBO J. 29:3496-506.
28. Inagaki, S., Miura-Kamio, A., Nakamura, Y., Lu, F., Cui, X., Cao, X., Kimura, H., Saze, H. and Kakutani, T., 2010. Autocatalytic differentiation of epigenetic modifications within the *Arabidopsis* genome. The EMBO Journal, 29:3496-3506.
29. Johannes F, et al. (2009) Assessing the impact of transgenerational epigenetic variation on complex traits. PLoS Genet 5(6):e1000530.
30. Kakutani T, Munakata K, Richards EJ, Hirochika H (1999) Meiotically and mitotically stable inheritance of DNA hypomethylation induced by ddm1 mutation of *Arabidopsis thaliana*. Genetics 151(2):831-838.
31. Kazi S, Shultz J, Afzal J, Hashmi R, Jasim M, Bond J, et al. 2010. Iso-lines and inbred-lines confirmed loci that underlie resistance from cultivar 'Hartwig' to three soybean cyst nematode populations. Theor Appl Genet 120: 633-644.
32. Kim, Y. H., Kim, K. S., and Riggs, R. D. 2010. Differential subcellular responses in resistance soybeans infected with soybean cyst nematode races. Plant Pathol. J. 26:154-158.
33. Klink V P, Hosseini P, Matsye P, Alkharouf N W, Matthews B F (2009) A gene expression analysis of syncytia laser microdissected from the roots of the *Glycine max* (soybean) genotype PI 548402 (Peking) undergoing a resistant reaction after infection by *Heterodera glycines* (soybean cyst nematode). Plant Mol Biol 71: 525-567.
34. Klink, V. P., Hosseini, P., Matsye, P. D., Alkharouf, N. W., and Matthews, B. F. 2011. Differences in gene expression amplitude overlie a conserved transcriptomic program occurring between the rapid and potent localized resistant reaction at the syncytium of the *Glycine max* genotype Peking (PI 548402) as compared to the prolonged and potent resistant reaction of PI 88788. Plant Mol. Biol. 75:141-165.
35. Klink, V. P., Overall, C. C., Alkharouf, N. W., MacDonald, M. H., and Matthews, B. F. 2007. A time-course comparative microarray analysis of an incompatible and compatible response by *Glycine max* (soybean) to *Heterodera glycines* (soybean cyst nematode) infection. Planta 226:1423-1447.
36. Krueger F, Andrews S R (2011) Bismark: a flexible aligner and methylation caller for Bisulfite-Seq applications. Bioinformatics 27: 1571-1572.
37. Lawrence M, Gentleman R, Carey V (2009) rtracklayer: an R package for interfacing with genome browsers. Bioinformatics 25: 1841-1842.
38. Li X, et al. (2012) Single-base resolution maps of cultivated and wild rice methylomes and regulatory roles of DNA methylation in plant gene expression. BMC Genomics 13:300.
39. Lister R, O'Malley R C, Tonti-Filippini J, Gregory B D, Berry C C, Millar A H, Ecker J R (2008) Highly integrated single-base resolution maps of the epigenome in *Arabidopsis*. Cell 133: 523-536.
40. Liu, S., Kandoth, P. K., Warren, S. D., Yeckel, G., Heinz, R., Alden, J., Yang, C., Jamai, A., El-Mellouki, T., Juvale, P. S., Hill, J., Baum, T. J., Cianzio, S., Whitham, S. A., Korkin, D., Mitchum, M. G., and Meksem, K. 2012. A soybean cyst nematode resistance gene points to a new mechanism of plant resistance to pathogens. Nature 492: 256-260.
41. Locasale, J. W., 2013. Serine, glycine and the one-carbon cycle: cancer metabolism in full circle. Nature reviews. Cancer, 13(8), p. 572.
42. Lopez Sanchez A, Stassen J H, Furci L, Smith L M, Ton J. (2016) The role of DNA (de)methylation in immune responsiveness of *Arabidopsis*. Plant J. 88: 361-374.
43. Mahalingam, R., and Skorupska, H. T. 1996. Cytological expression of early response to infection by *Heterodera glycines* Ichinohe in resistant PI 437654 soybean. Genome 39:986-998. 10.1139/g96-123.
44. Martinez-Medina A, Flors V, Heil M, Mauch-Mani B, Pieterse C M, Pozo M J, Ton J, van Dam N M, Conrath U. (2016). Recognizing Plant Defense Priming. Trends Plant Sci. 10:818-822.
45. Matzke M A, Mosher R A (2014) RNA-directed DNA methylation: An epigenetic pathway of increasing complexity. Nat Rev Genet 15(6):394-408.
46. Mauch-Mani B, Baccelli I, Luna E, Flors V (2017). Defense Priming: An Adaptive Part of Induced Resistance. Annu Rev Plant Biol; 68:485-512.

47. Meksem, K., Pantazopoulos, P., Nijiti, V. N., Hyten, D., Arelli, P. R., and Lightfoot, D. A. 2001. 'Forrest' resistance to the soybean cyst nematode is bigenic: Saturation mapping of the Rhg1 and Rhg4 loci. Theor. Appl. Genet. 103:710-717.
48. Mitchum, M. G., 2016. Soybean resistance to the soybean cyst nematode *Heterodera glycines*: an update. Phytopathology, 106(12), pp. 1444-1450.
49. Miura A, Nakamura M, Inagaki S, Kobayashi A, Saze H, Kakutani T (2009) An *Arabidopsis* jmjC domain protein protects transcribed genes from DNA methylation at CHG sites. EMBO J 28:1078-1086.
50. Mosher R. A et al. Uniparental expression of PolIV-dependent siRNAs in developing endosperm of *Arabidopsis*. Nature 460, 283 (2009). doi:10.1038/nature08084 pmid:19494814.
51. Niederhuth, C. E. and Schmitz, R. J., 2017. Putting DNA methylation in context: from genomes to gene expression in plants. Biochimica et Biophysica Acta (BBA)-Gene Regulatory Mechanisms, 1860(1), pp. 149-156.
52. Quinlan, A. R. and Hall, I. M., 2010. BEDTools: a flexible suite of utilities for comparing genomic features. Bioinformatics, 26: 841-842.
53. Rambani A, Rice J H, Liu J, Lane T, Ranjan P, Mazarei M, Pantalone V, Stewart C N Jr, Staton M, Hewezi T. (2015) The methylome of soybean roots during the compatible interaction with the soybean cyst nematode. Plant Physiology. 168:1364-1377.
54. Regulski, M., Lu, Z., Kendall, J., Donoghue, M. T., Reinders, J., Llaca, V., Deschamps, S., Smith, A., Levy, D., McCombie, W. R. and Tingey, S., 2013. The maize methylome influences mRNA splice sites and reveals widespread paramutation-like switches guided by small RNA. *Genome research,* 23:1651-1662.
55. Reinders J, et al. (2009) Compromised stability of DNA methylation and transposon immobilization in mosaic *Arabidopsis* epigenomes. Genes Dev 23(8):939-950.
56. Rigal, M., Becker, C., Pélissier, T., Pogorelcnik, R., Devos, J., Ikeda, Y., Weigel, D. and Mathieu, O., 2016. Epigenome confrontation triggers immediate reprogramming of DNA methylation and transposon silencing in *Arabidopsis thaliana* F1 epihybrids. *Proceedings of the National Academy of Sciences,* 113(14), pp. E2083-E2092.
57. Robinson M D, McCarthy D J, Smyth G K (2010) edgeR: A Bioconductor package for differential expression analysis of digital gene expression data. Bioinformatics 26: 139-140.
58. Saze H, Kakutani T (2007) Heritable epigenetic mutation of a transposon-flanked *Arabidopsis* gene due to lack of the chromatin-remodeling factor DDM1. EMBO J 226 (15):3641-3652.
59. Saze H, Shiraishi A, Miura A, Kakutani T (2008) Control of genic DNA methylation by a jmjC domain-containing protein in *Arabidopsis thaliana*. Science 319: 462-465.
60. Saze, H., Tsugane, K., Kanno, T. and Nishimura, T., 2012. DNA methylation in plants: relationship to small RNAs and histone modifications, and functions in transposon inactivation. Plant and Cell Physiology, 53(5), pp. 766-784.
61. Schmitz, R. J., He, Y., Valdes-López, O., Khan, S. M., Joshi, T., Urich, M. A., Nery, J. R., Diers, B., Xu, D., Stacey, G. and Ecker, J. R., 2013. Epigenome-wide inheritance of cytosine methylation variants in a recombinant inbred population. *Genome research,* 23(10), pp. 1663-1674.
62. Schmitz, R. J., Schultz, M. D., Lewsey, M. G., O'Malley, R. C., Urich, M. A., Libiger, O., Schork, N. J. and Ecker, J. R., 2011. Transgenerational epigenetic instability is a source of novel methylation variants. Science, 334(6054), pp. 369-373.
63. Slotkin, R. K. and Martienssen, R., 2007. Transposable elements and the epigenetic regulation of the genome. Nature reviews. Genetics, 8: 272-285.
64. Slotkin, R. K., Vaughn, M., Borges, F., Tanurdžić, M., Becker, J. D., Feijó, J. A. and Martienssen, R. A., 2009. Epigenetic reprogramming and small RNA silencing of transposable elements in pollen. Cell, 136: 461-472.
65. Smit, AFA, Hubley, R & Green, P. RepeatMasker Open-4.0. 2013-2015, world-wide website: repeatmasker.org.
66. Smith, Z. D. and Meissner, A., 2013. DNA methylation: roles in mammalian development. Nature Reviews Genetics, 14(3), pp. 204-220.
67. Springer, N. M. and Schmitz, R. J., 2017. Exploiting induced and natural epigenetic variation for crop improvement. Nature Reviews Genetics. 18(9):563-575.
68. Sun Z, Guo T, Liu Y, Liu Q, Fang Y (2015) The Roles of *Arabidopsis* CDF2 in Transcriptional and Posttranscriptional Regulation of Primary MicroRNAs. PLoS Genet 11(10): e1005598.
69. Supek, F., Bošnjak, M., Škunca, N. and Šmuc, T., 2011. REVIGO summarizes and visualizes long lists of gene ontology terms. PloS ONE 6, e21800.
70. Taudt, A., Colome-Tatche, M. & Johannes, F. Genetic sources of population epigenomic variation. Nat. Rev. Genet. 17, 319-332 (2016).
71. To, T. K., Saze, H. and Kakutani, T., 2015. DNA Methylation within Transcribed Regions. *Plant physiology,* 168(4), p. 1219.
72. Trapnell, C., Pachter, L. and Salzberg, S. L., 2009. TopHat: discovering splice junctions with RNA-Seq. Bioinformatics, 25:1105-1111.
73. Wang, H., Beyene, G., Zhai, J., Feng, S., Fahlgren, N., Taylor, N. J., Bart, R., Carrington, J. C., Jacobsen, S. E. and Ausin, I., 2015. C G gene body DNA methylation changes and evolution of duplicated genes in cassava. Proceedings of the National Academy of Sciences, 112 (44), pp. 13729-13734.
74. Wang, X., Hu, L., Wang, X., Li, N., Xu, C., Gong, L. and Liu, B., 2016. DNA methylation affects gene alternative splicing in plants: an example from rice. Molecular plant, 9(2), pp. 305-307.
75. Wibowo A, Becker C, Marconi G, Dun J, Price J, Hagmann J, Papareddy R, Putra H, Kageyama J, Becker J, Weigel D, Gutierrez-Marcos J. (2016) Hyperosmotic stress memory in *Arabidopsis* is mediated by distinct epigenetically labile sites in the genome and is restricted in the male germline by DNA glycosylase activity. ELife 5, e13546.
76. Young L D. (2001). Registration of 'Fowler' soybean. Crop Sci 41:257.
77. Zilberman, D., Coleman-Derr, D., Ballinger, T. & Henikoff, S. Histone H2A.Z and DNA methylation are mutually antagonistic chromatin marks. Nature 456, 125-129 (2008).

What is claimed is:

1. A plant cell comprising an overexpressed gene, wherein the overexpressed gene comprises a protein coding sequence of SEQ ID NO: 1 operably linked to a heterologous promoter or SEQ ID NO: 2 operably linked to a heterologous promoter and said plant cell is resistant to infection by soybean cyst nematode (SCN).

2. A plant cell comprising an overexpressed gene that comprises a protein coding sequence of SEQ ID NO: 1 or SEQ ID NO: 2 operably linked to a heterologous constitutive promoter or a heterologous root specific promoter.

3. The plant cell of claim 2, wherein the plant cell is a soybean plant.

4. The plant cell of claim 1, wherein the plant cell is in a plant part and the plant part is resistant to infection by SCN.

5. The plant cell of claim 4, wherein the plant part is a seed, endosperm, ovule or pollen.

6. The plant cell of claim 1, wherein the plant is a soybean plant or other cyst nematode-host plants.

7. A plant comprising a plant cell of claim 1, said plant being resistant to infection by SCN.

8. The plant of claim 7, wherein said plant is a soybean plant.

9. The plant cell of claim 1, wherein the heterologous promoter is root maize NAS2 promoter, maize Cyclo promoter, maize ROOTMET2 promoter, CR1B10 promoter, CRWAQ81 promoter, or maize ZRP2.47 promoter.

10. The plant cell of claim 1, wherein the overexpressed gene comprises a protein coding sequence of SEQ ID NO: 1 operably linked to a heterologous promoter.

11. The plant cell of claim 1, wherein the overexpressed gene comprises a protein coding sequence of SEQ ID NO: 2 operably linked to a heterologous promoter.

12. A plant comprising a plant cell of claim 1, wherein the overexpressed gene comprises a protein coding sequence of SEQ ID NO: 1 operably linked to a heterologous promoter, said plant being resistant to infection by SCN.

13. A plant comprising a plant cell of claim 1, wherein the overexpressed gene comprises a protein coding sequence of SEQ ID NO: 2 operably linked to a heterologous promoter, said plant being resistant to infection by SCN.

14. The plant cell of claim 3, said plant cell further comprising an inactivated gene encoding an aspartate aminotransferase protein and/or an inactivated gene encoding a transcription regulator of the NOT2/NOT3/NOT5 protein, wherein the gene encoding the aspartate aminotransferase protein comprises the protein coding sequence of SEQ ID NO: 3 and the gene encoding the transcription regulator of the NOT2/NOT3/NOT5 protein comprises the protein coding sequence of SEQ ID NO: 4.

* * * * *

SEQUENCE LISTING

<160> NUMBER OF SEQ ID NOS: 213

<210> SEQ ID NO 1
<211> LENGTH: 1248
<212> TYPE: DNA
<213> ORGANISM: Glycine max

<400> SEQUENCE: 1
atgggctctg gaaatatact accttcttct ggcagctctg acatgtctat ctccgagctc 60
cgcgagaagc accattggga gctagaaaat ctgactctga ccacacaacc tctcaaaacg 120
ttgaaattct tcacattagc tgttattcaa tacatcaaga aaacagcaat atatctattg 180
gcaaaaggtg gatgggttat gcttttcagt gttgcagttg ggactcttgg catagtgctg 240
atgacccttg gttgcctcca tgagaagcat cttgaggagc ttcttgaata ttttcgcttt 300
ggactgtggt gggttgccct tggggttgct tcttcaattg gtctaggatc tggtttgcac 360
acatttgtcc tatatttggg tccccacata gcactgttta caataggagc agtgcaatgt 420
ggccgagttg atttgaaaag tgctccttat gatacgatac aattaaaaag aggtccttct 480
tggcttgata aagactgttc tgagtttggg ccaccattat tccagtcgca ggttccgctt 540
agcagcattt tgcctcaagt tcagctggag gctattctat ggggtattgg aacagctata 600
ggggagcttc ctccttactt tatctccagg gcagcacgct tgtctggtgg gagagtagat 660
gccatggaag aattagacag cgaagataaa agagtcttga gtcgaataaa gtgctggttt 720
ctatcacact cgcaacattt gaatttcttt actattctag tgcttgcttc ggttccaaat 780
cctctatttg accttgccgg catcatgtgt ggacaatttg gcattccatt ttggaaattt 840
tttcttgcaa ccttgattgg aaaggcaatt attaaaactc acatacagac gatattcata 900
atctcagttt gcaacaatca acttcttgat tggattgaga atgaatttat ttgggttctc 960
agccacatac ctggttttgc atctgtcttg cctagagtga ctgctagtct ccatgcaatg 1020
aaagataagt atctgaaagc accccatcca ctttccccaa ataaacaggg gaaaaaatgg 1080
gatttttctt ttgcttcagt ctggaacact gttgtgtggc tcatgcttat gaacttcttt 1140
gtcaagatag tgaatgcaac ttcccagagg tatctgaaga aacagcagga gacacagctt 1200
gctgcattaa cggaaaagtc taccccaaca gactcagacg cacaatga 1248

<210> SEQ ID NO 2
<211> LENGTH: 1362
<212> TYPE: DNA
<213> ORGANISM: Glycine max

<400> SEQUENCE: 2
atgagacacg tggttatttt ttctttcaat ttcttgctgc tttgtgtctt catttctgct 60
ataacaagca caaaaagtga agtatctagc acaaatgaag aacaatcatt ttcttaccat 120
atcaaagctt tggaattcat atggaaacat ttgggctatc aacatgtgtg gccagaaatg 180
gaatttagct ggagaattgt tgttggaacc ttgattggaa tcttgggagc agcatttgga 240
agtgtagggg gagttggtgg tggtggcatc tttgtgccaa tgctaatcct cattattggg 300
tttgatccaa aatcagcagt tgctatttca aagtgtatgg tcacaggtgc agccatctca 360
gcagtattct tctgcatgaa gcaaaggcat cccacacttg atgaacccgt tatcgactac 420
gatttgatgt tgctaataca accaaccctc atgcttggaa tcagcatagg agttattttg 480
agtgtaatat ttgctgattg gatggtcaca attcttctaa ttattctatg tatagtgaca 540
tcaatcaggg cattcttcat gggtgctgac acatggaaaa aggaaaccaa aatgaaagag 600
gtgagcatcc ttggcaacat gtattggaag gagtttgtac ttattttcat tgtctggctc 660
gcatttgtga actatacagt ttcctgttca gtcacatact ggatacttat tttgtcacag 720
ataccaatta ctgtaggatt ttatttgtac caagcaagag ccctatatca ggggagagct 780
gcaggatctc aacacacaca ttggccattg caccatctat ttctagctag catttgttct 840
ctgttagctg gaattgttgg tggacttctt ggtacaggtt ctggatttgt tatgggtcct 900
ttatttctag aagtgggaat tgctccacag gtagcaagtg ccacagccac ttttggaatg 960
atgtattcat catctttatc tgtcatacaa tattacctgt tgaatcgttt tcctgttcct 1020
tatggtaaaa ttaaacttaa ttcacattgt acccttctat tatttctgaa tggttttcaa 1080
aggcaacata aacttattca agtaattttt atgcatgttt caacctgttt tgcagctctc 1140
ttccttactc ttgtggctgc aattgcagca ttcctaggac agtatctcat tgacaagctt 1200
gttaatatct tccaaagggc ttctttaatt atttttgtct tggccttcac aatatttgtt 1260
agttcaattg cattaggtgg agtcggcata tcaaacatga tcttgaagat tcaaaggaat 1320
gaatacatgg gatttgataa tttttgcagg aatgatacat ag 1362

<210> SEQ ID NO 3
<211> LENGTH: 1392
<212> TYPE: DNA
<213> ORGANISM: Glycine max

<400> SEQUENCE: 3
atggcttctt cgtttctatc cgcagcttcg cacgctgtct caccctcttg ttctctgtcc 60
accacgcaca agggaaagcc catgcttgga ggcaacactt tgagatttca caaaggaccc 120
aattccttct ctagttcaag gtctagaggt cggatctcta tggctgttgc agttaatgta 180
tctcggtttg aaggcatacc tatggctcct cctgatccaa ttctcggagt ttccgaggcg 240
tttaaggcag acaatagtga tgtcaagctc aatcttggag ttggggcata cagaacagaa 300
gaactacagc catatgtgct taatgttgtt aagaaggcag agaatcttat gctggagaga 360
ggggataaca aagagtatct cccaattgag ggtttggcag catttaataa ggcaactgca 420
gagttgttac tcggagcaga caacccagca atcaaacagc aaagagttgc cactgtccaa 480
ggtctttctg gaactggttc tctgcgacta ggtgcagctc tgatagagcg atattttcct 540
ggggcaaaag ttttgatatc agctcctacc tggggtaatc acaagaatat tttcaatgat 600
gctagtgtcc catggtctga gtaccgatat tatgatccca agacagttgg gttggatttt 660
gagggcatga ttgaagatat aaagtcagct ccggaaggat cttttatctt acttcatgga 720
tgtgctcata atcctactgg tattgatcca acacctgaac agtgggaaaa aatagctgat 780
ttaattgaag aaaagaacca cattcccttt tttgatgttg cttaccaggg gtttgctagt 840
ggaagccttg atgaagatgc agcttctgtg agactgtttg tggcacgtgg catcgaggtt 900
cttgtagctc aatcttacag taaaaatctc ggtctctatg ctgaaaggat tggagcaatc 960
aatgtgattt catcgtcacc agaatctgca gcaagggtaa agagccaact gaaaaggatt 1020
gcccgaccaa tgtactctaa tccaccggta cacggggcta ggatagttgc cgatgttgtt 1080
ggaaacccag ttctctttaa tgaatggaaa gcagagatgg aaatgatggc tggaaggata 1140
aagaatgtta gacagcagct atatgatagt attacttcaa aagacaaaag tggaaaggat 1200
tggtcattca tacttaagca gataggcatg ttctcattca ctggcttgaa caagaaccag 1260
agtgacaaca tgacaaacaa gtggcacgta tacatgacaa aggatggaag gatttccctg 1320

-continued

```
gcaggattgt cgttggctaa atgcgaatac cttgcggatg ctattattga ttcatatcat   1380

aatgtcagct ga                                                        1392


<210> SEQ ID NO 4
<211> LENGTH: 90
<212> TYPE: DNA
<213> ORGANISM: Glycine max

<400> SEQUENCE: 4

atggatataa taagtcttgc ttgggctact ttaatggtag ctttttcatt ttctcattcc     60

ctcgtagtat ggggaagaag tggactatag                                      90


<210> SEQ ID NO 5
<211> LENGTH: 798
<212> TYPE: DNA
<213> ORGANISM: Glycine max

<400> SEQUENCE: 5

atgtctaaga acaagctctg cacacccctt tcaacccttc tgagacgcac tttaacttca     60

tttccccaac acttcacttc caatttctct cagatcaaac tctctcttca tgactcatca    120

ctaccgtttg cacccccttc tcataacccc acctgcgatt actattattc tctcggattt    180

ttcaggaaaa gcctatgctc aaaatctgct gaggaaatcc aacgtggatg ttggaattgc    240

cacactgtcc ctcattcgga acctttcctt gtttgtgagt catgtcggtg cattcagcct    300

gtggatagct ccgttgacta ttttgacata tttggggtgg agaggaagta tgacatagag    360

ggtgagaatt tggagggcaa gtacaaagat tggcaaaaga aactgcatcc tgatttagta    420

cattcaaaat ctcagaaaga aagagatttt gctgctgaac aatctgcaag ggtcattgat    480

gcataccgta ctcttagcaa gcctttgtca agaggaattt acttgctaaa gctttatgga    540

gaagaagttg atgaagaaca gacaatttca gattcagaat tacttgcaga gattctggaa    600

atcagggaag cagttgaaga agcaactaac tctgagactt tgaatcacat tctctctgag    660

atgcaggaga agctacataa ttggtccaat gcctttggtc atgcttttca aagccaaaac    720

tttgaagaag caaaaaatggc aattaggaga atgacttact atagtcgtgt aattgatgaa    780

gttgtaaaga agctttga                                                  798


<210> SEQ ID NO 6
<211> LENGTH: 2895
<212> TYPE: DNA
<213> ORGANISM: Glycine max

<400> SEQUENCE: 6

atgccggaaa ataaaagcga gaatcgtgct aaaatagaaa gtttctggga aggtgcttta     60

aaggatattt acgaagaaac actaatgtat gataataatg atgtggtcca cagtccggat    120

gaatgcgttg atcctgaaac acgaaaaata aaagtcccta aatcagagtt tgttaagaca    180

tataaaaata gcgtcttttc tcttctggac cgttatagat atgaaaataa tgatgcacaa    240

acattagaat cgcttcagag agaaattgag gatctgactt tgaacttctc tgaagatagt    300

atttataaaa ctagtcctaa cattatggta atgttaacta aaaacaactt gccaagtgct    360

aaggaattcc ttcgtggaaa gtatcttatg gataaagaat atcccggcag aatgaccatt    420

tatgcagaaa gtcgaagtgg tgatagtcta gaaaccagcg gctcagagct atccgatgag    480

gagaataaaa atctaagatg tgtactatct gaaagtgata agtcgttgtt ggtagagtta    540

ggcgagcact ccattgagtg cctactggtt cacaccctag gccatctgtt taatctggaa    600
```

```
aatattgtca gtcttgctag tttggttgat cgtatagaac gcaatgtaag ggattatgcc    660
tcatcgtcaa cattgtatta taatagtagg gtatgtaatc taagtatgga tgctgttgat    720
aaaggtacta aagcatctaa aactagagct tatccctttg gtacagcatt agttgaattt    780
ttagtgagtc gtggtctatt gcgcttagta acatataatg ttgatttatt aaatttctct    840
gatgatagtg gtccaaagac tgttgtcaaa aatgttgtca aaaagggcca taattactat    900
aggagctctt tagtatatgc cgaatgcttg tttaaccccg cattacttcc tataaagtta    960
aacctaccta tggtatttcc acctaaagat tgggagcccc acaaacctga acagaaacgt   1020
aagttgttac atatatctga tatatatggt ggttatttaa gcaaccctac gggccaaatc   1080
tacagcactc aacggagtat gagttctccc gatgcgaaga atttcttcat ctatttcggt   1140
gaaaataagt atcaagaaag tcataataag caaaataagt tttgtactag catcagtagc   1200
ttacagcgtc aatcctttaa aataaatagt aatttcctta attttatatt agaaaatagg   1260
gaattattag aagaatgtgg ctacttgatg cccgaatttc tttcaaaggt aatactagcc   1320
catgcctcca ggaaacttag aagtcatttt gaaaagaata aggatattca aacaatatac   1380
aaatttagtg atgtgtacgc tctattaata aagaatatgc agcgggcacg ttatgagtgt   1440
acgattttag atctggcaaa ggcctactct ggatattctt tatattttcc agcatttatt   1500
gacttcaaag gtcgaatcta tcgcagcggc atctttcact tccacgagcg ggatttagcc   1560
cgaagtctac tattaataga ttgtaaagat aatatagaat attcttcccc tgaaattaat   1620
aattatctaa atatgtatct aaccgcaact gcattcctct atcaatcata taaatatgag   1680
gaggatgctc taaatgatat aaataataaa ttattaccat tacctaatct agagtgtaaa   1740
gagaacttta aaacgtattt aaagacttta gtgatagaat cacggatggc taaacggcca   1800
ttccaatatt tatctaatat ttacctttta ttattatcat tatcatcatc ggatttaatg   1860
tctttcgttg atctgtataa ttgtgttcct gtaactcagg atgctagcgc tagcgcatat   1920
caactgatgg cttatttcct cctggataag aattttgcga aactaacaaa tctttttgat   1980
accggcagcg gtgagatatt tgacatctat tctcacatga gaattgaatt aatttcattc   2040
atcaaagact ctcttagtga ggagaatcct gagctatgcg caattttgga tagggtccta   2100
actaggagta tagttaagca aatatatatg ccaattatat atggtaaaac agctaatagc   2160
acaactaagg atcttatagt gagtctttgc caagatctct tgccaaaaga atgtactata   2220
ctgtcggttc tatgcttcaa attttggcaa gaaaaataca gttttatgta ttcgtttatc   2280
cagctgatca gcctggtagg tcgggtatgc tcttacctag atcgaccagt cttgtacagc   2340
acagaatatt ttagcacatc ccaggattat aaaaagatgg aaaaacactc agttagagtc   2400
ttcaactctt acttgaaaaa ggcccataat gtcacactct cgtttccctc aaaagagcgg   2460
gataagagga aaagtggggt atccacattc attaacttca ttcatcaaaa ggacgcgcaa   2520
attgctatgt ctattgcctt ctatgagaac tcatataata tacctctgta cacagttcac   2580
gacaacttca taacaaatat gcattattgt aaatatatat ctaaaatcta tctacatgtc   2640
ataaaggaaa tggggccccc tcttaaaatc attaaccgct ttatttataa aaatattatg   2700
gagccggcta tagcgaaggg cctctataat aatgtaaaag gctacaattt gaagtctttt   2760
gatgaaagga tcataccaga gcctatttta gatgagttct taaaaattgg actcatttct   2820
ccagaagatg tcacgaatgc agctggttta aaaaaaataa acaataagtt gaaacaaaga   2880
tatcaactca tataa                                                    2895
```

-continued

<210> SEQ ID NO 7
<211> LENGTH: 1014
<212> TYPE: DNA
<213> ORGANISM: Glycine max

<400> SEQUENCE: 7
atgaatcctt ctctcacttc ttcctcaacc ttgtcgtcgt cttcttcgtc ctggttctcc 60
ggaatcgttc gagttggccg ttccaacagt gtcaaaatgt ccaataactc cgctgctgca 120
ccctcctccg acactgccgg ccccgtcgtc cgcaaaaatc agttccgagg tgttcttttc 180
aagtacggtc ccaatcctat tcaggttgca tttaagactg gtgatttcaa gcggcaagtc 240
atttttattg gtggattgac cgatggtttt ctagctactc catacttgga acctctggca 300
attgctctgg accatgagaa ttggtcgtta gttcaattcc ttatgtcatc ttcatacagt 360
ggatatggca cctccagctt gcaacaagat gctaaggagc tggatcagct gattaattat 420
ttaattaaca aagaagactc tgaaggtgtg gcattacttg ggcatagtac tggctgtcag 480
gatattgtgc attacatgcg cacaaatttt gcttgctccc gagctgttcg tgctgccatc 540
tttcaggctc cagtcagtga tcgggaatat caagctacac tccctcatac agcttctatg 600
attgacttgg ctgctaagat gataagtgaa ggccgaggtc tagagttaat gccaagggaa 660
gcagatccta gtgccccaat aactgcctat aggtatcact ccctttgttc atataatggc 720
gatgatgaca tgttcagttc tgacctgagt gatgaccagt tgaagatgag acttgggcat 780
atgtctagca cacattgtca ggttatattt tcaatggctg acgaatatgt gccagattat 840
gttgataaga aagctctagt tgagcggtta tgcagagcga tgggaggagc agagaaagta 900
gagattgaat atggaaatca ttccctctct aacagagttg aagaagctgt tgatgctatt 960
attgacttct taaaaagaga gggacccaag ggatgggacg atccatggag ttaa 1014

<210> SEQ ID NO 8
<211> LENGTH: 780
<212> TYPE: DNA
<213> ORGANISM: Glycine max

<400> SEQUENCE: 8
atggctgaat tcacagaaaa tttgcaaaac atttcctcat catctccatt cttagacatt 60
gatccaagca tggaactcct aaaccaattc atagggatga accaattata tgtgctagac 120
aactcaaact tgatgcctta tttctcctgt gataccttct tgggccccca agaacctgag 180
tttccaggaa acttggaaga agattttcct tttctcttcc atcatgtcaa ccacaatgca 240
cctcctgttt ccctccccat tttccaagca gaaaatgaga tccatgaagg taataagagg 300
aaatcaatgg atcttcttga gaccagtttt gctaattcaa cttctgcagt ttctgagact 360
ggaagcaaga tcaaacatag ttctggaaga ggaaagagac tgaaaaacaa tgttacagaa 420
gaagaggaga aagcaaagga agtggttaat gccagggcta gaagaggtca agctactgat 480
agtcacaatt tagcagaaag ggttagaaga gggaaaatca atgagaaatt aaggtactta 540
caaaatattg ttccaggatg ttacaagaca atgagtatgg cagtaatgtt agatgaaatc 600
ataaactatt tcctttcttt ggagcttaca gcagcaagta ccttttatga cttcaattcc 660
gagatagatg cttttgaaac aatgcagaga tcaagggcat acgaggcaaa agagttaggc 720
aagtataaaa gagaaggaca tggaggagtt tctctccttc aaccaacatg gcacctttga 780

<210> SEQ ID NO 9
<211> LENGTH: 1569

-continued

<212> TYPE: DNA
<213> ORGANISM: Glycine max

<400> SEQUENCE: 9
atggaaagaa gggttgtaat tattggagca ggaatcagtg gccttggtgc ctgcaaatac 60
cttctagagt ttggatttaa cccaattgtc tttgaagttg atgatggtgt tggaggacta 120
tggagacata ccatggactc caccaagctc caaaacaata aacaaatgtt ccagtttatg 180
gattttccat ggccttcttc tgtgaaagaa gataatccaa gtcacaagca agtgctagat 240
tatgttaact cctatgctga acatttttcc ctcattcctt acattagatt caacttcaaa 300
gtcattgaca tagattatgt tggtggagag tctagtgaag aaatgaagtc atgggaattg 360
tggggtggta atggcaggcc cttttgctcc aagggaactt ggcatattgc tgtgcaacat 420
accaaaaatt tatccataga gatgcatgag gccgagtttg ttgttctttg cattgggaaa 480
tatagtggtt ttccaaacat tcctgaattc cccccaggaa aaggcccaga agttttcaat 540
ggcaaggtta tgcactccat ggactactcg aatttggaca atgagactgc tgctgaactg 600
atcaaaggaa aaagagttac aataataggc tcacagaaat ctggtcttga tctagcagct 660
gaatgtgcga atgcaaatgg agtgaagcat ccttgcacag ttatccaaag aaccgcacac 720
tggtttcttc cagattttaa cttttggggt gttattgctg gattcttgta cttcaatcgc 780
tttgcggagc ttttagttca caagccagga gagtccttcc tacttggcct tgttgccact 840
ctgctttcac catggagatg ggaatttct aaacttgttg aaactactct aaaatggaag 900
ctgccattga agaagtatgg aatggcaccc aatcacagct ttcttcagga tctctccaca 960
tgtctgtttg cggtgtatcc tgataacttt tttgacaaac taaaagaagg atccatcatt 1020
atgaagggat cgcaaaactt tagcttttgt agagaaggtg taatcattga cggagaagct 1080
aagcccctgg aatcagatat tgtatttttt gccactggat acaaaggtga ccaaaaaatc 1140
aaaaacatat tcaaatctcc actcttccaa aagtacatca ttgggcaagc aacctcaaca 1200
gttcctctct acagacaaat aattcaccct cagatccccc agttggcaat aataggatat 1260
gccgagagcc catcaaatat atttgcctcg gaaatgaaaa gcttgtggct atcacatttc 1320
ttggatggaa acatagagtt gcctagtata agagagatgg aaaaggacgt gaaattgtgg 1380
gaagacaatt tgaagcaata tggtgggaaa tattattgga aaacatgcat tgctcattgt 1440
ggcatatggt atcatgatca attgtgcaaa gacatgaagc atgaccctag aaggaagaat 1500
ggcctttttt cggagttgtt tgaaccatat ggccacgctg attacgcagg tcttactcgt 1560
aaaagataa 1569

<210> SEQ ID NO 10
<211> LENGTH: 528
<212> TYPE: DNA
<213> ORGANISM: Glycine max

<400> SEQUENCE: 10
atgggagacg aagcaagtga agagcatcaa aggtcgctag cagctccttt catatttttc 60
gtggttctcg catttcagtt tgcttctcat tggattgatc actttaagaa gagtggatct 120
gacaaagaaa aagaaactaa gttgcgtgga gaaataaaag agcttttgaa ggaggcaagc 180
tcactgtcac agccatcaac ctttgcacaa gcagcgaaac tcaagagact ggcagctgca 240
aaggagaggg aactggcaaa gtgtcaaaat ttacatcaca aggatgatgc tttgtattca 300
aaagttctgc tcatctcaaa ggttttaaca tatttaattc tgcttatctg gttttggagt 360

```
gttcctgtct ctagcatatc tcaacaactt gtgcaaccat ttgggagatt attatcttgg    420

aggactggag gggttcaaaa tagcaatatt atggttggga taataccttg gctgatagtg    480

tctaccaggg ttagcagatt tatttgtaga ctcacctatg gcaaatag                 528


<210> SEQ ID NO 11
<211> LENGTH: 1062
<212> TYPE: DNA
<213> ORGANISM: Glycine max

<400> SEQUENCE: 11

atgcaaatgt ctcaaaaaca taaaatgtcc tatgactcta gcaggttcag cattgagcct     60

gtgcaaaatc tggggtcatg ttgcttcctg caaagtggga acctagacta ctcctcatcc    120

tctgataacg gtagccatgc aacctaccct tctgtttgta ttttcgaaca atattgcacc    180

ctggaatctt ctacaaacaa caatatccct tccctaaact ctccatctac tgtcagtttc    240

tcacctaaca atagtccagt ctcaaagctg cattcaaaag catatgtgtt gagttcacaa    300

aatttgcttg aaattgttaa tgaatcgcta gaaaacaaat ctttcttgac acttaacgat    360

gatgagctga ggcacaagat aagagagctt gaaagtgcta tgttgggaca tgatacagat    420

attctggata cctatgatac cataattcca aaagaatctg attcgttttt gaaagaggca    480

gaaaggtgga agaggatggt ggcaaagata tctagagggg atttaaaaga gatgctttgt    540

acatgtgcaa aagcagtggc aggaaatgat atggagacaa ctgaatggtt gatgtcagag    600

ttgcgtaaaa tggtctccgt ctccggcaat ccaatccaac gattgggagc atacatgttg    660

gaggctcttg ttgcaaggct tgcctcttca ggaagcacaa tcttcaaagt cttgaaatgt    720

aaagagccta ctagtagtga actcctttca cacatgcatc tactttatga aatctgtcca    780

tatctcaaat ttggttacat gtcagcaaat ggagctattg ctgaagtcat gaaggaggaa    840

agtgaagtcc acattattca ttttcagatt aaccagggaa ttcagtgggt aagcctaatc    900

caagctgttg ctggcagacc tggagcaccc cctaagatta gaataacaag ttttgatgac    960

tccacttcag cttatgccat ggaaggaggc cttgaaattg ttggagcaag gttatcaagg   1020

cttgcacaat catataatgt accctttgag tctaattgct aa                      1062


<210> SEQ ID NO 12
<211> LENGTH: 1143
<212> TYPE: DNA
<213> ORGANISM: Glycine max

<400> SEQUENCE: 12

atgtttacaa atgtaaaaga agaagaaaaa aaaaaacaaa aaaagaaaga gctaacgcaa     60

cccaaaccca aagtatcaat ctcctctact tccatttcca gtggtcactc actcagccac    120

tgtgcttctt cttcttctct ttctccctct ctcctcttcc caatgccctc tctccacctt    180

ctccccggcg ccaccaccgc ccccaactcc acattcctcc tccgccccca ttcccctctc    240

ctcccctcca aaccctaac ccccaaaaaa cccaaaccca aaccccccag tgccctcctc    300

cagtggaacc gcaagcccga gctctccggc tccatcccgc gcgtcaccgt cattacctcc    360

ggaaagggcg gcgtgggcaa gaccaccacc accgccaaca tcggcctctc cctcgcccgc    420

ctgggcttct ccgtggtcgc catcgacgcc gacgtcggcc tccgcaacct cgacctcctc    480

ctcggcctcg agaaccgcgt caactacacc gtcatcgagg tcctcaacgg cgactgccgc    540

ctcgaccaag ccctcgtccg cgacaagcgc tggtccaact tcgaactcct ctgcatctcc    600

aaaccccgct ccaagctccc cctcggcttc ggcggtaaag ccctcacctg gctcgtggac    660
```

gcgctgaaag cgcgtccaca gggctcccct gacttcatcc tcatcgattg ccccgccggc 720
atcgacgccg gcttcatcac cgccatcact cccgccaacg aggccgtcct catcaccacc 780
cccgacatca ccagcctccg cgacgccgac cgcgtcaccg gcctcctcga atgcgacgga 840
atccgggaca tcaagatgat cgtcaaccgg gttcgaaccg atatgataaa aggagaagac 900
atgctgtcgg tgttggacgt gcaagaaatg ttagggttgc ccttgcttgg ggctattcct 960
gaggacactg aggttattag aagcaccaat agaggctacc ctcttgtgct caacaagcct 1020
cccactctgg ctggcttggc gttcgaacaa gccgcttgga ggctcgtgga gcaggatagc 1080
atgcaggccg tggtggtgga agaacaaccc aaacgagggt ttttctcctt ttttggtggg 1140
tag 1143

<210> SEQ ID NO 13
<211> LENGTH: 1038
<212> TYPE: DNA
<213> ORGANISM: Glycine max

<400> SEQUENCE: 13
atgggcgaac aaccaaaccc ttggaacata ctacagcctc aggtggcgaa gagccgacat 60
cgaggtgcca aaccttccca tccatgtgag atcttaggga agatcagaaa cctttgcacg 120
cctccgttac ctttagggag gcttacgccc catagaaact atctacctga gactatccct 180
cggctcgtag gtcctggaac aaggaaaagc ccaaagccaa tcccaggaaa tagtgaagct 240
tcatatggtc tttctgtcca agtgcaggta gtccgcatct tcacaaacat gtctatttca 300
ccgagtctct ctccgaggca gtgcccaaat cattatgcct ttcatgcgga cgttatagtt 360
acggtcgccg ttcaccgagg cttcggtcat cggatcccct gtcatctggt cactaacttc 420
cttgaccttc cggcacttgg caggtgtcag cccccataca tggtcttacg actttgcgga 480
gacatgtgtt tttgcctcct ccatccctcg agtccaataa agggtagtac aagaatattc 540
accttttgtc catcgactac gcccttcggc cggatcttag gccttgactc accctccgtg 600
gatgaacctt acgaaggaac ccttgggttt tcgaggcatt ggattcttac caacgtttat 660
ggtacactcc cctaccgatt catttttaca ccccacagct ttggcagatc gcttagcccc 720
gttcatcttc ggcacaagag cgctcgatca gtgagctatt atgcattctt tcaagggtgg 780
ctgcttctag gaaaacctcc tggttgtctc tgcaccccta cctcctttat cactgagcgg 840
tcatttaggg gccttagctg tattagagtt tgcctcgatt tggtaccgct ctcatggccc 900
gcaccgaaac agtgttttac ccctagatgt ctagtaaact actgcacctc aacggatttt 960
agggagaacc agctagctct gggttcgagt ggcatttcac ccctaaccac aacttatcca 1020
ctgattcttc aacattag 1038

<210> SEQ ID NO 14
<211> LENGTH: 1905
<212> TYPE: DNA
<213> ORGANISM: Glycine max

<400> SEQUENCE: 14
atgtcatcat caaccacaag cagcagcagc agcaacaaca acatgagcga cgtcgatcgt 60
ttgttcgcat cttttaagtg cggtttaaca cctccaaaat ctgctacgag ggaaagaaaa 120
cgaagcaaga ggagactgga gcaggtgagt tcaaaccacg agactccatc ggaatctccg 180
ggtccaagat cgcctgaaga ggaactgaga accccttat cacgcatcag aaaaaccaac 240

-continued

```
attgaatctt ctattgagaa acttaaatca gcagtaacca gagcacaaag cattggttgt    300
gggaaacagt tctctccaat tgtattttat ggatctccct gtggcatccc tcccaaaaag    360
ccaacccgta tgttatggcg aatgttacgt gagatatgcc ccaatgtctc tcagcaaaat    420
atattgagca taaggaagga agtttggatg acattcccaa ggcaggatga agcaatgaag    480
tttgccaaag gacaagaaga tgttcatgtt ttcagctatc aagaccactt taatggccaa    540
agaaggttcc ttgtgtctac atatacagaa ttctggcgaa ggtacaataa tatgaatccc    600
aaattccgtc atcattatga agtcattcaa gcgggtttac catgtcacct ttattttgat    660
ttggagttta ataagaaagt caacacagga aagaatggag aagaaatggt tgatctcttg    720
atatcagtgg ttctagaagc cttccatgaa aaatatgcaa ttcaaggaga ccacgattgg    780
gtagtagaac ttgattcttc aaatgaagat aagttctctc gtcatataat agttcgcata    840
ccaaagactg catttaagga caactctcat gcaggtgcat ttgtttcaga aatatgctca    900
agaattctaa atgcaaggga gaaagataaa agttttgaaa aattgtttgt aatgaaagac    960
tctagcaaca atgaatctgc aggccaactt tttgtggata ctgctgtata ttcacggaat   1020
cgttgttttc gtctccctct ttcttcaaaa gcaggaaaaa gatcagttct tctgccaaca   1080
aagcgattta agtgcaagga cttgggtgaa gaagacatat tcatggcttc cttgatctgc   1140
aatatggatg ttgattgcaa aacgtatctg gtctgcaaaa cagacttaga ttgtgtgaaa   1200
actctgcatt ttgatacaga ggagaatagt aatgttagta attccaccca aattcctcca   1260
gaatttacat tgggtactag cacaagtgat gtttcaacta catacttcat gggaaagtca   1320
ccattcccat ttctggacaa atttatactg tctgttgcct ctgtcgggaa tataccagga   1380
aacattcata gctggtatta tttctcggaa tttggattga tggtctacag catgacaaaa   1440
aatagatact gtgagcgaat tggcagacag cataaaagca ataatgtgat atatgtggtt   1500
gatctacgaa tggcagtgta ttatcagaaa tgtcatgatc ctgactgcag aggttatcga   1560
tctccctcac gtcaaatccc agttcatgtg ttctccaatc cttcagatgt aattggttcc   1620
tttgggttgt tagatgatga acagccagta gatgataagt tgagacatca acttgatgac   1680
aacaaggagc aaaatctttt acaattcaaa gacactgttg aggacaactc caatgattca   1740
tggtggctag aagccataag agttgtcgag gatatggaaa ataagcaaac aaagacagag   1800
caggaggtaa ttgatgaaga tgaggagtgg tggcaggctg tagaaagtac tgcatcccag   1860
gttgaactta cctgctccag tcaacaagaa ctctgcgcaa tctaa                   1905
```

<210> SEQ ID NO 15
<211> LENGTH: 2142
<212> TYPE: DNA
<213> ORGANISM: Glycine max

<400> SEQUENCE: 15

```
atggaattga aaaagggcaa gcttgccagg ttctacacgg atggtaaaaa gcataagcaa     60
tcgttttggg gagcaagagc aactgagcct ccagcactta aacctagcaa tttgctacca    120
ctagggaaaa atagaattgc tgaaacattt agaattggag gatcgaaggt gttcccggag    180
gaccatgagc cgtggcgtaa aagaatactt gacccgggta gcgatattgt gttgaaatgg    240
aaccgggtct tcatagtttc atgcctggtg gctctttttg ttgatccatt gtacttttat    300
ttgcctagtg taatagaaaa cacagggtct acatgtgtaa ggacagacct aacactgcgc    360
attgtcgtga cctttcttcg cactattgca gaccttttt atctgttgca cctgataatt     420
aagtttagga cggcatatgt ggcaccaagc tcacgggtat ttggcagggg tgaacttgtc    480
```

atggacccaa agaagattgc aaggagatat ataagatctg atttcttcat tgattttatt 540
gccacactcc ctctacctca gatggtcatt tggtttatta taccagcaac aagaacccct 600
caaactgatc acaagaataa tgcgcttgca ttgattgttt tgcttcaata tgttccgaga 660
ttatatttga tttttccatt aagttctcaa ataatcaaag caacaggagt ggttacgaag 720
actgcttggg caggagctgc atataatttg ctgttgtata tgttagctag ccatgtttta 780
ggggcagctt ggtatcttct atccgtggac cgatacacta cttgttggaa atccttttgc 840
aaaaaggaac atgatcctga aaattgcttt ctttatctag actgcacttc gttgaatatt 900
aagctgcgcg agatatgggc aaatagtaca agtgtgttta gcagctgtga tcccagtaat 960
gataatatta atttcaagta tggaatattt gaaaatgcag taaagaaaca tgttgtctct 1020
tcaaacttta tcccaaagta cctttattgt ttatggtggg gattgcaaca attaagttct 1080
tatgggcaga atctagaaac tagcacgttt attggagaaa catcatttgc tattgtcatt 1140
gccatcttgg gtcttgtatt attttcccat ttaattggga acatgcagac ttatttgcaa 1200
tcaattacta taaggcttga ggagtggagg cttaagcgaa gagacacaga ggagtggatg 1260
aggcatcgcc aactccctga agatttgaga agtcgtgtta gacgatttgt tcaatataaa 1320
tggcttgcta ctcgtggagt tgatgaggaa accattctac gtgccttacc tgctgatctt 1380
cgccgtgata tacagcggca tttgtgctta gaccttgtta gaagagttcc cttcttctca 1440
cagatggatg atcagcttct ggatgcaata tgtgagcggc tggtatcgtc tctgagcact 1500
caaggcacct acattgttcg tgagggtgac ccggtgactg aaatgctttt tatcattaga 1560
ggtagactgg atagttctac tacaaatggc ggccgtagtg gtttcttcaa ctcaatcata 1620
ttgagacctg gagatttttg tggggaggaa cttctttctt gggctttact ccccaaatcc 1680
accattaatt tgccttcttc aactaggaca gttaaagccc taagtgaggt tgaagctttt 1740
gctcttcggg ccgaagacct caagtttgtt gctaatcaat ttaggcgcct tcacagtaag 1800
aagctgcagc acacttttcg attttattcc caccattgga ggacttgggc agcttgcttt 1860
atacaggctg cttggcgccg atataagaaa aggatgacta tgaaagacct cagtttgagg 1920
gaaaccattc ctttagacga agcagtagct ggtgagagaa aacatgggga ctattctgct 1980
ggttcaaatt caactcagac taaattgaac cttggggcta caattcttgc ttcgagattt 2040
gctgctaaca cacgaagagg ggctctgaag atgaaagatg acatgcccca gttacagaag 2100
cctgaagaac ctgacttttc cactgaagct gacgatgatt ag 2142

<210> SEQ ID NO 16
<211> LENGTH: 1068
<212> TYPE: DNA
<213> ORGANISM: Glycine max

<400> SEQUENCE: 16
atgaaacggt tttcaaagt ggtggagaaa gattcagatg ggtctgtgaa gaagccaaga 60
gagaatgatt cggaggctga agaaagtaat gagaagaagg agccgttgaa gtttatgact 120
tggaatgcca acagctttct ccttcgagtc aaaaacaact ggcccgactt caccaacctc 180
atcaccactt ttgatcctga tctcattgcc atacaggaag tgcggatgcc tgctgctggt 240
gccaagggcg cgtctaaaat tcagggagaa ataaaagacg atacaagcgc ggccagggaa 300
gaaaagaaga ttttgacacg tgcactttct gctccacctt ttgggaacta tcacgtttgg 360
tggtctcttg cagattcaaa gtatgcaggg acagcactac tggtgaaaaa atgcttcaag 420

-continued

```
ccaaaaagtg ttgttttcaa tcttgataaa ttagcttcaa agcatgaacc agatggtcga    480

gtaatcctag ttgaatttga aacacttcgt ttattgaata catatgtacc aaataatgga    540

tggaaagagg aggcaaactc atttcaaagg agaagaaaat gggacaaaag gatactggaa    600

tttgttacac aaagttcaga caagccttta atatggtgtg gggatctgaa tgtcagccat    660

gaagagatcg atgtgagtca tccagacttt ttcagtgtgg caaaactcaa tggttatatt    720

cctccaaata aagaggactg tgggcagcct gggtttacct tgtctgaaag aaaacggttt    780

ggtaccattt taagagaggg gaagctggtg gatgcctaca gatttctgca tgaagataag    840

gacatggagc gaggtttctc atggtctgga aacccagtgg gaaggtatcg tggaaaacga    900

atgagaatag actacttttt agtttcagag aagctaaaag aaaggattgc tgcatgtgaa    960

atgcgtggac atgggataga gttagaaggt ttctatggaa gtgatcattg tccagttacc   1020

ttggagctct ctcctagttc taactctcaa aatgaggatc caatataa                1068
```

<210> SEQ ID NO 17
<211> LENGTH: 1089
<212> TYPE: DNA
<213> ORGANISM: Glycine max

<400> SEQUENCE: 17

```
atggctattc gtgtaacctt ttccttttcg ggctatgtcg cccagagcct cgcctcctcc     60

gccggcgtgc gcgtcgccaa ttcgcgttgc gtccaggaat gctggatccg tacgcgcctc    120

tctggcgcca cccagaagac ggatctagat tcctccgccg gcggagtccg caattttgcc    180

gggcccaagc ccaactgctg ggcccagtcc acttactcca ccctcaccgg ggagttcctc    240

ggcgacggct gcaagagccc aatcatattg ggcctgattt cgatcatgaa gtcaacggcg    300

ggtgtgtctg ggtcatccgc ggcggctgcg ggtattttcg gtatttcgcc cttcaaaacc    360

acttcgatcg ttcccttctt gcctggttcg aagtggcttc cttgcaacga gtccgttccc    420

gaccccacca cttcctggga ggtcgacaaa ggtggcacgc gacgcgtcgt ttcggacacc    480

gaatccaatt ttgccaagac tagttggctt tcgcggttga tgaacgtgtg ttccgaagac    540

gcgaaggctg cgttcactgc tgttactgtt agtttgctct ttaaatcgtc cttggctgaa    600

ccaagatcaa ttccctcttc ttctatgtac cctactcttg aagtaggtga ccgtgttcta    660

accgagaagg tttcgttctt ctttagaaag cctgatgttt cggatatagt catttttaaa    720

gcgcctcctt gtttagagga gtttggtttt agttcgtctg atgtgtttat aaagaggatt    780

gtggctaagg ctggggacac tgttgaggtg cgtgatggga aactactggt aaatggtgct    840

gctgaagaac ggcaatttgt agtagagcct ctagcttatg agatggatcc aatggttgtg    900

ccagaaggat atgtgtttgt aatgggagac aatcggaaca acagctttga ttctcataac    960

tggggccctc tcccagttga gaacattgtt ggtaggtcca tgtttcgcta ctggcctcca   1020

tccaaagtat ctgacactga taccctaagt aaactcccac ctgggaacaa acctgtggca   1080

atttcttga                                                           1089
```

<210> SEQ ID NO 18
<211> LENGTH: 2115
<212> TYPE: DNA
<213> ORGANISM: Glycine max

<400> SEQUENCE: 18

```
atgttgacaa ttctacgtca tgccacacgc aaaagagtaa gagcaacact tattaaaccc     60

ccaccgaatc tactccaaat ctcatccact tcagtaaaca gtcacactta cactatcaca    120
```

-continued

```
cagcattact ctcactcaac aacaatgttg ccgccagcgg gaaccatcgt attcaacacc    180
gtcggaagag tccaatacgg tttcgacgtt ttctctgtcg acctcaatca ccaacagcct    240
ccgccccacg ccaccgcaga ccaccgcctc accgacggtg tctcgattaa cttcaacgca    300
caattcatta acccccaaaa cgacgtcgtc ttcgtatccg aaagaaccgg gtcgccccgc    360
ttctacatta caaaacccga cactaaaccc cagcctttac cctttctgcc caacgctctc    420
ttccacgatc gcccaatcgt taaaaacgga aagctctact tcgtttccac gcacgaagaa    480
aacgacgccg ttttcactag ctggagcgcc gtttactcca ccgccataga tgactccacc    540
gccaccgtca agagactcac cccgcgcggc gaggtggact acagccccgc cgtctccctc    600
accgggaaat tcctcggcgt cgcttcttac cgctctcgcc gctggcaaac caacgatttc    660
cgcgaactcc aaacggagat cgtcgttttc cccgagtccg atccaaaaaa ccgagtcacg    720
gtgagcgagc gcggtggctg gccatcgtgg tcccaagatt caaccatttt cttccaccga    780
atcgccgaag atggatggtg gagcatcttc cgcgtcgatt taaccgattc cgaactttca    840
gaatctcgaa actcgccgat tcgcgtcacg ccgccggggt tgcactgttt cactccggca    900
gctttccacg acggaaagcg cgtcgcggtc gcaactcgcc ggagagaaag caatttaagg    960
cacgtcgaaa tcttcgatct cgaatcgcaa acgttccaac gaatcaccga agacataaac   1020
cctaacttta accattacaa cccgttcgtc tcgttggact ctcgccacct cgggtaccac   1080
cgattccgag gcgagtcgat tcagggcgag ccaatatacc cgcacctcga caaagtcctc   1140
tctccggttc gcgacctaca gttactcaga ctcaacggtt cgtttcccac cttctccccc   1200
gacggcgatt tcatcgcttt caaccacggc ttagacggca acgttaacgg cggcgttaaa   1260
atcgttaaat cgaacggttc caaacgctgg acgttgctca aaggacgaac gtgcttccac   1320
aacgcgtgga gcccaacgga gaagaacgtg atatacacct ccgtcggtcc aatcttcgag   1380
tcggtttata aaacggttca aatcgcgcgc atcgagttcg acccggttca tttaactaac   1440
gaccgtgaag aggttccgtt taagttaacg attctcacga gagaagacac agggaacaat   1500
gcttttccgt catgctcccc tgacgggaag agcattgtgt ttcggtctgg aagggaagga   1560
tacaagaact tgtacatagt tgacgctgtt aaaggggagt ttgacggcgg gataaggagg   1620
ttgacggagg gggagtggat cgatacgatg ccgtgttggt cgccgaaagg ggatttgata   1680
gcgttttcat cgaacaggca tgaccctaag aatagtgagg tgtttgggat atatttggtg   1740
gggccaaatg ggagtgggtt gaggagggtt gaggtggcaa agggggtcga aggaatgaaa   1800
gagaggttga accacgtgtg cttcagccgc gacggagagt ggttgctgtt cacggcgaac   1860
ttgggtggcg tgagtgcgga gccggtgggg ctgccgaacc agtttcagcc gtatggggat   1920
ttgtatgtgg tgaggttgga tgggagtggg ttgaggaggc tgacgtgtaa tgcgtatgag   1980
aatgggacgc ccacgtggca ccatggggat ttggcgctgt gtgctcctag agaagatgat   2040
ggcgaaggag gtcaggattg ggataagttg aagggtgagt ttcaagaacc actttggatc   2100
acgtgtgata tttga                                                    2115
```

<210> SEQ ID NO 19
<211> LENGTH: 2463
<212> TYPE: DNA
<213> ORGANISM: Glycine max

<400> SEQUENCE: 19

```
atgagcacaa gtgtgcttcc ctctctcctg ttcttcctag tcctcatcct cttgctactt     60
```

-continued

```
gacccttctg aacccgaaaa cgtagccatt tactggggtc aaaacgccga cgagggaact    120
cttaatgaaa catgtgcaac agggacatac tcgcatgtaa tcatagcctt cctttccacc    180
tttgggaatg gccagacccc tcaactcagc ctggctgatc attgtgaccc ctctactaat    240
gggtgcacta agattgggag agagattaag aattgtcaag agcaagggat cacggtgatg    300
ctctctattg gaggaggatc tggtaattac tctataactt ccgatgagga tgccaacaat    360
gtgtccaatt atttgtggga taatttcttc ggtggcttct cctcatcacg cccatttggt    420
gatgcagttt tagatggcct tgactttgac atcgcgctgg gtgataatac atctttcatg    480
gcaaatcttg cacaatatct caaatcaaat tcagattcac agacgataca acaaaaacaa    540
ctacctgcat ctttgtactt gtcagcagca cctcagtgtc cgtttcctga tgctaggctg    600
ggttcggcca ttggtaccgg cattttttgac tatgtctggg tacaattcta taacaaccct    660
tcgtgcagtt atagccaaaa caatttagat aactttctaa aatcatggag agagtgggcc    720
acatcattga aagtaggtaa actgtttctg gggttaccag cagatgaagc tgcagctccg    780
gccggaggtt atgttccggc tgatgtatta atgtctaaga tcttacctga aataaacaag    840
tcaacaaatt atggaggtct catgttgtgg tcaaggtact acgataaaat tagtggatac    900
agtacccgca ttcaaaatcc tctaagaaat gggacagcaa accctctatg cacacggaaa    960
agtcaagcat gtaggagcca tgagggcggt ttcgcggagc ttcttggtta catgtccacg   1020
ctcggtatca aagtttatga agacgacaac aatggaacac agtgctgtga gatcatatgt   1080
aggaacaact gttcctgcga cgcgtttgct cccttaaatc acattaacaa tactagtact   1140
ggatgtcaga tatggctcaa aggaaccaaa tttgttagag cttctggaaa tatagctctg   1200
ccaatcaacg tttctgttgc attgctggaa cacaaagtaa acagctggtg gatttggctc   1260
atcgttgggg tgggagcagc ttttgtaata cctgtgatat tctatttatc gcgtgccttc   1320
ctgagaaaat acaaagcaaa agtggagaga aaaaagatgc agaagaagtt attacatgac   1380
attggaggta atgcaatgct tgcaatggtg tacggcaaaa ccataaaaag taataacaag   1440
ggaaagacta acaatgaagt tgaactattt gcttttgata ccatcgttgt tgccacaaac   1500
aatttctcag ctgcaaataa gttaggagag ggtggttttg gtcctgttta taagggaaat   1560
ctaagtgatc agcaagaagt agcaataaag cgactttcta aaagttcggg acaggggcta   1620
atagagttta cgaatgaagc caaactcatg gccaaactcc agcacactaa tctggtaaag   1680
cttttagggt tctgcatcca gagagatgaa agaatattgg tctatgagta catgtctaac   1740
aagagcttag acttctacct atttgattcg gctagaaagg atttgctaga ctgggaaaaa   1800
cggttgaaca tcattggagg aattgctcaa ggacttctat accttcataa gtattcaaga   1860
ctaaaggtga tacatcggga cctaaaggca agcaatatat tgcttgatca cgagatgaat   1920
gctaaaatat ctgactttgg catggctcga atatttggag taagagtatc agaagaaaac   1980
acaaatagag ttgttggtac atatggatat atggctccag agtatgcaat gaaaggtgtt   2040
gtgtccatca aaacagatgt gttcagcttt ggtgtgttgc tactagagat acttagtagc   2100
aaaaagaata atagtcgcta tcattcggat cacccactca acctcatagg atacgcgtgg   2160
cagctctgga atgcaggcag agctctggag cttatagact caacgttaaa tggattgtgt   2220
tctcagaatg aagttttcag atgtattcat attggcctct tgtgtgtaca agatcaagca   2280
acggatagac ctacaatggt agatattgtt tcatttctat caaatgatac aatccaactt   2340
ccccaaccaa tgcagccagc atacttcatc aatgaggttg tggaagagtc agagcttcct   2400
tacaaccagc aagaatttca ttccgaaaat gacgtaacaa tttctagtac gcgtgcaaga   2460
```

taa 2463

<210> SEQ ID NO 20
<211> LENGTH: 552
<212> TYPE: DNA
<213> ORGANISM: Glycine max

<400> SEQUENCE: 20
atgccaattg ttcagaaatt gtatgatacc tgcaaggcat ctttgtctcc tgagggaccc 60
atttcagagg aagctctgga aaaagttcga atcattttag ctgagttgaa gccttctaat 120
gtgggtcttg aacaagaggc gcaattgatg gaaatcttct gtaggtctcc aggttctgtt 180
atcccgcttc ataatcaccc cggaatgact gttttgagca agcttcttat tacttgtaag 240
gtcatatgct gggtttactc tgggttcgat gatccatctc aagcaagacc agcaaaactt 300
atgaaagatt gtctgatgag tgcaccctgc aacacaacag ttcttcatcc aagcaaaggt 360
ggcaacattc attgtttcaa agccttaacc ccatccgctc tctttgacat tctttcccct 420
ccttactcat cagaagatgg aagacactgc tcatatttca ggaagtcaac taggaaagat 480
cttccaggtg ttgagcatga tcagctgagt ggggtaaagc catctgaaat aacctggtca 540
gaagagatct aa 552

<210> SEQ ID NO 21
<211> LENGTH: 3180
<212> TYPE: DNA
<213> ORGANISM: Glycine max

<400> SEQUENCE: 21
atgataaagt atttcaattt caatcgagga agggacaatg ccgccgatgc ctcaccggcg 60
gcgacgcctt cttcgtcccc ggtgaccggt ccggcgaggc caattcgcct tgtctattgc 120
gatgagaatg gacggttccg catggacccc gaagccgtcg ccacgcttca gctcgtcaag 180
gaacccgtcg gcgtggtctc tgtgtgcggc cgtgctcgcc agggcaagag tttcattctg 240
aatcagcttt tggggaggac tagtggattt caggtagcat caacacatcg accatgtacc 300
aaaggactat ggttgtggag tgcaccgttg aagaggactg cccttgatgg aacagagtac 360
aatctcctgc tattagacag tgaaggaata gatgcttatg atcaaacggg aacatacagc 420
acccagatct tctccttagc tgtccttttg tctagcatgt tcatttataa ccagatgggt 480
ggtattgatg aggctgccct tgatcgactt tctcttgtca ctcagatgac aaagcacatt 540
cgtgttagag catctggagg aaggagttct acatctgaac tgggacagtt ttcccctatt 600
tttgtttggc ttctaagaga cttctatttg gacctcgtag aagataacag aaaaataaca 660
ccccgtgact atctggaaat tgctttgagg cctttccaag ggagtggaaa agatataact 720
gctaaaaacg agattcgaga ttccattcgg gctttattcc cagatagaga atgcttcact 780
cttgtgcgac ctctgaacga tgaaaatgat ctacagcgac ttgatcagat atcgttggaa 840
aaattacggc ctgaatttcg atctagcctg gatactctga cgaagtttgt ttttgagaga 900
gcaaggccaa aacaagttgg ggcaactatg atgacaggtc ctgtgttgat tggaatcact 960
gaatcttatc tggatgctct caatcatggt gctgtgccta caatttcttc ctcctggcag 1020
agtgttgaag aagctgagtg tcgtaaagct tatgattctg ctgccgagat ttatatgtcc 1080
tcttttgact gtactaagcc tcctgaggag gctgctttga gggaagcaca tgaaaaggca 1140
gttcgaattt caatggcagc ctttactgct agtgctgtag ggttggttc agtaagaaca 1200

-continued aaatatgaag gcatgctgca gaaattcctc aaaaaggcat ttgaggatta taagaggaat 1260
gcgtatatgg aagctgatct acaatgctct aatgccatac agtctatgga aaagaggcta 1320
agggcagctt gtaatgcttc cgatgcaaag atagataatg ttgccaaggt tcttgatgct 1380
cttttatgtg aatatgaaaa atccattcaa gctccagaga agtggcaaaa acttgctgtc 1440
ttcttacaac aaagttttga aggcccggta ctagacctaa ccaggagact gataaataaa 1500
gttgaatctg acaagagttc tctcagttta aactatcgat tgactgaaga taagattgcc 1560
ctgcttaata agagactgga aaccagtgaa agtgaaaagt ctgagtatat taaacgctat 1620
gaggatgcca tcaatgataa gaagcaacta actgatgaat atatgaatcg cattactgaa 1680
ctgagggcta gctgtcgctc attggatgag agatattcta gcttatcaaa aacattggat 1740
tctaccaagc aagaatccat ggattggaaa agaaaatatg aacaagtttt atcaaggcat 1800
aaatctgagg aagaccaagc tagttctgaa atagcagccc tcaagtcaca tagtagtgct 1860
gctgaagcaa ggttggctgc agcaagggag caatcccagt ctgctcagga ggaggctgaa 1920
gagtggaagc ggaagtatga aattgctgtt agagaagcaa aagctgctct agagaaggca 1980
gcaattgtgc aggagtacac aaacaagcaa tcacaattga gggaagatgc tttaagagag 2040
gaattttcta gcactttggc tgaaaaggaa gataaaataa aggagaaaac tgccaaaatt 2100
gagcatgctg agcagtgttt aacaactttg aaattggaat tgaaggctgc tgagtcaaaa 2160
ataagaaatt atgagtcaga gatatcacca ctgaggcttg aaattaaaaa gttgattgag 2220
agattgaaaa ctgaaaatgc tagggctcag tcatatgaga aggatgtaat ggtaattcaa 2280
caggagatta accatctaaa ggagaagtac aacaccgagt gcataaaatt tgaggaagtt 2340
caggaaagat gtcaaattgc tgaaaaagaa gctgtaaggg ctactgaagt agctgacaaa 2400
gctagggctg aagccaactt ggctcagaag gagatgagcg agatgcagag gcttgcaatt 2460
gagagactgg cacatattga aagggctgag aggaaaattg aaaatttgga gagggagaaa 2520
gataatttgg aaggtgaatt gcaaagagtg agggattcag agaaagatgc acttgttagg 2580
gtttcaacac tagaggaaaa ggtgggacag agagagaagg atatagattc actcttggag 2640
aaagatggaa cacagaggcg aaatagcaca cagattcttg atcaactttt ggaaacagaa 2700
cgtgaagcat gtgctcaggc aaatagcagg gccgactctc tctctctcca gttacagtct 2760
gcacaagcaa aaattgattc tctccatcaa gaactgacta agtttcaact gaatgaaaca 2820
atattggaca gtgagctaaa aactgcctct cgtggaaagc gtttgagggt agatgatata 2880
ggtgtagaat ctggtcagga catggattcg agccctagaa tcttaagggg aactaagaga 2940
tctaagagta catctagtcc acttaagttt tcacatctgg aagatgttag ttccattgga 3000
ggtgatgaag acaactatag tcagcaaact aacgaggatg attataaaaa gtttaccatc 3060
cagaagctca agcaagagct gacaaaacac aactacggtg atcagctgct tgagttgaag 3120
aatcccaaca agaaagctat ccttgctctg tacgagaaat gtgttcttca gaagtcatag 3180

<210> SEQ ID NO 22
<211> LENGTH: 960
<212> TYPE: DNA
<213> ORGANISM: Glycine max

<400> SEQUENCE: 22
atggcttatg aaccaccatt cctcgagacc tacaagaccc ttgtgcaaca acacttaggg 60
gattcaagga atgagttcat agtagagaga tgtgatatac ctttgatcga ccttggccgg 120
ttaagtcttg agagagaaga atgcatgagg gaaattgcag aagctgcaag agaatggggt 180
ttctttcaag ttgttaatca tggaatttca catgagcttc tgaagagcct gcaaattgag 240
caaaagaaag tgttctatca accctttctg aacaagtcat caacacaagg caaagcttac 300
aggtggggga atccatttgc taccaatctg agacagctgt catggtcaga agcctttcat 360
ttctatctga cagacatctc aaggatggac cagcatgaaa ctctgagatc aagccttgaa 420
gtttttgcaa taacaatgtt ttcccttgcc caaagcttgg cggaaatact agtttgcaaa 480
ttgaatacga aatccaacta tttccgagag cattgcttgc caaaaagttc tttcattcga 540
ctgaatagat accctcaatg ccccatatca tcaaaggtgc atggcttgtt gcctcacagt 600
gacactagtt ttcttaccat tgtacatcaa gaccaggttg gggattgca attgctgaaa 660 gatggaaaat gggttggtgt caagcctaat ccacatgccc tggtggttaa tattggtgac 720
ttatttcagg cattgagtaa tggtgtttat aaaagcataa aacacagagt ggttgctgct 780
gagaaagtag agaggttttc tatggcattt ttctattccc cctctgagga ggcaattata 840
caaagccaaa tcaagccacc tatctacaga aaattcactt tgagggagta tagacaacaa 900
acagagaaag atgtcaagca aaccggggat aaagtggggc tctctagatt tcttctgtag 960

<210> SEQ ID NO 23
<211> LENGTH: 525
<212> TYPE: DNA
<213> ORGANISM: Glycine max

<400> SEQUENCE: 23
atgttaggat ttgacgatgg tgattctgat tccgacaacg agcaggcact gtttgggaag 60
tacccggagc tacagatgtt taagtgggag aacagtctca ttcaccttcc ttccaattta 120
tcatctttgt tattgccgca gacaccactg tttcactgtg agcgtgaaga aaccctcagg 180
gttcaccctc ctccctttct tccgttgcaa gaaaccctcg atcatctgtc agcgaacact 240
gcccctactc aggacatcac ccatcttcaa caggcacgcc cagcgaaccc accccccact 300
tcatcaccat ctcccaatct ctgcaagaga tggaccaatg aagaacacag gctgtttctt 360
gaagggcttg cctactttgg caagggtgat tggaagaaca tctcaaaaca tgctgttaag 420
acaagaacca agactcaagt tgctactcat gcccaaaaat atttcttca cataaaggaa 480 aagggaaagg gaaaaagaaa gagcctcttt gacatggcct tgtaa 525

<210> SEQ ID NO 24
<211> LENGTH: 4827
<212> TYPE: DNA
<213> ORGANISM: Glycine max

<400> SEQUENCE: 24
atggaacctc ctgtcgtgag atccaggggc cgcccacgca aacggaggag agaagacgaa 60
gcaaccgtca ctggtgacgc gaaaacgctt cccgaggcaa agaagacgac gccggttgca 120
ttgattggac gatacgtgct aaaagagttt cgaagaaaca cggttcttct aggcaaagtc 180
gcgcgttatg ttagtggact gtacagagtc gtatatgaga gtggcggttt cgaggattta 240
gatagcaacg agattcgtag gatacttctc cttgatagtt atttcgacga cgatttgatt 300
cggaggaagg ttgaattgga ggaatcggtg ttgccgaaga tcacagcaga ggaaccggag 360
aaaggttcga gcgaattgca aggtgaatta tcggttgaca atgaagagga acgagctgag 420
acggatgatg atgaggccag ggattcgagt tccggtgcgg aaatgccgga aaaggcgata 480
ccgtcgccgc tgatgctgcc gccgtcttcc ggaacaattg gcgtgccgga accgtgtgtt 540

-continued

```
ttgaatctct tttcggttta cggattttta agatcgttta gcattcgcct gtttcttagt    600
ccgtttactt tggacgagtt tgttggtgct ttgaactgta aagtttcgaa tgcgttgctt    660
gatgcaattc acgtttcgct gatgcgtgtt ttgaaacgtc accttgaaaa catttcacca    720
gatggctcgc ggcctgcaac aaaatgcctt aggtgcagtg attggagttt ggttgatgct    780
ttgacttggc ctgtttttgt gtttcagtat ttagcaattt ttggatacac aaaaggacct    840
gagtggaaag gattttatga cgaaatcttt tatggcgagt attatttatt gcctgcaagt    900
aggaaattga cgatattgca aattctctgt gatgaagttt tggcgtctga ggagctaaaa    960
gctgaaatga acatgcgtga agaatcagag gttgggattg atcatgataa tgaagattgc   1020
cttcctgctg aaaatgggcc tagaagagtc catccaagat attccaaaac tactgcctgc   1080
aaggatgctg aaactaagaa gtatgtttca gaattgaatg ctgaggagga tgatgttgat   1140
ggcaatggag atgaatgtcg cttgtgtggc atggatggga ccttgctttg ttgtgatggt   1200
tgtcctgctg tttatcattc aaggtgtatt ggtgtgatga agatgcatat accagaaggg   1260
gcatggtatt gtccggagtg caaaatagat atgattgggc ctactattgc acggggaaca   1320
tcacttaaag gggctgaagt attcggaaag gatttgtatg ggcaagtttt catgagtact   1380
tgcaaccact tactggtgct caatgtcaac agtgatggct tttgtcttaa atactacaat   1440
cagaatgaca tacctagagt tctccaagtc ctttatgcat ctgagcaaca tagacctata   1500
tacaatggta tttgcatggc gatgttagaa tattggaata tttcagaaaa gttcttaccc   1560
atttgtgtca gtagactaac tcctatggtc gaagaagagc ataaagctgt tagttcggtg   1620
aaggaagaat acagtttaat gtttgggaat gggatttgtg gtgataattt ggtgccatct   1680
cttgatgctt cattggttac aactcgaagt cctgctcctg gaagcagtgg caatgcaaga   1740
actactgtga atctgaagct taatgaggaa actgcaatgg attcgactgt ttcaactgtt   1800
aaccatcatc actctgaccc aaagtgccaa aattctgtta ataggtcagc tgcagtaagc   1860
cctgtcaagt gctccttggt aagcagacaa tttaataatt atgggcacgc aaatgacgta   1920
gggttgccta tgaatttgtc tttgcaaact aaaggcgacc aatctggttt tggaaagtgc   1980
aaaggcagtt taactaatga ttttgtgtac atgggttgct cctataaacc acagtcatat   2040
attaattact atatgcatgg tgatgttgct gcgtctgctg ctgctaacct ggccgttctt   2100
tcttcagagg attctagatc agaaggtcat gtgtctggca acttggggaa agcaacatct   2160
ggaaacactt atttgctagc aaaagcattc tcccaaacag cttcacgctt cttttggcca   2220
agttctgaaa agaagcttgt ggaggttcca agagagaggt gtggctggtg catttcttgc   2280
aaagcctctg tttcaagcaa gaaaggatgc atgttaaatc atgctgctat aagtgccacc   2340
aaaagtgcaa tgaaaatcct ttctggtctt gctcctgtaa ggagtggaga aggaatcatc   2400
cctagcattg caacatatgt tatgtatatg gaggaaagtt tacgtggctt aatagttgga   2460
ccctttctga gtgaatgtta tagaaagcat tggcgtaaac aagttgaacg agccaaatca   2520
tttagtgata taaagcccct tttactcaaa cttgaggaga acattcgaac aattgctttt   2580
tgtggagact gggtgaagtt gatggatgat tggttggctg aattttctac aatgcaaagt   2640
gctacatgta ctcttggaac aacacaaaaa cgtgcaactt gtgggaagcg taagaaacag   2700
ttatctatca ataaagttac agttggtggt tgtcaggaaa attttgcatg gtggcatggt   2760
gggaaattta ccaaatctgt atttcagaaa gctgttttgc caaaatccat ggtaaaaaaa   2820
ggagcccgcc aaggtggttt gaggaaaatt tcgggtatat tctatgctga tggctctgag   2880
attcctaaaa gaagcaggca gctagtttgg agagctgcag ttcaaatgag taggaatgca   2940
```

-continued

```
tctcagctgg cacttcaggt ccgatatcta gattttcata tcagatggag tgatctgatt   3000

cgtcctgagc ataacctcct ggatgtgaaa ggtcaagata ctgaagcttc tgcttttagg   3060

aatgcaaata ttcgtgataa aaaatttgca gagggaaaat ttttgtacag agtagccttt   3120

ggaatccaga aacatcttcc ttctcgggta atgaaaaatg ctgaaataga gcaaggtccc   3180

gaaggaatgg aaaaatattg gttttctgaa acacgcattc ctttatattt ggtaaaagag   3240

tatgaagtac gtaatggaaa agtgctatct gagaaagagt acatgcatat tacatctcat   3300

atgcacaaaa ggcggttgac agctacctac aaggacatat ttttttacct tacctgcaag   3360

agagacaagt tggacatgtt atcatgctct gtatgtcagc tgggtgtttt aattgggaat   3420

gctctcaagt gcagtgcttg tgaaggttat tgtcacatgg ggtgttccgt gagttcgaca   3480

gtctctacat gtgaagaagt tgagttcttg gccacatgca aacaatgtca tcatgccaaa   3540

ttacttactc aaaaacagtc ctgttatgaa tctccaacta gtcccttact tttacaagga   3600

caagaacgta gcacttcggc agttctgaag ggccaaggc ctaatggtga tggtcaagga   3660

ttgatgtctg ctaagacaaa gaatagtcga cttgacatga aacgagttgc ttctgatttc   3720

cctttggaaa caaaaggccg tagcagaagt tgctcttggg gtattatatg gaaaaagaag   3780

aataatgaag atacaggctt tgatttcagg ctcaagaaca ttcttctaaa ggaaggttca   3840

ggcctgcctc aactggatcc tgtttgtcgt ttgtgccata aaccatatag atctgatcta   3900

atgtatattt gctgtgaaac atgcaaacat tggtatcatg ctgaagctgt tgaacttgaa   3960

gagtccaaac tttttgacgt gctgggcttc aaatgttgca agtgccgcag gataaagtcg   4020

cctgtgtgtc cttactctga tttgtacatg atgcaagggg gcaagaagtt gctcacaagg   4080

gcttcaaaga aagagcactt tggggcatat tctgattccg gtacacctat cgacatgaga   4140

acatgtgagc ctgcaactct tatctatcct gcaggggatg tctctagaca agacaatgat   4200

cctctgtttt tctccctttc aagtgttgag ctgattacag aactccagtt agatgcagat   4260

gatgcaggta atactgtctc tggtccaggg cttccgaaat tacctaaatg ggagggggag   4320

aataatggtt cttttatagg taatcttcat gctgagtttt caacaagcaa tgcaatggtg   4380

tccaaatctg taaaagattt atcacctgta gaatatggct ctgcggactg caatcttctg   4440

aataactctg aaattgtaaa ttttgatgaa ttggtggatt ttgaacctaa tacctacttc   4500

tctctgactg aactgctcca ctcagatgat aatagtcaat ttgaggaagc caatgcatct   4560

ggggacttct cagggtattt gaaaaattct tgtacattag gtgttcctga agaatgtggg   4620

actgttaatt tagcatccaa ctgtggatct acaaattcgt tacaaggaaa tgttaataaa   4680

tgtcggcaat gttcacaaaa ggaaccggcc cctgatctct cttgtcagat ttgtgggatt   4740

tggattcaca gccattgttc accttgggtt gaatcaccat ctcggcttgg tagttggaga   4800

tgtggtgatt gccgggaatg gcgatag                                        4827
```

<210> SEQ ID NO 25
<211> LENGTH: 2625
<212> TYPE: DNA
<213> ORGANISM: Glycine max

<400> SEQUENCE: 25

```
atgaacagaa aaattaatga caggttgaaa ccggagaaag cttctttgtc atacgctgat     60

tttcatcatg aaattaccaa aaatgtggaa gacaactctt taaaacctta ccgaaataag    120

caaaagcaag caacttatcg aagggcaagt gaggaagatg agctggttaa gtatatgtcg    180
```

-continued

```
aatctaccag gttacttaga gaagggagaa aaaattcccg ataaagcttt gaatgttggg    240

gtgcttgatt gggccactct acaacaatgg cagtacagcc ataaacattt gcccttaagt    300

agccggagct cgacatctac tggtaataca tcatcttctg tttcagcaga ggaattatct    360

ggtaattcta gcaaaggtcc tgtttgttct ccttcacgtc aaagaatatt tcgtccgtcg    420

ctgaaatctc acttcatggc atctccaatg caagactact ctgcatctgt caaatcctct    480

ggagggagtt ttggaaattg tcagaatctt agaggtgggt gcagtaatat tgacacacac    540

ggcaaatatg ctcaagttgg tgatcatctt tcccaaaacc atcctgctag tataccaaaa    600

ggatgtgaca ggagacaact gaatccacat attagtaaag aaagtgatat cttgccaaat    660

gggggaatgt atgaggcagc atcacatact acgactgaaa tgagctctca agatgataga    720

ccagaaaaga aagtggagaa tttcagacaa ccaaacattg atgctgatga gcaagttatg    780

cttgggaaaa gcaaacctat tgttcttatt ttgcctagag acattcccca gaataatcat    840

tgtgaagttc ctgatatgca aacatccttg ggtcaaaagc taggaagtcc cactggaaca    900

agattttcag aaaaacctaa ggaacctccc tgtagatatc caaattccaa tatttccaaa    960

acatgtcctc tgccagatga aattagagga atccgttatc agccggaaag gtcaggatct   1020

agttccacag atccagaagg tattaaaatt cctgcttcta ctttatcagc acctgtacca   1080

gtcagaacag ggataataag tccatgcaga tctagaaagg ctgaggaaaa gaaacacaac   1140

attggtgcat cttcatctgc aaatgggtct ctcaagggat tagatcagaa agtaacaact   1200

gagaaaccaa gaagttcttc accttttcgg cgatttagct tcagcattgg ctttacaggt   1260

aaaggttctg gctgtaaaga ggttgcacat gtgccacatc agagctccat agcagcactt   1320

aaatctagtt cagaaaatgt gagaggttat gctagctcaa aaatttcagg caatgataaa   1380

cctggtaatg ctgtcaaaag caggtctagt agccctttaa ggagactact ggatcccctg   1440

ctgaaaccga agacatcaga ccatcgctcg gtggagtcat ctcaaaaaga ttcagtggta   1500

ataaagaaga attgtaggtc agctaatggg ggatttgcta tggagaaaga actggacagg   1560

gaccagaggg ttggttgtac aaatacagca attaatacag ttgatttatc aaagaacaag   1620

aagtatgtgc cgtcaacgtt tcaagctctt ctaagaattg ctgtgaagaa tggtcagccc   1680

cttttcacat ttgctgttga caataatagc aacattcttg tggccacagt gaagaacttg   1740

gctgtctcaa aggaagacga atgcaatcgt atctatacat tttcacctt tagggaggga    1800

aaaaagaaga acggaagttg gatgaatcaa gcaagcaaaa cccaaggtcc cgattatatt   1860

catcatgctg ttgcccaaat gaaggtttct gattcacacc attatgattc aactagccag   1920

aattgtgtgg actcctctac atcaaaagag tttgttttgt tttctgtaaa gttaaagcag   1980

ggagatgctc aggtcactga ctacaaacca aatgatgagc ttgctgctat tgttgtcaaa   2040

tcagctaagg ctgtcaattt tatcaattat gcacatcaga gcagtcgcca gaatgacagt   2100

caagatctac atgtaacagt tgtgctccca actggggttc acagttttcc aagtaacgga   2160

ggaccttcat cactgattga gcgctggaga acaggtggat catgcgactg tggtggttgg   2220

gatatggctt gtaaacttaa gattcttgca aatgaaagtc aagcatgtag aaaatcaaga   2280

atatcaaaag cttgtttccc acatccattt gagcttttcc tccaggtgaa tgaccaagac   2340

ctagagaacc agcctgcttt cagtttttcc ccctttaagc ctggggtata ttcggtagct   2400

tttgattcct cattctcact tttgcaagca ttctccatct gcatagcgtt agttgatggc   2460

ttgatctcat atgaactttc tggatcaaga aactacatcg aaggaaaaaa ttcgagagaa   2520

actctgttgg tgcaaacaga tgaactaaag gcttttggca aattagagga cattcctgca   2580
```

-continued

```
agttatgttg cttatcctcc cctctctcca gttggtaggg tctaa                 2625


<210> SEQ ID NO 26
<211> LENGTH: 1983
<212> TYPE: DNA
<213> ORGANISM: Glycine max

<400> SEQUENCE: 26

atggatccct cacgccgtgc cccacgcgcc gtgatcgacc ctataccgaa gatccgccaa     60

gtggggttct ttgccccgcc cgagcgctct cagtcgggtc ctcccgaccc gacccactcc    120

tctcccccga tctccagctc cctctccccg gtcatgatcc cgcccccgcg ccacctctcc    180

gacaacctcc ttctccacgc cccccgcccc gcctcctccc ccctctccgc cgccgctgcc    240

gccggaggaa gcggaaactc ctttgactac ggcgcggtct tcttccccgc cccgctctct    300

cccgcgatac cgtcgtcttc gtactccagc agaatcatcg ccaccaccgg cgagggaggg    360

ttcttcaagg ggaacggcgc cggcggcgga aaggtggcgg cgtcatcgtt ccctcgcgga    420

ggattcgact tgacggcgat gaagaaggcg gcggcggcga gtgttgtggt gccggcgagc    480

gagttgacta cggtttccgt ggtaaatgat tcgctcggga ttcctgaaaa agaaaaagga    540

aataaagcag gagggtcagc agtggaagtg aaagaccaac ctaatagttc aaagcagcag    600

aaacccaaac tctcaaaagc tgaaagacgt gcactccaag aatctcaacg ggctgcaaag    660

gctgctgcaa aggtgaaggg aagtaaggca tctggaactg tggctacaat gaatgcaaaa    720

ccagctaaag ctgtaaagcc tgcacagaaa gttgataatg cagcagttgc agcgtctgaa    780

aagaagggag gtgagattcc accagaaaag gatagaaaga aagatgctcc tcaaccacgc    840

atgcagtatg acgacaagag tcgagtggag aaagctaaac gtcgtgcagt ggtgaaacaa    900

actgaagcta ggaatagagt tgagttgttc aggcatttgc cacaatatga gcatgggagt    960

cagcttccag atctcgaggc aaagtttttc catctttctc cagtgcaccc ttctgtttat   1020

aaggtgggtt tgcaatatct aactggagat atagctggtg gcaatgctcg ttgtattgca   1080

atgcttcaag cattccaaga ggccatcaaa gactacaagg ttccacatga gaagactctt   1140

gtgagagact tgacagcaaa aattagtagt tatgtatcat ttcttattga atgtcggcct   1200

ctgtcaatca gcatgggaaa tgcaattcgg tttcttaaaa gtcatatagc caagctacct   1260

ttgaccttgt ctgaatcaga agcaaaagct tctctccagt cagatattga gcgttttata   1320

agtgaaaaga ttatacttgc caacaaggtg atagtgaagc atgctgtcac caaaataaga   1380

gatggtgatg ttcttctaac atatgggtcc tcatcagctg ttgaaatgat actattacat   1440

gcacatgagt tggggaagca gtttcgtgtt gtcgtagttg actctcgtcc aaagcttaga   1500

gggcaactct tacttcgcag gcttgtggag aaaggtctta gctgtacata tactcatata   1560

aatgctgttt cctacataat gcatgaagtt actcgggttt ttctgggtgc ttcagcagtt   1620

ttgtctaatg gaacagtata ttcaagagta gggactgcat gtgttgcaat ggttgctcat   1680

gcattccgtg tacctgtcat agtatgttgt gaggcctata aatttcatga acgggtacag   1740

ttggattcaa tatgctcaaa tgaacttggc aatccagatg tcatttcaaa tgtactgggt   1800

agagaggatg taaaacactt ggatggctgg gccaatattg aaaatctgca acttttaaat   1860

ctggtttatg atgcaacacc ttcagattat gtttcaatga ttgtcacaga ttatggcatg   1920

gttcccccca caagtgtgcc tgtgattgta agagaatatg ggagagaaca ggtctggata   1980

taa                                                                 1983
```

<210> SEQ ID NO 27
<211> LENGTH: 4596
<212> TYPE: DNA
<213> ORGANISM: Glycine max

<400> SEQUENCE: 27

```
atggatcaca ggccgaaatc caaggactca ctctcttact ccactctctt caatctcgag     60
cctttgatga actttcaact tccaaaacaa gatgatgatt ttgattatta cgggaatagt    120
agtcaggatg agagcagaga cagcgaaggt ggggggatta caaatcacgg taatgggaat    180
gtgcatgaaa aggaagtgaa tttgttcaag aagaggagat ggtctctaaa cagtgacaac    240
gaggagaaga ccagttttta cggggcacac atgacggagg agcgatatcg atcgatgctg    300
ggagagcata ttcagaaata caagaggagg tttaagggta ccttgagtag tcccgcccaa    360
aatcaggctg ctgctccact tgtgaaaagc aacacgggac taaaagctcg caagtcaggg    420
aatgagcaca ggggaggagg attacatgtg gcggagagta catcggaatg gatgaatgat    480
tccagttctc agaaacctgg aaactaccgc gatgcagatt tctcaccaca atatggcact    540
gataggatta tgtatgaacc tgcatctttg gatattgggg atggaatcat ttacaagatt    600
cctccggtct atgataagtt ggctggagct ctgaacctcc caagcttctc ggatatccat    660
gttgaggatt tttacttaaa gggtactttg gatttgggct ccttagctga aatgatggct    720
gctgataaaa gatttgggaa cagaaaccga gcaggcatgg gagaagcaat accacaattt    780
gaatcactgc aggcacgact gaaggtcatg tcagcttcta attcagctca taaattcagt    840
ctgaaaatgt ctgatgttga tttgaattcc tccattccgg agggggcagc gggaagtata    900
aggcgatcta ttttgtctga gggtggagta ttgcaggtat attatgtgaa ggttttggag    960
aaaggtgaca cctatgagat cattgaaaga agcctaccta agaagcaaaa ggtgaagaaa   1020
gaccctgctt tgatcgagaa ggaggaaatg gaaagatgtg gaaaaatttg ggcaaatatt   1080
gtaagaagag acataccaaa gcatcatagg aacttcacta tttttcatcg aaagcagctc   1140
attgatgcca agagggtctc agagacttgt caaagagagg tcagaatgaa agttagtaga   1200
tcccttaaat ggacaaggac tgtcggtatg cgcacccgga aactagctag agacatgtta   1260
ctgttctgga aacgaataga caaggagatg acagaagtga ggaagaggga ggaaaaagaa   1320
gctgctgaag ctttgaggcg tgaacaggag cttcgagagg caaagaggca gcagcaaagg   1380
cttaattttc ttatacaaca aactgagctg tacagccact ttatgcagaa caagtcgaac   1440
ttactatctt cagaaacttt acccaaggaa gatgaagatg cagatgatca agatgcactg   1500
gttgactctt cagatgtgat gcccgatgag gaggtagatc ctgaagaggc tgaattgaag   1560
aaggaagctt tgaaggctgc acaagaagca gtttctaagc agagaatgtt gacaagtgct   1620
tttgacactg aatgcttgag gctgcgccaa gctggtgaaa ctgattcact tccaccagat   1680
gttgctggag cgagtaatat tgatttgcaa accccctcca ccatgccagt ggcatccact   1740
gttcggacac ctgaattatt taaaggggtt cttaaagaat atcagctaaa aggtcttcag   1800
tggcttgtta attgttatga gcagggttta aatggtattc tagctgatga gatggggctt   1860
ggaaagacca ttcaggccat ggctttttttg gcccatttag ctgaggaaaa aaatatatgg   1920
ggaccttttc tggttgttgc acctgcttct gtattaaata attggaatga ggaacttgag   1980
cgcttctgcc ctgaactgaa aagacttcca tattggggtg ggctttcaga gaggacagta   2040
cttaggaaaa gtattaaccc aaaggatctt tatcgtaggg aagctaaatt tcacattctc   2100
atcacaagct accagctatt agtatctgat gagaagtatt ttcgtcgcgt gaaatggcag   2160
```

-continued

```
tatatggttt tagatgaagc ccaggctatc aaaagtgcaa ccagtataag atggaagaca   2220
ctcctcagtt ttaattgtcg gaatcgccta ctgctgactg gtacacccat tcagaataat   2280
atggctgagt tatgggctct tcttcacttc atcatgccaa ctttatttga cagccatgag   2340
cagtttaacg agtggttttc taaaggaatt gagaaccatg cagaacatgg gggtacttta   2400
aatgagcacc aacttaatcg attgcattca attctaaagc ctttcatgct gcggcgtgtt   2460
aaaaaggatg tgatttctga gcttactaca aaaactgagg ttactgtgca ttgtaagctg   2520
agttctcggc agcaggcttt ctatcaagca attaagaaca agatatctct tgctgagttg   2580
tttgatagta atcgtgggca gctcaatgag aagagaattc tgaatttaat gaacattgtt   2640
attcaactaa ggaaggtttg caaccatcca gagttgttcg aaaggagtga gggaagcaca   2700
tacctttact ttggagagat tccaaattcc cttccacctc ctccatttgg ggagatggag   2760
gatgtatatt attctggtgg tcacaacccc atatcatatg agataccaaa acttgtctat   2820
caagaaatta tacaaagttc tgaaactctc agctcagctg ttggtcctgt tgtctccaga   2880
gaatcttttc ataaacattt taatattttt agacccgaaa atgtttatcg gtctgtcttc   2940
tcagaagata tgtacagtaa aagtggaaat tttggtttta cccatatgat ggatttgtct   3000
ccacaagagg tgacatttct ggctactggt tcttttatgg agcgactact attttctatg   3060
atgagatggg aacaaaaatt cattgatgaa gctgtagact ttctaacgga gaccatagat   3120
gatgatccgg aatgtagtta ccttgagaaa gaaaaagtga gagcagttac acgaatgtta   3180
ttggtgccat cgagatctga gaccctggtt cttcaaaaaa aattgcaaac tggacccagc   3240
catgctcctt ttgaggcctt ggtcgtcccc catcaagata gggtgttatc aaatgccagg   3300
cttcttcact ctgcttacac atatatccca caaagtagag ctcccccgat tggtgctcac   3360
tgctcagata gaaacttctg ctataaaatg attgaagaat tacatgatcc ctggattaag   3420
aggttgcttg tggggtttgc acgtacatct gataataatg ggcctagaaa gccagatagt   3480
cctcatcatt taattcaaga gatagattct gaactacctg tttctcagcc tgctcttgag   3540
ttaacacaca gtatttttgg gtcttctcca cctatgcgga attttgaccc tgcgaaattg   3600
ctcactgact cgggaaagct ccaaacactt gatatattat tgaaacgctt acgagcagaa   3660
aatcatcgtg ttctcttgtt tgctcagatg accaagatgc tgaatatttt ggaggactac   3720
atgaactata gaaaatatag gtattttaga cttgatggat catctactat tcaggaccgc   3780
agagacatgg tcagagactt tcagcatagg agtgatattt ttgtgttctt actgagtaca   3840
agagctggtg gattgggtat caacttgaca gctgctgaca cagtcatatt ttatgagagc   3900
gattggaatc caacattgga tctacaggca atggacagag ctcatcgttt gggtcagaca   3960
aaagatgtta ctgtttaccg acttatatgt aaagagacag ttgaagagaa gattcttctt   4020
agagctagtc agaaaagtac tgtgcagaac cttgtcatga ctggtggttc tgtcggtgga   4080
gatcttttag ctcctgagga tgttgtatca ttgcttctag atgatgttca attggaacag   4140
aaattaaagg aaatccctct tcaggtaaag gataagcaaa agaaaaaaca acctatgagg   4200
ggtattcggg taaatgaaga cggtgatgca tcgatggaag atctaacaag ctctgtagcc   4260
cagggtacat cagataatga tctttccatg gatccagagg gttcaaagtc tagtaataaa   4320
aagagaaaag ctgcctcaga taagccaact tcaaggccaa agaactctca aaagatgagt   4380
gaatttagta ctatgcctat ggacggtgaa ctggatgatc ttgatccagt gggtcagaaa   4440
cccaagagac ccaagaggat aaagaagaat gtgaatgaaa agtttgaaga tgcttttact   4500
```

-continued

```
tggactgcta gcttggtccc agagcagtcc cagtttccac ctccacgaga ttttagtgtc   4560

gggggttcta aagcagaatc aggccaagac aactga                             4596


<210> SEQ ID NO 28
<211> LENGTH: 3483
<212> TYPE: DNA
<213> ORGANISM: Glycine max

<400> SEQUENCE: 28

atgaaggttg aaattgaagg cagccacagt gattatgctg aatctgtttc cagacaacca     60

gaaaatagag gaagattgga atccaagaag aaactgaaga aagtgaggtc aataaggctt    120

gtaagattgc caagcaagag atcatccacc agaggaggga gacaccgcca tgattatctc    180

ttcattgaca cagaaagttt agaggggcca acaccaattg aaatggtaga tgcatcacca    240

aattacatga aggctaccag cagttctcat gcaaaagata gtattcagaa tacacaaaga    300

atactattca caaagaagac tttgacaaga atgtctacta ctttgaaact gaagagaagt    360

ctgaccagaa agttatctgg aaggactgaa ccaaagaggg aactgaagtc ctcaagatca    420

atcaagtttg cagctgtcaa gggccaaaaa tcaacaagaa agttttatga atctaattat    480

ggaagtgatg accagaattg gaaaagtgca agtgatgctg gtaacaaact ccagagagtc    540

ataaccagaa gattaagctt gaagcccgtg aggatcttag caaagatgcc tactttcaaa    600

tcaaagaatt cttccatgga gagaggcaat cagatatctc aatccccata cacaagcttg    660

cttagagcca cttgtacttc tgctctcaag gattcccatt ttcctgagaa aattgacctc    720

cctcaagagg gaagtgactc tcaaggagta tcagctgtga aggtttgtcc atattcttac    780

tgctcacttc acggtcaacg ccacaccaat ctgcctccac tgaagcgctt tgtgtcaatg    840

aggaggcgca cgttgaagag ccaaaagcca acaaaaatgg attgtcaacc tgacactaga    900

tcaaagcaga ttggtaatgc aaagaaagcc gctcagaaaa ctcaaactgt ccacaaagaa    960

gatggaagat ctcattttca gaacaagaaa aagctggcta ggggcttatg gattaggcct   1020

catggcactc cagcatccac agtttctgaa ggtgtggaat caacatcaac agatagagtc   1080

gagttttctg ctcctgatac tgagatattg gagagagaag taactaacac tggcaacaca   1140

agcaaaaata tgaagctgga ttgtgaagta ctgaagatga gttctttaca gaaagagtct   1200

acacatgcta gcactactga tatggcaagg ggaatgcagg aaagagataa aaaatttgtc   1260

aaaatgtggc agttgatgta taagcatgct gtattgagta acacaggtga aaataagcag   1320

caatttgatg ggaaggacaa ggaaggaaga gagcaagatt tctttgcaac taatgaagtg   1380

aacaactctt gtcgtgatga ttgtgataca gatcaggata tggatgagga aaataaggat   1440

gcaattgagc tggtgcagaa agcatttgat gaaatccttc ttccagagcc tgaagacctc   1500

ttttctgatg atcaattcaa atctgaaggc attgattcag atgtggtaca cttagaaaag   1560

agtgaagttg agagaaaaag gaatacttca acatccacag aatctccaac agcacagagg   1620

atggggacca aacctgacca aagagcacca agaagctgga gcaatctgaa gaagttaatc   1680

ctcttgaaaa ggtttgtgaa tgcattagag aaggtaagaa acatcaaccc caaaagacca   1740

agacgttttc cttctgatgc taacttagaa atagaaaaag tttttctcaa gcaccaaaca   1800

gcggaagaga agaagaatgc tgaggaatgg atgcttgact atgcacttca aaaggttgtt   1860

tctaaacttg cacctgctca aagacaaaaa gtgacacttc tagtaaaagc ttttgaaaca   1920

attctgccat ttcaagttgc tgaaaatagt ccacggtttt ctccaacaat ggaacctcaa   1980

gcaaatccag ttcaacccct tgacaattcc tcaaatcaca gcgaggaaga aacatcattt   2040
```

tctcatgata gcagtatgga actgacagaa aatactagtg atgatccaat gccagaactg 2100
cacaatccta ctacgctcaa agaaagatgt cttgagtctc ttgattttcc tggaaccgag 2160
acagtcaaga atatgcctgc ctttggagct actgaagaag acttgagtgg aaagcaaagt 2220
ttagctggca gttatgataa tgaggagaag atatcaagtg acagtgataa tatttatctt 2280
gtagagatca aagatactac ctcaagttcc ttaaatgagc cagttgaaat tataagaagc 2340
agtcatgagg aggctccaac caatgaaaca gtcaatgatg ttccagaaga tttgctatcc 2400
agtgtgaata cagaaaatcc agatatcaaa tctgagtcac ctggaagaga tgttgaaacc 2460
aagaatctga atggtgataa tggggaaaaa atttccatgt ccaaaagttt agtcctagaa 2520
ggtttagtta gatcactcag atctaatttg attggttcag gagcacctgt aaacgaacca 2580
actgccaaca acagaaaaga aggaattgaa aatgttaaac aggaaactga gactcttgaa 2640
gagttcccta caaaggaaca atctgaagct catattagtg ctgttgtaga acctgagacc 2700
cctgtagaga aacagaataa cacaggattg tggtacttgg tgtataagca catggtatca 2760
aatatggatg aaaacaattc cgagtcacta attgatgggg cagatgaaaa agagtcaggg 2820
tttgatggga gcagaacaag aggagcttcc ttctctcatg aaagtacacc cgtgactgat 2880
gaagagatga aatttaagga ccatgtcgta gctgatccag aagttgcacg ccaacagaat 2940
gaagccatca agatggtaga agaagcaatt gattcaattc ttccagatga tcaggatgac 3000
ttatcagaca aggaatcact cactgacagc acaatttcag acaactccaa acaatccaac 3060
agaactgaaa gagtatacag tgaaggcctg aaccaaaaag aagaacagat ggaatccggg 3120
aacggaatga tccaaaaaca agaagaatca gcaccaaagg agcaaaacaa aacaaaccag 3180
aaaatgtcta caagctggag caatcttaaa aaagtgatcc tgcttaggag attcatcaag 3240
tcattggaaa aagtaaggaa attcaaccca agagggccta gatatctacc tctagagcct 3300
gattcagaag ctgaaaaagt taacttaagg catcaagaca tggaagaacg aaaaggtacg 3360
gaagaatgga tgcttgatta tgcacttcga caggttgttt ccaaattaac ccctgctagg 3420
aaaagaaaag tggagctgct ggtggaagct tttgaaacag tcatgccaac tataaaaact 3480
tga 3483

<210> SEQ ID NO 29
<211> LENGTH: 219
<212> TYPE: DNA
<213> ORGANISM: Glycine max

<400> SEQUENCE: 29
atgccaattg ctctaagtag aagggatcta ttgggttgtg ctgaaactgg tagcggaaag 60
actgctgctt tcacaattcc tatgatacag cattgcttgg cccaacatcc cattcggcgc 120
aatgatggtc ccctggcatt aattttggct cctagaagag aacttgctca acaaatagaa 180
aaagaggtga catgtaataa ttttagaact atatcctaa 219

<210> SEQ ID NO 30
<211> LENGTH: 825
<212> TYPE: DNA
<213> ORGANISM: Glycine max

<400> SEQUENCE: 30
atggaaatcg ttccgattcc cgccgattcc tacaatctcg gcttcatcgg cgccggaaaa 60
atggccgagt ccattgccag aggcgccgtc cgctccggcg tcttgccgcc ttctcgcatt 120

-continued

```
cgcaccgccg tccactccaa ccccgcccgc cgcgacacat tcgaatcctt cggcgtcacc    180

gttctcccct caaacgacga cgtcgttcgc gaaagcaacg tcgtcgtttt ctcggtcaaa    240

cctcaactag tgaaagacgt ggtgttcaaa ttgacgccgc ttctgacgaa gaacaagctt    300

ttggtttcgg tcgctgctgg taccaaattg aaagatcttc aggaatgggc tgggaacgac    360

agatttataa gagtgatgcc taatacacct gctgctgtag gcgaggcagc atcagttatg    420

agcttggggg gatctgcaac agaagaagat ggaaatatta tagccaaatt gttagggtca    480

attggcaaaa tatggaaagc tgaggaaaag tattttgatg ctataactgg cctgagtggc    540

agtggtcctg cttatgttta tttagcaata gaggctttgg ctgatggagg agtagcagct    600

ggtttaccac gtgatctttc attaagtcta gcttctcaaa ctgtattagg agcagcatca    660

atggtcatcc agactgggaa acacccagga cagctcaaag atgacgttac ttctccgggt    720

gggacaacaa ttacgggcat tcatgagtta gaaaatggcg ggttccgtgg gacactgatg    780

aatgctgttg ttgctgctac taagcgcagc agagagcttt cctga                    825
```

<210> SEQ ID NO 31
<211> LENGTH: 237
<212> TYPE: DNA
<213> ORGANISM: Glycine max

<400> SEQUENCE: 31

```
atgtttggtg ggcatggagg tttattgaag gagtttgtgt atgtgggaat tgggttactg     60

gactataaag aagaccgaat tttggcaaag acaatatggt ataagattca atttggacta    120

tttcgaagct attgcaagat aaagttagcg ttgggctctt ctagcatact tcgagtcatg    180

aaaaggcgtg taggggtatt cattttactt gaagaaagct tcaaaataat gatttga       237
```

<210> SEQ ID NO 32
<211> LENGTH: 414
<212> TYPE: DNA
<213> ORGANISM: Glycine max

<400> SEQUENCE: 32

```
atgcatacta tagagtttca aaagcgagga ctccctcacg tgcatttatt tctatttcta     60

catctagata ataaatatcc atcttcaact gacattgacg agataatatc agtagaaata    120

ccttccccatg aagatgaccc agaactctac agattggtgg aaaatcatat gatacatggc    180

ccatgcggaa ttttacaacc caactctcca tgtatgaaag aaggcaaatg cagtcatttt    240

tatcctaaac aatttcagcc tcagactctt ttggattcaa acggttatcc agactatcat    300

agaagaaaca atggtcattc aatttcaaag aatggtgtta tcattgataa cagatatgta    360

gtaccttaca atccaaaatt actaaaaaaa atatcaggca catataaata ttga          414
```

<210> SEQ ID NO 33
<211> LENGTH: 1473
<212> TYPE: DNA
<213> ORGANISM: Glycine max

<400> SEQUENCE: 33

```
atgagggagc catcgtcggt gggattcgaa ggcaacggcg ccgtttcttc gccgccgcaa     60

gctctcctcg agagactgaa agactacggt caagaagacg ctttcgccct ctggtacgag    120

ctctcttacg aggaacgcga gtttctcatc aaggacattg agagtttaga tctttcgaga    180

attgaccgga ttattcggtg ctcgctgcga tctcaaggac tgccggcggc ggccattgag    240

cctgtgccgg agagcagtgt gtcgacggtg gaggagagaa gccaagagga tcgagagaga    300
```

-continued

```
tggtggaaaa tgggattgaa ggccatttct gatggcaaat tagctgtgtt gcttttatct    360

ggtggccagg ggactcgact tggaagttca gatccaaaag gatgtttcaa tattggactt    420

ccatctggaa aatcactttt tcaacttcaa gctgagagga ttttgtgtgc acagagacta    480

gctgctcaag ctacaaatga gaattctgct tcttcagtgc aaatacactg gtacatcatg    540

accagtccat tcactgatga ggcaacacgc aaattctttg aaagtcataa atttttttggt    600

ctcgaggcag aacaggttac ctttttccag caaggaacaa tcccttgtgt ttccaaggat    660

ggtagattta ttatggagac tccatacagg gtagcaaagg ctcctgatgg gaatggtgga    720

gtgtattcag ctctgaaatc taccaaatta ttggaggata tggcctcaaa aggaattaag    780

tatattgatt gctatggagt tgacaatgca ctagttcgag ttgccgatcc aacttttttta    840

ggttacttca ttgataaagg tgttgctgct gctgcaaaag ttgtccgcaa ggcatatcca    900

caagaaaagg ttggtgtgtt tgtaagacga ggtaaaggtg gtcctcttac cgtagtggaa    960

tacagtgagt tggaccagtc actagcttct gcagtcaatc aagcaactgg ccgtcttcgt   1020

ttttgttgga gtaatgtctg cttacacatg ttcactctgg attttctgaa tcaagtggca   1080

aatggccttg aaaaagacag catttatcat cttgcagaga agaaaatacc ttccatacat   1140

ggatatacaa tgggattaaa acttgaacag tttatatttg atgcatttcc atatgctcct   1200

acaactgcac tttttgaggt gttacgggag gaggaatttg caccagtgaa aaatgcaaat   1260

ggatccaatg ttgacactcc agacagtgcg aaactacttg ttcttcgact ccatactcgt   1320

tgggtagttg ctgcaggtgg cttcttaaca cattcagtgc ccttatatgc aacaggtgtt   1380

gaagtgtcac cactctgttc gtatgctggt gaaaacctgg aacctatatg tcgaggaaga   1440

acatttcatg caccttgtga gatctcattt tag                                1473
```

<210> SEQ ID NO 34
<211> LENGTH: 1302
<212> TYPE: DNA
<213> ORGANISM: Glycine max

<400> SEQUENCE: 34

```
atggcgaata aactgaatat aaggctagga gaaccaactc tggtgccacc agcagaagaa     60

acggaaaagg gtctttacta cttcctttca aaccttgacc agaacatagc acatccagtt    120

cgaacggttt acttttataa taagtctgca tgtagaggga acgaggaagc agcacaagta    180

ataaaggatg ctttgtcgaa ggttcttgtt cactattacc ctatggctgg aagattggcc    240

ataagttcag aagggaaact gatcatagag tgcacaggtg agggtgttgt gtttgttgag    300

gctgaagaag caaactgtgt gataaaggac ttgggagatt tgacaaaaca acctgacctt    360

gaaactcttg gaaaactggt ttatgatatc cccggtgcaa ccaacatgct tcagatacct    420

cctttgctaa ttcaggtgac aaagttcaaa tgtggtggat ttgttttggg cgtaaacgtg    480

aaccattgca tggttgatgg tataagtgct atgcaattcg tgaacgcatg ggtgagaca    540

gccagaggca tggacttgag catttcacca gttctggacc gaactatact aagaacacga    600

aatcctccaa agatagagta tccacaccac gaattcgacg aaattgaaga tgtatcaaat    660

gtcacaaaag tctatgagga agagatcctc tacgagtcct tttgtttcga cccagataag    720

cttgagttgc ttaagaaaat ggccacatca gaagatggtg ttgtaaagaa gtgctctact    780

tttgaagcac ttacagcttt tgtgtggaga gctagaagtg aagccttagg gatgcacatg    840

gaccctaatc aacaaaccaa gctacttttt gctgttgatg gaaggtctaa attcgtgcct    900
```

-continued ccaataccaa aggggtactt tggcaatgct attgtgtttt caaatgctct atgcaaggta 960
gaggagttag tgaataatcc actgtcattt agtgtgggat tggttggcaa agcaattgac 1020
atggtgacag acagttacat gagatctgct attgactatt ttgaagtgaa aagatcaagg 1080
ccttccttaa ctgcaacact tttgatcaca acatggacta ggataccttt ccgaagtgca 1140
gatttcggat gggggaagcc cttctttttt gggcctgtaa ctttgccagg gaaggaagtc 1200
attttgttct tgtctcataa cgaagaaagt aaaagcataa acgtgctcct aggtttgcct 1260
gcttctgcca tgaaaaggtt tgaaaggctg atggagatat ga 1302

<210> SEQ ID NO 35
<211> LENGTH: 828
<212> TYPE: DNA
<213> ORGANISM: Glycine max

<400> SEQUENCE: 35
atgttttgga gtgacctcgt gagtctgatt gtcttactcg ccactgcttc ggatcctgca 60
cctctacaat ttctggccct atattctggg tgtgccatgg gggaatattt ccatgataat 120
ggaatgcacg cattaataat ctatgatgat cttagtaaac aggccgtggc atatcgccaa 180
atttcattat tgttacgcca accaccgggc cgtgaggctt tcccaagcga tgttttctat 240
ttacattctc atctcttaga aagagccgct aaacgatcgg accagacagg tgcaggtagc 300
ttgatcgcct tacccgtcat tgaaacacaa gcgggagacg tatcggccta tattccaacg 360
aatgtgatct ccattactga tggacaacta tgtttggaaa cagagctctt ttattgcgga 420
attagacctg ctattaacgt cggcttatct gtcagtcgcg tcgggtctgc tgctcagttg 480
aaagctatga aacaagcaca atatcgcaaa gtcgccgcct ttgctcaatt tgggtcatac 540
cttgatgttg cgactcaggc attactcaat agaggtgcaa ggcttacagc agtactgaaa 600
caacctcaat attcaccact tccaattgaa aaacaaattc tagtcattta tgcagctgtc 660
aatggatttt gtgatcgaat gccattagat aaaattcctc aatatgaaag agacattcta 720
acgactatta aaccagaatt actacaatca ctaaaaggtg gactaactag caaaagaaaa 780
atagaactag aaaaattctt taaaaaaaag gtggaactta ctacataa 828

<210> SEQ ID NO 36
<211> LENGTH: 1632
<212> TYPE: DNA
<213> ORGANISM: Glycine max

<400> SEQUENCE: 36
atggtccaaa ccttttctct tccggctcca atctctcaat ggcctcaagg acaaggtttt 60
gcttctggcc ttgtaaacct tggtgaaata caagtttcca aagtcacaag gtttgagttt 120
atttcgagca gcagtgttat gctagacaca aaaaaagctg ttacattctt taggcctgtg 180
ggagtaccag aaagtttcca tatccttggt cactattgtc aacccagtgg caagcctttg 240
catggttttg tacttgttgc caaaatttgc tctcctcaaa atgctgatac gatacctcct 300
ctgaagaatc cccttgattt taagctagtt tggagtcata atgcagcaag tatggaaatt 360
ccaggtgtat acttttggct acctgaacct cctgaaggtt acaaggccct tggctatttg 420
gttactaaca aacatgacaa gcctttgttg gatgaaatgt gttgtgttcg tgctgacctc 480
accgataaat gtgaacctta ccgccaaata ctcgctgctg gttctagaat tccagagttt 540
tcatttcagg tatggagttt aagaccttgt gaccgtggca tgttagggaa aggtgtttct 600
gttggtactt ttttctgcag caatggctgg accatgggag aagagctact acctgttgca 660

```
tgcttgaaga acctgaatcc tgtgctacca gcaatgccag atttgcaaca aatacatgca    720

cttattaagc attatggccc tactgttttt tttcatcctc aggaaaaata cttgccatct    780

tctgtggatt ggtttttcaa caatggagcc atgctgcaca aaaagggtgt gtctaaagga    840

gagggaattg atgcaagtgg ctcaaactta ccaagtggag gaacaaatga tggccagttt    900

tggatagact tgccaagtga tcatgataga aagaattttg tcaaacgtgg agacttgaag    960

agttcaaggc tttatgttca tgtgaaacca gctcttggtg gaacttttac tgacattgca   1020

atgtgggtgt tttgtccttt caatggacca gccactctga aaattggaat taagagcatt   1080

cctctgagca aggttggaga gcatgttggt gactgggagc attttacact tcgtatatgc   1140

aacttcagtg gagaactcta tagtatatac ttttctcagc acagtggtgg tgaatgggtt   1200

gatgcctatg acttggatta tattaaaggt tacaataaag ctactgttta ctcatcaaaa   1260

tgtggacatg caagttaccc tcatccaggg acctatatgc aaggttcttc aaaacttggg   1320

attggcatta ggaatgatgc tgctcgcagt aatttgtatg tggattctag tgttcactat   1380

gagcttgttg cagctgagta tcttgaaaat gatgtcactg agcctcaatg gttgcagttt   1440

atgagagagt gggggcccaa aattgtttat gatacaaaaa ctgagttgga taaggtaatc   1500

aatgctcttc ctcgcatgct tagatattcg gtgaggaact tatttaacaa gtttccagtg   1560

gaactttatg gtgaggaagg tcccactggg ccaaaagaga aaaataattg gatacaggat   1620

gaaagatggt aa                                                       1632
```

<210> SEQ ID NO 37
<211> LENGTH: 591
<212> TYPE: DNA
<213> ORGANISM: Glycine max

<400> SEQUENCE: 37

```
atgacgacta ggaacgggaa aataaaaaat ttcactttga atttcggacc tcaacatcct     60

actgctcatg gtgtttcacg accagtattc gaaatgaatg gagaagttgt ggaacatgca    120

aaaccacata ttggatcact ctacactgcc tacacacgaa ttagctttcg agggactgag    180

gaattagtag agtgcaaaac ttatcttcaa gctttacctt attttgatca tttagaggaa    240

catgctcatt cttcagccgt agagagactt ttgaattgcg aggtaccatt atgggctcaa    300

tatatacgag tgttattccg tgaaataact cgaatttcaa atcatttgcc tactttaact    360

actcatgcta tggatgtggg agcatcaact ctgtccctat gggcttttga ggagtgggag    420

aaattgttgg aattctatga aagagtctcg ggagctagga tgcatgccag tttcatacga    480

ccaggtagag tggcacaaga tctgcctctt ggcttatgtc aagatattga ttgcttcaca    540

caccaatttg cgtcttgtat cgacgaatta gaagaggtgt caactggcaa c             591
```

<210> SEQ ID NO 38
<211> LENGTH: 1413
<212> TYPE: DNA
<213> ORGANISM: Glycine max

<400> SEQUENCE: 38

```
atggactgga ggcgctggac taagaataag aagaaccacc accaccctcc gccgcagctg     60

caaccgcgct tggagcgcct caacgccaaa aaaggcatca attaccaatc accaccttct    120

cctccttccc cttcttcttc ttcttctcac ttggatcgcc aaaccagctt ccgcctcttc    180

ggcttcgacg gcgaattcga ccgcatcttc cagaccctgg gcctctccgg cccagaagac    240
```

ttctccatcc ccaccgctga ctgggaagcc cacaaggccc gcttatctgg gcccaccacc 300
actcctcctc ctcacacgct tcctcccact tcccagattc aagacgatga cgtttcggtt 360
cccgctgcgg tttcttcttc ctccccttgg tcttccgggg agcactacgt gggcaggggc 420
agtgtcggta gattgaattt gagacacggc gaaaggagcg tgcttttcac cgattccgat 480
tccttcacta cttcacacga cgatgacagt gatgttggtg gagagaggga gagagcgggt 540
ctcgcttcta attctgcagc cgctgatgag ttggttattc cgtttaactc atccaacgag 600
tggtttagac agactttcgc ttcgtggcag aaaggtgacg tcttgggaaa tgggtccttc 660
ggaactgtct atgaaggctt caatgatgat ggattctttt ttgcggtaaa ggaggtgtct 720
ttgctggatg aaggtggcca gggaaaacag agctttttc aacttcagca ggaaatatct 780
cttttgagta agtttgagca taaaaacata gttcgatatt atggctcaaa caaggacaaa 840
agtaaattat atatattcct tgagcttatg tcaaaagggt cattggcaag tctctatcaa 900
aagtatcggt taaacgattc tcaagtttct gcatacacaa ggcagatttt atgtggcttg 960
aagtatcttc atgatcataa tgtggtccac agggacatca agtgtgctaa tatactggtt 1020
aatgtaaggg ggcaagtcaa gcttgcagat tttgggttgg caaaggcaac aaaatttaat 1080
gatattaaat caagcaaagg ctctccatac tggatggccc cagaggttgt taacttaaag 1140
aatcaaggtg gttatgggct agcagctgat atatggagct tagggtgtac agttttggag 1200
atgttgacaa gacagcctcc ctattctgat ttggaaggaa tgcaagcatt atttcggatt 1260
ggccggggtg aacctccacc tattcctgaa tatttatcta aggatgcccg ggatttcatc 1320
cttgaatgct tacaagttaa cccaaacgat cgtccaactg cagctcagct attttatcat 1380
tcttttctaa ggagaacagt tctatctccc tga 1413

<210> SEQ ID NO 39
<211> LENGTH: 2397
<212> TYPE: DNA
<213> ORGANISM: Glycine max

<400> SEQUENCE: 39
atgccaatgg cgtgcttctc cattctctct cctcctcatc ccactctcac tctcactctc 60
ctccctccct cccactctca atgcggcggc ttcaccgtta gagttagtgt tgctctcacc 120
gaaaggctct cccagcacca caagaccaat tccattattc cttcaactcg cgctgctgcg 180
aatggtggcg gtttcgagac agaaactgcg gtggtggaaa agcctcaatt gaagactctc 240
ttccaagctt ccagaggcta cccttccccc tttggtgcca ctgttcgaga cggtggggtc 300
aatttcgcca tttcctctct caacgcactt tccgccactc tctgtttctt tactctctct 360
gatttccaga ataatcgagt gacggagtat gttcctcttg atccgttgat taataggact 420
ggaggtgtct ggcatgtttt ccttaaagga gattttagag atatgcttta tgggtacaaa 480
tttgatggca agttttctcc tctagaggga cattactttg actcttctca tatactactg 540
gacccgtatg ccaaagcagt tataagcaga ggggagtttg gggctttagg acctgatggt 600
aactgctggc cccagatggc tggcacggta ccttctgagg atgatgagtt tgactgggaa 660
ggagatttgc ctctcaagta tccacaaaag gatcttgtta tatatgaaat gcatgtgcgt 720
gggttcacaa agcacgagtc gagcaatacc aagttccctg gtacatacct tggtgtggtg 780
gagaagcttg accacttaaa ggaacttgga gtaaattgtc tagaattaat gccatgtcat 840
gaattcaatg aactggaata ctatggtcac aattctgcac aaggagacta cagggtcaat 900
ttttgggggt attcaaccat caattacttc tccccaatga tcagatactc atctgctggc 960

```
atacgaaact gtggccagga tgggattaat gaaattaaat tcctgatcaa agaggcgcac   1020
aaacgaggaa tagaggtcat catggatgtt gttttcaatc atacagctga ggggaatgag   1080
aatggtccca ttatttcttt cagaggtgtc gacaacagta tgtattacat gttagcaccc   1140
aagggggagt tctataacta ttcaggatgt gggaacacgt tcaattgcaa ccatccagtt   1200
gtgcgacaat ttatagttga ctgcttaaga tattgggtaa cagaaatgca cgtggatggt   1260
tttcgctttg atcttgcttc tattatgacc aggagtagca gtctctggga tggagctaat   1320
gtatttggtg ctccaataga aggtgacttg ttgacaacag gaacccctct aagcagccca   1380
ccattaattg acttgatcag taacgatcct atactttgtg gagtgaagct tatagctgaa   1440
gcctgggatg ctggtggcct ctatcaagtt ggcactttcc ctcactgggg tatttggtca   1500
gaatggaatg ggaagtatag agacacggtg cgcctgttta tcaagggtac agatggcttt   1560
gctggagctt ttgctgaatg cctttgtggg agtcctaatt tatatcaggg aggaggaaga   1620
aaaccgtggc atagtattaa ctttgtatgc gctcatgatg ggttcactct agctgatttg   1680
gtgacctata acaacaagaa taatttgtca aatggagaag acaataatga tggagaaaat   1740
cataataata gctggaactg cggacaggag ggggagtttg tcagtacctc ggtgaagaaa   1800
ttgaggaaac gacaaatgcg gaattttttt ctttctctca tggtttccca gggagttcca   1860
atgatatata tgggcgatga atatggacac acaaaaggag gaaataacaa tacctattgt   1920
cacgataatt atcataatta cttccaatgg gacaaaaagg aagaatcctc atcagacttc   1980
ttcagatttt gtcgccttat gactaagttc cgccaggaat gtgaatcgct aggcttagct   2040
gacttcccaa cctctgagag gctgcagtgg catggtcatt ttcctggaaa gccagactgg   2100
tctgaaacca gccgttttgt ggcttgtacc atggtagatt cagtgaaggg agaaatatac   2160
attgctttca atatgagtca tttacctttc acagttacct tgccggagcg tcctggatac   2220
aaatgggaac ctcttgtaga caccagcaag cctacaccat atgatttcct cactcctgac   2280
cttcctggaa gagatattgc catacaacag tatgctcagt ttctggacgc caatatgtat   2340
cccatgctta gttattcttc cattatcctc ttgcgcattc cagatgaaaa tctgtag      2397
```

```
<210> SEQ ID NO 40
<211> LENGTH: 3144
<212> TYPE: DNA
<213> ORGANISM: Glycine max

<400> SEQUENCE: 40

atgtcgaaaa ctccgaagga gaaggaaacg gaggagcctc tgccagacca cctccgctgc     60
gggcgcacgg acgggcggca atggcgttgc cggcggcgag tgaaggagaa tctgaagctc    120
tgcgagattc actacctcca aggtcgccac cgccagtaca aggagaaggt tcccgagtcg    180
ctgaagcttc agcgcaagcg caaatctaac aacaacaaca acaacaacaa cgaggaagaa    240
gaagaagaag aagaagaaga gaaaccagag cctgataaga agaatgttct cgacgacaat    300
gtcgaatcta gggcacggag aacctcgaga atcgtgaaga agaagcgcat gctttctgag    360
gattccgatg cttcagcttc ttctcctccg gcgaggaaga aggcgctgaa gcagggcgat    420
atgcagttgg agctcttgag gatggtgctg aagagagagg ctgagaagaa caaaaacaag    480
agcaagagca agaacaagaa gaacaataac aaaaagaaga ataagaagaa ggaaaagagg    540
aggaaggagg aaaaagagga attgtgttac actaaagaag agttgagaag agaattgcca    600
aatggagtaa tggaaatctc tccggcttca ccgacgcgtg attacaacaa tgtaggttcg    660
```

-continued

```
cattgtgatg tcaaagttgg tgttgatagt aaaactgtta ctccgcgtta ctttaggtcc    720
aagaatgttg atagagtccc cgcggggaag ttgcagattg tgccgtatgg atcaaacttg    780
aaaaagggta agaggaagaa gtgtcattgg tgccagagaa gtgagtctgg gaatctcatt    840
caatgttcga gctgtcagag ggagttcttc tgcatggatt gcgttaaaga gcggtatttt    900
gacgctgaaa atgaaattaa gaaggcatgt ccagtttgtc gtggaacttg cccttgtaag    960
tattgctctg caagtcaatg taaagacagt gaaagtaagg aatgtttgac tggtaagagc   1020
agagttgata gaatattgca ttttcattat ttgatctgca tgctccttcc agtactaaag   1080
caaataagtg aagatcagaa tattgagcta gaaacagaag taaaaattaa agggaaaaat   1140
atttctgata ttcaaatcaa gcaggttgaa tttggatgca gtgagaaaaa ctattgcaat   1200
cactgcaaaa cacccatttt ggatctccat agaagctgtc ctagttgttc atatagccta   1260
tgctcaagtt gttgtcagga attaagtcaa ggaaaagctt ctggagcaat gaactcatcc   1320
gtgttcaagc gacctgataa aatgaaacct tgcagtgcta gtgagaacca tactttggag   1380
gagagagcca catctattgg caatttaact gatacttcag tattgcctga gtggacaaat   1440
ggtaatggca ttgatagtct atcatgccct cctacagagc ttggtggttg tggtaaaagc   1500
caccttgagt tgagatctgt tttcccttcc agttggatca aagagatgga agcgaaggca   1560
gaagaaattg tttgcagcta tgactttcct gaaacttcag ataaaagttc aagttgctca   1620
ttgtgttttg acactgatca tggtactaac agatataagc agttgcaaga agcagctcta   1680
agagaagatt ccaatgataa ttacttgttt tgtcccacag tgatggacat cagtggtgat   1740
aactttgagc actttcagaa acactgggga aaaggccatc ctatagttgt ccaagatgcg   1800
ctccgaagta cctcaaacct cagttgggat ccactgacca tgttctgtac ttatcttgag   1860
cagagcatta caagatatga gaacaataaa aacttgcttg aatcctgttt ggattggtgg   1920
gaggtggaaa ttaacattaa gcagtacttt actgggtctg tcaagcgtcg tcctcagaga   1980
aacacttggg atgagatgct gaaactaaaa gggtggcttt cttcccaaat atttaaagag   2040
cagtttccag ctcattttgc tgaggtaatt gatgctctac cagttcaaga atacatgcat   2100
cccctctgcg gtcttctgaa tttagctgca aatttgccac atgggagtgc aaaacatgac   2160
attgggccat atgtctacat ttcttatggc tctgctgaca aagaaactga ttcagtgaca   2220
aagctctgct atgactcata tgatgtggtt aatattatga cacataccac agatgccccc   2280
ctctctacag aacaacttac aaaaataaga aaactgctaa aaaagcacaa aactctgtgt   2340
caaatggaga ctattgctac tgaggagcca cgggaacaga aattgaatgg aatggcatta   2400
ttgcatggtc cagaaacaga gcgaaaaggc tcatggagta tggtcgaaga aggaatgaac   2460
tttttcagga gagtcaatag aacatcttgc atctcaactg aagctaaaaa agtttctagt   2520
cagagcatgg acagcaatgg agaatgtgat ttcatttctg attctgattc tggatccact   2580
ttacttctcc ttgggactgt tcaaactgct gaattgtcaa agcacaataa tcctagaaat   2640
ccctttgaaa gctcaaaaag acataaaaaa aagtttactg agcatttggg tgcccagtgg   2700
gatgtctttc gcagacaaga tgttccaaag ctcatcgaat accttaaaag acattatgct   2760
gaattttctt atacccatga ctatgacaag aagatggttc atccaattct agatcagagc   2820
atttttcttg acagtactca caaaaagaga ctaaaggagg aatttaagat tgaaccatgg   2880
acttttcagc aacatgttgg acaagctgtc atcattcctg ctggatgtcc ataccagatg   2940
aggaattcta agtctagcgt tcatgcggta ttggaatttg tgtcccctga aaatgttact   3000
gagggtatcc agttgattga tgaggtccga ctattgcctg aagaccataa agcaaaagca   3060
```

gacctgctgg aggtaaagaa aatggcgctt catagcatga atacagcaat taaagaagta 3120
cgtcagctta caagcaaaac atga 3144

<210> SEQ ID NO 41
<211> LENGTH: 2322
<212> TYPE: DNA
<213> ORGANISM: Glycine max

<400> SEQUENCE: 41
atgagcacct ttgaatcatc aacaacaaga tcctttgttt ctgtagaatc aacaacacca 60
attgaaggaa cggaagctga caatgtgaat agggactcat tgttccgagg gtgtgtattg 120
gaagggagat gggacttcat tcttacggca tataaaaacg atagtcacta tcacaaaatt 180
aaaataaacg aaagcagagg cacagcacta cacgtggcag tgaatgatgg caaagtggaa 240
cttgttaaca ctctcgttgg tgcaatctta aaccatgaag ggatggatgt gctgagggat 300
gatagtgcat tgaaaacaac caatgagaga ggggacactc ctttgcacct tgcagcatca 360
agagggttca atgctatgtg caagtgcatc ataggggagt ctgaggaaag gaaggatttg 420
attagggtta ggaacaataa gggtgaaaca cctctcttcc gggctgtgct cacatgccat 480
acaaagacct ttgtgtactt ccatcatgtt tccaaagata ttccacttag gaactatgat 540
ggggatacca tccttcacca tgccatttgg agagaattct tggatttggc aattataata 600
actcattgct atcctgaact tgttgacatg cgaaacaaag atggagccac tcctctcaaa 660
gttcttgcct ctaagccttc agccttcaag agtggaagca atctcccatg gtggaagcaa 720
attctatatt atggtatact cgtagaacaa ctagacgcag aaaaggcaat aaaatcctat 780
atggataaag ttgacaaatt tgaggccgac attgaactca aagtgaatat acattcagaa 840
agtagtgaag ccaacaaagc acaaaaattt gtggaaaaac agtatgctac ttctgttcgg 900
tttgtaaaga gtgctgttcg attagcattc aaagtcctta gcctctcggg attgggtgtc 960
actgcacagg acttgaaagc aataaagaag ataaggcaga agcacagatg gagtcgtcaa 1020
ctcttgaata tttttatgga aagaccttat gagtcgtaca ttggaattac tgggggtcga 1080
ccatttttga gagaagacag agacttaggg caacccgtta ttacccaaca acagttacaa 1140
atggtgggtg gtgcagctag ctcagggcaa caagaaaaca atagagtgga atccgcagca 1200
aaaaatgagg aaaaggagac atttgtggca gtggcaaaag ccggcatagt tgaacttgtg 1260
aatgagcttc acaacaaagt accaagtacc ttccatgaca ctaactctcc tgagaaggaa 1320
aacttactga ttgtggcaat gaagaacatc aaatacaaaa taggagaaca ccatgttgac 1380
aaaaaggaga ctgcattttt ggcagcggct aaatacggca ttgtggagat tgtatttgca 1440
cttcaatcca aaataccaag tgccgtgcat gaaaccaact ccaacaatga aaacgtgttg 1500
cttgtggctg tgaagaatag acaaaccaaa gttgttgagg tgttaaggaa acatatggat 1560
aaggaactct ttgatagctt gattttagaa gtggataaca gggagaacac tgtgttgcac 1620
ttggcagctg gaactggaac tacaagcaac agtgaaagga cctggcagat tgctggtgct 1680
gccatgcaaa tgatgtggga tatcaagtgg tatcagtaca ttagagccct agtgccggag 1740
cacttcgttt tcagaaccaa caaagacgat aaaaccgcag gcgaaatctt caaacaaaaa 1800
cacaaagacc tggtgaaaga aagctccgag tggctaaagg aaacctccaa ctcctgctcc 1860
gtcgtcgccg ccctaatcgc gggcgtctcc ttcgccacat cgagctccgt ccccggtggc 1920
accgagaagg gcaagcccga acttgaaggc cagccagcct tcgacgtctt cgccatcgca 1980

-continued

```
tcgctcatcg gcctctgctt ctccgtcacc gccctcatca tgttccttgc cattctcact   2040

tcgcgaaaac aggccccaga cttccgcaag agcttgccct tgaagcttct ctttggctta   2100

agctctctct tcgtgtccat tggctcaatg cttgtttcgt tttgcgctgc gcatttcttt   2160

gtgctcaagg acaagtacaa gaacattttg ttccccgttt atattgctac ttgtttgcct   2220

gtgaccttct atgcggtggt gcagtttccg ttgtatgctg atcttcttaa agccattttc   2280

aagaaggtgc cacaacccag tattaccagc agccaatttt ag                      2322
```

<210> SEQ ID NO 42
<211> LENGTH: 2055
<212> TYPE: DNA
<213> ORGANISM: Glycine max

<400> SEQUENCE: 42

```
atgaagagaa cgaaaagtga tcctcccaac tcgaggaggt ttagattgtc tcattttttg     60

tttggcattg gggtgttgta cttgttgttt gtgtcatgta agtttccaca gtttttgaga    120

attgtatcaa cgttaagtgg ggatgggagt gaagataggt tggagggggc agctgttggg    180

gactctgaag attcagattt gagtaaatct tttgtgagtt ctgtttataa agatgcattt    240

cacaggagat tggaagataa tagggaccag gagggtgccc ccttgagacc aaacacggag    300

ccaaagaagg aggaagagcg tcttccggaa tctccgaagc agattccact gcgatatggt    360

aggataactg ggaagataat gcgggaatat aagaggacca atgatttgtc tgtgcttgag    420

aggatggcgg atgaggcgtg gatattggga ttgaaggctt ggaaggaagt agataaggtt    480

gatgagaagg gttcgatgaa aaactcggtc cttgatggaa agcccgagtc atgcccttct    540

tgggtgtcaa tgaatgggga tgagttgatt aaaggagata gtttgatgtt tcttccctgt    600

gggcttgcag ctggttcttc aatcactgtg gtggggacac cccatcatgc tcataaggag    660

tatgttcccc agcttgccaa gatgaagaga ggtggagggt tggttttagt ttcacaattc    720

atggttgaat tgcaagggct gaagtcagtg gatggggagg atcctccgaa gattcttcac    780

ttgaatcctc gaataagggg ggattggagc agacagccag taattgagca taatacctgt    840

tacagaatgc actggggaac ctctcaaaga tgtgatggtc taccgtctgg ggatgaagaa    900

gaaatgcttg ttgatggata cagacggtgt gagaaatggt tgcggaatga tattatagat    960

tctaaagagt ccaagacgac atcctggttt aagcggttta tagggcgtga gcaaaagcca   1020

gaaatgacct ggccatttcc tttagttgag ggcagaatgt ttgtccttac attgcgtgct   1080

ggtgttgatg gataccatat taatattggg ggccgccatg taacttcatt tccatatcgg   1140

actgggttta cacttgagga tgctacagga ttggcaatta aaggggatgt ggatgttcat   1200

tcaatttatg ctacttctct tcctacttcc catccaagtt tctcacctca aagagtactg   1260

gaaatgtcag agacctggaa agcctcacct ttacctaaac atcctattaa actttttatt   1320

ggagttcttt cagcttcaaa tcactttgca gaacgtatgg cagttagaaa gacatggatg   1380

caatcagctg caatcaagtc ttcagatgta gtagcacggt tctttgttgc actgaatcca   1440

agggcggaag taaatgcagt gctgaagaag gaggctgctt actttggtga tattgtcatt   1500

ttgcccttta tggaccgcta tgagcttgtt gtgcttaaaa ctgtgggcat tagtgagttt   1560

gggattcaga atgtgactgc tgcatatgtt atgaaatgtg atgatgatac atttattagg   1620

gttgatactg tcttggaaga aattgagaag gtaccccagg gaaaatccct ttatatgggc   1680

aatctcaatc ttcggcatcg gcctctgagg aatggcaaat gggcagtcac ttatgaggaa   1740

tggccagaag aagtatatcc tccttatgca aatgggcctg catatgtaat ttctagtgat   1800
```

attgttactt tcatccgatc tcaacacaag gataggaaac taaggctgtt taaaatggag 1860
gatgtaagca tgggaatgtg ggttgagcga tataacaata ccattgcagc agtccagtac 1920
tcccacaatt ggaagttttg tcagtatgga tgcatggagg gctacttcac tgcacattac 1980
caatcaccaa ggcagatgat ctgtctttgg gacaaattgt caagaggtcg agctcgttgc 2040
tgcaacttca gatga 2055

<210> SEQ ID NO 43
<211> LENGTH: 1284
<212> TYPE: DNA
<213> ORGANISM: Glycine max

<400> SEQUENCE: 43
atgggaacct cggtggcgga tctagctccg ggtctgtcac ggaagctgaa gaaggttcaa 60
gaatctcgga tcgacacgcc ctatctcttg tcttcgctca acacgctctc ttccttctac 120
gacgacaaca ctcctcaggc gcgtcgcaac ctccgatcca ccatcgagaa gcgcgccctc 180
tccatcaact gcgaattcct cgacgcttcc cacgccgcgc agctgataaa tgcacttaga 240
gaagaagagc tgaatgaaaa ctttttcaag gcattgtctc atgtccaaga gattcatgcc 300
aattgcaaag tgttgcttag gacacatcat cagcgtgctg gtttagagct gatggatatg 360
atggctgtgt atcaagaagg agcttatgag cgcctatgca gggaaagatc tgtccttttc 420
aaatattgtg cagaagaggt agccaatatg agacacaacg cactatttag aagatttata 480
agtgctctta cacgtggagg acctggtgga ttgcctcgac caattgaagt gcatgctcat 540
gacccactac gatatgtcgg tgatatgcta ggctggttgc atcaggcctt ggcatctgaa 600
cgtgaacttg tagctgtatt acttgatcca gatacaatta ccgattctgg tccaaagcaa 660
ttctccaata actctgagga tggctctggg aagacagaat ctgacttgat gtttgttctt 720
gatagaattt ttgaaggatc tcaaccaagt cttatagtat cctacaaact cagtagtaca 780
cttgaatttt actgctacac tatctcagat ttacttgggc gagaaactgc actttgtaat 840
acactatggg cactgaaaga tgctgctcag aatacatttt ttgatatttt gaaaggccga 900
ggggaaaagc ttttgcggta tcccccactt gttgctgttg atctttcccc gccaccagca 960
gtgacggaag ggtatctgt acttcttgaa attatcgaca actacaacag catgatggtt 1020
cctgcttctg gccaaaaacc tgcttttggt ccagttatat ctgctatact ggatccaata 1080
gttcagatgt gtgaacaagc agcggaggca cacaagtcaa agggagctgg ccactcatca 1140
agaaggagtg ggatgagttt tgactgtggt caacttacta aatcatcagt tgatgcaatt 1200
ttgtcaaata gtagctctgt gtcttcctca ctggtctgtt cttactcctt ctctcttaag 1260
ttttacagat atttgttgcc ttaa 1284

<210> SEQ ID NO 44
<211> LENGTH: 3102
<212> TYPE: DNA
<213> ORGANISM: Glycine max

<400> SEQUENCE: 44
atgttgtctg aattgggaag aagacctatg cttgggagta acgagggttc ttttggtgat 60
gaattggaga aggagatagg gatgttactt cgtgagcaac gcagacaaga ggctgatgat 120
cgtgagcgag agcttaatat ttttaggagt ggatcggcgc ctccaactgt ggacggttct 180
ttgagtgccg taggagggtt gtttgctggt ggtggtggtg gtggtgctcc tgctgccttt 240

```
tcagagtttc gaggaacgaa ggatgtgaat gggattgctt ctgaggaaga gcttaggtct    300
gatccagcgt atctttcata ctactactcc aatgtgaatt tgaatcctag gctgccacct    360
cctttgctgt caaaggagga ttggagattt caacaaagac ttaaaggtgg agcttctgct    420
ctaggtggaa ttggagatag gaggaaagta aacaggactg atgataatgc tggaagatcg    480
ctttttgcta ccccaccagg ttttaacatg aggaaacaag agagtgaggt ggataatgaa    540
aaaacaagag gttcggccga gtggggtggt gatggactga ttggtttgcc tggactaggg    600
ctgagcaaac agaagagctt tgcagaaatt tttcaggatg atttggggca taatacctct    660
atcggatgcc ttccttcccg tccagccagt cgtaatacat ttgatgacac tgatatcatt    720
agttctgctg aagcagagtt ggctcatgtt caaggatcat ctgcagccca aaatgttggc    780
ttaccagctt catattctta tgctgttgca gtaggatctt ccttgtcaag aagcactact    840
cctgatccac aacttgttgc tagggctccc agtccctgca tcacgcctat tggtggcggc    900
agagccattg cttctgacaa gagagctatt gccaatccag atgcatttaa tggtgtttca    960
tctggcatca atgagtcagc agatcttgtg gctgcattgt cagtgatgaa cttgtcagca   1020
gattatgtgt tagatggtgc aaaccatttg ccatcacagg ttgaatcaga tgtagatagt   1080
cataagagat atctttttgg taggctaggt ggtcaagatc atgggaagca acaggcttat   1140
ttaaagaaat ctgaatcagc acacttgcaa aattcaagta agagcagcag gagtgggtca   1200
ggtctcaaca atccatcctt ggataggcag gttgagctac aaaagtctac cgttccttcc   1260
aataactcat atttcaaagg atcgcctacc tcccatttta gtagaggagg aagtatgcca   1320
cttcagtacc agcctttaga tggtacaaat tcatcattta ctaactacgg tatgagtggc   1380
tatgctggaa atccagcact ggcatccttg atgactaacc aacttggcac tggtaatctg   1440
ccacccttgt ttgaaaatgt tgctgcagca tcagcaatgg cagcccctcg aatggactcg   1500
agaattcttg gaggtggttt ggcttctgga gctgctgctc catctgatgt gcataatctt   1560
ggtaggatgg gaaatcaaat tcaaggcagt gctcttcagg ctccttttgt tgatcccatg   1620
tatcttcagt acctgaggac acctgagttt gctgcagcac aacttgctgc tctcaatgac   1680
ccctctgtgg acaggaacta cttgggcaat tcatacatga atttgcttga gctccagaaa   1740
gcttatcttg ggtctgtcct ctcacctcag aaatcccaat acaatgtacc gccgggtggt   1800
aaatcaggca gcttcactcc tcatggttat tatggaaatc ctgcatatgg tgctgggttg   1860
tcttacccag gaagtcctat ggcaaactct gttgtgtcca cttctccagt tggatctgga   1920
agtcctgtta ggcacaatga actgaatatg catttttgctt ctggaatgag gaatttagct   1980
ggggtcatgg gaccttggca tgtagataat gagaacattg atgaaagttt tgcttcttct   2040
ctgttggaag agtttaaaag caataaaacg aagtgttttg agctgtctga aattgctggt   2100
catgttgttg aattcagtgc ggatcaatat gggagtcgat ttattcaaca aaagctagaa   2160
acagctacta cagaagaaaa aaacatggtt tatcaggaaa tcatgccaca tgcccttgct   2220
ttgatgactg atgtctttgg taattatgtg gttcaaaagt tttttgagca tggacttgca   2280
tcccagaaaa gagaattagc caacaaactt cttggccatg ttctggcact tagccttcaa   2340
atgtatggtt gccgtgtcat ccagaaggcc attgaagttg ttgatctgga tcagaagata   2400
gagatggttc aagagcttga tggtaatgtt atgcgctgtg tacgtgatca gaatggtaat   2460
catgtcattc agaagtgtat tgaatgtgtt cctgaagatg caatccactt tattgtgtca   2520
acattttttg atcaagttgt gacactctca acccatccat atggttgccg ggtgatacag   2580
agagtgctgg aacactgcaa agaccctacg acacaacaga aagttatgga tgaaatatta   2640
```

ggagcagtta gcatgttagc tcaggatcag tatggcaact acgttgttca gcatgtgctg 2700
gaacatggga agcctcatga acgttcttct atcataaagg aattagcagg caagatagtt 2760
caaatgagtc aacagaagtt tgcctccaat gttgtggaga aatgtttgac ctttggtggt 2820
ccttctgagc gccaattact agtgtgtgag atgcttggca ccacagatga aaatgagcct 2880
cttcaggcga tgatgaaaga tcaatttgca aattacgttg tacaaaaggt gctggaaact 2940
tgtgatgatc aacaacgcga gctgattctt taccgaatta aggttcattt gaatgcattg 3000
aaaaagtaca cctatggaaa gcacattgtc gcccgtgtgg agaaacttgt tgctgctgga 3060
gaaaggagaa ttgctgctca ggctcctcct caacctgctt ag 3102

<210> SEQ ID NO 45
<211> LENGTH: 747
<212> TYPE: DNA
<213> ORGANISM: Glycine max

<400> SEQUENCE: 45
atgaccaacc caatctctga gactgaaatc cccgacgaaa cccaaagccc caacgccatc 60
cccgaacaat gcccacaaga accaccacta caccccgacc cccaattctc cgaaacccta 120
accctccccg atcctaattc ccccaatcct aaccaagacc aagattctac catgcaaggc 180
ccgatcccca ccaccctcac cgtcgtcgac gacgacgacc ccgagcccga cgcctccacc 240
ggcgctgcga ctggaggcgg cggcggcacc accaccagac gcacgacgaa gcggaagaaa 300
ggcccgaaga gaaccgcgct agagagaagg tctcgcgaga agctccaggt aatcgtcgca 360
accctaaagc ccattccttt cactccagca aaaaccctcg atttcgagag gcaccagagc 420
ctcttgcagc ggctggggct ctgggacttc gtccacgtcg agctcgattc ggggctccgc 480
ggcgatctcc tcgcccagct catcgcgagc tacgtcccca ccagtcggtg cagctacgtc 540
aacggggtta ggatcaatgt gaaccgcgcc gatctaggcc gcgccttgaa gcttccggtg 600
aagaagactg gttgcggtgg tggtgccacc gcagattcga tagactccgc ggaatctata 660
gcgtttgttg aggaggtggt gtatagttgg atgcttctgc atgatgatga agcttacatc 720
atgcctaatg atgaaacaaa attttaa 747

<210> SEQ ID NO 46
<211> LENGTH: 675
<212> TYPE: DNA
<213> ORGANISM: Glycine max

<400> SEQUENCE: 46
atgactgcag atgacggtaa aatattattt gatgaagaag agctcaaaat gatcctagat 60
tttaagagag gtgaggacta tattgaggtt ctttgtggcg ctacaaacaa aaaatatgga 120
gattatgttg ggaggctaaa aattaataac gaaggtcaat atttcatcac ttgtgagtgt 180
tgccttgagt gtcccttggt gaatgtcact ctagaagcat ttgagaaaca tgctttaagg 240
gaagggagcg gaaggtggaa gagaaacatc tgggttcatt gtgaagacga agacaaagtt 300
ccactctgga agacacctct gataaagtat tatacacacc aggcaaatgt ggctaaccgg 360
aaagactctg caatgaggaa acaaaacttt cacagggatg agttcctacg ttgcacgaga 420
tgcgggaagg agcgcaggtt ccatctcaag agcagaccag acattaagaa ctaccatgat 480
gcttcaaaca acaaatgctg gaattgttct ctttggcctt atcaaaaatc aagtctgaaa 540
gcaagcaggg gctgttctcg ttcttcaact tgcctaggct gctcaacttg ttactgtgaa 600

-continued gggtgcatca agtgccgctt tgaggattgc aattgccaag aatgcagaga ctttatgcta 660
tatgctaaac cttaa 675

<210> SEQ ID NO 47
<211> LENGTH: 513
<212> TYPE: DNA
<213> ORGANISM: Glycine max

<400> SEQUENCE: 47
atggttgatg gttctattct tgtaactaaa agatgtttga gagaggactt atgctcaaag 60
aaaaggagtg gaagctattc tggagagacc ataaaaaggc aaaggggttt tgacctagaa 120
aggcctgctg agagagacat tttttatggc ggctatgatg aacatgaggc aggacttacc 180
tcctacacta cactagagag atgcaaaata tgcagcaaca atgatgatgg ttatgatgaa 240
gacatggaag tggatttgac tctaagcata ggaggaggaa gccaagttaa taataacaag 300
aatagtagta gtaagaaacc ttatctgctt ccattagggt gctcagactc acccaatagg 360
aaaactaagg acctaaattc ttctgtctct ttccaatcct acagggtggg agatttcagt 420
gaccccacca cccctatgag cagctcaagt gtgacatttg atcaagagag aaaggggcca 480
cattggcttt ctcaaggttt aaagcttaaa tag 513

<210> SEQ ID NO 48
<211> LENGTH: 1338
<212> TYPE: DNA
<213> ORGANISM: Glycine max

<400> SEQUENCE: 48
atgaagcagc tcggcgagaa cgtggggagt ttagacgcgg ccattgagca attgctgaat 60
gcggagaagc atgcgaggct cgccggcgac gtcgccgcca ccagaaacgc cgtcaccgaa 120
attttacggt tgtgcttcga agcgcgtgcc tggaaaactc tcaatgacca gattgctctc 180
ttgtccaaac gacgtggcca gcttaagcag gctgtgacag cgatggtcca acaggctatg 240
caatatactg atgagacacc ggatcttgaa actcgtatag aactcatcaa aaccttgaac 300
agtgtatctg caggaaagat atacgtcgag attgagagag ctcggttgat caagaaactt 360
gcaaaaatta aggaagaaca aggacttata gctgaagctg ctgatttgat gcaagaaatt 420
gcggtggaaa cttttggcgc catggctaaa actgagaaaa tcgcattcat tcttgaacaa 480
gttcgtttgt gtctagactg ccaggattat gttcgtgcac agatactctc aagaaagatt 540
agtacgagag tgtttgacgc tgatgttaca aaagaaaaga aaaagcctaa agaaggtgat 600
aatgttgttg aagaagctcc tgcagatatt ccatctctac cagagttgaa gcggatctac 660
tatgaactaa tgattcggta ttattcccat aaaaatgatt atcttgaaat ttgccgttgc 720
tacaaggcaa tatatgagat tccatctgtc aaagaaaatc ttgccgagtg gattccaatc 780
ctgaggaaaa tatgttggta tttggttcta tccccgcatg atccaatgca gtcaagtctt 840
ctcaattcta ccttggagga taagaatctg tctgagattc caaactttaa gttactgttg 900
aaacagttgg tcactatgga ggttatccag tggacaactc tttgggattc atacaaggat 960
gagtttgaga atcagagtaa cttaggaaag aatttgggtg aaaaagcagc tgaagatctg 1020
agggaaagag taattgaaca taatattatt gttatatcaa aatactatgg aaggactact 1080
ttgaagagac ttgcagagct tttgtgtctc agtgttcagg aagctgagaa gcatctttca 1140
gatatggttg tgtctaaggc attggtggcg aagattgata gacccatggg aatagtttgt 1200
ttccaaagag ccaaggatag caatgacgtt cttatctcat gggcagcaaa cttggagagg 1260
ctgcttgatc ttgtggagaa gagctgccat caaatacaca aggaaaccat ggtgcataaa 1320
gctgccttga aggtttaa 1338

<210> SEQ ID NO 49
<211> LENGTH: 948
<212> TYPE: DNA
<213> ORGANISM: Glycine max

<400> SEQUENCE: 49
atgagtttgt cgcaattggg ggaaatcttg tctcgtcttc ccatgaaacc tttgatccaa 60
ttcaagtgtg tgtgcaagga atggaactcc ttgatttcag aaccctattt catcaaattg 120
caccttagca aatctgctgc aaaggacgat ttggaacacc ttcaattgat aaaaaatgtc 180
tgcctcggat ccatccctga aatccacatg gaatcgcgtg atgtaagttt gatattccat 240
tccctacaaa ttgaaacgtt cttgttcaat ttcgcaaaca tgccaggtta ccatctggtc 300
ggttcatgta atgggttgca ttgtggggtt agcgaaatac cagaaggata ctgtgtttgt 360
ttctggaaca aggcgacaag aacaatgttt gggtttggct atgatccgtc aagtgacaaa 420
tacaaggttg tagcaattgc gttgactatg ctctcacttg acgtatctga aaagactgag 480
atgaaagttt atggcgaggg tgacagtagt tggagaaacc ttaaaggttt tcctgttctt 540
tggactttac ctaaagttgg tggagtgtat ctgagtggaa cccttaattg ggagacttgc 600
atatcactgt ttcttcccga tgatttttgc ttttttgata caaatattgg agtttttaga 660
gactcgctgt gcgtttggca agatagcaac acccatattg gcttgtggca gatgaggaag 720
tttggagatg acaagtcttg gattcaatta ataaatttta gttatttaca tcttaatatt 780
cgtccttatg aagaaaaatc catgatttta ccattgtgca tgcctaacaa cggagacttc 840
ttcatgctga aattcactag aaatgctgat gatgaatacc aaacaattct gtataaccag 900
ggggatggta agtctcaagt ttctgtcgtt ccctcagata gtttcaga 948

<210> SEQ ID NO 50
<211> LENGTH: 231
<212> TYPE: DNA
<213> ORGANISM: Glycine max

<400> SEQUENCE: 50
atggccattt atcgaatcgt tgcaatcgat gctcgatctc aaagagaggg aagagatctt 60
caaaaattag gtttttatga tccaataaag aatcaaacct atttaaatat tcctgttatt 120
ctatatttcc ttgaacgagg tgctcaacct acaggaattg ttcaggatat ttcaaaaagg 180
gctggtgttt ttaaggaact tagctcaaat catcaaacga aatttcatta a 231

<210> SEQ ID NO 51
<211> LENGTH: 1566
<212> TYPE: DNA
<213> ORGANISM: Glycine max

<400> SEQUENCE: 51
atgaagaaat ttacgatact tctttaccct ttgagttgtt ctgccggatc ggtcgctcaa 60
gacctttggt ctctacccgg acctgatgaa aaaaatggga tcacatctta tggactcgtt 120
gagaataatt ctgatctagt tcatggccta ttagaagtag aaggcgctct ggtgggatcc 180
tcacatatag aaaaagattg cagtcagttt gataaggatc gagtgacatt gcttcttcgg 240
tccgaaccaa ggaatctctt aaatatgatt caaaatggat cttattctat cgttgatcaa 300

-continued

```
agatttctct atgaaaaata tgaatcggag tttgaagaag gggggggggg agtcctcgac    360
ccacaacaga tagaggagga ttttttcaat cacatcgttt gggctcttag aatatggagc    420
ccttggggct ttctatttta ttgtattgaa aggcccaatg aattgggatt tccctattgg    480
gccaggtcat ttcgggacaa gcggatcatt tatgatgaag aggatgagct tcaagagaat    540
gattcagagt tcttgcaggg tggaaccatg cagtaccaga cacgagatag atcttccaaa    600
gaacaaggct tttttcgaat aagccaattc atttgggacc ccgcggatcc actctttttc    660
ctattcaaag atcacccttt tgtctctgtg ttttcacatc gacaattctt cacagatgaa    720
gagatgtcaa gggaacttct tactacttcc caaacagatc ttcctacatc tatatataaa    780
cactggttta tcaagaatac gcaagaaaat cattttgaat tgttgattca ttgtcaaaga    840
tggcttagaa tcaatagttc attatctaat ggatttttcc gttctaatac tctatctgag    900
agttatcaat atttatcaaa tttgttccta tctaacgaag cgctattgga tcaaatgaca    960
aagacattgt tgagaaaaag atggcttttc ccagatgaga tggttgttgc tatctgctcc   1020
aataacgaat cattgatccc ctatatcgat aatacacatt ccagtttggg aacgtccggt   1080
gccaaagtca ttgaatggtt atttgatgca attagaactg atttgaatga aaaaacaata   1140
gtaaatggaa atagaacaaa gtgtattaga ataaacaaaa tccgtaaaaa agttcctcga   1200
tggtcataca aatttattga cgaattggaa caacgggagg gaaaaaatga agcagaaaat   1260
tatcaaattc gttctagaaa agccaaacgt gtagtcattt tgactaataa atctaatttt   1320
tgtaagaagt acgatactta taatcctaca agagatactg ataacgctga aaaaaaaaat   1380
gaattggctt taatacgtta ttcccaacaa ttggattttt ggcgagacat aatcaaagga   1440
tctatacgtg ctcaaaggcg taaaacagtt acttggaaat tttttcaaaa aagggtgcat   1500
tccctccttt ttttggataa aattgaaaaa cctttattct tttcttttga tagtttcaaa   1560
tcatga                                                               1566
```

<210> SEQ ID NO 52
<211> LENGTH: 612
<212> TYPE: DNA
<213> ORGANISM: Glycine max

<400> SEQUENCE: 52

```
atggcctctc tttttcttag acaggctctg ctcctccgcg tttgcttcca caactaccaa     60
cgcttcaccg ccggaggcgt cgccgcacgt caccggctgt ggtgcagcgc agccgccaac    120
ctaccgtcag acgaagcgga gaagaaaaca aactccggcg gcatcagcaa cagctccttt    180
gcacggaaag ctcagtatcc tccgtcaagt gaagcgcggt gggaggacga ccccgattac    240
cgcaaatgga aggacaaaga aaaggagatt ctcagcgaca ttgaacctat cgttgttctc    300
gccaaggata ttctccactc acgaaggtac atggatggag cgcgattgaa tgaggaggac    360
gagaaggcta tagttgagaa gctccttgca taccatccac attctgaaga taagattggg    420
tgtggccttg aatccattat ggttgaccgt catccccaat atcgacaatc aaggtgtctt    480
tttgttgtaa gaactgatgg tggctggatt gatttctcct atcagaagtg ccttcgggaa    540
tacattagag ataagtaccc tactcatgcg gaaaggttta ttagagaaca ttttaagcgt    600
gggagtggtt ga                                                        612
```

<210> SEQ ID NO 53
<211> LENGTH: 2691
<212> TYPE: DNA
<213> ORGANISM: Glycine max

<400> SEQUENCE: 53

```
atgtattatt ttcagcacaa tcctggatta cctgctactc gtcatcgtag gatagcaagc     60
tctttcaggg ataactctct ttttcagata ttccagatat cattaacttc tctcttccag    120
ttaaaatctg atgctgggag caagttgcag gagctgtctc ttatgctttc ccttagttgt    180
ttatcatttg attttatggg gacatcgtat gatgaaagtt cagatgaaat tggtactgtt    240
caggttccat ctggttggaa gcctacccta gaggattcct caacactgca aatctttttt    300
gattattatg caatgaatca aatgttttcg aaagaggcat tggagtgctt gttgcgtctt    360
gcttctacta gacgatcatt gttttccaat gatactgctc gaatgaagtt tctgtcacac    420
ttgatgctgg gcaccaaaga aattttgcaa actggaatag gtcttgctga tcatgataac    480
tatcatgcct tttgtcgtct tctcggccgc tttaaagtaa attatcagtt atccgaactt    540
gtgaatgctg aaggctatag tgaatggata cgcttggtag cagagtttac attaaaatct    600
ttgcattctt ggaagtgggc tggcagcagt gtttactacc ttctaaattt atggtctaga    660
tcagtgacgt ctgtgcggta cctcaagagt gacaaaccta acctgttaga tgaatatgtg    720
cctaaagtta ttgaagggtt tgtatcatca agatttgatt cattgcagtc tgaactatca    780
gatgaacttg gtgaaaatcc tcttgacaat gttgaagtac ttcaagatca gcttgaattt    840
tttcctttcc tctgcagatt ccagtatgaa agttgcagtt cgtatttgat gaagatagtg    900
gagcctatca tgaaaagcta tatgaacgaa atccatgtgg atagttatga actctctgta    960
actgaatcca aacttgcttg gttcacacac atagttgctg caattctcag aacaaaacag   1020
atttctggtt ctagtggaga atcgcatgag atacttgatg cggagatttc agcatgtgtt   1080
ctgcagttga ttaatatttg tgacagtggg tttcacagta agaggtatgg agatgtgagc   1140
aagcaaagac ttgatcgtgc tatactaact ttcttacagc atcttagaag gtgttatatt   1200
ggtgatcagg ctgtgtattc ttccaagcag ttatatacca ggctatctga acttcttgga   1260
ctgcatgatc atctcctact actaaatgtt attgtgggaa agatgactac taacctaaag   1320
tactacacta agtgcaagga ggttattgat cataccttaa atctctttct ggaaatgaca   1380
tctggataca tgtcaggaaa actgcttctt aaattggata ctgttaaaca catactatcg   1440
aatcagaata gggaccaatt ccctttcata gaaaattggg aatgtttccg cagcagaaca   1500
accctgtact atactattgg catgctgata ttcttggaag atagcctact gaaatttaaa   1560
tctgcaatgg aacctttctt acaggttttt gttagattgg aatcaacacc tgaagcattg   1620
ttccaatcag atgctgtaaa atatgcattc gttgggttga tgcgggacct tcgaggcata   1680
gcaatggcta ctaatagccg tagaacgtat gggttccttt ttgattggct ttatcctgca   1740
cacatgcccc ttcttttgaa aggaattaca cattatgctg atattccaga ggtaacaact   1800
cctttactga aattcatggc tgaactggtg ctgaacaaat cccagcgctt gaattttgat   1860
tcttcttctc ctaatgggat actacttttc cgagaagtta gtaaattgat tgttgcttat   1920
ggatcaagaa ttttgcctct tcctaataaa gcagacttgt acacatccaa atacaaggga   1980
atatcaattt gtttgataat tcttacaaga gcactatccg ggaactttgt caactttggc   2040
atttttgaac tttatggtga tagagcactt gttgacgctc ttgatatcac tgtaaagatc   2100
atattatcaa ttcctttggc tgatattttt gcatttcgga aggtcgcagc agcttacttt   2160
gcattcttgg agtctctctt cagttgtcat ttgtcatttg tcttgagttt ggataaaact   2220
acatttatgc ttgttgttgg atctctcgaa tctggcctta aagatagcga gaaaatatca   2280
```

-continued

```
tcacagtgtg cctctgctat tgacaacttg gctacatttt atttcaccca tgttactgtt   2340

ggagagtcag ttacctcacc tgctgctctt aatttagctg gactcctttc tgattgtgct   2400

gagcttttct ctagaatatt gagaacccta tttgaagttg ttatatttga gaaccgtggc   2460

aatcattgga ctcttagccg agccattttg agcatgatac taatcagtga agagatgttc   2520

acaaatgtca aggctcaaat tttggtttcg tatccaccag acctacacca gcggttttct   2580

ttgtgcttta ccaagcttat gacagatgtg atgctcagct tggatttaaa gaacagggaa   2640

aaattctctc agaatctgat cagattcaag tctgagtttt gtgccaaata a            2691
```

<210> SEQ ID NO 54
<211> LENGTH: 1170
<212> TYPE: DNA
<213> ORGANISM: Glycine max

<400> SEQUENCE: 54

```
atgggttata ttgggactca cggtgttgca gctctgcaca gatataaata tagtggagta     60

gatcattcct atgtggccaa atatgtacta caacccttt  ggagtcgctt tgttaatttt    120

ttccccctat ggatgcctcc aaacatgata actcttatgg gatttatgtt cttactactg    180

tctgcattgc ttggttatat atactcccca caattggaca cagctcctcc aagatgggtt    240

cattttgctc atggactact tctgttttta taccagacat ttgatgctgt tgatgggaag    300

caagctagac gaacaaattc ctcaagccca ttgggggagc tctttgatca tgggtgtgat    360

gcacttgctt gcacatttga agcattggct tttgggagca cagccatgtg tggaagaact    420

actttctggt ggtggttaat atctgcaatt acattttatg gtgcaacctg ggagcattat    480

ttcaccaata cacttatact gcctgttata aatgggccta cagagggtct tatgataata    540

tacatctgtc actttttcac tgctatcgtg ggtgctgagt ggtgggttca gcaatttgga    600

aagtctttgc cattcttaaa ttggcttcct tatcttgggg gaatcccgac attcaaagct    660

atattgtgtt taatgatagc ttttggtgtt acaccaacag tcacatgcaa tgttagtaat    720

gtttacaagg ttgtgaaggg aaagaatgga agcatgccac ttgcattggc aatgctttac    780

ccatttgttg tacttgtggg aggagtgctt gtgtgggatt atttgtcacc atcagacatc    840

atggggaaat atccacattt agttgttata ggaacaggac ttactttcgg atatcttgtg    900

gggaggatga ttttggcaca cttatgtgat gaacctaagg gtctgaaaac tgggatgtgc    960

atgtccctca tgtttctccc attggccatt gccaatgtac ttgcatccag gctaaatgat   1020

ggggttcctt tagtagatga gagactagtt cttcttggtt actgtgcatt ttcagtgaca   1080

ctatacttgc attttgccac atcagtcatt catgaaatta ccaatgccct gggaatatat   1140

tgtttcagga taactaggaa ggaagcttga                                    1170
```

<210> SEQ ID NO 55
<211> LENGTH: 2745
<212> TYPE: DNA
<213> ORGANISM: Glycine max

<400> SEQUENCE: 55

```
atggagttca gacatcgaaa ttacagtgcc gagcttgaat ctcacgcgct ccctcgccta     60

cgcgccggag ctcatcctct ctctgctcca cctccacctc cacctctctc ccaggttgat    120

gccatagatt gtgggaacac tgatttctat gatccactga gaggaactaa taatgatgca    180

aatgccgccc ctcctgatca tgacaacttg aatgaagctg ctgatcatat gccaacaaag    240

gagtggacct ctttcaggag attactaacg cagaggtttc ctgtctccaa aatggtttcc    300
```

```
gttgcttcaa tgcccgatgt tttaacgaga agtggaaaat tacttgagaa atcttcaaca    360
aatatgcact tggaggaatt ggaggatcca caaaaattcg cagacgaggg tgtcaagacg    420
attacgtggc aggagtatgt ttctcgacta catgaactca aagatgaaat tactcgttcc    480
tggcttgctg aagatcgagt gacatcctta aagttatcca taaaggttgc taagcttctg    540
atggatacgt cagtatttga gttttatcct acacttttg ttcttgtcac agatatcatg    600
gatatgcttg ggaacctggt ttggcaacgc ataaagcgga aagctgagtt ttccgaagat    660
ggagctttac gctgcaactt agcagaaaac tttcaagcaa gggatatttg tgctgatgcc    720
aaagaaactt gctataactg gttcaacaaa attggtgctg tgcaagagct tcttccacgc    780
atttacttgg agctggcaat attgccttgc tggcggtttt tgcttgagca acctttagac    840
agcctccgac gcttggtaat gatgataaga ggattaggag atccagtagc atctgcatat    900
tgccgtcttt atatggctca ctgtgctcag aagctgcctt cacatgatat aggctatctt    960
gttacatgtg tcaatgacat cagagttgtt ttgatgcaaa tcttgtcagc caatgaaaga   1020
actcataaaa atgttaaact caacaaaaaa ttgcaagtca gtctgatgga accaaccatt   1080
gagtatatta tgaagtgtat atttactggg ttgtctcaga gacaagtcaa tgaagtttta   1140
tcagagtttg gattgatgaa gaatcaacag gatttgggga gtgtttcatg tgtttcaatc   1200
attcttcatc atttactgaa ggaactccct atagaagtag ttagttccaa tgttgtgcag   1260
atccttcatc tcattgaatt tagcaaggat aattcctttg atcagcatat gaattacaga   1320
ttgcttggat tcaggctgta cgaaagaaaa tcccctgttg atattgttga tgctgtgtta   1380
gataaagtta ttcaggttat tgctctgtat gatagccttg acgaatacct gaaggttgta   1440
gatgcttata ctgatcttat tcttcagaat cagatggata accatttgaa aatcattttg   1500
gaaggcattt caaagcgtac ttggaataaa ggagttacag aggatgaaat gccgagcttg   1560
caatctcttg tggtgaagct tctgtctcat tttaagcatc tggaagatgt gttttctctg   1620
gatcagtttc ctgaaatctt ggatgtaatg tatggcaagt cacaggatgt tgtctttttg   1680
catatcctta atatggcgac aaggaatggt cgcattagtg atccgacgag catacagttg   1740
ctttttgaaa tttctctggc tctacataat aatatagagt ttatgaacat gaaagatgat   1800
gatggccaag tggcatgttc aatagctcgc tttgtgcaca tggtagatta tggaacagag   1860
atggaacacc atttagcatt tctggttgat tgccgaggag cttttggtag attaaatgag   1920
cttaaggaaa ctcttgttca ctctagcaat tctttagcaa ttcaagcttt gaaatgtgct   1980
aagaaacatc tgaattttgt caaatcctgt gttacattta gtgaagtcac aataccttct   2040
atttctgctc acaggcagtt tgatcttttt ctagaaactg cagaggttgc attcttaggg   2100
ggcttggttt ctcattcaga tggattgatt gattcagcaa tcagctgttt gcataccttta   2160
gacataattg atggcttccg aactccaact gatgttgaag gactagtttc atctattaga   2220
aagctatgtg gcttcttaat tatggttcca ggttgtactc ttagtttacc agtcacctat   2280
ttcccaaata gcttatttac attgatcagc tcccggtctt ggtttgaacc aaaaatgagg   2340
gcacaaattt tttctgctat catattatta ttgacaactt tatcacaaaa gagactgcca   2400
tatcatgcaa attcacagat tccaggcaat gacatgttat actacgggga ttcatcgtac   2460
aaccaagagc ttgtttcttt gtctaaactt gttcttgaga acctgcttag tgccgttcaa   2520
caagaacctt cccaggctgc tcgaggaatt atggcacttg aagcttgcaa ttgcattgct   2580
tcttctttca tgctaagcaa tgagttattg tcttcttgtc ttacactggt cgaaactgcc   2640
```

aagtcatgtt tgagtgccaa agacagatac ctccagtcaa ccattcaact tttaaacaag 2700
caatcgccaa cttctgtagg gactatggtg tctacttttg tatga 2745

<210> SEQ ID NO 56
<211> LENGTH: 555
<212> TYPE: DNA
<213> ORGANISM: Glycine max

<400> SEQUENCE: 56
atgtcatctc caagcaagag aagagaaatg gatgtaatga aactgatgat gagtgattat 60
gcagtggaga ctataaatga tggactcaat gagttcaatg tggagtttca tggtccaaaa 120
gaaagccttt atgaaggtgg agtctggaaa attcgtgttg agcttcctga tgcttacccg 180
tacaaatccc cttctattgg ctttgtgaac aaaatattcc acccaaatgt tgatgagcta 240
tctggctctg tatgcttgga tgtcattaac caatcttgga gtccaatgtt tgatcttcta 300
aatgtttttg aagtttttct tccccaactc ttgctttatc caaatgcttc agatcctctc 360
aatggtgatg cagcatcgtt aatgatgaag gataaaaagc tatatgacca gaaagttaaa 420
gagtattgtg agcggtatgc taagaaggaa aacattagca actctacagc tgaagagagt 480
ggagatgagg aagacatcag tgaagaagaa agtggatcta gtgatgatga aattcctggt 540
cgcgctgatc cttaa 555

<210> SEQ ID NO 57
<211> LENGTH: 2355
<212> TYPE: DNA
<213> ORGANISM: Glycine max

<400> SEQUENCE: 57
atgctttcag gggtgaaatt catttcccgg gaccaggtgc atgatgagga cttggattct 60
gtctcgaaag aaaggaaaaa atcagatagg aggagggaaa agaataagag gaaaaggagg 120
agctctaggg acagctctga tgatgatgat gatgggcttg agaagataaa gaaaggatct 180
agaaagaaga agtggtattc gtcggatgaa gactctttga tttacacaac tgaaagtgag 240
agtgagaaag atgaaaagaa gaggaggagg agagcgaaaa agaaaaggga tgatggttcg 300
tcacgtgatt ctggcgaaag gtcaaaagga agatcacgat ccaggagtgg taaaaaagaa 360
tatacatctg aggatgagga agactcttat tcttctgatg gtagtgatag tttttcgggt 420
cttaaaggta agcaccaaaa gtcagataga aaagatggga gtaagaggaa caagatcgaa 480
ggtggcacgg taaattctac aagtgagatg gaaattgcaa gaaaagaaat gggattggat 540
tggatgctta ggtctgaaag taagaagcct gtagttacgg aatcagagga aaaactgtca 600
gaggaggttc ctgttgagga gtcaaagaag gcaaatccta aggaactgaa tccatatttg 660
aaggataatg gaagtggata cccggaagaa agtggagcta aagttggtgc cgaccaactt 720
ctatcttctt cccttgttgg ggatggagga gcaagttgga gacttaaagc cttaaagcgt 780
gcacaagagc aagcagctcg agatggacga agattcaatg aggttgtgga agaaaggtgg 840
agttctcttg gtgagttgac tgcagctgtt gcatctcatg cagctgcccc agctcgtgct 900
catctgcgtg ctataaaaaa tagacaaaga gggataactg aagaaaattc acaagattct 960
gataagcatg gtcgaaggga ttctaaaagg caggactact taaaggatgt ttctgttcgg 1020
caccatgaaa tgaaagcacc taaagttcga gattctttgt cttggggaaa gcgaaagagc 1080
caacaagtgg tagctgaggg tgccggggtc atctctgctg cagtatctag cctaaataag 1140
tttgccaatg atggaagctt tatgcatgat tttggtagca agatgagtaa taattctgac 1200

```
ggctctgttt tggatagtag tgaattagaa aaggtttcgt tggaagctaa tagacctgaa   1260

gaaagtagtg cagtagtcaa gaatgagatg agtgaaaacc agttggcagc taaggttatg   1320

caacttcgtt tgaagggaaa gcatgaagaa gctgacaaac tgatgcaaga agcaaaagtt   1380

atgaacacaa agcaaggaaa tcaagaccat tcaattagat caagaaccga gggaagttct   1440

agcaggtatg ctatgcagaa aatatctgct gagcagaaga aaggagagga tgatgctgat   1500

atgcatcttg ctcgcaagat catgcataac aagcagttta gggcttctac tcaggctgat   1560

gatgaatatg actttgagga tggtccaagc agaaagagta gaaagaagca aggaggtgat   1620

gatcacaaga gtatccaaaa gaagacaaat cgattcttga ctcagcaaga gcgctgccta   1680

ttttgtttag aaaatccaaa tcggcctatg catcttgttg tttcaatcgc aaatttcaca   1740

tatcttatgt tgccaaagtg gcagcctgtg gtgcctggtc attgctgcat tttaccaatt   1800

cagcatgaat cagctacaag aactgtggac gataatgtct ggacagagat tcgaaacttc   1860

aagaagtgcc taattatgat gtttgctaag caagagaagg aggtagtgtt tcttgagact   1920

gtgatgggat tggcacagca acgacggcat tgtatggttg agtgcattcc tttaccccaa   1980

gatattgcca aagaggctcc tttgtacttt aaaaaggcta ttgatgaagc tgaagatgag   2040

tggagccagc acaatgcaaa gaaacttatt gatacaagtc aaaagggatt gcgcaattca   2100

attcctaagc actttccata ttttcacgtt gaatttggtc taaacaaggg ttttgtccat   2160

gttattgatg atgaaaagca gtttaacatc agccttggct tgaatgtcat aagaggcatg   2220

ctacatttgg cagaggagga catgtatagg cgacgacgct acgaggctgt ggaggtacaa   2280

aagcaagcag ttgaaagctt ttccaaagag tggaaacatt ttgactggac aaaacagctt   2340

catgaaactt cgtaa                                                    2355
```

<210> SEQ ID NO 58
<211> LENGTH: 264
<212> TYPE: DNA
<213> ORGANISM: Glycine max

<400> SEQUENCE: 58

```
atgagaacca ctcaacgtgc tttggtgggt ctatttgtct taattctcac gcacttcatc     60

attttctcta tagtttcaat gactactgag actagaagta atctgatagg taggtgccca    120

ccacggaagc tgctagatcg tgtctcctac ttctctgcaa gtttagataa attaaaaata    180

gtttatgagg ctcctcagag atcagtaaat acaagtttaa ggaagaatcc tccaagcaac    240

tcaaacccaa cccataacaa gtga                                           264
```

<210> SEQ ID NO 59
<211> LENGTH: 2592
<212> TYPE: DNA
<213> ORGANISM: Glycine max

<400> SEQUENCE: 59

```
atgggttcat tctctggcac ttgtgaaatt gtcgaagcaa gggaagacct aaatacagag     60

aaagatacgg ggatatatca gtccaattct ggatatagcc tggatgagaa atttcagaag    120

catcctgtgc agaaactggg atataagggt aatctagatg atgatattaa taagctgttt    180

gagtcaatta ctcttaaatc ttcctcaagg gatttgggct ttatacatgg tacaagccct    240

aagatgaaaa gtgcattgaa aaaaccaatt gcagtgggtg cttctcggtc cccacgagtt    300

ggaccttctg agcctgtgac tttgaagcag gcactaagag acctatgtat atctaaggca    360
```

```
tcagaaatgg cttccatgaa aagattatca aagtcaactg cttctccacg aatatctgag    420

gttgggaaga tacatacatt gtacaattca gttgtagttg aaggtagacg atctgagcct    480

tctaatgttg agagtaaagg tagtacaagt gaaatatctc tagtgccaga agagagcaac    540

tcactttctt tggataatgc ttaccagtct cgttcaactg ttaaaagcac ttcgctgagc    600

ccaaatgttc aatcttccaa aattgctgtt gcaattgcaa ttacacaaaa tgatactggg    660

gcttcattga tgccaagtga cctggctagt tcatcaagta aagttggggt tctatcaccg    720

tcatcagagc ctgctcaaat agagaaacaa acatctgaat cttcttcatc tagttgtaac    780

accaatggaa gtaaattaga gttgcccgaa aatgcttctt cccctaaaaa gataggaaat    840

aaagcctctg catcaaagaa tgggcggaaa ggtaggttac aaacagtctc ttcctcatct    900

acttcggtaa atggcaatag agtgtgcaaa ctgtcacgca atgcccctcg tacagtcaaa    960

tcaattatca agaacaaaaa ttttggaaag aaaaaagtaa agcaggattc agtttctgct   1020

ttatttgatc ctacatgcag tgaagtaaat gacaagtcag tttctggtac aactcaactt   1080

gtttgtgaga gatgttggtg tgctattgaa aataacaaag gtattacatc attggactct   1140

atcagtcctg gagagggaat aaactctgtt aataactctg gcgctgcatc agctggctgt   1200

aatagcagca gagaagttac aaaagtgaaa aagaacaccg tattgaaaga gcaacttgaa   1260

ttttctcaaa gttcaaagag tagccaaggt gactacagta gtagtacaag taccagtgat   1320

gagagtaatc tcagtgggtc tagttgtggc aataggcctc acatgtcaaa ggatgttaga   1380

tggaaagcca tacgccatgc tcaaattcag aatggagtct tgggcttgag acacttcaat   1440

cttttgaaga agctaggttg tggagacatt gggactgtat atcttgctga actaattggc   1500

aaaagttgtt tgtttgctat taaggtgatg gacaatgagt tttggcaag aaggaagaag   1560

atgcctaggg ctcaaactga acgagaaata ttgaggatgc tggatcatcc ttttcttcca   1620

acactgtatg ctcagtttac atcagataat ttgtcatgtc tggtcatgga gtattgtcca   1680

ggtggtgatc ttcatgttct acggcagaag cagcttggca gaagtttttc agagccagca   1740

gcaaggtttt atgttgccga agtccttctt gctttggagt acttgcacat gcttggagtg   1800

gtttaccgtg atttgaaacc tgaaaacatt cttgttcgag aagacggcca cattatgctc   1860

acagattttg atctgtcgct aaggtgtgat gttagcccaa cacttctgaa gtcatcttat   1920

gtggatcctg ctaagatttc tggtccttgt gcacaatcga gttgcattga gccattctgt   1980

attgaaccag cctgtcaagt tccgtgcttc agcccaagac tcctacctcc tgccgcaaaa   2040

gcaaggaaat taaaaaatga ccttggtgct cagctcagat cattgccaca gctcgtggct   2100

gagcccacag atgcaagatc aaattcattt gtcggtactc atgaatactt ggcgcctgag   2160

atcatcaaag gagaaggaca tggagctgca gttgactggt ggacatttgg tgtttttcta   2220

tatgagcttt tatatggtag aacacccttt aaaggttcta ataatgaaga aacattagcc   2280

aacgtggtgt tgcaaggtct cagattccct gacaccccat ttgttagtat ccaagcgagg   2340

gatctcatta gagggttgtt ggttaaagag cctgaaaacc gtttgggttc agagaaaggg   2400

gctgctgaga taaaacagca ccccttcttc gaaggcctta attgggcgtt aatacgttgc   2460

gctatcccac cagaactgcc agacttgtgt gaatttggag tttcagagat gaccccacag   2520

tcccagggaa agggtgttaa gtatgtagag tgcaatgcag caggagagct agttgaattt   2580

gagttgtttt ga                                                       2592
```

<210> SEQ ID NO 60
<211> LENGTH: 2184

<212> TYPE: DNA
<213> ORGANISM: Glycine max

<400> SEQUENCE: 60
atggagggaa tgtgggagaa cattcttgga aagcatcagc agtcgctgaa atccctattc 60
ctccgaagca agccttcttc ccccaacgcc gacgccgccg atgactatgc caattccccc 120
aaacccatcc ctcagctctc tcctctcgcc aactccgtcg tctctcgctg ttccaagatc 180
cttggaatgt cgacacagga attgcaacac tgcttcgatt cggaactccc catgggcgtc 240
aaagagcttc tcacctacgc cagacacctc ctcgagttct gttcctacaa agcgcttcac 300
aaactcattc aaatctccga tttcttaaac gacaaggatt ttcatcgttt aaccttcgac 360
atgatgctcg cttgggaggc tcccagcgtc cacaccctcc cagataccccc tacttcaagt 420 tcaagtaaag aggaaaccgc aggggacgag gatgaggcct ccttgttcta ttcgagttcc 480
accaatatgg ctcttcaggt cgatgacaag aagacggttg gtttagaggc tttctcgcgg 540
attgctcctg tgtgtattcc cattgccgat gttgtaactg tccacaatat cttccatgca 600
ctcactagta cctccgcgca ccgccttcat tttcttgttt atgacaaata cctaagattc 660
cttgacaagg ttatcaagaa ttctaagaat gtaatggcca catctgctgg aaatcttcag 720
cttgcagaag gagagatcat ccttgatgtt gacgggacaa ttccaactca accagttctt 780
caacatattg gaatcactgc atggcctggg cggttgaccc tcaccaatta tgctctgtac 840
tttgagtcac tgggagttgg tgtatatgag aaagctgttc gatatgatct gggcacagac 900
atgaaacagg tcataaagcc tgatctaact ggacccctcg gtgctcgcct tttgataaa 960 gctgtgatgt ataagtcaac ttctgtagca gagcctgttt attttgaatt ccctgaattt 1020
aaagcaaact tgcgtcgtga ctattggttg gacattagtc tggagatctt gcgtgcacac 1080
aagtttatca ggaaatacta ccttaaggag gtacaaaaaa cagaagtgct tgccagggct 1140
attctgggca ttttccgcta ccgtgcagtc agagaagctt tccagttttt ttcatcccac 1200
tataaaactt tactttcgtt taacctagct gaaactcttc cgcggggaga cataatcttg 1260
caaaccatgt caaatagctt aacaaatttg actgttgttt ctggtaaaca tgatattcct 1320
gcgactgtag atacaaaaag gcaaccggca gtgtctccgg tagcagttat ggcacttttc 1380
tatcttggat acaaatcaaa aaaggtgact gatatttgtg aggaagcaac ttttgtcagt 1440
gatatccgag ttggtgagat acatcccttg gaagtggcag tgaaaaagtc ccttctggac 1500
actggaaaag cggaagctgc gcaggcaacc gtggaccaag tgaaggttga aggaattgat 1560
acgaatgttg cagtaatgaa ggaactacta ttcccagtca ttgtatctgc taaccaacta 1620
cagcttttgg cctcatggaa agacttttac aaatcagcag cctttttgct actctcctgt 1680
tatatgatta taagggggtg gatccagtac tttctgccat ccatttttat gtttatggca 1740
attctcatgc tctggcgaag gcatttcaga aagggaagac cattagaagc ctttatagta 1800
actcctcccc caaatcgaaa tgctgtagaa caactgctga cattacaaga ggccattaca 1860
cagtttgaat cgcttattca agctgcaaat attattctcc taaaattgag agctcttcta 1920
cttgctatat taccacaggc tacagagaag gttgcactat tacttgtatt cctagcagca 1980
gtgtttgctt ttgttcctcc aaaatacata tttttggtgg tattcgttga gttttacaca 2040
agggagatgc catataggaa agagagcagt gatagatgga taaggaggat tagagaatgg 2100
tgggacagaa taccagctgc tcctgtccag ctcgttaagc ctgttcatga atccaagaaa 2160
aatgagtcca agaaaaaaaa atga 2184

<210> SEQ ID NO 61
<211> LENGTH: 2097
<212> TYPE: DNA
<213> ORGANISM: Glycine max

<400> SEQUENCE: 61

```
atgccgtcgg acaccgtcgg caacgtggct ctggtcccct tcaccggaga ctcgccgcca     60
gcggtatacc ctctccacca cggcctcgct cctccgatta gtcgtctctc catctcctgg    120
gcccgcggca gctccctccg cctctccctt ttcgccggcg ccgccgccaa ggtcgttgaa    180
gtgaagctcg ccggcgaaga ttcggagatc cctgacgctc actggcgccg aatcgcgtac    240
ggctccgttg cgccgtttgc gctgcttcag agtcggagga gctccctttc tgctctcttg    300
aagactcctt ctccctatcg ttcggattgg tgggagcatg tgcttcagta tagcaaagag    360
ataggttcac ttcttggggg gccaaagttg cctgctagtc ctataattga ggacccaaat    420
gtaattgcta agagaggtga agagcctaca tctttgaaag ctgcgtggga gttaattgaa    480
atattttatg tggacaagca atctcaagca tggctacctg aaaggcttgt tgattggtta    540
gctgattatg ccagcctctt tactagtaca catgaaacaa ttcatggcaa gcttgtggat    600
tttcagaaag aactagttaa catacaggtg attgaggagg atcccagata ttgggacttg    660
ttgtcatctg cactgtcagt tggttggctt gatattgtgg tgaaaatgct gcggttgcat    720
ggatcttacc aattagatca gctcagtaat cgggagttgg aaaatggact tgtagaggct    780
gttgctgttc ttatttccaa aatgccccgc atgcgtcctg aatctgttgg aaagttaggt    840
gaatgctata aatccaaacc tgacttcatc aaggcctggg aaaaatggag gtcacaaatt    900
acaaaactgg attgcagtcg attctggatt caatgtgata atcaacaaac tcgtgagggc    960
ttgagaaact tgctacaaat tatgctgggt aacactgaga gtctctgcat ggctacatgt   1020
tattggattg aattatatat ttctcatttc ctgtacataa ggccatttac aatgggaata   1080
gaaagcatgt ataatttggc ccagaaatgc atccagttga aaccacgatc tagtacccat   1140
aggttgtcag tacttatgat tggaattctt gaagaaaata ccgaggttgt tttagctgag   1200
tgttccagag aatttggccc ttggttggtg gcacatgcca tagaactgtt gactgcaggg   1260
agtgagcaag cagagattct tctgcatgag gagcgttata acttgggggg aatcagcata   1320
gtggaactac atcggcttgt atatgctcaa attctatcgt cacatgcatt gacctggcaa   1380
attgctccta tatatttaac atcatgcatg aagcaaggaa tgggcttgtt agagaattta   1440
ttgtacaggc aatctgctca acataatgat gtgttgctta agaacattga gatatgccgt   1500
ttgtatgagc ttgatcatat tagttcaaat atcatgaaga ttgctggagt acatcactgg   1560
aagcatggcc ataagggtgc tggagtattc tggcttcaac aagcccaaga cgcaagttgt   1620
cttgataaga ttgcccaaca gttatttgat tctgttggaa agtctatatc tgatgaaagc   1680
ttcaagcaat gggaaggcat gattgaacta ttgggttctg aatctaagcc tgctggggga   1740
cttgaatttt tgcacaagta tagggatttc aagaaatccc ttcagaaggt atctagtgga   1800
aaatcaactg atgcagcaag gcaagctgta ggctccctca tactgcttat gaaaaatcca   1860
tctactcctc agcgcttttg gttgcctctt ctgtatgact cgttgaagtt acttaattgg   1920
caggattgcc ctcttctaag tgtctctgag accaatcttc tgctgaacaa acttcatgag   1980
ttatctctgg cgaagctgcg accgcaccat actgagccta gcttacctcc tgatgcacta   2040
agctctatta ggttggctct agctacaaat cttggtcaag ccatacttga tgaatag      2097
```

-continued

<210> SEQ ID NO 62
<211> LENGTH: 1221
<212> TYPE: DNA
<213> ORGANISM: Glycine max

<400> SEQUENCE: 62

```
atgggaagtg cacgaactct acaatataag ttgagcttct acaactgttc ttcagttgag      60

catcaatacc tgagaaactc tgaacagtca ctgtcagact cacaagatat gatctcctat     120

ccaatttatg tttctgatct tgacgacagt gtgctcagat tggacctaac atcttgtacc     180

aaaatgtttg acatcgttac accagttttg gcttacggga tgcagcgaaa ttcgttggat     240

ttgagatggt tcgaagcaaa ttctagtaag tgcaaagcaa aaggaaagaa atgtaaatgg     300

aagaacaaca aaggtgacat tgaatgtttc gactgcaagg acaaacaaaa aactattcgt     360

gttcccaaat cttttattta ctctactaca tgttcgattc ttttggggtt catagttatt     420

gccattttta agatcatata ccattttaga cagaaagaag aggaccaagc aagggggaag     480

aagttcttag aggaatacag ggcagaaaag cctgcaagat ttacttatgc tgatgtgaaa     540

agaatcacag gtggttttaa agacaagtta ggggaaggag ctcatggggt tgtattaaga     600

ggaaaacttt caattgagat tctgagggaa aaagggaaag agttcatcaa tgaattggaa     660

attatgggca aaatccacca catcaatgtg gttcgtttgc ttggctattg tgctaaagga     720

atccatcgtg ctctggtcta caatttcttt ccaaatggtt cgctacaaag catcatattt     780

ccaccagatg ataagcagga tttccttggc tgggagaagc tgcagaacat tgctcttggt     840

atagctaaag ggattgagta tcttcaccaa ggttgtaacc atcccattat tcactttgac     900

atcaatcctc acaatgtgtt acttgatgac aacttcactc ttaaaatttc tgattttggc     960

ttagcaaaat tgtgttccaa gaatcctagt ttggtgtcca tgacagcagc tagaggaacc    1020

ttcggataca ttgcacctga agttttctct agaaactttg ggaatgtgtc ttataagtct    1080

gatatttata gttacaaaat attgttagac atgtcttctc cacaagattt ccatgtgttg    1140

tatgcagatt ggatgcatga cctagttcat ggagatgtgc atatccatgt tgaggatgac    1200

ggtgatgtta aaattgcata g                                              1221
```

<210> SEQ ID NO 63
<211> LENGTH: 1914
<212> TYPE: DNA
<213> ORGANISM: Glycine max

<400> SEQUENCE: 63

```
atgatcactg gtaaggatat ttatgatgtt ttcgcggcta ttgtgcccct ctacgttgct      60

atgatattag catacggctc agttcggtgg tggaaaattt tcacacctga tcaatgttct     120

ggcataaacc gcttcgttgc tgtgttcgca gttccacttc tttctttcca cttcatctcc     180

tccaatgacc cttatgctat gaactaccac ttcatagcag ctgattgtct tcaaaaagtt     240

gtcattttgg gtgctctctt tctatggaac accttcacaa aacatggtag cctagactgg     300

acaatcaccc tcttctcact ttcaaccctt ccaaacacac ttgtcatggg gatccctcta     360

ttgaaggcca tgtatggaga cttctcaggg agcctcatgg tccaaattgt ggtgttgcaa     420

agtgtgatat ggtataccct catgctgttc atgtttgaat atagaggtgc aaaactcctc     480

atcacagaac agttccctga gactgcaggc tccataactt ccttcagggt tgactcagat     540

gttgtctcac tcaatggtag agagccactt caaacagatg ctgagatagg agaagatgga     600

aaacttcatg tggttgttaa aagatcagca gcttcttcca tgatatcttc attcaacaag     660
```

tctcatttaa cttccatgac accaagagca tctaacctca ctggggttga gatctattct 720
gttcagtcat caagagaacc aaccccaaga ggttcgagtt tcaaccaaac ggatttctat 780
gccatgttcg caagcaaggc accgagtcca aaacatggct acacaaacag tttccagagt 840
aataatggtg gtattggtga cgtttactcg ttgcagtctt caaaaggggc aacgccaagg 900
acttctaatt ttgaagagga gatgttgaag atgcacaaga agagaggagg gaggagcatg 960
agtggcgagt tgtttaatgg gggtttggtt tcttctaatt acccgccacc gaatccaatg 1020
ttttcagggt ctacgagtgc tgctggtggc cccaagaaga aagatagcag tggtggcggt 1080
ggtgctgtag cacctaacaa ggagttacac atgtttgttt ggagttcaag tgcatcacct 1140
gtttctgagg ggaatttgag gcatgcagtt aatagagctg cctctactga ctttggaact 1200
gtcgatcctt ctaaggctgt tccacacgaa actgttgcct caaaagctgt tcacgaattg 1260
attgagaaca tgagccctgg tcgtagaggg agtggagaga gggagcctga aatggatgaa 1320
ggagccaaaa ttcccgcaag tggatctcca tacacttgcc agaagaaggt ggacatggaa 1380
gatggcaatg caaacaaaaa ccaacagatg ccacctgcaa gtgtcatgac aagacttatt 1440
ctcatcatgg tttggaggaa actcataaga aatcctaata cttactccag tcttttggga 1500
ctcacatggt ctctcatatc atttaggtgg cacattgaaa tgccaactat tgtaaaaggt 1560
tccatctcaa tactgtctga tgctggtcta ggaatggcca tgttcagtct aggtctattc 1620
atggcattac aaccgaagat cattgcctgt ggaaaatctg tggcagcatt ttcaatggct 1680
gttaggttct tgacaggtcc agctgtgatt gctgcaacct caataggcat cggactccgt 1740
ggagttcttt tgcatgttgc aattgtccag gctgctcttc cccaaggtat cgttcccttt 1800
gtgtttgcca aagaatacaa tctccatgca gatatactta gcactgcggt tatatttggg 1860
atgctaattg cattgcccat aaccatactc tactacgtgc tgcttggagt ttaa 1914

<210> SEQ ID NO 64
<211> LENGTH: 2451
<212> TYPE: DNA
<213> ORGANISM: Glycine max

<400> SEQUENCE: 64
atggacgctg ccaaagaaga atttctcaga gactttggtg aacactacgg ctaccctaac 60
ggccccaagt ccgttgatca aattcgagct actgaattca agagattaca attacaagat 120
cttgtatact tggatcatgc tggggcaact ctatactctg acctgcaaat ggaatctgtt 180
ttcaatgatc tcactactaa cctatacgca aatcctcaca gccaaagtga ctccagttct 240
gcaactcttg acattgtcaa gaacgcccgc cagcaggtcc ttgactactg caatgcatct 300
cccaaagaat acaaatgtat atttacttct ggggcaacag cagcgctgaa gctggtagga 360
gaggcttttc catggagttg taacagtagt tttatgtata caatggagaa tcataatagc 420
gttcttggaa taagagaata tgctcttggt caaggagcag cagccattgc agtagatatt 480
gaaggagaat tacatcctga aatatcagga gaaacaatta ctacaaagat atcaccacac 540
caggttcaga ggagaaaagt agctggatca ctgaaagaag agccaacagg tgatgtgtat 600
aatttgtttg cctttccatc agagtgcaat ttctcagggt tgagatttga cttggacttg 660
gtgaagatta ttaaggaaga ctcaagcaag atcttgggaa tttcttcagt ttgccaaagt 720
ggacagtgga tggtcttaat tgatgctgca aagggatgtg ctaccatgcc acctgatttg 780
tctaagtatc ctgcagattt tgttgctatc tcattttaca agctgtttgg ctatccaact 840
gggcttggag ctctcattgt tcgaaatgat gctgccaagt tactgaagaa gacttatttt 900

-continued

```
agtggaggaa cggttagtgc atcgattgct gatattgatt tcattaaaag aagggaaggt    960

attgaggaac tgtttgagga tgggactgtt tcatttttga gcatagtatc tatccgccat   1020

ggcttcaaaa tcctgaattc tttaactgta tcagcaatat caagacatat agcatctctt   1080

gccttgtata cgaggaaaat gctcttggcc atgaggcatg gcaatggatc tagtgtctgc   1140

atcctctatg gacaccataa ttcaatgaaa ctgtgtcatg aaatgggtcc aataatttca   1200

ttcaacttga aacggcctga tggctcttgg tatggatacc gtgaagtgga aaagctggca   1260

tcactttcag gaattcagct aaggacagga tgcttctgca atccaggtgc atgtgcaaaa   1320

taccttggct tgtctcattt ggatcttatt tcaaatactg aggctggtca cgtttgttgg   1380

gatgatcttg atataatcaa tggtaaacct gttggagctg taagaatatc ctttggctac   1440

atgtcaacat atgaggatgt caagaaattt gttgattttg ttgcaagttc cttcatgtca   1500

cctcaaattc acattgacca tgggaatcaa atgaaaggcc ttgataaggg ttttgtggat   1560

actggttatt atctcaaatc aattacaata tatccaataa aatcctgtgg aggtttcagt   1620

gcaagcagtt ggcctcttag caacaatggc ttgacacatg atcgcgagtg gattctcaaa   1680

agcctaactg gtgaaatact tacacagaaa aaggttcctg aaatgggctt tataagcacc   1740

tttatagacc tcagtcaggg aatgttgttt gtagaatctc cacgttgtga agaaagattg   1800

caaattcggc ttgagtcaga tgtttatggt gttatagagg agattgaact atatggacag   1860

aggtacgagg tatatagtta tgacaatgag accaattcat ggtttagtga agccatcggt   1920

aaaacttgct ctttgttacg gtattctagt ttcgatcagg attttatgtt aaataagatc   1980

aaaggtgcag ccacatgtag agatccgaag aacaaactta attttgccaa tgaagcacag   2040

ttcttacttg tatctgagga aagtgtttct gacctaaata gaagattaag ctcagatgta   2100

cagaagggca tatatggaaa agtgatgcaa gtcagtgcaa gtaggtttcg tcccaatctt   2160

gtggtatctg gaggtaggcc ttatgctgaa gatggatgga gatacattag gattggaaac   2220

aagtatttca gttcgcttgg gggatgtaat cgatgccaga taatcaacct tacaataaat   2280

gcgggacaag tgcaaaagtc aaatgaacct ttggcaactt tagcatccta caggagggta   2340

aagcagggaa aaattttgtt tggtatactg ctgaaacatg tttctattga cggagagcag   2400

caaaaaggtg atttctggct tcatgtgggc caagatgtgc atccggatta a            2451
```

<210> SEQ ID NO 65
<211> LENGTH: 576
<212> TYPE: DNA
<213> ORGANISM: Glycine max

<400> SEQUENCE: 65

```
atggccagtg aggcagaatt caggaaggag gaggtgaccc ttcaagttga tggttccact     60

ggccgtataa ttgtgaaagg cgaaaggcaa acaaatgaac agaaacgagt tcagtttgag    120

ctggcctttc cattgcctcc agattcagat gtggataaca tatccggaaa ctatgacagt    180

gaaatccttc acgtgcatgt ccccaagcaa gcttcacatc aagagcacaa caaagaaagt    240

agtgatatag agaaagcttc aaattatggc agtgttgaaa tgccacaaga aattgaaagt    300

gaggaacaca atgttgttga tgagggaagg aatcatggtc atgaacaaca taaggaagat    360

agagagaaga agaaagaaag aagaaatgaa aatgcacaac acatggatga ttattattct    420

aaaaaattga caagtaagtt ggagcaaaaa cgcgacatgt caagagctct agaggaggtt    480

ttgatgagaa acaagggagt tgttacaact gcagttgtgg ccttttcttt tgggttgtat    540
```

gtatctaata agttccattc atggaaagaa ccataa 576

<210> SEQ ID NO 66
<211> LENGTH: 447
<212> TYPE: DNA
<213> ORGANISM: Glycine max

<400> SEQUENCE: 66
atggcatcga agcggatctt gaaggaactc aaggatctcc aaaaggatcc tcctacctca 60
tgcagcgccg gtcctgttgc tgaagacatg tttcactggc aagcaacaat tatgggtcct 120
ccagacagtc cttatgctgg aggtgttttc ctagtcacta ttcatttccc tccagattat 180
ccctttaagc cacccaaggt tgcattcagg acgaaggtat ttcacccaaa tataaatagc 240
aatggaagca tttgccttga catattgaag gagcagtgga gccctgcgct aactatttca 300
aaggtgttgc tctcaatttg ttccctgttg acggacccta atcctgacga tcctttggtc 360
cctgaaattg cccacatgta caagacagac aggaacaagt acgagtcaac tgccagaagc 420
tggacccaga aatatgccat gggttaa 447

<210> SEQ ID NO 67
<211> LENGTH: 432
<212> TYPE: DNA
<213> ORGANISM: Glycine max

<400> SEQUENCE: 67
atgcatactt tcttctttct gccttcttta ttggacatgt tcattgattt ttcaaagcca 60
gaaacgaaaa gggcactgct aaacaaaagt tctgaggata aaatacaaaa gtatggtagg 120
tccaaagctg gatctcgtgt ggttccatat caagaagatg agagccaaga ctcagttcct 180
gtcagtatcg tctctaaaga tctccaaagg aatgacaaag agagtgaaga tctccaaagg 240
aatgacaaag agagtgaaga tttatggctg atccgtgatc agttacatca aattgagaac 300
cagcagtcaa gtctacttga tcttctgcag catgaaggtg cttctcaagc ctttgaagat 360
gctcaaaaga agatgaaaag catatcagaa acagtgataa tttgcagcat gaaggtgctt 420
ctcaattctt ga 432

<210> SEQ ID NO 68
<211> LENGTH: 1842
<212> TYPE: DNA
<213> ORGANISM: Glycine max

<400> SEQUENCE: 68
atgccagaga agaagaacaa gaaagtttct ttcaccgaag aagatgctgt tacgctcatg 60
cagaggtacg acgcaactac ggtgttcact ttacttcagg aagtggcgca ttaccctcac 120
cccaagattg attggtgcga gttggtgaag aaaagcgcga ctgagatttc taacgccaga 180
gaatatcaaa tgctatggcg gcacttggcg tatcgccatt ctttgcctga aattttcgaa 240
gatggggatg aacctttgcc tcatttccag gatgatgata gtgacctaga gtgtgagcta 300
gaagcatttc cccctgtaag tgtggaatgt gcatcagagg ctgctgcatg tgtgaaggta 360
atgattgctt ctcgtacact gagtgaatct gcccctagta gctcaacaat agaggctcca 420
ttgactataa atgttccagt ttgccattca tctagaactc ctattgaaaa ttcacagccc 480
tctaatttga tgcaagggac aagcattatt tttccagtta ccgttcagag acagacactg 540
ccaactatat catcgacaga tggtatagaa accaagggaa tagttggtgg taacatggct 600
tccaaaagaa aaagaaaggc atggtcagaa gaagaggaca tgcagctacg agctgctgtt 660

-continued caaagatggg gtgaagggaa ttgggcaacc atggcaaaag gagacgactt tcctattaag 720
agaagtgcta cacagttggc tcagaggtgg agcattttac gaaagaaaga tggttgtaca 780
aatacaggaa ccataaccag cacacagtat actactgctg aacagctggc aactcgacac 840
tctttatctt tagcccttga tatgccattc aaaaagttaa ctgctcctgg aatgactgat 900
gttaagccat ccacatcagt taaaaatcaa gcgcagatta gaaatactac agagaaggta 960
tccagtagtt tagtaccacc tcaacagcca tctcaacaag ctttgttggg atcctctgat 1020
ttgcatgcaa aatccaaatt agcagatgaa aaaccagtct tgaagggtaa tctaatttca 1080
gatcatgtgg taaaatctgc cacagcaact ttggggacac gagttgatcc cctttcaaat 1140
actatatcac aaattaaagt tgctcaagta aaaaatgcta cagataccaa gccagcagtt 1200
agctctttga caaaaccatc catttctacc aatttgcctt ctgacccaaa gaacaaacat 1260
gttacctctt tggctgataa aggtgctcaa gtaaaacatg ccgtggatac taagcctgct 1320
gttagctctt tgataaagcc atccatttct accaatttgc cttctgaccc aaagaacaaa 1380
catgttaccc ctttggctga taaagttcca ttgaagcaag ttgttaatcc cacaaaagag 1440
ttaaaagttt ctgatcccag caccacacca aaagagaagg tacaagaaaa tgagcctcct 1500
aaagttacca ctggaagcca ggttgatagc agcctagaga aggggagatt tgaaaaaggt 1560
ctagagacga gcacacctct tgttaaaatt agttgtggtg aggaagtttc aaaagataaa 1620
gcaaatccag tagtagtgtg tgaagagcaa ggaagtgtta agaaggccac tgagaataac 1680
aacattgaca aggggagtca aaatttagat catgacaaga agatagattc tattaatcaa 1740
agttcaaatg atcaaaacgc gaatgataaa catgtaaatt tgccagtaca agatgaactc 1800
agcctaagtg ccaaggtagt aaaaagtgat ggggaatgtt ga 1842

<210> SEQ ID NO 69
<211> LENGTH: 1197
<212> TYPE: DNA
<213> ORGANISM: Glycine max

<400> SEQUENCE: 69
atggctgaag cagaggatgc cgtaagacgc cgtaatgcgg tcgccgagta tcggaagaaa 60
cttctccagc acaaggaatt ggaatccaga gtccgatccg tcagggagaa tttgcgagct 120
tcaaagaaag agttcaataa aacagaagat gatttgaaat ctcttcaaag tgttgggcag 180
attattggcg aagttctcag gcctcttgac aatgaacgcc tgattgttaa agcaagcagt 240
ggtcccaggt atgtggttgg ttgccgcagt aaagtggata aggaaaaatt gacttcaggg 300
acaagggtgg ttcttgatat gacaacactc accataatgc gagctcttcc tcgagaagtt 360
gatccagtag tttacaatat gttgcatgaa gatcctggta atatcagcta ctcagctgtt 420
ggtggcttat ctgatcagat cagggaattg agggagtcaa ttgaactgcc tctaatgaat 480
cctgagctct tccttcgagt tggaattaaa cctccaaagg gtgttctcct ttacgggcct 540
cctggtactg gtaaaacatt gttagctagg gcaattgcaa gtaatataga tgcaaatttc 600
ctaaaggttg tttcaagtgc cataattgat aagtacattg gagaaagtgc caggttaatc 660
agagagatgt ttggttatgc acgtgatcac cagccttgca tcatttttat ggatgagatc 720
gatgccattg gaggtcgccg tttcagtgag ggaacaagtg cagatcgtga gattcagaga 780
acgctaatgg agctgcttaa tcaacttgat ggatttgatc aacttggaaa ggttaaaatg 840
ataatggcaa caaaccgacc tgatgtactt gaccctgctc tcctgcgtcc tgggagattg 900
gatagaaaaa tagaaatccc tctgcctaat gaacaatcaa ggatggaaat tcttaagatt 960
catgctgctg gtatcgctaa gcatggtgaa atagactatg aagctgttgt gaagcttgca 1020
gagggattta atggggctga tcttcgaaat gtctgcacag aagctggaat ggcagcaatt 1080
cgtgcagagc gtgattatgt gatccatgaa gattttatga aggctgttag gaaactgaac 1140
gaggcaaaga aacttgaatc cagtgcgcac tacagtgctg attttggtaa agactag 1197

<210> SEQ ID NO 70
<211> LENGTH: 1134
<212> TYPE: DNA
<213> ORGANISM: Glycine max

<400> SEQUENCE: 70
atggagtccg aactcaaaga cctcaattcg aagccgccga acggcaacgg caacagcgtt 60
cgcgatgacc gtcctctgct gaagccggag cctccggtct ccgccgacag catcgccgat 120
atggagaaga agttcgccgc ttacgtccgc cgcgacgtgt acggcaccat gggacgcggc 180
gagttgccga ccaaggagaa gctcttgctc ggtttcgcgt tggtcactct tctccccatt 240
cgagtcgttc tcgccgtcac catattgctc ttttattact taatttgtag ggtttgcact 300
ctcttctctg cgcccactgg cgaagaggaa caggaagatt acgctcacat gagtgggtgg 360
aggagaacca ttattgtttc gtgtggacgc gccctctcca gactcatgct tttcattttc 420
ggcttttatt ggatccccga atcgaactct gcctctcagg aagacaagag tcggcagccc 480
gaagagttga ggagacctgg cgtaataatt tctaatcatg tgtcgtactt ggatattttg 540
tatcacatgt cttcctcatt ccctagtttt gttgctaaga gatcagtggc taaacttccg 600
ctagtcggtc tcatcagcaa gtgccttggt tgtgtctatg ttcagcggga atcaaggtca 660
tcagacttca agggtgtttc agctgttgtc actgacagaa ttcgagaagc tcatcagaat 720
gagtctgctc cattaatgat gttatttcca gaaggtacaa ccacaaatgg agagttcctc 780
cttccattca agactggtgg ttttttggca aaggcaccgg tacttcctgt gatattacaa 840
tatcattacc agagatttag ccctgcctgg gattccatat ctggagtgcg ccatgtgata 900
tttctcctgt gtcagtttgt gaattatatg gaggtgatcc gattacctgt ttaccatcct 960
tcacagcagg agatggatga tcccaaacta tacgctaata atgttagaag gttgatggct 1020
actgagggta atttgatact ttctgatatt gggctagctg aaaaacgaat atatcacgct 1080
gctcttaatg gtaataatag cctgcctagt gttttgcatc agaaagacga atga 1134

<210> SEQ ID NO 71
<211> LENGTH: 174
<212> TYPE: DNA
<213> ORGANISM: Glycine max

<400> SEQUENCE: 71
atgacttcga tctcgccaac tccggcagat ttgcgattgt atttacagta tgcaactttg 60
gctttgccat ggtttatgat tgttgttgat ctctatataa tgtgcatttc attgattgtt 120
tttgtatacg aagagggagt agaagtgaag ggagaagaag atatgtatat ttga 174

<210> SEQ ID NO 72
<211> LENGTH: 6126
<212> TYPE: DNA
<213> ORGANISM: Glycine max

<400> SEQUENCE: 72
atggccgata acatggaaat cgatacaccc tccgattccc aaccgctcaa gcctcgcgat 60

```
cgagtcgttc ggaggcttgc ccagtttggt gttcctgagg aacagctcga ccaacctggt    120
ttagttgctt ttgttaagga taagagggcg ttgatacctg agctggtgtc tgtgatattg    180
cctactgatg cggaagtggc ggatgcatgg caagctaaat tgtcttctaa gaagacggcg    240
gtgggtgtga tcatgaagaa gaggtttaac gagagcatgg cgtggttgca gtggttgata    300
tttgagggcg acccaggtgg cgcactgaga aggctttcca agatgtctga tgggcagagg    360
ggtgtctgtg ggtctgtttg gggcaacagt gatattgctt acaggtgtag gacatgtgag    420
cacgacccaa cgtgcgcaat ctgtgttcct tgttttgaga atgggaatca caagggccat    480
gattactttg ttatatacac gggcggcggt tgctgtgatt gtggagatgt aacagcatgg    540
aagcgtgagg ggttctgctc gatgcataag ggtgcagagc agatgcaacc acttccggag    600
gaattcgcaa actctgttgc tcctgtgctt ggttcccttt tcaattcttg gaaagtcaag    660
ctaacattgg caagtgagtc ggttaatgaa aaaaatcatg cagcaaatga gctaacttat    720
gccgtggttg atatgctttt agaattttgc aagcatagtg agagtttgct cagttttgtt    780
gctaggttgt tgttctcttc taatggttta attaacatgc tggtgagagc tgagaggttc    840
ttaactgagg ttgtagtgaa gaaactccat gagctactcc tgaaattgtt aggagaacca    900
aattttaagt ataattttgc taaagatttt ctcacttact atccaactgt cataaatgag    960
gccacaaaag acagcagtga ctctcctcta aagaagtacc cactactatc cacgttctct   1020
gtacagatac ttactgtgcc cactcttacc ccacgccttg tgaaggaaat caacctacta   1080
accatgctgt tgggatgctt tgaaaatatt ttcatttctt gttctgaaga tggacgctta   1140
caggtttcca tgtgggtagg tttatatgag acaactatac gtgttattga agatattcgg   1200
tttgttatga gccatgtggt agtgcccaaa catgtaacca atgaccagca agatatctca   1260
agaacatgga tgagacttct ttcctttgta caagggatga accctcaaaa gagagaaaca   1320
ggtcaacata tagaagatga aaatgagcat gtccatttgc cttttatttt agggcattct   1380
attgccaata ttcacactct attggtggat gggtcatttt ctgatgctag caagggggaa   1440
atggatgcag aaattgtttg gagctcttgt aagaatgatt cagatgatgg agataatcta   1500
aggcatgcaa aggtaggacg gagatctgag gaaagctctg catgtaatgt gaccagtggg   1560
aatagtgcct tagcttctag aaagtttcgt gagataaaag ctgatgactc ttctcagctg   1620
cctcttccac gttctgtcac tttgttgata tatgagtgtt taagggctat tgagaattgg   1680
ttgagagtcg agaatacccc tggtgtaatt cctaatgcac aatctccgaa cagtggtgct   1740
gtctgtgatg acaatttttc agcatttaag agaacaatat ctaagtttgg aaggggtaga   1800
tatacatttg gtaggcttac aagttcaatt gaagatcatg gtaagcagtg ttctgaaaat   1860
aatgcaattg attcagaaaa tacctatatt cgtcccactt ttgatgataa tgccatggaa   1920
gaagatttcc ccttggaatc agatggtcca cgtttttttat cattgcctga ttggccacaa   1980
atagtctatg atgttagttc ccaagatata tctgtacaca ttccattaca tagattgctt   2040
tccatgctgt tacagaaggc aatgaaaaga tatttttgtg aatctgaagg gtcagatgtg   2100
actcatgttt cttcagctaa ttcattgctg actagctaca atgacttctt cgaacaagct   2160
ttacgaggaa gtcatcccata tggtttctct gcctatgtaa tggagcatcc attgcggatt   2220
agggtctttt gtgctgaagt ccatgccgga atgtggcgta aaaatggaga tgctgcttta   2280
ttatcttgtg aattgtatag atcagtacgc tggtctgaaa aatgtctgga gcttgatcta   2340
tttcttcttc agtgttgtgc tgcactagct ccagaggatc tatttgtcag tagacttctg   2400
```

-continued

```
gagcgctttg ggttgtcaaa ctacttatgt ctaaatcttg aacggtctag cgaatatgaa   2460
cctgttttgg tccaggaaat gcttactctt attattcaga tagtaaaaga acgacgcttt   2520
agtgggctaa ctactgctga atgtttgaaa agagaactaa tttataagtt atccattggt   2580
gatgccactc atagtcattt ggttaagtct cttcctcgtg atctctccaa atttgaacaa   2640
cttcaagaca tcttggatac agttgctgtt tattccaatc catctggatt taatcagggt   2700
atgttttctt tgcgatggtc attttggaaa gaattggatt tgtatcatcc acgttggaat   2760
tcaaaggatt tacaagttgc tgaagaaaga tacttgcgct tctgcagtgt ctctgcacta   2820
accacccaat tgccccagtg gaccaaaatt catcctcctc taagggggat agccagagta   2880
gccacttgca aagttgttct acatattatc cgtgctgtgc tattttatgc tgttttcact   2940
tttaaatcat ctgaatctcg tgctcctgac agcgttcttc tacctgctct acatttactg   3000
tcattatcat tagatatctg ttttcaacag aaagaatcta gtgagaatac atgccatgat   3060
gtgtcacatc ttcccataat tgccctctct ggagaaataa ttgagagttc ttttggtgaa   3120
caaagcttgt tgtcacttct tgttttattg atggaaatgc acaggaagga aaatgtcgac   3180
aactttgtgg aagcaggtgg ttgtagtcta tattctctga ttgaaagctt actgaagaaa   3240
tttgctgaga ttgacaacag atgcatgacc aagttgcaaa aacttgcccc tgaagtagtc   3300
agccatattt ctgaatgtgt tccaactaga gactcaagtg tctcatcgtc ggcttctgat   3360
agtgagaaac gcaaggcgaa agctcgagag aggcaggctg caataatgga aaaaatgaga   3420
gcccaacagt ctaaattctt ggccagcatt gattccactg ttgatgatgg ttcacaactt   3480
ggtcatgaag gtgacttaga cactgagcaa gatgtagaag aatccgattc taaacaagtt   3540
gtttgctccc tttgtcatga ccacaattca aaacatccta tctctttttt gattcttctt   3600
cagaaatcta ggctcgtgag ttccgttgac aggggtcccc catcatgggc ccaactttgc   3660
cgatcagata aagatcggac acctatcatc aacaccaacg agatggatac attgcctatt   3720
aactgtaatt cagttagttt gggatcaact tcatcttccc acttaagtca atttgttcag   3780
aatgctgcaa aagaattagc ttcttgtggg aaacctgggg aagttcttac ttttctgcaa   3840
tatgtcaaga ataagttccc agctttgtca aattttcagc tcccagacac atattatcat   3900
gataaagaaa atacaccata tacttttgag actttagaac agggtatgta cttctccgtg   3960
cgtgatgaaa tgcatgatct tctgctatct tcgaatttgt tgaatgagga tgagaaagtt   4020
tcaactgtgg gagggaattc aaattttata atagacactg gatctgtatt gcttgggaaa   4080
tatacagccg atcttgtgca agagatgtca gaagtttctt ctgtgtctga aaatgcttct   4140
aatgagactg cttctgtaga atcaacatca cagcatccag catatgatgg atttggccct   4200
acagattgcg atggagttca tctttcttcc tgtgggcatg cagtacatca aggatgtctt   4260
gatcgatatt tatcttcatt aaaggaaaga tctgtcagaa gaattgtttt tgaaggagga   4320
catattgttg acccagatca gggagagttt ctctgcccag tgtgccgcag acttgcaaat   4380
tgtgtcttgc caactttacc tggagaatta cagaagcctt tcaagcagtc taccatcttg   4440
agtactagtt caataaatac tgcacccccc ttagctgaat tgagtgaatt gacttattca   4500
cttcgtctcc atctaggctt aaagcttctg caatctgctg ccaatgcagt tgggaaggat   4560
aaattcctaa atgctattcc tttgcatcac attgatagaa ctagaacaaa tcttgaaaag   4620
ttcatatggg ggctttctaa aatgtattcc ccttgcaaag aagaaaagct atcaagattt   4680
tccagactaa accactcaat gctgatgtgg gacactctca agtactcttt gacatcaatg   4740
gagattgctg cacggtgtgg aaagacttct tttacaccaa actttgctct tagtgcattg   4800
```

```
tatgaagaac tgaaatcttc aagtggcttt atattatccc tgatgctgaa acttgttcaa   4860
aagacacgaa gtaataattc tcttcatgtt ctacaaagat ttagaggtgt tcaactcttg   4920
gcagaatcaa tttgttctgg ggtttccctg aattacgcaa ataatgacga gtctgggaga   4980
ggtgatatgt taagtatctt aaagcaaatt gaaatggact tgtcaaacac caacattagc   5040
ttttggagtc aggcttcaga tcctgtactc ctccatgacc ctttctcaac attgatgtgg   5100
gttctttttt gtctaccaca cccatttttg tcatgtgaag aatccttgtt atccctagtg   5160
catgttttct atatagtagc cgtaacccag gctataattt tgtattatga gaaatctaaa   5220
gataaaccat caagggaatc agctctttca gattgcctga ttaccgacat atataacgtt   5280
atggatgagt ctggatatgc ccaacagtac tttgtgtcaa attattttga ccccaatgtt   5340
gatattaaaa acgctattcg gaggtttact tttccttact tgagaagatg tgcgttgttg   5400
tggaagatac tctattcttc tatcccagca ccattctgtg atgaggaaaa tatattggat   5460
agatcatgga atgccccaaa ggacataatg gactgggcca atattgagat atttgaggtc   5520
gctaaaattc aagagctcga gaaaatgttc aaaattccct ctcttgatat ggttctcaag   5580
gatgaacttt caagatctac agtctctatt tggtgccatc atttttgcaa ggaattcgac   5640
ttgcgcagaa ttcaacaaaa tatgcatgta acacctgctg ttccatttga gttaatgaga   5700
ttgcccaatg tttatcagga tcttttgcag aggtgtatca aacagcgctg ccctgaatgc   5760
aaatcagttc ttgatgaccc tgctttgtgc ctactgtgtg gtagattgtg ctctccaagt   5820
tggaaatcat gctgcaggga aagtggatgc caaactcatg ctgtaacctg tggagctggt   5880
actggagtgt ttctgttgat taagagaaca acaatcctac tacagagatc tgcacgtcag   5940
gccccctggc cctctcctta cttagatgct tttggtgagg aggattttga aatgcatcga   6000
ggcaagccac tttatctgaa tgaggaacgc tatgcagctt tgacttatat ggtcgcttct   6060
catggtctgg accggagttc cagggtcctt ggtcagacca ctattggttc cttcttcctg   6120
gtttag                                                              6126
```

<210> SEQ ID NO 73
<211> LENGTH: 1341
<212> TYPE: DNA
<213> ORGANISM: Glycine max

<400> SEQUENCE: 73

```
atgtatggcg gtgatgaagt atcagctata gtaattgact tgggttcaca cacttgtaaa     60
gctggttatg ccggtgaaga tgctcccaag gctgtgtttc cctctgttgt tggagcaatt    120
gatcaaatgg atgttgatga agcagataat ggtgaaaaga accctggctc tgctccggaa    180
tcaaataata ataatgttag aaatgctgat tctgacaagg ccaagggaaa gaggaaattg    240
tatgtaggat cccagtcctt ggggtaccgc agagaccata tggaggtgct gtctccattt    300
aaggatggag ttgttgctga ctgggatatt gttgacagca tatgggatca tgccttcagg    360
gagtgcctat tgattgatcc taaagagcat cctatgctcc ttgcagagcc ctcttctaac    420
tctcaacaac agagagaaag gacagtggag catatgtttg agaagtacaa agcacctgca    480
ttatttttgg caaaaaatgc tgttctgact tcttttgcat cagggcgtgc tacgtctgta    540
gttgttgatg gtggtggagg ctcaactaca gttgcaccgg tacatgatgg ttatgttctt    600
caaaaggctg tggcaacctc tccaattgga ggagaatttc ttacagactg cttgatgaaa    660
agtttggaaa gcaagggtat tatgataaaa cctcggtatt ccttcaggag aaaggaaata    720
```

```
cgccctggag agtttcagac agttgatctt gaatttccca atactactga aagctacaaa    780
ctcttttccc agagggtgat tgctagtgat atcaaggaat gtgtgtgccg tgctccagat    840
actccatatg atgagagtgc gtattcaaac attccaatga cctcatatga gcttcctgat    900
ggccagacag ttgaaattgg agctgacaga tttaagatac cagatgttct tttcaatcca    960
tccctggttc agtcaattcc tggcatggag agctttgcag aaattgctcc ttcagttcgt   1020
ggcctgcccc aaatggtgat tgaaagcatt aataagtgtg atgtagacat tcgaagagag   1080
ttgtttaata gtatactgct tgctggtggt acagcttcaa tgcaacaact aaaggaacgc   1140
cttgagaaag acttgttaga ggaatcccct caagctgcca gagtaaaagt attggccagt   1200
gggaatgcta ctgaaagaag gtttagtgtt tggatcgggg gtagtatatt ggcatctctt   1260
ggctccttcc agcaaatgtg gttctccaaa tccgagtatg aagagcatgg agcttcatat   1320
atccaaagga agtgtccatg a                                             1341
```

<210> SEQ ID NO 74
<211> LENGTH: 1899
<212> TYPE: DNA
<213> ORGANISM: Glycine max

<400> SEQUENCE: 74

```
atggctagta gttcagatga gaggtatgtt tggccttgga caggcattgt tgccaacata     60
tttgggaagc caaagcatga accagtggag tgtgatagca tgtattggct gagaaagttt    120
gaacaataca aacccgaaga ggcttatgtt ttgcattgtg cagaagatcc aacagggtac    180
gttgtgctgg aatttggtac agaatggact gggttctcgc aaatgatgaa gttagataca    240
gattttcttg ttgatcatca tggaaaaaag gattattatg agtcaaggaa aatgggttat    300
tcgtcaggct tatttggttg gtgtgcacag gcagaagatt acaactcaga agggcttgtt    360
ggaaattttc tccgtcagaa agctgagctg aaaacaacct ctatggttgc acaagagtca    420
ttgaatgaaa aaactgaaac tctggatcat ttgtatgggg aaataggctc tgtaaacaaa    480
aagattagtg agatggaatc gaagtacatt gaggactaca tgtcattgga taaaatgatg    540
aaagagattg agaagaagag agacttgctt caccagactc gtgctgaaga tgatcatgta    600
aattgtgctc cagtgttgaa gtcgatcgta atgcgtggac gtgaaattac ttataaagcc    660
atggaaaaaa ataaaaaatt gcaacaagag atagatacaa tgaatgatga actcgatcgc    720
tggtgtcaac aactgattga acaagaaaag tcaactatac aacaaaggag aaaatttgag    780
gaagaaaaga aaagccaaat ggaatcacta attttagcaa cagagaagca gatgaaggcc    840
agaagtgatg ttctcagttt gcttgaaaag catcagatgg agaaaaaagc tgtcagtgat    900
gcactgttga agcttgaaaa agagatggga aatgaacaaa agttgaattt agaaattgct    960
gaactagagg aacaactcaa ggttttgaag tgtgtgaact tggaggaagc tgatcatgag   1020
aataaaagaa agatagaaat agaagagata gaagaaaaat tggaggacat gatttttgat   1080
atgtccgtaa aagatgatga aaatcaagct ttgaagaaga aggtacaaga agctaaaatc   1140
gagctagaag atgctaggca acaaattatt aagctattgg ctgttggtac tgttttatca   1200
caattaatgc tttccgtgca aaagctaatt gaatgcattt gcttgacaat tcaggaatta   1260
ccacagttct tgaaaggggt tactaagatt caaataaaaa aaattgggga ggtcagtgct   1320
aggtcattta aaaaagtgtg catgaatagg tataaaaata acaaaaaagc atcatcggag   1380
tctgtcaaac tgtgcgcaaa gtggcaaaaa gaaattctgg attcaacatg gcaccctttt   1440
aagattgttg atgtcgaagg gaaggaaata caggaagaaa ttgatgaaaa tgatcctaaa   1500
```

-continued

```
ttattatctt taacaaatga tttgggagag gaggcatacg ttgctgtggt gacagctctt   1560

aaggaattgc ctgagtatca tcattctgat gatgctgaga acacccataa ttcaagtgag   1620

aaacaagtga tacctgagat atgggactcc caaaatggac gtagagccac cgtaactgaa   1680

gctttgaatg ttggaaatgg agtcggaatc gcctgcatga aggaagaaac aaaaagaata   1740

aaaggaaaag agaagaagat tcagatgaga aaaatggaga aagagaagat tgagggagaa   1800

aacacagagg gagaaaacac aacaacagat aaaactcagg agagagaaga aagagtaatg   1860

gataagatac acacaattat gagtattaag cggaattaa                          1899
```

<210> SEQ ID NO 75
<211> LENGTH: 273
<212> TYPE: DNA
<213> ORGANISM: Glycine max

<400> SEQUENCE: 75

```
atgatttctt caatgaaaga agtagccgag tcattgaaag aatttgttga agtgactaag     60

aagaagatgg agaacaaaaa aaagatggag ataaaagaag ctcaagaagt ggtacatgaa    120

gtggtgagtg agctagataa tatacctaat tttaatggtg cacttagaca tagagcaatt    180

gattggttga cagaaaatcc cattaagttt gcgattataa aagctcttcc attggatgag    240

aaagaggatt acatcttatc ttttatgcct tga                                 273
```

<210> SEQ ID NO 76
<211> LENGTH: 996
<212> TYPE: DNA
<213> ORGANISM: Glycine max

<400> SEQUENCE: 76

```
atgctgctag ctcaacccat ttcctctct cgcaactttc ccactctcaa caaccgaaac     60

tcgagaactt ctcttcaact tcacaaccct cctgcactca taagagtttc accgcaaaga    120

acgccaataa tagcctcttc tggttgtttt ggttgcttcg taaaaccgct tgatgtcaga    180

accaaaacct cgctgggtgc gttttttaag aaaagaaagg gttgtgcaca tatttgccat    240

agtttgaagg aagagagcga ggttggtggg aatggcaata atggaagaga ctggacgacc    300

tccattttgc tctttctact gtgggctgcg ctaatgtact atgttttctt tctcacccca    360

aaccagaccc cgtcaaggga cacgtatttc ttgaaaaagc tcctgaatct gaaaggagat    420

gatggtttca gaatgaatga agtgctagta tcattgtggt atttaatggg cttgtggcca    480

ttggtatata gcatgctctt gcttccaacc ggaagaagct caaaaaacaa tattcctgta    540

tggccattcc tgatactttc atgttttggt ggtgcatatg ttcttcttcc atatttcgta    600

ctttggaaac cgccagctcc tcctgtcgaa gaaactcagc ttaaaacatg gcctttgaat    660

ttcctggaat caaaagtaac tgcaatgata tcacttgcgg caggggtagc catcataact    720

tatgctggtc tagctggaca agatgtgtgg aaagaatttt accagtactt cagggaaagc    780

aaatttatcc atattacgtc cattgatttt attatacttt ccacatttgc accgttttgg    840

gtttacaacg atatgactgc tcgaaaacgg tttgacaaag gttcttggct ccttcccata    900

tcattgatac catttttagg gcctggttta taccttctcc tgcggccatc attatcaaca    960

gtggccattt cacagactcc tgttgagcca gagtaa                              996
```

<210> SEQ ID NO 77
<211> LENGTH: 2337
<212> TYPE: DNA

<213> ORGANISM: Glycine max

<400> SEQUENCE: 77

```
atgaaaaatg agaaaagtgg gattgaatgt tcaggtgggg ttttgtttga ttatggaggt     60
gtggaacctg atggaggttt ggttattgaa tttaatgatg gttttcggag tgagctgggg    120
tgtgagaatg ctagggatgt tgctgaaaat ggtttgctga gctttgcgtt gaataatgtg    180
actcaagggg gtgataatga tgcggttgag tgtacgcagg aggttaagaa tgatggtttg    240
gtgaatttaa gcgcggttgt ggagaatgat ggcaagagaa atggtgctga tagtttggtt    300
actaaagatg gcatggaaga ttcacgtgcc atagaagttg caacctacca attacaagat    360
gggattccgt gtatggaagc tgtggatgtc aacgctgaag aatctttgca tgtgaaagac    420
ttgtcaagga attgcctgga gctaaaacct tcatgtgagc cagcctttca ggtagatgca    480
aatgtagatg tgatgcagaa tcaaaccgtg gtcgttgatg tttctgaagg actatttgag    540
aatattcaaa atgagtgtca tggttttgat cttgttgtgg atcttaattc ttacaaaagc    600
atgcataagg ttggcacgta ctggggatca gtgtcttcgg aaatgaattt ctgtgtgtct    660
gatttagtat ggggaaaggt gactggccat ccttggtggc caggtcagat ctttgatgcc    720
tcagctgcat cagagaaggc aaagaagcac ctcaaggaag gctgtcacct gatagcgtat    780
tttggggatg gaacatttgc ttggaatgat gtgtcaatgc ttaaaccatt tcagacacat    840
ttttcacaaa tggagaagct gagcaatttg gaaaatttcc accatgctgt tgattgtgct    900
ttagatgagg tctcgagacg ggttgagttc agcctatcct gccattgcat gcctgaagat    960
gtgctttcta agattaaaac tcaagtaatt agtaatgctg gaatcaacaa tcagtcgtgt   1020
agaagaaatg gaggggacag aattatgaat gcaatgtctt ttgaacccat gaaacttgtc   1080
aattttgtta aatcattagc acagtcgcca cttgttgaat ctgataggct ggattttgta   1140
attgcacgtt cccaattgtc agccttctat tgctcaaagg gttattctca actacctgag   1200
ttcccagtgc ttggtgtgtt gttcgagaat gatatggaaa ctctactcat gagggagaaa   1260
gagcaatgtg attatcaaac ccatgtcagc tttttgcaac aggatcacaa gcacatctct   1320
ggggatagca agtggcacgg gaagaaactt aaacttctgt cagatttgat gtctgagaag   1380
ggcttctgta tttcaaatgg tgaaggcaca tcagaacagg aggctaagtc agttccacag   1440
cgtcgaggca ggaaaaggaa gacagctttc aatacttcag aagattattt ccataattcc   1500
caaaatggaa ggctcaccca attacagtat gcttctacaa atgacatgag gtctcaactc   1560
tgcttggctg ccaaggatcc aactggagaa agttgctcta gtgacatggt acatttcttt   1620
gcagaattta gaaaattcat tagccatgat tattatgctt ccctggatca ggaaatgtct   1680
ttggaacgaa tgaactatga tgagaccgga gtaacctcta cagcagcatt ggcttctatg   1740
acacctgcaa tggagccttg cagtgattct tattggactg atagaataat ccaaagcatt   1800
cccaaggagc tatcattgac aaaataccag aatgagagag tggttttttt acctgagact   1860
ctaactgagg ctaatcctct ttctttcaag ttgcaaccgt ctgctgaaac taccacagat   1920
ttatgttata agcagcaaga tactgataga aatcttggat cagaatcttc taagcttgtg   1980
gaacatttgg atgggagttc taaagagaac ttctgtccca ctgctctgac actgaaattt   2040
acaaacttcg attctgttcc ttcaacaacc gatctcaaca acatttttgg ccgctttggg   2100
ccactgattg aatcaaagac tgaactgcta gagaggacaa accgtgccag agtggttttc   2160
caaagacgtt cggatgctga aactgccttt agtagtgctg gaaaatacag catatttgga   2220
ccttcacttg ttagttaccg cctcaagatt ttgcctcgta agccaccaca aggtacagga   2280
```

aagcgaggca gaaaaagaag aaaagaaaca agttctgtgg atggcacagc agtttga 2337

<210> SEQ ID NO 78
<211> LENGTH: 276
<212> TYPE: DNA
<213> ORGANISM: Glycine max

<400> SEQUENCE: 78
atgctcacga ctcatcttca ctctcgaccc ttctcttcat cttcacaatc gcgctcttcc 60
cttctcttca tcttcacgca accgcaccgt aagtcgttgt gccacccacc acaagctcat 120
tgctccacta gaccaggtct acgacttgcc agctgtcgct gcacctgggt cccattttcg 180
aggattaggg taatttggaa gccattggat gggtttgaac ccggcatacg aagtggaggt 240
gaagcgtgtg tcgcagatat tagtggcgtt cgttaa 276

<210> SEQ ID NO 79
<211> LENGTH: 3867
<212> TYPE: DNA
<213> ORGANISM: Glycine max

<400> SEQUENCE: 79
atggttctct caaccgaggg cgcaacaaac tccgtcgagg tggtggcgtt cagtttccta 60
acggacgacg agatacggcg gagcagccgc gtgaagataa cgaacccgat tctgattttt 120
aatttaagtt gtacttattt tacatgtctt gaattgagtt gtaagtcttg tggtcaaaca 180
actaaacatt gcccagatca ttttggtcac attgagcttg tttcccctgt ctacaaccct 240
ttgacgttca atattcctag caatattcta caaagaactt gtttctcttg ccatcatttt 300
cagtccctta gaaaagaggt ggatattcgt gcattccaat tggagcttat aatgaaaggg 360
gatattatca tggccaaaaa tttggaatct attatcacag aaaaaagcaa ttctgttcta 420
aggaaattcc tgacgaaaaa acataagtgt caagaatgtg gagctgagaa tcctagaatc 480
agtaaaccaa cctttggatg gttttatatg gttttacaat gcaatatatc cttgggagat 540
gcccatctaa ataagtcaga tccctcaaag gttctaagct ggtggatgga tcttcagcaa 600
tctgtaaaca tgctatttga caataaaact gcttctggca agagagatgt ggctactgga 660
atttgtcgat tgctggagaa gaaggaaggc atctttcggc agaaaatgat gggaaagatg 720
gtttattttg catgtcgctc tgtcatatca ccagatcctt atttagcagt caatgaaatt 780
gggattcccc catattttgc tttaagatta tcagtgactc cttggaatgt agtgaagtta 840
aggaatgcta tccttaatgg tgctgaatcc catcccagtg cttctcatta tgctgataaa 900
gtatcaatag tcaagcttcc accaaaaggg aaggagatat ctgaccatga gtttgaaggg 960
aaagttgttt atcgccactt gaaggatggc gatgttgtgc ttgccaatcg acagccaaca 1020
ctccataaac ctagtataat ggcacatata gttcgcgttc taaaggggga gaaaactgta 1080
cgcatgcact atgcaaactg tagggttact acagttaata acttctttgt tttatttttt 1140
ccccttcgtg atctctgtac ttataatgct gattttgatg gtgatgagat taatgttcat 1200
tttccacaag atgaaatttc tcgggctgaa gcttacaata ttgtaaatgc taacaatcaa 1260
tatgtgaaac ctacaagtgg ggatccaatc agagctttga ttcaggatca tattgtaagt 1320
gctgctcttc ttacaaaaaa ggatactttt ctaagctatg aagagttcaa tcaactactg 1380
tacagttctg gtgtatccat ggctgggcta ggctcattct atggcaaaca tgggcagaaa 1440
gttttcatgt caaattctga gagtgaaatg tttcttgcat tgctatacta tatcaccaga 1500

-continued

```
ggttcaccat catttactgt tgagaagaat gcaaaaatcc catctaattt tttcaagact   1560
cggatcagga aggggaaaag atacactcaa gatacatcaa aaaagaagga aaagcctgat   1620
gaggataaat tattgatata taaaaatgac ttggtgctgc aagaacttta tggatcaaat   1680
gttgctggca acctactttc cgcattaagt cggttattca ctaccttttt acagatgcat   1740
gggttcacat gtggagtaga tgatcttatg ttaacagaag gaaaggatgt tgaaagaatg   1800
aatcagctta atagttgtga gataattggt aacagtgttc atcgtgaatt cattagagtg   1860
aagaatagtg acaatataga ttcagtcaca ttgcaattga atattgagaa aaaaatacgc   1920
agtaatggag aagcaacctt aacatcagat aggaagatga caaacaagct taactcaaca   1980
acaagctcag gtatattaaa ggagctacta tctgaaggaa tattgcaacc ttcaggaaaa   2040
aattgtattt ctcttatgac tacatctgga gctaagggta gtatggtaaa tttccagcag   2100
atatcttctc atctaggcca gcaagagttg gaaggaaaac gagtcccacg catggtttct   2160
ggaaagacct taccctgctt tcctccctgg gattgttccc ctagagcagg agggttcatt   2220
attgatcggt ttcttactgc ccttcaccct caggaatact actttttga tactgcagtc    2280
aaaacatctc ggagtggtta cctgcaaaga tgcctaatga aaaaccttga gtgtcttaaa   2340
gtttgttatg accatactgt ccgtgatgct gatggttcaa ttattcagtt tcactatgga   2400
gaagatggtg ttgataataa agaattggtt tatagcaact attgccgtca gctagacaga   2460
tccagtccat atattaacaa attacctgat gctcttgaag gaaaagcaga aaaattctca   2520
aaacagagaa atcttggttc tatggagcat gcagatttcg taagattgat agagcataag   2580
tatgtctcat gtctcactca accaggtgaa ccagttggtg tattagcttc tcaatctgtt   2640
ggagaaccgg caacgcagat gacagagaga ggggaggaat caagttactc caagagtaac   2700
tctaaaatga gttttctttt aattgtttta acgaaaatcc tgatggctgc tgcacgtgat   2760
atcaaaactc catttatgac atgcccttg agacatgaga aatctataaa tttgaagaag    2820
atcactgtag ctgacataat taagagtatg aaagtttctg ttgtaccagt aactgttctt   2880
ggtggtcaga tttgcagtat atataaactt gtaatgaagc tatataaatc taaacagtat   2940
ccagaatata ctgatattac ccttgaagac tgggaggaaa ctctaagggt taactttgtg   3000
agagactctg aagatgctca cgacaatgga tcagaatctg agaaaaaagg tcaaagtaat   3060
gatgaagatg atgatggtgt tgttgttgaa gacactgaag ggaatgaaga tcttggatca   3120
gatgcacaaa agagaaaact acaaggtact gatgaggttg attatgagga tggtcctgaa   3180
gaggaaacac atgatgaaaa gaaaaaatct gaaccaacaa aaagatatga ctgggcaatt   3240
tttgtggaag ctaaagggat gcattttgag atccacttta gatttactgg tgaacctcac   3300
attttgttaa ctcagattgt tcagagaaca gccaagaagt tttgcctcca aaattttgga   3360
aaggttggtg aatgtaaagc tattacatgt aaagaaagtg gagtaatcta ctatggtaaa   3420
gatgacagaa aaggggatga gatttcagcc tttgagaaag aagaaatacc agcacttcag   3480
acatcagggg tacattttaa aacattttgg gagttggaag atgatctgga tgtgaggtac   3540
atttattcaa acaacgtgct tgctatgcta aatgcttatg gggtggaagc agccagggag   3600
accatcatca gggaagtaca gaatctcaat gccgacttta tgacacactc tggtggctac   3660
tgcctgatga acagaacggg gagcatagca gactcaacat ccctttcat caaaatgtgc    3720
tttgagacag ctgccaaatt tattgttgaa gcagcttatc atgggcaagt ggacaatttg   3780
gagacaccat ctgctagaat ttgtattggt ttgccagtga agatgggaac tgggtgccat   3840
gacttgatac agaagctgga gatatga                                       3867
```

<210> SEQ ID NO 80
<211> LENGTH: 2175
<212> TYPE: DNA
<213> ORGANISM: Glycine max

<400> SEQUENCE: 80
atggcacatg ttcttctgct tcgccctcct ctgcttcgcg tcatgtcctt tcgcttcatc 60
acctcctttt ccttccactc gcgcctttct tcattccctt cttctactct ctccaaaacc 120
aggacgagtt ttcctctgag aaaattttgg gctccctgtt cggttccaaa tgcggtcact 180
ccaagggcgt ttatgtcttc tatctcgacc accgaagctt ttcacaatag tgaaagtccc 240
acagcttata gttctgatca aattcaggtg cttgaaggct tggaccctgt gaggaaaagg 300
cccgggatgt atattggaag caccggccca cgagggttgc accatttggt gtatgaaatt 360
ttggataatg ctgttgatga agctcaagct gggtttgctt ccaagattga tgttgtttta 420
cttgcggatg attctgtgag catcacagac aatggtcgcg ggattcctac tgacttgcat 480
ccagttacaa ataaatctgc cttggagaca gtgttgacgg tcttgcatgc tggtggaaaa 540
ttcggtggtg ccaacagtgg ctactctgtt tcaggaggtt tacatggtgt tggtttgtct 600
gttgttaatg ctttgtctga gttgctagag ataacagttt ggcgtgatgg aatggaatac 660
atgcaaacat attctcgtgg aaagccagtg tcaattctga aatgccttgt gcttccagat 720
gaaaggaaag atcttcgagg gacacgtgtt agattttggc ctgacaaaga agtattcacc 780
actgctattc agtttgatca caacacaatt gccggacgca ttagggaatt agctttcctc 840
aacccaaagc ttacaatcac gtttcggaaa gaggacaatg atccagaaaa agttcaatat 900
aatgaatatt tctatgctgg gggattggtt gaatatgtga aatggcttaa caccgataag 960
aaagctcttc atgatgttct gagttttaga aaagaaacag atggcatcac agttgatata 1020
gcttttcaat ggtctgaaga tgcatattca gatacaatac tgggatatgc taatagtata 1080
cgcactattg atggtggcac tcatattgat gctatgaagg cttctataac aagaactctt 1140
aatagtcttg gaaagaagtc caaagttatt aaggagaagg atattactct aagtggcgag 1200
catgtgagag agggtctaac atgtgttgtc tcagtcaagg tcccaaatcc tgagtttgaa 1260
ggacaaacaa agacaaggtt aggaaatcca gaggtgcgaa aagtggttga tcaatctatt 1320
caggaatatc ttactgagta tttagaattg catccggatg ttcttgattc agtactttct 1380
aaagctctta atgcttttaa ggcagctctg gcagcaaaaa gagcaaggga attggtgaga 1440
caaaagagtg ttttgagatc ttcatccctt ccaggaaaac tagctgattg ttcatctaca 1500
gatcctgaag aatgtgaaat ctttatagtt gaaggtgatt cagctggagg aagtgctaag 1560
caagggcgtg acaggcgctt ccaggccatt ctccctctga ggggtaagat tctgaatatt 1620
gaaaggaggg atgaagcagc aatgtacaaa aatgaagaga tccaaaattt aattcttggt 1680
cttggtctcg gggtgaaggg agaggatttt aagaaagatg cactccgata tcataagatt 1740
attattttga ctgatgctga tgtggatggt gcccacatcc gaacactgct actgacattt 1800
ttcttcagat atcagagggc tttgtttgat gaaggttgca tatatgttgg tgttccacca 1860
ttgtacaagg ttgtaagggg aaaacaagtg cactattgct atgatgatgc tgaccttaaa 1920
aagcttcaaa gatcattccc tcctaatgca tcatacaaca tgcaaaggtt caaagggttg 1980
ggagagatga tgcctttaca actatgggaa acaaccatgg atccagaacg caggttattg 2040
aagcaattaa aagttgagga tgcagcagaa gcaaatattg ttttttcctc tcttatgggt 2100

-continued actcgggtgg attttcggaa ggaacttata cgaaactctg caagcatgat tgatcttgat 2160
cagctagata tttga 2175

<210> SEQ ID NO 81
<211> LENGTH: 543
<212> TYPE: DNA
<213> ORGANISM: Glycine max

<400> SEQUENCE: 81
atgataattg gggtcaggga agagtgccgc attcgagagc aggacttgtg caatttccag 60
gtcatcaacg aaactcgcca acgcttcgga agattcttct ttcgccgacg tttccttgaa 120
tctctgtgga gggacgttga catgaacagg cttaaccatc atccttctga tgatctggat 180
ttgataattg tgtcacatgg gctggcatct cgtgttttcc ttatgaagtg gttcaagtgg 240
acagttgaac agtttgagct tctgaacaat tttggaaatg gtgagttccg ggtgatacag 300
ttgggagtgg tggagattgg agaatacagc ttggcagttc atcacacgga cgaagaactg 360
cttgaatggg ggctctctcc tgatatggta gctgatcaga aacggcgagc cagtgccggc 420
aagggtgact ggaatgatca atattcctgg taccttgatg cttttttta tcaccttcct 480 gactctgatg atgagaatgt ggacaaacat gacgagacag attctttgag tgaatgttca 540
tag 543

<210> SEQ ID NO 82
<211> LENGTH: 1776
<212> TYPE: DNA
<213> ORGANISM: Glycine max

<400> SEQUENCE: 82
atgaacctgt tactcccact ccctcatcac cataaccatc tctcattctc ccaaagccca 60
tttctccaca accccatcaa acccctccat ttcctcccca accctcccgc acgtgcgagc 120
acaataatcc gcatgggcgg gggtccccgc acgtaccccg gaggcgtgtc gaagtgggtg 180
tggaagcgca tgcaggcgaa gaaggccaag cagcttatga aggcgcgcct ctgccgggag 240
cggcagatat acgagatgcg gaagcgggcg gagctcaagg cggcggtgtc ggagctggag 300
cggccgtggg aggttgtcga gagagaggcg tcggcgtcgg cgccgaactt gttctcaatt 360
ggggcggatg agcaggtgaa ggtgcttgct gacaggttcc agaggccagg cgggtttgac 420
ttgtggagtg agagggatgg gccggtgctg tttgagagcc ctgatgagct gccctctgct 480
aggtttttcc ccaaaggggt tgtgcatagt gtgaagcctt ataggagggt tgatgggtat 540
ggattggtga aggatgctga tggagatggg gagatgggtt tgttgaaggg aaatgatttt 600
ggtggaggtt tgagggaatt gggtgatggg ggtttgagtg gattggagga tgttgatagg 660
cttgaattgg aagatgatga tgatggagaa tgttcatctt ctgatgtgag ttatgggagt 720
gatggtggat tgagaaggaa tgagaatggg gggaggtttt tgtctgatga tgttggtagg 780
tctagcaatc gagggcgagg gcaagggcaa tcttctcgaa attatgggag gaatggagcg 840
gatggtgatg gcagaatgag gaagaatggg aatgggagaa ggtttttgtc caataatgtt 900
gatcggtcta gcggtggaga acagtcttct cctttgaatt atggcgggga tggaatggat 960
ggtgatggta gattgaggag gaatgggaat gggaggaggg ttttgtctga tgaggatagt 1020
agcgatggaa agcggtcttc tcatttgagt tatgggagga atggagtgga tggtgatggt 1080
gatggtggat tgagaaggaa tgggagaggg agaaggttaa tgtcatctgg tgatggaggg 1140
caatcttctc gtttgaatta tgggaggaat ggagcggatg gcaatggtag attgagaagg 1200

-continued aatgggaatg agaatggaag gaggattttg tctgatgatg atggtaggtc tagtgatgga 1260
gggcgatctt ctcgtgtgca ttatgggagg aggaatggat tgaattttga tggaagaatg 1320
agaaggaatg agaatggaag taagtatgtt gtgcagggtg ttgacggggc tgatggtgga 1380
gaaagtttgc cccattcttc aagctctgga aggtatggag caagttttga tggcagattg 1440
aggaatagtg ggagtggaag gagggtttta tccaaggatg ttgatgggtc tggtgatggc 1500
ggattgagga gtaaggagaa tggaaggagg tttatgtcaa agaatgttga tgggtctaat 1560
gggttgtatt caggggggagc tagttctgtc aggaaacaga gagggggtaa ttccattgga 1620
ggcagaagtc gaggaaagta tactaatagg acttcagagt atgcctcacc aagaggtaga 1680
gatgcaaatt ctgaagttta tgacatggat ttgcaacaag atgggagtta tgggttcagg 1740
aagaagcgtg agcaacctga ttctacaagt tggtag 1776

<210> SEQ ID NO 83
<211> LENGTH: 3621
<212> TYPE: DNA
<213> ORGANISM: Glycine max

<400> SEQUENCE: 83
atggaggata gtgttagtag cagcaacatg aatgccacca atgtggcgca agctatacac 60
accgcccttg attgggcctc tactcccaac gcgagacaaa acgccgtcgc ttttctcgat 120
tccataaaaa acggcgatgt acgggtatta gcaaacacat cattccttct ggtgaaaaag 180
agctggtcat ctgaaatccg gttacatgcc tttaaaatgc tgcagcattt ggtgcgctta 240
cgttgggagg aattaagacc tgcagagcac aagaactttg caaatctttc tgttgatttg 300
atgtctgaga ttgctgatcc ttgtgaaaat tgggctctca aaagccagac agctgccctt 360
gttgctgagg tagttagaag agagggtctt aatttatggc aagaaatgct tccatctttg 420
gtttctctat ccagcaaggg tccaatagaa gcggagttgg ttgcaatgat gctgcggtgg 480
cttcctgaag atattacagt tcacaatgaa gacttagaag gtgaccggcg aaggctactt 540
ttgcgtgggc taactcaatc attgcctgaa attttgcccc tattatacac tttactagaa 600
aggcacttta cagctgcaat gaatgaagct ggtaggaaac agatggatat tgccaaacag 660
catgctgcca ctgtaacagc tactctaaat gctgtgaatg catatgctga gtgggctcca 720
ttgtcagatt ttgctaagtc tggcatcatt catggttgtg gtgtactact atctgcaccg 780
gattttcgtc ttcatgcttc ggagtttttc aaacttgtct ctccaaggaa gaggcctatt 840
gatgcatctg cttctgaatt tgaccaagct atgagcagca tctttcaaat attgatgaat 900
gtatctagag aatttttgta tagatctggt tcaggtcctg ggtccatgga tgagggcgaa 960
tatgaatttg ctgaatttat atgtgaaagt atggtgtcgc tgggttctta taacttgcaa 1020
agtattgctg gtgatagcac catacttcca ctttaccttg aacagatgct gggatttttc 1080
caacatttca agtttggtat tcattttcaa tccatgcact tctggctggt gctaatgagg 1140
gatttgatgt caaagccaaa aaattccaca cattcagctg ctgacagttc agctgtgagt 1200
agcacaggtt ctggagaagt tgaaaatgct aagaaaaaga ctctaagctt tgtgagtgat 1260
gatttttgtg gtgcaatttt agatacatct ttccctcgca tgctcaagag agagaaaatt 1320
ctgcatgaga ctgccatttc tttaggggca ttagagttgt ggagtgacga ttttgagggc 1380
aagggaactt tcagccagta tcgttctaga ctgttggagt tgattaggtt tgtttccttt 1440
tacaaacccc tgatagctgc tactaaagtt tctgaaaaaa ttgatacaat catcaaaggt 1500

-continued

```
ctcttgcttt catcagcacc aactcaggac ttagctgtga tggaaagcat gcagttggct   1560
ttagagaatg ttgtaaatgc agcttttgat ggatcaaatg actttaccaa ggcaaatgct   1620
gaagttcagt tagcattatg tagaacgttt gaaggtttac ttcaacaatt tatttcctta   1680
aaatggacgg agcctgcact tgttgaagta cttgttcact atttggatgc tatgggcccc   1740
tttttgaagt atttcccaga tgcagttggc agtgttatca ataaattatt tgaactttta   1800
acatctattc cccttgtaat caaggatatg tcaatgcata atgcacggca tgcaaggctg   1860
cagacctgta catcatttat tcggatagca aaaactgctg acaaaagcat cttgcctcat   1920
atgaagggta ttgctgatac aatgggatgt ttgcaaaggg agggtcgttt gcttcaggga   1980
gagcataatc ttttaggtga agcttttctt gttatggctt cttctgctgg gatccaacag   2040
caacaagatg ttttaaggtg gttactagaa cctttgagca ttcagtggac acaatcggag   2100
tggcaggata aatatttgtc aggtccacac ggtttggttc agttgtgctc agatgcgcct   2160
gttatgtggt caatttttca tacattgaca ttctttgaga gggcacttaa gaggagtgga   2220
ttgaagaaag ccaattggaa ttcagaaaac agctcaacac caaactcaac tcctttaaat   2280
ccaatggcct ctcacatatc atggatggtg actcctctct tgaaactact gcgctgtata   2340
cattcccttt ggtctccatc tgtaagtcaa gctttacctg gtgaggtcag agctgcaatg   2400
gtcatgggtg atgttgagag gttcagtctt cttggagaag ggaactctaa attaccaaag   2460
ggtgtcacag atggatctaa ggttgacatg aataaagaag gatatgctga acccaatgaa   2520
tcagatatac gaaactggtt taaaggcatc agagacagtg gatataatgt attgggtttg   2580
tcaacaaccg ttggggattc ttttttcaaa tatttggatg tgcactctgt tgctgttgca   2640
ctaatggaga atatacagtc aatggagttc aggcatataa ggcagcttgt tcattccact   2700
ttgattcctt tggttaaaaa ttgtcctttg gatatgtggg agatttggct ggaaaagctt   2760
ctacacccat tgtttgtcca tgctcagcag gcacttagct gttcatggtc tagtcttcta   2820
caagatggta gagcaaaggt tccagatgtt catgacattc ttagtggatc agacttgaaa   2880
gtggaagtga tggaggaaac aattctgagg gatctcacac gtgagatgtg ttcactcctc   2940
tctgtcattg cttctcctcc ccttaatact ggaatccctt ctttggaaca atctgggcat   3000
gttagtcgat tagatatgtc ttctctaaaa aacttggata cagttgcatc atgctccatg   3060
gttggtttcc ttctaaagca tgaaggtctg gcccttccaa cactacgaat gtgtttggaa   3120
gcttttacat ggacagacgg tgaagctgtg actaaaattt cttcatattg ctctgcattg   3180
gtagttcttg cgatagtaac aaatcacgca gaactcattg aatatgtttc tagagatctt   3240
tttacatcca ttattaaagg tttagccctt gaatcaaatg caataatcag tgctgatcta   3300
gttggcattt gtcgtgaaat atttgtttac ctttgtgata gacacccagc tcccaggcag   3360
gttttgatgt ctctccccaa tattaccact catgatttag ttgcctttga ggaatcttta   3420
acgaaaacat tcagtccaaa ggaacaaaag cagcttacga gaagcttgtt tcaattagca   3480
actggtaaca aattgaaagc acttgcagca cagaaaaccg tgaatatcat tacaaatgtt   3540
tcaacaagac cgcgcccagc caatgctcct gagtccaaag ttgatgatgg tgatgttgtg   3600
gggttggcag ccatcatgtg a                                              3621
```

<210> SEQ ID NO 84
<211> LENGTH: 786
<212> TYPE: DNA
<213> ORGANISM: Glycine max

<400> SEQUENCE: 84

-continued

```
atggtgaaaa caaagcagaa gcgcacagga aaagttcctg gtaaaaaaag tggtacttct     60

tcacattgcc ttgttaattc tggaaacggt gacaatcagc atgaggatag tgattggatt    120

atagtgaaaa agcagagagt taccattctg gtgcctgctg cacctcttaa tgagagatca    180

ttaacagcaa accaaggacc aaatcacatg catcttatgc ctcctgaaat agcaagtaac    240

catgtgcagc ttcccatgga aacatctacg atgcatcctt caggtaatga acatgagaag    300

gccactttgg ctctccgaaa ggagactcgt gccgagagaa gagctccccc taccttacct    360

aaaccaactg tggtcaatcc accgtcttta gatgaaataa tagaatcaga aaatccacat    420

caaacgaaca gtttgaagtc acataaacta cttggaattt ctgatacatc aaaagttatt    480

aagcagccca gaacactact tgcaccaaga aggtcctcca acttggaaac tctgaataaa    540

agcttaagag catcaaacct tgagaggaag ctcgaaagag ccggtggact tagcaaatgg    600

ctgacatcgc ttggactggc gcaatttgtg agaatttttc aggggaatag tctcagtaag    660

tatcagctgg taaatctaac catgaaaaaa ctcaaggata tgggcgccag tgcagtggga    720

cctcgcagga aactgatcca cgccatggac tgtgtttgtc agccatattg ctttgaggca    780

ttgtaa                                                               786
```

<210> SEQ ID NO 85
<211> LENGTH: 2382
<212> TYPE: DNA
<213> ORGANISM: Glycine max

<400> SEQUENCE: 85

```
atgttcaaat tcttgaaaga ggtggtgagt ggatctggca cgggcctcaa agatctccca     60

tacaatatcg gtgaacctta tgcttctgct tggggctctt ggcttcattt tcgcggcacc    120

tccaaggacg atggttctcc ggtgtccata ttttctctgt ctgggagcaa ttctcaggat    180

ggacatttag ctgcggggcg taatggcgtt aagcgtcttc gcactgttag gcatccgaat    240

attttgtcgt ttcttcacag caccgagatt gaaaccgtcg acgctggttc tcccaaggtt    300

acaatttata tggtgactga gccagtgatg ccgctgtccg acaagattaa ggagttgggt    360

cttgaaggta cacaaaggga tgaatattat gcttggggcc tgcatcagat agcaaaagct    420

gtgagcttct taaataatga ttgtaaactt gttcatggta atgtttgctt ggctagtgtt    480

gttgtcacac aaactttgga ctggaaactc catgcttttg atgttctatc agagtttgaa    540

gggagtaatg aagcttcctc tggacaaatg ctgcaatatg cttggcttgt tggatcacaa    600

tacaaaccaa tggaactggc aaaatctgac tgggctgcaa ttaagaagtc tcctccatgg    660

gccattgatt cttggggcat gggttctcta atctatgagc tattctctgg tatgaagttg    720

ggcaaaacag aggagttacg caacactgtc tccattccca agtctctgct tccagattac    780

cagcggctac tgagttctgt gccctctcgt agattaaata catcaaagct tatagaaaac    840

agtgagtatt ttcaaaataa gttggtagac acaatacatt tcatggaaat tcttagtttg    900

aaagatagtg ttgagaaaga caccttcttc cgcaagcttc caaatttggc agaacagctt    960

cctcagcaga ttgtgttgaa aaagttactt cctttattag cttctgcgct tgaatttggt   1020

tcagcttctg cccctgcttt gactgcattg ctgaaaatgg gttccagtct ttctgctgag   1080

gagttccgtg tcaaggtgct tccaacaatt gttaaacttt ttgcatccaa tgaccgagct   1140

attcgagttg gccttcttca acatattgat cagtttgggg agtcattatc agcacaagtt   1200

gttgatgagc aggtttaccc tcatgttgca actgggttct ctgatacatc tgcttttctg   1260
```

```
agggaactta ctctcaagtc catgctaatt ctggctccaa agctgtctca aaggaccttt   1320

tcaggatcat tattaaagca tatgtcaaag ttacaggttg atgaagaacc agctatacga   1380

acaaatacta ccatcttatt gggaaatatt gcaagccact taaatgaagg gacaagaaaa   1440

agagtgttga taaatgcatt tacagtccgt gctttacgtg ataccttttcc ccctgctaga   1500

ggagcaggca ttatggcttt atgtgcaacc agttcctact atgacatcac agaaattgct   1560

actcggattc ttcctaatgt tgttgtactc acaattgatc ttgatagtga tgtgcgatct   1620

aaggcatttc aagctgttga tcaatttttg cagatggcga agcaacatta tgaaaagaca   1680

aatacagcag aggctactga gggtacagcc attggaatct cttcacttcc aggaaatgca   1740

ggtttacttg gatgggctat gagctccttg actcttaagg gtaaaccttc tgatcatgct   1800

ccagttgctt ctgtcagttc tagtgcacgt actccaacat cttccaatgc cagcccagct   1860

gtagatgctc cttcaacagc acctgttcgt gttagctcca caccagattt tgctgaacac   1920

cttgtcccta catccccaac gtcaacagat ggctgggggg aactagagaa tggactaggt   1980

gaaaatgaca aggatgggtg ggatgatctg gaaccacttg aagaaataaa gccaactcca   2040

gctcttgtaa acattcaagc agctcaaagg aggccagttt ctcaacctgt ttcacagata   2100

aaacaagcct caagtttgct atccaaaagt acgccaaagt tgagcaagga tgaagatggt   2160

gatttgtggg gttccatagc agctcctgct ccaaaaatcat caaaaccttt aagtttgaag   2220

tcaactgtaa ctgacgatga tgatccttgg gcttccattg ctgctcctgc acccactact   2280

aaggccaagc ccttatcagc tggtagagga aggggtgcta aacttgctgc tccaaagtta   2340

ggtgctcagc ggataaaccg gacaacatca tccgggatgt aa                      2382
```

<210> SEQ ID NO 86
<211> LENGTH: 969
<212> TYPE: DNA
<213> ORGANISM: Glycine max

<400> SEQUENCE: 86

```
atggagagca tagagcacag aacggtggaa gtgaacggca taaagatgca tgttgcagag     60

aaaggagaag gagcagtggt gttgttcttg cacggcttcc cagaactctg gtactcatgg    120

cgccaccaga ttctagctct gagctccctc ggttaccgtg cggtggcacc tgatctccgt    180

ggctacggtg acacagaggc cccttctacg gtgaacagct acacgtgttt tcatctggtg    240

ggtgatatca ttgctctcat cgactctctg ggtgtggaca aagtgttcct ggtggctcat    300

gattggggtg ccatcatcgg ttggtacctc tgcttgttcc gaccagacag aatcaaggct    360

tatgtgtgcc tcagtgtccc cttccgcccc ttcctcggaa gaaaccccaa acagaaaacc    420

gttgactttt tccattcctt gtatggagat gactactaca tctgcagatt ccaggaacca    480

gggaagatgg aagctgagat ggctggcgtt gacactgcgt atctgatgaa gaacatactt    540

acaacgcgca aaaccggtcc acccactttt ccaaaagggg agtatggaac tggatttaat    600

ccagttactc cagacacctt gccctcttgg atctctcaag aagatcttga ttattatgtt    660

actaaattca acaagactgg cttctctgga ggcttgaact actacagaaa cctcaattta    720

aattgggaac tgacagcacc atggactgga gcaggcatcg tagatgtacc ggttaagttc    780

atcacaggtg gcgttgactt ggtgtacact tctccgggga tgaaggagta tatccacaac    840

ggtggtttca agaaagatgt gccaacttta gaggaagtgg tggtgcagga aggggttgca    900

cacttcaaca accaagaagc agcagaggac gtgagcaatc acatctacga cttcattaag    960

aagttctga                                                            969
```

<210> SEQ ID NO 87
<211> LENGTH: 2184
<212> TYPE: DNA
<213> ORGANISM: Glycine max

<400> SEQUENCE: 87
atgtccaaac ctcaaaatga tccccttgtg caatcggaaa caacttgtgg aacacttctc 60
tatgaacttc agataatatg ggatgaagta ggggagtctg agtctgacag agatagaatg 120
ctgtttgagc ttgaacaaga gtgtctagaa gtatacagaa ggaaggtaga tctggcaaat 180
cggtctagag ctcaattaag gcaggcaatt gctgattgtg aggcagaact tgcagccatt 240
tgttcatcaa tgggagagag accagtgcat attcgacaga ctgatcaaaa tgctggaagc 300
ctgaaggaag aacatgcaag aattcttcca cagttggagg agatgcaaaa aaggaaaatt 360
gagcgtagaa atcaatttat agaaattcaa gagcagattc aaagcatttc aattgaaata 420
tatggtccta gagagtatat tcctgctgtc gaagatgaaa ctgatttatc cttgagaaaa 480
cttgaagaat tgcacaggca gctacatgca cttcagattg agaagagtag tcgcttaaag 540
caggtccagg agcacctgtg tacattaaat tctctttgtt tagtgcttgg ttttgacttt 600
aagcagacaa ttaatggaat tcatcccagt ttagtggact caaaaggatc taagagtgta 660
agtaatgata ccattcagca attagctgtt gctatacaag aactgcggga agttaaatta 720
cagagaatgc agaagctcca agatcttgcg actacaatgt tggagctctg gaacttgatg 780
gataccccta ttgaagagca acagatgttt cagaatgtta catgtaatat agctgcttca 840
gaacatgaag taactgaacc aaacaccttg tccgtggact tcatcaattt ggttgaggtg 900
gaagtagcta ggttagaagc gttaaaatca agcaagatga aagagcttgt attaaagaaa 960
agaacagaac tggaggagat ttgtcgaaag actcatttga tcccagaaat agataatgca 1020
gtggaatctg ctgttgaggc catagaatct ggatctgtgg accctgcttt cgtgcttgaa 1080
caaattgaac ttcagatttc ccaagtcaaa gaggaagctt tgggcagaaa agagatactt 1140
gaaaaggttg agaaatggtt ggcagcgtgc gatgaagagt cttggcttga ggagtacaac 1200
agggatgata atcgctacaa tgctgggaga ggtgctcatc ttactctcaa gcgagctgag 1260
aaagctcgtg ccttggttaa caaaattcca gcaatggtag atggtctgac ttcaaaaact 1320
atttcatggg agaaggaaaa aggcattgag ttcacatatg atggtattcg tctactttct 1380
atggttgaag aatacaatat attacggcaa gagaaagaac aagaacgtcg taggcagcgg 1440
gatctgaaga aactccaggg acaaatgata gctgaacagg aggcactata tgggtcaaaa 1500
ccaagccctt caaagcccca aagtgttaaa aagggaccta ggatgtcgac cggaggaggt 1560
gcagctagta gaagagtctc tctgggagga gcaatgcttc aaactcctaa accggattca 1620
aaatctactc actcacgtgc catgagaaag gttgataaag tgcaccaaat tgagcatcta 1680
aattacctgg atgatggcat ttcaggttta tcagcagcta gaagagggct ggatattgct 1740
ggcgctcctg ttaaaaagca ctcatttggt gctgggactc aaatcataga atctcctctg 1800
atacgacaac ctttttctcc catctcttct aacagtgtat cttcaaaagc taatgtggca 1860
aatgctacag atgaactgag taaacagaat gagaagttgc agagaacagt gtcgcttaac 1920
aatgggccat ttactactcc ctccaagaca gttcctactg tggtagatga agagaatagg 1980
actccaaata ttcctgcccc agctacccct tcgacagtat cagttccaat gaatatggcc 2040
atgactccag ttccttcttc aattttgaag aacgtaagct tgaattcaac tcccatatca 2100

-continued

```
gttccttatg gaaataatga cttggttcag gaggttgaat attcattcga ggaaaaaagg   2160

ctcagttact atatgttagc gtga                                           2184


<210> SEQ ID NO 88
<211> LENGTH: 222
<212> TYPE: DNA
<213> ORGANISM: Glycine max

<400> SEQUENCE: 88

atgccttctg atcctgtgtg gaactatcgg ggaaacttgt taaaaatgct ggaattggta     60

gtcttccaca ggtggtccaa acctctctgt tctttgttgt tctcagttga aacttacatc    120

gatcccttac tgaaaacctc atgccaaaac aaagtcacta aactggaagg gaacttccat    180

cgcggagcaa aacgaaggaa acttacatca atcctgttct ga                       222


<210> SEQ ID NO 89
<211> LENGTH: 966
<212> TYPE: DNA
<213> ORGANISM: Glycine max

<400> SEQUENCE: 89

atgtcgaagg tggtttgtgt caccggagcc agcggcgcca tcggatcatg ggtggtccta     60

ctcctcctcc agcgtggtta caccgtccat gccaccgtcc aagatatcaa ggatgaaaat    120

gagacgaaac atttggagga aatggaagga gcaaagagtc atctccattt ttttgaaatg    180

gatcttcttg acatcgactc cattgccgct gccataaagg gttgttccgg cgtaatccac    240

cttgcatgtc ctaacatcat tggtcaagtc gaagatcccg agaaacagat attggaaccg    300

gcgataaaag gaacggttaa tgtgttgaag gcggcgaagg aagcaggggt ggagcgcgtg    360

gtggcgactt catcgatttc gtcgattatg ccaagtccta attggccagc tgataagatt    420

aagggagaag agtgttggac ggaccttgaa tactgcaagc aaaaggggtt gtattatccc    480

attgcaaaga ctctagcaga gaaagcgggt tgggactttg cgaaggagac aggttttgat    540

gttgtcatga taaaccctgg tacagcattg ggccctctgc ttcctccaag aatcaattca    600

agcatggctg tgcttgttag tgttctcaaa gggggcaaag agacctacga ggacttcttt    660

atgggaacgg ctcacttcaa agacatagca ttggcacata ttttggcact tgagaacaag    720

aaagcagcag gaaggcactt gtgtgtggaa tctattcgtc actttagtga tcttgtggac    780

aaggttgctg agttataccc tgaatacgat gtggctaagt tgccaaagga tacccaacca    840

gggttgttga gagcaagtgg aaaggatgca tcaaagaagc tgattgattt aggtctagaa    900

ttcactcctg ttgagcaaat catcaaggat gcagtggaga gtttgaagag caggggctat    960

gtctaa                                                               966


<210> SEQ ID NO 90
<211> LENGTH: 963
<212> TYPE: DNA
<213> ORGANISM: Glycine max

<400> SEQUENCE: 90

atggataccc tttcaaggat tagattcctc cccacttgtt acagtcttca gttcccaaaa     60

atctctgcat tatctcgttt cccaaatgct ttttccacag ccactcccct ggtttcagtg    120

ctaagagtaa gagctggtcc tccttcagtg agtgatacag atgaggatgt cttgcaaata    180

ttttttaagg agagagaatt aaatggggat tttatatcaa gagcttccga tttattatgg    240

agaagagatt tcagaagttc tggtgattat gatattagcg agctcaccga caacacttct    300
```

```
caacaaatag agcagatcat agagactgac agtgatggtg gttttttgaa acttacaaga    360
acccaagagt ggctaacagg tgacaattct ccaccaataa acaagaaggt gactgctaag    420
gcattacagg acagcagtgc aagacgcatg aaactgaaca tgctcaaata tgaatctctc    480
aagagggaat tactgcttct atctgtgggt attggactgg cttgtagtgg atattgcttg    540
gttatttttt ccgtacaggc tgctataagt tatgcgattg gagtcctttt cagttgcttg    600
taccttcaac tcttgtatca acatgcagac aacctatcca gtgaagatgt tcctcaaata    660
ttcaagaaaa agaagtcgaa gaaaattggt ataagaagtg aagaccttga agatttcttg    720
gagaggacaa tcaagggtag cggtatatct ctttcatctc ccaggctagt tattccagca    780
acaatatatg ggctttggat tctgtttcat cagtatttta ccaatgacat tttgatttc     840
cagcttgtgc cagccatgtt cggaatgttt gtctacaagg ctgctgttct ggtgcaagct    900
tatagagaca atgaaggttt acggtttgta tttcccgaaa atgaagatgg atcaagctat    960
tga                                                                  963
```

<210> SEQ ID NO 91
<211> LENGTH: 555
<212> TYPE: DNA
<213> ORGANISM: Glycine max

<400> SEQUENCE: 91

```
atggctaagt actatgatat tgatgatatt atcattgagg aagagactgt gtcagttata     60
tttcagaggg ctgcatctgg agtgggaata gatcccagtt cttcaatcct tattgaaaca    120
ggttcaaaag ttgaactgcc gttttggctt gctcatgagt tacagttgag acaagcagta    180
tcagtcaatg ttcctccttg tttcaatcaa aaaacaaggc aggagctcca tgctgattct    240
gcaggtgtgg atctgaggtc cagatgtcca tttttctatg aatttggttg caagatagca    300
cccatagttg gcgaccgaac cattgggttt ctgttgttga ctgcatttaa gagtaggtac    360
aaggaaattc tcaccaaggc acatactgta gcatttgcac ctggttccaa attttggact    420
attctaacaa aagaagagat ctacttgtat gagacagctc aatctgcaat ggcatctttc    480
aagaagtggc gaatgggggg acccagattt cagatagctt ctgttctggg aagaaagaga    540
aaatctaagg aatag                                                     555
```

<210> SEQ ID NO 92
<211> LENGTH: 1392
<212> TYPE: DNA
<213> ORGANISM: Glycine max

<400> SEQUENCE: 92

```
atgggaatcg atcaacttcg gtggcggtgg tggaacgccg tcgttttgat cggaatggtc     60
ggcgttacag tagtaaccgt taccggttcc gacagtcacg agaagcagga acaagtggtg    120
tctcgaattg ccttcggatc atgctccaac cagagcgctc ctcagcccat ctgggatgca    180
gtggtggact tccatcccca aatttttata tggctgggtg ataacattta tggagacttc    240
aaacgccctt tcaaaatatt tggacaggaa aggactgttg gaccgtggaa gaatgttcca    300
cgatttgttc cttcctctga gcaggaaatg aaggctggat atgaaaaagc taagtctaat    360
cctggctatg ctcgactcca acagaatgct aaggttattg gtacatggga tgatcacgat    420
tatggattaa atgatgcagg gaaagaattt catggaaaaa taaccaacca aaagttgctt    480
cttgatttct tggatgaacc tcaagatagc ccacggcgga aacaggctgg tgtatatgcc    540
```

-continued

```
tcatatacgt atggtcctgt aggtagagat atcaagattg tcctcttaga taccagatat    600

cacagagacc ctgtaggaag tgatggaacc attttgggga attcacaatg gttgtggttg    660

gagacagagc tcaagggtcc accaacagct cttaccataa ttggatcttc tattcaggtt    720

atatcaaatc tttcagctac cattcatcca ttgttcgcaa tggaatcatg ggtcgttttt    780

ccaaaagaaa gagatcgcct ttttaaatta atcgctgata gtaagagggc tggagtattt    840

tttattagtg gagatgttca ctttggggaa atcacgagat atgattgtgc tttggactat    900

ccactatatg atttaacctc aagtggggtt actcaatcag ttgaggaggt tgtcccacct    960

ttcttgcgtt cttttgtgag atttgtggca tggttgaccc catctactat gagagttaag   1020

gacgaaaatt gcagatacaa atcttgtatt tatggtcagc caaactttgg aactattgag   1080

atagattggg actctcaccc agtgactctg aaattcaaag tcagggacaa ggatagtgtc   1140

acagttacag ggttgatgt ttcattaacg gaattacaac catcaaattc agagatttta   1200

gacagggtaa aagcagagca taataattca aagcattgca cccttgaagt tagtctgcca   1260

tggattgtaa gatatcgcct ggcaatcttg ttcttttcca ccttatttgt gatgtttgtt   1320

gcattcctag tgctagttta cacttgcttc agactttgcc gacttgaaag ctgcaaaaga   1380

aagcacgatt ga                                                        1392
```

```
<210> SEQ ID NO 93
<211> LENGTH: 180
<212> TYPE: DNA
<213> ORGANISM: Glycine max

<400> SEQUENCE: 93

atgccactca aacccagagc tagctggttc tccccgaaat gcattgaggt gcagcagttg     60

actagacatc tagaggtaaa gcactatttc gatgcgagcc acgagagtgg tactaaatcg    120

aggcaaactc tgaatactag atatgacctc aaaataacaa gggtcaagtt cggccagtga    180
```

```
<210> SEQ ID NO 94
<211> LENGTH: 3864
<212> TYPE: DNA
<213> ORGANISM: Glycine max

<400> SEQUENCE: 94

atggtcctta tgaaatcgtt ctctaggctc taccaggtga atccgaatta tcgaatggca     60

tccaataatc cttacgagat aatggacgat gagggatttg actgggaagc agctgctaga    120

gaaatcgacg tggtttgcca gacgaccagt gacgtaaagg gaaagggaag ggtttttgag    180

aagagaaagc agcaatccac tctcgataag ttcatatcta ttgccaatgc caatgccgaa    240

aaggaaaccc caccaccgca gttccaagaa gatgaccaaa gccctgcttt catccaccac    300

attgacaccg aggctgccaa aacttggata tatccagtta atgttcctct ccgtgactat    360

caatttgata ttacccagtc cgcacttttc tcaaacacat tggtggcctt gccaacggga    420

cttggcaaaa ccctcattgc cgctgttgtt atgtataact acttcagatg gtttcctcaa    480

ggcaaaatag tctttgctgc tccttctcgg ccacttgtca tgcagcagat agaagcatgc    540

cacaatattg tgggaatacc tcaagaatgg acagttgata tgactggtca gctaagtcct    600

cccaaaagag ctcaattttg gaaaacaaag cgagttttct ttgtcactcc acaagtgttg    660

gaaaaggata ttcattctgg tacatgtttg gtgaagtact tggtatgttt ggtgattgat    720

gaagctcaca gagcaatggg aaattacgct tattgtgaag ctgttcgcga gttaatgtct    780

gtaccagtac agctgagaat attagcgtta actgcaacgc caggatcaaa gcaacagaca    840
```

-continued

```
gtccaagctg tcattgataa tttgcatatc tccagacttg aatatcgcag tgaaactgac    900
catgatgtta tctcatatgt tcacagtagg aagatagaat tgatacagag atctttgttg    960
caatattacc aggttgcaat gggcccagaa gcggtagaaa taaacaataa gtttatggaa   1020
gtaatacgcc ctatagtagc caggcttaca aatattgggg tcattcagaa cagagattac   1080
cgcactttga gcccttgtca attacttgaa ataagggaaa agtttcgcca acggcctagg   1140
caagatcttt ctcatgtcaa ctatgaagat gttgaagggt attttggcgt tctcattact   1200
ctttattaca tccataagtt gctctcaagt cacggaataa ggccagcaca tgagatgctt   1260
gagagaaaat tgaagcaagg atattttgca aaatttatga gtaaaaatga agttattctg   1320
aaagcaaggc agctaatgca gcaaagtttg tctcacggag catctagtcc aaaattgtcc   1380
aaaatgctag atgtattact ggagcatttc aaaactaatg atccgcaaaa ctccagggta   1440
attatcttct ccaattacag agaaagtgtc agggatataa tgaatgcact tggagatatt   1500
ggggaattag tcaaagctac tgagtttatt ggtcaaagtt cagggaaagc aatgaaaggt   1560
cagtcccaaa aagttcaaca ggctgtgctg aagaaatttc ggtctggcgc ctataatgtt   1620
attgttgcta catcaattgg tgaagaaggt cttgatatca tggaagttga tcttgtcata   1680
tcttttgatg ctaatatttc accactcaga atgatccagc gaatggggag aacaggaaga   1740
aagcatgatg gacgagtcgt agtttttgct tgtgaaggga cagagttgaa gggctacttg   1800
caaaaacagg caaagagcaa gactataagt aaacacatgc gaaatggggg cataaatagc   1860
tttacctttc atcctagtcc aaggatgatt cctcatgtcc ttaaaccaga agttaaatgc   1920
gttgagctgt ccattgagaa atttattcct cgtccaaaga atgtgaaaga tgatgagctc   1980
cacatttctc catcaaagga caaactaact gttgcggaaa ttgatttact tgaaacatat   2040
tttcacccta ctgtggaaaa caatagtaga atgtctctta ttgcctttcc ccactttcag   2100
acctttcctt ctagagtgca taaagtgaag cattcctctg gaacattgat gcttatagac   2160
atgatgcagc gcttgcaagg actagtatca tttccagaag atgacaaaac ttcttcactt   2220
caggaagatc tgtgtttggg acatggtaag ccagtcacca ctaccgaact tgatgaagct   2280
aaaaaggaca atgaatcgtg ctctaggcat aaaatgagaa ggaatttagt ctctgttaat   2340
tgtctggaga tggattcgtg tcatttgggg attcaaagca aagacttagt tgacctaact   2400
cgacaagatg gtactttctg tgacttgggt aagaatcaag aggaagcatg tgagggtgat   2460
gagacaattc ctgaaactcc aattgctaag agaagtttgt caaatgaagg agataatgat   2520
ggtcaaatgg taaatcttgt ggagattgag acttcttcat tggctgcaaa tgcatgcatt   2580
aatggcatga gagatgaaga acttagtcca cgtttaacta atttgattag aagtggtgtt   2640
gttccagagt ctccggttga cgaaagaggg aaatcaagat acaattctat catacgtgat   2700
tttgtgttac ctgttcatct ccacaaagaa caggatgtta gttctttaag ctctagtgaa   2760
actaaagagg tcattattga taagggcacc aacaagaatg tctgtacttc ccccattaat   2820
gaaactcaaa gccctttact tgacctgaaa aattgtgcaa ttagaagagg acgagtcttc   2880
ctttctcaaa ttgaggaagg ccatgcacat aacactgatc caagcttcag cgaagaagca   2940
tatccagcag attgtggtga aatgtccgaa agcattaaac ctgcacgcaa atttaaaagg   3000
ttgcggaaag ctgaagatac tgaaagaaat atgaatcaga aaaacaataa actttttgct   3060
tcaacagcaa actttctcaa accatcttct gcctccaatc ctgcacaata taagcatggc   3120
caaggtaaaa ggaaatcaac acacaatgtg agagacttca ttgaggagga agccgaagta   3180
```

-continued

```
tcttcagatg gctatgtatc taatgatgaa gatgatgagg aaggcagttc atttgacagt   3240

ttcatagatg acaggaccaa ccctacagca gccagtcagc ctgaagctag tagaatggac   3300

atgatggcaa tttacaggcg ttctttgctc agtcaaacac caagtaatgg agggcttgat   3360

ctttgtgcca cctttactcc tgaccgtgtg actatggcag ccagtattag tgaaagtgag   3420

gattctacag ggaagacagt ggatcacttc cacgcagagc caaccaaaca gtcagcaaat   3480

cggactttgg aatctgttag tatcaaccag ataacctcag aagcagtggc ttcaacttgt   3540

tatcctatgg gaactgggac agagacaaga agtcacaaac gaagattggc attttaccat   3600

tctggacact tcccaaatat gaaccttcaa cgagaatttg aacttcaatc aaagaaagac   3660

gtagtgcaca ctgatgcaac tacagatgtt ctatgtgatg atcaatttta taatgatctt   3720

gatcttgacg agttggaggc acaagcaaca ttgcttctaa aacagaaatt agatttgtct   3780

aatcagaaac aagatacggt ccctcaatct cacacatcca atcttgatat ttttcagtct   3840

ccatcatttg accttgggat atga                                          3864
```

<210> SEQ ID NO 95
<211> LENGTH: 2949
<212> TYPE: DNA
<213> ORGANISM: Glycine max

<400> SEQUENCE: 95

```
atggaactca ccatcccacg caaccccaac cctcttctcg tttcctcacc cccaccactc     60

tctcgaaacc ccaacgtctt caccttaacc gtgccgcgcc gccgcagaag gattcggttt    120

cgggtctcgg ccgccgcgga gcccgatggg ccgtcgtggt cgcaatcgct gctgcgcggg    180

tcacggcggt tttggggaaa gtttggggaa atggtaaaga aggagacggg tctcgacttc    240

gaaaacagga gtgtgaagaa agttggcgag tttgtgaacg gagatgaatt gcgaaggttg    300

gggactgatt gggtgtttcg gtttgtcgat tggaatcgtt gggaacggtg gaagaatatc    360

aaggattggg aacctaagcg aattggtgca ttggttcttt acatttttgt tgtgacattt    420

gcttgtagag gagtatatgt aacaattcaa gcacctttcc taagtcgcca gaaaaaagag    480

ttgacagaag cttacatgga agcgttaatt cctgaaccat cccctaccaa cattaaaaga    540

tttaaaaagg gtatgtggaa gaagacaatg ccgaaaggcc tgaaaatgaa aaagcttatt    600

gaaagacctg atggaacact tgttcatgat acttcttatg ttggagagga tgcatgggag    660

gatgatcgag aggctcctga ggagcgtgta aaacaaatta tagaggatga tgaaaggtta    720

aacaaagaag agaagaaaga gttaacaaaa ggcttgggca tttcaggtga agttcaaact    780

gatggcacat ggcgtgatag acttaataaa tggagagaga tccttagtaa agaacgtttt    840

tctgagcaag tggattcctt aaatgccaaa tatgtagttg aattcgacat gaaagaggtt    900

gaaaatagtc ttcgcaagga tgtggcagaa aaggtgacac ccactcaggg tacaagggct    960

ttgtggatag ctaagagatg gtggcgctat cgccctaaac ttccttacac ttatttcctt   1020

gacaaactcg atagttctga ggtagcagcc gttgtcttta ctgaagactt gaaaagattg   1080

tatgtgacga tgaaagaagg ttttccattg gaatttgttg ttgatatccc tcttgatccg   1140

tatatgtttg agattattac aagttccgga gttgaagtag atctccttca gaagcgacag   1200

atccattatt tcatgaaggt tgtgattgca ttagtacctg gaatactgat tctctggctt   1260

ataagggagt ctgtaatgct tctacacatt actaacaaga ggtttcttta caagaagtat   1320

aatcaactct atgatatggc tcatgctgaa aatttcatca tgccagttgg agatgttggt   1380

gaaacaaaat caatgtacaa ggaagttgtg ttggggggtg atgtctggga tcttcttgat   1440
```

-continued

```
gagttaatga tctatatggg aaatcctatg caattctatg aaagggatgt gcagtttgtt   1500

cggggtgttc tactctctgg acctccagga actggaaaaa cactttttgc caggacgctt   1560

gcaaaagaaa gtggattacc ttttgtattt gcttcaggtg cagaattcac tgatagtgaa   1620

aaaagtggtg cagctaggat caatgagatg ttttccattg ctaggagaaa tgcaccttgt   1680

tttgtatttg tggatgaaat agacgctatt gctggaagac atgctaggaa ggatccacgg   1740

agaagggcaa cttttgaggc tcttattgca cagcttgatg gggagaagga aaaaactggt   1800

gtagaccgtg tatccctcag acaagctatc atatttatct gtgccacaaa taggccagat   1860

gaattagatc ttgagtttgt tcgtgctgga cgtattgatc gtcgtctgta cattggtttg   1920

cctgatgcaa agcagagagt tcaaattttt ggtgtgcaca gttccggaaa gcaacttgca   1980

gaggatgtgg attttgacga gcttgtcttc cgtactgttg gattctctgg agcagatata   2040

agaaaccttg tcaacgaatc agcaataatg tcggtgagaa aagggcattc caaaattttc   2100

cagcaagata ttattgatgt actagataaa caactgcttg agggtatggg tgtccttctg   2160

acagaggaag agcaacaaaa atgtgaacaa aggttatcct ttgaaaagaa gagactgctt   2220

gctgttcatg aagctggtca tgtagtgcta gctcacttat ttcctcggtt tgactggcat   2280

gcattttcac agctcctgcc tggtggtaag gaaactgcaa tatctgtatt ttatcctcga   2340

gaagatatgg tagaccaagg ctatacaaca tttggttaca tgatgatgca aatggtagta   2400

gctcatggtg gtcgatgtgc tgaacgtatt atatttggtg atgatataac tgatggtgga   2460

agtgatgatc ttgaaaagat aacgaagatt gctagggaga tggttatcag tccccaaaat   2520

aaaaagttgg ggttaattgc tttaacaaaa agggttggct taaatgatcg accagacagc   2580

ccagatggag agttgataag atatagatgg gacgatcccc aagtaattcc tgctaatatg   2640

acactagagg tgtctgagct tttacaagg gagttgacaa ggtacattga agaaacggaa   2700

gaacttgcaa tgaatgcttt aaggaataac aggcacatcc tggacttgat tgtgagggaa   2760

ctattggaga ggtcaagaat aaccggattg gaggttgaag aaaaattaaa ggaaatgtct   2820

ccagtaatgt tcgaggactt tgtgaagcca ttccagataa atccagatga gaagggacca   2880

ttaccgcata atgatcggct acgatatcag ttacccgact tgtatcctgc tcctctccat   2940

agatgttga                                                           2949
```

```
<210> SEQ ID NO 96
<211> LENGTH: 1158
<212> TYPE: DNA
<213> ORGANISM: Glycine max

<400> SEQUENCE: 96

atgaatacga taacgacgac gacgatgacg atgagtgtat taaacatcta tggctatggc     60

tatggtgttg tagctgttgt tgtgttcctt atattattgc tttggcagcg tcacagattt    120

ttcttcgctt catctccgtc gtctccatcc acttcattac tgctcttcga ttctatcaat    180

tcaaactcaa actccagaag cagaacctca aattttgtga cagatgcaga tttgaaattt    240

ttaatggaga ttttggatga gaagctcggc agtgataaat gggaggatgt tctagataaa    300

agaaaccatc atctaagcta cagtgtgaaa tgctgcaggc ctaagaatgg tcccctgaaa    360

tatttgagca agactgtgtt caatgacatt tcatcagaga tgctaagaaa cttctacatg    420

gacaatgatt acagaaagca gtgggataaa acactggttg agcataaaca actgcaggta    480

gacaaatctg atggtactga agttggtcat acaattaaaa agttccctct tttaaagcct    540
```

-continued agagaatatg tgctagcttg gaagttgtgg gaggggagtg ataaaacatt ttactgtttt 600
atgaaggaat gtgagcatcc tttggcacca cgacagagaa aatatgtacg agttgagttt 660
tttagatctg gctggcaaat aagagaagta cctggtagca atgcctgtga gatcacaatg 720
tttcatcaag aagatgctgg tttaaatacg gagatggcta agctggcctt tcgcaagggc 780
atatggaact atgtatgtaa gatggataac gcgcttagaa gatactctgt tataggctat 840
catttatcaa gttcagttac cacttcaatc gatttaatgc agaaggtacc tgcttgcttg 900
gacactattt cgagtaacat ctctccagca aatcctaccg tcttccatga tcaagttact 960
gatgaatctc aaattaggat gatccaaaga aggccatcaa gaaagttgat agccaatggt 1020
ttgttgcttc tagggggtgc tactgctata tgcctgtctc gtggtcactc tagcctaggt 1080
gctaaagttg ccatggcata catcataaac aaacttagta agcgtggtgc tagatcaaac 1140
caaagcaaac aaagttga 1158

<210> SEQ ID NO 97
<211> LENGTH: 834
<212> TYPE: DNA
<213> ORGANISM: Glycine max

<400> SEQUENCE: 97
atggacgccg ccggcttaga ttccgatggc cgtgaattca aaacccccga ggacatgtgg 60
agggaacagg cgggtgaccc tagcaagaag acccagtggt atcgcgacgg cgtctcctac 120
tgggagggtg ttaaggcaaa tatggatggg gtattgggag ggtttgcaaa tgtgaacgag 180
cctgacataa cttgcagtga ggatttcttg aacattctct tctctgaacg ttttcatgct 240
gctgatgcca gacaccaacc acttgttgtt cttgattgtg gttctggcat tggcagagtc 300
accaaaaatc tgttaataag atacttcaat gaggttgatc ttctggagcc agtatcacat 360
ttcttagaga ctgcacgtga aactttggct ctaggatgtc agacaaattc agatatgcac 420
aaagcagtta atttttactg tgttcctctt caggatttta caccagatac tgcaagatat 480
gatgtaatat ggattcaatg gtgcattggt catcttacag atgaagattt tgtttcattt 540
ttcaagagag ccaaggttgg cctcaaacca ggtggatttt ttgtcctgaa ggagaatatt 600
gccagatctg gatttgtgct tgataatgaa gaccgaagtg ttacaagatc tgatttgtac 660
ttcaaagagc tattttctcg atgtggattg catgtttaca aatcaaagga tcagaaagga 720
ttccctgaag aattatttgc tgtgaagatg tatgcattaa ctacagaccc tccaaagaag 780
gctccccgag caaaatccaa aacatcaact aatagaccta gaactattat gtga 834

<210> SEQ ID NO 98
<211> LENGTH: 1200
<212> TYPE: DNA
<213> ORGANISM: Glycine max

<400> SEQUENCE: 98
atgcgaagct gcatcatcaa cctctggatc gtggcggcac tcgtcgtccc cgtgctcctc 60
tctctcagaa gccctcgagg cgaaacccaa acccaaacca cttcttcttt ctccgattct 120
tctacctttt ctttgaagct tgcaaatgga tttggcttct atgctgtctc tttccctttc 180
aaccaaagga tacgtgatgg gtccaatctc gaatacgatt tctataggga cacgtgtccc 240
caagcggagg gtgttgttcg ttcggcgctc actcgcatat acttcgacca cagggacgtt 300
gcacctgctc tgcttcgtct cttcttccac gattgcttca tcgaggggtg tgatgcttct 360
ttgctgttgg atgagaacaa tggtgataga aaccgttcgg tggagaagca ggctgtgcca 420

-continued aatcagacat tgagaggttt tgacaaaatt gagctgataa aagaagaggt ggaacaagca 480
tgtcccggga ttgtgtcttg tgctgacata cttgctcttg cagcaagaga ttccattctt 540
ctggctggtg gacctttcta tccagtttta acaggaagaa gggatagcca tcaatcattt 600
tttgaggaag caactgatca gattcccaga cctgatgata acgttacacg cacactaaat 660
ctcttcaatc tcagaggatt caatgcaaga gaaacagtca gccttcttgg aggacacaac 720
attggcaaaa tcggctgcga cttcattcag caaaggctgt acaactttca aggcacagga 780
caaccagacc ccagcatccc cctcgatttc cttcgccaga tgaggctaaa ctgcccagac 840
agcaagaaca gcagcaccag catagacgag tttacgatct caaagccagt gagcagtgat 900
ttccactcca aaatggggat gtcatacatg caggcactgt catcttcagt gtcatcagga 960
gcatcatttg acactcacta ctaccagagc ctgctaagag gaagagggct tcttttcgcg 1020
gatcagcagc tgatggccga gcagaaaacc gccagattgg tctctgctta tgcttcagat 1080
gatggatcaa cctttcgaat ggactttgct agggtcatgt tgaaaatgtc taaccttgat 1140
gttctaactg gacttcaagg tcaggttcga gtcaattgct cactacctgt gtcttcttaa 1200

<210> SEQ ID NO 99
<211> LENGTH: 3282
<212> TYPE: DNA
<213> ORGANISM: Glycine max

<400> SEQUENCE: 99
atgtggtata atgaaagaac atcaaagcat aaaaatagta gaagctcgag attcagctta 60
tgttacaaat caattaaccg ttcaagagga cctcctacaa ttagaattaa gggtcaacca 120
tgtcaccgca tagatagttt attaccaatg tctggaaaag aatccaaatt tgcacaatta 180
tatatctttg acacagataa tgaagttaaa aatataatta atgccatcag ccagcatgat 240
ggaattcaac cgcaaattgt ttcaagttta gctgaaatgc tggataaaca caatgtgcat 300
gctaaaagtt ttaggatggc tagagataga ttggcaaata gtgatgtcga taatgtcaca 360
ttaagattga tatctactcg tgaaaaggat ggtcggacat acaatgttcc aattgtttca 420
gaagttgctg cacttattgt aggtgatttt aatcccaact caagaagaga tattattctt 480
gagactcaaa atggacacta tctaggccta caattccctc tgcttttccc ttatggtaaa 540
gatggatata ggcctgacat acttcaccgt gcaacaccag gcaacaaaaa aagagagaga 600
aatcctcaaa ctttatttca ttctagaaga ctatttcaaa aattcattgt tgaagcatat 660
accatggttg aatcggaaag actcaactac atcaggaaca accaaaagaa acttagagtt 720
gacaagtatt gttgcttaca aaattcactg gatgctggga caagccaagg tttaaataaa 780
cgcaagagag taattttgcc tcctaccttt gttggcagcc cccgctacat ggatcagcta 840
tactttgatg gtatggcgat atgcagccat gttggtttcc caaatctttt tatcacttta 900
acatgtaatc caaattggcc agaaatccat agattacttg cgccattgaa tttgaaacca 960
gcagatagac cagacattat ctcacgagtt ttcaagttga aatatgaaga aatgctttca 1020
gacctaacaa agaatcacct acttggaaaa gcagtggcat gtaaattggt gcaaaatcat 1080
atggctcatg gcccatgtgg aattatacgc tctgaatctc catgtatgaa agaaggaaag 1140
tgtagcagat tttatcctaa aacgttccaa cctcgcaccc ttttagatcc aaatggttat 1200
ccaatatatc ataaaagaaa tgatggtcgt acaatttcaa agaatggtgt tatcattgat 1260
aatagacaca tcgtacctta taatccaaag ttactgaaaa aataccaagc gcatgtcaat 1320

-continued

```
attgaatggt gcaatcaaag tacttcaatc aaatatttat tcaaatacat aaacaaaggg   1380

tacatttctc cctgtgaagc tgcttggaga atttttagtt tttcaataca tgctaggaag   1440

cctgttgttg aaagattata tttccatctt ccaggccaac acagtgttct ttatgaggac   1500

catgatgata ttgatgatgt cctatccaag ccaagcattt cagatttcaa atttttagct   1560

tggatgaacg ccaacaaatg tttttcagaa ggaagaaatc tgacttattc agaattcgtt   1620

tcaaagtttg tatataatca aaagactaga tcatggcaac ttagaaagaa aggatgcact   1680

attggaaggc ttatatgggt cccaccaatg acaagagaat tgttttattt gaggatgatg   1740

cttactgctt gcaaaggagc aatttcattt gaggatatta gaactgttac aaatattcaa   1800

taccctacat atagagaagc atgcttttcc atggggtttt tacaagatga tagagaattc   1860

gttgaagtaa tcaaagaggc aaaggattgg ggcacaacta attatttgag gaaattattt   1920

gtgttgatgc ttttaacaga attacacatc gatgataatc atctgagtaa tttggcattg   1980

ctagagattg aacaattgtt gcacgtaaat caaaaatcac ttaaagacta tccttcaatg   2040

ccatatcctc aggatgctga ttgcacgtcc tatctagcca atagcctgat attagcagaa   2100

ctaaattaca ataaggatga taccagatca gaatttcagc aactttttc atccatgata   2160

gatgaaaaaa catcaattta taaacaaatc attgaagccg tcaacaaaaa tcaaggtggc   2220

atgtttttcc aatatggatt tggaggtaca ggaaaaacct tcatatggag aacattggca   2280

acttcattga gagcaaacaa tcaaattgtt attatagttg cttccagtgg catagcttct   2340

ctattgttac caggcggcag gactgcgcat tcaaaattca aaatacctgt acccattttt   2400

gaagactcaa catgcaacat tcatcaagga agtgaattag ctgaattggt aaatcaaaca   2460

agcctaatta tttgggatga agcaccaatg gctcacaaat tttgttttga agcgcttaac   2520

caaagtttaa gagatataat taaaactaaa cccaactcaa ataaaatatt tagaggtaaa   2580

gtcatcaaca atgaacaatc accaaatgaa caagaaattg ccgcatttgc taagtggatc   2640

cttgacattg gagatggaat tattggacat gaaaatgatg gctattccac aattgaaatc   2700

cctgaggacc tgttgataac tcaatatgat gattcaatcc atgccatagt tgactcaaca   2760

ttcccagatt taacacagca tcacaacgat ggtcagtact tcaacagtag ggcaatatta   2820

gcttcaacca acgaaacagt cgaacaggtc aatgattata tactatcatt aatcccagaa   2880

attatcatag gtgagtacat ggaataccta agttctgact ctatagacaa atcaaaaact   2940

agtgaaagct gtcattttca aacaataact attgaattcc tcaattcatt gatgatatct   3000

ggtctgccaa atcagtttat caagcttaaa ataagaactt ttataatgct tttaaggaac   3060

ttagatcaga ctcaaggcct gtgtaatggc actagattaa taactacaag attggcaaag   3120

catgtaatta cggctgaaat catttctggc aaaaattcag gtcatatggt ttacaaccca   3180

agaatgttca tgtccccttc acaatcacca tggcctttta aacttttaag gaggcaattt   3240

ccaatcatgt tgtcttatgc aatgacaatt aacaaatctt ag                      3282
```

<210> SEQ ID NO 100
<211> LENGTH: 2112
<212> TYPE: DNA
<213> ORGANISM: Glycine max

<400> SEQUENCE: 100

```
atggattcgt ggctcaaagc cgctgaaggt ttatttgaag ttgtagatcg acgagcgaag     60

gctgttgcca gtgacttatc agaggagcag ggtgatctta agtctccagc atcaaatggg    120

caaggatctc agggcaagaa gacaaaatca aaaccaaagg ctcaaaaggg actatccgac    180
```

-continued

```
tcatcaacta caattagtga tactactcag gagaaaagtg gatctccatc agcacctgcg    240

gacatagcaa cttcaataga caaagttgat cctgaaataa ttgatgggag cgcttcaaca    300

tctacaaacc aaccaaagga gccacgacct agcgatgcaa catcaccctt gttaggctct    360

tcattatcaa aaatgctagg cgatgatgtt ggtaaacatg acccagatga tgtggaaaca    420

ttagtaaatg atgctgatat tggagttgcc actattgctg ctaatggtga tactgtccaa    480

gagagtgctt cagatgtttg tgagatggat cctcctccag ctcccaaaga aattgagggc    540

cccagtgatg aacccactag tactgggcaa attatcaaat ctagagattt agatgccagt    600

aaaaatgtgg atatagagaa atctgaatct gtggcttctg acacagctcc taataatgat    660

actatactca aagattctga tgtaaaactt gaatctgttg tggatgaaaa aagccaagag    720

gatcacaaaa ctgatatctc ccccaaaaaa gtacaggatc aacttgatga ggctcaagga    780

ttacttaaaa caacaaaatc tactggtcag tctaaagagg caaggttagc tcgggtctgt    840

gctggattgt catcccgtct tcaagaatac aaatctgaaa atgcacagtt ggaggaactt    900

ctcacttcag agagagagct gagtaaatca tatgaagcta gcataaaaca gctacagaag    960

gatttgtctg aaagtaaaag ggaagtgacc agagttgaat caaatatggt tgaggctttg   1020

gctgcaaaaa atgctgaaat tgaggcactt ttaagttcga tggatgctgt taagaggcag   1080

gctgcattgt cagaaggaaa tctagcttcc ctgcaggcaa gcatggaatc aatgatgaga   1140

aatcgagaac taagtgaaac aaggatgatg caggctctaa gagaggagct agcatctgct   1200

gagcgaagag cagaagagga gcgtgctgca cataatgcta ccaaaatggc tgctatggaa   1260

agagaagtgg aattggagca cagagcagtt gagtcatcca ctgcacttgc aaggatacag   1320

agagtagcgg acgagaggac agcaaaagcc acagaacttg agcagaaagt ggcacttctc   1380

gaggttgaat gcgcatcttt aaatcaagaa ctacaagata tggaagcccg tgtgcgccgg   1440

gaacaaaaaa aggcaccaga agaggcaaat caagtaattc agatgcaggc atggcaggaa   1500

gaattggagc gtgcacgtca aggtcagagg gaagctgaaa acaagctatc atccttggag   1560

gctgaaatgc aaaaaatgag agttgaaatg gctgccatga agagggatgc tgagcattac   1620

tcacgtcagg agcatatgga gttagagaaa cgctatcggg aactgactga ccttttgtac   1680

tacaaacaaa ctcaattaga aaccatggtc agtgaaaaag ctgctgcaga gtttcaattg   1740

gaaaaggaaa ttaagcgtct tcaggaagca aaggcagagg cagaaagaag tagagtttct   1800

cgtcgagcat catcatcttg ggaagatgag actgaaataa aatcccttga gccgcttcct   1860

ttgcatcacc gtcatttggt cggtgcaagt attcagttgc aaaaggcagt gaaactatta   1920

gattctgggg ctgtcagggc cacaagattt ctctggcagt atccaacagc tcgagttatt   1980

ttatttttct acttggtgtt tgtacatctc ttcttgatgt atctcttgca tcgccttcag   2040

gtacaagctg acacattggc cgctagagaa gttgcagaat ctatgggact ttctaaccag   2100

aatttaccgt ga                                                        2112
```

<210> SEQ ID NO 101
<211> LENGTH: 3273
<212> TYPE: DNA
<213> ORGANISM: Glycine max

<400> SEQUENCE: 101

```
atgtttcgtt ctgcaagatg gagaagcgag aagaacaggg tcaaagctgt tttcaagctg     60

cacttccatg ccacccaggt gtttcaatct gggatggatg cattggtgct gtctatagtt    120
```

-continued

```
ccaggggaca ttggaaagcc aactacgaaa ttagagaaag ctacagttcg agatagaact    180

tgtagatggg aaaatccggt ctatgaaact gttaagttta ttcaagaacc caagactggg    240

aaaatcaatg acaaaatata tcattttttg gtttcaacgg ggttaccaaa agctagttcc    300

attggggagg tttctatgaa ttttgctgat tatgtggaag ccactaagcc ctcctctgtc    360

gctcttccca tcaggatttc tcactgtgat gctgttttgc atgtatcaat tcagaggctg    420

caagaaaacg gtgatcgaag agaggaagaa gaatgtgaag atgtgaaact aaagtccgat    480

gataggagct caaggaatca attaagcaac ggcaatacgg atgaaacaag tagaagttgt    540

tcttctgaag atgtgtctgc caaagcaatc atcaatagag ctgaattgag ttctaattat    600

aggacatcta gtggctctga tatgacattg tcaagttctg atgacagctc tggatttgat    660

actccccggg aaattggacc tagaaaaaag aacatccacc tcaacacaaa aaggtttctt    720

ccagacccag ttttacacca tgcttcagaa cctcaaaacc ttgctctcaa tgcctcaaca    780

tcaatgcatg ttgtacatca gagatcacac tgggactggt cagcgggttc ggagcatagg    840

ctaagtacag atgattcaac atatggttct catcataatt ctctcccgaa ggaaagcaac    900

caacaacctt ctcctttaga gattgaaagt ctcaaggctg aacttgctgc tttggccagg    960

caggtgaatg tgtcagactt ggaattacag accctcagga agcaaattgt gaaggaatgc   1020

aaaagagggc aggatcttgc gaaagaagtc atcgtcttga aagaggaaaa ggaagcactc   1080

aggacagaat gtgacaatct caggtctttt cagaaacgca tggatgaggc caaagtgagg   1140

aacagatcac aattggaagg tggagatctt catgctcttg ttgaagaaat aagacaagaa   1200

ttggattatg agaaggacct aaacgcaaat ctccgattac agttaaagaa gatgcaagaa   1260

tctaatgtcg aactggttct tgcagtgcaa gatctggatg aaatgttgga gcagaaaaat   1320

agggacatat ctaaccattc ctatataaat gagcaggata aaaattccca agagaaaagg   1380

aaaaacctct ctaaatgtga aacggatgat gacgaagaac agaaagcatt ggaggagctt   1440

gttaaggaac acactgaagc cagtgagaca cacttactgg agaagaaaat agtagacctc   1500

tatggtgaaa tagagatgta taggagagac aaagatgagt tagagatgca gatggaacag   1560

cttgcactgg actatgagat actgaagcag gaaaaccatg gccttgcata taagctggag   1620

caaagcgatc tgcaagaaca gttgaaaatg cagtatgaat gttcatctcc tcctgctaca   1680

atgaatgaca ttgaaaacca catcaagaat ctggaagatc aactcaagga acaatcagaa   1740

gacttctcaa attctctggc taccattaag gcacttgaaa gccatatcag aggattagag   1800

gaggaaatgg agaaacaagc acaaggattt gaagctgatc tagaagcagt gatgcatgac   1860

aaagttgaac aagagaaaag agccatccaa gctgaggaag ctttgcgaaa gaccagactg   1920

aaaaatgcta aaactgctgg gaggcttcaa gaggaattcc aaaggctctc ctcgcaaatg   1980

accaccacat ttgatgtgaa tgagaaggct accatgaaag cattgacaga agcaagtgaa   2040

gtgcgtgcac agaaaagatt actggaagaa aagctgcata atgtcaaaga agaactggag   2100

tcatctaaag ctgattatga ggtaaaactg aaccaacttt cgaaccaaat agatacgatg   2160

aaagttcaga tacaacagat gttgttggaa attgaggaca agtccaagca gcttcaaaat   2220

cagaagaagc acgaggaacg agttattagg gatttctcta atgagatcgt gttactaaaa   2280

tctgagaatg gaaagcttaa tgaggatatt tcatgcttac atgatcaagt agaaggaaaa   2340

gaaattttaa gaactgactt ggaagctatg aaaaaatcaa ttgaggaatc tgaggcactc   2400

gtacagaaag gaactgtgga aagaaatgaa ctggtgggta caattgcatt gttgaagaag   2460

gaggcagaac agtcacttaa tgagctaaac agaatgagac atcttaagga taaaaaagaa   2520
```

```
aaagagatta gagtcttgca atcagagttg gaggctgtta gagctcagta cagtgacctg   2580

aaactctctc tttctgagga cgaaattgag aaagaaaaac tacaaaagca agttttgcag   2640

ctaaagggtg aattgaagaa gaaagatgat gctttaatca gcaccgagaa gaggttcagg   2700

gaaagtaatg gacgtgcaca acttactgat ggaactaaaa atattccaaa gaacaaaaaa   2760

actgcttcag ttcctcagaa ttcaaaggaa atagccagtc tgagggagaa aataaaaaca   2820

cttgagggaa tgatacagtc aaaggaaact gccttggaaa cttcaacaac ttcattcttg   2880

aagaaggaaa aggaactcca gaccaaaatt gaggagctgg aggacaaatt ggaggaattc   2940

aaccaaagta ttgctttgca gaaggtggtt caggatagaa gtacagttga gcatctcaat   3000

gctgctgcat cttcctctgg ggttgcattg ttattcaaga gtaacgtaaa cttgccggag   3060

aaagaagcag gaacctccat aatggatact tcagatagca ttcttgctga cttattaacc   3120

gagctaacat cattgaagga gagaaacaaa tcaatggaaa gcgaacttaa agagatgcaa   3180

gagagatact tagaaatgag cctcaatttt gccgaggtag aaggtgaaag acaaaagctc   3240

gttatgactg tacggaatct ccagaaaggc taa                                 3273
```

<210> SEQ ID NO 102
<211> LENGTH: 339
<212> TYPE: DNA
<213> ORGANISM: Glycine max

<400> SEQUENCE: 102

```
atgaaatttt ttgttgttcc tcctgcttgg tcaaattcaa attttttgcc tttcatttct     60

attgcatgtt catcattttg tgtgcttcgc ttttgtgctt ttccaagacc taattttttt    120

ggtttctggg gtttttcctg tgacggtcga atggttcaca taagtttctc atatgttctt    180

ccatgtgttc ttcgattgtc tgcttttttt tgtgtgttcc tcacccttct tgactgtggt    240

ccaacatttt gggtttcttg gggttttgcc ggtcagattc gaatgtttcc catatgtttc    300

ccctattttt gttgcatgtt cttctattct ttgctttaa                           339
```

<210> SEQ ID NO 103
<211> LENGTH: 651
<212> TYPE: DNA
<213> ORGANISM: Glycine max

<400> SEQUENCE: 103

```
atggcgaaaa cgaggccagg cagaaaggac gtggactcat acaccataag aggaaccaac     60

aagatcgtcc gagctggaga ctgtgttctg atgcggccct cggacacgtc gaagcccccct   120

tacgtggcgc gcgtggagat gatcgagcag gataatagga acaacgtgaa ggtgcgtgtg    180

aggtggtact acaggccgga agagtcgatt ggtggtcgga gacagttcca tggtgcgaaa    240

gaactgttcc tctccgacca ctacgatgtg cagagcgcgc acaccattga gggcaagtgc    300

gtggtgcact ctttcaagaa ctacactaag cttgagaatg tgggtgctga ggattactat    360

tgtagattcg agtacaaggc cgcttctggg gcttttaccc ctgaccgtgt tgctgtgtat    420

tgcaaatgtg agatgcctta taacccggat gatctcatgg tacaatgtga agggtgcaag    480

gattggtacc atcctgcttg catgggcatg actattgaag aagctaagaa actagatcat    540

tttgtatgtt ccgaatgttc atctgatgat gatatgaaga aaccccaagc tacattttct    600

gcatcactgg gagctgatgg caaggtggag ccgaagcggc ggaagagatg a             651
```

<210> SEQ ID NO 104

<211> LENGTH: 1491
<212> TYPE: DNA
<213> ORGANISM: Glycine max

<400> SEQUENCE: 104
atgagtagta cacaggtgcc aaagaaaaga gtggcatttg tgctgattga tgggttggct 60
gatgtgtcac tgccaaggct tggatacaag actcctcttc aggctgcaaa actgcccaac 120
ttggatgcca tagcatctgc tggagttaat ggactaatgg accctgttga ggttggctta 180
gcttgtggaa gtgacactgc tcatctttcc ttgttgggtt atgatcctag agtttattat 240
cgtggccgag gagcatttga atccatgggg gcaggattgg ccatgtcacc tggtgatatt 300
gcttttaagt caaacttcgc aactcttgat gagaaaactg gaatagtcac cagtaggaga 360
gccgacaggc actttgaaga agaaggtccc ctactttgtg ctgccctgga tggaatgaag 420
ctgccatctt tccctcaata tgaagtcaga gtcaggtatg caacagaaca tagatgtgga 480
gtggttgtta aaggaccaaa tctgagtgga aatatatcag gaacagaccc attaaaggac 540
aaccgcttac ttttgaaagc agaagcttta gatgattctc atgaagcaag gaacactgct 600
gctgttgtta acgagctgtc caaggaaata acaaaaattt tggtttctca tcctgtgaat 660
gctaaacgtg ctgcagaagg gaagaacata gcaaatgtag tcctttttaag aggctgtggc 720 attcgaattg aggttacacc atttataaat agacatggtt tgcggccatg catggtagct 780
ccaacgaaaa taattgctgg cctgggctta tcacttggta ttgatattct agatgctcct 840
ggagcaactg ggactatcg aactttacta acatcaaaag catcagcaat agctaaggca 900
ctctcagctc ctttacagtc ctgtcccaga gtttttgttc ctggagagga tgagcttaaa 960
gcaggccggt cagatggcta tgactttgga tttcttcata ttaaggcaat agatgatgct 1020
ggccatgaca aggcgagcat cctcaaggtc aaagcattag aagctgtaga taaagccttg 1080
gggcagttgg caaggcttct ctgggaggca gaatcaacag gaaagtttca gtttttcctt 1140
tgtgtcacag gagatcactc tactccagta gaatatggag atcatagctt tgaatcggtc 1200
ccgttcacaa tttgccggtt gaaagacttt gttggtgcaa ttggggaatc caccatttcc 1260
aaaacttctc ttgacccatt tcctattccg agtgttaagt cgggtgaaga cttgcttgat 1320
gatttggaaa cagaagagag aagagacaaa tgttgtcaag cttatagtgg tgattcggtt 1380
tatgagctaa atgaagtggc agctgcaaag ggatgtctgg ggcgtttccc tgggggagaa 1440
atgatgggaa ttgtaaagaa attccttaac ttagatgcgg gaactgctta g 1491

<210> SEQ ID NO 105
<211> LENGTH: 1434
<212> TYPE: DNA
<213> ORGANISM: Glycine max

<400> SEQUENCE: 105
atggatacta agtcggctgt agaattaatg gagtcttccg cagaggttca tttttctgga 60
tttcacatgg atggttttga gcaaagaaag gctagcatag aacaaccaac aacctcagaa 120
actgacatgt ataaacaacc ttttgtcata ggtgttgctg ggggtgcagc atctggcaag 180
acaacagttt gtgatatgat tattcagcag cttcatgatc aacgagttgt acttgttaat 240
caggattctt tttacaataa cttgacggag gaggaactta caagagtaca agattacaac 300
tttgaccatc ctgatgcttt tgatactgag caattgctac gcgttatgga caagttgaag 360
catggcgaag ctgtagatat tccaaagtat gattttaaga gttacaagag tgatgacatg 420
ttaagaaggg tgaacccttc agatgttata attttagaag gcatccttgt tttccatgat 480

```
ccacgtgttc gggagttgat gaatatgaag atatttgttg acacagatgc tgatgttcgt    540
ttggcaagaa ggattaggcg tgacactact gagaagggtc gggatattgg agcagttctt    600
gatcagtatt caaaatttgt gaagccagct tttgatgact ttattcttcc aacaaagaag    660
tatgctgata taattatacc ccgtggagga gataatcatg tggccattga tttgattgta    720
cagcatattc gcacaaagct tggtcagcat gacctgtgta aaatatatcc taatttgtat    780
gtcattcagt caacttttca gatacggggt atgcataccc tgatacgtga tgccaagaca    840
acaaagcatg attttgtatt ttactctgat cgattgattc gattggttgt ggaacatggt    900
ttggggcatc tgccatttac agaaaagcaa gtaatcactc ctactggttc tgtatacact    960
ggtgttgatt tttgtaaaag gttgtgtggt gtctctgtta tcagaagtgg ggagagtatg   1020
gagaatgctt tgagagcatg ctgtaaaggt atcaagattg ggaaaatttt aattcacaga   1080
gaaggtgaca atggtcagca gctaatatat gaaaagttgc caaatgatat ctctgatagg   1140
catgtgttac tgttggaccc tatacttggc acagggaatt cggctgttca agcaatttct   1200
ttactcataa aaaagggtgt acctgagtcc aacattatat ttcttaatct catatctgca   1260
cctaaaggtg tgcatgtggt atgcaaaagt tttccaagaa taaagatagt aacatctgag   1320
attgagattg gtttgaatga agatttccgt gtcatacctg gcatgggcga gtttggagat   1380
cggtactttg gaacagatga tgatgatgag caagtggtag tttcttccca gtag         1434
```

<210> SEQ ID NO 106
<211> LENGTH: 465
<212> TYPE: DNA
<213> ORGANISM: Glycine max

<400> SEQUENCE: 106

```
atgagtttcc gtcattccat catgaacgct cttcccattc tcctcttctt cctcttcgtt     60
tctgcattag tttctgcgaa gaaaactggt gatgtgacgg agctgcaaat tggcgtgaag    120
cataaaccag tatcatgtga agttcaggca cacaaaggtg acagagtcaa agtacactat    180
aggggaaaac tcactgatgg aactgttttc gattctagct ttgaaagaaa taatccaatt    240
gaatttgagc ttggtactgg tcaagtgatc aaaggttggg accagggatt attgggaatg    300
tgtcttggtg agaagcgtaa gctgaaaata ccatcaaaac ttggctatgg agagcagggt    360
tccccaccca ctattccagg tggtgctaca ctcatatttg acgctgagct tgtgggagtg    420
aacgacaaaa gtttaggcga aggaaaagga aacaacgaac tgtag                    465
```

<210> SEQ ID NO 107
<211> LENGTH: 1698
<212> TYPE: DNA
<213> ORGANISM: Glycine max

<400> SEQUENCE: 107

```
atgtcagact ccttggtccg tgtttcaaga cgggccgaat ggggagccca caggccgacg     60
ccaggagcgc gcaggtgccg aggcacgcca agggcgcgcg ctgccatcca caatcgcgat    120
gatgacgtct ccacgagcat atcaacagcc cgggcttggg ccaccatcgc aatccgcgtc    180
ggtcaatgtc ccgagtcgat cggcggaccg gctctcaccc tttcggtgat aattcatcaa    240
ttgtctgggt gtgccagatt ctcgctgcaa gaattgaaca taggaggaaa tcaaatcaat    300
ggtacgcttt ctgacctttc aatattctct gccttgaaaa cattggatct ttcagaaaat    360
caattaaacg gcaaaattcc agagagtacc aaattgccat atctattaga gtctttgtca    420
```

-continued

```
attggatcaa actctttaga aggtggaatt ccaaaatcat ttggggatgc atgtgctttg    480
cgctcgttgg acatgtccaa taatagcttg agtgaagagt tttcaatgat aatccatcac    540
ttgtctggat gtgctagata ttcattggaa caattatctc taagcatgaa tcaaatcaac    600
ggcacactac ccgacctctc aatattctca tctttaaaaa aattatatct ttatggaaac    660
aagctaaatg gagagattcc taaagatatt aaatttccac ctcaactgga gcaactagat    720
ctgcaatcaa attccttaaa gggtgtgctc actgactatc atttcgctaa tatgtctaag    780
ttatacttct tggagttatc tgacaactct ttattggcct tggcatttag ccaaaattgg    840
gtcccaccat ttcagttgcg cagcatagga ttgcgatctt gcaagctagg tccagtattt    900
cccaaatggt tggagacaca aaatcaattt caggttgaaa ctttgtacga attagacctt    960
tcaaataatc atttctctgg aaaaaattcct gactgttgga gccatttcaa gtcattaact   1020
tatttggact taagtcacaa taatttttca ggaaggatac ccacgtccat gggatctctt   1080
cttcatcttc aagcattgct attgagaaac aacaacttaa cagatgagat acctttctcc   1140
ttgaggagtt cagaacaaat gttcaaaaat aatgtgttac tacttttaaa aagcattgat   1200
ctctcaagca atcacttttc tggagaaatt ccactggaaa tagaggattt atttggattg   1260
gttttattga atttatcaag aaaccatttg accggaaaga ttccttcaaa tattggaaag   1320
ctaacatcac ttgaatatct tgatttgtca agaaaccagt ttgttggttc aattcctccg   1380
agtcttactc aaatttattg gctcagcgtg ttagatttgt cacataacca tctaactgga   1440
aaaattccaa ccagcacaca gttacagagt ttcaatgcct cgagttatga agataatctt   1500
gatctttgtg gaccgccact tgagaaattt tgtattgatg agagaccaac acaaaaaccc   1560
aatgttgaag ttcaagagga tgaatattca cttttgagtc gtgaatttta catgagtatg   1620
acatttggat ttgttataag cttttgggtg gtgtttggct caatcttatt caagcgttct   1680
tggagacatg cctatttc                                                  1698
```

<210> SEQ ID NO 108
<211> LENGTH: 1293
<212> TYPE: DNA
<213> ORGANISM: Glycine max

<400> SEQUENCE: 108

```
atggcaccga agcgcgttta tgaagcatgg aaaggaagta ataaattcct atttggagga     60
aggttgatat ttggaccgga tgctaggtca ctgcttgtca ccttgttgct gatcattgtt    120
ccagttattg tcttttgtgt atttgtagca aggcatcttc ggcatgaatt ttcttcatat    180
aatgcaggat atgctatttt ggtggtggca gttctcttta atatttatgt gttgattctt    240
ctctttctta cttcctctcg tgatccgggc gttatcccaa ggaatttaca tccaccagag    300
gaagagttcc gttatgactc ttcagtttct gttgaaattg gggacgcca aactccgagc    360
cttcagttcc ctcgaacaaa agaagtaatg gtaaatggcc attctgtgaa ggtgaaatat    420
tgtgacactt gtatgctcta tcgtcctcct cgttgttcac attgctccat ttgcaacaat    480
tgtgttgaac gttttgatca ccattgccct tgggtgggcc aatgtattgg gctgaggaac    540
taccgttact tctttctgtt tgtttcttcg gcaactattc tatgtatcta tgtgttttcc    600
atctcagctt tttacatcaa ggttctgatg gatcattata aggggacagt ttggaaggca    660
atgaaagaat cccctgcatc tgttatatta atggcatatt gtttcatctc tttgtggttt    720
gtcggtggac taactggctt tcatttgtac cttattggca caaatcagac tacctatgag    780
aacttccgct acagagccga taacaggatc aatgtttaca atctgggttg ttttaacaat    840
```

```
ttcctagaag tattttgtac aaaagtgaag ccctcaagga acaatttccg agcttttgtt    900

caagaggagg taccgaggcc accccctccg gtcatttccc gggaacccga accagatctg    960

ggtggtggag atccacgttc taaagttgaa gacgatctag atatcggtga agacctgtta   1020

aagatatcac agcgtcggaa tattgaagaa attgacgagg acatccggag cagaggaagc   1080

aatggacctc cccataatac ttctgaagta gattcagttt tgggttcaga tcgccgggcc   1140

ccaacaattc gatctgaagc aaggcactca agtgagggaa gaagtgaaag ctgggaaatc   1200

gggtctgagg tccttgccaa ttcaactgta actgaaagca gaagctatgt tgtatcaaag   1260

gaggtgcgcc aaaaacttgg gggttctttc tga                                1293
```

<210> SEQ ID NO 109
<211> LENGTH: 336
<212> TYPE: DNA
<213> ORGANISM: Glycine max

<400> SEQUENCE: 109

```
atgtggtcat tggataggga cccttcacct cttcctccct tagacaatca gtcatttgtg     60

gaactaatat tgaagtcaac aaaagttgac ttaaagacac cctgtagttt tgagtttcgg    120

cttcgcatct ctctcaatgc tgacaaccta attttgattc cgcaagtcag aaacactgct    180

aacaaagcat tttctttttc ctttacacta tgcaactatt tatcggtatc agatatcagg    240

aaaaaaaaca acatccctgc tgcacaaatt aatatccaac actctcaagc tttccagttt    300

caaactgtgg gcgctgaatt tgctttgtct ttctga                              336
```

<210> SEQ ID NO 110
<211> LENGTH: 456
<212> TYPE: DNA
<213> ORGANISM: Glycine max

<400> SEQUENCE: 110

```
atgagtgaca tgttaacaac atttacgaag aagaaagagg tggataccat catcagagac     60

acctttgata aagtcgtggt cctccgcttt ggtcgtgcct ctgaccttgt ctgtctccag    120

caagatcaca ttctttctaa agcagcaagg gatgtgtcca agtttgccac tgtggcactg    180

gttgatgttg actctgagga gattcaagtc tatctcaagt attttgacat cactttgata    240

ccatctacag tgttcttttt caatgctcat cacatgaaaa tggattatgg gactgctgat    300

catactaaat ggattggtgc tttttacgca aagcaagact tcgtagatgt tgtagaggca    360

atatttagag gagcgatgaa gggaaagctt attgtgaatt gtcctctccc gccagaaagt    420

ataccaaaat ttcagatact atacaaggat gtctga                              456
```

<210> SEQ ID NO 111
<211> LENGTH: 429
<212> TYPE: DNA
<213> ORGANISM: Glycine max

<400> SEQUENCE: 111

```
atgctttgtc ctctagtccc gcttattcta agtctatcta agtctatggt agagctagag     60

cccgggaagg ttctccatga cagacaagaa aggtttttttg gtcccttagt agtaatagta    120

gttactccca gccccttttcc tttacagaat aacaaaaaag tttatttgtt gcatccgagg    180

ttcaaagctc tgctcataga agggatggag acaactactt ttagaatgag agaggcatgg    240

accaatggtg tcaaaaaaaa aaaggcattt attttgtcca atccaatcac agcttattcc    300
```

-continued

```
gcctacacct tctttgccga aagcccttgt ttgtggctat cttctacatt ctctgccatc    360

ttccgtcatc cccttgatcg actatcccta aagcaaagag ccaatgccag cgaatcttct    420

aagccataa                                                            429


<210> SEQ ID NO 112
<211> LENGTH: 6546
<212> TYPE: DNA
<213> ORGANISM: Glycine max

<400> SEQUENCE: 112

atggccacta agtctcaagc aaactccagg agaatgtatt catggtggtg ggacagccac     60

attagcccca aaaattcaaa atggctccag gaaaatctca cagatatgga tgccaaggtg    120

aagcaaatga ttaagcttat tgaagaagat gcagattcct ttgccaggag agcagaaatg    180

tattataaaa aacgcccaga gcttatgaaa atggttgaag agttttaccg ggcatatcgg    240

gcattggccg agagatatga tcatgcaact ggagtgatcc gccatgccca taggaccatg    300

tccgaggcat ttcctaatca agttcccatg atgctgacag atgatttacc tgcagtttct    360

cctatggaga ccgagccaca tactccagaa atgcgccacc ctgaaagtgc ctttcttgat    420

ccagatgaac ctcaaaagga tgcttctgct cctttccatg ctatcaaaag aaatggtggt    480

tatgctggtg aaccctattc tcctttgaac aaaaccggtt tgaagcagct caataatcta    540

tacatccctg gagaacatga aaatcttcca aagtttgcta gaagggggct caatttttttc    600

gagacgcagg aggagagtaa tgagaaaaac agtggaaaca acaacaattt gtcccagtct    660

gaacgtgtga tgaaagctga gacagaaatt ttggccttga agaaagccat tgccaaatta    720

gaagatgaaa aggaagctgg cttgcttcag tatcagcaga gtttggagaa attgtctaat    780

ctcgagttag aagtgtctac tgcacaagag aattctcaaa gacttgatga gcgagcaagt    840

aaagctgaag ctgaagttca agccttgaag gaagcccaaa tcaaattaca ggctgaaagt    900

gaagctagtc ttcttcagta ccacgaatgc ttggagaaaa tatctaatct ggagaaaaat    960

atttcttttg caaaaaagca atcaggagaa cttaatgaac gagctactag agctgaaact   1020

gaaactgagt ccctaaagca ggaccttgct agagtagaag ctgaaaagga agctaccctt   1080

gttcaatata accagtgctt agagacaaca tctaaactgg aggagagaat aaaagaagct   1140

gaggagaatg caagaaggat taaggagcat gcagatatag cagaaaaaga aatcaaggct   1200

ttgaaattag aagtcactaa acttaatgaa gaaaaggaag atgccactct ccgttatcag   1260

caatgcttgg agataatttc cagtttggag tataagctct cttgtgctga agaggaggtg   1320

cgtagtctaa attccaagat agttgatggg gttgaaaagt tacagagttc tgagcagaag   1380

tgtcttctct tggagacatc aaatcacatg ctgcagtctg aattacaatc tttggcacaa   1440

aaaatggggt ctcaaagtga agaacttaac gagaagcagc aggaattggg tagactttgg   1500

ggttgcatac aagacgagag actgcgattc atggaggctg aaactgcttt ccaaactctt   1560

cagcagttgc attctcagag tcaggaagag cttagatctc ttgcttctga acttaccagt   1620

aaagtggaaa tactggggaa tgtggaatca cgtaagcagg ctttagagga tgaagtactc   1680

agggttagcg aggaaaaaaa aattctaaat gaggtcaaaa tttcttcatc tttgtccata   1740

caaaatttgc aggatgagat tttgaatttg agggaaacaa tagagaaagt tgaacaggag   1800

gtggagcttc gaattgatga aagaaatgct cttcagcaag aaatttactg tcttaaagag   1860

gagcttaatg atgtgaataa aaaacatgaa gccatgatag aggaggtcag gtcaactgac   1920

atagacccac agtgctttgg atcatctgtg aaaaaattgc aagatgagaa tttaaggttg   1980
```

-continued

```
aaggaaactt gtgcggctga caaaggagag aaagaagctc ttttggtaaa attggaaaac   2040
atggagaaac ttctggagaa aaatactgtt ttagagaatt ccctttcaga cttgaatgcc   2100
gagctggata gtgtgagagg aaaagtaaat gtgttggaag aaacatgcca atctcttcta   2160
gaggagaaat caaatcttgc tgctgagaag gccaccttgt tttctcagtt acagtccaca   2220
actgaaaagc tggagaagct atcagaaaag agcaacctat tggaaaattc actgtttgat   2280
gtgaatgctg aacttgaagg attaagggtg aagtccaagg tattagaaga cacatgccaa   2340
tcacttgacc atgagaagtc cagtatcttt caagagaaag aaactttagt ttcacagttg   2400
aacataactc atcaaacact gaaagatctt gaggaactgc acagtttatt ggaattgaag   2460
catttggaac taaaaggaga aagggagtct gcacttcaaa aggtagaaga gctactagtt   2520
tccttatatt ctgagaggga agagaattcc agagttttga aattgaatga agatgaattg   2580
gctgagaagg aattacaaat tcatattcta caagaagatg caaattgtaa gaaaaaggaa   2640
tatgaggagg aactggacag agctatacat gctcatcttg aaattttcat cttgcagaaa   2700
tgtgttgatg atttggagaa aaagaacttc tcccttctag ttgagtgtca gagacttttg   2760
gaggcttcca gaatgtctta caaaatgata tctaaattgg agactgaaaa tgttcaaaag   2820
caggttcatg tgaattctct gtctgagaaa attaaaatac taaggattgg gttgattcaa   2880
gtgttgaaga ctcttgacaa taacggtggg catttcagtg aagatatgtt tgaagaagac   2940
caaatgctcc tgaaccacat atatggaaaa cttcaggaga ggcagaaatc ttttgacaca   3000
gttttcaatg aaagccaaca aatggccatt gagaattcaa ttctgattac attcctagag   3060
cagttgaaac taaaggtaga aaatcttgtg acacaaagag attcccttga tgaggatttc   3120
agtatccagt ctaagcagtt cttggcattg caaatagagg tccaaaaggt gttggaaaat   3180
aatcaggagt tgaagttgac aataagcaaa ggagcggaga gaatggaagt aatgacaact   3240
gagatagaca atctacggaa gcagctgtca gacttggaaa agagtcacaa caatttacag   3300
gaggatagtt gcaagatatt ggaagagaag aagtccttga cgagaagttt tctatatctg   3360
ggtgaagaga aaagtaactt ggaagaagaa atatgtgtca tgatccatga gacaatagct   3420
caatctaata tttccctgat ttacgagaat gttatctttg aaaagctcct ggaacttaaa   3480
gagctaggtg aagatcttga taaacattgt tcagcaaata atgaccttga tgagagatta   3540
aaagtaatgg tgtgcaaatt agaaaatgca gaaatggaaa attcacatct taaagagtca   3600
ttcataaagt caaatgttga actacattta gttgaatcta tcaatgatca attgagctgt   3660
cagattagtg atgagaggga gatgttgcat caaaaggaaa atgagctgtt ggaagcagct   3720
gagatgtttc gtgttttaca tactgagaaa acagaattgc aaagaatggt ggaagatgtc   3780
aagattaaat atgatgaagc cagggcgatg cttgaagaac aggctaatca aattttgaaa   3840
ttgtccacag acaaggatca tcaaaatgaa gagctcacat gcctgtgtga agtgaaccag   3900
aagttggagt ctgaaatggg gtacctacgt caagagcttg gagaaactaa actgagggaa   3960
aagaagctag gtgatacagt acttaaggga acaaatgaga ttgaacaatg ggaaactcag   4020
gcttcaacac tctttgctga acttcagatt tccgctgtca atgaaacatt attagtggga   4080
aaggtctctg agctagctga gatgtttcgt gttttacata ctgagaaaac agaattgcaa   4140
agaatgatgg aaaatctgaa gattaaatac gatgaagcct gggtgatgct tgaagaacag   4200
gctaatcaaa ttttgaaatt gtcctcagac aaggatcatc aaaatgaaga gctcatatgc   4260
ctgtgtgaag tgaatcagaa gttggagtct gaaatggggt acctacgtca agagctcgga   4320
```

-continued

```
gaaactaaac tgagggaaag gaagctaggc gacgaagtac ttaagggaac aaatgagatt   4380
gaacaatggg aaactcaggc ttcaacactc tttgctgaac ttcagatttc ttctgtcaat   4440
gaaacattat tagagggaaa tgtctgtgag ctagctgaga tgtttcgtgt tttacatact   4500
gagaaaacag aattgcaaag aatggtggaa aatctgaaga ttaaatatga tgaagccgaa   4560
gtgatgcttg aagaacaggc taatcaaatt ttgaaattgt ccacagacaa ggatcatcaa   4620
aatgaagagc tcatatgcct gtgtgaagtg aatcagaagt tggagtctga aatggggtac   4680
ctacgtcaag agctcggaga aactaaactg agggaaagga agctaggtga tgaagtactt   4740
aagggaacaa atgagattga acaatgggaa actcaggctt caatactctt tgctgaactt   4800
cagatttctg ctgtcaatga aacattatta gagggaaatg tctgtgaact agctgagatg   4860
tttcgtgctt tacatactga gaaaacagaa ctgcaaagaa tggtggaaga tctgaagatt   4920
aaatatgatg aagccagggc gatgcttgaa gaacaggcta atcaaatttt gaaattgtcc   4980
tcagacaagg atcatcaaaa tgaagagctc atatgcctgt gtgaagtgaa tcagaagttg   5040
gagtctgaaa tggggtacct acgtcaagag cttggagata ctaaactgag ggaaaagaag   5100
ctaggtgatg aagtacttaa gagaacaaat gagattgaac aatgggaaac tcaggcttca   5160
acactctttg ctgaacttca gatttttgct gtcaatgaaa cattatttga aggaaaggtc   5220
tgtgagcttg ccgatgcatg tgataatctt gaacacagaa actactccaa agacatggaa   5280
actgaacatc taaaagaaag agttagcaag ctggaagttg aaaatggaag actgtgcgaa   5340
caattagctg cttatgttcc tgctgccagt gctttgaatg attgtataac atctctggag   5400
atgcagagtc ttgcacatga aaagcctcac gactatgaag aatcaaagca ttttcaggtt   5460
aaaagtttgg tgaataatga atgcactgaa aatggtcgac aaacagatga agatcagact   5520
gttatggcac cagatgcact ctcttatttc caagacatgc agagaaggat caatgcaatt   5580
gcaaggacag ttaagcagtt aaatgaaagt cttaaaccga agaatgaaga gaacattcaa   5640
gcaagcaagc atgttactca agcagatcaa gcaaggccat ctatcccagt taccgagatt   5700
gaagttctgc cgaaagacat catgcttgac caaatatccg aatgttcgtc gtacgggata   5760
agtaggagga gagaaattct tgaggctgat gatcagatgc ttgagttgtg ggaaacagca   5820
gataaggatg ccacgattgg caagcaagct gaaaagacac agaagatggc tgctggcaat   5880
catcaaagag gaacaaccaa ggaacccaaa aataggtatc cttcaacaga ttccttggtg   5940
gaaaaagagt tgagtgtgga caagttagag gtctcaagaa gattgacact accacgcgaa   6000
gaagggaacc aaagcaagat tttagaaaga cttgattctg atgcacagaa gttgacaaac   6060
ctccaaatca ccatacaaga tttgatgaag aaagtagaga taaatgagaa gagcacaaaa   6120
ggaaaaagtg ttgagtttgg tgaggtgaaa gggcagcttg aagcagctca ggagaacatc   6180
acaaagttgt ttgacgccaa ccgcaagttg atgaagaatg tggaagaagg taccgtgtct   6240
tctgttggga aggatgcagc agagttaggt gaaattggaa gtgtcagcag aaggagagtt   6300
tcagaacagg cacggagaga atcagaaaaa ataggacaat tgcatttgga ggtgcaaaga   6360
ctgcagtttt tactgctgaa actaggtgaa ggaaaagaaa acaaagagaa aacaaaaacg   6420
gctgatcgaa gtccacgagt ccttttgcga gattatctct atggcgggac gagaaccaac   6480
aaccaaaaga agaagaaaaa gctaccgttt tgttcatgtg tgcgacctcc caccaaggga   6540
gattga                                                              6546
```

<210> SEQ ID NO 113
<211> LENGTH: 993

-continued

<212> TYPE: DNA
<213> ORGANISM: Glycine max

<400> SEQUENCE: 113
atggcaagaa gagatcttga aagtggcggt ggagtaacca agaacaacag aagtgcagag 60
gaaaactact ctgcgcccga atcttcccat gtttatgatt ctgagaccca ttggacatca 120
tggctcgtgc ccatgtttgt ggttgctaat attgctgtct ttgttattac catgtacatc 180
aacaattgtc ccaggaacaa cattcgtttc caaggtcgct gcgtggcaag gtttcttgga 240
aggttctctt ttcagcctat gcaggagaat cccttgcttg gtccttcttc ttcaacattg 300
accaagatgg gagctcttcg atgggataat gttgtgaata gacatcaggg atggagactt 360
gtcacttgca tttggttaca tgctggggtt attcatttgc tggctaatat gttgagtctg 420
gtcttcattg gcattcgcct tgaacaacaa ttcgggttta ttaagattgg aatcatatac 480
ttggtgtctg ggtttggtgg aagtgtactg tcgtctctat ttatcagaga ccacatctct 540
gtgggtgctt ctggtgccct tttggactt cttggcgcaa tgctgtctga acttatcaca 600
aactggacta tatattccaa taaagcaatg gctttaataa cccttctagt gatcattgta 660
atcaaccttg gcattggcat tttgccacac gtagataatt ttgctcacat cggaggattc 720
ctggtgggat tactccttgg ctttattttg ctgccacgtc ctcagttcgg ttggttagag 780
cagcgacgtc ttcctgccgg tgttcagatg aagtcaaagt acaagactca ccaatatgtt 840
ctaggggttg tgtctcttat tctgttgatt gcagggttat cgactgcatt ggtgatgcta 900
tttcggggtg agaaagggta tgaccactgc cattggtgtc gctacttaac atgtgtccct 960
acttctaaat gggaatgcag caatgacagt taa 993

<210> SEQ ID NO 114
<211> LENGTH: 1383
<212> TYPE: DNA
<213> ORGANISM: Glycine max

<400> SEQUENCE: 114
atgaacccca acgatggcaa caactctccc agtcccaagc ccttggagat ggtcaacccg 60
gttcctccgt ttctttctaa gaccttcgac ctcgtcgacg ccccgactct cgacccgatc 120
atctcgtgga actccacggg cctcagcttc gtcgtgtggg accctctcga gttcgcgaga 180
attgtccttc ctcgacattt caagcacaac aacttttcca gcttcgttcg ccagctcaat 240
acttatggat tccgcaagat tgacacagac aagtgggagt ttttcaacga agctttccag 300
cgagggaaga agcacttgct gaagaacatc caaaggcgca ggtcatctca atcccagccg 360
gttggtagct atattggaat cggatcttct accgaggcag gggggtcaga ggttgagatt 420
gagatagaaa ggcttaggaa agaaaagact atgctgatgg aagaggtggt tgatttgcag 480
caagagcaac gaagaacagc tcaccacgca ggagaagtga atctaaggct ccaatctgca 540
gaacaaaggc agaaacaaat ggtttctttc cttgccaagt tgatccaaaa ccccgccttt 600
ttagcccgcc ttagacataa gaaggagcaa aaggaaatag attctccaag agtggtaagg 660
aagtttgtca aacagcacca tgaaactgga acaacaacaa cagcagaaac tctccaagaa 720
gggcagatag tgaggtatca acctgattgg agaaatatag ccatgtcttc tgaaactcca 780
aaactaagtt cagtttccat tgaacaatct cctcactacc tttcacaggg tttggcagga 840
gaaatgagtg tagtaggtgc agaagacctt actgctcaaa ttgacaatat tgtatcagat 900
gatttggctg cagtgcacgg gattacgccg tctcaagaaa tgatgattgg agaaggatca 960
tctacctttg gagctgaaga ccccctcttc aaagggaaga gtgtcatgag tccaattcta 1020
gaagttcctc cagagtattt tccttccttc ccagagggtt tgaccaagga gaagaaagac 1080
tttcaagatt tttctgctct tggaactgaa ggcatgataa agctagaaga tatatgggac 1140
tctggcctca atgttagtgg tgctgcttta agcagtggga atgagctgtg gggcaatcat 1200
gtcaactatg aagagtttcc acaatttgga gtcacaagtg gtatgtctga ctcagatatc 1260
tgggatattg gcttaggaag ttttggaatt gatacgtggc caactgatga accttctctt 1320
ggtgaaacag atggtcaatc tggtcagcca aatgaagata ggtctaagaa ttttgatcca 1380
tag 1383

<210> SEQ ID NO 115
<211> LENGTH: 1083
<212> TYPE: DNA
<213> ORGANISM: Glycine max

<400> SEQUENCE: 115
atgaagatct tcattatctt tagtatcacc ttcacatgtg gtatttttgg aaatgttaat 60
tcaaatgtca atcctctccc gtatgaagct attttcaatt ttggtgactc tataagtgat 120
acaggaaatg ctgctgccta tcaccatgtt cccaaggatg gtaaaagccc ttacggctca 180
acatacttca aacatccatc gggacgtttg tcaaatggac gattgatcat agattttata 240
aatctcacca aaggtcaaga cattaggcat ggagtaaatt ttgcatttgc tggtgctggt 300
gcacttgata tgaactattt cacaaacaat agactcaagg caccagcaac aaataattca 360
ttaagtgttc aacttgattg gtttaagaag ctcaaacctt ccctgtgcaa aaataaaaaa 420
gagtgcaata actacttcaa aaaatcattg tttatagtag gagaaattgg tggaaatgat 480
attaatgcgc ctatctcgta taacaatatt tctaaacttc gtgaaatagt tcccccaatg 540
attgaagaaa ttaccaaggc caccattgca ttaatagaag aaggagctgt agaggtagtg 600
gtgccaggaa actttccaat tgggtgtaat tctggtgtct tgacagtggt gaatagtggc 660
aacaaagatg actatgatca atttgggtgc ttagcagctt acaatgtttt cattaaatat 720
tataattggc ggcttaatca agccatagag gcactaagac aacaaaaaaa ccatgttaag 780
ataatatatt ttgattatta tggtgatgcc agacgtttat ttcaagcacc acaaaaatat 840
ggcttttcat ctagtaagaa tgagactttc agagcatgtt gtggaacagg cgagccttac 900
aatgttgatg aacatgcacc ttgcggaagt ttgacttcaa caatttgctc tgatccttca 960
aaacatataa attgggatgg agctcacttt actgaagaag cttataaact aatagcaaag 1020
gggctagttg agggtccttt tgcaagccct tctcttaaat ctcctctttt taagatagta 1080
taa 1083

<210> SEQ ID NO 116
<211> LENGTH: 3906
<212> TYPE: DNA
<213> ORGANISM: Glycine max

<400> SEQUENCE: 116
atgcagaact atcaacatgc aaagagatct gattctgcaa aagccaggat caacagaaaa 60
cgtattatgc agcagaagcg acatggtcat gctcagtcat cttcacaacc aatagttaac 120
tgcacttcag aatataatag atattctgat cttggtgatc aactcatcca atgtagatat 180
tgtaatgcac aaatgtggta tgatgaaaga atatcaaaaa ataagaattg tcataatcca 240
aggttcagtt tatgttgtgg agatggaaaa gttgaattgt cattattaca aaatctaccc 300

```
caatatctcc aacaacttct atttcatgat gataccattg atagtaaaaa ttatcaacat    360
aacttacgag catacaacat gatgtttgcc tttacttctg ctgaaattaa gctagataaa    420
acaattaata attcaaaagg acctcctaca atcagaatac aggggcaacc atgccataga    480
ataggcagtc tattaccaat gcctgggaaa aaacccaaat ttgcacagct atatatcttt    540
gacacagaaa atgaagtgca aaatagaatt aatgtcatga gtcaatattc cggaattcag    600
agtcatattg tttcagcttt aagtcacatg ctcgatcaac acaattctca tgctaaaagt    660
tttagaatgg ccagagatag attggcaggt gatcaaccca ataatatcaa attgcaactc    720
atagctgctc ggggaaaaga tggtcgtgca tataatatgc ctaatgttcc ggaaattgtt    780
gcacttatta ttggcgattt tcatccaggc tcaaaaagat atattattgt tgaaactcaa    840
aatggagaat tacaaagaat ccatgaactt caccctagct atctaccact acagtatcct    900
ctactctttc cttatggaga aacggatata gagctgacat acttcacccg aaaccgtctg    960
acaatgagag agtggtttgc ttatagattt cagtctaggt caaatgaagc acagacttta   1020
ttgcattctc gaaaattatt tcaacaattc attgttgaag gttatacaat ggtggaatct   1080
gaaagactta gctatatcag aaacaaccaa aagaagctta gagttgataa gtattctagc   1140
ttacaaactt cattggatac tagaatggct aaaggcttaa ccaagggaaa aagagtcatc   1200
ttaccctcaa cgtttgttgg gagctcacgt tatatggatc aactttactt tgatggtatg   1260
gcaatatgca gtcatgttgg ttttccaaat cttttgatta ctctaacctg taatccaaat   1320
tggcctgaaa ttcgtagatt actttcacct ttgaatctca aaccaacaga caggccatat   1380
attgtatcac gaattttcag attaaaatat gaacacatgc tgtcagactt aacaaatggt   1440
caattaatag gaaaagtggt tgcatatatg aaatacagaa ttatacttac catcgtaact   1500
ttatcttttg tggatcacaa atatgcatac tatagacctc agactctttt ggattcaaac   1560
ggttatccag tctatcgtag aagaaacaat ggtcattcaa tttcaaagaa tggtgttatc   1620
attgataaca gatatgtagt accttacaat ccaaaattac tgaaaaaata tcaggcacat   1680
ataaatattg aatggtgtaa tcaaagtact tcaatcaaat atttatttaa atacataaac   1740
aaaggctatg acagggtgac tactgttatg ctttctgata gcaataacgc aactcaaaat   1800
gtaaatattc aaaatgatga acttaaagaa tatctagatt gcagatacat ttctccttgt   1860
gaagctgctt ggagaatatt tgcttttcca atccacggca gaaagcctgt tgttgaaaga   1920
ttgtattttc atcttccaga tcaacacatc attctttatg aagatcatga tgatatagat   1980
gatgtactat cgaaaccaac tatttcagat tcaaaattcc tagcttggat gaacactaat   2040
aaagatttgg atgaggccag gaatctaact tattcacaat ttgtgtcaaa gtttgtacca   2100
ccaaccacag aagaattgtt ttatttaaga atgatgcttg gcagctgcaa aggacctact   2160
tcatttgagg atatcaggac tgttgcgaat atccaatatc caacatatag agaagcatgc   2220
tttgcaatgg gctttctaca agatgacaga gaatatgttg aggcaatcaa agaggctaag   2280
gactggggca caactaatta tctaaggaaa ttaagtaatg atgatactct tagaaatttg   2340
acattgattg aaattgaaca actattgcac ataaaccaaa gatcactaaa agactatcct   2400
acaatgccat atcctcagga tatcaatctc acatcctacc tacaaaacaa cttggtgtta   2460
tcagaacttg actacaacca tgatgcaacg agatcagaat ttgagcatct tttgcatcc   2520
atgacagatg aacaaaaaac aatttatcac agaattatcc aagttgtcaa caacaatgaa   2580
ggtggaatgt ttttcctata cgaatttgga ggcataggaa aaacattcat atggagaaca   2640
```

-continued ttagcaagtt cattgagagc agagaatcaa attgtgatta ttgttgcttc tagcggaata 2700
acctctctat tagtaccagg aggcagaact gcacattcta gatttaaaat tcctatacca 2760
atttttgaag actcaacatg taatatccat caaggcaccg aattagcaga attactgaac 2820
cagacaagtc taataatttg ggatgaagta gcaatggccc acaaattttg ttttgaagcg 2880
cttgatcaaa gtttaagaga tattatcaca aataaatcaa actcaaatca aatatttgga 2940
ggcaaagtta tagtatttgg tggagatttt tgtcaaatac taccagtcat cccaagagga 3000
acccgctcag acattgtaaa tgcagcaatc aattcatcct atctatggga ttcatatgaa 3060
atattgacct tgacaaaaaa catgcggtta cacagcaatc tagaatcagt tgatgaacaa 3120
gaaactgcca catttgctaa atggattcta gacattggag atggaattat agatgatgaa 3180
aatgatggtt atgctacaat tcaagttcct gctcatcaac tcattactca atatgatgat 3240
ccaatcagtg ctatagtgaa atcaacattc ccagacttag atcagcacca caataatcct 3300
gaattcttta aatccaaggc aatactagct tcaacaaatg aaacagtaga acaaatcaat 3360
cattacgtgc tatccttcat tccaggtgac cacatggaat atctaagctc ttattcggtt 3420
gataaatcag aaaccaatga agatttgtat ttccaatcaa ttactactga attccttaat 3480
tcattgaaca catccggttt gccaactcat tctatcaaac ttaaaattgg aagtcctata 3540
atgctgttaa ggaacctcga ccaaaatcaa ggtctatgta acggtactag attagtggta 3600
acaaagatgg caaaacatgt aattgcagct gaaattatct caggtaaaaa cattggcctc 3660
gctgtttata ttccaagaat gtcaatgtcc ccttcacaat caccctggcc gtttaaacta 3720
ttaagaagac aatttccgat tatgctatct catgcaatga caattaacaa gtcacaggga 3780
caatcactat ccatggttgg actttatttg ccgaaaccgg tattcactca tggccaatta 3840
tatgttgcat attcaagggt caactcagca aaaggattaa aaattctgat tcatgatgat 3900
gagtag 3906

<210> SEQ ID NO 117
<211> LENGTH: 990
<212> TYPE: DNA
<213> ORGANISM: Glycine max

<400> SEQUENCE: 117
atggtgacgg accaagatat agcgaaaggg gtggagtccc tactgcgtca ctctgaccca 60
aactccataa ctacggtaaa cggcgtcgtt cagcagctgg aggccaaact agggttagac 120
ctctctcaca aggccagttt catcagagac cagatcgatc atcttctccg gtcacagcca 180
cagacatttg ctcctcaccc tcctccactt cacaaagact attttgcccc tcacacccaa 240
ctgcacttcc caaccaccca ctttgctccc cattttgccc tccatgacga gatcaacttc 300
ctgcagcacc cccaccctcc tccaccgcgt aaagtcgaga cctttcctcc tcaaaatgtt 360
gcccctcctc aagtgcccaa agaaagtgtg caaactggaa gcaaaagaag aggtggtgct 420
ggtggtctaa acaaagtttg tggtgtttct cctgaacttc aggcggttgt tggtgagccg 480
gcaatgccaa gaactgaaat tgtgaggcag ctgtgggcat acataaagaa aaacaacctc 540
caagatcctg gtaacaaaag aaagataatt tgtgatgatg ccctgcgttt ggtatttgag 600
acagactgca ccgatatgtt caagatgaat cagttgctag ctaaacacat tatcccactt 660
ggtcctacaa aggagtcaca ggctaaacga gtgaaggtgg atactgaaat taagactgaa 720
agtgctgaac ctgctccatc taccgtggca atatctgaag cgcttgccaa atttttgggc 780
actgagggaa gagagatgca acagtctgaa gccataagac ttgtttggga gtacatcaag 840

```
cttcaccatt tggaggatcc tttaaattca atggtgatat tatgcgatgc aaagcttcaa    900

gagctacttg gatgtgaaag catttctgct ttaggaatac cagagatgtt agcacgtcat    960

catctattta aacagtctga cacccgttag                                      990
```

<210> SEQ ID NO 118
<211> LENGTH: 780
<212> TYPE: DNA
<213> ORGANISM: Glycine max

<400> SEQUENCE: 118

```
atgtctagta agaaggaaga gaaatctcag gctgcggctg aaagaatcaa ggctgcagcc     60

ctgagtgctg cgaaaggcct tagtcgtgcc caggctgaaa gggctgcgac tgcagctgcc    120

cgaaacgtca atgcttatgg gcagaaggaa gaagggccca gcagatggca ggagaaaagg    180

gaagcaaaga ggcagatgta tttgatgagt accgaaaaag ctgttaaatt gggggaaaga    240

aaagacctca agcctgcaat gtcggcagcc ggtggattgg ctcagtgcca aaagtgtttc    300

caaagtggcc actggacata cgaatgcaag aatgaacggg tttacatttc aaggccatcc    360

cggacccagc aacttaaaaa ccctaaattg agggtgaatg tgtctgtgac ttatgatttg    420

gatgataata ttcctgatgc taaggaggaa aaggcaaaaa caagttccaa aaaaaccaaa    480

aggaagcatc ggaaggactc tgattctgct agtgatagtg aggattctgt tttcgagact    540

gatagtggca gtgggtcatc atctgttacg ggatcagatt attcttcaga aagtagttca    600

ggttacagtt catcttctga ttcagaggag gaacggagac ggaggagaaa gaagaagcag    660

aagagaggga gacgcaagag gtacacttca tcagaatcat ctgattcaga ttctgcttca    720

gactctgatt ccgatgataa aagcagccgg agaaagaaga ggaataatcg aagacgttga    780
```

<210> SEQ ID NO 119
<211> LENGTH: 2001
<212> TYPE: DNA
<213> ORGANISM: Glycine max

<400> SEQUENCE: 119

```
atgtcaatgt cggattccga ttcctcctcc tcctcttatg gcgctgaata caagagtctc     60

aaacaagtta gccgcgaccg attattacat gaaatgctta ggtcagcgaa aacaggagat    120

tcaaaatcta catggaaggt actcataatg gacaaactta ctgtgaagat aatgtctcat    180

tcttgcaaga tggctgatat cactgatgaa ggtgtttcat tagttgaaga catatacaag    240

cgaaggcagc cattgcccac cttggatgct atatacttca tccagccaac cagagagaat    300

attattatgt ttttgtcaga catgtctgga aggaaaccct tgtataggaa ggcctttgtt    360

ttctttagtt cacctattgc cagagaattg gttatggaaa ttaaaaaaga tgcacaggtg    420

ttacctcgta taggtgcttt gagagagatg aacttggagt attttaccat agatagtcag    480

ggcttcatta caaacaatga gagagcttta gtggagctat ttggggatga ggagaataat    540

cgtaaagctg ttgcatgttt aaatgtgatg gctactcgga ttgcaacact tttgcttca     600

ttaagagaat ttccttttgt ccgctttcgt gctgccaagt ccctagatgc aaccacaatg    660

actaccttcc atgatcttat tcctacaaaa cttgctgctg gtgtctggga ctgtcttatg    720

aaatataaaa aaactatacc taatttccct cagactgaga cctgcgagtt gctcatcatt    780

gatagaacta ttgatcagat tgctcctgtg atacatgaat ggacatatga tgccatgtgc    840

cgtgatttgt tgaatatgga gggaaataaa tatgttcatg aggttcctag caagactggt    900
```

-continued

```
ggtccacctg agcgaaaaga ggttctcttg gacgatcatg atcctatatg gcttgaactt    960

cgtcatgcac atattgcaga tgctagtgaa cggctgcacg agaagatgac caacttcatt   1020

tcaaagaata aagctgcaca aatccaacat ggttcaagag gtagtggtga aatgtcaaca   1080

agggacttgc agaagatggt tcaagcactt ccacaataca gcgaacaaat tgacaagctc   1140

tccctccatg tagagattgc aggaaaaatt aacagaatta ttagggagtc aggacttcgg   1200

gaacttgggc agctggagca agatcttgtt tttggagacg cagggatgaa agatgtgatc   1260

aaattttta ctacaaacga agatacaact cgtgaaaata agttgcgctt gttaatgatt   1320

cttgcgtcca tatatcctga gaaatttgag gctgaaaagg gtctgaattt aatgaaggta   1380

gcgaagttga cagatgagga tgcaattgca ataaataatt tgagaatgct tgggggagaa   1440

cctgatacca aaacgacttc gacgagttct tttgctctta aatttgatat gcacaagaaa   1500

aagcgtgcag caaggaaaga tcgatctggt gaagaggata catggcagtt atcacgtttt   1560

tatcccataa tagaggaact catcgaaaaa gttagcaaaa atgaattatc aaaactggac   1620

tatccttgtc taaatgaccc aagtccaact ttccacggta caacttatgc tgtaccagta   1680

actcacaatc ctcctgctca ttcaatgaga tcaaggcgca caccaacttg ggctcgacct   1740

agaggctctg atgatggata ttcaagcgac tcggtgctaa aacatgcatc cagtgatttc   1800

aagaaaatgg ggcaacgaat atttatattc attgttggtg gagcaaccag atctgagctt   1860

aggatatgcc acaagcttac tggtaagctg aagagggaag ttattctagg ctcgtcaagt   1920

atcgatgatc ctgcacaata tattacgaaa ttgaagatgc tgacagcaca ggaactttca   1980

ttggatgatc tccagatatg a                                             2001


<210> SEQ ID NO 120
<211> LENGTH: 1332
<212> TYPE: DNA
<213> ORGANISM: Glycine max

<400> SEQUENCE: 120

atggcttctt caaaatcaaa ggttagaagg gcatgttctt tcaccaacct cctccttagc     60

tgtttgaatt tctcactctt tatcctctct gcttcctcat ttgcacccac tattctcctc    120

aagatgcccc caacttcatt cggcatggct ctccttatgg tctctggcat ctcactcctc    180

tcatcttttg tgggcttcta ctccccgctc acacacttct gttacctcac tcacatttca    240

cttctactag cctcattaat aggacaagtg ctgaccatat tggccttgtt cacaaaagag    300

aaagcaagca tgtcccttct gaagtcacca agggacccca aagaagccaa acttttggtg    360

aggctggagt gtggggcatt gatggcaatg ttcatgctgc agtgtgtggt gctgatgctg    420

ggttgtgcag tgcatagttt ctgggtgaag gattatgagg aactcgaagc agagaaagcc    480

gcctcggcga ggaagaggag taggagaatt gcggaggtgc aagaggaatc catggctaat    540

gctagcaaga tggcagaaat caaagctaaa gagttggatg agaaaatgaa aagcaagacc    600

atcgacactg acttcttgaa cacgaagaag aaacaagttt cgttccaact ttcgagtttg    660

atcacaccac ctgtctccac tgtgaggttc tgcgatctca actttggccg cttgcaacct    720

tccgatgaag aattgggtcc tcacaaaaga tttgagtttg gcaacttcgt tgcacgagaa    780

gccctgcttg aggaagagta ttggtctgca gcgtgcctaa gggcagaaga gtgggcaaat    840

cgaacagata aactatatgt tgttgatcgg cagaggaatt ttgctgaaca ggaatttaat    900

gcgataaaaa agcggtgcaa ggagctacaa gacggtcaca gtagcacatg catcatcacg    960

gttaggaagc cacaaaagaa tgtaaaactc ccaataatag aaagtgttgt aggaactctt   1020
```

gatttgaata tcatatattt gcggcgaggg gagacctttc ctgggatcga ccgaacagca 1080
tcaagcagat atggttatat tgcaaacttg tgtgttgcca aatcacttta tcgcaagggt 1140
gttgcaagca aaatgttgta ttttgctgtg gagtctgcaa aatctactgg tgtgtcacgt 1200
gtgtatgcgc atgtggacag aaacaataaa cctgcccaaa tattatacca aaacttaggg 1260
tttgagataa ttgacactgc aaaccccctg ttgttgaaaa atcaaacatc cttgctttac 1320
ttacagatgt ag 1332

<210> SEQ ID NO 121
<211> LENGTH: 1209
<212> TYPE: DNA
<213> ORGANISM: Glycine max

<400> SEQUENCE: 121
atgtcttgtt gggcatgcaa aaaatgcacc tttgtgaatc tcccttctca aaaaggggaa 60
tgcgaaatct gcttttcccc cgcgtcccca ttgtcaatgg gtccttcttg ttcttcgtcg 120
cccccaaaat ggtcgtgcaa ggcctgcact ttcttaaacc cttacaacaa cccttcttgc 180
gaggtctgcg ccactcgatg ctccgttctc tccctttcca atctcaccga cttgaatgac 240
gccaccgatc acgattcttc tgtcggttct gttttctttc ctcttcgaac ctgcaacaag 300
agaaaggcca ttgatgatga cgattcttct gaggtcatca atttcaaggt caagccatcc 360
aatatcaccg gtgatgagaa tatcgacaca ggaaaagcgt ttaagatatt gagttacaat 420
gtttggttcc gggaagactt ggagttgcac aagaggatga aggctattgg cgaccttgtt 480
cagttgcatt cacctgactt tatctgtttc caggaggtta ctcccaatat atatgacatt 540
ttcaagggat ccgcttggtg gagtgtgtat tgttgttcag tttcttctga gatggcttat 600
tcaagaccct acttttgtat gctgttaagc aaactgcctg tgaaatcatt cagcaataag 660
cccttcagca attctataat gggaagagaa ctttgcattg ctgaggttga agctgcaagt 720
ggcaagccat tggttattgc cactagccat cttgagagtc cctgtccagc tcctccaaaa 780
tgggatcaga tgtacagcaa ggaaagagta gtgcaggcca atgaggctat aaaccttctc 840
aagaaacagc caagtgttgt ttttgggggga gacatgaact ggaatgacca acaggatggt 900
caatatcctc tacaagatgg atgggttgat gcctggtctc agctaagacc aaatgaaagt 960
ggttggactt atgacaccaa gtcaaaccag atgttgacag gcaaccgtac tctccaaaag 1020
cgattagatc gctttatttg ccaattcact gattttaaga taaccagtgt tgacatgatt 1080
gggatggaag caatacctgg tgtttcatac aacaaagaaa agaaagtaag aaaggagata 1140
aaacaactgg tactcccagt tttgcctagt gatcattatg gcctgctttt gacaatttct 1200
agtaagtaa 1209

<210> SEQ ID NO 122
<211> LENGTH: 3000
<212> TYPE: DNA
<213> ORGANISM: Glycine max

<400> SEQUENCE: 122
atggctgaga ccacaaaata cattcccaac tcacaattag agcttgaaga gatattgaat 60
gaagcagaac atcgatggct tcgacctgct gaaatatgtg agatacttcg caatcataag 120
aagtttaaat taacaccaga tccacctgtt atgcctccag ctggatcact attcttgttt 180
gatcgaaaag cacttcgtta ctttcgcaag gatggtcacc ggtggaggaa gaaaaaagat 240
gggaagactg taagagaagc tcatgaaaag ttgaaggctg gtagtgtgga tgtcttgcat 300
tgttactatg ctcatggtga ggataatgaa tacttccaac ggagaagtta ttggatgctt 360
gacgagcagt tagagcacat tgtccttgtg cattatcgtg aaattaaaga gggctgcaag 420
tctggcatct cacatttgcc tgtagttcca gtaaccctgg ttggtagttc tcaaaatact 480
tcagtgcttt cctctaccaa aataaattca ccaatatctc tagttcagac atctttcaca 540
tcaagtgcaa ataaagttta tcagaatgga cgagcctcag agcatgagga tgtcaattca 600
aagaatggtc ctcaagcctc ctctcatgct cagcctatca gcaattatgt acttcacagt 660
gcaccttggc ttacacatga agctgcaggg ttttctgagt tgttaaggaa ccccttgatt 720
tcatcatggc catcttcttt ccctagctac tctcctggta ctggcttgtc tccctggacc 780
tcaattcaga actctagcag aaacacaatt aatatgcatg atggaaagca tcatgttgaa 840
gcctctgaag cagacttaac tgttcgtaag ctaagcaatg ctgggttaga ttctgttcac 900
cgaatgcaag atggtgtaat tttcagagat aggctcatca ctgacatgtg cgtccagcca 960
gttatagatt tgcctactgt taatcaggtg aaaaacgagc atggtctgga ttcatttcat 1020
gctcaagtcc atgatcataa tgatcatcca gttgttgcaa ctactaaaat cctagttgaa 1080
caaaaacttc aagatggtgg tttatacaat gatgaatcag aacaagttga atatggagaa 1140
atgaagaaac ttgatagttt tggaaggtgg atggataagg aaattggtgg agactgtgat 1200
aattccttga tggcttcaga ttctggtaat tattggagca cacttgatgc tcatagtgag 1260
gataaggagg tatctagttt acgccacatg cagttggatg tggattcatt aggtccttct 1320
ctttcccaag aacaactatt tagtatccat gacttttctc ctgattgggc atatactgga 1380
gttagaacaa aggttttaat agttggcaca tttctgggga gtaaaaagcc ctctagtgag 1440
accaaatggg gatgtatgtt tggtgaaatt gaggtttcag ctgaagtttt ggcggataat 1500
gtcataaggt gtcagactcc tttgcattca cctggacgtg taccattcta tattacctgc 1560
agtaataggt tagcctgcag tgaggtcagg gaatttgaat ttgatgaaaa tccaaccaaa 1620
tttttaggtc ctgagggtat taaaatctca ccagaagaag aggtacgact tcaaatgcga 1680
cttcttaaac tagtagactt gggacctgac aataagtggt tgaagtgctc cgtttcagaa 1740
tgcgaaaaat gtaaactcaa gggaacaatg tattccgtga gagatgatag tggagtattt 1800
gaagaaactt tccagattga tggaattggt catataaacc atagagatat attatttcag 1860
agattagtga gagacaagct ttatgagtgg ttgatatata aggttcatga aggaggaaaa 1920
ggaccacatg tgttggatga tgaaggacaa ggagtaatac atttggcagc ggcacttggt 1980
tatgtgtggg ctatggcccc attagttgca gctggtatca gtcctaactt cagagactct 2040
cgtggaagaa caggacttca ctgggcatca tattttggga gagaagaaac tgttattgtg 2100
ctagttcagt taggtgcaac cccaggtgct gttgaggatc cgacatcagc atttcctcga 2160
ggacaaacgg cagctgattt aggttcaagt agaggacata aaggcattgc tgggtatttg 2220
gcagaggcag atctgacaaa tcaattatct gtattgactg tcaaggaaaa tgaaactggc 2280
aacattgcca caacaatagc agctaacagt gctcttcagt ctgttgaaga tgactcatct 2340
agtatgacaa tggatgagca acattatctc aaagagtcac ttgctgtgtt tcaaaaatca 2400
gctcatgcag ctgcttcaat cctagcagcc tttagagcaa ggtcattctg tcagagacaa 2460
ttagcccaaa gtagcagtga tatttctgaa gtacttgacg tagttgctga ttctttgagc 2520
aaggtacaga acaagggtca ctttgaggat tatttacatt ttgcagcttt aaagattcaa 2580
aagagatatc ggggatggaa aggaagaaag gatttttga agatacgtga ccgcattgta 2640
aaaatccagg ctcatattag aggacaccaa gttcgtaagc agtacaaaaa agttgtgtgg 2700
tctgttagca ttgtggaaaa agcaatcctg cgctggagac ggaaaggggc tggtctgcga 2760
ggattccggg ttgggcagcc agttggtgtt gtggttaaag atgccgagaa aagtgacgag 2820
tatgaatttc ttagcattgg gaggagacaa aaatcagatg atgtaaagaa agctctagat 2880
agagtcaagt ccatggttcg taacccagag gcaagggatc agtatatgag gctcatcatg 2940
aaatatgaaa agtttaagat tgatgatgga ggaagcagtc aatcacagca tgtcggttag 3000

<210> SEQ ID NO 123
<211> LENGTH: 429
<212> TYPE: DNA
<213> ORGANISM: Glycine max

<400> SEQUENCE: 123
atgaggaaca gtatggatac taataggaag gaagtcacct cacagtttgc ggagtttcga 60
tcctatgaag gccaggttat gtatgttggg gagaagattg ttccgatcaa gcttgatctt 120
tgtgttaatc atacgctcgt gaaggaccaa tttttatggg acttggacaa ctttgagagt 180
gatcatgaag agtttgccaa aatctctaca aggacacgag cattgaatat cccgaggttg 240
gagaaaattg caattcaaag tgtggtttca gcaagagaaa ccagaatgag caacaagggt 300
cgtcgagggg ctgaatatac tccagtcagg aaaagaaagg agtgggacgt atatgaacct 360
attgtcgacc tactatccaa cgaggaagtt gatgccattg aagcaaagga agagagaaat 420
ttctggtga 429

<210> SEQ ID NO 124
<211> LENGTH: 561
<212> TYPE: DNA
<213> ORGANISM: Glycine max

<400> SEQUENCE: 124
atggcttcct ctctacacaa ctatgttctt gctatcttac ttttggccat aacccaattc 60
aaaaccacat ctgcgggctc ccatcaccac ctccagcacc tcaaatccct tcacttctct 120
ctgtttcaac acgagaccat aaacaaaacc ggatacatca tagtggatgg tataaaagga 180
ggagcagggg tgactcaaac cacaacccct tttggcacct tatttgcctt tcaggaccct 240
ttgactgttg cagccaacag gtcctccaaa ctagttggga ttgcagaagg gactacagtc 300
acatctagtc tcgacgggct tcggagcatt tcgatcgcca agctaaccct gcgtttgaag 360
caccacaagg gctccctttc cattgttggt gtcacaaaca atgtcaaacc ctctgatctt 420
ccagtggtag gaggcactga agatttcatg tttgtgcaag gctatattag tacttctcca 480
gttgatctca agggtcttac tgttgtctac aagattgagt ttcatcttta ctggcccca 540 tatgcaactc aagcctcatg a 561

<210> SEQ ID NO 125
<211> LENGTH: 2034
<212> TYPE: DNA
<213> ORGANISM: Glycine max

<400> SEQUENCE: 125
atgccacgat ctagttccgc cgtgcaccac caccgtcaga gctccgataa cttcatgttc 60
gacgctcacg gaaggtggtt acactcttcg gcttacgcgc aggagctcgg gactcgatct 120
tcgagcttga ggagaaacga cgatgatcgc gttttaacca gtggcttgct tgatctgcat 180

-continued

```
tctttcgata ccgagctttt acctgaggga caaagttttg atggctacga gtcgattctc    240

tctggcaaca aacttgtacc aaggtctcgg ggcttgcctg agagccatct ccttaaaagt    300

gtctcagcag ataaagagag agcaaacaat gttgccaaga tcaaagttgt ggttcggaag    360

agaccactaa ataagaagga aatagcaaag aaagaggaag acattattta catagattca    420

aattttctca cagtgcatga aagaaaactc aaggttgact taacagaata tattgagaaa    480

catgagtttg tttttgatgc tgtgctgaat gaagatgttt caaatgatga agtgtatgct    540

gagactgtgg agccgattgt tcctttgatt ttccaacgaa caaaagcaac ctgctttgca    600

tatggtcaaa ctgggagtgg gaagacatat accatggaac cattgcctct caaagcatcc    660

cacgatattt taagattaat gcaccacaca taccggaacc aaggtttcca actgtttgtt    720

agtttcttcg aaatatatgg ggggaaactt tttgatctcc tcaatgaacg aaaaaaactt    780

tgcatgaggg aggatgggaa acagcaggtt tgcattgttg gcttgcaaga atatagagta    840

tctaaagttg agacaatcaa ggaatttatt gagagaggta attccacaag aagtactggt    900

acaactggag caaatgagga atcctctcga tcgcatgcta tacttcagct ttgtatcaag    960

agatcagctg atgggactga atcaaagcct acccgacttg tgggcaaact atcttttata   1020

gatctggctg gaagtgaacg tggtgcagat acgacagata atgataagca gactaggatt   1080

gaaggggcag aaataaataa aagtttactt gctctgaaag aatgcattag agccctagac   1140

aatgaccaag ggcatatccc tttcagagga agtaaattga ctgaagttct gcgagattct   1200

tttgttggtg attcacgcac tgtaatgata tcatgcattt cacctagctc aggttcatgc   1260

gagcatactc ttaacacatt aagatatgct gacagagtta agagcctgtc aaaagggaac   1320

acctctagaa gggatcctct ttcttcctca aaccttagag actctactgt gttgcctggc   1380

tcttcagttt tatctcatga tgataccttg gaggatgaaa caacatatgt ttccagtgac   1440

aagaatcgat ttggttggcc caaacagcta gaaagggaac cctctcctcc gaataatgtg   1500

gaccgtgttc caagtggtag aatgggggga aatttgatac catctgtgta ttctgatcca   1560

caaaatggtc aaagaggcag tcaaaaggcc agaactgcaa atgaatatga ttacctagga   1620

ccaacatatg aacaggatag aacgagaaaa acaagtaaga gggtggataa caaccaatta   1680

tctgccgtgg gggacaagag gaagatagaa tctcgtgtta aacttgtgga tgaattgcat   1740

tttgaggcta atcattctga tcctgacgat aatttaaatg ccctcctgaa ggaagaggaa   1800

gatctcgtaa ctgctcaccg gagacaggtg gaggaaacaa tagacattgt tagggaggag   1860

atgaatttac tcgttggagc tgaccaacca ggaaatcaac tggatgatta tatttccaag   1920

ttgaatacta ttttatcact aaaggctgca ggaatctttc aattgcagac acagttggct   1980

caatttcaga gacgcttaaa tgagtataat gttgtcgtaa cgtctggtaa ttga         2034
```

<210> SEQ ID NO 126
<211> LENGTH: 990
<212> TYPE: DNA
<213> ORGANISM: Glycine max

<400> SEQUENCE: 126

```
atgagcaaaa gagctaataa gaggaaagcg aagcaagacg aacagcccaa acaacgcaag     60

aagcgatcca caacaattaa acctgccgag cacgaagagt acttcgagga tcagcgcaac    120

ttggaagact tatggaggga aacattccct gtcggaacag agtgggatca attggattct    180

gtgtatcaat acaagtggaa tttctctaac ctggaaaatg cgtttgaaga gggtggtgta    240

cttcatggga aaagggttta tctctttggt tgcaccgagc ctcaactggt ctggttcaaa    300
```

gatgaaagca aagttgtctg catacctgtt gttgtagctg ttgtatcacc tttcccaccg 360
tctgataaaa ttgggattaa ctcagttcag agagagttcg aagagataat tcccatgaaa 420
caaatgaaaa tggactggat tccatatatc ccccttgagg accgagaaag ccgagttgat 480
agattaaagt ctcaaatatt tatcttaagt tgcacccaaa gaagggctgc attgaaacat 540
ctgaagttgg atcgtgtaaa gaaatacgag tattgcttgc cttacttcta ccatccgttt 600
aaggaagatg aacttgaaca gagcactgaa gttcaaataa tatttccagc agagccaaag 660
ccggttttct gtgaatttga ttgggaatta gatgagcttg aggagttcac tgataagctc 720
atagaggagg aggagttatt ggaagatcaa aaagatacct ttaaggaatt tgtcaaagaa 780
aaagtacggg aagcaaagaa agctaataga gaggcaaggg aagctcgaag aaaagccatt 840
caagaaatga gtgaggaagc tagagctgca tttgagaata tgagatttta taagttctac 900
cctgtgcaaa gtccagatgc acctgatgta tctaatgtta agtctccatt cataaacagg 960
tattatggaa aggctcatga ggttctgtaa 990

<210> SEQ ID NO 127
<211> LENGTH: 2808
<212> TYPE: DNA
<213> ORGANISM: Glycine max

<400> SEQUENCE: 127
atgctccaca acaagtcctt cgtcaagaaa accaaaggtg gcaaagtcat aaagcaagtg 60
cgggagcact acctgcgcga cgatatatac tgtggcgcac cgttttgcac cgtttgcgat 120
tcttccagtg ctcgcctcag tgcttcgcct tccatcattc tcgtcgtcga caccaatgtc 180
gttctcaacc agattgattt gctggagaat ccggcaattg acgatgttgt ggtgttgtcc 240
attgtgttgg aagaggttaa gaacaagaac atgtctgttt acaaccgtat aagagctatc 300
tgtagcaatt ccatgaggaa gttctttgtt ttttccaatg aataccacag ggatacatat 360
attaaggaaa tgagtgggga aactaaaaat gataggaatg atagagctat tcgagtggct 420
actcagtggt atcagaatca tcttggtggt gcagtaaagg tgttgctttt aactaatgac 480
aaagagaaca aaaggaaggc tagtgaagag ggtattttgg ccgaaacagt tgagtcatat 540
gtgaagtctt tggaccaacc tgatttactt gatctgcttg tgcggcctgc atctgaagat 600
gtggacatgg aagaggttga agatcttaga ccatccaaga ggaaagtcat ctactccgag 660
cataagccga tgtcagaaat tacttctggt ttgcatcgtg gaatatatca tcaagggaaa 720
cttcgtgtta accgttataa tccatttgaa gcatatgttg ggagtgagag cattggtgat 780
gaaataatta tttatgggcg ctcaaacatg aatcgagcat ttgatgggga tattgtggca 840
gctgaacttc tgcctcagga ccagtggcaa ggagtctcat ctctatctat agcccatgaa 900
gaagacgagg atgaggatga agatgttcat ctagctccaa atagtgctga tgatgcacct 960
agaactattt ctcagcaggg ttcttctgaa caagtaaatg ctgtgcccag tcgtccttct 1020
ggtcgtattg ttggcattat aaagagaaac tggcattcgt attgtggatc tttggagcca 1080
atgcctatgc ctgcagggag tggtggtatt gcccatgcct tgtttgtctc caaagatcgc 1140
agaattccca agattcgaat ccaaacccgt caacttgaga accttttgga taagaggatt 1200
attgtggcag ttgattcttg ggatcgtcag tctcgatatc catcaggcca ttatgtgcga 1260
actatagggg agataggtga tagagatact gaaagcgagg tggttttgat agaaaatgat 1320
ataaatacac ggccattctc ttcacaagtg ctggcatgct tgccaccatt gccatgggta 1380

```
gtctcttctg aagatttgtc taatccaatc aggaaggatt tgcgtcatct gcgtgtcttc   1440

agtgtggacc ctccaggctg caaggatatt gatgatgcac tccactgtca cgtccttcca   1500

aatggaaact ttgaagttgg agttcatatt gctgatgtga ctaattttgt ttatcctggc   1560

actccccttg atgatgaggc tgcacaaagg ggtacgtctg tctaccttgt tgagcggcgg   1620

atagacatgc ttcccaaacc tcttacggag gacatatgtt ctcttcgttc tgatgtggaa   1680

aggcttgcat tctctgtcat atgggaaatg acacccgaag cagatattat tgccacctca   1740

tacacaaaaa gtgtcataaa atcttctgcg gcattgtctt atgttgaagc acaggcaagg   1800

atggacgata gtcgattgat ggatccgatt actgcagatt tgaggaatat gaatagttta   1860

gctaagaaaa tgagattaag gcgtattgag agaggagctt tgactcttgc atctgctgag   1920

gtcaaatttc aaattgacac ggagactcat gatccacttg atattggaat gtaccagatc   1980

cgggaggcca accaaatggt ggaggagttt atgcttgcag ctaatgtttc cgttgcacaa   2040

caaattctta aaagttttcc attgtgctca ttattaaggc gtcatccaac accaacaaga   2100

gagatgcttg aacccttact acggactgct gctgcagttg gcttgcactt ggatgtctcg   2160

tcatcaaaag cgttggctga ttctcttgac catgctgtgg gtgatgatcc atacttcaat   2220

aagttaatcc gtatactggc aactaggtgc atgactcagg cagtttattt ctgcagtggg   2280

gatcttagcc ctccagaata tcatcattat gggcttgcag ctcttttgta tacccatttc   2340

acatcaccta taagaagata tgcagtagat gtcattgtgc acaggctact tgctgcttct   2400

ttagggatat ccaagttacc acctgtattt caagacagtc tccagctcac tagtattgca   2460

gacaatttaa attatcggca caggaatgcc cagtatgcag ggcgggcatc tgtagagcta   2520

catactctaa tttatttcag gaagaggcct acagacacgg agggtagaat agtgaaaata   2580

agatctaatg gatttttttgt gtttgttccc aaatatggca tagaaggacc tgtatatttg   2640

acaaaagcag aaaagggaag tggagaatgg tatgtagatg agcaacagca gaagattaaa   2700

aagatggatg gtagcctttc atacaacgtt ttgcagacag tccaaattca catggaggtt   2760

gtggagcctc agcctaaccg gccaaaactt cagcttaccc tcatctag                2808
```

<210> SEQ ID NO 128
<211> LENGTH: 999
<212> TYPE: DNA
<213> ORGANISM: Glycine max

<400> SEQUENCE: 128

```
atgagcatgt taggcctgag agacctagtt ctcatagctc aaaccccttc ttcccttcac     60

caccaacacc aaggccaacc catttcagaa aaccagactc acactcacac tccaaacctt    120

cctttgcctt cttcagcagc ttctctcagt gttggctttg gaattttccc tctcctcact    180

gccacaccat gtgtgccaca gcctcatcaa aacaatgagg ttcaagagtg tggtggtggt    240

ggtgccaata gtaacactac caccaccaat tattggaacc tcaagatgtg ccaagaagtg    300

aataatcctc caaagaaggg tgtgatcaac gtggctgatc atgatgatga gaagggtgtg    360

atggagagtg aggaaaacgg ggtctatggg cctgacttta gggtgtgcca agattgtggc    420

aacagggcta agaaagattg cgtctttaga agatgcagga cttgctgcaa gggacgtggg    480

tatgattgta acactcacgt gaagagcacg tggatcccct ccgttcgccg ccgcgagcgc    540

gagatcacgg tggcttccgg tggcggtgtt ggcggcaatg gtggttgtaa gaggccaaga    600

gctgtggtgg ggtcatctca aaatgccact tctcatagtt ccaactctaa tgctacaact    660

cctaagagct tagctactag ctcttttcat caagatgcta gcttcaagca gtctttaccg    720
```

ggtcatgttc gtgcaccagc agtgttcaag tgccatagag tctctgccat tgggaatggt 780
gaagatgagt ttgcatactt ggcaacggtc cagattagtg ggcatgtgtt caaagggttt 840
ctctatgacc atggtgttga tgggaaaacc gcaaatgtag tcccttgtgt ctcggaactg 900
cagctgggaa acaattgcag tgggaagaac agagaatgtt cctctgcaat tgcaattggg 960
gttgcaaata acaatgcata ccctgcttct gcgagttga 999

<210> SEQ ID NO 129
<211> LENGTH: 783
<212> TYPE: DNA
<213> ORGANISM: Glycine max

<400> SEQUENCE: 129
atgcgagcac agacgctgat gacacagtgg tgcacaagag cagcaacgtg tggccaattg 60
aggatgagca ctaacaccaa cacccccaaa cacgatggtc tcgacgccat tttcaaacat 120
aagcgcttac ttcgaacgca ggtcagaaaa accctaaaat ccatccaacc ctccctccga 180
tctcaccaag ataacaccgt tcaagacata gttttgggag ctccgtggtt caaatccagt 240
cgcaggctat gcgcgtacat aagctgcgct gctcttcgcg aagtcgacac tttaaaaata 300
ttgtcacaaa ttttgcaaca taacaatgct actgatggaa agaaactcta tgtgccgcgc 360
gtggaggata agaatagtca catgcgtatg ctccacatat cgggaattga tgatctcatt 420
gcaaactcaa tggacatctt agagcctgct ccggttgatg ttgatggaaa tgcgcgtgaa 480
gatgttatgc aggcaaatga tccagttgat ttgttccttt tacctggact ggcatttgac 540
agatctggaa gacgtttagg tcgtggcaga ggttactatg atacattcct gaagaattac 600
caagaccttg caaagacgcg gaattggaag cagcccttgc ttgttgcact gtcgtattcc 660
gaacaaatac tggatgaagg actaatacca atgacttcat ctgatcttcc agttgatgct 720
cttgtatctc cggaaggtgt gattcccatc agtaaaactg ccttaaacag catggatctc 780
tga 783

<210> SEQ ID NO 130
<211> LENGTH: 216
<212> TYPE: DNA
<213> ORGANISM: Glycine max

<400> SEQUENCE: 130
atgatcatcc ccgttcgttg ttttacctgt ggaaaggtca ttggaaacaa atgggacacc 60
tatttggacc ttctccaggc agattacagt gaaggagatg cactggatgc attgggattg 120
gttcgatatt gttgtaggcg catgcttatg acccatgttg atctcattga gaagttgctc 180
aattacaaca ctctggacaa gtctgatccc aattaa 216

<210> SEQ ID NO 131
<211> LENGTH: 3051
<212> TYPE: DNA
<213> ORGANISM: Glycine max

<400> SEQUENCE: 131
atggtaacaa gaagtacatc aagattagtc aatgttatta atgaggatag tgatcaaaat 60
tctgataata caactgaagc agaaaactca aatacagttc cagaagcaat tataaaccca 120
attaattcta aacaagggaa aaccccatcg aaattatact accaacatcc aactgcccct 180
gtccttctac tagaagaaag aggagaaaat aatttcaaga gtttttctgc aaataacatc 240

-continued

```
tatgagtgga atatagatgc tcaaacagaa tacaatatca tgaatacact ccaacatatg    300
acaatggtag ccacaactta ccaaacctcc catgaattca agactgatct caatggtaaa    360
gtcattacta atgatgatga taaagagatt cctaacgctg ttaacacctt aatctttaca    420
atagcacaac attttattgg agacccatct ttatggaaag ataggtctgt agaattatta    480
tcaaatctta agtgtagaac cttagcagat tttagatggt acagggatac tttcttgact    540
agggtctata ccagagaaga tagtcaacaa cctttctgga aagaaaaatt tctagctggt    600
cttccaagat ctttaggaga taaggttaga gataaaatcc gtagccaata caatggagat    660
attccatacg aaagtttaag ttacggtcaa ttaatttctt atgtccaaaa ggtagcctta    720
aaaatttgtc aagatgaaaa aattcaaaga caattagcta aagagaaagc ccaaacaaag    780
agagatttag gatctttctg tgaacaactt ggcttgccag cctgtccaaa acagaagaag    840
aagacctcta gaaaagaaac ccatgaaaat aaggtagtta ccaaaaagag atttccaagg    900
aggagatact cgcacaagcc ttcaactagt aaagaaatag aaaacccaaa acaaaaatta    960
aaatctaaag taacatgcta taactgtgga aaacaaggtc acattagcaa atattgtagg   1020
ttaaaaagaa aattaagaaa tcttaatcta gaaccagcag ttgaagaaca cattaataat   1080
tttctcatgg aatgttcgga ggaagaagaa acagaaactt cattctcctc tgatgaaaat   1140
ctcaatctaa ttcgacaaga tgatccattg tcatctacag aggatgaaag acaaatcaat   1200
actttaacaa gagaacaaga cctcctgttt gaagcaatta attctatacc tgacccccag   1260
gaaaagaaaa attttctaga aaagctcaag aaaacattgg aagtaaaact tagacaaaaa   1320
gatattatta tcaataacaa atttgatgtt tgtaacattc ttagaaggtt agaaaatact   1380
tcagctaaac caacaacaat ccaagacctc caaacagaaa tcaataatct taagaaagaa   1440
gtaaaagaac ttcgtcagca acaagaaatt caccagaata tcctttctca actcgaagaa   1500
gaaagtgatt ctgaaagcat cgctaacagt gacacaaacc acatagaaaa tccagaagat   1560
aatatgttta tgggggccga ttcaaattgt atcttagaag gattaatccc aacaaaattc   1620
ttcgaaaaaa catcagagaa gttaggcaca gcaaatggat caaaattaaa aattaatttt   1680
aaactgtcaa atgcaattat agaaaatcaa ggccttagga tcaacacaag ctttcttttg   1740
gtaaaaaacc ttaagaatga aatatcaaag gaaggaataa ctacaaatta tttaggaaga   1800
aaaattatat ttgatttttc cactaaacca atctccagaa acataaatca catagcaaat   1860
aaaattaacc aaatcaattt tttaaaagaa gtatctttta gtaatattca aaaccaacta   1920
gaaaaacccc aaataaaaga aagaattcaa tctttgttga aacatattga atcaagtgtt   1980
tgttctgatt tgccccatgc cttttgggat agaaagaaac acattgtcga tctcccttat   2040
gagaaagact tcagggaaaa acaaatttcc accaaagcta ggccaattca aatgaatgaa   2100
gaacttcttc aatattgtca aaaggaaata aaggatttgc ttgacaaagg tctaatccag   2160
aaaaatgtaa agaatcttgc atcaaaacaa atttttgcta gatggcaagc aattttaagt   2220
gtctttgatt ttcaaataga atacataaat ggcacctcaa attctctaca tgactacctc   2280
acacaatatt gggacaaaaa tcccttcaaa gccactgcta agtcttttcc ctcgggattc   2340
cattacagac caacatacct caacaagaca ataaagtttt atgaatttat tttagttgat   2400
acaaaatcag tatccattaa acacttcaaa gatccaaaag accaaagcct aaatacccat   2460
tctacaatcc aaatcctaaa agtaatgcaa ccaaggcatt acggatctaa tctcaaccaa   2520
cccaaaaagt tttttgcacc ttttgaccca gcaggatata cttattggga ctatattaat   2580
gcctggacta atgtgttctg gcatcagaac aataaataca aacattcatg gctaatctac   2640
```

ttcaaaaata atacctacag atatggaaga atagaaaata ataaacaata tccatctttg 2700
caaagacatg catttgtcaa atggtggact cagtttgata cttcaaaggt ggctcctgac 2760
caagtcaaca actggtttca gagtcaccct gaacttctca aaccagctga cctagaaaca 2820
tcgttgtttt ttaaccaaaa atctcaactt gtagtctttc tagcaagctc caaatccaag 2880
gagagtcttg caaagaatct caatgaagtt ctccaaatgc ttcaacaaga agaagaggaa 2940
gaatcttcaa agaaagaagc tgaatcttct gaagattttg atgaccaaga tgatgatccc 3000
ttctaccaga atgaggatga ttgtttcggc atctcacttg aagaagatta a 3051

<210> SEQ ID NO 132
<211> LENGTH: 378
<212> TYPE: DNA
<213> ORGANISM: Glycine max

<400> SEQUENCE: 132
atggcaaatt atgaggtcaa tcttatacca atgactactc ctgtattcac tcaagccaat 60
gatgctgacc tgtccaaact gtcaatccaa atagttcttc catttgacaa agaaacagaa 120
agtttgccaa atcctaatca agaaacagct cgcttgagaa aggttgaagg aggcattgtt 180
gcaataatga agtttagcgg aaaacccaca gaggatattg ttcgtgaaaa ggagaaaacc 240
ctgcgtgcca atattattaa agatggtctt aaacctcagc ctggttgttt gcttgcacgg 300
tacaatgatc caggtcgaac atggaccttt ataatggtat gctgcaaaac ctgcttgagt 360
gtgtcagttg atttctaa 378

<210> SEQ ID NO 133
<211> LENGTH: 726
<212> TYPE: DNA
<213> ORGANISM: Glycine max

<400> SEQUENCE: 133
atggaatccc aattaattga tggtaatgat gagatggaag tttctgggga tgtgggtttg 60
agtacgtgtg aagttcagat gcatcaagaa acatatgaag tggatccaaa tgaggggtgt 120
agagtactag agagttcttc ttggggagag ttgggtatct gtgaagatca tgctattcag 180
gaaccatatg aaggcatgga atttgaatct gaagatgctg ctaagctatt ctatgatgaa 240
tatgcccggc gattaggatt tgtcatgcgt gtgatgtctt gtcgacgctc agaaagggat 300
ggtaggattc ttgcccgcag acttggatgt aataaagagg gttattgtgt cagcatccga 360
ggtaaatttg cgtcagttcg taaacctagg gcaagcacaa gggaaggttg taaggcaatg 420
attcatatca aatatgataa gtctggaaaa tgggtgataa caaagtttgt gaaggatcat 480
aatcatccat tagtagtctc tccacgtgaa gcacgccaaa caatggatga gaaggataag 540
aaaattcagg aattaacagc agagcttcgg cttaaaaaac ggttgtgtgc aacatatcaa 600
gaacagttga cttcttttat gaaaattgtt gaagagcaca atgagaagct atctgccaaa 660
attcatcatg tagttaataa tcttaaagaa tttgaatcca tagaagagct tttgcaccag 720
acataa 726

<210> SEQ ID NO 134
<211> LENGTH: 2172
<212> TYPE: DNA
<213> ORGANISM: Glycine max

<400> SEQUENCE: 134

```
atggcggagg agaagagggc gccgtcgtcg ttcgtgaaga aaggcgaccg gcaaatgttc     60
acggtggagc tctggccagg tgagaccacc atagtttcgt ggaagaagct gttgaaggac    120
gctaacaagc acaacggatc cacttcggcg ccacaacacg tcgcaatcgc tccgggtcaa    180
cctgtggagg ttgaagaaac agatccttct cagccaaacc gtttcagtgc tgtaatagag    240
aagattgagc gcctttacac gggtaaggac agtagtgatg atgaggatct gcttgatgtt    300
cctgatgatg atcagtatga tactgaagac tcttttatag atgatgctga actggatgaa    360
tattttgagg ttgataattc tgcaatcaaa catgatgggt tctttgtaaa taggggggaaa    420
ttggaacgca taaatgaacc tcctgtacta cctaatcagc aaccaaagaa aaggcgcaga    480
aaagatatat tgaagaatgc tggtgaaaac aatgatggtc atggatcaaa taaaaatgta    540
aaagttggca ggccagcatc tgccaaaaca gcttcactac aggcaaagaa tatgttaaat    600
ttatctgaga atttggttgc acctggtgac catattgaag acttgaaact tccaaatcaa    660
tcggatgtct ctggaattat ttcgaaaaag aaaactgctg atactaaacc aatattgaac    720
ccttctgtct ctttgaaaac atcaagtgat gatgctcctg ctgtaacaga tgcaaaagat    780
gttgacaagc agaagatagg agcttttcaa tctaagaaca ttagtgataa atatatagat    840
ggaagtggat cgtttgatgc atctcatcat aaatacaatg aaaaaagtgc atatgctcat    900
tccaaatccc aacctggaag accctcaagt aatattgatg atatcaattg gacaaaagaa    960
aaaaatggta tgcgtgaact gccagatctt aacttgtctg agggaaagtc tgctacccaa   1020
gcaacaaagt ctgaaaacat gcacaagaaa gagggttcta gtgttaggcc aaaaacttca   1080
atgcttgaaa aggctcttcg tgagttggaa aaaatggttg cagaatctag gccaccagca   1140
gtggataacc aagaggctga tgctacatcc caggcagtca aaaggaggtt gcctagagaa   1200
ataaagctaa agcttgctaa agttgctaga ctagcggcaa cgcacgggaa agtatcaaaa   1260
gagttaatta accgtcttat gagtattctt gggcatctga ttcagctaag aacattaaag   1320
agaaacttaa aaataatgat caatatgggt ctgtcagcaa agcaggagga ggataatagg   1380
tttcaacaga taaagaagga agttgttgat ttgattaaga tgcaggcccc aactctggaa   1440
tccaagcagc agctgaaagg tgaagcatct ggtgattttc aagaatttgg tactgatgga   1500
aaaccaataa ctaaaaggaa gtttactatg gatgctgcat tggaggacaa gatttgtgat   1560
ctctacgatc tttttgtaga tgggttggat gaaaatgccg gtccacagat tagaaagttg   1620
tatgctgagc ttgcacagtt atggcccagt ggttacatgg acaaccatgg gatcaaacgt   1680
ggaatttgca gggcgaaaga gaggcgcaga gcactataca acaaacataa ggatcaggag   1740
aaaattaaga ggaaaaagtt gctggcacct aagcaacagg agaacgttcg atttgatact   1800
aatacaatta cttcacagca gaacctacga gagagatcag ctccagagtc tagcagtcat   1860
gcttatactt cagggaacaa gcaagtttct aatacaagca ccccaagtcc aatgaatggt   1920
ctaaaacaag aaaaagcaaa gggaagttca agcagttccg tggatgatgt cagggttgca   1980
gatggtgttt tgacaaagaa ggtaaagaga aaaccagaac ttgagttgga aggagcacat   2040
ttaggtcctg agaaagtagc ttccttgcag ggagaagaaa gacccaggtc cctaaagcag   2100
tctacagggc cacttcccac caaatcaaat cttcagccaa catctctgcc tgatcttgaa   2160
cagtcaagct aa                                                        2172
```

```
<210> SEQ ID NO 135
<211> LENGTH: 477
<212> TYPE: DNA
<213> ORGANISM: Glycine max
```

<400> SEQUENCE: 135
atgggtgttt tcacattcga ggatgaaatc aactcccctg tggctcctgc tactctttac 60
aaggccctag ttacagatgc cgacaacgtc atcccaaagg ctcttgattc cttcaagagt 120
gttgaaaacg ttgagggaaa tggtggccca ggaaccatca agaagatcac tttccttgag 180
gatggagaaa ccaagtttgt gttgcacaaa atagaagcga ttgatgaggc taacttggga 240
tatagctata gcgtagttgg gggagatggg ttgccagaca cagtggagaa gatcacattc 300
gaatgcaaat tggctgctgg cgccaacgga gggtctgctg ggaagctaac tgtcaaatac 360
caaaccaaag gagatgctca gcccaaccaa gacgacctca aaattggcaa agccaagtct 420
gatgctcttt tcaaggccgt tgaggcttac cttttggccc atcctgatta caactga 477

<210> SEQ ID NO 136
<211> LENGTH: 2370
<212> TYPE: DNA
<213> ORGANISM: Glycine max

<400> SEQUENCE: 136
atgaggagat tttggttga tagagcaagt attgagaatg tgaatgttgt acaacaagaa 60
gccgaattag aaccgccacc taatgtggtt aatgagttta acccaaatga gattgtgcgt 120
gatccaggtc ataggaaaca aattaatgag tatgctccag atattcaaga tcaagtgagg 180
agggcatata tattgaaggg tccaatgcaa ccacatttgc caagctttcc tcgtactcca 240
tttcgaagtg tttctagagc atttagtaaa tcatggtata agaattacac atggttagaa 300
tacagtgaga tcaaggatgc agcttattgt ttttattgct ttctctttaa gcaacccggg 360
agggccgaac actttggttt tgaagtcttc actaaaagcg gatatagaga ttggaagcat 420
gcatctcaag gcttgaaaga tcatgttggt agtcataata gtttgcacaa ctcatgtgtc 480
aagcactacg atgattataa taatcaaaga caaagtgtga caagtaagtt tgctaaagca 540
accaaggaat cagaagaatt gtataagatt cgtttgactt gttctttaga ttgttcaaga 600
tatctcatag cacaaggcat ggctttccgt ggccatgatg aatcctctac ttcactaaat 660
aagggcaatt ttagagagat ggtagattgg gtaaaatctc agaatgaaca agtgagggat 720
gcttttgacc gtggtggaaa aaattgcaca atgacttgcg gtgacattca aaaggagctt 780
gcaacgtgtt gtgcacatga agttaccaag gtgattatgg aagagcttgg tgatagacaa 840
ttctccgtgc ttattgacga gtcacgtgat atatccgtca aagagcaaat ggcggtgatg 900
ttgaggtttt tgaatgacaa agggaatgtt gtggaacgat ttattgctct acatcatgtc 960
acagatactt catctaagtc attaaaggat gctctttatg gtattcttga taagtacaca 1020
ttatctattt caaggatacg agggcaagga tatgatggag cttcaaatat gagaggtgaa 1080
tttaatggtt tgcaaagaaa aattctagat gaaaatcctt atgctttcta tgtccattgt 1140
tatgctcacc gtttgcaatt ggttgttgtg tctgttacta gtagttgctc atctattcat 1200
gatttctttg agtacatcac cttgattgtg aatacaacaa gtgcatcttg taagaggagg 1260
gatgctttga cagaggcaca acacaaagat attttaaata aacttgagag tggtgagata 1320
tctagaggaa ggggcttaca ccaatcatct agtctcacta gacccgggga tactagatgg 1380
ggttcacatc atactacatt gcttcgtttg gatcaaatgt ggtcctccgt gttaaaggtg 1440
cttagtatgg ttgatgaaga tggacgtgga ccatctcaag cagcaggttt gatagaaaaa 1500
atggagagct ttaaatttgc ttttattttg aggttaatgt taaagttgtt tggtatcaca 1560
aacgagcttt caaatatatt gcaaagaaaa gatcttaata ttgtgaatgc catggaatta 1620
gttgatgttg tcaaagctcg gttgggcaca atgagagaga gtggctggaa taattttttt 1680
gccgatgtcc aaggattttg tgttgctaaa agtattctgg taccaaatat ggatgacgaa 1740
ataccagttc ggggtcgttc aagagcagaa gggaggacta tcactaatct tcatcattac 1800
cgtgcagaga ttttttatgt tgctattgat aaaatatgtg tggagatgga tcaccgcttt 1860
agtgaaggaa gtaacattat acttgattgt ttctcatgtc ttgaccccaa gaactctttc 1920
tccaagtttg atgttgataa gcttgctcgt cttgctgata tttatcatgc agacttttct 1980
gatgatgacc gaggaacaat tagggatcaa cttgaaactt atgtgcttca agtgagaaga 2040
aatgcttctt tttccacttg tgaagatgtt caaagtttgg ctatgaagat ggttcaaatt 2100
gagaaacatt tggtatttcc attggtttat aaacttattg agctagcttt gatattgccg 2160
gtgtcgacag catccgttga aagagctttt tcagcaatga agattatcaa gtctaaattg 2220
cgcaataaga tcaacgatgt gtggttcaat gacttgatgg tatgttacac cgagcgggag 2280
atattcaagt cacttgatga tattgatatt attcgaacat ttaccgcaaa gaagtctcgg 2340
aaaggacact tgcctcgtaa ttttatttaa 2370

<210> SEQ ID NO 137
<211> LENGTH: 336
<212> TYPE: DNA
<213> ORGANISM: Glycine max

<400> SEQUENCE: 137
atgggttttt atctatcgga ccaattctta caaaatcctc cattgacaaa aaagcctcca 60
agaaacttga gaccatgcat gaagacagac aacaataaaa tcaacatcaa gaagtccaag 120
accataaaaa ttgaccgtgt tgagacaagc ctcaaagaat cgagtcgcga cttgtctctc 180
ttcaagttca agtctggggg tgtggtggct ctagttctct ttgtggtctt tgggttgctg 240
aattcactct acgaaggcaa ggtagttgcc aaattgccct acaaaccttt tgtcatctct 300
ggtccccctg aatttaaagc cacattttgt atataa 336

<210> SEQ ID NO 138
<211> LENGTH: 864
<212> TYPE: DNA
<213> ORGANISM: Glycine max

<400> SEQUENCE: 138
atgggtggtc tttttgaggc tataactggt tatggtcttg gtgggtcttc tatggctttg 60
tttggaagag ttggtggagg tatctatact aaggctgctg atgttggtgc tgatcttgtc 120
ggaaaggttg aaagaaaaat ccccgaagat gatccaagaa atccagctag aaggcagtat 180
gacagtgctg gatttgagct ttttgacgtt ttcattcaca ttcttcatga tatagttcta 240
tttgaaatgc aacaatcttt aagatgttct acctatactt atcaggccct tgatgcggat 300
agcatggaca tggaaattga tttatctaat cttgggactg tgaacacaat gtttacagct 360
ttattcagca aaatgggtgt ccctatcaag actaccattt cagctaatgt tcttgaagaa 420
gctctgaatg gaacagaaga tagtgagaag actggcaagg tgacatctgc aggaatgtat 480
ttcttacatt ttcaagtgta tagaatggat tcgacggtga atgcgtgcta tgtgcagtta 540
gcaatggcca aggatcctga aggggccttc tttaaaaggt tggaaggtct tcagccttgt 600
gaagtctcgg aactaaagcc tggcactcat atatttgctg tttatggaga taacttcttt 660
aagtctgcta gctatatgat tgaggcagta tgtgcaaaat catatgaaga taccacccaa 720

```
aaactgaagg acattgaagc tcaaatttta agaaagagga atgagctacg ccaatttgaa    780

gcagaatata gaaaggttat tattctctta agtaatcagc tctcaggatg cgtcatctgt    840

gatcaagtat gcaaaaagcc ataa                                           864


<210> SEQ ID NO 139
<211> LENGTH: 1635
<212> TYPE: DNA
<213> ORGANISM: Glycine max

<400> SEQUENCE: 139

atgcgtatag tcattgagct gaagcgggga tcagatccat tgattgtttt gaataatctt     60

tatcgcttaa catctctgca atctacattt agctataata tggtgggcat tctaaatgga    120

caacctaaac aaatggggct gaaggaatta ctgcaggcat tcttagactt cagatgctct    180

gttgttgaga gacgtgcaag gtttaagtta tcacaagcac aagagagaag acatattgtt    240

gaggtatgtg ttcttattgg gtttgataat ctggatgggg tgattcgcat aatacgtgaa    300

gcttcaagta actcggctgc agcagctggt ttacgtaatg cattcagtct ctctgagaaa    360

caagctgaag ctcttttgga cattagccta agaagactgt cccttcgtga gagtggaaac    420

tttatggctg aacgtaaatc tttgatggaa caaatttcca agttagagga actgttgtcc    480

agcaggaaaa atatacttga gcttatagaa caagaagcaa ttgaaatgaa gaataagttt    540

tccaatccaa gaccttcaat gttggaggac acagatgatg gtcaacttga ggacattgat    600

gttattccaa atgaagagat gatattggca cttagtgaaa aaggttatgt gaaacggatg    660

aagccaaaca cttttaacct acaaaatcgt ggaacaattg gaaaatctgt aggaaaatta    720

aaagtgaatg attcgatgtc tgattttctc gtttttcgtg cacatgatca tgtcctatat    780

ttcagtgata agggaacagt atactcagct cgtgcctaca aaattcctga atgtagccgc    840

actgctgctg gtacaccact tgttcagatc ttatctttat ctgatggtga aagaattaca    900

tctattattc ctgtgagtga gtttgctgag gatcagtttt tgctgatgct tactatgcaa    960

ggttatatca aaagagtatc cttgaatttg ttttcatcaa tcaggtcaat cggaatcatc   1020

gctattcaat tggttcatgg tgatgagctg aaatgggtcc gtctttgctc aaatgatgac   1080

tttgtggcca tggcttctca caatggaatg gtcatgctaa gccaatgcac tcagattcgc   1140

acactaggta gaaatacgcg gggggcactt gcaatgagac taaaaaaagg ggataagatg   1200

gcaagtgtcg acattatacc atcagccatg tggaacaact tggaaacctc atcaaaattt   1260

cctgggagca atgcaaagaa ccaaaatggg ccatggctat tgtttgtatc tgagaatggt   1320

tatggaaaga gagttccttt gtgcagtttc cggatatcgt ctttgaatcg agttggtttg   1380

ataggatata agtttctgc tgaggatcgc ttggctgctg tttttgtgaa tggtgaaagt    1440

gatgaacaag tggttcttat aagccaaagt ggcactgtca acagaattaa ggttcgggat   1500

atttcaatac aatctcgatt tgcaagggaa gttattttga tgcgacttga tcattctgga   1560

aagattcagt ctgcttcatt gatctcagca acagattgtg agcctgagga agttcttact   1620

attgcacaag gctag                                                     1635


<210> SEQ ID NO 140
<211> LENGTH: 1248
<212> TYPE: DNA
<213> ORGANISM: Glycine max

<400> SEQUENCE: 140
```

```
atgctaaatt ttaataggac cagaagtcag cccaggtcta caagatctat gtctttggga     60
ggcatggatt atgtggatcc aaaaaggaag ggcaattttg ttggaaaagt ttttcttgct    120
gcagcattaa cggcattatg cattatcatg atcaagagat ctccatcttt gaatccccca    180
agtccgtttt ccatccgtga accaggtgtc actcatgttt tagtgacagg aggtgcaggc    240
tatattggtt cacatgctac cctacgactt ctgagggaaa attatcgtgt caccatagtg    300
gataacctgt cacgaggaaa tttgggtgct gttagggttc ttcaagagtt atttccagaa    360
cctggaaggc ttcaatttat atatgctgac ttgggagata aagaatctgt aaataaaata    420
tttttggaga ataaatttga tgctgtgatg cactttgctg ctgttgcata tgtgggagag    480
agcacactgg accctcttaa gtattatcac aatattacgt cgaatacctt gttggtattg    540
gagtctatgg ctaaatatgg tgtgaagaca ttaatatatt ctagtacatg tgcaacgtat    600
ggggaacctg aaaagatgcc tattatagaa ataacagaac agaaaccaat taatccatac    660
ggaaaagcca agaagatggc agaagatatc atctttgatt tttccaaaaa ttctaagatg    720
gcagtaatga ttctgagata cttcaatgtg attggatcag acccagaggg cagactaggt    780
gaggctccaa gacctgaact tcgagaacat ggtcgaattt ctggtgcctg ctttgatgca    840
gctcgtggta ttacaactgg cttaaaggtt agaggaactg actacaagac acccgatgga    900
acatgcatac gagactacat tgatgtaact gatttggttg atgctcatgt gaaggctctt    960
gaaaaggcac aacctggtaa agtagggatc tacaatgttg gcactggaaa gggtagatca   1020
gtgaaggagt ttgtgaatgc ttgtaaaaag gccacagggg tggacatcaa agtagactac   1080
cttccacgtc gacccggtga ttatgccgag gtgtatagtg acccttctaa gatcaaccgg   1140
gaactgaatt ggactgcaca atacactgac cttgagaaga gtttgcaggt tgcatggaaa   1200
tggcaaaaat ctcatcgtaa tggttatggc attttatctg caatctga                 1248
```

<210> SEQ ID NO 141
<211> LENGTH: 993
<212> TYPE: DNA
<213> ORGANISM: Glycine max

<400> SEQUENCE: 141

```
atggctaacg aaatccctca cgatgaggta gtgtgcgtta ccggcgccaa cggtttcatc     60
ggttcgtggc tggtccgaac cctcttggag aaggagaacc cacgctacac catccacgcc    120
accatcttcc ccggctccga cgcctcccac ctcttcaacc tccacccctc cgccgccagc    180
cgcctcaccc tcttccccgc cgacctcctc gacgccgccg ccctctcccg cgccatcacc    240
gcctgctccg gcgtcttcca cgtggcctcc ccctgcaccc tcgaggaccc cacagacccc    300
caaagagacc ttctcgaacc cgcggttcag ggcaccctga acgtcctaac cgccgcaagg    360
cgcgtgggcg tgcggcgcgt ggtgctcacc tcctcgatct ccgcgatggt gccgaacccg    420
gggtggccgg cggggcgggc cgcggacgag gcgtcgtgga cggacgtgga gtactgtaag    480
ggaaggggga agtggtaccc ggtggcgaag acggaggcgg agagggcggc gtgggcgttc    540
gacggcgtgg aagttgtggc ggttctcccg gcgacgtgtt tagggccgct tctgcagccg    600
gatctcaacg cgagctccgc cgtgctgcgg gagctgatga tggggtcgag ggagacgcag    660
gagtatcact ggttgggtgc ggtgcatgtg aaggacgttg ctaaagctaa tgttttgtta    720
tatgaaaccc ccactgctgc tggtagatac ctctgcacca atggtatcta ccagttttct    780
agttttgctg ccatggtctc tgaattgtac cccgaattcc ctattcacag gttcccagaa    840
gaaacgcaac ctggcctgac agcatgtaaa gatgcagcaa agagactaat ggacttgggt    900
```

cttgtcctca caccaattca agatgctgtg agagaagcag tggagagcct catagctaaa 960
ggcttcctgc aatgcacacc ctcacagagt tag 993

<210> SEQ ID NO 142
<211> LENGTH: 2664
<212> TYPE: DNA
<213> ORGANISM: Glycine max

<400> SEQUENCE: 142
atggcttcac attgcttcct tcgttttcct ccttccttaa accctaaata caaaagactt 60
cccaaacccc gttattaccc ttccatttcc tcgcgaattc aaaccccaaa acctgacaat 120
gacgacgaca atgacaaaac cccaaacgac aaccgcttcg acttcctcaa actctccgta 180
accctcactg tcatctctgc ctccctccct caacccgctg ccgctgccgc cgccgccacc 240
aggaaggtaa agaaacggtc accgaaaaaa caatcagcca aaaaagccga aggtctttcg 300
ccggaggagc taaaaacatg gacaagtggc cttcccgtgg tctccgatcg ccttccctac 360
agcgaaatta tcgaactgaa gaagagcggg aagctgaagc acataattaa acctaattcc 420
gcgaaattga ggcaacgtgg cgaagcagtt cttgtagttt tggacgattc gagagtgttg 480
aggacagtgt tgccctcgct tgagagccat agcaagtttt gggattcatg ggatgagttg 540
aagattgatt cagtgtgtgt gaatgcgtac acgccaccca tcaagagtcc agagttgcct 600
acctctctgt tggcaaacat ttgggtgccc ccttttgtgc agaaattcat tacttacgtt 660
tttgaagaga ggcaaacaaa gcccaagaag gagtccaaga aagcggcgga gtatagggaa 720
atgaggatgc agttgcagag ggagaaggaa gaggagctaa ggaagtcgag ggaagagagg 780
gagaccatgg agaggaacac gagggctcgg aagaaggagg aggagaggag gaagaagagg 840
gagatcagga agaggaagta taaggaatcc ttgcgccagg cgagtgaccg aaacgagaga 900
atggcgtatt tctggtctga tttggcaaat aatagcaatg tggccaatgc acttggggtg 960
cttttcttct acattttta caggactgtg gtgcttagtt ataggaagca gaagaaggac 1020
tacgaggaca ggctcaagat tgagagggcc gaggctgagg agaggaggaa gatgagggag 1080
ttggagaggg agatggaggg aattgaaggt gatgatgagg agggtgagca ggggaaaggg 1140
gaggagaatg cttatttgaa aatggccaag cagtttatga aatcgggagc gcgtgtgagg 1200
agagcacaga acaagaggct tcctcagtat ctagagagag gtgtggatgt gaagtttagt 1260
gatgttgctg ggctgggtaa aattcggctt gaacttgagg agattgtcaa gttctttact 1320
cacggagaga tgtaccgaag gaggggagtg aaaataccag gtggcatact tctttgtggc 1380
cctcctggag tgggaaagac attgctggca aaggcagtgg ctggtgaggc aggggttaat 1440
ttcttctcta tttccgcttc acagtttgtg gaaatatatg tcggtgtagg ggcttctcgt 1500
gtccgagcac tttaccaaga agccagggaa aatgccccat ctgttgtctt cattgacgag 1560
ctggatgctg ttggaaggga gcgtggcttg attaaaggtt caggtggaca ggaacgtgat 1620
gctactctta atcagctcct ggtgtcctta gatggatttg aaggcagggg agaggtgatc 1680
actattgcat ccacaaaccg accagacatt ctggatcctg cacttgtgag acctggcagg 1740
tttgatcgga aaatatatat ccccaaaccc ggtcttattg gccgcataga aattctaaag 1800
gtccatgctc gtaaaaagcc aatggctgaa gatgtggatt acatggctgt tgctagtatg 1860
actgatggaa tggtaggtgc agagctggca aacataattg aggttgctgc catcaatatg 1920
atgcgtgatt caaggactga gattactact gatgacttat tgcaagctgc acaaatggaa 1980
gaaagaggaa tgctagatag aaaggaaaga agcactgaga catggaaaca agtagctata 2040
aatgaagctg caatggctgt tgtggctgtg aactttcctg atcttaaaaa tatagagttt 2100
gtcacaattg ctcctagagc tggtagggaa ttgggttatg ttcgggtgaa gatggattca 2160
gtcaaattta atcaaggaat gctcacacgt caatcccttc ttgatcatat tactgttcaa 2220
ctagctcccc gtgcagctga tgaactttgg tttgggagtg gtcagttgag tacgatatgg 2280
gctgaaactg cagacaatgc taggtctgca gcaaggacat ttgttcttgg tgggctttct 2340
gagaagtatc acggaatgtc caatttctgg gtgtcagacc gaattaatga aattgattcg 2400
gaagcaatgc ggattgtcaa ctcgtgttat gaacgtgcaa aagagatcct cgagcaaaat 2460
agaacgctga tggatgcttt ggtgaatgag cttgttgaga agaaaagctt aaccaaacaa 2520
gagttcgtcc gtctagtaga gttgcacggc ttcctaaaac caatgcctct cagcatactt 2580
gacatacgag ttgctaagtg tagagaattc caaaaattga tcgatagtgg aaaggaaaca 2640
actagtttga gtagccacgc ataa 2664

<210> SEQ ID NO 143
<211> LENGTH: 1404
<212> TYPE: DNA
<213> ORGANISM: Glycine max

<400> SEQUENCE: 143
atggcagaga caccaaccct cagaatccac gaagtctgcc ccatctcgcc gccacaagaa 60
accccatcaa ccactattcc cttcaccttc ttcgacgtcc tatggctacg cctcccccca 120
gtggagcgtc tgttcttcta ttccttccca aacccaacaa caacctcttc attcttcgac 180
accaccattc tcccaaatct caaacactcc ctctccctca ctctccacca cttccctcct 240
ctcgccggca ccatcacatg gccacttcac acacccctcc ccctcatcac ctacaccccc 300
ggaaactcaa tcccccttcag aatcgccgaa tccaacgcag acttcaacac cctctcttca 360
aacctctcag aagttaacaa ccaccgccga aacctaatac cccacttacc cacttcccac 420
gaagaagctt cggtgttagc ccttcaactc acccacttcc caaaccaagg ctattcgata 480
ggaataacaa gccaccacgc agcacttgat ggaaagtctt caactttgtt catgaaatcg 540
tgggcgcata tttgttctta cctcaatacc tcaccggaag aaccgttgct gttttcacta 600
ccgaagcatc taacaccttc gtttgataga tctgtcataa gagacccttt ggggatcggt 660
gagatttacg cgaagtcgtg gacgagcttc ggtggagcca ccaatgaccg aagcttgaac 720
gtgtgggata ccctcggtgg aaatcaaacc gatttggtta aaggattgtt tgagttgaca 780
ccgttggata tcaagaagct gaagaagtta gcggagtcca agtttgttgt cggagacaac 840
aagaagaaag ttagggtgac atcatttacg gtcacgtgcg cttacctgtt gtcatgcgcg 900
gtgaaagcgg agcaacccaa ctgcgaaaga gtgccttttg tcttcaacgt ggactgtagg 960
gcgcgtttgg accccccaat tccggaaacg tacttcggga actgcgtcgt ggctttgttg 1020
gcttcggcca agcgagaaga gcttttgggg gaagaagcgt ttttcaaaag cgttataggg 1080
ataagcgagg agttgaacgg gttagagggt gacgtgttga acggcgcgga caaatggatt 1140
ccgaagattc aatcggtggt atcggagact cctaggttgt tctccgtcgc cgggtccccg 1200
aggtttgagg tttacggcat tgactttggg tggggaaggc ctgagaaagt ggatgtcaca 1260
tccgttgata aaacgggtgc gttttcgctc tcggagagta gggatcatag tggagggatt 1320
caaattgggt tggcgttgac caagaatcaa atggaggcgt tttctagggt ttttgctcaa 1380
ggacttgagt ccttggaatc atga 1404

<210> SEQ ID NO 144
<211> LENGTH: 1068
<212> TYPE: DNA
<213> ORGANISM: Glycine max

<400> SEQUENCE: 144
atgatgaatt ccacagaaga agagtatcgt ggctgcgaga ttatggagaa agatgttcat 60
gtcacgtttc tcgagttaat gtactattta ctcccatctc cgtacgagtc ccaagagatc 120
aaccatctca ctctcgctta ctttgtcatc tctggacttg acatcctcga ctctctccac 180
aaagttgcga aggatgctgt tgtcagttgg gttttgtcct tccaagctca ccccggtgcc 240
aagactgatc tcaatgatgg gcaattctat ggctttcatg gatccaaaac ttcacagttt 300
cctccagatg agaatggggt tttgattcac aacaacagtc acttggcaag tacttattgt 360
gccatttcca tattgaaaat tgttggttat gaattgtcca atcttgactc tgaaacaatt 420
gtgacttcta tgaggaacct tcaacagcct gatggaagtt tcattccgat tcatactgga 480
ggcgaaacag atcttaggtt tgtgtattgt gcagctgcca tctgtttcat gttggataac 540
tggagtggca tggacaagga gaaaaccaag gattacatat tacgttgcca gtcttatgat 600
ggtggctttg gattagttcc tggtgcagaa tcgcatggag gtgcaactta ttgtgctatg 660
gcatctctcc gattaatggg attcattgaa gataatattc tctcaagttg tgcttcatct 720
tctttgatag atgcgccatt gctgctggac tggatcttgc agaggcaggg aactgatggg 780
ggttttcaag gtagaccaaa taaatctagc gatacatgtt atgcattttg gattggagcc 840
gttttaagga ttttgggggg cttcaaattt gttgacaata aggctctacg tggatttttg 900
ctttcttgtc aatataagta tggtggtttc agcaaattcc ctggggagta tccagaccta 960
taccactcct actatggatt cactgctttc agcctgttgg aagaatctgg cttgaaatca 1020 ctttttttcgg aactgggaat cactgaaaat gctgcactgg cactctag 1068

<210> SEQ ID NO 145
<211> LENGTH: 810
<212> TYPE: DNA
<213> ORGANISM: Glycine max

<400> SEQUENCE: 145
atggcgatta ttcattattc agcagcttca cgttgttgca tgccatcgct gcatcgcgct 60
tcgccttctc gctcggttct cgcgccctca atcttcttct tccgcgacgc tgctccgacc 120
ctcaggctcg acgtctcggt tcggtcccag cctccaggtt cggacggctt cggcgaaccc 180
atcaataaca aacacgcttc tcgtgatgcc tccgttgggt tatccgcttc ttcttcttcg 240
tcggtcatcg attttctcac tctctgccac cgcctcaaga tcacaaaaag gaaaggatgg 300
gttaatcatg ggataaaagg tgctgaatcg attgctgacc atatgtaccg catggcttta 360
atggcattga ttgctggcga tgttccagga ttgaatcgag aaagatgtat taaaatagca 420
ctcgtgcatg atattgcaga agctattgta ggagatataa caccatctga tggtgtgccc 480
aaggctgaaa agagcagaat ggagctggaa gctttgaaca aaatgtgtga acttcttggt 540
ggagggatga gagctgagga gatcaaagaa ctttgggaag agtatgaaaa caattcttct 600
gtagaggcaa atcttgttaa ggattttgac aaggttgaga tgattctgca agctctggaa 660
tatgaaatag aacatggaaa agtgttggat gaattcttcc tttcaactgc agggaagttt 720
caaactgaaa taggaaaaag ttgggctgct gagatcattt caagaagaaa atctttatca 780

-continued gcaaaaagac caagttcata tagtggctga 810

<210> SEQ ID NO 146
<211> LENGTH: 2373
<212> TYPE: DNA
<213> ORGANISM: Glycine max

<400> SEQUENCE: 146
atgctatctt tcgccataac cactcatgct ttccccgtta ttgccattaa caaatggaag 60
cagagacata tgcaaaggca aatgcaaagg gtgtcacttt cagcttccat tcaccatgac 120
agcttgagag tgctcgaatg ggacaagctt tgcgacttgg tcgcttcctt cgccaccact 180
tccttgggcc gtcaagccct caaggatcag ctatggtctc ttaatcaaac ttttgaggaa 240
agtcttaaac ttctcgagga aaccaatgct gccgttgaaa tgaacaagca tggcactctc 300
agattgcact tggggcacct tgatgctatg ctggtcaaaa ccgccattca acatgcccgg 360
agaagtatac cagtgagtgg ttatgaggca cgggccattg tggctcttct gcagtgtgct 420
gagatcgtgc agggtgatct caaggctgta attaaggaag acaaagattg gcataatcgt 480
ttcatgcctc ttacagaagt gataatggag tttgtcatca atagatcttt aattaaagcg 540
atagagcaag tggttgatga agatggctct attaaggact ctgcgagtcc agcccttaag 600
caggcacggc aacaagttca agtgattgag agaaaggtac aacagttaat agagagcata 660
atcaggaatg aaaagagtga aacatcaacc cttgaagtga ataacattga tggcaggtgg 720
tgtgtaagag tagattctgg acagaagacc agttttaagg gtctattgtt gtccagtgga 780
tccggagttg gaagtactat agagccactt tctgctgttc ctttaaatga tgagttgcag 840
cgagcaagaa gtttggtggt aaaggctgaa gcagatgtgc ttttggcatt aaccaaaaag 900
ctggaccttg atgatattga gaagacattg aacagtttgg ttgaactaga tgtgatcaat 960
gctcgtgcta cttatggtct gtcatttgga gggtcaagtc ctcatatatt tctgccagat 1020
aggagtagct cttctactgc agaagcattc ttaccaagga gcgaaaatct ctatggacca 1080
ttacccagca aaagggaatg gacgctatat cttctaaaag cttatcatcc tttattgctc 1140
cagagacata aggagaaatt gcggaaggcc aaaaagaatg tcaatcttgc tacttcagat 1200
gctgcactgg acaatgctcc gccagtacct gttgattttt tggtatctca gaaaactcgt 1260
gttatagtta taactggccc taatactggt ggtaaaacca tatgtttgaa gaccgtagga 1320
ttggctgcta tgatggcaaa atcaggtctc tatgttcttg cttctgaatc tgcgcaaatt 1380
ccttggtttg attctgtttt tgctgacatt ggtgatgagc agtccttatc acaatctttg 1440
tctacgttct ctggccactt gaagcagata agtaatatta aatcacagtc aacaagccag 1500
tcgctagtgc tactagatga ggttggtgca ggaacaaacc ccccttgaagg agcagcacta 1560 ggaatggcat tattggaatc ttttgcacaa gacagttgtt tgttgactat ggctacaact 1620
catcatggtg aattgaaaac actaaaatac agtgatgagg cctttgaaaa tgcatgtatg 1680
gagtttgatg aagtgaattt gaagccaaca tacaaggttc tttggggtgt accaggccgc 1740
tcaaatgcaa taaatatagc cgagaggttg ggactaccat ctgttgttgt agatactgct 1800
cgtatgttat atggttctgc tagtgcagag atagatgagg ttataactga tatggaaagg 1860
ttaaaacaag aataccaaga actattggat gaagcacgtc attatctgag gcactccaga 1920
ggactttaca atagtctatt gaacaccaga aggaagatca tagaatatag tactaatcta 1980
agatttaaga agatgagaga tgtgtccgag gctgcagcga tggcaagatc catccttcac 2040
aagaaagtga gggaattgga tgcatcagct aagcaacctt cacagaataa taaaaccatt 2100
agcagctcta atttatcagc aaccaacaaa agccaaactg ttgcagagaa caaagaaccc 2160
actattgctg ataaaagtgc atcttctgtt aaagttttta atcgatcaag atcagataaa 2220
tctgggcctc ccaaggttgg tgatatggta catgtctctt ccctcgggaa acaggtgact 2280
gttttaaaag tggattcatc caaaggagaa attgtagttc aagctggaaa catgaagttg 2340
aagctgaaac taactgacat tcaaagatca tag 2373

<210> SEQ ID NO 147
<211> LENGTH: 474
<212> TYPE: DNA
<213> ORGANISM: Glycine max

<400> SEQUENCE: 147
atggcttctt cttcttcttc tctgtttcgt tccattccca tttcttttcc acacacccaa 60
tgcgctctca aatccccgcg cctctcgctt cgtgcttcgg ccactccgag ccagaaggct 120
cggttcgtcg ctcgccgcaa ggagtccgtt tcggttcggc aactccaacg ccccctaatt 180
gagtacatgc ggttaccagc gagtcagtat tcagtgttgg atgcagagag gattgagcgg 240
gtaaacgaaa acacgtttag gtgttacgtt tataggttca agttcttcaa ctttgaggtt 300
tgtcctgtgt tgttggtgaa agtggaagag caacctgatg gatgttgcat caagctcttg 360
tcttgcaagc ttgagggctc gccaatggtt gctgcacaga atgacaagtt tgatgcagaa 420
gctgaggcaa ttttcttgta ctcttctcta ggaaaggaaa gtgaaaacat gtag 474

<210> SEQ ID NO 148
<211> LENGTH: 960
<212> TYPE: DNA
<213> ORGANISM: Glycine max

<400> SEQUENCE: 148
atggtttctc gccatttggc ttcttcgctc ttcctctgtt tcctctgttt cgagatctct 60
gtttcgtccc ttcgattgcc cggtttggac caagacgcca aggccacgca tggatcggtg 120
ctaaggttga acagaggtgg ctcttcagtg aagtttgatc ccacacgggt cactcagctc 180
tcgtggagtc ccagggcttt tctgtacaag ggggtttttat ccgaggaaga atgtgatcat 240
ttgatagttc tggccaagga caagctggag aagtctatgg tggcagataa tgattccggt 300
aaaagcataa tgagtgatat cagaacgagt tctgggatgt ttctcaacaa ggcacaggat 360
gaaatagttg ctggtattga agcccgaatt gccgcatgga cattccttcc tgtagagaat 420
ggtgagtcga tgcaaatatt gcactatgag aatggtcaga agtatgaacc acattttgat 480
tacttccatg acaaagctaa tcaagttatg ggtggccatc ggattgccac tgtattgatg 540
tatttgtctg atgttgagaa gggtggggaa acaatttttc ccaatgccga ggcaaagttg 600
ttgcagccaa aagatgagag ctggtctgaa tgtgctcaca aaggatatgc agtaaagcct 660
cagaagggtg atgccttgtt gttcttcagt ctccatctgg atgcaagtac agatactaag 720
agcttgcatg gaagctgtcc agtcattgag ggcgagaagt ggtctgcaac caagtggatt 780
cacgtgagtg actttgaaaa accattcaag caagtggata atggagagtg tgttgatgag 840
aatgagaatt gccctaggtg ggctaaagta ggtgaatgtg acaagaatcc actttatatg 900
gttggtgggg aaggagtaag aggaagctgt atgaagagtt gcaatgtctg cacttcttaa 960

<210> SEQ ID NO 149
<211> LENGTH: 282
<212> TYPE: DNA

<213> ORGANISM: Glycine max

<400> SEQUENCE: 149
atgttgttct tctcgtactt caaggatttg gtggggaggg aagtaatcgt ggagctgaag 60
aacgatttgg ccatcaaagg aacattgcat tctgttgatc agtacctcaa catcaagctc 120
gaaaacacta gcgtcgtcaa tcaagaaaag taccctcaca tgctttctgt aagaaactgc 180
ttcatcagag gttcggtagt gagatatgtg caattgcctc cagaaggggt ggacattgaa 240
ttattgcacg atgccacaag aagagaagcc cggggcggtt ag 282

<210> SEQ ID NO 150
<211> LENGTH: 744
<212> TYPE: DNA
<213> ORGANISM: Glycine max

<400> SEQUENCE: 150
atggtctatt tccatagctc aatctctctc tgcaagttcg ttgatcaatc atctttcatg 60
gcgaattcaa tttgttctgc ggatttcggt tcgaaatcga gacaaatcaa tcaccttcag 120
aagaatcgga gaacccctag ttcatcatca tcatcatcat catcatcgaa ttcccttcag 180
attccaccct gtgatcgatc tcgatcggca atggttgatg ttgtgatgtt cattgctgtt 240
gtttgtgcct gtggcttttt gttcttccct tatgtagagt ttttggtgac aaagtgttac 300
gaggttatta agggtgttgt gtttttgatt aaggaggagg tttctgtggc accttggatc 360
tatatttcca tagggttgag tgttgtgttt gctgcattgg ccacgtgggc tgtggtggct 420
tgcaccacta ggaagtgtgg gaatcccagt tgcaagggtc tgaggaaggc tgctgagttt 480
gacattcagt tggagactga ggattgtgtg aagaatttgg cttctgcgtc gtcgaatgta 540
gcgaaagatg gtggtggtgg aacgaagaag ggtctctttg aattgcctcg tgatcaccat 600
agggagctgg aggctgagct caagaagatg gcaccaccaa atggaagggc tgtgctcgtg 660
ctccgggcga ggtgtggatg ttctgttggt aggttagagg ttccaggacc aaggaagcat 720
cttcgaaaga tcaacaagaa gtag 744

<210> SEQ ID NO 151
<211> LENGTH: 1611
<212> TYPE: DNA
<213> ORGANISM: Glycine max

<400> SEQUENCE: 151
atgtttaacc attctgcgct ccattattat tttctcctct tcttcacgtg cacgtgctta 60
gcacgacagc aatgccagtt caagcaggag tgccaactcg ataccatcca tgcactgaaa 120
cctgacaacc tcatcgaatc ccaaggtggt gtcacagaga catggaacgc tagccaccct 180
gagctatgtt gcgctggcgt cgcctttatc aagcgcacca tcaaccccaa tggccttcac 240
ttgccatcct acgttaatta ccccgaactc catttcgtac tccaaggtga gggagtgttg 300
ggaattgtaa ttcctggttg tgacgaaact tttgaagagc cacaacggga gagggaacat 360
gatcgccacc agaaggttcg ttacctgaag cagggtgaca tattcgcagt tccacctgga 420
attccttact ggacctacaa ctacgccaat gtttctcttg ttgtaattac cctccttgac 480
actgccaatt tcgaaaacca gcttgatcgt gtccccagaa gattctatct tgctgggaac 540
ccaaaagaag agcacccttg tggacgcaag caagaagaag gtaacaatat aaacatgttc 600
ggtggtttcg acccacggtt cttagcagaa gcatcgaacg tgaaggtggg gataacaaag 660
aagcttcagt cacacatagg tgaccaaatc ataaaagtgg aaaaaggtct tagcattatc 720
aggccaccct tggaacacga agttagagaa gcagaagtag aagaaaaacc caagacccga 780
gaacactgtg aatgccaaaa agaaagaaaa cacaaagaag gagaaggaga agaagaggtg 840
gtacaagaga aagaaataag aaagcgcaag caccacatag gagaacacga gggatgtggt 900
gaatgcgaag ataaagaaga ggaagagcaa agtagaagcc gagaacgcgg cgagtggcat 960
gaacataaag gacaacaaca tggaaaagaa aaaggaagag agagatataa ggaaggtggt 1020
gaagggagag tgcgtagcaa tgtgttggaa gaaatcttgt gcactttgaa gctgcacgag 1080
aacattgctg acccatcaca cgccgacata ttcaacccta gagctggtcg cgtacgcacc 1140
atcaatagct tgaccctccc cgttctcaaa ttgctccgtc tcagcgccca atgggttaaa 1200
ctctacaaga gtggtattta cgtgccacac tggagcatga acgcaaacag cgtggcctac 1260
gtgacgagtg gaggagggtg ggttcaggtg gtgaactccc agggaaagtc ggtgttcagc 1320
ggcgctgttg gaaggggtcg agtggtggtg gtgccgcaga actttgcggt ggcgatacaa 1380
gccgggaggg atgggatgga gtacatagtt ttcagaacaa acgacagagc catgatgggg 1440
acgctggtgg ggcccacttc ggccatcact gccatcccag gagaagtgct tgcgaatgct 1500
tttgggctga gcccggagga agtgagcgag ctcaagaata atagaaagga ggctgttttg 1560
tctagccctg cttctcatca ctctccaaat cccctcattg tcaccatgta a 1611

<210> SEQ ID NO 152
<211> LENGTH: 1455
<212> TYPE: DNA
<213> ORGANISM: Glycine max

<400> SEQUENCE: 152
atgagtaact ctacagagag aaagccacat gcactgttga caccattacc acttcaaggc 60
catatcaacc cattgttgag attagcaaag ctgcttcatc tgagaggctt tcacataacc 120
tttgtccaca ctgaatacaa cattaaacgc ttgctcaact caaggggtcc taaagccctt 180
gatggccttc aagactttca ttttgagacc ataccagata gtcttccccc cacatatggt 240
gatggtgatg tcactgaaga cgcagtgtct cttgctaaat cagtgagaga gaagatgctc 300
gtaccctttc gcgatcttct tgctcgtctt catgattctt ccactgctgg ccttgtacct 360
ccagttactt gcttggtttc tgattgttgg atgtttttta ctatacaagc tgctgaagaa 420
ctttcacttc ctattgctct attttcaccg atcagtgctt gttccttaat gtttgttttg 480
cactaccgtt ctctttttga taagggtctc ctaccactca aagataagag ttatttgaca 540
aatgggtatt tggacacaaa agtggactgg ataccaggaa tgaaaaactt taaactgaag 600
gacttgcctg agattatatg gaccatagat ccaaatgact tcatgttaaa atttctcatt 660
gaagtaggag ataatatgca aagaagctct gctattattt taaatacttt tgctgaactt 720
gagagtgatg tattgaatgg tctcacctct atgttccctt ctctttaccc cattggccct 780
ctcccttcat ttttaaacca aagtccacag aaccacttgg cttctctagg ttccaatctt 840
tggaaggaag atactgagta tcttgaatgg cttaaatcca aggaaccaaa gtctgttgtt 900
tatgtgaact ttggtagcat cacagttatg tctccagagc aacttttgga gtttgcttgg 960
ggtttggcca acagcaagag acccttttg tggatcatta ggcctgacct tgtcgtgggt 1020
ggctcaatga ttttatcatc tgagtttgtc aatgaaactt tagatagagg cctaatagca 1080
agctggtgtc cacaagagga agtgctgaac cacccttcaa ttggtggatt cttgactcat 1140
tgtggatgga actcaacaat tgaaggcatt tgtgctggcg tgccaatgct gtgttggcca 1200

-continued

```
ttttttgctg atcagccaat aaactgtaga cacatttgca aagaatgggg cattgggatt   1260

gaaattaaca ccaatgcgaa gagagaggag gtggagaaac aggtcaatga attgatggag   1320

ggagagatag gaaagaagat gaggcaaaag gtcatggaat tgaagaagaa ggcagaggag   1380

ggcaccaaac taggtggtct ttcacacatt aacttggaga aagtgatttg ggaagtgctg   1440

cttaaaaaaa attag                                                    1455
```

<210> SEQ ID NO 153
<211> LENGTH: 1341
<212> TYPE: DNA
<213> ORGANISM: Glycine max

<400> SEQUENCE: 153

```
atggcttctc gaaaccatga ggtatcaatg gtaaaggaga atggtggtgg tgggaacaac     60

ctgaaggggt tgagcaagga aatgagacat ggcagaacgg cacataacat gtcatcatct    120

tctttgcgca agaaatctga cctaactctt gtgtctaagg tttgctctgg ccatgtaagg    180

aatgtgttgg tgaatttgca agaggttatt cttggaacca agctctctat tcttttccct    240

gccattcccc tagccattgt tgctgaaggc tatggctttg gaagatcttg ggtttttgtg    300

ttgagtttac ttgggctcac accacttgcg gaacgagtca gcttcttgac agaacaagtt    360

gctttttaca ctggtcctgc agtgggagca cttttgaatg caacatgtgg gaatgctaca    420

gagctcatca tagcaatttt tgcccttagc cataacaaaa ttgctttggt caaatattct    480

ctcttgggtt ccataatttc taaccttctt ctggttcttg gaacctctct attcattggt    540

ggcctagcaa atcttagtca ggaacaaaaa tacgacagaa aacaagcaga tatgaacttg    600

cttatgttgt ttgtggcatt gctttgccac ttgctgccat tgttgtttca ttatgttggt    660

gcctcagcag ctgacactgg agactcatct ctgcagttgt caagagctgc tagcattgtt    720

atggtgattg catattgtgc ttaccttgtc ttccaactgt ggactcacag gcagctattt    780

gaagcccaga atgaagatga tgaagagggt ggcagtgatt cagaagcagt gataggattc    840

tggagtgggt ttacttggct ggttgggatg actatgacca ttgctttgtt gtctgaatat    900

gtggtgcaaa caattgagga tgcatctgat tcatggggtt tgtctgttag cttccttagc    960

ataatcttgc ttccaatttt tggcaatgca actgaacatg cagcagcaat catatttggt   1020

ttcaagaaca aactggacat ctctttgggt gtttctttgg gttcttcaac tcaaattagc   1080

atgtttgtgg ttcccctatg tgtgattgtt gcttggatta tgggtatcaa aatggacctc   1140

aacttcaacc tcctagaaac agcttctctt tctttggcaa taacaatcac agccttcgca   1200

ttacaggatg gaacttccca ctacatgaaa ggccttgttc tcatactctg ctatattgtt   1260

attggggcat gctttttcgt acaaagaaca ccccctaacc aaactaatgt ttctaacata   1320

acgcttaaat ccgcaaactg a                                             1341
```

<210> SEQ ID NO 154
<211> LENGTH: 3231
<212> TYPE: DNA
<213> ORGANISM: Glycine max

<400> SEQUENCE: 154

```
atggcagcag cactggtagg tggtgccttt ctctctgctt tccttgatgt ggttttcgac     60

aggctggctt cacgtgagtt tgttcacttg atccttggaa ataagcttag caagaagttg    120

cttcaaaagt tggagaccac tctcagagtg gttggagctg tgcttcatga tgccgagaag    180

aaacagatca caaacaccaa tgtcaaacac tggctcaatg atctcaaaga tgctgtctat    240
```

gaggccgatg acttactcga ccatgttttc accaaagctg ccacccaaaa gaaggtaaga 300
aacttttttt ctcgcttttc cgataggaag atcgttagta agttggaaga catagttgtc 360
acacttgagt ctcatttaaa actcaaggag agtcttgatt tgaaagagag tgcagtggag 420
aacttgtcat ggaaagctcc atcaacatct gtggaagatg gatctcatat atatggtagg 480
cagaaagata aggaggccat aatcaagttg ttgttggagg ataacagtga cggtagtgaa 540
gtgtctgtgg ttcctattgt gggcatgggt ggggttggaa aaactacttt ggcccaactg 600
gtgtacaatg atgagaatct ggtagagata tttgacttta aggcatgggt ttgtatttct 660
aaagaatttg atgttctgaa gatcacaaaa actatgatag aggcgattac tggagagcct 720
tgtaaattga atgatctgaa tctacttcat cttgaattga tggacaagct gaaagataaa 780
aaattcttaa ttgtcttgga tgatgtttgg acagaggatt atgttgattg gagtcttatt 840
aagaaaccat ttaaccgtgg gattaggaga agtaagattc ttctaacaac ccgcagtgaa 900
aaaacagcat ctatagtcca aactgttcac acctatcatc taaaccaatt gtcgaatgaa 960
gattgttggt cagtgtttgt gaaccatgcg tgtctttcct ctgaatcgaa cgagaacaca 1020
acaacactag aaaaaattgg aaaggagatt gttaaaaggt gcaacggact gcctttagca 1080
gcacagtcgc ttggaggcat gttgagaaaa aagcatgaca tcgtggattg gaataatatt 1140
ctgaatagtg acatttggga actttctgaa agtgagtgta aagttattcc agcactgaga 1200
cttagttatc attatctccc tccacattta aaacggtgct ttgtttattg ttccttgtat 1260
ccacaagatt accaatttga aaaaaatgaa ttaatcttgt tgtggatggc cgaagatctt 1320
ttgaagaaat caagcaaagg taggacttta gaagaggttg gtcatgagta ttttgacgat 1380
ttggtttcga gatcattttt ccaacgttca aacacaagta gaagtagttg gccttatggc 1440
aaatgttttg tgatgcatga cctcatccat gatctagcca catcactcgg tggagatttt 1500
tactttagat cagaagaact tgggaaagaa acaaagatca agaccaagac tcgtcatttg 1560
tcatttacga aattcaattc ttcagtcttg gacaactttg atgttgttgg tagagcaaaa 1620
tttctgagaa ctttttttgtc cattatcaat tttgaagctg ctccattcaa caacgaggag 1680
gcacgatgta tcatagtgtc gaagcttatg tacttgagag ttttatcatt ttgtgacttc 1740
cgaagtttgg attctttgcc tgattcaata ggtaaattga tccatctgcg ctatttagat 1800
ctttctgatt caagtgtaga aacactgcca aagtcattgt gtaatttata caatctgcaa 1860
actttgaagt tgcgtagttg cagaaagctg actaagttgc ctagtgacat gtgcaatctt 1920
gttaatttgc gtcatcttga gatattttgg actcctataa aagagatgcc gagaggaatg 1980
agtaaattaa atcatttaca acatctggat ttctttgctg tgggcaagca cgaagagaat 2040
ggaatcaaag aattgggagg actttcaaat ctttgtggtg aacttgaaat taggaagttg 2100
gagaatgttt cccaaagtga agaagcgttg gaggcaagga tgatggataa aaaacacatt 2160
aatagtttac agttggaatg gtctagattt aacaacaaca ggaccaactt ccaacttgaa 2220
atagatgtgc tttgcaagtt acagcctcac tttaacattg aatcgttgca aataataggc 2280
tatgaaggaa ccagatttcc agattggatg ggaaattctt cctactgcaa tatgattagt 2340
ctaaaattgc gtgattgtga caactgtagt atgcttcctt cacttggaca actaccttct 2400
ctcaaggtcc ttgaaatttc agtattgaat aggctgaaga ctattgatgc aggtttctac 2460
aagaatgaag aatgtcattc tgggacgtcc tttccctccc ttgaatctct ggccttttat 2520
ggcatgcctt gctgggaggt gtggagttcc ttcgattcag aagcttttcc tgtgcttaaa 2580

```
agtctttaca tacgtgactg ccctaagcta gagggaaatt tgccgaatca ccttcctgtt   2640
ctgaaaaaac ttgcgattaa gtattgcgag ctgcttgtct cttctctccc aacggctccc   2700
gccattcaaa gtttggaaat aagtgaaagc aataaagtag cactgcatgc gttacctcta   2760
ttggtagaga ctatagaagt agaaggaagc ccaatggtgg agtccatgat ggaggccatc   2820
actaacatcc aaccaacttg tctccggtct ttaacattaa gggattgctc gtcagccgtg   2880
tcatttccag gtggtcgttt acctgaatca ctgaagagac tatttttttgg tcaacgtcac   2940
cttggttttt tcggtcaatg cgacaaagct tgttaccagg aacaacttga ggcacttgcg   3000
gactcgcttg tcaggttttt catcattgac atgcaagctc agatggcaag agaccagaag   3060
gagatcctgc ttaagaactg ttggaatttg aatcagtggg aacttgcagc aagcaagcaa   3120
cagaagcaag gggtgcaat tagaaaacaa gaccaagaga gcaattacaa gacccactta   3180
cctcaaggat taggtgtgaa acaagcaggt gcatcatatc tggaagaatg a            3231
```

<210> SEQ ID NO 155
<211> LENGTH: 2451
<212> TYPE: DNA
<213> ORGANISM: Glycine max

<400> SEQUENCE: 155

```
atgcctccga agacggcgaa gcgagggtcc gcgtcgagcg cctcgaagag gggtggcaga     60
ggtggcaggg gaaccccgaa ggctgcacag aaccaacagc agcatgaaac tgcggaggag    120
acagtgaagg ttgaagagaa acaacaaccc gtggttgttg ttgctgctga ggaggaacag    180
cagaaggtgg tggtggaaaa agagattcct gctgttgaag agaacgagtc cgctgtggtt    240
attgaggata aggctattga catgaatcaa atggctccgg aggctgtgga agaaacgtcc    300
catgcggcta gtgggttgag cttggtgaaa aatgatgaag aggaggttaa ggagtccata    360
gatgaatatg agaaagatga acgcttagat ttggaggata atgatcctga gtatgaacct    420
gaggagtatg gtggagttga ttatgatgag aaggaaattg aacaagatga gggtcatgag    480
gtaggaaatg aagtagagga agaagaggct gaagataatg taggtgaaga agagggtgat    540
acaggtgagg aagaagtcga agatgttcat gacgaacttg agggtgaaga ggagcatgag    600
catgctggtg aggagcgtga gcatccagac tttgctgacg ttgaggaaga ggaacaccga    660
gaagtcgtga aggagaggca aaagcggaaa gaatttgaag tttttgttgg gggcttggac    720
aaggatgcta ctgagagtga tctgaggaag gcttttggtg aagttggggt ggttacagag    780
gtcaggttga tgatgaaccc tcaaactaaa aagaacaagg gatttgcatt cttgcgtttt    840
gaaactgtgg aacaagcaaa acgagctgta gcagagctca aaaatccagt gattaatggc    900
aaacaatgtg gtgtgactcc tagtcaggac agtgataccc tctatttggg aaacatatgc    960
aagacatgga caaaggaagc tttaaaagag aagttgaagc attatggagt caccaatgtt   1020
gaggatttaa ctttggtaga agatactaat gatgaaggaa agaaccgtgg atttgcgttt   1080
ttggaatttc cttctcgttc tgaagctatg gatgccttta agcgactgca gaggagggat   1140
gttgtatttg gagttgataa gcctgcaaaa gtttcttttg cagattcctt tattgatccg   1200
ggtgatgaaa ttatggcgca ggttaaaact gtgtttattg atgcattgcc tccttcatgg   1260
gatgaagatt atgtccggga tcttctcagg aaatatggtg agattgaaaa gattgagctt   1320
gccaggaaca tgccagctgc tcggaggaag gactacgggt ttgtgacatt tggctcacat   1380
gatgctgccg taaaatgtgc tgatagtatt acaggcacag agttgggtga gggagacaag   1440
aaggcaaaag ttagagcaag gttgtctaga ccactccaga gaggccgcgg aaaacacatt   1500
```

agtcgtgggg actatcgttc tagtcgggga tctggaatga tgacgcggcc ttcatggagc 1560
cgacctgcac ctcgttcttt tccttctcgt agtgtaagag gagttggaag tcgtgctcca 1620
cctgtcagac cagttagtgt gagagataga cgccctatga tgtccatacc tgcaagaagt 1680
aggccagtgc ctcctccatc tagatcttat gataggagac cagttgctcc tgcatatcca 1740
aaaagtagca tgaagagaga ttatggtcgg cgtgaggata taccacctcc aagaagtaga 1800
gttgctgtag attatggctc aagggttgct tctgaaagac gaacatctta cagggattat 1860
cctgctcgtg gtcctggcta caccgagctc cctagaagca catctcgtgc tgcaccaagg 1920
agaggctatg tggatgatgg gtatggccag agatttgaga gggctcctcc tcctcctcct 1980
cctccccatc taagttaccg tgaaggacgt ccccgagatt atgatgctct gtctggctca 2040
aaacgttctt atgctgctat agatgatgtt cctccacgat atgctgatac tggtgctcgc 2100
caatcaagag ctcgactgga ctatgactat ggcggtagtg cttcacagta tggagatgct 2160
tatggtgata gacttggaag atctagtatg ggatatggtg gtggcagcag aagttctatt 2220
tccagtcaag attcacatgg gttgtatagc agtcggcagg gcatgagtta tggaggaggt 2280
tcttttggta gtggtgatgt tggtggcatg tattcatcaa gttatggtgg tgattacatt 2340
tctcgtggaa gtgatgttgg tggcagctca tattcatcaa tgtattctgg aaggggtgtg 2400
ggtggtggta gcagttatat gggtggtggc ggatcaggat cttattattg a 2451

<210> SEQ ID NO 156
<211> LENGTH: 624
<212> TYPE: DNA
<213> ORGANISM: Glycine max

<400> SEQUENCE: 156
atgtacgctg atcgcgtgga gggtggagca aggaggccag tgaaggaacg ccttaatgat 60
gtgaatggtg tcagtggctc tactcgcccg cagcagcagc gtcaaatcac tggcaagagg 120
tcaaggcaag atgacaagtg ggaacatgat ctctttgaca atgacgaacc ccggatcact 180
aatcgcaaag ttagtgctca agatcttcgc ttcaagcttc aaaggaaggg tcttcaacct 240
gcatctcaga gtggaaagag ttctgcccca aacgtgctgg atctccgtga aaggctatca 300
gggacaatgg caccacaacc tacaaattat gatctgccta agacaaaagt tattaaacca 360
agcagtaaaa gtgttggtgt tgaggctcct gcagtgcaga tcaaaaggcc agctgaccca 420
gctcctaaaa agtcatggaa ggctggtcct tcagttgatg aatttttgcg gtccttgggt 480
ctcgaaaagt atctcataac ttttcaggct gaagaagttg atatgacagc tctcaatcat 540
atgactgatg aagatctcaa ggctatgggc ataccaatgg gaccaagaaa gaagatactt 600
ttagcactgg agtcgaaagt ctaa 624

<210> SEQ ID NO 157
<211> LENGTH: 8598
<212> TYPE: DNA
<213> ORGANISM: Glycine max

<400> SEQUENCE: 157
atgcatcacg tgtctgtcaa tattagtgat gaaaatcaaa gaggcagaag cggagattta 60
cttcttgttg ccaagttaga taattggggt atttggtggg tttcaatggt gaagcttgat 120
gaaagaataa acatagttca gtcagttgag tggatggatt tccaattttc tgataatctt 180
cttgtctgtc ttaattcttc tggcttgatt gttctctatt ctgcaatgtc cggtgaatac 240

-continued

```
atgacacatt taaatgtttt acaggagact tgtggcctta acccccattt taatttgcaa    300
gggttagaaa agttatattc acacgataat atatatgcta aacaagagtg tagcattaag    360
gataacatgt ctgaccagca gagtgattct tttaggagat cattcaagag gttagttgtt    420
gcttcacaca cctccctttt agctgtggtt gatgaatgtg gtgtgatcta tgtgatctct    480
ttgagggaat atatacctga caaaagttat tcatctgaga agttgcttcc acattgtcag    540
caatttgggc tgggaatgtt ggttggctgg ggagttggtg gttctgatat agatcgccaa    600
gcagtatact ccaatttatc tggacatttt caatcaaatg atttaaacat aaaacatgga    660
agtgttgctt ccttagacaa agctgtggca ggtaatgcac ttcagaaaac taatggctgc    720
acattcaaag aaaaggggaa tttggttggc tcctattcta gtggtttttc tgctacttct    780
aaagtaaata atggtcacaa atttcttggt tatgatgtgc aatcacctgt tatgagaaag    840
atattacttc ccaattttag agtctctgag gatgattcta tttgtttttc tcctttggga    900
attactattt tctctaaaaa gaagtgtgta aagaatcaga agggttctca gcttatccat    960
tttaatctgc aagtgaagtt agaagtccgt gatgacaact tcttagacag tgtatatgat   1020
gtataccact ttgatggaaa agatgttatt ggagaagcaa ttggttgcac attccaaggt   1080
tgtttttata ttgtgagaga tggtggtcta tcagtatata ttccctccat ttcaatttta   1140
tcaaattttc ttcctgttga gtacattggt tatcgtcaat caagtaagga tatggggatt   1200
tcagttctac ttaaagacaa tctaaaaata aaagaaccaa ccaaaaggtt ttctccttgg   1260
aaagttgaaa ttttggacag agttcttctg tatgaaggca ctgaaatggc agatcaattg   1320
tgtttgaaaa atggatggga catcaaagtt tctcgtattc gtcaattaca aatagcattg   1380
gactacttga aattttatga aatagaaaga tctttggaaa tgcttgtgga tgttgatcta   1440
gcagaagagg gaattttgag attgcttttt gctgctgtgt atcttatact taataaaggt   1500
ggcaatgata gtgaaacttc tgctgcttct aggcttcttg cactggccac ttgctttgca   1560
acaaagatgc tccataaata tgggttgcta caacataaaa aggatacatg catagcagag   1620
ggctttaaca agacgggatt actatctctt ccaccaattg aaccagttaa actaaaaact   1680
gaggtggatt ttgctcagaa actttgtgag atagctcatt tcttggagat catccgaaat   1740
ctgcaatgta gacataggtc aatatttcta agggccagtc aaggattggt cgacagtgga   1800
gaagagtcat ctttaataag tacagacatg ttgcaggaag aatcccaact ttcaattctt   1860
ccatcagatt tagagtcatt ggatgtgttg aaccaacatg agctttcttt tcctctacca   1920
ggcggcaaca ataatgaaaa tcttgtgctg gtgcctgttg attctgagtc tcatttggtc   1980
tcagatgaat ttggcagcat atctcattta accccattag aaggaatttt aggaaagaaa   2040
gttttgcctg tggaaaatcc aagagagatg atggcacgtt ggaagctaaa taatctggac   2100
cttaagactg tggttaggga tgctttgctc tctggccgtc ttcctttggc agttctgcat   2160
cttcatcaaa tgaatgattt cgttgctgat aaagagcctc atgatacttt tactgaagtt   2220
cgtgacattg gcagagctgt tgcttatgaa ttatttttga agggtgaaac tgaacttgct   2280
gttgctacac ttcaaagact tggagagaac attgaatctt atcttaaaca acttctgttt   2340
ggcactgtaa ggagatcctt gcgaatccag attgctgagg aaatgaaaag atatggttat   2400
ctaggaccat atgagtggaa gatattggat gatatgtcac tgattgagag tctctatcct   2460
agcagtagct tctggaaaac atataatcgc cgactgaaag aaatcagcat tgcaccggac   2520
tctgttttac cagtggaaaa taaattaagg ctcttgcata accattcatt tcatagtcat   2580
gtcattgaat gtggtgagat tgatggaatt gtctttgatg catggattga tattagtgaa   2640
```

-continued agttcctctg ctctggaagt tgatgaagat gatgctcatg ttggatattg ggccgcagct 2700
gctgtctggt ttgatgcctg ggaccaaaga actgttgatc gtatgatatt gaatcaatct 2760
gttcattcgg acaatcctat attgtgggag tcacaacttg aatatcatgt ttgccgtaac 2820
cactggaagg aagtctttag actgctggac ttgatgcctg catatgtcct atcggctgga 2880
agccttcaac tcaatttgga tcttttacag cctgcctcat ctttaggatg caatatgaat 2940
atgaagtctt ctaattatgg aaatttcttg tgctcttttg aagaattgga ttctgtattt 3000
atggaagttc cagatgtcca aatgtatagg ttttcacctg atatatgttc tgggtggatg 3060
aggatgcttg tggaggaaaa gcttgcaaaa agatttatat ttttgaagga atattgggag 3120
gggacattgg agatgataac tctcttggct cgttcaggtt tcatatctgg cagagataag 3180
atctgcttgg aggatgatct tactaagatg tcatctgtca gagatggagc tgtacaagct 3240
ttgcataaaa tatttgtaca tcactgtgca caatataact tgccaaatct tttggacctt 3300
taccttgatc atcatcgttt ggccctcgaa aatgattcac tttatgcatt acaggaaact 3360
gctgttgatt gtgaatgggc aagatggcta ctcttatcga gagttaaggg gtgtgaatat 3420
gaggcctcac ttgccaatgc tcgatcgata atgtcacgta atttagttcc tagaagtggc 3480
ctcagtgttc tggagttaga tgaaataatt cgaacagtcg atgacattgc tgaaggaggg 3540
ggagaaatgg cagccttggc aaccctgatg catgctgctg ttccgattca aagctgctta 3600
aatagtggtg gtgtaaatag gcatagttat tcctctgccc agtgcacatt ggagaacctt 3660
aggccaactt tgcaaaagtt ccccacattg tggcgcactc tcgttggagc atgtcttgga 3720
caagacacaa tggccttgct ggtccctaag gcaaaaactg ctttatccga ctatcttaat 3780
tggcgtgatg acatcttctt ctctactggt cgtgatactt cacttctaca aatgcttcca 3840
tgctggtttc ctaagcctat acgcagattg atacagcttt atgttcaggg tcctcttgga 3900
tgccaatcat tttcagggtt ccctacaggc gaaactttgc tgcacagaga cattgattta 3960
ttcataaatg ctgatgtaca tgctgagata aatgcaatct cctgggaggc aacgatccaa 4020
agacacattg aagaagaatt atatggtcct ttacttgagg aaaatggatt ggggcttgag 4080
catcttttac atcggggacg ggcattggct gcttttaacc aaattcttgg ccatagaatt 4140
caaaatctga agtcagaagg ggaatctagt acttcagctc atggacaaac taacattcaa 4200
tcagatgttc agacacttct ctcaccacta ggacaaagtg aagagactct actttcatct 4260
gttttgccaa ttgctattat gcattttgag gattccatgc ttgttgcttc gtgtgctttt 4320
cttatggagc tatgtggttt atcagccaac aaactgcacg ctgatattgc tgtgctaaaa 4380
cggatatctc tgttctacaa atcaagtgaa aataatgaaa atctcaggca attatcacct 4440
aagggatctg tgtttcatgc aatatcccat gaaggtgatg taacagaatc tcttgctcga 4500
gctttagctg atgaatattt gcacaaggat tctcctgtaa ctggtactga gactgtaagt 4560
aaacaacctt cacgagctct tatgcttgtg ttgcaccatt tggaaaaggc tagccttcct 4620
cggttggttg atggaaaaac atatgggtca tggctattaa gtggaaatgg tgatggaaat 4680
gagttaagat ctcaacgaaa ggctgctagt cagaactgga ctttggtaac aaatttttgt 4740
agattgcacc agcttccatt aagtactaag taccttgctg tattagctag agacaatgac 4800
tggattgaat ttttgtctga agctcagatt ggaggatatt catttgatac agtagtccaa 4860
gtggcatcaa aggagtttag tgatctgcgt ctccgacttc atatgttaac agttttgaga 4920
gcaatgcagt caaagaaaaa ggcaagcact gtattgttct tggattcact ggagaaaggc 4980

-continued

```
agtgaaacaa cctttcctga tgaaaacatg ggtgttccag ttgaactctt ccaaatatta   5040
gcagagtgtg aaaagcaaaa atgttctgga gaggctctct tgaggaaagc aaaagagttg   5100
tcatggtcaa tattggcaat ggttgcttca tgtttccttg atgtctcttc attgtcatgc   5160
ctgacagttt ggttggaaat tactgcagca agagaaactt catccattaa ggtgaatgat   5220
atcgcttccc agattgcaga caatgttgga gcagctgtaa atgctactaa tgccttgcct   5280
gtcggtgaca gagtacttac atttcattac aataggcaga gtcctaaacg tcgacggcta   5340
ataactcctg tttcactaga ctcctctgct tctgcaatat ctgacatctc tagctcttct   5400
ataagtgaaa aaatatttga ttcccaaggt aaaactatgg agaatgatag aaaaatagaa   5460
cattttggat gcattaatgt tcctagtaat tccgatgaag ggcctgcttc tctctcaaag   5520
atggttgcag tgctttgtga acaacaattg ttcttgccct tgctaagggc attcgagatg   5580
ttccttccat catgcccctt gcttccattc atccgcgctc ttcaagcatt ttcgcaaatg   5640
cgcctctcag aggcttctgc acatttgggt tccttttctg cacgaattaa ggaagaacca   5700
atctacttac aggaaaatgt aggaagagag gcgcagattg gggcatcatg gattagttct   5760
actgcttcaa cagctgctga tgctgtgctt tcaacctgcc catctcctta tgaaaaaaga   5820
tgcttactgc aacttcttgc tgctactgac ttcggtgatg gtggacatac tgcagcatac   5880
tatcgaagga tttattggaa aattaattta gcagagcctt tacttcgtaa agataatgag   5940
ttgcatttag gtgatgaaat ttcagatgat gcttcactct tatctgcact agagaataat   6000
aggcactggg agcaagcaag gaactgggcc aagcagttgg aggccaatgg tgcaccctgg   6060
aaatctgcta cgcatcatgt tactgaatct caggctgaat ctatggtagc tgaatggaag   6120
gagtttcttt gggatgtgcc agaagagagg gttgctttat ggagccactg ccacacacta   6180
ttcatcagat attccttccc ttctcttcaa gctgggttat tttttcttaa acatgccgaa   6240
gctgtggaga aagatcttcc tgcgagggag cttcatgaac ttttattgct ttctctgcaa   6300
tggctgagtg ggatgataag tctttccaat cctgtctgtc cattgcaact tctgcgtgaa   6360
attgaaacca aagtatggct cctggccgtt gagtctgaga ctcaggtgaa gagtgaagga   6420
gatttcaatt ttaccttttc caccagggag agtggtatca agaacgactc cagtattatt   6480
gatcgaactg ctagtataat agcaaagatg gacaaccata taaatacaat gaggagtaga   6540
attgtagaaa aatacgagtc cagggaaaat aaccaaatcc cccacaagaa tcaagtgatg   6600
gatgctggtc tttcaactac ttttgctggg aatatgaaga caaaaagaag ggccaaagga   6660
tacatggcat caaggcgccc acctcttgaa tccacagata aaaatgctga tactgatgat   6720
ggctctagta ctattggttt aaagaatgag ttgcagctgc aagaggaaaa cataaaagtg   6780
gaaatgtctt tttctaggtg ggaagaaagg gtcggaacag cagagctaga aagggctgta   6840
ctttccttat tggaatttgg acaaattgtg gccgccaagc aactacagta taaattctct   6900
cctgggcaaa taccatctga gtttagactt gttgatgcag ccttgaagct tgctgctatt   6960
tcaacacctc ctagcaatgt atcagtgcca atgcttgatg aggaagtgcg ttcagttatg   7020
cagtcatacg gtataatgaa tgataagcac tatgttgacc cgctgcaggt tttggagagt   7080
ttggtgacca tttttattga aggcagtggg cgtgggctgt gtaagagaat aatagcagtt   7140
ataaaagctg caaacacctt gggcctctca tttttgagg ggttcaacaa gcaaccaatt   7200
gaactactac agctgctttc gcttaaagca caagattcct ttgaggaggc caactttctg   7260
gttcagactc atccaatgcc agcggcaagt attgctcaaa tacttgcaga atcttttcta   7320
aagggtgtgt tggctgcaca tcgtggagga tatatggatt cacagaagga ggaagggcct   7380
```

gctccattgc tgtggagatt ttcggacttc ttgaagtggg cagagctttg tccctctgaa 7440
ccagaaattg gacatgcttt aatgcgtttg gtgattactg gacaagaaat accacatgcg 7500
tgtgaggttg agcttcttat tctgtctcac cacttctaca aatcatcttc ttgccttgat 7560
ggagttgatg ttcttgtggc ccttgctgca actagggttg atgcttatgt cttggagggt 7620
gattttccat gtttggctcg cttgataact ggagttggaa atttttatgc tctcaatttc 7680
attcttggca ttcttataga aaacggtcag ttggatcttc ttcttcagaa gtattctgct 7740
gctgcagaca caaacactgg cactgctgag gctgtcagag gatttcgaat ggctgttctt 7800
acatccttga agcatttcaa ccccaatgac cttgatgcat ttgccatggt ctacaatcat 7860
tttgatatga aacatgagac ggcagctctt ttagagtcac gtgcagagca gtcatgtgag 7920
cagtggtttc accgctacaa caaagaccag aatgaagact tgttggattc catgcgctac 7980
ttcattgaag ctgctgaagt tcactcttca atcgatgctg gcaacaaaac acgtaaggat 8040
tgtgctcagg cttcccttct gtcccttcaa atacgaatgc cagacttcca atggctttat 8100
agatcagaaa ccaatgctag acgagcgtta gttgagcagt ctcgatttca agaagctctg 8160
attgtagctg aagcttataa cctgaaccag ccaagtgagt gggctttagt actctggaat 8220
cagatgctta aacctgaagt aatggaggag tttgtggctg aatttgtggc agttttacct 8280
cttcagcctt caatgctgat tgatttagct aggttctata gagctgaagt tgccgccaga 8340
ggggaccaat cccatttctc tgtctggctc acagggggag gattgccagc tgaatgggct 8400
aaatatttag gaagatcatt caggtgctta ctgaagcgaa caagggattt gaagttgcgg 8460
atgcagttgg ctacagtggc aactggattt ggggatgtca ttgatgcatg tacagaagaa 8520
atggataagg tcgctgacaa tgcagcacca ctagttctga ggaagggtca tggtggagct 8580 tacctcccctt taatgtga 8598

<210> SEQ ID NO 158
<211> LENGTH: 912
<212> TYPE: DNA
<213> ORGANISM: Glycine max

<400> SEQUENCE: 158
atgacgaaga tcgttgatac cctaggtcct aaatctcgat cggtcgaggt tacttctgct 60
tgtcttaaag ctagaatgcc aggtttttct aagtgcatgg gaaatgtcta tttatgtccc 120
tacaatttgt gtatgcatgc attgctgttg gttaggtttc ttgtacgtga taggaaagaa 180
gttgagtgtt gcttactcta ttgttgttgc ctttgccagg tcatgatgga cacttttggt 240
gcaaagatgc atgccgatgg tcaggttgtt ctgactccta attggggaaa agaagcgtct 300
tcacaaatat tgcctatcaa tctcgatgga ctggcaatgt caatgacgaa gggagacacc 360
atttttattg gtcattactt gttcacagga agtgaaacta cttctgatgt catttgtact 420
atagagaatt tgacaacatt ggctgggtca ttgttcactt tgcatgcctc tcaaattcat 480
gttgacttgc ctaccctcag tgataaagac aatgagggag taaaacacaa aattgattat 540
ctatcattgt catatactag gcatgctgaa gataatttgg tcattgatct tcccccaaag 600
aaggtgagca tgactacacg tgttgtggat agcatgactg acaacttaag accaactcgt 660
gcagaagcca ctaatgttgc caatgctatt ttagatggaa gtgatgcaat acttctaggt 720
gctgagacct tatgcgggtt ataccctgtt gagactattt ccacaattgg caaaatttgt 780
gcagaagtcg agaaagtttt caatcaagat ctttatttta agaaaactgt caaatatgtt 840

-continued

```
ggagaaccca tgatccactt ggaatctatt gcatcctctg aagtacgagc agctattaag    900

gtgaatgaat aa                                                        912


<210> SEQ ID NO 159
<211> LENGTH: 5865
<212> TYPE: DNA
<213> ORGANISM: Glycine max

<400> SEQUENCE: 159

atgaatgatc tgatccgagg gaaaatggtg aacatggcct tgttactgag ttttctggtg     60

acggcgacgg tactggcgtc gtcgtctcac gctgcttcta gtggtcctca cattgccgac    120

gttaacatac tcttgccgcc gaaaatgacc ttccctgtcg attataggct ccaaggaagt    180

gacggttgct tccaatggtc atgggatcat catgatattc tgtctgttga gccagagtat    240

aattcaagca gcaagtgctc gactagtgca aggataagat ccattgcccc ttatagtggt    300

cggaaggaaa ctgctgttta tgctgcggat ttgcagactg gaattgtgat tcgctgcaaa    360

gtcttcattg acaacatatc aagaatacag atatttcata attctattaa acttgattta    420

gaggggcttg ccacactacg tgtccgtgcc tttgacagtg aagaaaatgt attttcctca    480

ttagttggct tacagtttat gtggagcctt atgcctgaag ccaacggatt accttgtcac    540

cttgttaatg ttccgctaaa ggattccccc cttagtgatt gtggaggact gtgtggtaac    600

ttagatatac aaataaaact tgaagacaat ggtgtatttt cagatctgtt tgtagtaaag    660

ggaattgaga ttggtcatga gattgtgtca gtgcatctgc tcgagccaca gttaaagaat    720

ttggctgatg agattgttct tactgttgct gaagctatgt cacttgatcc tccatcacca    780

gtctttgtcc ttgttggtgc agtcattccc tacaccctta aagtcatccg ggaaatgtt    840

cctcaagtgg tcaccttacc ctcagcacat caccaatggt ctgtctcaaa tgcttcggtt    900

gctcaggttg actcaaaaac agggctagca tatgcatgga acttgggaat ggcagctgtt    960

attgttgaag atactaggat tgctggccat gtacaagtgt cttcactaaa tgtggtccta   1020

ccagcttctt tatgtttgta tatatcacct ttatctagtt ctggtgatcc agtggaagga   1080

atcaaatcta ttgctctaac gacccgttgg tatgttgtat ctggccatca gtatcttatc   1140

cagataaagg tttttgcaca tgatcatgat gcgcaagaga tttatattac agagaatgac   1200

gatgttaagg tgtatgataa tgattctggt cactggaaaa cattttgggt ttcaaatgat   1260

attgctgtaa aacatggctg gcggaattct aaaatcttga aggcttattc accaggactt   1320

gaaaaattga cagcttcttt gagctatcct ggtggggctg atgacaaaaa ggagattatc   1380

aaagctgtgc aagaagtcat ggtttgtgat cgagtaaagt acaccttggg caatgaaagt   1440

ggaatcatct tactgccctg gtctcctggt gtttatcagg aggtggagtt aaaggctata   1500

ggaggttgtg caaaaaacagt gagtgactac aaatggctat cttcggactt gtctactgta   1560

tctgtgtcag cttttggtgt tgtccaggca aaaaaacctg gtaaagctac tatcaaagtg   1620

ttatctgtat atgattcact aaattatgat gaggtccttg ttgaagtctc cattccttct   1680

tctatggtta tgcttcacaa ttttcccgta gaaactgttg ttggatcgca tcttcaagct   1740

gccgtgacaa tgaaagcagc aaatggtgcc tttttctata gatgtgatgc ctttaattct   1800

ttgataaagt ggaaagctgg aagtgagtct tttgtaattg tcaatgcaac tcaggagttg   1860

ttatacttgg aaacagtgcc aaatactcaa ttccagtcat cagttgatgg ctctccttgt   1920

tcgtggacat atgtatatgc ttctaatcct ggtcaagctg tgatccacgc catattttct   1980

aaagaagatc accactacag tcttggtcct ggtgtattaa aagcatcttc acgtattgtg   2040
```

-continued

```
gcatatctac cccttattgt gcgtcaggca ggtgatggaa accaatttgg tggttactgg   2100
cttgatttgg ttcaagccga aagtaacaag cagtctcata gcttagagga gttatatctt   2160
gtacctggta caagtttaga catagtactt gttggtggac ctgaatggtg ggacaatggt   2220
gttgatttca ttgaaactgt agaagttttg gatgaaggga atgctctggc tgaagatgga   2280
gttctagtgc atcgggtctc tagtaatttg tatggagttt tatgtcaaaa actgggatcc   2340
tttaaacttc ttttcagacg tggaaatttg gtcggggatg accatcctct gccatcagta   2400
gctgaagttt ggctgtcagt aacatgcaac attccttctt ctattgtact tatagctgat   2460
gaaccagtga atgaacgaag aattattaaa gcagcagctc aagctgaacg tagttcaggt   2520
agacttcgtg ataccccctgt tattgtggca aatgggcgct ctattcgtgt atctgcagtt   2580
ggtatcagtg attcgggaga ggcttatgca aattcatctt ctctcagttt gaggtgggaa   2640
cttggcagtt gcgagggact ggcatattgg gattatgctt ttgatatagt gaagtctaac   2700
agttgggaga gatttctggt cttgcaaaat gaatcaggat tgtgcactgt tcgtgctact   2760
gttactgact ttgctgatag cttgggagat gatacatttc atcgatttac taaaactgaa   2820
aatgttctga cagatgcaat tcggttacag cttgtttcta ccctaagagt tgatccagag   2880
ttcaacttga tatatttcaa tcctaatgca aaggtaaatt tgtcaattat tggtgggagc   2940
tgtttcttgg aagctgttac aaatgattct caagttgttg aagttattca accaccatcg   3000
ggattagaat gcctacaatt gattttgtcc cctaaaggat tagggacagc taatctgact   3060
atatatgaca ttgggctaac ccctccacaa agagcttctg cgctcgttca agttgcagat   3120
atagagtgga tcaagatcat atcaggagca gagattagcc tgatggaagg aagtttgcaa   3180
actattgact tattggctgg tactaatggt ggaaataatt ttcatgcttc tcagtttgtt   3240
tacatgaatc ttcatgtaca tgttgaagat agtataattg agctggtgga tactgaagac   3300
ttctcaagtc ttgttggtgg acatgttaat gcaccaagtt ttaaaataaa ggggagacat   3360
cttggaatta caacccttta tgtcagtgct atacaacatt tgggacatgt aatacaaagt   3420
caagccatta aggtagaagt ttatgcagcc ccaagaatac accctcacga tattttccta   3480
ctacctggtg catcatatgt gcttaccatg gaaggaggcc caactctggg tgttcatgtt   3540
gagtatgaaa ttgacaatga taaaattgcg agtattgata gatattctgg acggctctta   3600
gcaagttcta ttggtaacac tacaattatt gctagtgtct ttgcaaatgg taatactgtg   3660
atttgtgaag cacggagttt tttaagggtg ggagttccat ctactgtcac attgcatgta   3720
cagagtgaac aacttgggat tggccgcaaa ttgccaattt atccgttatt tcctgaggga   3780
actttgtctt ctttctatga gctatgtaaa aattaccagt ggagtattga agatgaaaag   3840
gtattgagct tcaaggtggc agagaccttg catgaggata gtatccagtt gactgcttca   3900
gcaggaagtc aagttaatag ttattttgat gacaatgacc ttggttttat taatgtcttg   3960
tatggaagat ctgcaggcaa gaccaatgtt gctgtctctt tctcatgtga actttcaact   4020
tctgggtcaa ggacacagtc aaggttttac agttcatctt tatcagttac agtgattcct   4080
gatcttcccc tggctttggg agtccccata acctggattc ttcctcccta ttatacaatg   4140
acaagccctt tgccttcatc atcagaatcc cattctcaga atgatagtcg gaatcgcaga   4200
ggaaccatta gctattcttt attgagaagt ttggagaaaa atgaagctct gcaaaaagat   4260
gctatattca ttgatgcgga tagaattaaa acaaccaaaa gtaacaatct tgcttgcatt   4320
caagctaaag atcgtacaac tggaagaaca gagattgctt cttgtgtcaa ggttgctgag   4380
```

-continued

```
gtgactcaaa ttagaatagc cagtaaggag gttctgctca atataattaa ccttgccgtt   4440
ggtgcagaac ttgatcttcc aacaagcttt tatgatgctc taggaaatcc tttccatgaa   4500
gcatacaatg cagtaccttt ttatgctgaa actaactacc ctgatgttct ctgcgtaaac   4560
aaaacagctg atggaaaagg caatgtccat atcaaggcaa ttcagcatgg taaagctctt   4620
gtgcgtgtag caattagtga agatctgcaa aaatcagatt atgtgctgat tagagtgggt   4680
gcccatatat atcctcaaaa tccagttctt cacataggaa gtcctcttaa cctaagcata   4740
aaaggtttga gtgatacaat ttctggacag tggtttacca caaatggaag tgtaatatca   4800
gttgatacat tatctgggat ggccaaagct attggggaag gttcagcaca agtatctttc   4860
cattacggaa gattgagact acaaacaaca attacagtgt tgaaaggaaa ttatattttt   4920
gtgaatgctc caaaagagac gttaactaat gtcccgtacc cttcaaaagg atacaacttc   4980
tccgtgaaat tcagtgaatc ccttggtgca cctggagaaa agaagagaat tttattcaat   5040
tgtagagtag atccactatt tgtggggtat gtgaagccat ggctggatca ggactctggc   5100
aactcatatt gcttattttt cccttactca ccagagcatt tggtgcactc agtacctaag   5160
ttagaaggca tgaggccaga tgtatcactc tccatttctg cttcccttga acacgaacat   5220
gtttctggat ctgcttcagc actttttatt ggaggatttt ctataatgga gatgagcaag   5280
aattcgatgc agctgaattt gacgccaggc tctaacaaaa cttgcattac tgtcttggga   5340
aatactgatg ttgaaattca ctggcatcac cgagacttga ttatgatcag tctcatccat   5400
aaagaagatt ttggcattcg agggtttgca cggtatgagg tcaaattgct taaagccaag   5460
agattcaaag atagaatcat catcactctc ccagctaatg gccagagtgt ggagatagac   5520
atcaaccatg aacccgagga aacagcatca tccagcgtaa ccataaataa ggccttctgg   5580
gcaagcatcc tggggtattt gctgctgttg attttatcaa ttgctatcat cacacgtttc   5640
ttggacagac cagagagatc tcagcaaaca agttcttcag ttactactac tccaagcatt   5700
gcagcgccca caactcctga cagaagcacc ccatcatctg ttgtaaatga ctcctctcct   5760
cgaacacctc aaccatttgt agactatgta aggaaaacga tcgatgaaac tccatattat   5820
aagcgagaag ggagaagaag gattaatcca cagaacacgt tttag                  5865
```

<210> SEQ ID NO 160
<211> LENGTH: 627
<212> TYPE: DNA
<213> ORGANISM: Glycine max

<400> SEQUENCE: 160

```
atgaacttag tcgatacaaa gctatatgat agcacttcca ttttttgat tcggcaatat      60
gatctatgct atgatttatc attcatggac gttgataaga tccttccatc tagcaacacc    120
ttaggatggc acagccctaa agttaatgtc gaggttcaaa tgaaaaaaga cttatggtgg    180
atacctgggc accccgagac gaggaagggc gtagtaagca acgaaatgct tcagggagtt    240
gaaaataagg gcaagagaca acttggtgaa ttgaaacatc ttaatagcca gaggaaaaga    300
aagcaaaagc aattcctaga atgctgcacc ctagatggca agagtctagt aaccaaaagc    360
atcactagct tatgctttga cccgagtagc atggggcacg tggaatccca tttgactgga    420
catttaggga taaagcacta tttcggtgca ggccacgaga gcggtaccaa atcgaggcaa    480
actctgaata ctagatgtgt cctcaaaata acatggatca gggggtgcat agacaaccaa    540
gaggtttgcc tagaagcaac cacccttgaa agagtgcgta atagctcact gatcgagcgc    600
tcttgcaccg aagatgaaca aggctaa                                        627
```

<210> SEQ ID NO 161
<211> LENGTH: 291
<212> TYPE: DNA
<213> ORGANISM: Glycine max

<400> SEQUENCE: 161
atgagaatca tggcttcacc accagctctc tttacttcgt ttcctttgtc aattcttcct 60
ttatcctctc ctctctcaca caaaacaaca ttgcctctga aatctacatc attcaaggat 120
ccatcaacac aaaatgcagc ttctatgcca ttctttccag catatgccaa gggtagcagt 180
gtgggagaaa aacttgagac tagaaaacag attcaccatc aaattcttgc ccatttccct 240
gcttcgctgt tgctaaaatg cttctgtcaa tattgcttgc tccaactgtg a 291

<210> SEQ ID NO 162
<211> LENGTH: 4287
<212> TYPE: DNA
<213> ORGANISM: Glycine max

<400> SEQUENCE: 162
atgcagccag gcggtcgatc tcctaagcca gtgagcagtc caacatcaac atcacagtta 60
aaatctggtt cagatagtgt ccaaaacagt gtttcttcct tttcttctca tgttaagggt 120
aggaaaaggg agagggtaga tcaagggcaa gaatctgtaa agcgagaccg ttcaaccaaa 180
aatgatgatg gggattctgg taattttaag gcggatagca ttttgaagac agagattgcc 240
aaagtaacag aaaagggggg tcttattgat cctgaagggg ttgagaaatt agtgcagctg 300
atggttcctg atggaaatga gaaaaagatt gatttagcta gccggtcaat gcttgcagct 360
gtaattgcag caaccgagaa atttgattgc cttagtcggt ttgtgcaact aaagggtttg 420
cctgtatttg atgaatggct ccaagaggca cataaaggga agcttggtga gggtattggg 480
tctagggatg gtgataaatc tgttgatgac tttctttttg tattactccg agcactagat 540
aagcttccag taaaccttca ggctctacaa gcttgtaaca ttggtaaatc tgtgaatcat 600
ttgcgaactc ataaaaactt ggaaattcag aagaaagcca ggggtttagt tgacacatgg 660
aaaaaacgtg ttgaagctga aatgattata aatgatgcta ggtcttgttc agttcagact 720
gtcccctggc cagccagaca acgactttct gaagttgctc aaggtgggaa taaacattca 780
agtgggtcag ctgatgttgc catgaagagc tcagttacac agctttctgc atccaaaact 840
gcctctccga agattgcccc aggagagaat actacaagat ctacatctgc atctccaggg 900
tctacgaaat cagtgccttc acctgcaccc gcaaccgcaa acttgaaaga tggacagccc 960
catgctgcag ctgttagtgg ttcatctgat cttcctgtgg caaatgcaag ggatgagaaa 1020
agtagcagtt ctagtccatc tcataacagt caatcttatt caagtgacca tgccaaagct 1080
gggggtttct caggaaagga ggatgccagg agctctactg caatgagtgt gaataaggta 1140
tcaggaggct cttcacggca ccgaagatct atgaatggat ttccgggttc aactccatct 1200
agaaggcaaa gggaaactgg atcgagcaga aattcctcac acaagaattt aatttcagag 1260
aaaatatctc aatctggatt aagggaaaaa gcaaatgatg gaactcttct tgaggggcat 1320
actccgaagc tgattgttaa gatcccaaac cgaggtcgaa gtcctgcaca aagtgccacg 1380
gcaggttctt ctgatgatcc ttcaatcatg aacagtcgag cttcatctcc tgctctttca 1440
gagaagcatg atcagtttga tcgctgctca aaggaaaaga gtgattttta tcgagctaat 1500
attggtgcag acattaatac agaatcgtgg cagagtaacg atttcaaaga tgtattgact 1560

-continued

```
ggttctgatg agggtgatgg atcaccagca gccattactg atgaacagtg taggactggt   1620
gaggattgta agaaagtatc agatgtatct aagacaactt cttcatcacc tgggagtgag   1680
agtaaagcca ggaatttgca ggatgcttca tacagctcca tcaatgctct tattgaaggt   1740
gttaagtaca ctgaagctga tgatgttgga atgaatcttc ttgctcgtgt ggctgctgga   1800
gagatctcaa aatctgaatc gggaatgcca gctggatccc ctaaaaaaaa caccactaca   1860
attgaacagt catatgcagg taatgctgca gtagtcaagt cctctgaaga gtatcttgtt   1920
caggataagt gctactctaa tgctgaacat atgaagcagg attctagatc tggtgatttt   1980
gggacagatg atgatattcg ggcatttgaa gggaaagcta caggagaaca caatccatct   2040
agtatggatt tacaggttac tgaaactagt ttagaaagca aaggaaaatt aattgtaaaa   2100
tcatctggta catctgctgg cattcctgaa agcaccttcc aagaagtcag agatattgac   2160
tctagcaaac tggtaaagga aaagaaggtt gttgtgagag tggatgctgt caataatgtt   2220
gatgaggtca atgttgttgc aagagaaggt gaaacagagg caattgaaaa attgtcacac   2280
acctgtgaag aagttgatgt caagtgtgat aaccatgctt ctgaaggact aagctgtgac   2340
aaagagacag ctggcaagtc tcctgccact tgtgtgccct ctgactctgt aaaagcgaca   2400
gatgagaatg cgctccaatc atctggttac attgttgata aggttcctga atacctaaat   2460
gaaagggaat ctgaaaaaaa tgatgatatg gctgctcagg atcatgctaa gcagtctttg   2520
aagcaaaaaa atgagtctga aaatgatgct attatggtgc ccgagaacag aggtttatgt   2580
tcaggtgcaa ctggtcttga tgctgaatat gtggaagaga attcaggtac aaaagaggtt   2640
tgtgaccaag atgcaggagc aggacagata ctgcacacag atttacctag ctttccttca   2700
cgagaaatgg atcagcattc aggtcaaagg gattcaaaat tggctgccat ggaatcagag   2760
gaagcagagg aatgcacctc taccactgga gatgcctctt ctgcatctgt tgctggtgtc   2820
tcagaagtgg acacaaaagt tgaatttgat ttaaatgaaa ggctcaatgc agatgacggg   2880
aaatgtagtg agatacctgg gtctacacct gctgcaagat tggtcagtcc tgttccattt   2940
tctgcttcat ccatgtcttt tggtattctc tcgatcacag tggctgctgc tgctgcagca   3000
aagggcccct ttgtgccaca tgaagattta ttgaaaagta aaaaggagct tggttggaag   3060
ggatccgctg ctactagtgc atttcggccg gctgagccca ggaaagttat ggaaattcct   3120
cttgatatgt ctactacccc tattcctaat gatgaagcta gaaagcagag tcgggtacca   3180
ttggattttg acttgaatgt ttccgatgaa ataatacttg atgatctttc ttctcagaac   3240
tgtgctcgtc agactgattg tgtaactcgt tcagatgatg ggcatgatcc aaataaatca   3300
atggcctcac atgttcgttg ttcaggagga ctaggtcttg acttgaacct agtggatgga   3360
gcttctgacg tgggcaattg caccttaagc agtagtcata aaatggatgt accacttacg   3420
cagtttaaat cagccgccag tggtcctcca aatggaaaga tgagtgtcct tagggatttt   3480
gatctgaatg atggacctat agttgatgaa gtcaccactg aacatttgat gtccacacga   3540
tctgccagga atagtgtacc atctcaacct cctatttctg gacttaggat gagtaatgca   3600
gaagtaggca acgtctcttc atggtttcct tccactggga acacctattc agccgtaaca   3660
atatcttcaa ttatgtctga tagaggtgat aagccatttt caattgttgc ccctaatgtg   3720
tcagaaaggg tgttgggtcc tgcaactggc agcaacccat ttggacctga tatttatagg   3780
ggggcagttt tgtcatcttc tcccgcagtg ccatatcaat ctgcaccatt tcagtatcct   3840
gtcttccctt tcaattccag ctttcctctt ccatcagcat cattttctgg tggatcaact   3900
ccttatgtag atacaacttc aggagggagg ctttgcttcc ctgtagtaaa ttcacagctt   3960
```

-continued ataggttctg ttggtaatgt ttcagcccat taccccaggc cttacgttgt tagtttccca 4020
gatggtagca atagtagtgg tgctgagaac agtaggaaaa gggcaaggca gggtttagat 4080
cttaatgctg gacctggttc agacttagag gggagagatg agagctcacc tcttgtacca 4140
cggcaacttt ctgttgctag ttcacaggcc caacttgaag agcaagcaag gatgtttcac 4200
ttaagcagtg atgttcttaa aaggaaggaa cccgatgggg ggtgggatgg ctacaagcaa 4260
tcatcatggc agtaccataa tttgtaa 4287

<210> SEQ ID NO 163
<211> LENGTH: 567
<212> TYPE: DNA
<213> ORGANISM: Glycine max

<400> SEQUENCE: 163
atgaattgtc tatcattgtt caccttcctc tatgcaattt gtgcgcactc catcacctcc 60
acgacatatc cttccattct cgacatgaaa accggagagt gctccctccg cagcatcagc 120
atcggcgatg gtgttctggt ccctccgtgg cgagaagtgt acgaggagag gcgaatcttc 180
gacatcaccc acaggtatgt ccccgagatg ctggtgtggg actcgacaga ggggctcggg 240
caccacttcc tgtggctcga aaagagcatg aagaatggct cacgcgctaa caactccaac 300
atgaaggtcg gtgttcacac cgacacccat gttgacgcgc tcggtcacat ttacaacaat 360
tactatgacg tcgacttcgt ggttgactca cttgacctaa cactcctcaa tggccttaca 420
cttttggttg atgttccacg ggataaaaac attactactg aggttacgaa atccttgaat 480
atccctagag gtgtaagcca cgtgcttttc agaactttaa acactgatag gccactcatg 540
tttaagaaag aatttgacac aagctag 567

<210> SEQ ID NO 164
<211> LENGTH: 1422
<212> TYPE: DNA
<213> ORGANISM: Glycine max

<400> SEQUENCE: 164
atgttggacg agagcaagtt cgaggtacac ttcaaactgt gggcccttcg aatcccttgc 60
caacattgca agctcgccac gcgaatcctc aacggttact tgcttgacaa gccccgagtt 120
aaacccatca ccgaggaccc aacctgtgac aaaaaccgtt accttatact ctccgacaat 180
gttcacaatc aagaagaata tctttctttc agcggaaatt cttatttttt acttgatttg 240
aattggtggt tgagggcaga tttatctgat attccaaaac aaaagctaga tgagctcaag 300
ggcttgtgtg agattgaagt tgtgccctat tctttgactt tagggtattc ttactggagt 360
gcagatcatg tgctgaagca gatactgcct actggagtgg agcttctaac tgcaatccaa 420
acagccactg atggtcaaat tgcccattta aacctacatg atgagttact tccccacaaa 480
gatgttattg caaaggttat ttatgataaa aattatccaa gaatcaaaac tattgttaat 540
aaagttggaa ccattacaaa tgaatttcgt gtgccagagt ttgaaatttt agcaggagag 600
cataatatga ttacagaagt gaagcaatat ggtgccactt ttaggcttga ttacagcttg 660
gtttattgga attcgagatt ggaacatgaa cacaaaaggt tagtctcaat gttccaagct 720
ggagagacca tttgtgacat gtttgctggt attggtcctt ttgccattcc tgcagcacag 780
aaaggatgca tagtctatgc aaatgattta aatcctgata gcattcacta tctgaggatt 840
aatgccaaaa tcaataaggt tggtgattgc atttatgcat acaacatgga tgctagaaaa 900
ttcatctccc agatgatgga agtgccaaat actgaggtca cattagaaaa ctcacatgaa 960
gtccctattt tggatacacg agacaatgct gaatcaaatt ctaaaaatga gttgctaact 1020
gggaatggag aggctcatgg aactgacatc cttgaaggtg gtaggagaaa aggaagcgca 1080
aacaaaagaa tgagaggctc tgaaatctct gtcacaaaaa cttgggaaca tgttgatcat 1140
gtaataatga acctacctgc atctgctgtt cagtttctag atgcattcag gggattaatc 1200
cagaagaaat attggaaagg atgtctacca tggattcact gctattgctt cattagggca 1260
actgaaactc ctgagactat aatagctgta gcagaatctg ctttagacgc tcatatacaa 1320
gactcaagat ttcatagggt tagggatgtg gctccaaaca aggcaatgtt ttgtttaagc 1380
ttcaggttgc cagaagcatg ccttaaagaa gattgtccat aa 1422

<210> SEQ ID NO 165
<211> LENGTH: 951
<212> TYPE: DNA
<213> ORGANISM: Glycine max

<400> SEQUENCE: 165
atgaatccgc ttccttttca atctcctcct ccatggtttc caatattacc ctccgaacca 60
ccaaattcaa cttccttttg ggacaacaga aatgtctgcg atcgcctcag agaattgcaa 120
aacactctca atctcgcaaa ggcaatgcag aaggagctag agatgttgat gatgataaaa 180
gatggtaaag ggtcttcgga agatttaaaa catgcttcaa acgaaccttg tctttctggt 240
tttgtaaaat gtttagaaga caaaagggtt agtgtagaat cccaagaatc attggctgtg 300
gaagctgcaa attctttgac gtcaaagcta agagctcagc tggagccatt ccggtatgtc 360
gcggacgagg cgagtccgtg ggagcatgcc aaggaaattg ctaatagcaa ggtactgaag 420
atgaaagcaa ttgcgaagtc taaagccaaa gaagaggaga agaaagtaga ggctggggtt 480
gcacttatta agtacctaaa tcatttaatt tctcccttta tttttcaaca ttgtatgttc 540
gttagctcct caccatcaaa ttacttgctc ttttgttgtc tttgtcattt tctcccagag 600
gaggatgaca agtttcttga gaaagttcaa gctgctgtgg aagaagagga gcgtgaagct 660
ttggctgcac aaagagttca cagtgtgact gaagaggatc tgtgcagtga tgagaagaaa 720
tctagtaaaa taggacagat cagtgagagc gatgatcctt tggcaaattt acccattgag 780
ttctaccatt attatcatgg aagcaacaat gatatgggta cacttattga ggttagaaga 840
ggatggaatg cctatatcag accaggagga agccgaatac cagggcactg ggttcagcct 900
cttcctccag ctaatgagat atgggcatct tacttggtga gacctaaatg a 951

<210> SEQ ID NO 166
<211> LENGTH: 3285
<212> TYPE: DNA
<213> ORGANISM: Glycine max

<400> SEQUENCE: 166
atgccgacgc cggtcagtgt agtgaggcaa tgcttaaccg acgaggccgc gcgtgcactc 60
gacgacgcag tcgccgtcgc gcgccgacgc agccacgctc agacgacgtc gctccacgcc 120
atctccgcgc tcctggctct cccctcctcc gccctgcgcg acgcgtgcgg ccgcgcgcgc 180
tccggcgccg gcgccggcac cagcgccgcc cgattctccg ccgcatactc cccgcgcctc 240
cagttccgcg ccctggagct ctccgtcggc gtgtccctcg accggctccc ttcgtcgaag 300
tccacctccg ccggcgagga ggagccgccg gtgtcgaact ctctcatggc ggcgataaaa 360
cgctctcagg cgaaccagcg gcggcacccg gagagcttcc acatgttcca gcaaagccaa 420

```
cagggaacag catcgacgtc gtttttgaaa gtcgaactaa agcacttcgt tttgtcgatc    480
ctcgatgacc ctatcgtgag tcgcgtcttc gctgaagcag ggtttcggag ctgcgatata    540
aaactcgcct tgctccaacc gcctctgcct ccggttcagc accggttcaa ctggtcacct    600
ccggttttcc tctgcaacct cgacccggcc cagcccgacg aaaatattcg caggatcatg    660
gaagttctcg cgagaaaaaa caagagaaac cctttactta tgggcgttta tgcaaagagt    720
gctctaaagg gtttcgttga gatggttcgg aatggaaggg gaggttcggc attaggttcg    780
gagttgaggg tggttcgttt ggagagggag attggggagt ttgtgaaaaa gggtgggagt    840
ggggaagaga aatttggtgt taggttgaag gaattggaac agcaatgtga gggttctggt    900
tctggggttg ttgttagttt cggggagatt gaggtttttg taggggaaga tgttgatgtt    960
gatgttgtaa ggttcgttgt ttcgggttta acgaggttgt tggagattcg tggtgagaag   1020
gtttcgttgc tgggcgtggc ggaaacttct catgcttatt ccaagttctt gggattgttt   1080
cccaatgtag aaaatgattg ggatcttcat ttgctcactg tcacttctgc cactccttcc   1140
atggaaggac tctactcaaa atccagcttg atggggtcct ttgttccatt tggagggttc   1200
ttttctacac ctgaaatcag aagtccggta agctgtgcaa acgggtcttt tacacgttgt   1260
gacacatgca ataaaaaatg tgaacaagaa gttgcagatc ttctgaaggt agatccttca   1320
tctagttatt caacaagctc acactggtta caaaaggttg ttaacatgga cgcgcataga   1380
gggtcggacg tggcaaagac taatgaagaa aacacaagtt tgaatgataa aatcttggga   1440
tttcaaaaga aatggagtga tatttgtcag cgtcttcatc acacaagttc actacctcaa   1500
tttgatattt ctcaaacaag gtcccaagct ccaacagttg aggttttacg gtttggtctg   1560
gcttttaagg aaagcagcaa taaagaccca tcacacagtg aattccaata ttctagtcaa   1620
atttcctgca tgcccaaaga gttgcatagt atttttcctt cgaagcagtt atctgttcca   1680
ttaccttctg atacagtctg cattaatact ggaaccgatc atgttccaaa agtttcagag   1740
acactgcaaa ttcacatgaa caccccttgg gttgcccctt cccttatggc caataagagt   1800
gcacttgacc acagatcatc ttcattccgt actcctgtga ccacagattt aggattggga   1860
acgttatata catcaactgc tcaggatcca gataccccaa aactacaaga tcaaagaaag   1920
catcttcagc acctgtcaga ttctgtttca actgattgtg atggtatgaa tgaaaatact   1980
tctcaccgaa ttgctagatt ttcctgctct ggttcaaatt tggaaggtaa atttgattta   2040
gcagatttca agtctcttga tcgacttctc actgaaaagg ttggctggca ggatcaagcc   2100
atatgtgcta tcagtcaaac tttgtccctt tgtaaatctg gtgcaggaaa gcgtagaggc   2160
tcaaatggta gagcagacat atggttggct ttccttggac ccgatagact tggaaaaagg   2220
aaaattgctt cagttcttgc agagactata tttggaaacc ctgaaagcct aatctctgtg   2280
gatcttggct tccaggacag cttttaccca ttgaactcgg tttttgaata ccaaaaatca   2340
cgttgttatg atgtgcttag gaggaagaca attttggatt atattgctgg ggagttgagt   2400
aaaaagccac attctgttgt ctttcttgaa aatgtagata aagccgatgt tttggtgcag   2460
aatagtttgt tgcaggcagt aagaacaggc aaattttcat attcgcatgg aagggtgatt   2520
agcatcaata acacaatctt tcttgtaacc tcaactgtct gtaaaggtaa tggctctttt   2580
gttttggaag agtctaagat gtttctgag gaaagaatcc ttgaagccaa aagatgccaa    2640
atgcaattat tacttggaca tgcttctgag gatgccggaa gaattggtag cacaaatgtt   2700
aaggttgtac ccggaaaagg gttttccaaa tcatcatctc tgaacaaaag aaagcaggct   2760
```

```
gatattagtg actccaagga gggggcaaca agcaagatgc agaaacaaga cagtgaggca   2820
tctcgatcct atcttgatct aaatatgcct gtagaggatg gtgaagaggg tgtcaatgat   2880
gaccacgaaa gtgaatccat aacagaaaac acagatgcct ggttaagtga tttctttgat   2940
caaattgatg agaaagtggt gtttaagtca ttcaattttg atgagcttgc tgaggaagta   3000
ttaaaaagaa ttggcatgct atttcaaagg acatttggtt cagagcttca gctggaaatt   3060
gattatgagg taataacaca catacttgct gctgcttggt tatcagacaa gaaaaatgca   3120
gttgaggatt gggttgaaca tgttcttggc aaaggctttg ttgaagctca gcagaagtac   3180
cttcctgcag ctcaatatgt agtaaaactg gttaattgtg aatccatttt tgtggaagag   3240
caagctcctg atgtgtgcct tccagctaga attaacacgg actaa                   3285
```

<210> SEQ ID NO 167
<211> LENGTH: 2943
<212> TYPE: DNA
<213> ORGANISM: Glycine max

<400> SEQUENCE: 167

```
atggcatttc gatttggagt ccttattctt gctttgctaa tttgtttgag tgtcaattct     60
gtggaatctg atgatggagc aacgttgtta gagataaaga agtcattcag ggatgtggat    120
aatgttctct atgattggac tgattcacca tcatcagatt attgtgcctg gagagggata    180
gcatgtgata atgtcacctt caatgttgtt gcactcaatc tttcagggtt gaatcttgat    240
ggtgaaattt cacctgcaat agggaaactt cacagtttgg tctctattga cctcagagaa    300
aacaggttat cagggcagat accggatgag attggtgact gttcttcttt aaagaacctg    360
gacttatcat ttaatgaaat tagaggggat ataccatttt ctatttctaa gttgaaacag    420
atggagaatc tgattttgaa gaacaaccag ttgattggac caattccttc aactttgtct    480
caaattcctg atttgaagat tctagacctg gctcaaaata atcttagcgg agaaatacca    540
aggcttatat attggaacga agtattgcag tatctaggct tgagagggaa caatttggtt    600
ggttcactat caccagacct gtgccaatta actgggctgt ggtattttga tgtgagaaac    660
aatagcctga caggaagtat tccagagaac ataggcaatt gtactgcctt ccaggtcttg    720
gatttatcct acaaccaatt aactggagag ataccattca atattggatt cttgcaagta    780
gcaactttgt cgttgcaagg caataaactc tctggacata ttccatcagt gatcggtctc    840
atgcaagcac ttgctgtcct agacttgagc tgtaacatgt taagtggacc aattcctcct    900
atcttgggca atttaactta cacagaaaaa ttgtacttgc atggaaacaa gctgacgggc    960
ttcatccccc cagagcttgg aaatatgtca aagcttcact atttggaact gaatgataac   1020
catttaagtg gacatatccc acctgagctt ggaaagctta ctgatctgtt tgacttaaat   1080
gttgctaaca acaatctcaa ggggccaatt cctagtaatc ttagctcatg taaaaatctc   1140
aacagcctca atgtgcatgg aaacaaattg aatggatcaa ttcccccttc tttgcagagc   1200
ttggagagta tgacctcttt gaatctttct tccaacaatc ttcagggtgc aattccaatt   1260
gaactgtcac ggattggtaa tttggataca ttggatattt caaacaataa attagttggt   1320
tccatccctt cttcccttgg tgacttggaa catcttctga agttgaacct gagcagaaac   1380
aatttaacag gagttattcc agcagaattt ggaaatctta gaagtgttat ggaaattgat   1440
ctttcagata atcagctctc tggcttcatt cctgaagaac ttagtcagct tcagaacatg   1500
atatccttga gacttgaaaa caacaaatta actggcgatg tggcgtcact ttcaagttgt   1560
cttagtctct ctctacttaa tgtgtcctat aacaaactat ttggtgttat ccccacgagt   1620
```

aacaacttta ccaggtttcc ccctgacagt ttcattggaa accctggtct ttgtggtaat 1680
tggctgaatt tgccatgcca tggtgctcgt ccttcagagc gagttacatt atctaaggct 1740
gccattcttg gaattacttt gggtgccctt gtgattcttc ttatggtatt ggtggcagct 1800
tgccgaccac acagcccctc tccttttcct gatggatcat ttgacaaacc aattaatttc 1860
tcccctccaa agctagtgat tcttcatatg aatatggcac tacatgtgta tgaagatatc 1920
atgaggatga ctgaaaacct aagtgagaag tatatcattg gatatggtgc atcaagtaca 1980
gtttataaat gtgttcttaa gaattgtaag ccggtggcta tcaagaggat ctattctcac 2040
tatccccaat gtattaaaga atttgaaact gaactcgaga ctgttggcag catcaagcac 2100
cggaatttgg tcagtctcca aggctactcc ttgtccccat atggccatct cctgttttat 2160
gactacatgg aaaatggcag tctatgggat cttcttcatg gacctaccaa gaagaaaaag 2220
cttgactggg agctgcgtct aaaaatagca cttggagcag cacaaggact tgcttatcta 2280
caccatgatt gctgtcctag aatcatccac agggatgtga aatcatctaa cattatatta 2340
gatgcagact ttgagcctca tctcactgat tttggcattg ccaaaagtct ctgcccctcg 2400
aagtcccata cttctactta cataatgggc acaattggct acatagaccc tgagtatgct 2460
agaacttcgc atctcactga gaagtctgat gtgtacagtt atggtattgt tttactcgag 2520
ttgctaactg gaaggaaagc tgttgacaat gaatccaacc tccaccatct tattttgtcc 2580
aaggcagcaa ccaatgctgt gatggaaaca gttgatcccg acattactgc cacatgcaag 2640
gacctaggag ctgtaaaaaa ggtttatcag cttgctctat tatgcacaaa gaggcagcca 2700
gctgataggc caacaatgca cgaagtgaca cgtgtactcg gaagtctcgt gccatcaagc 2760
atcccaccaa agcaactagc tgacctacca cctgcttcaa atccatctgc caaagtgcca 2820
tgctacgtgg atgagtatgc aaacctcaaa accccacact tagtaaactg cccctcaatg 2880
agcacttcag atgctcaact cttcctcaag tttggagaag taatctctca aaacagtgag 2940
tga 2943

<210> SEQ ID NO 168
<211> LENGTH: 1455
<212> TYPE: DNA
<213> ORGANISM: Glycine max

<400> SEQUENCE: 168
atgggtttgg tggggattct gtgttcttcc gtatttcttt ttatcccaat tgagtctact 60
ggcagagcag agaatatgtg gcaccaaaac ttaggtctgg attccacggg aactgtgagt 120
tttacagtct tcagtgcaag tatatttgtg cttgttgctc ttgttctctc catgtattta 180
gtattcgagc atttagccgc ctataatcaa cctgaggaac agaagttttt gattggtctc 240
attttaatgg ttcctgttta tgcattggaa tcgtttttgt cagtattgaa ttctgatgca 300
gcatttaaca gtgaaattat ccgagaatgc tatgaagctt ttgcattata ctgctttgag 360
agatatttga tagcttgctt aggtggtgag gagaaaacaa ttcaatttat ggaaagcatg 420
agccgaacag aatccattat tcctcttctg aaagaagcat atgcatatgg agttgtagag 480
catccatttc ccttaaatct cttcttggag gattggaatc taggccctga gttctatcaa 540
tctgtgaaaa ttggcattgt acaatatatg atactgaaga tgatttgtgc aatagtggca 600
ataattcttg aatcttttgg ggtttatgga gaggggaagt ttgaatggaa atatgggtat 660
ccttacttgg cactagttct taactttagt cagacatggg ccctatattg ccttgtacag 720

```
ttctatgctg ttattaaaga taagttgaaa ccaatcaaac cattggcaaa gtttctaact    780

tttaagtcaa ttgtcttcct gacatggtgg caaagtgtgg ctgttgcatt tctttttttat   840

atgggagctt ttaggggatc attggctcag gagttgaaag cacgtattca agactacatc    900

atctgtatag agatggctgt ggctgctgtt gtgcaccttt atgtcttccc agcagaacct    960

tacaaaatgg gagagagatg tattcgtaac gtagcagtga tggacgacta tgcatcgcta   1020

ggatcgcctc tggaccctga ggaagttcaa gacagtcagc gctcaacaag aacgtggctg   1080

ggagcacata ataatcagag agaaaaaaat cctatgaaat ttacccagag tgttcgtgat   1140

gtggttgttg gaagcggtga aattattgtt gatgacatga agtttacagt ttcacatgtg   1200

gtggagcctg ttgaaagggg cattgcaaag ataaacaaaa ccttccatca gatatcagaa   1260

aatgtgaaac gccacgagca gcggacgcga aataccaagg atgattgtta ccttgttccc   1320

ttgcgaacgc aaatgtcaga attttctgac gttcacgata ctatgggtga aggaagtgtc   1380

agtgatagtg gtatgtccag ggtaaagcga cagcatttcc aatgcaaagc agcagccacc   1440

agaagtagaa gatag                                                    1455
```

<210> SEQ ID NO 169
<211> LENGTH: 3036
<212> TYPE: DNA
<213> ORGANISM: Glycine max

<400> SEQUENCE: 169

```
atgaggattg agcaagagag tgatggagtc tccgcttcca caaagcacct cgtctttgcg     60

tattacgtca ctggtcatgg ttttggccat gccactcgag tcactgaggt ggtgcggcat    120

ttgattcttg cggggcatga tgtgcatgtg gtcactggtg ctcctgattt cgttttcacc    180

tccgaaatac agtctcctcg cctaatcatt cgtaaagtgc ttttggactg tggagctgtt    240

caggctgatg ctttgactgt tgatcgtctt gcctctttgg agaagtattc tgaaacggca    300

gtaaagcccc gtgctcaaat cttggctcaa gaaaccgagt ggctgaactc tgtcaaagct    360

gacttagtga tctccgatgt tgtcccagtt gcttgtcgag cagccgcaga tgctggcatt    420

cgctctgttt gtgtgaccaa tttcagttgg gacttcatct atgcagagta tgtcatggct    480

gctggacttc atcatcgttc aatagtttgg cagatagctg aggactattc tcattgcgag    540

ttccttatcc gtctcccggg atattgccca atgcctgctt ttcgtgatgt tattgacgtc    600

cctctggtag tgaggaggtt gcacaaatct gcaaaagagg ttaagaagga acttggggta    660

actgatgatg tgaagctagt tattctcaac tttggtgggc agccatcaga attgaagcta    720

aaggaggaat tcttaccacc tggctggttg tgcctggttt gtggtgcttc agagactgca    780

gaccttccgt ctaactttgt aaaacttgct aaagatgcat atacgccgga cattattgcg    840

gcatctgact gtatgcttgg aaaaaattgga tatggcactg ttagcgaggc cttggcatac   900

aagtgtcctt ttgtctttgt acgtagagac tatttcaatg aagaaccttt tttgagaaat    960

atgcttgagt tttatcaagg tggtgttgaa atgattagaa gggatttact gactggtcac   1020

tggagacctt atcttgaacg tgcaataagt ttgaaaccct gctatgaagc aggcattaat   1080

ggtggtgagg tggcagccca catcctgcag gagacggctt ttggaaaaag ttatgcatca   1140

gataagctta gtggagcaag aagattgcgt gatgccatag ttcttgggta tcaactccaa   1200

agggcccctg gtcgagatat tacaatccca gaatggtatg caactgctga aaaccaactt   1260

ggccgctcaa cacctggttc ccctatggat gatggaagat ctgcgtttag cttggacatt   1320

gaaaactttg acattcttca tggagatatt caaggacttc cagatactgt ggcattctta   1380
```

```
cagaacctat ctgaattaca ggacaagcac actaggcggg agcgtaaggc tgcggctaat   1440
ctcttcaact gggaggaaga aatatttgta acaagagctc ctggaaggtt ggacgtcatg   1500
ggtggtattg ctgactattc tggaagtctt gtcctgcaga tgccaattaa agaagcctgt   1560
catgttgctt tacaaagaaa ccatccaagt aaacataggc tgtggaaaca tgctgaggct   1620
cgacagaatg acaaaggggg aaatccaact gctgtcctgc aaatcgtatc atatggctca   1680
gaattgagca atcgtggccc aacatttgac atggatttat ctgattttat ggatgaagaa   1740
gacaaaccaa tctcatatga aaaagcaaag aaatactttg ctcaagatcc ttcccaaaag   1800
tgggcagcat atgttgcagg ggcagttttg gtcttaatga ctgaaatggg tgttcaattt   1860
gaagacagta tcagcatgct ggtttcatct gcagtcccag aaggaaaagg cgtatcatct   1920
tctgcatctg tggaggttgc tagtatgtat gctattgcag ctgctcatgg attaaatatc   1980
agcccaaggg atctggccat actctgccag aaggtggaaa accacattgt aggcgctcca   2040
tgcggtgtca tggaccagat ggcttcttca tgtggtgaag ccaacaaact tcttgctatg   2100
atttgccagc ctgcagagat tgttggcctt gttgacattc ccagccatat ccgtttctgg   2160
ggaattgatt ctggaataag acacagtgtt ggaggtgcag actatggttc tgttagaatt   2220
ggcgccttta tgggtatgaa gatgataaag gccaaggcat ctgaggaatt gtctgagagt   2280
tgggctgcta atgggttgaa ctatgatgaa gtggaacaag atgacataga actacttaaa   2340
caagaaacct ccttagatta cttatgtaat ttgccacctc atagatttgt gactctttac   2400
gctaagacaa ttcctgagtc cattgtcggt gagacatttt tggagcaata tcaaaatcat   2460
aatgatcctg tcactactat tgatccgaag cgtacttacg gagttagagc tcccacaatg   2520
catcccatat ttgaaaattt ccgagtcgtg accttgaaag cacttttaac atctgcagct   2580
tcaacctatc agcttacagc cttaggagaa ttgctatatc agtgccacca cagctacggt   2640
acttgtggac ttggctctga tggaacagat aggcttgtaa acttagtgca agagttgcag   2700
cacagtgcag catctaaagc tgaaggtggg acattatatg gagccaagat aactggtggt   2760
ggttctggtg gaacagtttg tgtagttggc agaaactgtc tcaagagcag tgaacacatt   2820
tttgaggttc aacataggta caagaaagct actggttatt tgcccttcat ttttgaaggt   2880
tcatcacccg gtgctggaaa atttgggtac ctaaaaatac gtcgtcgagc taccccaaaa   2940
aaggctaacg ccatcaagga tgatggtgca ctcacctcag aaaaggctaa cgctagcaag   3000
gatgatggtg cagtcacgat gaagaataat agttaa                             3036
```

<210> SEQ ID NO 170
<211> LENGTH: 813
<212> TYPE: DNA
<213> ORGANISM: Glycine max

<400> SEQUENCE: 170

```
atggaggagt cttcttacac cggtcttccc actagccatt tgctcggttc agttcctgct     60
gtcgtaactg aagaaaataa tgcctcgaaa catgtggcca ccagtgcgaa tatgcaaata    120
ttccctccca acaatggagg agacagagga ccgggatata atactcttgg cagtcctact    180
gaagcctttg aacaacagcc agcaaacaac tggaggggag tctttagcat ctcatcttat    240
tcagagtatt tcaatgtaga cacggatgtt gtcctaatca gattgataag ttccttgaat    300
ccagttgctg gagacttttt cagcaagata gatgctaacc ctgatttata tgggcttata    360
tggatctcaa caacattggt ttttgtgctt gcctcgcttg gaaatctggc cacgttcctt    420
```

```
atgcaaaaac atgtggataa cagtacctct tggagctttg acgtcagcta tgtgaacgtg    480

gctgcatgct ctatctatgg ctatgcgatt gtggttccat tggcatacta cttcttcctt    540

cagtatatgg gttcaaatgc tagccttata aggttttggt gcatgtgggg gtattccctc    600

accattttca tcatgtcttc cttcctgttg ataattcctg ttgagtttct acggtgggtt    660

ataatcctcc ttacgggcgt tgcctcagca agctttgttg ccttaaacct gaggtcttac    720

atagaaggca atgaactttc agtggcgatt attgcagcat tttcttgca aatggctttg     780

gcaatcttca tcaaggtttg gttctttccg tag                                  813
```

<210> SEQ ID NO 171
<211> LENGTH: 456
<212> TYPE: DNA
<213> ORGANISM: Glycine max

<400> SEQUENCE: 171

```
atggggaacc aataccacca agcaacagat gggcttctga gccttttcac aaaggccaat     60

cacgatctct ctatggttca ccatcgtctc gaaaaggagt ttcagcaggt ttaccccgac    120

aacgctaacc ctatgaagct ggtttctaga atcaagaagg ttcaggaaga tatatcaatc    180

ttgaaggggc agtgccatga gcttctggct gctaagcagg atttgattga taaggctcag    240

agagttctgg tggagaacag aaatttggtg cagcgtatgc agccgtcctt gggcatctcc    300

ccctctggtg aagatgatgc tgcattcact aacttcaaac aggtaattga agaatggaca    360

gcacaagtaa gatccaaaac agggaatgaa acacatgatg ctgattctgg atatatcaac    420

aaactactat tctcagctat agttcaaagt aattga                               456
```

<210> SEQ ID NO 172
<211> LENGTH: 1119
<212> TYPE: DNA
<213> ORGANISM: Glycine max

<400> SEQUENCE: 172

```
atggcagatt cgatttgcag aacactgagg gatggagcgt tggagggaga gcttgcgcct     60

actctcacaa tcaaggactc cctcgcttca cctttcgcct ttcatgtatt ctctcacatt    120

ctacttcaac tctcgtcaca cgtcatagca caaaaatctc agtcacaggg tatagtaatt    180

gttgcacttt ctcggagtcc atcgtcttac acttctttgt taaagatgaa tgggatggat    240

gttgcttctt ctaataaatg gattcacatt ttggattgtt atactgatcc tcttggttgg    300

aaggataagg caaggaaatc tgcgaatgtt acggatcctt ctcagcaaat ttcgcttgct    360

actagttctt ataaaaccgt gaaggacgtg gataagttgt ttttggtaat tgctgaactt    420

ggcagaggat tggttggaga aaataaagcc cgcttctgtg ttgccataga ctcgctaagt    480

gaacttttga ggcatgcatc tatgcagtca gttgcaggcc ttctaagcaa tctgcgtagc    540

catgatcaaa tttcaagtat gtttggatta ttgcattctg accttcatga ggagagggct    600

gtggcagttc ttgagtacat gtcctccatg gtggccagtg tagacccgta tcatcattct    660

gcagatggtc agaaaaggtg tttagagagt tccttatatg atcaaaactt taccaaggga    720

aaatttaatg tcaggttcaa acgcagaaat gggcgagtta gagtaacgtg tgaagaattt    780

aaagttgagc ctggaggaat cagcttctca cctgtttcat cagtagatgg aaccgtcatt    840

gcaggcatag tgccaaaggt gcagttcaat ctccagctgt cagagaagga gcgaattgat    900

aggtcaaatg ttgtgcttcc ttttgaacac cagggaaatg gtaaaccaat acaaatttat    960

gatggtagaa gatcccttga agagagcaac agtgaggcaa atcccatttc aagtggtaaa   1020
```

aaggaggatt ctgccatggg tgaaattata tattttcgtg attcagatga tgagatgcca 1080
gattctgatg aggacccgga tgatgattta gatatatga 1119

<210> SEQ ID NO 173
<211> LENGTH: 2598
<212> TYPE: DNA
<213> ORGANISM: Glycine max

<400> SEQUENCE: 173
atggggggta taggtaagac aactgttgct aaggtcgtat atgccaaact atgttatgaa 60
tttgaaagtt gctgcttctt ggaaaatgta agagaacaat cgcagaagca tggattaaat 120
tatttacatg ataagcttct ctttgagctg ctgaaggatg aacctcccca caattgcaca 180
gctgaagttg taggatccaa atttgttttg agaaggctcg caaataaaaa agttttgatt 240
gtgcttaatg atgtgaatgg ttttgagcaa ttagaatatc tggcaagaga atttgtctgc 300
ttgggaccag gtagtagagt tattataact acaagagata agcatttgct tattcgaaga 360
gttgataaaa tacatgaagt caaggaattg aactttcaag attcccttaa gcttttcagc 420
ttagttgcat tcagagacag caatcctcaa atggaatata tagagctatc agaaagggca 480
gttgcataca ccaagggcaa tccattagct ctgaaagtgt ttggcttcac ttttccattc 540
caaaatatag aagtatggga aagtgcactt agcaaactca agaaatatct gaacgtacaa 600
atccaaagtg tgttacaatt gagttatgat gaattagatg atgcagagaa gaacattttt 660
ctagacattg cattcttttt tgaaggggaa aataaagatc atgtcatgag gctactagat 720
gcctgtggct tttatgcaac tatcggaata gaaacccttc aagataaagc tcttgtaact 780
atttcaaaag acaataaaat acacatgcat cagctgattc aagaaatggg cataatgtta 840
gacatgtctc aaattaggga acttcacttg agtgctgaca tcttcaaaaa gatggctaaa 900
ctaagattgc tcaaattcta ttctcccttc aatgggagat catgcaaaat gcaccttccg 960
acaggtcttg agtctcttcc gcacaaatta aggtatcttc attggaatga ataccctttta 1020 atgtccctac catcaacttt ctctggcgag atgcttgttc agcttcgcat gccacgtagc 1080
catgtaaaaa aactttggga tggattacag gatttcgtca acttaaaggg aatagacctt 1140
actgcttcca cgcagttgat ggagctccca gatttatcca aggcaacaaa gcttgaaata 1200
caaaatatcg cccactgcgt aaatttgagt catgttcatc cctctatttt atcacttgac 1260
acccttgttg attttgttct atatggttgc aagaaactca agagtcttca tttaagatct 1320
gtcaagtaca ttgtgctcaa tggttgcttc aatctacagg aattttcact gacctcagga 1380
gaaataaacg tgttgaactt gagagggaca gcaatcgaaa cattagcatt tccatcggtc 1440
gtctcagcaa aattgaaaag ctctctgtct gagttacctt ctctgacatg tcttagtgaa 1500
ctgaatcttc ataactgcag acagcttgac atgccaaatt tgcataacct acttgatgct 1560
ttgcgttctg tcagaaagct gattttggac gagtgttgta acttttctcg agtcccttgc 1620
aatatcaagc atctttggtg ccttgaatac ctgtccctaa gggattgcac ggggcttcga 1680
tttatacctc agcttccacc atctgctgaa catttagatg ccatcaactg cacatccctg 1740
gagacagtgt tgcctctaat gcctttgaga caaccgggac aaaatgacat aagcatttca 1800
tttgaaaact gcttgaaatt agatgaacat tcaaaatatg gtattacaga atatgccaac 1860
ttcacaatga agcatgttgc atatgcaaat gacagtggtt cacatcatct gaataaaaga 1920
ggtggtgctg tttgttttcc aggaagcaag gtgccagagt ggtttgaaaa caggacaaca 1980
acaccggctt gtgtaactgt tcaacttcct ccaccttccc acttgttggg ttttgctttc 2040
tgtgttgtgc tttctcagtt tcaatcaaat gctaagtatg agtatcatca gatagtatgt 2100
cgatggtgct tggaagatga aagccaagcc aatggtgatg agtgcatcac tgaaaaccta 2160
aatgtgtcat ttgaattcta tgttgaaact cataggtttt gtgagcctaa acacattggc 2220
ttgattggta tcaaagagtg tggggtctgt ccaatatata cttcaaaata ttacagtttc 2280
acaaaccaca gagaactgga catgatgttg gaacatagag ctagagagat tacaatggcg 2340
gtaggaaact ctgatgagac agaaagcaat ggcataaaaa ctcaggaggc taaaaagctg 2400
gatgaaaagg ttcgacgttt tgttgaacaa aagataggtg ttgagatgaa aaaggccaaa 2460
ttgaaggaga ccctggaaag atgtgaaggt caaaaaatga aactgaaaca agaggctaag 2520
aacaaggtaa ctgaaagtaa agagataatg ttggcgattg agaattctaa agccttgtat 2580
atgattctgc cctgttga 2598

<210> SEQ ID NO 174
<211> LENGTH: 1533
<212> TYPE: DNA
<213> ORGANISM: Glycine max

<400> SEQUENCE: 174
atggttgtct tttcgcgaag tgcgacgacg acgacgacga cgacgacgac ctatacgcgc 60
cacaacttaa tacgacaaac gaaaacctgc gttggcaata ataatagttt gtgttactct 120
gctactaaga aggctcctcc gcagaggatt cttggtggtg cacgtggcag tagagtgatt 180
cttgctgcca gccctcccac cgaagacgct ctagttgcca ctgaccctct caccaagcag 240
gatcttgtcg attatcttgc ctctggttgc aagcccaagg ataaatggag aataggtact 300
gaacatgaga agtttggttt tgagtttgga accttgcgtc ctatgaagta tgaccaaata 360
gcagaattgc tgaatggcat tgctgagaga tttgactggg ataaagtaat ggaaggtgac 420
aaaattattg gactcaaaca ggggaagcag agcatatcat tggagcctgg tggtcagttt 480
gaacttagtg gagctcctct tgaaaccttg catcagactt gtgctgaagt taatttgcac 540
ctttatcagg ttaaagctgt tgccgaggaa atgggaattg gatttttggg gattggtttc 600
cagccaaagt ggggaatcaa agacatacct ataatgccaa agggaagata cgacattatg 660
aggaattaca tgcctaaagt tggctctctt gggcttgaca tgatgttcag gacatgcact 720
gtacaggtca atctggactt tagttctgaa gctgacatga tcaggaaatt tcgtgcaggt 780
cttgctttgc agccaatagc aacggctctt tttgcaaatt caccctttaa agagggaaag 840
ccaaatggtt ttttcagtat gagaagccat atttggactg atactgacaa ggatcgcaca 900
ggcatgctgc cttttgtttt tgatgactct tttgggtttc agcagtatgt tgattatgca 960
cttgatgttc ctatgtattt tgtctatcgg aaacacagat atatcgactg tactggaaag 1020
accttcaggg acttcttggc tggaagactt ccttgtattc ctggtgaatt accaactctc 1080
aatgattggg aaaatcactt gacaactata tttcctgagg tcaggctgaa gagatatttg 1140
gagatgagag gtgctgatgg agggccttgg agaaggttat gtgctttacc agcattttgg 1200
gtagggttat tgtacgatga agtttctcta caaagtgttt tggatatgac agctgattgg 1260
actccagaag aaagacaaat gctaaggaat aaggttcctg taactggttt gaagacacca 1320
ttccgagacg gtttgctgaa gcatgttgct gaagatgttc taaagttggc aaaggatggc 1380
ttggaaagaa gaggcttcaa ggaatcagga tttttgaatg aggttgccga ggtggttaga 1440
acaggtgtca ctccagccga gaggcttttg gaattgtatc atggaaagtg ggagcaatcc 1500

```
gtcctggtgg tctctcattt gagcttcatt tag                              1533


<210> SEQ ID NO 175
<211> LENGTH: 2754
<212> TYPE: DNA
<213> ORGANISM: Glycine max

<400> SEQUENCE: 175

atggcgaaat cggggaataa gaatatggga tcaaccgcaa aagttcaccc ttccaatgat     60

cccgaactgg atcccgattc ttacgccctg gagaagttca gactctacga aaccagagcg    120

aggttttacc taatcggaag tgatcggaac aagaggttct tccgggtatt gaaaatcgat    180

cgatcagagg cgtgggatct gaatatcagc caagaccccg tgctgtattc tccccaggaa    240

atcaagagct tgctccagcg gattgctgaa ggtaacaggg ccactggcgg cctcactttt    300

gtcgctaagg ttttcgggat tgctggctgc atcaagtttc tcgagtccta ctatttgatt    360

ctcgttacta agcgcagaca aattggttct atttgtggcc atgcaatcta tagcatcaag    420

gagagccaat tgagaaccat tccacatgtt tcaattcaat ctgatttagc tcactctaag    480

actgagctca ggtacaaaaa gcttttgtct agtgtcgatt tgaccaagga tttttctttt    540

agttacaatt accctataat gcaaagtttg caaaagaacg tctcctccgg ctccagtcaa    600

gaggaaggga tgtcatatga taacattttt gtttggaatg cgtatttgac acaagcaatc    660

agatcaagat gcaataacac catttggacc gtagctttag ttcatggtca ttttaggcag    720

attcgtctat caatttttgg gagggacttc agtgtttcct tgatttctag acgatcgaga    780

cattttgcag ggacacggga aggattgaag gaggaggagc aacaaaccag gtacttgaaa    840

aggggtgtga atgatcgggg gagggttgct aatgatgttg agacagagca gattgtcctt    900

gatgaagaat caggctcttg caagggaaag atgagttcag ttgtgcaaat gcgtggatca    960

ataccgcttt tctggtcaca agaagcatca agatttagcc ccaagcctga cataattttg   1020

cagaggtatg atccaacata ccaagcaaca aaattgcatt ttgaagacct agctaagaga   1080

tatggcaatc caattattgt tcttaatttg attaagacag ttgagaagcg gcctcgagaa   1140

atgatgctga ggcgtgaatt tgcaaatgct gttgggtatc tgaaccaaat tctaccagta   1200

gagaaccatc ttagatttat tcactgggat tttcacaagt ttgcaaagag caagtctgcc   1260

aatgttttgg cagttttagg aggtgtagca agtgaagcgc ttgatttaac tgggttttac   1320

tacagtggta aaaccagcat cattaagaga gccaacaaga gcaatagaac aagcacaggg   1380

agggatactt cagtgagaga tctgagagct agttctgggg atcttgtgag gattgggaac   1440

agtaatgaaa tgctaaattc tgtggttaat caagacaaag agactgacat gaaccatcag   1500

aataaaaaag ataatttgg tagtgatgca ccacattttc agagtggagt tctccgtacc    1560

aactgcattg actgcttgga ccgtacaaat gttgcccagt atgcttatgg tcttcaagct   1620

ttaggacgcc agctccatgc aatgggtttg actgatgttc caaaagtgga tcctgatagt   1680

agtattgctg cagctctaat ggatatgtat caaagtatgg gagatgctct tgcccagcaa   1740

tacggtggct ctgctgctca caatactgtg tttccagaga ggcagggaaa gtggaaagca   1800

acaacacaat caagagagtt tttaaaatcc ataaaacgat actatagcaa tgcttacaca   1860

gatggtgaaa aacaagatgc aataaacttg tttttaggtt acttccaacc acaggaaggg   1920

aaacctgctc tctgggagct ggattcagat tattatctcc atgtatctgg gattggggat   1980

gatctaattc ctgagaagtg ttctgaacca aatatcagtc cttctggaag aggtggaatg   2040
```

-continued

```
gtattcatgc ctataccagc ttgtagagat gacttctctc gcataaagtt gacatcattt   2100

gacatgttaa ttgaaaagac ttgtagtaaa ataaaaaatg taagactatg ctgtgagcct   2160

gatcagagac caggtggggt ttctggaaac agtggtgtag cacctgatgc agctgagata   2220

cagctcaaaa gcccaaattg gcttttcggc cagagaaagt atgaagaggg ttcctctgct   2280

gcaaaagttg cttctcgtga atctggcgtt gaaggatctc atgctaatgg cttttgtgac   2340

ttgaattggc tttcctctgg caatgatatg aatgaagagg atgttttcca aaggtacctt   2400

acaatgacct caacaaatga ggccaacggt tggtatggag gtagtctcct cggcgatcaa   2460

gatgaaagca gtgagatata taaacattat gctgagttat gtcagggacc tgccttggaa   2520

cttttccaaa atgaccctga gaaggagcaa cactatgcag atgctttaag cacgagttca   2580

tatgaaattg ttaatgatgc tgtcgttgca gcagaaatgg aagcagctct aaaggagtat   2640

gaccaagttg gtgctgacct tgggattatt cccaaatctt gtaaattcta tgttgatgat   2700

ccgagctggc tgacgagatg gttaactggg gacgaaaaag taccaaggat atga         2754
```

<210> SEQ ID NO 176
<211> LENGTH: 708
<212> TYPE: DNA
<213> ORGANISM: Glycine max

<400> SEQUENCE: 176

```
atgggggata gtcagtattc gttttctctc accacattta gcccttctgg aaagcttgtt     60

cagattgagc atgctttgac ggctgtcggg tctggacaaa cgtctttggg aattaaagct    120

gcaaatggag ttgtcattgc taccgagaag aaattgccat ctatattggt tgatgaagca    180

tcagtccaga aaattcagtt attaacacca aatataggtg tcgtatatag tggcatgggt    240

cctgattttc gagttttggt tcggaaaagc aggaaacaag ccgagcagta tcaccgttta    300

tataaagaac caattcctgt cactcaactt gtcagggaag ttgccgccgt aatgcaggaa    360

tttactcaat ctggtggtgt taggcctttt ggagtgtccc tgctagttgc tgggtttgat    420

gataacgggc cacaattata tcaggtggat ccatcaggtt catatttttc ttggaaagct    480

tctgctatgg ggaaaaatgt ttctaatgca aagacgtttc ttgagaagag gtacacagat    540

gatatggagc ttgatgatgc agtccacaca gcaatattga ctctgaagga agggtttgag    600

ggacagatct caggaaaaaa cattgaaatt ggcataattg gagctgataa aaagttcagg    660

gtattgacac cagctgaaat tgacgactat ttggctgaag tagaataa                 708
```

<210> SEQ ID NO 177
<211> LENGTH: 1836
<212> TYPE: DNA
<213> ORGANISM: Glycine max

<400> SEQUENCE: 177

```
atggctgaac catcatctaa tgttgcaaca aggaaaaata ggacagaccc tggttggaag     60

tattgtcatc cacttgtgga aggggataca aacaccattg tttgtaatta ctgtggaaaa    120

atcacccagg gaagaataac gagagccaaa gaacacttga ttgggaagtc gagtaacgtt    180

gcatcttgca agaaaactcc accagatgta gtcgaagagc tcaagggata tatggctaac    240

aaaaaaagtg gggccactta caatagtact ggtggtggta atatgccaaa tataagagat    300

tttgaattta gtgaaccaat tggatgtgat gaaagtgaag atgagtttga ggactctagc    360

aatgctactg ctttggccgc aaagacaaag tgtgcatcaa tatattgctc gctttggtac    420

caagctggtt tgtcattcaa cctcattaaa ttgaaaagct ttgagaatat ggttgcagtc    480
```

```
attggtcaat atgggccacg tttgcccatt ccaagctatc atgatatcag agttccactc    540

ctgcaaaagg aagttgaata cactgaaaat ttgatgaaag gccataggga gcaatgggtc    600

aaatgcatca ttaatttttt ggttaactct caagctggta caatgttttt gaagtctgtt    660

gatgactctg attttgtgaa gacaggtgaa aagtttttttg agttgcttga tgctattgtg    720

gaggaagttg gagaagagaa cgttgttcaa gttgtaactg ataatgggag caactatgtc    780

ttagcgggta agttgttaaa ggacaaaacg aaacatattt attggaatcc ttgtgcagcc    840

cattgtattg atttgatgct tgaagacatt gggaagcttc ccttgataag gaagacaatt    900

agaagggcaa ttaatccagt tgggtttatc tatgtccatt ctagtacctt aagcttgttg    960

agaaattgta caaacaagag ggaattggtg agacatgcta ttactagatt tgtcacttct   1020

tatctaacct tagaatggtt ccacaaagag aaagttaata ttagaaagat gtttatttct   1080

gatgaatgga tcttaagcaa gttatctaag gagcctaagg ggaaagaagc tgcaaaggta   1140

gtgcttatgc cttctttttg gaatagtgtg gtttacactc ttaaagtcat gactccactt   1200

gtcaaagtgc ttcgtcttct ggatggtgaa aggaaatcaa ccatgggcta tatttatgaa   1260

gcaaaggaca aggcaaaaga aacaactata agtctttcaa caacaacgaa agcaactgcc   1320

tacttcttaa attcagagtt attttatgac aacactgatt tggagtttga ttttgaggtc   1380

accaatggat tgtttgatag cattaagaag ttggttccac aatttgatgt gcaacagaaa   1440

attctaactg agttgcatct ttacaagatt ggtgctgaac actttggttc ttacatattg   1500

tggcaaatgt ttgggtcaca aactccaaat ttgcaaaagc tagctattaa aattttgagt   1560

ttgacttgca gtgcttcagg atatgaaaga aattggagtg tatttgagca aattcattcc   1620

aaaaaaagaa ataggcttga gcacaagaag ttgcatgatt tggtgtttgt caaatacaac   1680

caacaattga agcaaagata taatgcaaga gatgaaattg atccaatttc tcttaatgat   1740

tttgatgcgt ctgatggaga agagggagag ggaaatgctc cactacctta tgataacaat   1800

gaagaggatt atgttgggat tggagaagat gattag                              1836
```

<210> SEQ ID NO 178
<211> LENGTH: 948
<212> TYPE: DNA
<213> ORGANISM: Glycine max

<400> SEQUENCE: 178

```
atgtcgaacg atattggatt cttcgacctc aacacgggcg ccaagatccc ttccgtcggc     60

ttgggaacat ggcagtccga tcctggcctc gtcgctcaag ccgtcgctgc ggccatcaag    120

gttggttacc gccacattga ttgtgctcaa atctatggca atgagaaaga gattggctct    180

atgttgaaga agctgtttga ggagggtgta gtgaagcgtg aggatttgtg gattacatct    240

aaactatgga atactgatca tgctccagaa gacgtaccac tggcattgga caggaccttg    300

aaagatttgc agcttgatta tgtagatttg tatcttatcc actggccgac ttcaatgaag    360

aaaggatcag ttggctttaa tcctgaaaat cttgtgcaac caaacatacc taacacatgg    420

aaggcaatgg aagcactcta tgactccggc aaggctcggg ctataggtgt aagcaatttt    480

tccaccaaga agctggcaga tttgctggca attgctcgtg ttcctcctgc tgtcaaccag    540

gtggagtgtc atccttcatg gcagcaggac aagctgcagg ctttctgcaa ttccaaagga    600

gtccacctca ctggatattc acctttgggt tcccctggaa caacctattt taaaagtgat    660

gtccttaagc acccaattat aaatatggtt gcggagaaac taggcaagac tcctgcacaa    720
```

```
gtagctcttc gctggggact gcaaatgggc catagtgttc ttcccaagag tactaacgaa    780

acacggataa aggaaaattt tgatgtttct ggctggtcta tacctgagga cttccttgct    840

aaattttctg agattcaaca ggcaagatta ctcaggggta ccacatttgt ccatgaaact    900

tacggtgcct acaaatctgt cgaggaatta tgggatggtg aaatctaa                 948
```

<210> SEQ ID NO 179
<211> LENGTH: 2703
<212> TYPE: DNA
<213> ORGANISM: Glycine max

<400> SEQUENCE: 179

```
atgtttggcg ggggcggcgt gagcgtgaga atggaggaag aggaagatga agtgggttgg     60

tgttcttctg attcgggcga cggcgacggc gacgacgata tcgaagaacg gaaatctcag    120

aatgtggatg ccttgctcag gggcaacctc gtggtgaaga gacaatcgtt gctaccgcga    180

cttctatcag tatcgcaagg agcggctgtt tgtagaaagc ccttcaaacc tccatgctct    240

aaatctcatg cttccgcttc cgcttacaat caagacctta ctcgtaagct ttccgctcgc    300

aaaaggtttg ttccctgggg ttcttcctct cctattccta ttcctattcc tagatctgcc    360

ttagacgact ccaaattcaa tgttgctgtt gctgttgctg atgttgccga ggagctcaag    420

ccctctttgc ctcccgggat tgatcctctc gtattgtggc accctcaaga ctccgaggat    480

gctaatgcta attttaccac cataacagtt gatccgttgc ttgttcgtta ccttcgtcca    540

catcagagag aaggggttca gttcatgttt gattgtgtct caggcctgtc taccacacca    600

aatatacacg gatgcatttt ggcagatgat atgggtttgg ggaagacatt gcagtccatc    660

acattactat atactctact ttctcaaggg tttgatggca aaccaatggt tcgaaaggcc    720

atcattgtga ctcctaccag ccttgtcagc aattgggaag ctgaaatcaa aaagtgggtt    780

ggagaaagag ttcctcttgt tgctttatgt gaaagcacaa gggaagatgt catctccggg    840

attgacaatt ttacaagtcc caaaagcaat ttacaggtgc tcattgtttc atatgagaca    900

tttcgaatgc attcgtcaaa gtttagctct actgactcat gtgaccttct catatgtgat    960

gaggctcaca gactgaaaaa tgatcagacg ataacaaacc gggcattggc agctctcccc   1020

tgcaaacgta gaattttgtt gtcaggaact ccccttgcaaa atgacttaga agaattcttt  1080

gcaatggtta actttactaa tcctggaata ttgggtgata ttgcacattt tcgacgttac   1140

tatgaggcac caattatttg tggaagagaa cctgctgcca ctgcggaaga gaagaagcta   1200

ggtgctgaac agtctgctga attaagtgtc aatgttaacc ggttcatatt aagaaggact   1260

aatgcattgt tatcaaatca cttaccacct aagatagttg aagttgtttg ctgcaagttg   1320

actccactgc agtcagaact atataaacat tttatacaat ccaaaaatgt taagcgggca   1380

attactgaag aactgaagca atcaaagatt ttggcctaca taacagctct caaaaagttg   1440

tgcaatcatc caaagcttat ctatgatacc atacgaagtg ggagtccagg aacttcaggt   1500

tttgaggact gtatccgatt cttccctcct gaaatgttat ctggaaggtc tggctcatgg   1560

acgggagggc atggagcatg ggttgagcta tcagggaaaa tgcatgtctt agcaagatta   1620

cttgctcatt tacgtcagag aacaaatgac cgcattgtcc ttgtctcaaa ctacactcag   1680

actcttgatc tttttgctca attgtgtcgg gaacgaaggt accctcactt gaggcttgac   1740

ggctctacat caatcagtaa aaggcagaag ttggtcaact gctttaatga tccatccaag   1800

gacgaatttg tttttctctt aagcagcaag gctggtggtt gtggactcaa tttgattggt   1860

ggaaatcgac ttgtcttgtt cgatcctgat tggaatccag caaatgataa acaagctgca   1920
```

gcaagagtat ggagggatgg acagaagaaa agagtttata tttatagatt tttgagtgcc 1980
ggaacaatag aagaaaaggt ctaccagcgt cagatgtcaa aagaagggct gcaaaaggtc 2040
attcagcagg agcaaaccga tagccttgtg gcacagggta acttgctttc aacagagaat 2100
cttcgtgatt tgtttacttt tcatgagaac atcaagtcag agattcatga aaacatgcaa 2160
tgcagtcggt gtcaaacatt tgatggccct cgaagcactg aagcccagtc aacaataaca 2220
gatagtgaat ctgatgaaga aacctctgat attggtggat ttgcagaaat tgctggctgc 2280
ttacagaatt taaaaagatc agaaaagcag gtagggagcc cattggaaga ggatttagga 2340
agttggggcc atcatttttt cccaacttct gtaccagatg ctatacttca ggcttcagcc 2400
ggtgatgagg tgacttttgt cttcacaaac caagttaacg gacgactggt acccgttgaa 2460
tctattatga gtcccaagct acagcaaaag gatccaaaaa aggaattact caagtcaaag 2520
cagaacggta aacaaaagcc cactcctttt tctttacata acagactacc attgcagtct 2580
gcttctgtcg ggattactaa aaacatctcc atgaatgtgg catttaagcc ccagtactct 2640
cttgtaagta aagtattgcc acagaaaaga tcatgtcctg ctaatatcaa tgatgataat 2700
tga 2703

<210> SEQ ID NO 180
<211> LENGTH: 1674
<212> TYPE: DNA
<213> ORGANISM: Glycine max

<400> SEQUENCE: 180
atgtattctc attgggttcg attgatgctt ctcattgctt gcattcttcc agctttggtt 60
gaatgcagag agaggcacta caaatttcat gtggtgtcta aacaaactaa tagattgtgt 120
tcaagcaaat ctattgtcac cattaatggc aagttcccgg gacccactct ttacgccagg 180
gaagacgata cagtgttggt caaagtcatc aaccaagtca atcacaacgt taccatccat 240
tggcatggtg tgaggcaatt gagaactggt tgggctgatg gacctgcata tgtcacacag 300
tgcccaattc aaccagggca aacctatgta tacaatttca cactcacagg gcaaagagga 360
acacttttgt atcatgcaca tgttaattgg ctaaggtcaa ctctctatgg tgccttggtt 420
atcttgccaa agagaggtgt gccttatcct ttcccaaaac cagatgatga gttggttgtg 480
gtattaggag aatggtggaa atctgataca gaagctgtaa tcaatgaagc actcaaatca 540
ggattggcac caaatgtctc agatgctcat actattaatg gccttccagg gacagttacc 600
aattgttcta cacaggatgt ttacaacctg cccgtggaga gtggaaagac ctaccttttg 660
agaattgtca atgctgcact caatgaggag ctattcttca aaattgctgg ccacaagctc 720
actgtggtag aagttgatgc cacatatgta aagccattca agattgaaac aattgtgata 780
gcccctggcc aaaccaccaa tgtgcttcta aatgcaaacc aaaaatctgg caagtacttg 840
gtagcagctt ctccattcat ggatgctcct gttgctgtgg ataacttgac tgccacagca 900
acattgcact acaccggcac tcttgctgcc acccccacaa ttctcaccac cccacctccc 960
aaaaatgcta cccaaattgc caacaacttc atcagctctc ttagaggcct taactccaag 1020
aaataccctg tcaatgtccc attaacagtt gatcactcac ttatcttcac tgttgggttg 1080
ggaattaacc cttgtccatc ttgcaaagct gcaaatggga gcagggtggt ggctgctatc 1140
aacaatgtta catttattat gccaaccatt gccttacttc aagcacatta tttcaacatc 1200
aaaggggtgt tcaccactga tttccctgcc aatccacccc atgttttcaa ctactcaggg 1260

-continued cctggaccag ccaatttgaa caccgaaacc ggcacaaagg tttacaggct accattcaac 1320
gccacagttc aggtggtgct acaagacaca ggaatcattg cacctgagaa ccacccagtt 1380
catcttcatg ggttcaattt ctttgttgtt ggaagaggag taggcaattt caaccccaaa 1440
attgacccta agaactttaa ccttgttgat cctgttgaaa ggaacactat tggagtacca 1500
gctggagggt ggactgcatt tagattcaga gcagataatc caggagtttg gttcatgcac 1560
tgccacttgg aggtacacac aacatgggga ctaaagatgg cctttttggt ggacaatggc 1620
aaaggtccta agcaatcagt gataccccca ccaaaagatc ttcccaaatg ctaa 1674

<210> SEQ ID NO 181
<211> LENGTH: 3441
<212> TYPE: DNA
<213> ORGANISM: Glycine max

<400> SEQUENCE: 181
atgttggata gtgttctttc catcagagca aagattgtag aatatattgt gggtccaatt 60
ttacaccatg caaaatactt gtgttgtttc aacaactttg ctgtgaatct cccaaatgcc 120
aaaagagaat tggaattgac cctagagcaa gtgaaattac gagtaagaga agccactatt 180
aggattgaaa aaattgaacc aactgttgaa gaatggctag aagaagttga gaaagtttta 240
gcagaagtgc agattctcga aggaagagtt ttgaaagtga caaagagtag tttcataagg 300
caatgtcgat attttcttgc aaaagaaatg gtaagaaaaa taggacaaat gaatcagctc 360
aaatgtaaca agttagagcc cttttctagg agtattaacc ttccagacat gaagtactat 420
tcttccaaag attttgttct ttccaattca acagaatcaa cttacaacaa gcttttggaa 480
acattaaagg ataaaaatgt tagcataatt ggactagttg gaatagaagg ctcgggaaga 540
actactttgg caaatgaggt gggtaagaaa gctgagaagt taaaactttt tgagaaggtt 600
gtcatgacaa cagtctctca aaatctcaat atcataagca tccaagaaca aattgctgat 660
aagttgggtt tcaaattaga ggaagaatct gaggaaagta gagcaaaaac attatcacag 720
agtttaaggg agggcacaac acttctaatc ttggatgatg tatgggaaaa gctaaacttt 780
gaagatgtag gtattcctct caatgaaaac aacaagagtt gtgtaatact cctaacaact 840
caaagtagag aaatatgcac ttctatgcaa tgccaaagta taattgagct caatcgttta 900
accaacgagg aatcttggat tttgttcaaa ttgtatgcca acataactga tgactctgca 960
gatgctttga aaagtgtggc aaaaaatatt gttgatgaat gcgaaggatt cctaatttca 1020
attgtgactt tgggaagcac actgaagaag aaaagtttag gagattggaa gtcagcattg 1080
aaaagactac aagattccaa accattggtt attacaaaag gcctaaaaat tcctcatgta 1140
tgtcttcaat taagttatga taacttgaca gatgagttaa ccaagtcgtt gcttttgttg 1200
tgttctatct ttccaaagga ccatgaaatt gatttggaag atttatttcg atttggaagg 1260
ggactgggac taactaagac ttctgaaaca atggaaaaat caaggaggga gattgaaata 1320
gccgttaaca tcctaaagga ttcttgtttg ttgttgaaag ttagtaataa agaaagggtg 1380
aaaatgcatg acatggttcg tgatgtagcc ttgttgatgg catctgaaag gggtcaagca 1440
atgttggcaa gtactgcaat ggatctaaga atgttggtag aggatgaaac actaaaagat 1500
aagagagcaa tatccttatg ggatttgaaa aatggtcaac ttcctaatga taatcaattg 1560
aattgtccaa cactagaaat tctcttgctt cattctccaa aggctggctt tgaagtatct 1620
aatttgtgtc ttgaaaggtt gaaagttctt aaaatactgt cattcttaac atgtggctat 1680
acgtggaagt tgcctcaatt tagtccatca cagtacattt tatcattgcc acaatcaatt 1740

```
gagtcattaa aaaatcttca aactctgtgc ttgagaggct ataagctagg tgacatctca   1800

attttggaaa gtctacaagc actcgagatt cttgacttgc gtggttctta tcttgaagaa   1860

ttgcctaatg gaattgtaga gttgaagaaa ttgaagcttt tggatttgta caattgttgg   1920

attgagaaaa ataatgctta cgaggttgta ggacgtttgc aactagagga attgtatttt   1980

catttattct cgtataaaga agacattcca cataatgttt ctttctcaag attgcagagg   2040

tatgttattg tactagatca tagaccatat tccttccacc taaagacaga aattatggaa   2100

gagcatagac catctagagc tttgtacata aatggtttga atgcatctac tcaaaggttt   2160

atatcattac caatcatgga tctattttta agagcagagt accttcattt gaagcatctg   2220

aagggaggtt acaaaaatct tatcccatcc atggatcaac aaggcatgaa tcagttgatt   2280

gccttagtcc tcgaatattc tttagatata gaatacctct ttgatagtac tatgattacc   2340

accaaagatg tttttttgtc caaacttgtt actttaaggc taaatggcat gcatggcctt   2400

caagaagtgt ttcatgacca gttttctcta tgctctctgg aaaatttaca agaactaatc   2460

atagaaaatt gtgcacaatt gtacagcata tcctttccaa ggtactcaaa tctatgcagt   2520

atcaaggtct taagaatata caattgccca gtcctaactt ctctcttcat gccatccatt   2580

gtcaaaactc tagtgctgct ggaggttcta aaaatatctg agtgccataa attgaagtac   2640

ataatagaag aagtcaaaga agggactatt aacagacaaa atcatgcatc tatgacgctc   2700

ccaaaattaa gtatcattga tattgaagga tgtgaaaggt tgaaatatat attgcctgtg   2760

tgttttctgg gagagctagt tagtttgcaa aggatgagca ttcgaaaatg tagcgagttg   2820

atgtatgtat ttggaaatga aaaggagcat gatctttcag cgtaccaaca ccagagtaca   2880

taccattgct tgtatccaaa tttgcttaat ttggatactt tcaagttgga ttccttacca   2940

aatcttgttg acttttggcc tgattactat cgtccgcgtt tactaaattt gaaagagggt   3000

cgatgcactg agtgtcccgg actgtccaat tcagcgcgta aggtggtgat ttatttaaac   3060

ttgcgccaag acataactgc aacggataag gtgggtaaag tctcctctca taggacacaa   3120

caggatacca ctataggcaa gaccatcaga cgtcttaagg gaattttaga tcgtgctgag   3180

atgacttcat cgactcaaga atcaattgct ccttcttcat ccaacaatgc ctatgaggat   3240

atagctagag ctcaacaaca agttgcagaa gctcaaaggg atgcatcaat tgctcgacaa   3300

gaaactactg ttgtaagtca tctgcttgag caaatgatgg aaaagttggc agtaaatgag   3360

cagataggat tacaaaagag ggcccatgag cacgtgggac tacagagggg aacccagcaa   3420

gagccagagg aagatggata a                                              3441
```

```
<210> SEQ ID NO 182
<211> LENGTH: 642
<212> TYPE: DNA
<213> ORGANISM: Glycine max

<400> SEQUENCE: 182

atgattaatt tgaggaagct tgttcagagg tcactgtctt tagaagcact tcgcaacttg     60

gtgcctcata ttgaagcctt agccttatct gccatgaact cttggggtgg tgatggccaa    120

gtcattaaca catttaagga aatgaaaatg ttttcttttg aagttggaat cctcacagtt    180

tttggccatc tagagccgcg tttgagagag gagctaaaga agaattaccg gattgtggac    240

aatggttaca aatcctttcc aatgtgcatc ccaagaacac aataccaaaa ggcactattg    300

gctagaagga gacttagcaa gattatatgt gacataattt gtgagaggaa ggagaagaag    360
```

ttgtttgaaa gggatctctt gagctgctta ttgaattgga aaggtgaagg gggagaagtg 420
ttatctgatg accaaattgc agataacatt attggggtgc tttttgctgc tcaggacacc 480
acagctagtg ccatgacatg ggttgtaaag tacctgcatg atgaaccgaa acttctggag 540
tctgtaaagg ctgagcagaa ggcaattcac aagtctaatg aaggtaacct accactgagt 600
tgggatcaga ctagaaacat gcgaattact cacaagacct ga 642

<210> SEQ ID NO 183
<211> LENGTH: 264
<212> TYPE: DNA
<213> ORGANISM: Glycine max

<400> SEQUENCE: 183
atggccgaag aatttgtgaa tgactttgtt catcaaaatg gcatcactgt cataatccac 60
aatcccccca aaggtgatgg ggagaaaaag accaaaattt ggataatatt agttgttgtg 120
gtggggctaa tatgccttgg aatccatata tttctggtat ggaggtttaa gagaaaacct 180
aaagcaattt catcagcttt tggttacaac aacaatagcg aaatactagt cattgatcta 240
acgaggagta cagacttatc ataa 264

<210> SEQ ID NO 184
<211> LENGTH: 3753
<212> TYPE: DNA
<213> ORGANISM: Glycine max

<400> SEQUENCE: 184
gcaggttaca aagatattgg aaatcctatt tggcaatgca agcaatgtaa agcaaagatg 60
tggtatgatg agaggattaa caaagataaa cagacaaaaa atccaaagtt ttcattatgt 120
tgtggtgatg gtaaaataca actgccaata ctacatgatg ctccgcaacc cttgtggcag 180
ctactctttg acagcagaga ctcacaagta aagaaattcc aacaaaacat acgtttatac 240
aacctaatgt ttgcattcac atctctcggt gtcaaagtag acacatccta taatactgga 300
agaggtcctc ctacattgcg catacatggt caatcgcatc accttattgg aagcctccta 360
cctataccgg ataactcacc aaagtttgca caactatata tttatgacac ggagaacgaa 420
gtcaacaata ggctttcaca ataccctata aaaaataatg ttgatgaaga cattataatt 480
ggtatcaaga atatgctaga tacccacaat ccatatgcac aaaaattcag aatggcaagg 540
gataaactag actcttctgc agtgtgtgac ctgaaactaa aactcattag tgacagacaa 600
actgatggca gattatataa tttgccaaat gcttctgaag tggctgcttt aattgttggt 660
gatgagcata caacaaataa caaagatatc atcattgaga agcaaacagg catgctacaa 720
agaataaatg aacttcatcc tacatattta cctttgcaat atcctctttt gtacccacac 780
ggtgaagatg gctacagacc aaacattctt cataacatca tccgcatagc catgctgcaa 840
agaggaacaa agatgcaatc aagggataat gaagcacaaa caatacttca ttcaagaaga 900
ttgtttcacc aatgggttgt tgatgggtat tgtatgattg agtctcaaaa actaaactat 960
gttagacaac atcaacaaga actccgagtt gccaagtaca tcaatttaaa ttactgtaat 1020
aatcagccct taacccaagg taatgaaaaa ggtaagagaa ttatactacc aagttcgttc 1080
gttgttagtc agagatatat ggaacaattg tattttgata ggatggcaat ttgtgcccat 1140
gttggatttc ctgatctatt tttgacatta acgtgtaatc cagtatggcc agaaatacaa 1200
cgacaagttg aaaagtcaaa tcttacagct catgattgcc ctgatgttat gtcacgggta 1260
ttcaaaataa aactaaacca gttgatgcat gatcttaaga gtggacatgt atttggtccc 1320

-continued

```
attcttgcat acattgacaa cataattttt gctgaaatac caaacaagga cacatatcca   1380
gaattgtatc aaattgtctc caaccacatg atgcatggtc catgtggact agctaataaa   1440
agggcaccat atatggccaa tggcaagtgt ttcaggtttt tcccaaaaaa gtttcagcca   1500
gccacaattg ttgaccaaga tggttttcct gtttatagaa gaagagacac cagacggatt   1560
gtgcaaaagc agggtgttca tctcgataat caatttgttg tcccatatag tccacatttg   1620
ctactcaaat atagaacaca cctaaatttg gaatggtgca atcaaagtac ctcaataaaa   1680
tatttgttta agtacatcaa caaaggatct gatcggatta cagctgctat tgtcaatgac   1740
caaaaccagg atggcacaca caatcaggtt catgatgaaa ttaaacatta tcttgactgt   1800
cggtatgtgt cgactcctga agcatgttgg aagatttttc cattcccaat gcatgggcat   1860
gcatcggcag ttgaacgtct ttatttccac ctagaaaatc aacagcctgt ttactggaaa   1920
gatagtcaag aaattggcac agtactggct aagagtacaa tcaaagaatc aatgttcaca   1980
gcttggatgg attctaataa aatataccat catggacgat atcttactta tgctgaatat   2040
gtgtccaaat ttgtttatga tgcacgaaaa agatgctgga aaccaaggaa acaaggaaat   2100
actattggca ggctgatttg ggtgcccccct tccagtggag agttattcta catgaggatg   2160
atgctttgct ctgctaaagg atcacaatgt tacgaagata ttagaacagt agaaaatgtt   2220
gtctatcata cattcagaga agcatgcttt gcaaaaggtt ttctaggaaa agcaaacact   2280
tggggaactc cacactatct taagaagtta tttgtgaagc tgctatttat gaataccatg   2340
gataggccag aatatgtgtg gaaacaaact tggcaatgga tgacagatga tattgtattt   2400
aatcatagaa gacaagattt tccttcaatg ccatacccac taggatatgc cgccaacacg   2460
caccaaaata atctcatcta caatgaattg acttacgaca gagacatatt ggtcgccgaa   2520
tttgacaaat gctaccagtc gctaacagat gagcaggctt ctatttttaa taagattatg   2580
catgtggttg caactcaatc aggtggagtt tattttctat atggatatgg tggcacatgc   2640
aagacatttc ttcaagtggg attgcctggc ggtagaacaa cacattctaa gtttgctatt   2700
tctgtccctg caacaaaaaa ttctacatgc aatattcatc aagggactcc aatgtgtcac   2760
agatacagta ttgaggccct tgacaaaagt ttacaagaca tcatgcacaa cagcaatcct   2820
tttggaggaa aggtcattgt ttttggtggt gatttccgtc aaattctacc tgttgtgcca   2880
agaggtaatc gttctgacat tgtctatgca actttaaatt catcttacat ttggaaccat   2940
tgtcaaattc taaagctgac taaaaaaatg cgatttcaat caaatcctac tgaccattcc   3000
aacttggatg aactaaaaca attttttgag tggttgctag acataggtga tgcaacatat   3060
ccagacttat tacacaacta caacaatggc gatttcttgc aaaaaagagt tgtccttgcc   3120
tctacaaaag atgttgttga taaaataaat gactatgtcc tgtctttgat tcctggtgag   3180
gagaaagagt attgtagtgc tgattctatt gacaaatcag atgaactact caatcctgca   3240
tttggagtac taacagttga atttctaaac tcattgaaga catcaggcat accaaatcac   3300
aagctcataa tcaaggttgg tatgcctacc atcctactac gaaatctgga ccaagctgat   3360
gggttatgca acagaactag gcttattgtt acaagacttg gttcaagtgt tgttgaagtg   3420
gagattatta ctggacccaa cataggccat agaacataca ttccaagaat gaatctttct   3480
ccctctgatt caccatggcc attcaagcta attagaagac aatttccatt catggtttca   3540
tttgcaatga caattaacaa atctcaggga caatcgttgg cacatgttgg attgtatttg   3600
ccaaccccag ttttttctca cggccagtta tatgttgcac tttcacgagt tcaaagcaaa   3660
```

aaagggctcc acattcttat tcatgataat caaggcactc ccaaaaatac taccattaat 3720
gtagtataca aagaagtttt ttcaaactta taa 3753

<210> SEQ ID NO 185
<211> LENGTH: 1947
<212> TYPE: DNA
<213> ORGANISM: Glycine max

<400> SEQUENCE: 185
atgcctccaa atttgttgcc tatcgttgtt acatctatta gaacaaggat cgaagaaggg 60
ttttggatga aaagtgatcg aagtagtctg ctgcaggcag ctgctattgg ttgcttgaca 120
ttagctttgt ctacttcacc atcttctgct caaataagga agatgctcta tgatgaggtt 180
tcttcaggtt atattgtgac tgaaaagaag tctggtgttc tttctacgtt atttgaatat 240
tcaatgcaat ggagttgccc aaccatttgc cttgaggccc ttcaggcact taaagctgta 300
tcccacaatt atcctaacat agtgtctgct tgttgggaaa aagtttctgc tattgtgcat 360
ggcttcctta gtactgtgtg ccttgaagct ccttccaggc agtcaagtga tcatgttggt 420
agtccttctt catttaataa tgaaaaagtt ctgatcactg ctattaaggt tctggatgag 480
ggtcttcggg cagtctctgg atttcaagga acagaagatc tttcagatga taaattgatg 540
gatattcctt ttgcatctga ttgcattagg atgaagaaag tgtcatctgc tccatcatat 600
gagctagagt gcaaagatga tgttatagtc aactttgaat cttgtggatc aggaagtcag 660
cagtggtgtg aggcaattga gaagcatatg cctcttattt tgtgtcactc ttcagcaatg 720
gtgagagctg catcagttac ttgttttgcg ggtatgactt cttctgtatt catttgtttt 780
tctaaagaga aacaggactt catattgtct tctttagtgc atgctgctgt acatgataat 840
gtgccatcgg tgagatctgc tgcttgtcga gccattggta tcatttcatg ttttccacaa 900
gtgtgtcaga gtgcagaggt acttgacaag tttatccatg ctgttgagat taacactcgc 960
gatgccctaa tctcagttag gataacggct tcatgggcat tggcaaatat atgtgatgct 1020
atttgtcact ctgatagaat actcccctat gggcaaatgg gttcaaactc caatacccag 1080
gtgattgtat cattgagtga atgtgctttg catcttacta aggatggaga caaggtcaaa 1140
tctaatgctg taagggctct tgggtatatt tcaagaatct taaaatcttc aacatcaaaa 1200
ttccaaggca cgtcagcggg tcaccatgac cgcatgactg atgcgtatct caatagtgag 1260
aatctaatgg tgtgtcaaca gaattgtgca tcagattctc tgcaagattt gaataggcta 1320
gagagaatag ttcatgcatt tatttcttgc attactactg ggaatgttaa ggtccagtgg 1380
aatgtttgtc atgctctagg caacttattc ctcaacgaga cattaaggct gcaagatatg 1440
gattggactc cagttgtgtt tggtgttctt ctgcaactat tacgtaattc atcaaatttt 1500
aaaatcagga tacaagctgc agcagcattg gctgtgccaa tgtcaatgca agattatggc 1560
ctatcctttt cagagattgt gcaatctgta gagcatgtaa tggagaatat tgacgatgac 1620
caaatttctg ggccatcaaa tttcaaatac agggtttcgt tacaaaagca gcttaccttg 1680
acaatgttac acattctacg ctttacctca agcacaaatg atcaaaacct gaaagatttt 1740
ctagtgaaga aagcatcgat ccttgaagat tggttcaagg gattatgctc atctggcgag 1800
ggcatgctcg atgttcaaga taagtgcatt gcagaccgaa agagggtttt gatatctggt 1860
gcgctacagt cgttgattga agtatacaaa gaaaaacaac aggatgcgat agctcagaag 1920
tttgaggaat tgaagaacaa tatgtaa 1947

<210> SEQ ID NO 186
<211> LENGTH: 255
<212> TYPE: DNA
<213> ORGANISM: Glycine max

<400> SEQUENCE: 186
atggaaaaaa gtttgtctcc tagaagcaaa acaaacggag ggtggttttc atgttggggg 60
cgtctcaaat tgaagcttcc atggtcgaag agaacaagca cttataaacc cattggtggt 120
tttaactatg accctttaag ctatgctcaa aactttgacg agggatggga ggaggatgat 180
gaagaatctt tacatcgcgg gttctctgct agatatgcag caccttcctc acataataaa 240
ttgctcaagc aatga 255

<210> SEQ ID NO 187
<211> LENGTH: 1530
<212> TYPE: DNA
<213> ORGANISM: Glycine max

<400> SEQUENCE: 187
atggatttga agattcaaca tattaaatgg gtggggaata tttaccagaa gtttgaagca 60
gtgtgtcagg aggtggatga tattgtaggc caggatgcag ttaaatatct tgagaatcag 120
gtccaaaatg ttggagacag tgtgaaaaag ttctattctg gagttgtaca tgagctactt 180
ccttttccta cctcggctga ttcaaaatat gaatctcatt cagtggcttt gacaaataat 240
attggctttc cagttgagtc agttgttggt cataaagata ataataaaaa aagggatgag 300
gaaaatccca ccaataatgt tatcaagtca ttacaggaat ctagtgccat tgatattgct 360
aacaatcagc aagttggtgt tcctatcaag cacaaactta ttgatgaaac ttgttcagat 420
tccctggagg tggaagattc ttacataact caggaagagg tcggtgatga ttcaagagaa 480
acttccgggg ctaagaaaga aaagttgaat acaagcattg aagaggtttc tgttgagtct 540
gtgcctaaat cgatgaactt gatgtctctt agagagaaag aatcccttga attccctata 600
cacagtgaat cttattctga ttcttctgac agcgggtgtg aagattcaat cgcaaaaaag 660
gataacatag atgtgactgt ggaacaaaac tcatgtttgg ttgttgaaaa aaatgctatg 720
aattcatcca cctcagaagt gttgagttcc cagtctcttg acggggaaga atcaattaaa 780
gtttccttgt tcagtgaatc atctgatgct gttgatgagg atacccatga catactagct 840
gaagtttcac ctgatgcttc tgtgtcaagc gaaagaccta ttatcacaat gacagaacct 900
ttatgctcca gaaacttcat aacttctgac agtctatatt caaagtcact cggaagctac 960
cccttggaaa ttgaatcttg caaaaacaat tcaggtgatg ctactctgtg tatttcagat 1020
agttccatga tgcatatatg ttgtgaatca tccccccatg tagctcgtca aatcatggaa 1080
tcccaggatg gacttgcttt ctctggctac tgccaatctc tggaatcaaa tgataaatca 1140
ctgttcagct ctgttgaatc cagtttggaa gacattgatt tgaatgatga tccaaagctt 1200
gaggaaaact gtgtatttgt ggacgatagt gaactctatg cagtctcttg tagagcccaa 1260
aagcttagat catataagaa aagaattctg gatgcatttt cttcaaagaa gaggttatca 1320
aaggagtatg aacagctagc aatatggtat ggagacaccg atattgagcc aaaacaagga 1380
ttttcacaaa cttcattgcc atttatctcc agaacgtaca tggactcgaa gaatgtgcaa 1440
gttcagcgtg cttctgaaac tgagtgggag ctgctatatg catataggat ttcattccat 1500
gcatcaggga ctccaggtag gcaccagtga 1530

<210> SEQ ID NO 188

<211> LENGTH: 1914
<212> TYPE: DNA
<213> ORGANISM: Glycine max

<400> SEQUENCE: 188
atggaatcaa gcatggatgg aagatcctct ccccatttgc tgatgcttct ttgctttgct 60
tcatttcttc aaatatgtca ctcagcatcc caactgaaga gctacattgt ctacactggc 120
aatagcatga atgatgaggc ttctgcgttg actctttatt caagcatgct acaagaagtt 180
gcagacagca atgctgagcc caagttagta caacaccact tcaagcgtag tttcagtggc 240
tttgttgcta tgctaacgga ggaggaggcc gatagaatgg ctagacatga tagagttgta 300
gctgtctttc ctaataaaaa gaagcaactc catacaacaa gatcatggga ttttattggc 360
tttccactac aagcaaatag agcaccagct gaaagtgatg tcatcattgc agtacttgac 420
tctggaattt ggcccgaatc tgagagcttc aatgacaaag gattcggtcc accacctagt 480
aaatggaagg gcacctgcca aacttctaaa aatttcacat gcaataataa aatcattggg 540
gctaagattt acaaagctga tggatttttt agcgatgatg atccaaaatc tgtgagggat 600
atagatggtc atggcactca tgtagcatca acagcagctg ggaacccagt tagcacagct 660
agcatgttag gccttggtca gggaacagca agaggtggcg cgacaaaagc acgcattgct 720
gtgtataaag tgtgttggtt tgatggttgt tctgatgcag acatacttgc tgcatttgat 780
gatgcaattg cagatggggt tgacataata acagtttctc ttggagggtt cagtgatgaa 840
agctacttta gagatgtaat agccattgga gcatttcatg ctgtgagaaa tggagcatta 900
acagtaactt cagcaggaaa cggtggtcca agaccttcct ccctatccaa cttttcgcct 960
tggtcaatta ctgtggctgc tagtaccata gacaggaagt ttgttaccaa ggttgaatta 1020
ggtaacaaaa tcacctatga gggtacctca ataaatacat ttgatctcaa gggagaattg 1080
tatcctataa tttatggtgg agatgcacca aacaaaggcg taggcataga tggatcgtca 1140
tcaaggtttt gcttcagcgg ttcgttggac aaaaagttag ttcatggtaa aattgttctc 1200
tgtgatagca gaagccaagt gtcaggccct tttgatgctg gtgctgttgg ggcattggta 1260
caaggtcaag gttttagaga tattcctctc tcttttccat tgcctggatc ttaccttgcc 1320
ttgcaggatg gtgtctctgt atatgactac ataaactcta caaggactcc aactgcaacc 1380
atatttaaga ctgatgagac aaaagataca atagctcctg ttgtggcctc tttctcttca 1440
aggggcccaa acattgttac acctgaaatt ctcaagccgg atttagtggc tcccggagtt 1500
tcgattctag ctagttggtc tccagtttcc cctccttctg acattgaagg tgacaacaga 1560
acattgaatt tcaatataat ctcaggaact tcaatggctt gtccacatgt ttctggagcc 1620
gcagcgtatg ttaaatcatt tcatccaaca tggtctcctg ctgctattcg ttcagctcta 1680
atgacaacag ctaaacaact tagtccaaag actaaccttc aggcagaatt tgcatacggc 1740
tcaggccaaa ttgatccttc caaggctgtg taccctggtt tagtatatga tgctggtgaa 1800
atagactatg taaggttttt atgtggacaa ggctatagta caaggactta caactcatca 1860
caggagataa cagtagctgc cctgaaacaa agaatggttc agcaagggat ctaa 1914

<210> SEQ ID NO 189
<211> LENGTH: 996
<212> TYPE: DNA
<213> ORGANISM: Glycine max

<400> SEQUENCE: 189
atggaaatct tgtctcgtct acccgtgaaa cctttgatcc aattcaagta tgtgtgcaag 60
ggatggaact ccctgatgtc agatccctat ttcatcaaat tgcaccttag caaatttgct 120
gcgaaggacg atttggaaca ccttcaactg atgaaaaatg tctgcctcgg atccatccct 180
gaaatccaca tggaatcgtg tgatgtaagt tcgttattcc attccctaca aattgaaacg 240
ttcttgttcg atttcgaaaa catgccaggt taccatctgg tcggttcatg taatgggttg 300
cactgtgggg ttagcgaaat accagaagga taccgtgttt gtttctggaa caaggcgaca 360
agggtgatat ccagagaatc gccaacgctg tctttttccc tgggcattgg tcgtagaaaa 420
atgtttgggt ttggctatga tccgtcaagt gacaaataca aggttgtagc aattgcattg 480
actatgctct cacttgacgt atttgaaaag actgagatga aagtttatgg cgcgggtgac 540
agtagttgga gaaaccttaa aggttttcct gttctttgga ctttacctaa agttgatgga 600
gtgtatctga gtggaaccct taattgggtt gttattaagg gaaaagaaac cattcattct 660
gaaatcgtaa ttatttatgt tgacctggag aaggagactt gcagatcact gtttcttccc 720
gacgattttt gctttttga tacaaatatt ggagtattta gagactcgct gtgcgtttgg 780
caagatagca acacccatct tggcttgtgg cagatgagga agtttggaga tgacaagtct 840
tggattcaat taataaattt tagttattta catcttaata ttcgtcctta tgaagaaaaa 900
tcgatgattt taccattgtg catgtctaac aatcgagact tcttcatgct gaaattcact 960
agaaatgctg atgatgaata ccaaacaatt ctgtaa 996

<210> SEQ ID NO 190
<211> LENGTH: 2208
<212> TYPE: DNA
<213> ORGANISM: Glycine max

<400> SEQUENCE: 190
atgagtgagg aagaaccagc gaatgaagtt tctaagattg attcaaatgg aaagagcttg 60
cagaagataa ttttggatga aattactgag aaagaggatt tggaaactga tggaggaaaa 120
gtcttggaga acaatggaat caaagagttg aaagaaaata ttgtaaaaga aattgaagat 180
aagaaaactg atagtgtgga aaaggtagaa gaggacaaga aagttggtgt tgtggaagaa 240
gcaaaagagg ataagaaaga agatggggtg aaagaagcaa aagaggataa gaaagaagac 300
ggggtgaaag aagcaaaaga ggataagaaa gaaggggtgg aagaagcaac agaggataag 360
aaagaagatg gggtggaaga agtaaacgag gataggaaag aagatggggt gggagaagta 420
aaagaggata aggaagttga tggtgtgtca tgtgtgaaag aagttgagga ggatggggaa 480
gttgatggtg tgaaaaaagt agaagataaa aaaggtgatg agttgaaaga aatagaagag 540
gataagaaag atgatcatat atctgaaaat gataaaatgg atgaagacac tgagattaag 600
gaaacaatgg aaggtgaacc agaaaatgga aaagaggaat ctgagaaacc agtagtagat 660
gctatggaag tggagggtgg tattaaggag aaggaggaga gcaaagaaaa tgagaaagtt 720
gaagtggtga tggaggagga tgagaaggat gaagatgagg ataaggataa tattgataag 780
tcaaaagaag agaaggcaga agatagtaag ggtgagaaag gatcaaaaaa acgtgggaga 840
gggaagatca atggggagaa agtgaaagaa aaaagaaaag aactgaagaa aacagagcca 900
aggactccta ctattgatcg ccctgtgcgg gaaaggaaat cagttgagag gttggtagca 960
tcaattgata aagatgcaac caaagaattt cacattcaaa agggccgtgg tacacccttta 1020 aaagatatac caaatgtggc atttaaatta tctagaagga agactgatga taccttcaaa 1080
ttgctccata caattctctt tggaaggaga gggaaggcag ttgaaatcaa gagtaatata 1140

-continued

```
tcaaggtttt ctggttttgt gtggcgtgac aatgaggaaa agcaaatgat taaagtaaaa   1200

gaaaaacttg acaagtgtaa taaagagaag ttactggaat tctgtgatgt gcttgacata   1260

acaattaaca aggcaacaac gaggaaggaa gatattattg ctaagcttat agacttttta   1320

gttgcccctc atgcaaccac aactgtgtta cttgcagaaa aagagaagcc cagtaaggga   1380

acaaagcgca agcgtgttgt aaaacggggt tcatcaagat ctgggacaac ttcaagacgt   1440

tctgtgaaga ggcagaagaa aaacgaagat tctacagtag cgcggagaaa gagtgcatct   1500

gacacagatg agtcagagga agacaagaaa gatgaagaaa acgaggagga aaatgaaatt   1560

ggtgttgctg acaaatctga ggatgaaaca ccagagaaat ctgaaagtga agacaaaagt   1620

gattctggga gtgaatctga agatataaaa gaaaagaaaa aaccttctaa aacatcatcc   1680

acaaagaaag aatctgctaa gaaaagtaaa aatgaaaaaa ttacagttcc caataaatct   1740

cgctcaccac caaaaagagc acctaagaaa ccatcatcca atctctcaaa gtctgatgaa   1800

gacagtgatg aaagtccaaa ggtcttttca aggaaaaaga aaaatgagaa aggaggaaag   1860

caaaagacgg caacaccaac taaatctgcc tccaaagaga aaactgcaga aaaggttact   1920

agaggaaaag gcaaaaagaa agagaagtcg agccccagtg acaatcagtt gcgtgatgcg   1980

atatgtgaaa ttcttaaaga agttaacttc aatacggcca catttaccga cattctgaag   2040

aaacttgcta aacaatttga tatggatctc actccgagaa aggcatctat aaaatccatg   2100

attcaggaag agctgacaaa actagctgat gaagcagatg acgaggacag agaagaggat   2160

gctgagaaag atgaagcccc atctacaggc caagaggttg aaggctga                2208
```

<210> SEQ ID NO 191
<211> LENGTH: 336
<212> TYPE: DNA
<213> ORGANISM: Glycine max

<400> SEQUENCE: 191

```
atggagtttt gccccagttg tggtaacatg ctacagtatg aattgcctta tatgggtcgc     60

ccttcaagat ttttttgttc tgcttgccca tatgtttgcc acattgagaa tagggttgag    120

atcaaaagaa agcaaaggtt ggtgagaaaa gagatagagc ctatattctc cgaggatgac    180

atgacaaatg caccatcaac tgaagcgacg tgcccatttt gcggtcatgg taaagctgct    240

ttcaaagaat ttcagactcg atcggctgat gagccagcaa ctctatttta taagtgcttg    300

aacaatgact gtaaaaaaca atggcgtgaa ggttga                              336
```

<210> SEQ ID NO 192
<211> LENGTH: 174
<212> TYPE: DNA
<213> ORGANISM: Glycine max

<400> SEQUENCE: 192

```
atggttcacc gcaacaattc ctccttcttc gacaccacct ctttcccctt gtaccttcct     60

cacaacatcg tggctctttg tttgccctct ttcctttgtg cttcgctatt gatgagatca    120

acacaacaaa gatattggaa tctccatcat gggttgatca ttgataaagc ttga          174
```

<210> SEQ ID NO 193
<211> LENGTH: 2532
<212> TYPE: DNA
<213> ORGANISM: Glycine max

<400> SEQUENCE: 193

```
atgtcaggct atttagatat tgggtatcca ataatgcagt gtaaacaatg ccaagcaatg     60
```

-continued

```
atgtggtatg gagaaagaat gcttaaacat aggcatggta ccaatccaaa gttcagtttg    120
tgttgtggaa atgacaaggt ccaacttcca ttattacaaa caccacctcc attgttagca    180
aaacttgatg actttattaa cgatggaaga ggaccgccaa caatttgtat ccaaggccaa    240
ccatgtcata ggattgggag tctattacca atgcccagaa aagaatcaaa attcacacaa    300
ttgctacaat tcaaacccat ggaagcgcat acagatttac attcaaggag actattccaa    360
caatttagtg ttgatggcta taccatggtt gaatcagaga gactttattt cataagaagt    420
atccaatcaa aattaagggt cgacaaatat tgtgatttgc gtgaaacatc taatcatggt    480
gctactcaag ggtcaaacag aggcaagcgt gccattttac cttctacatt tgttggtagt    540
cgtaggtaca tggatcaatt atacttcgat ggtattatca tattcatgta caccattgaa    600
ttccaaaaaa gaggtatgcc atatgcacac ttactcctat ttttgcatcc attgagcaag    660
tatccaacgc ctaaagatat cgacaagatt atatgtgctg agataccatc aaagaatgaa    720
caaaatgaac tttactcgct ggtccaggca cacatgatac atggttcgtg tggcatagcc    780
aaccaatcat caccctgcat gaaggatgga aattataggt gttggaaacc atgcaaaaaa    840
gggttcacac ttggcaggtt aatttggatt tcacctaccc ttggagaatt atattaccta    900
aggatgatgt tgccagtgtg caaagggcct acctgttatg aagatataag aacaatggaa    960
aatattgtgt atcctacatt tagagatgct tgttttgcat taggctttct tcaagatgat   1020
aaggaatatg ttgaagcaat taaagaagcg aaagattggg gtacaagtca tcacttgaga   1080
aaactttttg ttacaatgct aatcacaagt tccattaata aaccagagca ggtttggaaa   1140
caaatatggc attggttagc tgatgatatt ctatattctt tgcaactgaa tgatgatgaa   1200
ttgaaaaatt taacttcatt ggagattgag aaatttttgc gtgcgagtgg aaagatctta   1260
aaggactatc caccaatatc atgcatagct gcaaaattgt caagttatat aggaaattgt   1320
ttgatacact tggaactaca ttttgatctt gctgaattag atgctgaatt caaaatatta   1380
ttctctgctc ttactaccct aagagcaaag aaaaaaattg ttttggtagt tgcatcaagt   1440
ggaatttcat ctttattact acctagtgga agaacaacac attcaaagtt taggattctt   1500
ctaccaactt tagatgactc agtttgtaat ataacccatg ggagtgactt agatgagttg   1560
cttaaagtta caagtttgat tatatgggat gaagcaccaa tggtgcacaa attctgtttt   1620
gaagcactaa acaaaacctt aaatgatatc atgaaaatta gtgatgatag tgacactgtt   1680
ttcagaggaa aaatagttgt tttttgtcaa attcaaacac tacacatgca actggagtta   1740
caaactttgc aaaatgaatc cttcaaattg gagatggaaa ttccaaaaga attgtttatc   1800
ctgaattaca ctgatccaat tgatgttata gttaaatgta aataccctaa tcgaaggcaa   1860
cattacaagg attcagagtt tctacaatcc agggctattt tagcatcaac taatgaaact   1920
gttgaccata ttaatgatta tgtattatct ttgatctcag agagagaata cctaagctca   1980
gatttaattg aaaaagctaa aacaatagaa agtgaaaggt ttagcacaat aactatggaa   2040
tttctaaact ctttgtcaac ctctggtctt ccaaatcata agattaaggt caaggttggc   2100
tcaccaataa tgttgttaag aaacttagat caaaatgaag gcctatgtaa tggtactaga   2160
ctaattatca caagttttgc caaccatata attgaagcta aaatcatgac aggcaaaggc   2220
caaggcaaca aagtgtacat tcctaggagg tcaatgtctc catcacaatc accttggcct   2280
ttcaaactca taagaaggca attcccaata attgtctctt atgcaatgac cataaatgaa   2340
tcacaaggac aatcattagc aagtgttggg ttatatctac ctagactagt atttagtcat   2400
```

-continued ggccagttgt atgtagcatt ttctagggtg caaatgacaa atggactaaa agtaataata 2460
caagataaag ataaaatgcc ctcaagtaca acaactaatg tagttttcaa ggaggtgttc 2520
cagaacttat aa 2532

<210> SEQ ID NO 194
<211> LENGTH: 1290
<212> TYPE: DNA
<213> ORGANISM: Glycine max

<400> SEQUENCE: 194
atggatccag cgttacccat tgtagcgtta tcgcttctct tgggtgccat catcgcattt 60
ctctttttca gcacctacta ccggaagcgg caatccgaaa tccaatctat cgccgatccc 120
aatcccaaac ccttatcctc caaagcccct cccaagaagc ctctctccaa accccattcc 180
tccgacaagg atcaaaacaa gcgacatcat ccgttggatt tgaatacctt gaagggtcat 240
ggtgatgcag tgacagggat atgcttctcc cccgatggac gaaatttggc aacagcttgt 300
gctgatggag ttgtgagagt atttaagttg gatgatgctt caagtaaaag tttcaagttt 360
ctgaggatta atttgccagc cggtggtcat ccaacagcag ttgcattttc tgatgatgca 420
tcctccattg ttgtggcgtc ttatactctg tccggctgtt cattatacat gtatggagaa 480
gagaaaccta aaacctctga agataaacca caaacaaagc ttcctctccc agaaattaag 540
tgggagcatc acaaagttca tgataagaaa tcaataatta ctatgtttgg agcctccgca 600
acttatggca ctgcggatgg aagtacaatt gttgcctcat gttcagaagg gactgacatc 660
attctttggc atggaaaaac tgggaagagt gttgggcatg ttgatacaaa tcaattgaaa 720
aataacatgg ctactatatc acccaatggt cgttttattg cagcagcagc atttactgca 780
gacgtgaaga tctgggagat tgtatatgct aaggatggat ctgtgaagga agttttaaat 840
gttatgcagc ttaaggggca taagagtgct gtgacttggt tatgctttat gccaaactct 900
gagcaaataa tcactgcatc caaggatggt tcaatgagac tatggaatat caatgttcgt 960
tatcatcttg atgaggatcc gaagacgctg aaggtgttcc taattcctct tcatgattct 1020
tccggtacta cactgcacta tgaccgcctg agtgtttccc ctgatggaaa aattttggct 1080
gcgacccatg gctccacact gcagtggtta tgtgttgaga ctggaaaggt tctggataca 1140
gctgaaaaag cccatgatag tgacatttca tgcatttcat gggctcctaa acccattcca 1200
atgggaaatg aacaagtttt ggttttagcc acagccagtg ctgacaagaa agtgaagttg 1260
tgggcatctc catctatccc ttcatcatga 1290

<210> SEQ ID NO 195
<211> LENGTH: 3177
<212> TYPE: DNA
<213> ORGANISM: Glycine max

<400> SEQUENCE: 195
atggctctgc gatcattctc ctatgacgtg ttcctcagct tccgagggga agatactcgt 60
tatggtttca ctggcaatct ctacaatgtc ctccgggaaa ggggaattca caccttcatt 120
gatgacgagg agctccagaa aggggatgaa atcaccacag cacttgagga ggcaattgag 180
aagtccaaga ttttcatcat cgtgctctct gaaaactacg catattcctc cttttgctta 240
aacgaactca ctcacatcct taactttact gaggggaaga atgatccgtt ggttttgcca 300
gttttttata aagtgaatcc ttcatatgtc cgacaccaca gaggtagtta tggagaagca 360
ctggctaatc atgaaaagaa gttgaactct aataacatgg agaaacttga gacgtggaag 420

```
atggctctgc gccaagtgtc taacatttct ggccatcatc tccaacatga tggtaataaa    480
tatgaataca agttcattaa ggagatagtt gaatcggtgt ctagcaagtt taatcgtgat    540
catttagatg ttccgaatgt cctggttggg ctagagtcac cggtgcgaca agtaaagtcg    600
cttctggatg ttggacgtga tgatgtcgtc cacatggtgg ggatccatgg actcgccgga    660
gtgggtaaaa caacacttgc tgtcgcagtc tataattcca ttgctgatca ttttgaatct    720
tcttgctttc tagaaaatgt gagagaaact accaataaga aggggttaga agatctccaa    780
agtgcctttc tttctaaaac agctggagaa attaagttaa caaattggag agaaggaatt    840
accataataa agtgtaagct caagcaaaag aaggttcttc tgattctaga tgatgttgat    900
gaacataaac agttacaagc gattattggc agccctgatt ggtttggtcg tggtagtaga    960
gtcatcatca ccactcgaga cgaacatttg ttagcgcttc acaatgttaa aataacatat   1020
aaggtgagag agttgaatga gaaacatgct cttcaattac ttactcacaa ggcttttgag   1080
ttggaaaaag aagttgatcc aagttaccat gatattttga atcgagcgat aacttatgct   1140
tcaggcctcc cattagctct agaagtaata ggttccaact tacttgaaaa aagtatagaa   1200
gaatgggaat ctgctctaga tggatatgaa agaattcctg ataaaaagat ctatgacata   1260
cttaaagtaa gctatgatgc tttgaatgaa gatgagaaaa atatttttct tgacattgct   1320
tgttgcttca aagcttataa attggaagag ctccaagata tactttatgc tcattatggt   1380
cattgcatga aatatcatat tggggtgttg gttaaaaaat ctctgataaa cattcatggg   1440
tcatgggatt ataaggtcat gagattgcat gacttgatag aagacatggg taaagaaatt   1500
gtccgaagag aatcaccaac aaatcctggg aaacgtagca ggttatggtc ccatgaggat   1560
ataaatcagg ttttacaaga aaataagggg actagtaaga ttgaaatcat atgtatgaat   1620
ttttcctcat ttggagaaga agtagaatgg gatggagatg ccttcaagaa gatgaaaaat   1680
ctcaaaacac ttatcatcaa gagtgattgt ttttccgaag gtcccaagca tcttcctaat   1740
actttaagag tattggaatg gtggagatgt ccttcacagg attggccaca taattttaac   1800
ccaaagcaac ttgctatatg caagttaccc gatagtagct ttacatcagt cgggttggcc   1860
ccattatttg aaaagaggct cgtgaatttg acaagtttaa ttttggacga gtgtgatagt   1920
ttaacagaga taccagatgt atcttgtctc tcaaatttgg aaaatttgtc atttagaaag   1980
tgtcggaatt tatttacaat tcaccattca gttggtttat tggaaaagct taaaatcttg   2040
gatgctgaat gttgcccaga gcttaagagt tttccaccgt tgaagttgac ctctcttgaa   2100
aggtttgaac tttggtattg tgtcagtctc gagagttttc ctgaaatatt aggaaaaatg   2160
gaaaatataa cacaactttg cttgtatgaa tgtcccataa caaaactccc accttcattt   2220
cgaaatctta ctcggcttcg atccttaagt cttggacacc atcaccaaac tgagcagtta   2280
atggactttg atgctgccac cctcatttcg aacatctgca tgatgccaga actggatggt   2340
atttcagctg acaatttgca atggaggcta ttgcctgagg atgttttgaa attgacctca   2400
gtcgtgtgtt caagcgttca atctcttact ttgaaactgt cagatgagct tcttccgcta   2460
tttctctcat gttttgtaaa tgtgattgat ttagagctat cagggagtga attcacagtt   2520
attcccgaat gcatcaaaga atgccgcttt ttatctaccc ttactttgga tcgttgcgat   2580
cgtcttcaag aaattagagg gattcctcca aacttgaaaa ctttctctgc aatggattcc   2640
ccagccttga cctcctcaag cataagcatg ttgctgaatc aggaactgca tgaggctgga   2700
gacaccgact ttagtttgcc aagagtacag attccacagt ggtttgagca caagaatccg   2760
```

```
ggacggccaa ttcgtttctg gttccgtaac gatttcccag ccatagttgc ttgcattgct   2820

aagtcagatt ttcagggagt tttcgattat ccagatctca gcgtgttcat taatggaagg   2880

gaacataaac attacggtcg taccccctgtc cttgaaaaac cttgtacagt tctttttcat  2940

cttctaatag aagatgattt agatgtatca ctgttagaga acgaatggaa ccgtgcagag   3000

attgtatgtt atggttcatg ggacgaatgc ggaatccatg tattgaaaga gctaagtagc   3060

atggaggata ttcgattcac tgatcctttt agaaaagaaa aatttgtagt tcagaggttg   3120

cggttcggga aaaagcaaag gttagcaaga gtgaagttgt tgagacacaa tttgtag      3177


<210> SEQ ID NO 196
<211> LENGTH: 3312
<212> TYPE: DNA
<213> ORGANISM: Glycine max

<400> SEQUENCE: 196

atggctgcaa caacacgttc ccgtgcatcc atctacgatg tgttcctaaa cttcagaggg     60

ggagacacac gctatggttt cactggcaat ctgtacaggg ctctttgtga caagggaatt    120

cataccttct ttgacgaaaa gaagcttcac agaggagagg aaataacacc tgcacttttg    180

aaggcaattc aagagtccag gattgctatt actgtgcttt ctaaaaacta tgcttcttcc    240

tcattttgtt tagatgaact tgtaaccatc cttcactgca agagtgaagg gctgttggtt    300

ataccggtct tttacaacgt agatccttct gatgtcagac accagaaagg tagttatgga    360

gtagaaatgg ctaagcatca gaagaggttc aaagctaaga aggagaagct gcagaaatgg    420

aggatcgctt tgaaacaagt agctgacttg tgtggatatc atttcaaaga tggagatgca    480

tatgaataca agtttatcca gagtattgtt gagcaggttt ctagggagat taatcgtgct    540

cctttacatg ttgcggatta tccagttggt ctagggtcac aagtgataga ggtaaggaag    600

cttttggatg ttggatccca tgatgttgtc cacattatag ggatccatgg aatgggcggg    660

ttaggaaaaa caacacttgc tctggcagtt tataatttga ttgctctcca ttttgatgaa    720

tcctgttttc ttcaaaatgt gagagaagaa tcaaataaac atgggttaaa acaccttcaa    780

agcatccttc tttcaaaatt acttggggag aaggacatca ccttaacaag ttggcaagaa    840

ggagcttcaa tgatacaaca taggctccaa cgaaagaagg ttctcttgat tttagacgat    900

gttgataagc gcgagcaatt aaaggctatt gttggaagac ctgattggtt tggtcccggt    960

agcagagtca tcattaccac tcgggacaaa catctgctaa aatatcatga ggttgaaaga   1020

acctatgagg tgaaggtttt aaatcagagt gctgctcttc aattgcttaa gtggaatgct   1080

tttaaaagag aaaaaattga tccaagttat gaggacgtct tgaatcgtgt agtaacttat   1140

gcttctggcc ttccattggc tttggaagtc ataggttcca acttgtttgg aaagactgta   1200

gcagaatggg aatctgctat ggaacattat aaaagaattc ccagtgatga aatcctagag   1260

attctgaaag taagctttga tgctttgggg gaagaacaaa agaatgtttt tcttgacatt   1320

gcttgttgct tcagagggta taaatggaca gaggttgatg atatactccg tgctctttat   1380

ggtaactgca agaagcatca tattggggtg ttggttgaaa aatctctcat aaagcttaac   1440

tgttatggta ctgatactgt tgaaatgcac gacttgattc aggacatggc tagagaaatt   1500

gagcggaaga gatcaccaca agagccaggg aagtgcaaga gattatggtt accaaaagat   1560

ataattcaag tttttaaaga caacaccgga actagtaaaa ttgaaatcat atgcctggat   1620

tcctccatat ctgacaaaga agaaacagtg gaatggaatg aaaacgcctt catgaagatg   1680

gaaaacctta aaatacttat tattagaaat gacaaatttt ccaaaggtcc caattatttt   1740
```

ccagaaggtt tgagagtact ggaatggcac agatatcctt caaattgttt accatctaac 1800
tttcatccga acaatcttgt tatatgcaag ttacctgaca gttgtatgac gtcgtttgag 1860
ttccatggcc catcgaagaa gttcgggcat ctaacagttt tgaagtttga caactgcaaa 1920
tttttaacac agatacctga tgtatctgat ctcccaaatt tgagggaact ttcatttgaa 1980
gagtgtgaga gtttagttgc agttgatgac tcaattggtt ttctgaataa acttaaaaaa 2040
ttgagtgcgt atggttgcag caagcttaag agttttccgc ctctcaactt gacctctctt 2100
caaacacttg aactttctca atgttccagt cttgaatatt ttccagaaat aataggagag 2160
atggaaaaca taaagcatct ttttttgtat ggccttccca taaaagaatt gtcattttca 2220
tttcaaaatc ttattggact ccgttggtta accctgagga gctgtggaat tgttaagtta 2280
ccatgtagct tagcgatgat gcccgaactg tttgaattcc atatggaata ttgcaacagg 2340
tggcaatggg tagaatcgga agaaggtgaa aaaaaagtgg gctcaatacc atcttcaaag 2400
gcacatcggt tttcggccaa ggattgcaat ctatgtgatg atttttttt aacaggtttc 2460
aagacctttg ctcgtgtagg acatttaaat ctgtcgggga ataatttcac aatccttcct 2520
gaattcttca aagaattgca attattaaga tcacttatgg tgagtgattg cgagcatctt 2580
caggaaatta gaggtcttcc accaaactta gagtatttcg atgcaagaaa ctgtgcatcc 2640
ttgacttcct cgagtaaaaa catgctttta aatcagaaac tgcatgaggc tggaggaacc 2700
aattttatgt ttacaggaac aagtatacca gagtggttcg atcagcaaag cagtggacct 2760
tcaagttctt tctggtttcg taataaattc cctgccaaac ttctttgtct tcttattgca 2820
cctgtgtcta ctgggattgt tgtccttaat ccaaaggtgt tcatcaatgg caaatttcaa 2880
gaaattcggc cctattttgg aagacacgag ataaaaagta ggttgaactt ggatcataca 2940
tatatctttg atctccaagc gtctgctttc ataaataata atcggtttga agaaatggct 3000
agggaaaagg aatggaacca tgtggaggtt agatatcaaa gtgtgttagc ctatgaaaaa 3060
gaaaagagag aagaaggtgt cttagactta gagagctcaa tcattaaggc aagtggaatc 3120
catatattca aagaaagcag tatggaggaa gatattcgat ttgatgatcc ttatctcagc 3180
agttctgcat cagaaagccc atcgttgcta caaaccatag cctttgggaa acgcaattcc 3240
atagcttttt tcttattttt ttcatgtttt ttattttatt attttggttt cagttgtcaa 3300
aaattcactt aa 3312

<210> SEQ ID NO 197
<211> LENGTH: 1272
<212> TYPE: DNA
<213> ORGANISM: Glycine max

<400> SEQUENCE: 197
atggcgacgg ctgaagatgc tccagtgctc cctgaggacc tcatagtgga aattctgtca 60
tgggttgaag tgaagaatct catgcgattc aggtgcgttt ccaagtcctg gaattccctc 120
atcttcaatc ccacattcat taaattgcac cttcaaaggt cctcccaaaa catccacatc 180
ctgttaacat ttgaccaaga ttcatcgaac ccctacccgt accatgatga taactacatc 240
tccgtcgttg ccgcaccctg ctctatacag cgtttacttg agaacccatc atccactatt 300
tataatatag ttcattttct cgaggctcag tcaacatcat catcgtccac tatttatttt 360
gatgtttgtt accgatttaa gcacacttat ttgttcttgg gtgtatgcaa tgggttggtt 420
tgcttgcttg attgtttgta tgaggatgaa tttgaggaat actgggtccg atttggaac 480 ccggccacta gggccatgtc cgcagattcg ccccacttgc gtgtccattc gagcaattat 540
aaacttggag acattgctgt gaagcatgcg tttgggtacg atgattcgag tgacacttac 600
aaggtgttgg cgatcctttt taacgttaaa tcacaagatt gggagctgag agttcactgc 660
atgggtgatg acactggttg gagaaatgtt ttgacttgtt ctgcttttcc cattttgcaa 720
caagtttatg ggcagtttgt gagtggcact cttaactggc tagcacttga caattcgtcg 780
ggttctgatc attatcaatg ggaaactgtc actgtcgatc agttagtcat tttttcctat 840
gatctgaaga acgagacata cagttatttg tcgatgcctg atggtctttc tgaaatctct 900
cttgacgagc cttatcttgg ggttttgaat ggctgccttt gtctttctca tgatcacagg 960
cgaaccaatc ttgttgtttg gctaatgaga gagtttggag ctgaaaagtc ttggactcag 1020
ttgctgaatg taagctatca tcatcttcaa gttctagatt ttccaccttg tccagtggta 1080
cctttgtgca agtctgaaaa tgacgacgtc ctgttgctgg aagactatgg aggtggtgca 1140
gaatttgttc tggttgataa gagagataat agtatagacc gcatggaagg tttcaacaat 1200
ggattatcgt ctttctctgc atttgtctct catgattatg ttcaaagttt ggttttgcca 1260
tatcgaaatt aa 1272

<210> SEQ ID NO 198
<211> LENGTH: 2661
<212> TYPE: DNA
<213> ORGANISM: Glycine max

<400> SEQUENCE: 198
atgggagcta gtcgaaagct tcagggcgag attgatcgtg ttctcaagaa ggttcaggaa 60
ggcgtcgaag tcttcgatag catctggaac aaggtttacg acaccgataa tgccaaccag 120
aaggagaagt tcgaggctga cctgaagaag gagattaaga agctgcagag gtacagggac 180
cagattaaga catggattca gtccagtgag atcaaagaca agaaggttag tgcctcatat 240
gagcaggctc tggtggatgc acgcaagatt attgagcgtg aaatggaaag attcaagatc 300
tgtgagaagg agacaaaaac aaaagcattc tccaaagaag gcttaggtca acagcctaaa 360
actgatccta gagagaaggc taaatcagag acaagggatt ggttgaacaa tgtggttggg 420
gagttagaaa atcaaatcga taactttgaa gctgagcttg agggactttc tgtcaagaaa 480
ggaaagaaca ggccacccag attgacacat ctagaaacat caattactcg gcacaaggct 540
catataaaga aatgtgaatt tatcttgagg ctactagata atgatgaact aagtccagag 600
gaggttaatg atgtcaagga tttcctggat gactatgtag accgtaatca ggaggacttt 660
gaagaattta gtgatgttga tgagctatat agttcattac ccttagacaa ggtggagtca 720
attgaagata ttgttacaat tccccctggt cttgctaagg tggcacctgt gcttagcttg 780
aagccttctg tggtagcatc agcttcagca tcacaaacat ctgagcaagc tgatgataca 840
gcttcccagg atagcaattc tgatattgtt gcaggaactc cacctcctaa aagtagtata 900
gttagtccta ctactacaac accagcaggg aatttttcta ctcctgtttc tatgaatgtt 960
cccatgccta acttgtcgag tccaccagcc attgcgtcag ccatgcctgg ttcaaattct 1020
gttcggagtt ccttggagat tagtagtcct gtcaatgctt catcttttgt aaatcagtct 1080
agcactatga aggaggaaga gattaatagt ttccctggcc aaagaccatc tccatcactt 1140
tctgatgttg cacttgtaag gaacatcagc agaaacagct tatcaaatca agcaacaaat 1200
aacatacctc ttgtttctgg caatatggtt tccagcaatg ggccccttgg ttcagtccct 1260
tcagcatctg aaataaccaa gagaaacata ttggtagttg atgatagact cggaagcaat 1320
gggatggtgc agcctcttgt atccccttta agtaatagaa tgatcatgcc tcaggttgca 1380
aggcctaatg atggaacttc ctcagttgac tctagtagtg tcaacgaagc tgcaactgta 1440
tctgggagag ttttctcccc ttctgctgtt cctggcatgc aatggagacc tggaagcccc 1500
ttccagaatc agaatgatgt gggtcagatt cgtggaagaa ctgaaatagc tccagatcaa 1560
agggaaaggt atttgcagaa gttgcagcaa gtgcagcaac aagggcaaag tgcccttctt 1620
aatatgccat cttttgtagg agggaattct aagcagtttt ctgctcagca acaaaatcct 1680
ctcttacagc agttcaattc tcaaggctca tctgttgctt ctcaatctag cgtgggactt 1740
ggagtccagt caccaggtct tagtggtatt gcttccacct cattaccgca gccacccaat 1800
tctgtccatt ccccatctag ccaacaatca ttgctattag ttgtttccaa agatgcagat 1860
gttggaaatt ctaaggttga cgagccacaa ctacatattt ttcctgatga ttcggggact 1920
gaatctactg ctagtactgg gattggcaaa aatttcgtga atgaagatga attgaaatcc 1980
acatatgccg tagattctcc tacaggagta cctgcctctc ttccagagcc tgctcagact 2040
tctagagata ttgatttgtt tcctggccaa cctttacaac caaatcagcg tagtggtaac 2100
cttggtgtta taggaagaag tttgactgac cttggagctg ttggtgacaa cttcagtgca 2160
tcaactgcta attctggcgg agttcgtgat caattatata atttgcagat gcttgaggca 2220
gctcacctca aacttccaca acctaaggac tcagaacgtc ctaggaccta tactcctaaa 2280
caccctacga taacacctcc tagttttcct caagtacagg ctcctattgt taataatcct 2340
gctttttggg agagagtagg tattgaacaa tatggcactg ataccctgtt ctttgcattt 2400
tactatcaac agaacactta ccaacagtat atggctgcaa aagagctaaa gaagcagtct 2460
tggagatatc accggaagta taacacatgg tttcaacggc atgaagagcc aaaagttgca 2520
acagatgaat atgagcaagg aacatatgtg tactttgatt tccatattgc aaatgatgat 2580
ctgcaacatg ggtggtgtca aagaatcaag accgacttca cctttgaata taattatctt 2640
gaagatgagc ctattgtcta a 2661

<210> SEQ ID NO 199
<211> LENGTH: 1536
<212> TYPE: DNA
<213> ORGANISM: Glycine max

<400> SEQUENCE: 199
atgtacttgg aaatctcctc tctaagtcta tgtatacatg tccaatgtcg tgggagtcag 60
gaaaagttga ttccctcatg ggatgaagcg atagagaatg gtttgcgaga attggggtgg 120
tcggggatgg cgcaatgcat ccttgtgtcc attgctatgt gctttgatgc acagcagtcc 180
ttcatggcaa tctactccga cgactaccca acatggcact gcacagagac agcatgcacc 240
tcatcacgtt ctgacatatg caagcttcca aagtcctctt gggcatggga tggaccctct 300
tctaagacaa tcatatcaca gtttggcctt gaatgtgcag gcagcttcat cacaggttta 360
cctcaatctt ctttcttcgc cggttgcctt atcggttcct ttcttcttgc ctccttggct 420
gatacatctc ttggaagaaa gaacctcctc ttgctgtctt gtttatcaat gtccatatct 480
tctatcttca ttgtcttctc caccaatgtt tggatctact ccgcctttaa attcctcatc 540
gggttttggc gttcatccat cggaacatgt gttctggtgt tgctgactga gaaagtgagc 600
actgagtgga ggttcacagt gggaattgtc gaatatttct gcttcacatt ggggtatatg 660
atcttgcctg gaatagctta tataaacaag aattcttcat ggaaaactct ctatgtgtgg 720

-continued

```
acatccattc ctgccatttt ttactctatc attgcttacc tttttgttac cgagtctcca    780

aggtggcttc tcatgcaagg tcgagagcaa gaagccatgg caatgcttaa cggagtttct    840

tcagtagaaa atggtgctaa tttaactgct agcctgctga aagttcctgc tgctaaacaa    900

aagtcttcaa ttttccaact ttactcatca atagcagagt tgtttgagag aagttgggct    960

cttaaacgga tggtggccat tatggtgctt ggtcttggga ttggaatggt gtattttggc   1020

atgcctttgg ccgtcgggaa cttaggattt gacatttact tggcagttgt gcttaatgcc   1080

ttgatggaaa taccttcttg tgtagtcacc tacttcttgg aaaactacag aagaaagcca   1140

tctattcttg cattttcagt agcaagtggg atatgctgtg tattgtgtgt ggtcgtaggc   1200

agtgggcagc aggtagctaa ggtggggata tcattggtag cctttttag tgctgtcacg   1260

gcttataatg tgtttctcat ttacattata gagttgtttc ccaccagcgt aaggaacacc   1320

acaacctcat tggtgaggca agcaactgta tttggtaaca tattcatccc atttttgata   1380

tctgcaggaa ggaaaaatga tattttctcc tatggcgtat ttggagtagt tataatatca   1440

tcctgtttga ctttagtctg tttgccagag accacaggaa tagcactttg tgataccatg   1500

gatcaacaag agaaaaagca cagcttatct gtgtaa                              1536
```

<210> SEQ ID NO 200
<211> LENGTH: 960
<212> TYPE: DNA
<213> ORGANISM: Glycine max

<400> SEQUENCE: 200

```
atgaaacacc tcctgcaatt cgtgtctacc acctccaatc tcaccagctt tgcagtgttt     60

cagaagcatt tgaatgccaa gacattggtt tgtccaactg tgaaagcaat ggggtctaaa    120

agaccctttt caaattcatc aaaaccctcg tcaccatttg ttgaggacaa gaagaatgtg    180

aagcttaaag ggttggaagc cagccttggt tccaagaagc ttgttgttga ggagaatgat    240

gttaatagct attcgattga gcttgagaga ttaagaaatg acccaacaat agtagacacg    300

gtgactgttc aggaactccg gaaaaccttg aagagattta acgtccctgc caaaggtcgt    360

aaagatgata ttttgtctgc ctggaagagt ttcgtgggca gtaacatgtg tgaactagat    420

tctcatgcac aagaaaaaaa atggccatgg atttcttctg aaaatgcatc tgtagaagtg    480

gaggctaaaa aagtattgga tgaagaccat attgaaaatg tcaatgaaaa tcccgagata    540

tctgaactta accaggctaa gagaaggtta aaacaatcag aatctgagag aaaaactatc    600

aaagtgacaa caaagaagaa agtttcattg aaatcagacg aggattcaga ttttaagcct    660

tccagggcaa agagaaaagt atcttcagat gttgctagca ttgttgtaca gtcagaggaa    720

atcagtacag ctactattca aactgaacca tggacagttc ttgcccacaa gaagcctcaa    780

aaaggttgga ttgcttataa tcctagaact atgagacccc cacctcttgc tcaggataca    840

aaatttgtca agcttttgtc atggaatgcc aatggattga gagcattgct aaaattagaa    900

ggattctcag cacttcaact tgcccaaagg gaagactttg atgtattgtg tttgcaatag    960
```

<210> SEQ ID NO 201
<211> LENGTH: 1194
<212> TYPE: DNA
<213> ORGANISM: Glycine max

<400> SEQUENCE: 201

```
atgtcccaca gaaacgtggt cacctggacg gccatgatct ggcaacaacc atatgagtgc     60

atggagtgtg tttcctcaaa tgctcagaga tggggtgaac cccactgctt tcaccatatc    120
```

```
atctttttttg aaggcctctg taagggtttg aaagctcttc catgtggcca gttagttcat    180

gctttggcct tcaagattgg tgtccaagga tcatccatat atattgataa tgcacttatg    240

gatatgtatg ccacttgttg caataggatg gatcatgcaa ggatggtttt cgatgatatc    300

acaaccaaga ctgatgatga aggagcgtta agtctcttca gcttctcaat tgcagctaaa    360

gcttgtgcat caattggatc gggtattttg ggcaagcagg taaatgctgc agtggttaag    420

catggatttg agtccaacct tcctgtcatg aattccatac tggacatgta ctgcaagtgt    480

cattgtgcat ctgaggaaaa acaattattc tctgaaatga ctcataaaga taccatcaca    540

tggaatacct tgatagctgg atttgaagca ttggattcca gagagtctct ctgcatattt    600

tctgcagtag gtgcatgtgc taacttagca gttctgtatt gtgggcaaca gcttcatggt    660

gtaattcaaa atgctatgca caaatttgtc tcctggactt caatgatgat tgaatatggg    720

gatcacggat acggtaaaga ggctgttgag ttattcaatg aaatcgtcag atcaggtatt    780

aaaccagata agatggtatt tatggcagtt ctaagtgctt gtagccatac tggactagtg    840

gacgaaggga tgagatattt tatattaatg accagctatt atgatgtaac ccctgatata    900

gaggtatatg aatgtgtggt tgatttgctt ggacgtgctg gaagagtaaa ggaagcttat    960

caactaatag agagtatgcc atttaatcca aatgagtcta tctgggcagc ccttcttgga   1020

gcttgtaaag tgcataaaca acccactctg gatatgaagc caaatagtgc aggaacttat   1080

gcgttgttat caaatattta tgctgctgaa ggaaactggg ctgattttgc cagctcaacg   1140

aagttgagaa gtattaaaaa taaaagtgag tcggggagga gtggattgaa ttga        1194
```

<210> SEQ ID NO 202
<211> LENGTH: 309
<212> TYPE: DNA
<213> ORGANISM: Glycine max

<400> SEQUENCE: 202

```
atgattcata aggataaatt cccttatgaa aacactaatc aaatccttgc ttcctgtttt     60

ttcattctct ttgtgactag aaaagatgtg aaggctacct gcggaatacc tgaaatagct    120

tttgcaacat ttgagaacat ggaatatgga gaagattaca tgaagcctga tacagagaca    180

tacaattggg ttattcaagc ttatactaga gctgaatctt atgacagagt acaagatgtt    240

gctgtgttac ttggcatgat ggttgaggat cacaaacgta tacagccaaa tgcgaagacc    300

catgcgtaa                                                            309
```

<210> SEQ ID NO 203
<211> LENGTH: 213
<212> TYPE: DNA
<213> ORGANISM: Glycine max

<400> SEQUENCE: 203

```
atgtccctaa taaatatagt cctaattaat gctatggatg tttccttagt tgtcaatagt     60

ggcactgtag tgccaaagca gtgtggagtg acactgggcc gttacaagga ggccatagca    120

tctcagttta gttgtgcggc tgtcacaact gctatcacgg agtggccgaa atcacggtgg    180

agcaggtgct ttgtggacgc tacattgaaa taa                                 213
```

<210> SEQ ID NO 204
<211> LENGTH: 2859
<212> TYPE: DNA
<213> ORGANISM: Glycine max -continued

<400> SEQUENCE: 204

```
atggttagcg gcaacatttt tcattgtaga aaaaactcgt ggcctccgca agagtatatc     60
agtaaatcca ctttgcagct gtttgattat gatagttctg ctccccctga acaagcttgg    120
agaaggagat taaacagcca tgccaatctt cttaaagaat ttagagtaac ttttacggaa    180
gctataaaaa tggttcgatt aggtatacgc atttggtcat atgttaggga agaggcttct    240
catggaagga aagcgcctat tgatcctttc actcgagaaa gttgcaagcc atctgcatct    300
caaggagttc cacttggagg gatgggggagt ggcagcatat caagaggatt tagaggcgag    360
ttccgacaat ggcaaattat tcccagctta tgtgaagcat caccagtcat gtcaaatcag    420
ttctctattt ttataagtag agagggagga aagaaaaaat ttgcatcagt cttggctcct    480
ggccagcatg aaggtttagg atctagcagg aaacctgatg atcagggcat atcatcgtgg    540
ggatggaatc taagtggcca gcactcaacc taccatgctt tgtttccaag agcttggaca    600
gtttatgatg gtgagccaga tccagaacta aaaatatcgt gtcggcagat atcgccgttc    660
ataccacata attatagaga aagcagtcta cctgctgctg ttttcgttta tacgttggtg    720
aatactggta aggaaagagc taaagtcagc cttctgttta cttgggcgaa ttccattggt    780
ggaagctcac actcgtcagg agatcatgtg aatgaaccat tcaaagctga agatggagtc    840
tctggtgtac ttctatatca caagacagcg aaaggaaacc ctcctgttac ctttgccatt    900
gctgcatgtg agacacagaa tgttaatgtt tctgttttgc caagttttgg gctgtctgaa    960
gaaagtagta tgactgcaaa acacatgtgg agtaaaatgg tgaaggatgg gcaatttgac   1020
caggagaatt tcaattctgg acctagcatg ccctcatcac ctggagagac actttgtgct   1080
gctgttgcag cttccacatg ggttgaaccc catggaaaat gcaccgttgc atttagtctt   1140
gcatggtcat ctccaaaagt aaagttcgtg aaaggtagca ctttcaacag gagatataca   1200
aaattttacg ggacttctga gaaagctgcg gcagacttgg cccatgatgc attgacacat   1260
tacaatcggt gggaagaaga gattgagaaa tggcagaatc ctgttcttaa ggatgaggcc   1320
ctacctgaat ggtacaaatt tacattattt aatgagctgt actttcttgt tgctggagga   1380
acaatttgga ttgactctcc tgtgctatct tcgaatatgc ggaatgacca ggatcgagta   1440
agggagttag aaagtgcagt tgtgaaagaa actgaagata aaatgagcga ccgaaaaagg   1500
acagttgtgg agagtacaac ggatagtacc tatgattctg ctgttattac aggacatgat   1560
cgtgcagatg aaaaattgta tgaagatgat gatgatgttg gaagattctt gtacttggaa   1620
ggagtggaat atatcatgtg gtgtacatat gatgtgcact tctatgcctc atttgccctt   1680
cttgagctct ttcctaggat tgaattaaat atacagcgtg actttgctag agctgtcttg   1740
tgtgaagatg gaagaaaagt aaagtttctg gcagagggaa attggggcat tcgcaaggtt   1800
tatggagcgg tgccacatga tttgggggaca catgatccat ggcatgaaat gaatgcctac   1860
aacatccatg atactagcaa gtggaaggac ctgaacccaa aatttgttct tcaggtgtat   1920
cgagattttg ctaccacagg tgatttgcaa tttggagtag atgtgtggcc tgctgtccgt   1980
gctgcaatgg agtacatgga acaatttgat agagatggtg atggtcttat tgagaatgat   2040
gggttccctg atcaaacata cgatacatgg acagtccatg gtgtgagcac ttactgtggt   2100
tgtctttggc ttgctgctct acaagctgca gctgtaatgg cccttgaact aggtgacaga   2160
gaatttgcag aaacatgtaa aaggaagttt ttgaaggcta agccagcatt tgaagaaaaa   2220
ttgtggaatg gtacgtattt taactatgac agtggatcaa gcggtaacag taaatccatt   2280
caagcagatc aattggctgg gcagtggtat acagcatcct cagggctgcc ctcccttttt   2340
```

-continued

```
gaggattcta aaatcaaaag tgctcttcgg aaggtttatg atttcaatgt aatgaaagtt   2400

aaaggaggca gaatgggtgc tgtaaatggc atgcatccca atggtaaggt ggatgagacc   2460

tgtatgcagt ctcgagaagt atggacaggt gtgacctatg gtcttgctgc tacaatgata   2520

cacgcgggaa tggaagaaga ggccttcaca actgctgagg gaatatttct agcaggctgg   2580

tcagaagatg gatatgggta ctggtttcag acaccagagg catggacaat ggatgggcac   2640

tacaggtccc ttatgtatat gaggccccta gctatttggg gcatgcaata tgcaataaat   2700

cggcccaagg caattctaga ggcccctaaa atcaatatca tggacagaat ccacttatct   2760

cctgttattg gaggatactc tcataatgaa acaggtgtga ggaagattgc aacaaaagca   2820

ggatgcttta gcaattctgt atttaattgt gcttgctga                         2859
```

<210> SEQ ID NO 205
<211> LENGTH: 1674
<212> TYPE: DNA
<213> ORGANISM: Glycine max

<400> SEQUENCE: 205

```
aacgttctgc tgttgagaaa caacttaaat ttgagtccag atattgctga agtctcacaa     60

gagaaattgc tttcattggt tgctgaaaga ttaattgatt caaatagtag tgtgaatggc    120

aaagatgcag gctatgttga aaatcaacaa cagaacattg ctgatgcaat tgacttactc    180

cctaggcttg ctactggaat tgatgtaaat ataaaattta ggagaatagc tgattttgaa    240

ttcactcgag agtgtgccat atttgatctg ctggacattc ctttgtatca tggctggatg    300

gttgatcctc aggattatga cactgcgaat gcaattggat caaagtccta taatgccctt    360

atgggagagc ttgtctctct tgaaacacta aacatgaatg tccatcatga aaataatcca    420

gaagattgtg ttgattttgt ggctgcaaca actgctactc ttggagttcc ttctcccagt    480

ctttcaaaag ccaggtcgtt tgattattct tctcattcta tttctgatca tatacaaaga    540

aaaggtgatc tagaagaaga ggcagagttg ttgagagtct tgaaaatgtc cgaggctgaa    600

aatgatcctg ttgtaggtca cataaatgga ggagaaattt ctgtcagtat ggatagaaat    660

atgtgtgatg aggaggttat aaatacggat tctggagata aattaggaaa tagcactggt    720

gctgaatctc ttgacctgaa taatgtgatt gagaacaacc ttgatgcatt ggttcagaat    780

gagagtgaag atatcccata tcctgaaaaa cactctgtct ctttgtttga gtgccgtgca    840

gatgtttctg gaggagatgg aaaagtccat gatcaatcca ctcctacaac tatagatcat    900

gaagttgtag atgaatctca tggacctgat gccacagtat tatcattctc atcccctggc    960

catacaaatt cagattcatc tagtgtcaga tatcatcaaa ctgatgtttc tggagcattg   1020

acttcatgtg ttcaagggag tgagcccata tatgaaggag aggaatgtgt gttggataca   1080

agaactggaa attttgagga tcgtgaactt gtttatgaag gtgaggtggt acttgcagaa   1140

cagtctgaca aaaacacctt agctgctcct gatctaagag ctaaggatga acttactcca   1200

gaacaaggtg aattgatcaa gagtttcttg aggaataacg ccagccagtt gacattttat   1260

ggtcttttct gtttacaata tgggcttaaa gagcgtgaat acaccatgtt caagtttgag   1320

ggtgagctct atcttctagc cacggaacaa ggttacataa atcaacctga tctggtctgg   1380

gaaaaactga atgaggtcaa tggtgataca ttgtttttga ccagtaattt caaggaattc   1440

aaggtagaaa accatgaaag tagcacttgg gatgagaaca atgctctgac cagcactgtt   1500

gactatcttg ccagcataga tagtgcaaca catgcaagct tagatatcaa ttctgatcta   1560
```

-continued caattagcaa tagccttgca acaacaagag tttgagcaac agccaccacg ccaggataat 1620
tcacagcagc aatcatccat tagcggtagc tctagactgg tcacaggtcc caag 1674

<210> SEQ ID NO 206
<211> LENGTH: 873
<212> TYPE: DNA
<213> ORGANISM: Glycine max

<400> SEQUENCE: 206
atgggattta gaattagcag ttcctcctct tcatcatgct tttgtttgca acgtgcgctt 60
cttcctccgt taacagcgat agccacttct actcgtgcct tgaggaggag taattgcata 120
ccaagttgtt cagtatctta tcaaaagttt gttgagtttg cattggatga aaccaaacgc 180
cacactcact tgatcccttc gcctttacag gaaaagttca gtttcatgaa ttccaaggat 240
gttaaaggaa gttttagtat gctatcattt gaagctgcaa aaattaggct tctacgaagt 300
ttgatcattc agacagaaac aatgcaggtt ttggatttta ctgtctttcc aaaagcagaa 360
tatgatgtcc ccatattttg tgctaacttt ttcacctctg ctaaaacaaa cattattgtg 420
ttggacctta accctgtgca tgatatcatc aatcagtatg agtacaagga gaagtacttt 480
aaaagcttaa ttcctcttgg ccttaaatat gctgaggtat ggttggaatt gatatgcaaa 540
gcagttaaag agacagatga atctcagatt ttccacaatc tcgaagcaca acatagatat 600
ctgacatgga gagctgaaaa ggatccagga cgaggtgttt tgaagaagct gattggtgac 660
acacttgcca aggatatgtt gagaagcttt ctctttaatg gagtcgatga acttggaagc 720
aaaacattca atgattattt tccacagtac tgctgtcaag agggaaatct aaataaaaaa 780
ggcaatatta ttgggaagtc ctttgaaaat cgcccttgga atgctagagg agaatttatt 840
ggatccttca gctggattga cgttgatgtg tag 873

<210> SEQ ID NO 207
<211> LENGTH: 2103
<212> TYPE: DNA
<213> ORGANISM: Glycine max

<400> SEQUENCE: 207
atggcttcgg agactgagac gttcgctttt caggccgaga tcaaccagct cctcagtcta 60
ataatcaaca ccttctacag caacaaggag atctttcttc gtgagctcat cagcaatgcc 120
tctgacgctt tggacaagat tcgatttgag agtcttacag acaagagcaa gcttgatgct 180
cagccagagt tgttcattca cattattcct gacaagacca acaacacatt gtctatcatt 240
gacagtggta ttggcatgac taaggctgat ttggtgaata acctcggtac tattgcaagg 300
tctgggacca aggaattcat ggaagccctg gctgctggtg ctgacgtgag catgattggg 360
cagttcggtg ttggtttcta ctcggcttat cttgtagctg ataaggttat tgttaccaca 420
aagcacaatg atgatgaaca gtatgtctgg gagtcccatg ccggtggctc atttactgtg 480
acaagagata catctggtga gaaccttggt aggggaacaa agataacttt gtttcttaag 540
gaagatcaac ttgagtatct tgaggaacgc cgtctgaagg atttgataaa gaagcattct 600
gaattcatta gctatccaat ttctctctgg attgagaaga ctactgaaaa ggagatttct 660
gatgatgagg atgaggaaga gaagaaggat gaggagggta aagttgaaga tgtggatgaa 720
gataaggaga aggaggagaa gaaaaagaag accattaagg aggtatctca cgagtggtca 780
ttggtgaaca agcagaagcc tatttggatg aggaaacctg aagagattac gaaagaagaa 840
tatgctgctt tctacaagag tcttaccaat gattgggaag agcatttggc tgttaagcac 900
ttttctgttg agggtcagct ggagtttaag gctgtcctct ttatccccaa gagggcacct 960
tttgatctct ttgacaccag gaagaagcct aacaacatca aactgtatgt ccgccgtgtc 1020
ttcatcatgg acaactgtga ggagttgatg cctgaatatc ttagctttgt taagggtatt 1080
gtggattctg aggatcttcc tctcaacatt tctagagaaa tgctgcagca gaacaagatc 1140
ctgaaagtca tcaggaagaa cttggtcaag aagtgcattg agatgttctt tgaaattgct 1200
gaaaacaagg aagactataa caagttttat gaagccttct ctaagaacct gaaacttggt 1260
attcatgagg attctcagaa caagacaaag ctagctgaat tgctcaggta tcactccact 1320
aagagtggtg atgagatgac cagcctcaag gactatgtta ccaggatgaa ggaaggacag 1380
aatgacatct actacattac tggtgaaagc aagaaagctg tcgagaattc cccctttcctt 1440 gaaaagctta agaagaaggg atacgaggtt ctctacatgg ttgatgctat tgatgagtat 1500
gctgttggcc agcttaagga atttgaggga aagaagttgg tctctgctac caaggaaggc 1560
ctaaaacttg atgagagcga agacgagaag aaaaagaagg aagaactaaa ggataaattt 1620
gagggtcttt gccatgtgat caaggatgtg ttgggtgaca aggtggagaa agttgtggtg 1680
tctgatcgtg ttgtggattc tccttgctgt ctggtgacag gtgaatatgg gtggacagcc 1740
aacatggaaa ggattatgaa agcacaggca ttgagggaca gcagcatggc tggatacatg 1800
tcaagcaaga agacgatgga gattaaccct gagaacccca tcatggagga gctgaggaag 1860
cgagcagatg ctgataagaa tgacaagtct gtgaaggatc tcgtgctctt gctctttgag 1920
actgctcttc taacttctgg gttcagcctt gatgatccca acactttcgg taacaggatt 1980
cacaggatgc tgaagcttgg actgagcatt gatgaagatg ctggtgaagc agatgctgac 2040
atgcctcctc ttgaggacgc tgatgcagat gctgagggta gcaagatgga agaagttgat 2100
taa 2103

<210> SEQ ID NO 208
<211> LENGTH: 1869
<212> TYPE: DNA
<213> ORGANISM: Glycine max

<400> SEQUENCE: 208
atgctctctc gctctctcag acctcgtcac atactctcct ccctccgttc attacccttt 60
accctaaacc caaacccaaa ccctaaccct aaccctaacc gaacccctcc aatccgagcc 120
tccacacacc gtcccttctc ttcttcatgg ctgtccgaac ctggaaaccc aatcatccaa 180
tggccctcac tacccccacc aaaacccact ccgaacccaa acccaaaccc aaacctaaac 240
cccacacccg accctccctc tcccaaccca aacgctctct ccgtcatctc caacctcttc 300
gccgaccctt ccctctcgcc cggcccggcc ctccacgccg agctcgaccg ggctgggatc 360
gagccggacc cggcccttct gctcgccgtg ttcgatcgct tcggctcgtc gcccaagctg 420
ctgcactcgc tcttcctctg ggcccagacg cggcccgcct tcaggcccgg ccccaagctc 480
tttgacgccg tagtcaacgc gctcgcgaag gcgagggagt ttgacgccgc gtggaaactt 540
gttctccatc acgccgagaa agacggggaa gaagaaggag aaaaagaaag gttggtttcc 600
gttggaacct tcgctatcat gattcggcgc tacgctcgtg caggtatgtc caaacttgca 660
attagaacat atgagtttgc cacaaataac aagtcaattg tggattctgg ctcagaaatg 720
agtttattgg agatattgat ggattcactt tgtaaagaag ggtctgtgag ggaagcttca 780
gagtatttcc tttggaaaaa ggagttggac ttaagttggg ttccttctat tcgggtttat 840
aacataatgt taaatggatg gtttcgattg cggaaactca agcagggaga gagactttgg 900
gcagagatga aggagaatat gagacccact gttgtgacat atggtaccct tgtggaagga 960
tattgtcgaa tgcgccgtgt cgaaaaggca cttgaaatgg ttggtgatat gaccaaagaa 1020
ggaattgcac caaatgcaat tgtgtataat ccaataatcg atgcactggc cgaagctgga 1080
agattcaaag aggcattggg tatgttggaa cgttttcatg ttttggaaat aggccctact 1140
gattcaacat acaattctct ggtaaagggg ttttgtaagg caggagatct tgtaggtgct 1200
agtaagattc ttaaaatgat gataagtagg ggtttcctcc caagtgctac cacttataac 1260 tacttttta ggtacttttc aagatgtaga aaaatcgagg aggggatgaa cctgtataca 1320
aagttgattc aatctggtta taccccagat cggttaactt accatcttct ggtgaagatg 1380
ttatgtgaag aggagaagtt ggacttggca gttcaagtta gcaaggaaat gaggcataat 1440
ggatatgaca tggacttggc tacgagtacc atgttagttc acttgctttg caaagtgcgt 1500
aggttggaag aggcttttgt ggaatttgag gacatgatac ggaggggtat agttcctcag 1560
tatctgactt tccagagaat gaaagctgat ttaaagaaac aaggtatgac tgaaatggct 1620
caaaaacttt gcaagttgat gtcttctgtt ccttattctc cgaatttgcc aaatacttat 1680
ggtgaagtca gagaagatgc atatgcacga agaaaatcta taattcggaa agccaaagca 1740
ttttctgata tgctgaagga ctgtaaggac cctagtgaac ttcgtaagca tagaagttca 1800
tcagaaaata ctgtctcaag cacaaacagt ttgatagagg atattgagag aaaaagaaat 1860
acaggatga 1869

<210> SEQ ID NO 209
<211> LENGTH: 2898
<212> TYPE: DNA
<213> ORGANISM: Glycine max

<400> SEQUENCE: 209
atgccacttg ctgaattgta tgatcctgct agaggttatc ttgtgaatga tacatgtgtt 60
gttgaggctg acatttctgt gcgtaaagat atggattggt catatgattc aaaaaaggaa 120
actggttatg ttggactgaa aaaccaagga gctacatgtt atatgaattc tctgcttcaa 180
acattgtacc acatttctta tttccgaaag gctgtgtacc atatgcccac gactgaaaat 240
gatatgccat cagggagcat ccctctggca ttacaaagtt tgttttacaa attgcagtat 300
agtgacacta gtgtggcaac aaaagagtta acaaagtctt ttggatggga tacatatgat 360
tcgttcatgc agcatgatgt ccaagagctt aatagggttc tttgtgaaaa gctagaagga 420
aaaatgaagg gaactattgt ggaaggcact atacagcaat tgtttgaagg acaccatatg 480
aactatattg aatgcatcaa tgtggattat aaatcaacaa gaaaagaatc attttatgat 540
cttcagcttg atgtcaaagg ctgtaaggat gtgtatgctt cttttgataa gtatgtggaa 600
gtggaacgac ttgagggtga taacaagtat catgctgaga actatggttt acaggatgct 660
aggaagggtg tgttgttcat tgatttccct cctgttcttc agcttcagtt aaaacggttt 720
gagtatgatt ttacgcgaga cactatggta aagatcaatg accgctatga gttccccttg 780
caactagatc ttgataggga taatggcaaa tatctatctc ctgaagcaga cagaagtatt 840
cgcaattttt atacacttca cagtgttttg gttcacagta gtggggtgca tggcggacac 900
tactatgctt acattagacc aacactatca aatcaatggt ttaaatttga cgatgaacga 960
gtatcaaaag aagatccaaa gagggcttta gaagaacagt atggtggtga agaagagtta 1020
cctcgtataa atcctggctt caaccactct ccttttaaat ttacaaaaca ctcgaatgca 1080
tatatgcttg tctatgtacg tgagagtgac aaggataaaa taatttgtaa tgtggatgag 1140
aaggacattg ctgaacacct tagaatgaga ttaaagaaag aacaagatga aaaggagctg 1200
aagaggaagg agaaggctga ggctcacttg tacaccacca taaaggttgc ttgtgatgaa 1260
gatctacgtg aacagattgg aaataatata ctctttgatc ttgtggatta tgataaagta 1320
cgaagttttc gtgttcaaat acaaatgcct tttatggttt tcaaggaaga aattgccaaa 1380
gagttcggta tacccatcca gtatcaacgt ttttggttgt gggcaaagcg ccaaaacaac 1440
acatataggc caaatagagc actgacacct caggaagaag cacaatcagt tggactgcta 1500
agagaagttt ccactaaagc aaataatgca gagctgaagt tatttttgga actagaaatg 1560
gggcaggatt tgcgccctat tcctcctcct gagaagtcaa aagagaatct cttgcttttc 1620
tttaaacttt atgaaccttc aaatgagaag cttcggtatg ttgggcggct tttgtgaag 1680 agtagtggga agccagaaga tatattggta aaactaaatg aaatggctgg atatgctcct 1740
gatcaagata tagacatgtt cgaggagata aaatttgtgc ctaatgtcat gtgtgaacgg 1800
gttgacaaga aatccacatt ctttgggagt cagcttgagg atggtgatat tatttgcttc 1860
caaaagtccg tccaaactgg aagtggagag cgatatcgct atccagatgt tccttctttc 1920
ttggaatatg tgcacaaccg tttggttgtt cgctttagga ctttggagaa accaaaggag 1980
gatgaattta gtctggagct gacaaagctt gacacttatg acaatgttgt agaagaagtt 2040
gctcaacata ttggtttgag tgatccttct aaaattagac tcacatctca taactgctac 2100
tcccagcaac ctaaaccaca gtctatcaag taccgaggaa tggaacattt gtcagacatg 2160
ctgattcact ctaatcagac ttctgatatt ctatactatg aagtattgga tatccctctg 2220
ccagaattgc aatgcctaaa aactcttaaa attgctttcc atcatgatac caacgatgaa 2280
gttgtgattc atactattag attaccgaga catagtactg tgtctgatgt aattaatgat 2340
cttaaatcaa aggtagattt atcacatcct gatgcagaac ttagattgct tgaaattttc 2400
tatcacaaga tctataagat tttccgtgtc agcgaaaaga ttgagaacat taatgatcaa 2460
tattgtgctc tacgagcaga ggaggttctt gaagaagaga aaaaccttgg cccgcatgat 2520
cggttgatcc atgtttatca tttcttgaaa gacacaactc aaaatcagca gcaagttcag 2580
aactttggac atcctttttt attggttatc catgagggtg agacattaac tgaagtcaaa 2640
ttgcgaatac agaaaaagtt gcaagttcca gatgaggagt tttcaaagtg gaagtttgca 2700
tttttgtcat ttggtcgtcc tgagtacctt caagattcag atattgtttc agctcggttt 2760
cagaggaggg atatctacgg tgcatgggag caatatctcg gactggaaca cactgacaat 2820
gcttcaaaaa ggtcgaatgc tgccaatcag atctttgctc ctaactaccc tccccccaaa 2880
tggcaatggc aaaaatag 2898

<210> SEQ ID NO 210
<211> LENGTH: 151
<212> TYPE: RNA
<213> ORGANISM: Glycine max

<400> SEQUENCE: 210
gacaccaaag auagggauau uaaacgaaug gaauuaguau auggauguaa uauaaugaaa 60
uagagccacu uuuggguucc cuaugaaaug aggcauagaa aggagccacu gugaagaagu 120
uuuacgaguu acgaaggaaa cuucgaguuc a 151

<210> SEQ ID NO 211

<211> LENGTH: 3248
<212> TYPE: DNA
<213> ORGANISM: Glycine max

<400> SEQUENCE: 211

```
atatcttcaa catgattttc tttttaaaac tctatttgta gacatataaa gtttttcaag     60
ataattttcg tttgttctaa aaaaatttc tttttgttct tttagaaact aagaataatt    120
tatacatatt tgtaagggtt attacaatta gtggtttgtt tatacatcct tttctttttt    180
ttttataaga tagttataaa ccagtaaaag taggaagagt ggatacaggt agtgtacaca    240
tgtttcaact aatcgaataa tcagtatgta aattcaacaa catcaattct ataaagtaaa    300
taaaaaattg aaaaagataa ttgatttttt taaacaaatt aataaccatt tattaaaaaa    360
aattattgaa caattataga ggattgtatg aaatttaatt atcaagtttg ttataaaaat    420
ttacaactga agattcaata tcaaaaaaaa aatataaaat aagattaaag tagaagaact    480
atataaataa ctaaaaagag tattaaaata ataaaaagat agcatatata aaaaattgat    540
gttgatgaaa ataatttgta aattaatgtt gaatattttt ttagtaagtt gtagatatag    600
atataagata tattttacaa atttttcctt taaaggtgca ctgttaaaga tttcgtagat    660
gaataaaaca ttttaattat agaatttaaa cttgtattat tagtaagttt tgtattaatt    720
attaataaac tggtaaattg aagtaggcat tgatactgtg ggccactaaa ctggtaaatt    780
tataaaataa aagtgttgaa tataaaacta aaaattttta attaaaagaa ttaaataaag    840
atactctaaa ttttaaactt tcatactaaa aaaaattaca gataatttga aattttctta    900
tgaggcgtgt acactattat attaacaaac aatgttaact tataaatata ttacactaat    960
gacactccca tttttttcc cttttttttg tacacattaa actgctttag aattcttatt   1020
attcacataa aatgaggtgg aaaattaaac aattaaacta tacattaaat gattttactt   1080
actgtcaata gattatttgc taaatcattt ataaaatata taaatattaa taaacgttta   1140
tatatatttt atatttttta tacgtaaaaa atatttttaa acaaatattt attattttta   1200
tatttaatta tatatttact tatcagtaag ttttgaaaat gaaaagtttc taatttttaa   1260
ttaaaattaa gttatttatt aattgatatt gaacttatat ataaatataa aaattgcaat   1320
taatttttca aactcacaat ttattttatt aaatttaact cacctattag ctaaacttta   1380
ataattagta atactaatta tcatacgtca tgtaatctta taaaataaac ttgttagtta   1440
attttgttag attttatgtt aatatgttcc cttttcatca accgtttttt tttttacgtg   1500
ctataaagaa aatgttatta ataaattttt agatctttta aaataaaatt caactaactt   1560
tacaacaaat tattattaac aaatttaatg ataggatgaa ttgtgtatta ataaaaataa   1620
aacagtaaat aaaatatagg ttttaatatc agatgtttag atattatcta ttaattttac   1680
aatacgaaac tttaagtact aattttattt atattgaaaa aattttgttt atatataaag   1740
tttataattt tttattatag tgttgttaga tcaaaaaatt tgtttctatt tgctataatt   1800
gattattaat ttccttattt aaaaaattac taaatattaa agtctttaat aaaccactaa   1860
aaaaatgatt aaactactca gaacttagaa ctaactatca aatgttaaag tttttggtaa   1920
catgacaaaa taattaaact gggtgctaaa ttcgggtatt attgtaccat ataatcagac   1980
taggctacta ttttctttct tacccgagac ctttatatga tggaagaaga ccgtcgagac   2040
tgtacagata gaggctcgag gcgctcttcg tggtaaccct cgatctttta gactgagact   2100
ggtgtgttgg agagttttgc aactttaaga agtgtaatcg acaataagtt atgtagttct   2160
tttgtcgtta tatagataac cgttttccac ctacccaata cgaaaagtca caacgtcaac   2220
```

cctgagaacc gtatcacgac tactgggaac caacggaggt actcttcgta gaactcctcg 2280
aagaacttat aaaagcgaaa cctgacacca cccaacggga accccaacga agaagttaac 2340
cagatcctag accaaacgtg tgtaaacagg atataaaccc aggggtgtat cgtgacaaat 2400
gttatcctcg tcacgttaca ccggctcaac taaacttttc acgaggaata ctatgctatg 2460
ttaatttttc tccaggaaga accgaactat ttctgacaag actcaaaccc ggtggtaata 2520
aggtcagcgt ccaaggcgaa tcgtcgtaaa acggagttca agtcgacctc cgataagata 2580
ccccataacc ttgtcgatat cccctcgaag gaggaatgaa atagaggtcc cgtcgtgcga 2640
acagaccacc ctctcatcta cggtaccttc ttaatctgtc gcttctattt tctcagaact 2700
cagcttattt cacgaccaaa gatagtgtga gcgttgtaaa cttaaagaaa tgataagatc 2760
acgaacgaag ccaaggttta ggagataaac tggaacggcc gtagtacaca cctgttaaac 2820
cgtaaggtaa aacctttaaa aaagaacgtt ggaactaacc tttccgttaa taattttgag 2880
tgtatgtctg ctataagtat tagagtcaaa cgttgttagt tgaagaacta acctaactct 2940
tacttaaata aacccaagag tcggtgtatg gaccaaaacg tagacagaac ggatctcact 3000
gacgatcaga ggtacgttac tttctattca tagactttcg tggggtaggt gaaaggggtt 3060
tatttgtccc ctttttttacc ctaaaaagaa aacgaagtca gaccttgtga caacacaccg 3120
agtacgaata cttgaagaaa cagttctatc acttacgttg aagggtctcc atagacttct 3180
ttgtcgtcct ctgtgtcgaa cgacgtaatt gccttttcag atggggttgt ctgagtctgc 3240
gtgttact 3248

<210> SEQ ID NO 212
<211> LENGTH: 3362
<212> TYPE: DNA
<213> ORGANISM: Glycine max

<400> SEQUENCE: 212
cctcgctcct tacagtagtt acagatgtcc tttggattga catgagtctt ctttttttcct 60 ttaaacacct ttttcttgat gttgttgtta gagttagaga ctacaagacc agatccattt 120
gattcttcag aatttccaag tgctttagat cgaagttccc ttgagtataa gctggatttc 180
acttcctcca tggtgacaca ttccttacca acactaagag aattgacaaa gctctcatat 240
gatggtggta aagaggctaa caaaatcacg acaacatctt catcctctat cttaacatct 300
atatctctta attccatcaa aatagagttc agttcatcaa gatgatcctt aagagatgta 360
ccttctttca tgtgtaaaaa aaatagttgc cttttcaaga agagcttgtt gcatattgac 420
ttggtcatat atagcttttc caacttgagc cataagccac ttgcaatttc tttatttgca 480
acctcatata aaacttcatt aggtaaagaa agcaagatta gtgagtgagc cttttcttct 540
tgttccgcaa gttctccaat ctttaaaaca gaggcctttt cttttgattc agaagccact 600
ggtttcttca tagatgcaga agcaacagga gcccaaacac gttgttcctt caacaaagca 660
cacatcttga tgtgccatag attgaagttg tttttttccat tgaatttctc aattctaatt 720
gtgtttgaca taatttcttg agtgtccttg atcacaatga agcaacgaaa gataccagaa 780
acaagactca cacaacttga tcttcgtatt caaacgagaa tcttgaattc ccttgatcgc 840
aacttgagct cttgatacca atttgttatg aaagtgatga agaacaaaca agaacagcag 900
tagcaacaaa acaatatgtc atacacaaaa ttgcagtaaa atgaaagaga gtaaagagag 960
aaaagaacac atagaattta cgtggttcac ccttaatcag gctacatcca cgaggagggg 1020

-continued

```
cagaaagatt ttatttctga tgcaattcaa aaggaagtgc ttcccaatac agaacaaccc   1080
ttccttatat aagaaaagga tcagaaaaaa caaaacaaaa caaaataaca gaattaactg   1140
ccatatagat tttagtcaca acctaacaac actattgatg aaattttcct aaaataaaaa   1200
taagatagtg agagagaaat agtaatttat aaagtagtta tagaagtaaa ataggacaaa   1260
aaaaggattt tagccacaat ccaacaacac tattgataaa attttcctga aataaaaata   1320
agatagtgag agagaaatag tgatttataa agtagttata gaagtaaaat aggacaaaaa   1380
aatatgtata ccaaaacttc atataatctc tgcatatagt tatagatatt tttgaatttc   1440
tctcgttttt tttttcttta cctctttcta tttttcattc ttacacccaa aaaatgagat   1500
ctacatctaa cattttccat tttttttttg tgaagaaaca ttttcctttg tctccggcat   1560
tcctccacca gcacattttt agccattgga ttaatccgat cactgagatt aaaatttaaa   1620
aaaaaaaata ttattgctgg cctttggaag aatccaaaag acacattcgg tgtgtcaatt   1680
caacatactt tttgctacta gaaaccagct cgtagggccc tttaatttct aattcagaca   1740
ctcaaaccat gcgttcaact actattctta tccgagtcca cacatagcat tttatttttta   1800
aatcataata taagccatgt catgtgccaa atttccttga agctatttaa tatttcaaaa   1860
tatactacct cctttgttga ataaccttcc atttcttagc tgtcacattt tgtcaatcaa   1920
ttaacaagtg cgtctttttt aatcgcatcc ctcttgtggc tttccttcca tttttgcagg   1980
agcaatttgg cgggttgatc atgagacacg tggttatttt ttctttcaat ttcttgctgc   2040
tttgtgtctt catttctgct ataacaagca caaaaaagtga agtatctagc acaaatgaag   2100
aacaatcatt ttcttaccat atcaaagctt tggaattcat atggaaacat ttgggctatc   2160
aacatgtgtg gccagaaatg gaatttagct ggagaattgt tgttggaacc ttgattggaa   2220
tcttgggagc agcatttgga agtgtagggg gagttggtgg tggtggcatc tttgtgccaa   2280
tgctaatcct cattattggg tttgatccaa aatcagcagt tgctatttca aagtgtatgg   2340
tcacaggtgc agccatctca gcagtattct tctgcatgaa gcaaaggcat ccccacacttg   2400
atgaacccgt tatcgactac gatttgatgt tgctaataca accaaccctc atgcttggaa   2460
tcagcatagg agttattttg agtgtaatat ttgctgattg gatggtcaca attcttctaa   2520
ttattctatg tatagtgaca tcaatcaggg cattcttcat gggtgctgac acatggaaaa   2580
aggaaaccaa aatgaaagag gtgagcatcc ttggcaacat gtattggaag gagtttgtac   2640
ttattttcat tgtctggctc gcatttgtga actatacagt ttcctgttca gtcacatact   2700
ggatacttat tttgtcacag ataccaatta ctgtaggatt ttatttgtac caagcaagag   2760
ccctatatca ggggagagct gcaggatctc aacacacaca ttggccattg caccatctat   2820
ttctagctag catttgttct ctgttagctg gaattgttgg tggacttctt ggtacaggtt   2880
ctggatttgt tatgggtcct ttatttctag aagtgggaat tgctccacag gtagcaagtg   2940
ccacagccac ttttggaatg atgtattcat catctttatc tgtcatacaa tattacctgt   3000
tgaatcgttt tcctgttcct tatggtaaaa ttaaacttaa ttcacattgt acccttctat   3060
tatttctgaa tggttttcaa aggcaacata aacttattca agtaattttt atgcatgttt   3120
caacctgttt tgcagctctc ttccttactc ttgtggctgc aattgcagca ttcctaggac   3180
agtatctcat tgacaagctt gttaatatct tccaaagggc ttctttaatt atttttgtct   3240
tggccttcac aatatttgtt agttcaattg cattaggtgg agtcggcata tcaaacatga   3300
tcttgaagat tcaaaggaat gaatacatgg gatttgataa tttttgcagg aatgatacat   3360
ag                                                                  3362
```

<210> SEQ ID NO 213
<211> LENGTH: 2449
<212> TYPE: DNA
<213> ORGANISM: Glycine max
<220> FEATURE:
<221> NAME/KEY: misc_feature
<222> LOCATION: (432)..(531)
<223> OTHER INFORMATION: n is a, c, g, or t
<220> FEATURE:
<221> NAME/KEY: misc_feature
<222> LOCATION: (1991)..(1991)
<223> OTHER INFORMATION: n = a sequence of between 3 and 13 nucleotides

<400> SEQUENCE: 213
ttaccctcga aattcaattt actttatcca ctttagtcga tacttcctct atcacgttca 60
aaatagtaca cttcgattgt aagattggtt atatagttat atttatataa aatgactatt 120
ttttagtaag gttgttggta cttggtgtgt tttttagtct ttaccggtga ctgggcgaac 180
gtcgggacat ttgttccaag gtcgaagaag ttgttgttga gctactcgac gtgcgcagaa 240
ggaacgtttg tggtattcgt ttgtagttgc aatttttaaa aaaatagttt gggccctgga 300
acaaagggct tggttgggga ataaaaagaa ttggattttc ttcgaattgg attgttggaa 360
taattgcatt ggaccaaaag aaggctttca cttaaattac aaccagaagg gctttgaccg 420
ttcacgttca gnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn ngtcccgaat 540
tcccaagtta gcttccgaag ttagcttcgg tgttccgaca gatgtcccaa gttacgaact 600
ttgactttgt tgtttatgca actcccgttc gctcttacca cttcccaagt tagcttccag 660
tgttccgaca gatgtcccaa gttacgagtt cccaagttac gatccagagt cacgacacaa 720
gtttcctttt ctgttatgca actcccttcg ccaaattaaa agtaaaaaaa aacaaaattg 780
agatgcagcc aaaaatgact tttggccgca tttacaatat cggacattgt aagattccgc 840
caaaaaatat tggcggaatc taacgttcag catcttacgt ttaataaagt gtttttaatg 900
tttttacggt ggcaagttga ataatctcgc caaggattta ttggctgcat ttaaaccata 960
gcatttttcg gaaaaaaaat catcactgaa agagggggtt gtttagtttt gaagtaagga 1020
aaagaaacta aggcaattta atggtaattt gtgtccatga aagtgcggac acacaagtgt 1080
taaaaataaa aggacgttgt aaaaaacaat tttaactata taaaaaagtt atagagaatc 1140
ataggcgtaa tatattgtgt gttgtgttat tgtttttaca ttattgtgtg ttatacataa 1200
aactttaact tcatatagat attaagtgaa atcaataaag ggaaatatta ttacacggtt 1260
acggaaccta cgtgtgtatg taccattgta agataaagtt tttaataaaa aacaaaattt 1320
tttaaaaatt ttttatgaaa agaaaatttt taaattataa cttatttcac taaaaatttt 1380
aacaaaattt taaacataag aaaaagacgg atataaaaga taacaaatta tattaagtaa 1440
aataacttat gtattatgta ctaattaaaa ttttttaatg tgaattaaaa aattacttta 1500
atacaaaaaa ttaaaaaaat cttttattat tttaatattt tttcgtacgg atgtttaatc 1560
atttcaacca aaattaaaaa gatgtacagt gaaacaacta aattttgtat tttaactgag 1620
atacatatta actagcttcc aaaaagaaaa aattagatta cacttttcac ataaataata 1680
aatgaaatta aatcgacaca attatttaat aattatgtat cagggcaatt taagttaata 1740
cgtttgaatt ttagtcagaa tctaaaccat ggttattctc aattaaacaa tggttacttc 1800
tctctcttcc aatatcctct ctcttgttac ttaactttca attaaacaat gtatttttc 1860

-continued

```
ttaatgtata ttaattagta attatgtata atatgtggac tttacctaag gatctttatt   1920
ttttttata ttttaagtac aattaacaca acgaagcgaa agagatatcg aacgaggaga   1980
aaatctatta ngaaggtgtt cggatcgagc ttcttccttc tctattctcc cgggatacct   2040
tttacaccag tctttaggta ttatctcagg ctggtgttga tagcttaatt aatagaagta   2100
cgtattctta tgatctaata ggtcatattt tctaactttt tagtagagtt tggagagaaa   2160
aagaaaagat aacgttaaag acctaagaaa aagataacgt taaaaaccta ataatatatt   2220
gctaaaaagt tgaaaggtaa aaggttttaa aaggtaaata tctttatcta tctgatcttt   2280
gctgtagaga atagagttac tgtggtttct atccctataa tttgcttacc ttaatcatat   2340
acctacatta tattacttta tctcggtgaa aacccaaggg atactttact ccgtatcttt   2400
cctcggtgac acttcttcaa aatgctcaat gcttcctttg aagctcaag               2449
```